(12) United States Patent
Callewaert et al.

(10) Patent No.: US 9,598,682 B2
(45) Date of Patent: Mar. 21, 2017

(54) HYDROLYSIS OF MANNOSE-1-PHOSPHO-6-MANNOSE LINKAGE TO PHOSPHO-6-MANNOSE

(75) Inventors: Nico Luc Marc Callewaert, Hansbeke-Nevele (BE); Wouter Vervecken, Landskouter (BE); Petra Sophie Tiels, Merelbeke (BE); Han Karel Remaut, Boutersem (BE); Kathleen Camilla Telesphore Alida Maria Piens, Ghent (BE)

(73) Assignees: VIB vzw, Ghent (BE); Universiteit Gent, Ghent (BE); Oxyrane UK Limited, Manchester (GB); Vrije Universiteit Brussel, Brussels (BE)

( * ) Notice: Subject to any disclaimer, the term of this patent is extended or adjusted under 35 U.S.C. 154(b) by 615 days.

(21) Appl. No.: 13/499,061

(22) PCT Filed: Sep. 29, 2010

(86) PCT No.: PCT/IB2010/002589
§ 371 (c)(1),
(2), (4) Date: Sep. 6, 2012

(87) PCT Pub. No.: WO2011/039634
PCT Pub. Date: Apr. 7, 2011

(65) Prior Publication Data
US 2013/0158239 A1 Jun. 20, 2013

Related U.S. Application Data

(60) Provisional application No. 61/246,847, filed on Sep. 29, 2009.

(51) Int. Cl.
C12P 19/14 (2006.01)
C12N 9/24 (2006.01)
C07K 14/00 (2006.01)
C12P 21/00 (2006.01)

(52) U.S. Cl.
CPC ............ *C12N 9/2488* (2013.01); *C07K 14/00* (2013.01); *C12P 19/14* (2013.01); *C12P 21/00* (2013.01); *C12P 21/005* (2013.01); *Y02P 20/52* (2015.11)

(58) Field of Classification Search
CPC .................................................. C12N 9/2488
See application file for complete search history.

(56) References Cited

U.S. PATENT DOCUMENTS

| | | | |
|---|---|---|---|
| 4,307,717 A | 12/1981 | Hymes et al. | |
| 4,352,883 A | 10/1982 | Lim | |
| 4,353,888 A | 10/1982 | Sefton | |
| 4,407,957 A | 10/1983 | Lim | |
| 4,704,362 A | 11/1987 | Itakura et al. | |
| 4,837,148 A | 6/1989 | Cregg | |
| 4,879,231 A | 11/1989 | Stroman et al. | |
| 4,882,279 A | 11/1989 | Cregg | |
| 4,883,666 A | 11/1989 | Sabel et al. | |
| 4,929,555 A | 5/1990 | Cregg et al. | |
| 4,968,733 A | 11/1990 | Miller et al. | |
| 4,976,859 A | 12/1990 | Wechs | |
| 5,084,350 A | 1/1992 | Chang et al. | |
| 5,158,881 A | 10/1992 | Aebischer et al. | |
| 5,272,070 A | 12/1993 | Lehrman et al. | |
| 5,284,761 A | 2/1994 | Aebischer et al. | |
| 5,585,089 A | 12/1996 | Queen et al. | |
| 5,798,113 A | 8/1998 | Dionne et al. | |
| 5,800,828 A | 9/1998 | Dionne et al. | |
| 6,110,703 A | 8/2000 | Egel et al. | |
| 6,265,185 B1 | 7/2001 | Muller et al. | |
| 6,699,658 B1 | 3/2004 | Wittrup et al. | |
| 6,803,225 B2 | 10/2004 | Contreras et al. | |
| 6,872,392 B2 | 3/2005 | Nakamura et al. | |
| 7,029,872 B2 | 4/2006 | Gerngross | |
| 7,259,007 B2 | 8/2007 | Bobrowicz et al. | |
| 7,262,287 B2 | 8/2007 | Kang et al. | |
| 7,326,681 B2 | 2/2008 | Gerngross | |
| 7,390,884 B2 | 6/2008 | Segal et al. | |
| 7,422,742 B2 | 9/2008 | Greenfeder et al. | |
| 7,422,890 B2 | 9/2008 | Gopalakrishnakone et al. | |
| 7,431,927 B2 | 10/2008 | Couto et al. | |
| 7,442,772 B2 | 10/2008 | Goddard et al. | |
| 7,449,308 B2 | 11/2008 | Gerngross et al. | |
| 7,488,591 B2 | 2/2009 | Miura et al. | |
| 7,785,856 B2 | 8/2010 | LeBowitz et al. | |
| 8,026,083 B2 | 9/2011 | Callewaert et al. | |
| 8,597,906 B2 | 12/2013 | Callewaert et al. | |
| 9,206,408 B2 | 12/2015 | Callewaert et al. | |
| 9,222,083 B2 | 12/2015 | Callewaert et al. | |
| 9,249,399 B2 | 2/2016 | Vervecken et al. | |
| 2002/0127219 A1 | 9/2002 | Okkels et al. | |
| 2002/0137125 A1 | 9/2002 | Zhu | |

(Continued)

FOREIGN PATENT DOCUMENTS

AU 2012206984 8/2012
EP 1408117 4/2004

(Continued)

OTHER PUBLICATIONS

GenBank Accession No. NP_630514 (Sep. 2008).*
GenBank Accession No. AAO78636 (Oct. 2007).*
H. Guo et al. "Protein tolerance to random amino acid change", PNAS 101(25):9205-9210 (2004).*
Abe et al., "In vitro oligosaccharide synthesis using intact yeast cells that display glycosyltransferases at the cell surface through cell wall-anchored protein Pir.," *Glycobiology*, 13(2):87-95, print Feb. 2003, ePub Nov. 2002.
Ackerman et al., "Highly avid magnetic bead capture: an efficient selection method for de novo protein engineering utilizing yeast surface display," *Biotechnol Prog.*, 25(3):774-783, May-Jun. 2009.
Almeciga et al., "Production of an active recombinant human N-acetylgalactosamine-6-sulfate sulfatase enzyme in Pichia pastoris," *Molecular Genetics and Metabolism*, 111(2):S19, Abstract 11, Jan. 27, 2014.

(Continued)

*Primary Examiner* — Rebecca Prouty
(74) *Attorney, Agent, or Firm* — Fish & Richardson P.C.

(57) ABSTRACT

Described herein are methods and genetically engineered cells useful for uncapping a mannose-6-phosphate residue on an oligosaccharide.

21 Claims, 126 Drawing Sheets

(56) References Cited

U.S. PATENT DOCUMENTS

| | | |
|---|---|---|
| 2003/0147868 A1 | 8/2003 | Treco et al. |
| 2003/0186374 A1 | 10/2003 | Hufton et al. |
| 2004/0018588 A1 | 1/2004 | Contreras et al. |
| 2004/0018590 A1 | 1/2004 | Gerngross et al. |
| 2005/0014270 A1 | 1/2005 | Picataggio et al. |
| 2005/0064539 A1 | 3/2005 | Chiba et al. |
| 2005/0170452 A1 | 8/2005 | Wildt et al. |
| 2005/0265988 A1 | 12/2005 | Choi et al. |
| 2006/0014264 A1 | 1/2006 | Sauer et al. |
| 2006/0030521 A1 | 2/2006 | Defrees et al. |
| 2006/0040353 A1 | 2/2006 | Davidson et al. |
| 2006/0148039 A1 | 7/2006 | Kobayashi et al. |
| 2006/0286637 A1 | 12/2006 | Hamilton |
| 2007/0037248 A1 | 2/2007 | Bobrowicz et al. |
| 2008/0171359 A1 | 7/2008 | Botes et al. |
| 2009/0069232 A1 | 3/2009 | Callewaert et al. |
| 2009/0186011 A1 | 7/2009 | Vellard et al. |
| 2010/0291059 A1 | 11/2010 | Sakuraba et al. |
| 2011/0201540 A1 | 8/2011 | Callewaert et al. |
| 2011/0207676 A1 | 8/2011 | Callewaert et al. |
| 2012/0135461 A1 | 5/2012 | Cook et al. |
| 2013/0053550 A1 | 2/2013 | Geysens et al. |
| 2013/0096281 A1 | 4/2013 | Rychaert et al. |
| 2013/0158239 A1 | 6/2013 | Callewaert |
| 2013/0190253 A1 | 7/2013 | Callewaert et al. |
| 2013/0195835 A1 | 8/2013 | Callewaert et al. |
| 2013/0243746 A1 | 9/2013 | Vervecken et al. |
| 2013/0267473 A1 | 10/2013 | Piens et al. |
| 2013/0295603 A1 | 11/2013 | Piens et al. |
| 2015/0031081 A1 | 1/2015 | Vervecken et al. |
| 2015/0337273 A1 | 11/2015 | Geysens et al. |
| 2016/0251693 A1 | 9/2016 | Piens et al. |
| 2016/0279254 A1 | 9/2016 | Vervecken et al. |

FOREIGN PATENT DOCUMENTS

| | | |
|---|---|---|
| FR | 2954349 | 6/2011 |
| JP | 57-054588 | 4/1982 |
| JP | 2002-369679 | 12/2002 |
| JP | 2004-313074 | 11/2004 |
| KR | 20040062304 | 7/2004 |
| WO | WO 92/19195 | 11/1992 |
| WO | WO 95/05452 | 2/1995 |
| WO | WO 96/04378 | 2/1996 |
| WO | WO 96/21038 | 7/1996 |
| WO | WO 98/01473 | 1/1998 |
| WO | WO 98/01535 | 1/1998 |
| WO | WO 98/48025 | 10/1998 |
| WO | WO 99/36569 | 7/1999 |
| WO | WO 99/37758 | 7/1999 |
| WO | WO 01/49830 | 7/2001 |
| WO | WO 01/88143 | 11/2001 |
| WO | WO 02/18570 | 3/2002 |
| WO | WO 03/029456 | 4/2003 |
| WO | WO 03/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2005/100584 | 10/2005 |
| WO | WO 2005/106010 | 11/2005 |
| WO | WO 2008/100816 | 8/2008 |
| WO | WO 2008/120107 | 10/2008 |
| WO | WO 2009/033507 | 3/2009 |
| WO | WO 2009/105357 | 8/2009 |
| WO | WO2009137721 A1 | 11/2009 |
| WO | WO 2010/099195 | 9/2010 |
| WO | WO 2011/039634 | 4/2011 |
| WO | WO 2011/061629 | 5/2011 |
| WO | WO 2012/042386 | 4/2012 |
| WO | WO 2012/042387 | 4/2012 |
| WO | WO 2013/098651 | 7/2013 |

OTHER PUBLICATIONS

Andrés et al., "Use of the cell wall protein Pir4 as a fusion partner for the expression of *Bacillus* sp. BP-7 xylanase A in *Saccharomyces cerevisiae*," *Biotechnol Bioeng*, 89(6): 690-697, Mar. 2005.

Boder and Wittrup, "Yeast surface display for screening combinatorial polypeptide libraries," *Nat. Biotechnol.*, 15, 553-557, Jun. 1997.

Boder et al. "Directed evolution of antibody fragments with monovalent femtomolar antigen-binding affinity," *Proc Natl Acad Sci U S A.*, 97(20):10701-5, Sep. 2000.

Brady, "Enzyme replacement for lysosmal diseases," *Annu. Rev. Med.*, 57:283-296, 2006.

Brady, "The lipid storage diseases: new concepts and control," *Ann Intern Med.*, 82(2):257-61, Feb. 1975.

Carlson et al., "Function and structure of a prokaryotic formylglycine-generating enzyme," *J Biol Chem.*, 283(29):20117-20125, Epub Apr. 4, 2008.

Chao et al., "Isolating and engineering human antibodies using yeast surface display," *Nat. Protoc.*, 1(2):755-768, 2006.

Chiba et al., "Production of human compatible high mannose-type (Man5GlcNAc2) sugar chains in *Saccharomyces cerevisiae*," *J Biol Chem.*, 273(41):26298-26304, Oct. 9, 1998.

Cho et al., "Structure of the extracellular region of HER2 alone and in complex with the Herceptin," *Nature*, 421(6924):756-760, Feb. 2003.

Davidow et al., "Cloning and sequencing of the alkaline extracellular protease gene of Yarrowia lipolytica," *J. Bacteriol.*, 169(10):4621-4629, Oct. 1987.

Dragosits et al., "The effect of temperature on the proteome of recombinant Pichia pastoris," *J. Proteome Res.*, 8(3):1380-1392, Mar. 2009.

Fournier et al., "Scarcity of ars sequences isolated in a morphogenesis mutant of the yeast Yarrowia lipolytica," *Yeast*, 7(1):25-36, Jan. 1991.

Fujii, "Antibody Affinity Maturation by Random Mutagenesis," *Antibody Engineering*, vol. 248, pp. 345-359, 2004.

Gasser et al., "Engineering of Pichia pastoris for improved production of antibody fragments," *Biotechnol. Bioeng.*, 94(2):353-361, Jun. 2006.

Grubb et al., "New strategies for enzyme replacement therapy for lysosomal storage diseases," *Rejuvenation Res.*, 13(2-3):229-236, Apr.-Jun. 2010.

Klis et al., "Cell wall construction in *Saccharomyces cerevisiae*," *Yeast*, 23(3):185-202, 2006.

Landgrebe et al., "The human SUMF1 gene, required for post-translational sulfatase modification, defines a new gene family which is conserved from pro- to eukaryotes," *Gene.*, 316:47-56, Oct. 16, 2003.

Lin et al., "Display of a functional hetero-oligomeric catalytic antibody on the yeast cell surface," *App. Microbiol Biotechol.*, 62(2-3): 226-232, print Aug. 2003, Epub Mar. 2003.

Matsuoka et al., "Analysis of regions essential for the function of chromosomal replicator sequences from Yarrowia lipolytica," *Mol. Gen. Genet.*, 237(3):327-333, Mar. 1993.

Nicaud et al., "Protein expression and secretion in the yeast Yarrowia lipolytica," *FEMS Yeast Res.*, 2(3):371-379, Aug. 2002.

Pignède et al., "Characterization of an extracellular lipase encoded by LIP2 in Yarrowia lipolytica," *J. Bacteriol.*, 182(10):2802-10, May 2000.

Rakestraw and Wittrup, "Contrasting secretory processing of simultaneously expressed heterologous proteins in *Saccharomyces cerevisiae*," *Biotechnol. Bioeng.*, 93(5):896-905, Apr. 2006.

Rodriguez et al., "Production of recombinant human N-acetylgalactosamine-6-sulfate sulfatase enzyme in Pichia pastoris," *Molecular Genetics and Metabolism*, 108(2):S79-S80, Abstract 197, Feb. 1, 2013.

Ruiz-Herrera and Sentandreu, "Different effectors of dimorphism in Yarrowia lipolytica," *Arch. Microbiol.*, 178(6): 477-483, print Dec. 2002, Epub Oct. 2002.

Ryckaert et al., "Isolation of antigen-binding camelid heavy chain antibody fragments (nanobodies) from an immune library displayed on the surface of Pichia pastoris," *J Biotechnol.*, 145(2):93-98, Epub Oct. 2009, print Jan. 2010.

(56) References Cited

OTHER PUBLICATIONS

Shusta et al., "Increasing the secretory capacity of *Saccharomyces cerevisiae* for production of single-chain antibody fragments," *Nat. Biotechnol.*, 16(8): 773-777, Aug. 1998.
Shusta et al., "Yeast polypeptide fusion surface display levels predict thermal stability and soluble secretion efficiency," *J. Mol. Biol.*, 292(5):949-956, Oct. 1999.
Swennen et al., "Secretion of active anti-Ras single-chain Fv antibody by the yeasts Yarrowia lipolytica and Kluyveromyces lactis," *Microbiology*, 148(Pt 1):41-50, Jan. 2002.
Tajima et al., "Use of a modified alpha-N-acetylgalactosaminidase in the development of enzyme replacement therapy for Fabry disease," *Am J Hum Genet.*, 85(5):569-580 Epub Oct. 22, 2009.
Tanino et al., "Construction of a Pichia pastoris cell-surface display system using Flo1p anchor system," *Biotechnol. Prog.*, 22(4): 989-993, Jul.-Aug. 2006.
Ueda et al., "Cell surface engineering of yeast: construction of arming yeast with biocatalyst," *J. Biosci. Bioeng.*, 90(2): 125-136, 2000.
VanAntwerp and Wittrup, "Fine affinity discrimination by yeast surface display and flow cytometry," *Biotechnol. Prog.*, 16(1): 31-7, Jan.-Feb. 2000.
Vega et al., "Partial characterization of α-mannosidase from Yarrowia lipolytica," *J Basic Microbiol.*, 28(6):371-379, ePub Jan. 10, 2007.
Vernis et al., "An origin of replication and a centromere are both needed to establish a replicative plasmid in the yeast Yarrowia lipolytica," *Mol. Cell Biol.*, 17(4): 1995-2004, Apr. 1997.
Wang and Shusta, "The use of scFv-displaying yeast in mammalian cell surface selections," *J. Immunol. Methods*, 304(1-2):30-42, Sep. 2005.
Wang et al., "A new yeast display vector permitting free scFv amino termini can augment ligand binding affinities," *Protein Eng. Des. Sel.*, 18(7): 337-343, print Jul. 2005, Epub Jun. 2005.
Wang et al., "Construction of a novel Pichia pastoris cell-surface display system based on the cell wall protein Pir1," *Curr. Microbiol.*, 56(4): 352-357, Apr. 2008.
Yeung and Wittrup, "Quantitative screening of yeast surface-displayed polypeptide libraries by magnetic bead capture," *Biotechnol. Prog.*, 18(2):212-220, Mar.-Apr. 2002.
Ying et al., "Soluble monomeric IgG1 Fc," *J Biol Chem.*, 287(23):19399-19408, Epub Apr. 19, 2012.
Hamilton et al; Production of complex human glycoproteins in yeast; Science; Aug. 2003; 301(5637):1244-1246.
Akcapinar et al; Effect of codon optimization on the expression of Trichoderma reesei endoglucanase 1 in Pichia pastoris; Biotechnol Prog; epub Jul. 2011; 27(5):1257-1263; doi: 10.1002/btpr.663.
Choe-Min-Hui; Structural analysis of N-linked oligosaccharides assembled on recombinant proteins secreted from Yarrowia lipolytica Yloch1 and Yloch1 Ylmnn4 mutants; Thesis, Chungnam National University: Department of Microbiology; 2006; 39 pages; Republic of Korea.
Choi, et al., "Structural analysis of N-linked oligosaccharides assembled on recombinant proteins secreted from Yarrowia lipolytica Yloch1 and Yloch1 Ylmnn4 mutants.," XXIIth International Conference on Yeast Genetics and Molecular Biology, 09—Protein biosynthesis, maturation, modification and degradation, Yeast, 22:S131, 9-35, 2005.
"Arxula adeninivorans," Wikipedia [online] Jan. 13, 2010 [retrieved on Jan. 31, 2010]. Retrieved from the Internet: <URL: http://en.wikipedia.org/wiki/Arxula_adeninivorans>, 2 pages.
"Eukaryotes Genomes—Yarrowia Lipolytica," The European Bioinformatics Institute [online] [retrieved on Jun. 26, 2012]. Retrieved from the Internet: <URL: http://www.ebi.ac.uk/2can/genomes/eukaryotes/Yarrowia_lipolytica.html>, 1 page.
Aebi et al., "Cloning and characterization of the ALG3 gene of *Saccharomyces cerevisiae,*" *Glycobiology*, vol. 6, No. 4, pp. 439-444, (1996).
Akeboshi et al., "Production of Recombinant Beta-Hexosaminidase A, a Potential Enzyme for Replacement Therapy for Tay-Sachs and Sandhoff Diseases, in the Methylotrophic Yeast Ogataea minuta", *Appl. Environ. Microbiol.*, 73( 15):4805-4812, (2007)
Alessandrini et al., "Alterations of Glucosylceramide-b-Glucosidase Levels in the Skin of Patients with Psoriasis Vulgaris," *J. Invest. Dermatol*, 23(6):1030-1036, (2004).
Bagiyan et al., "The Action of α-Mannosidase from Oerskovia sp. on the Mannose-Rich O-Linked Sugar Chains of Glycoproteins," *Eur. J. Biochem.*, 249(1):286-292, (1997).
Baharaeen and Vishniac, "A fixation method for visualization of yeast ultrastructure in the electron microscope ," *Mycopathologia*, 77(1):19-22, (1982).
Ballou, "Isolation, characterization, and properties of *Saccharomyces cerevisiae* mnn mutants with nonconditional protein glycosylation defects," *Methods in Enzymology*, vol. 185, pp. 440-470, (1990).
Barnay-Verdier et al., "Identification and characterization of two alpha-1,6-mannosyltransferases, Anl1p and Och1p, in the yeast yarrowia lipolytica", *Microbiology*, 150:2185-2195 (2004).
Barth and Gaillardin, "Physiology and genetics of the dimorphic fungus Yarrowia lipolytica," *FEMS Microbiology Reviews*, 19(4):219-237, Apr. 1997 [print], Jan. 2006 [online].
Bennetzen and Hall, "Codon Selection in Yeast," *J. Biol. Chem.*, 257(6):3026-3031, (1982).
Bentley et al., "Complete genome sequence of the model actinomycete *Streptomyces coelicolor* A3(2)," *Nature*, 417:141-147, (May 2002).
Bobrowicz et al., "Engineering of an artificial glycosylation pathway blocked in core oligosaccharide assembly in the yeast Pichia pastoris: production of complex humanized glycoproteins with terminal galactose," *Glycobiology*, 14(9):757-766 (2004).
Boisrame et al. "Sls1p, an endoplasmic reticulum component, is involved in the protein translocation process in the yeast Yarrowia lipolytica," *J. Biol. Chem.* 271(20):11668-75, (1996).
Bretthauer, "Genetic engineering of Pichia pastoris to humanize N-glycosylation of proteins," *Trends in Biotechnology*, 21(11): 459-462 (Nov. 2003).
Burda et al., "Ordered assembly of the asymmetrically branched lipid-linked oligosaccharide in the endoplasmic reticulum is ensured by the substrate specificity of the individual glycosyltransferases", *Glycobiology*, 9(6):617-625 (1999).
Burton and Harding, "Hydrophobic charge induction chromatography: salt independent protein adsorption and facile elution with aqueous buffers.," *J. Chromatogr. A* 814(1-2):71-81, (Jul. 1998).
Callewaert et al, "Use of HDEL-tagged Trichoderma reesei mannosyl oligosaccharide 1,2-alpha-D-mannosidase for N-glycan engineering in Pichia pastoris.," *FEBS Lett.*, 503(2-3):173-178, (Aug. 2001).
Callewaert et al., "Ultrasensitive profiling and sequencing of N-linked oligosaccharides using standard DNA-sequencing equipment," *Glycobiology* 11(4):275-281, (Apr. 2001).
Carter et al., "Humanization of an anti-p185HER2 antibody for human cancer therapy," *Proc Natl Acad Sci USA*, 89(10): 4285-4289, (May 1992).
Chiba et al., "Production in yeast of alpha-galactosidase A, a lysosomal enzyme applicable to enzyme replacement therapy for Fabry disease," *Glycobiology*, 12(12):821-828 (2002).
Choi et al. "Use of combinatorial genetic libraries to humanize N-linked glycosylation in the yeast Pichia pastoris," *Proc. Natl. Acad. Sci. USA*, 100(9):5022-5027, (Apr. 2003).
Cipollo and Trimble, "The accumulation of Man(6)GlcNAc(2)-PP-dolichol in the *Saccharomyces cerevisiae* Deltaalg9 mutant reveals a regulatory role for the Alg3p alpha1,3-Man middle-arm addition in downstream oligosaccharide-lipid and glycoprotein glycan processing," *J Biol Chem.*, 275(6):4267-4277, (Feb. 2000).
Cobucci-Ponzano et al., "The molecular characterization of a novel GH38 alpha-mannosidase from the crenarchaeon Sulfolobus solfataricus revealed its ability in de-mannosylating glycoproteins," *Biochimie.*, 92(12):1895-1907, (Aug. 2010).
Codon usage table: Yarrowia lipolytica CLIB122 [gbpln]: 5967 CDS's (2945919 codons), *Codon Usage Database* [online], [retrieved on Jul. 10, 2012]. Retrieved from the Internet:< URL: http://www.kazusa.or.jp/codon/cgi-bin/showcodon.cgi?species=284591>, 1 page.

(56) References Cited

OTHER PUBLICATIONS

Connock et al., "A systematic review of the clinical effectiveness and cost-effectiveness of enzyme replacement therapies for Fabry's disease and mucopolysaccharidosis type 1," *Health Technol Assess.*, 10(20):iii-iv, ix-113, (2006).
Database Accession No. P41546, UniProt (online), "RecName: Full Transcriptionmanal Activator HAC1"; XP002509286, Nojima et al., Nov. 1, 1995.
Database UniProt[Online] Aug. 1, 1998, "SubName: Full=Putative secreted protein;" XP002628929 retrieved from EBI accession No. UNIPROT:069822 Database accession No. 069822, 3 pages.
Database UniProt[Online] Jul. 11, 2006, "SubName: Full=Alpha-1, 2-mannosidase, putative; Flags: Precursor;" XP002628931 retrieved from EBI accession No. UNIPROT:Q1ASW5 Database accession No. Q1ASW5, 2 pages.
Database UniProt[Online] Apr. 29, 2008, "SubName: Full=Putative uncharacterized protein;" XP002628930 retrieved from EBI accession No. UNIPROT:B1BZG6 Database accession No. B1BZG6, 2 pages.
Davies et al, "Nomenclature for sugar-binding subsites in glycosyl hydrolases," *Biochem. J.*, 321:557-559 (1997).
Fickers et al. "New disruption cassettes for rapid gene disruption and marker rescue in the yeast Yarrowia lipolytica," *J. Microbiol. Methods.* 55(3):727-737, (Dec. 2003).
Fickers et al., "Carbon and nitrogen sources modulate lipase production in the yeast Yarrowia lipolytica," *J. of Applied Microbiology*, vol. 96, No. 4, pp. 742-749, (2004).
Fickers, P. et al. "Hydrophobic substrate utilization by the yeast Yarrowia lipolytica and its potential applications," *FEMS Yeast Research*, vol. 5, No. 6-7, pp. 527-543, (Apr. 2005).
Freire et al. "Efficient monitoring of enzymatic conjugation reaction by surface-enhanced laser desorption/ionization time of flight mass spectrometry for process optimization," *Bioconjug. Chem.* 17(2):559-564, (2006).
Fujita and Takegawa, "Chemoenzymatic Synthesis of Neoglycoproteins Using Transglycosylation with Endo-Beta-N-acetylglucosaminidase A," *Biochem. Biophys. Res. Commun.*, 282(3):678-682, (Apr. 2001).
Gao et al. "UpGene: Application of a web-based DNA codon optimization algorithm," *Biotechnol. Prog.*, 20(2): 443-448, (2004).
Gellissen, et al., "New yeast expression platforms based on methylotrophic Hansenula polymorpha and Pichia pastoris and on dimorphic Arxula adeninivorans and Yarrowia lipolytica-A comparison," *FEMS Yeast Res.*, 5(11): 1079-1096, (2005).
Genbank Acccession No. XM_502922 GI:50550898, "Yarrowia lipolytica YALI0D17028p (YALI0D17028g) mRNA, complete cds," Oct. 29, 2008, 2 pages.
Genbank Acccession No. XM_503217 GI:50551486, "Yarrowia lipolytica YALI0D24101p (YALI0D24101g) mRNA, complete cds," Oct. 29, 2008, 2 pages.
Genbank Accession No. AAF34579 GI:6979644, "1,2-a-D-mannosidase [Trichoderma reesei]" Feb. 16, 2000, 1 page.
Genbank Accession No. AAO78636.1 GI:29340846, putative alpha-1,2-mannosidase [Bacteroides thetaiotaomicron VPI-5482] Feb. 8, 2011, 2 pages.
Genbank Accession No. AAO79070.1 GI:29341282, "putative alpha-1,2-mannosidase [Bacteroides thetaiotaomicron VPI-5482]," Feb. 8, 2011, 2 pages.
Genbank Accession No. AAO79099.1, "putative alpha-1,2-mannosidase [Bacteroides thetaiotaomicron VPI-5482]," Feb. 8, 2011, 2 pages.
Genbank Accession No. AF212153 GI:6979643, "Hypocrea jecorina 1,2-a-D-mannosidase (MDS1) mRNA, complete cds," Feb. 16, 2000, 2 pages.
GenBank Accession No. AF441127 GI:16974782, "Yarrowia lipolytica Mnn9p (mnn9) gene, complete cds," Apr. 11, 2003, 2 pages.
GenBank Accession No. AJ563920 GI:38488499, "Yarrowia lipolytica och1 gene for alpha 1,6 mannosyltransferase," Nov. 20, 2003, 2 pages.
GenBank Accession No. AJ865333 GI:56266607, "Trypanosoma brucei brucei glcasella gene for glucosidase II alpha subunit precursor," Oct. 25, 2005, 2 pages.
GenBank Accession No. BAA08634 GI:1171477, "alpha-mannosidase [Aspergillus saitoi]" Feb. 10, 1999, 1 page.
GenBank Accession No. NP_630514 GI:21224735, "hypothetical protein SCO6428 [Streptomyces coelicolor A3(2)]," Jan. 19, 2012, 3 pages.
GenBank Accession No. NP_812442 GI:29348939, "alpha-1,2-mannosidase [Bacteroides thetaiotaomicron VPI-5482]" Jan. 20, 2012, 2 pages.
Genbank Accession No. XM_499811 GI:50543289, "Yarrowia lipolytica YALI0A06589p (YALI0A06589g) mRNA, complete cds," Oct. 29, 2008, 2 pages.
GenBank Accession No. XM_500574 GI:50546093, "Yarrowia lipolytica YALI0B06600p (YALI0B06600g) mRNA, complete cds," Oct. 29, 2008, 2 pages.
Genbank Accession No. XM_500811 GI:50546682, "Yarrowia lipolytica YALI0B12716p (YALI0B12716g) mRNA, complete cds," Oct. 29, 2008, 2 pages.
GenBank Accession No. XM_503488 GI:50552026, "Yarrowia lipolytica YALI0E03190p (YALI0E03190g) mRNA, complete cds," Oct. 29, 2008, 2 pages.
GenBank Accession No. YP_003013376 YP_003013376, "alpha-1,2-mannosidase [*Paenibacillus* sp. JDR-2]" Jun. 15, 2012, 3 pages.
GenBank Accession No. YP_003120664 GI:256420011, "alpha-1,2-mannosidase [Chitinophaga pinensis DSM 2588]," Jun. 18, 2012, 2 pages.
GenBank Accession No. YP_003584502 GI:295133826, "alpha-1,2-mannosidase [Zunongwangia profunda SM-A87]," Nov. 21, 2011, 2 pages.
GenBank Accession No. Z49631 GI:1015863, "*S. cerevisiae* chromosome X reading frame ORF YJR131w," Aug. 11, 1997, 2 pages.
GenBank Accession No. ZP_01061975 GI:86143590, "putative alpha-1,2-mannosidas [Leeuwenhoekiella blandensis MED217]," Nov. 9, 2010, 1 page.
GenBank Accession No. ZP_01885202 GI:149279069, "putative alpha-1,2-mannosidase [*Pedobacter* sp. BAL39]," Nov. 9, 2010, 1 page.
GenBank Accession No. ZP_02866543 GI:169349605, "hypothetical protein CLOSPI_00343 [Clostridium spiroforme DSM 1552]," Nov. 9, 2010, 2 pages.
GenBank Accession No. ZP_03677957 GI: 224537418, "hypothetical protein BACCELL_02296 [Bacteroides cellulosilyticus DSM 14838]," Nov. 10, 2010, 1 page.
GenBank Accession No. ZP_04848482 GI:253571075, "conserved hypothetical protein [*Bacteroides* sp. 1_1_6]" Jun. 9, 2010, 2 pages.
GenBank Accession No. ZP_05522540 GI:256784109, "secreted protein [Streptomyces lividans TK24]," Dec. 9, 2010, 2 pages.
GenBank Accession No. ZP_06527366 GI:289767988, "secreted protein [Streptomyces lividans TK24]" Oct. 26, 2010, 3 pages.
GenBank Accession No. ZP_07083984 GI:300774115, "probable alpha-1,2-mannosidase [Sphingobacterium spiritivorum ATCC 33861]," Dec. 1, 2010, 1 page.
Gentzsch and Tanner, "The PMT gene family: protein O-glycosylation in *Saccharomyces cerevisiae* is vital," *Embo J*, 15(21):5752-5759, (1996).
Gerngross, "Advances in the production of human therapeutic proteins in yeasts and filamentous fungi," *Nature Biotech.*, 22(11):1409-1414, (2004).
Ghaemmaghami et al., "Global analysis of protein expression in yeast." *Nature*, 425(6959):737-741, (Oct. 2003).
Gonzalez and Jordan, "The alpha-mannosidases: Phylogeny and adaptive diversification," *Mol Biol Evol.*, 17(2):292-300, (Feb. 2000).
Gossen and Bujard, "Studying gene function in eukaryotes by conditional gene inactivation," *Ann. Rev. Genetics* 36:153-173, (2002).
Grinna and Robbins, "Substrate specificities of rat liver microsomal glucosidases which process glycoproteins," *J. Biol. Chem.*, 255(6):2255-2258, (1980).

(56) References Cited

OTHER PUBLICATIONS

Guarente et al., "A GAL10-CYC1 hybrid yeast promoter identifies the GAL4 regulatory region as an upstream site," *Proc. Natl. Acad. Sci. USA* 79(23):7410-7414, (1982).
Hamilton and Gerngross, "Glycosylation engineering in yeast: the advent of fully humanized yeast," *Curr Opin Biotechnol.*, 18(5):387-392, (Oct. 2007).
Henderson and Finn, "Human tumor antigens are ready to fly," *Adv Immunol.*, 62:217-256, (1996).
Hermans et al., "Human lysosomal alpha-glucosidase: functional characterization of the glycosylation sites," *Biochem J.*, 289 ( Pt 3):681-686, (Feb. 1993).
Hinnen et al. "Transformation of yeast," *Proc. Nat. Acad. Sci. USA* 75(4):1929-1933, (1978).
Howard et al., "Identification of the Active Site Nucleophile in Jack Bean alpha-Mannosidase Using 5-Fluoro-beta-L-Gulosyl Fluoride," *J. Biol. Chem.*, 273(4):2067-2072, (1998).
Hudson and Kortt, "High avidity scFv multimers; diabodies and triabodies," *J. Immunol. Methods*, 231(1-2):177-189, (1999).
Huston et al. "Engineered antibodies take center stage," *Hum. Antibodies*, 10(3-4):127-142, (2001).
Ichishima et al., "Molecular and enzymic properties of recombinant 1,2-alpha-mannosidase from Aspergillus saitoi overexpressed in Aspergillus oryzae cells," *Biochem. J.*, 339: 589-597, (1999).
Ito et al., "Transformation of intact yeast cells treated with alkali cations," *J. Bacteriol.*, 153(1):163-168, (1983).
Kornfeld and Kornfeld, "Assembly of asparagine-linked oligosaccharides," *Annu Rev Biochem.*, 54:631-664, (1985).
Kotula and Curtis, "Evaluation of foreign gene codon optimization in yeast: expression of a mouse IG kappa chain," *Biotechnology (N Y).*, 9(12):1386-1389, (1991).
Kuroda et al., "Production of Man5GlcNAc2-type sugar chain by the methylotrophic yeast Ogataea minuta," *FEMS Yeast Res.*, 6:1052-1062 (2006).
Laroy et al., "Glycome mapping on DNA sequencing equipment," *Nature Protocols*, 1: 397-405 (2006).
Lee and Park, "Enzymatic in vitro glycosylation using peptide-N-glycosidase F," *Enzyme and Microbial Technology* 30(6):716-720, (2002).
Liao et al., "Cloning, expression, purification, and characterization of the human broad specificity lysosomal acid alpah-mannosidase," *J. Biol Chem.*, 271(45):28348-28358, (Nov. 1996).
Lobsanov et al., "Modulation of activity by Arg407: structure of a fungal alpha-1,2-mannosidase in complex with a substrate analogue," *Acta Crystallogr D Biol Crystallogr.*, 64(Pt 3):227-236, (2008).
Luer and Hatton, "Vancomycin administration into the cerebrospinal fluid: a review," *Annals of Pharmacotherapy*, 27:912-921, (1993).
Madzak et al., "Strong hybrid promoters and integrative expression/secretion vectors for quasi-constitutive expression of heterologous proteins in the yeast Yarrowia lipolytica," *J Mol Microbiol Biotechnol.*, 2(2):207-216, (Apr. 2000).
Madzak et al., "Heterologous Protein Expression and Secretion in the Non-conventional Yeast Yarrowia lipolytica: A Review", *J. Biotechnol.*, 109:63-81 (2004).
Maras et al., "Molecular cloning and enzymatic characterization of a Trichoderma reesei 1, 2-alpha-D-mannosidase," *J. Biotechnol*, 77: 255-263 (2000).
Martinet et al., "Protection of mice against a lethal influenza challenge by immunization with yeast-derived recombinant influenza neuraminidase," *Eur J Biochem.*, 247(1):332-338, (Jul. 1997).
Merkle et al., "Cloning, expression, purification, and characterization of the murine lysosomal acid alpha-mannosidase," *Biochim Biophys Acta.*, 1336(2):132-146, (Aug. 1997).
Moreau et al. "Cell-free transfer of membrane lipids. Evidence for lipid processing," *J. Biol. Chem.* 266(7):4329-4333, (1991).
Moreau et al. "Trafficking of lipids from the endoplasmic reticulum to the Golgi apparatus in a cell-free system from rat liver," *J. Biol. Chem.*, 266(7):4322-4328, (1991).

Mori et al., "Signalling from endoplasmic reticulum to nucleus: transcription factor with a basic-leucine zipper motif is required for the unfolded protein-response pathway," *Genes Cells*, vol. 1, No. 9, pp. 803-817, (Sep. 1996).
Newman and Ferro-Novick, "Characterization of new mutants the yeast secretory pathway isolated by a [3H]mannose suicide selection," *J. Cell Biol.*, 105(4):1587-1594, (1987).
Orlean et al., "Cloning and sequencing of the yeast gene for dolichol phosphate mannose synthase, an essential protein," *J. Biol. Chem.*, vol. 263, pp. 17499-17507, (Nov. 1988).
Paulik et al., "Cell-free transfer of the vesicular stomatitis virus G protein from an endoplasmic reticulum compartment of baby hamster kidney cells to a rat liver Golgi apparatus compartment for Man8-9 to Man5 processing," *Arch. Biochem. Biophys.*, 367(2):265-273, (1999).
Platt and Lachmann, "Treating lysosomal storage disorders: Current practice and future prospects," *Biochim Biophys Acta*, 1793(4):737-745, (2009).
Poljak, "Production and structure of diabodies," *Structure*, 2(12):1121-1123, (1994).
Protein Data Bank, "Structure of the GH92 Family Glycosylhydrolase CCMAN5" Deposition: Sep. 29, 2010 [retrieved on Jul. 17, 2012]. Retrieved from the Internet: < URL: http://www.pdb.org/pdb/explore/explore.do?structureId=2XSG>, 2 pages.
Rexach and Schekman, "Distinct biochemical requirements for the budding, targeting, and fusion of ER-derived transport vesicles," *J. Cell Biol.*, 114(2):219-229, (1991).
Richard et al., "Tagging morphogenetic genes by insertional mutagenesis in the yeast Yarrowia lipolytica," *J Bacteriol.*, 183(10):3098-3107, (May 2001).
Smith and Waterman, "Comparison of biosequences," *Adv. Appl. Math.*, 2(4):482-489, (Dec. 1981).
Song et al., "Characterization of Genes Involved in N-glycosylation in Yarrowia lipolytica," *Yeast*, 20:S147 (2003).
Song et al., "Engineering of the Yeast Yarrowia lipolytica for the Production of Glycoproteins Lacking the Outer-Chain Mannose Residues of N-Glycans," *Appl Environ Microbiol.*, vol. 73, No. 14 (Jul. 2007), pp. 4446-4454.
Sreekrishna et al., "Invertase gene (SUC2) of Saccharomyces cerevisiae as a dominant marker for transformation of Pichia pastoris," *Gene*, 59(1):115-125 (1987).
Stocks, "Intrabodies: production and promise," *Drug Discov. Today* 9(22): 960-966, (Nov. 2004).
Tremblay and Herscovics, "Cloning and expression of a specific human alpha 1,2-mannosidase that trims Man9GlcNAc2 to Man8GlcNAc2 isomer B during N-glycan biosynthesis," *Glycobiology.*, 9(10):1073-1078, (Oct. 1999).
UniProtKB/Swiss-Prot: P06280.1 GI:113499, "RecName: Full=Alpha-galactosidase A; AltName: Full=Alpha-D-galactosidase A; AltName: Full=Alpha-D-galactoside galactohydrolase; AltName: Full=Melibiase; AltName: INN=Agalsidase; Flags: Precursor," Jun. 13, 2012, 26 pages.
UniProtKB/Swiss-Prot: P15291.5 GI:116241264, "RecName: Full=Beta-1,4-galactosyltransferase 1; Short=Beta-1,4-GalTase 1; Short=Beta4Gal-T1; Short=b4Gal-T1; AltName: Full=UDP-Gal:beta-GlcNAc beta-1,4-galactosyltransferase 1; AltName: Full=UDP-galactose:beta-N-acetylglucosamine beta-1,4-galactosyltransferase . . . " Jun. 13, 2012, 10 pages.
UniProtKB/Swiss-Prot: P26572.2 GI:311033399, "RecName: Full=Alpha-1,3-mannosyl-glycoprotein 2-beta-N-acetylglucosaminyltransferase; AltName: Full=N-glycosyl-oligosaccharide-glycoprotein N-acetylglucosaminyltransferase I; Short=GNT-I; Short=GlcNAc-T I," Apr. 18, 2012, 6 pages.
UniProtKB/Swiss-Prot: P27809.1 GI:127214, "RecName: Full=Glycolipid 2-alphamannosyltransferase; AltName: Full=Alpha-1,2-mannosyltransferase," Jun. 13, 2012, 8 pages.
UniProtKB/Swiss-Prot: P38069.1 GI:586137, "RecName: Full=Alpha-1,2-mannosyltransferase MNN2; AltName: Full=Calcium resistance and vanadate sensitivity protein 4; AltName: Full=Mannan synthesis protein MNN2," Jun. 13, 2012, 5 pages.
UniProtKB/Swiss-Prot: Q09326.1 GI:1169978, "RecName: Full=Alpha-1,6-mannosyl-glycoprotein 2-beta-N-

(56) References Cited

OTHER PUBLICATIONS acetylglucosaminyltransferase; AltName: Full=Beta-1,2-N-acetylglucosaminyltransferase II; AltName: Full=GlcNAc-T II; Short=GNT-II; AltName: Full=Mannoside acetylglucosaminyltransferase 2; AltName: Full=N-g . . . ," Jun. 13, 2012, 3 pages.

UniProtKB/Swiss-Prot: Q24451.2 GI:32130434, "RecName: Full=Alpha-mannosidase 2; AltName: Full=Golgi alpha-mannosidase II; Short=AMan II; Short=Man II; AltName: Full=Mannosyl-oligosaccharide 1,3-1,6-alpha-mannosidase," Apr. 18, 2012, 13 pages.

UniProtKB/Swiss-Prot: Q9Y7X5.1 GI:74698597, "RecName: Full=Uncharacterized protein C365.14c," May 16, 2012, 2 pages.

Vandersall-Nairn et al., "Cloning, expression, purification, and characterization of the acid α-mannosidase from Trypanosoma cruzi," *Glycobiology*, 8(12):1183-1194, (1998).

Verostek et al., "Glycoprotein biosynthesis in the alg3 *Saccharomyces cerevisiae* mutant. I. Role of glucose in the initial glycosylation of invertase in the endoplasmic reticulum," *The Journal of Biological Chemistry*, vol. 268, pp. 12095-12103, (Jun. 5, 1993).

Verostek et al., "Glycoprotein biosynthesis in the alg3 *Saccharomyces cerevisiae* mutant. II. Structure of novel Man6-10GlcNAc2 processing intermediates on secreted invertase," *The Journal of Biological Chemistry*, vol. 268, pp. 12104-12115, (Jun. 5, 1993).

Vervecken et al. "In Vivo Synthesis of Mammalian-Like, Hybrid-Type N-Glycans in Pichia pastoris," *Appl. Environ. Microb.*, 70(5):2639-2646, (May 2004).

Vocadlo et al., "Mechanistic insights into glycosidase chemistry," *Curr. Opin. Chem. Biol.* 12:539-555 (2008).

Ward et al., "Characterization of Humanized Antibodies Secreted by Aspergillus niger," *Appl. Environ. Microbiol.*, 70(5):2567-2576, (May 2004).

Wheeler et al. "Intrabody and Intrakine Strategies for Molecular Therapy," *Mol. Ther.*, 8(3):355-366, (Sep. 2003).

Yang et al., "Cell-surface display of the active mannanase in Yarrowia lipolytica with a novel surface-display system," *Biotechnol Appl Biochem*, vol. 54, No. 3, pp. 171-176, (Oct. 2009).

Yue et al., "Construction of a new plasmid for surface display on cells of Yarrowia lipolytica," *J Microbiol Methods*, vol. 72, No. 2, pp. 116-123, (Feb. 2008).

Zhu and Zhang, "SCPD: a promotor database of the yeast *Saccharomyces cerevisiae*," *Bioinformatics*, 15(7-8):607-611, (1999).

Zhu et al., "Mechanistic insights into a Ca2+-dependent family of alpha-mannosidases in a human gut symbiont," *Nat. Chem. Biol.*, 6(2):125-132. Epub Dec. 27, 2009 (2010).

Zimm et al., "Cerebrospinal fluid pharmacokinetics of intraventricular and intravenous aziridinylbenzoquinone," *Cancer Research*, 44(4):1698-1701, (Apr. 1984).

International Search Report and Written Opinion in PCT/IB2010/002589, mailed Aug. 5, 2011.

Written Opinion of the International Preliminary Examining Authority in PCT/IB2010/002589, mailed Jan. 31, 2012, 11 pages.

Written Opinion of the International Preliminary Examining Authority in PCT/IB2010/002589, mailed Apr. 23, 2012, 10 pages.

International Preliminary Report on Patentability in PCT/IB2010/002589, mailed May 30, 2012, 49 pages.

"Glycoside Hydrolase Family 38," cazy.org [online] captured Sep. 11, 2010. Retrieved from the Internet: <URL: http://www.cazy.org/GH38.html>, 1 page.

"Glycoside Hydrolase Family 47," cazy.org [online] captured Sep. 12, 2010. Retrieved from the Internet: <URL: http://www.cazy.org/GH47.html>, 1 page.

"Glycoside Hydrolase Family 92," cazy.org [online] captured Sep. 12, 2010. Retrieved from the Internet: <URL: http://www.cazy.org/GH92.html>, 1 page.

Aravind and Koonin, "The fukutin family—predicted enzymes modifying cell-surface molecules," *Curr Biol.*, 9(22):R836-R837, Nov. 18, 1999.

Bijvoet et al., "Recombinant human acid alpha-glucosidase: high level production in mouse milk, biochemical characteristics, correction of enzyme deficiency in GSDII KO mice," *Hum Mol Genet.*, 7(11):1815-1824, Oct. 1998.

Bourbonnais et al., "Production of full-length human pre-elafin, an elastase specific inhibitor, from yeast requires the absence of a functional yapsin 1 (Yps1p) endoprotease," *Protein Expr Purif.*, 20(3):485-491, Dec. 2000.

Cantarel et al., "The Carbohydrate-Active EnZymes database (CAZy): an expert resource for Glycogenomics," *Nucleic Acids Res.*, 37(Database issue):D233-D238, Epub Oct. 5, 2008.

Cardone et al., "Abnormal mannose-6-phosphate receptor trafficking impairs recombinant alpha-glucosidase uptake in Pompe disease fibroblasts," *Pathogenetics*, 1(1):6, Dec. 1, 2008.

De Pourcq et al, "Engineering Yarrowia lipolytica to produce glycoproteins homogeneously modified with the universal Man3GlcNAc2 N-glycan core," *PLoS One*, 7(6):e39976, 12 pages, Epub Jun. 29, 2012.

De Pourcq et al., "Engineering of glycosylation in yeast and other fungi: current state and perspectives," *Appl Microbiol Biotechnol.*, 87(5):1617-1631. Epub Jun. 29, 2010.

De Pourcq et al., "Engineering the yeast Yarrowia lipoytica for the production of therapeutic proteins homogeneously glycosylated with Man8GlcNAc2 and Man5GlcNAc2," *Microbial Cell Factories*, 11:53, 1-12, May 1, 2012.

Devos and Valencia, "Practical limits of function prediction," *Proteins.*, 41(1):98-107, Oct. 1, 2000.

Ettinger et al., "Intrathecal methotrexate overdose without neurotoxicity: case report and literature review," *Cancer*, 41(4):1270-1273, Apr. 1978.

Gagnon-Arsenault et al., "Activation mechanism, functional role and shedding of glycosylphosphatidylinositol-anchored Yps1p at the *Saccharomyces cerevisiae* cell surface," *Mol Microbiol.*, 69(4):982-993, Epub Jun. 28, 2008.

Gagnon-Arsenault et al., "Fungal yapsins and cell wall: a unique family of aspartic peptidases for a distinctive cellular function," *FEMS Yeast Res.*, 6(7):966-978, Nov. 2006.

Gatlin et al., "Automated identification of amino acid sequence variations in proteins by HPLC/microspray tandem mass spectrometry," *Anal Chem.*, 72(4):757-763, Feb. 15, 2000.

GenBank Accession No. XP_503768, GI: 50552716, "YALI0E10175p [Yarrowia lipolytica CLIB122]," Oct. 29, 2008, 2 pages.

GenBank, "Yarrowia lipolytica CLIB122 [gbpln]: 5967 CDS's (2945919 codons)," Codon Usage Database, [online], Jun. 15, 2007 [retrieved on Aug. 15, 2014]. Retrieved from the Internet: <URL: http://www.kazusa.or.jp/codon/cgi-bin/showcodon.cgi?species=284591>, 1 page.

Gilbert, "Glycoside Hydrolase Family 92," CAZypedia [online], Mar. 4, 2010. Retrieved from the Internet: <URL: http://www.cazypedia.org/index.php/Glycoside_Hydrolase_Family_92>, 3 pages.

Henrissat, "A classification of glycosyl hydrolases based on amino acid sequence similarities," *Biochem J.*, 280 ( Pt 2):309-316, Dec. 1, 1991.

Inoue et al., "Molecular cloning and nucleotide sequence of the 1,2-alpha-D-mannosidase gene, msdS, from Aspergillus saitoi and expression of the gene in yeast cells," *Biochim Biophys Acta.* 1253(2):141-145, Dec. 6, 1995.

Jacobs et al. "Engineering complex-type N-glycosylation in Pichia pastoris using GlycoSwitch technology," *Nat Protoc.*, 2009;4(1):58-70., Epub Dec. 18, 2008.

Komeda et al., "Construction of protease-deficient Candida boidinii strains useful for recombinant protein production: cloning and disruption of proteinase A gene (PEP4) and proteinase B gene (PRB1)," *Biosci Biotechnol Biochem.*, 66(3):628-631, Mar. 2002.

Kuroda et al., "Antibody expression in protease-deficient strains of the methylotrophic yeast Ogataea minuta," *FEMS Yeast Res.*, 7(8):1307-1316. Epub Aug. 22, 2007.

Le Dall et al., "Multiple-copy integration in the yeast Yarrowia lipolytica," *Curr Genet.*, 26(1):38-44, Jul. 1994.

(56) References Cited

OTHER PUBLICATIONS

Li et al., "Optimization of humanized IgGs in glycoengineered Pichia pastoris," *Nat Biotechnol.*, 24(2):210-215, Epub Jan. 22, 2006.
Liu et al., "Disruption of the OCH1 and MNN1 genes decrease N-glycosylation on glycoprotein expressed in Kluyveromyces lactis," *J Biotechnol.*, 143(2):95-102, Epub Jun. 24, 2009.
Mast and Moremen, "Family 47 alpha-mannosidases in N-glycan processing," *Methods Enzymol.*, 415:31-46, 2006.
Mille et al., "Identification of a new family of genes involved in beta-1,2-mannosylation of glycans in Pichia pastoris and Candida albicans," *J Biol Chem.*, 283(15):9724-9736. Epub Jan. 30, 2008.
Moreland et al., "Lysosomal acid alpha-glucosidase consists of four different peptides processed from a single chain precursor," *J Biol Chem.*, 280(8):6780-6791, Epub Nov. 1, 2004.
Nakadai et al., "Purification and Properties of Alkaline Proteinase from Aspergillus oryzae," *Agr. Biol. Chem.*, 37(12): 2685-2694, 1973.
Park et al, "Essential role of YlMPO1, a novel Yarrowia lipolytica homologue of *Saccharomyces cerevisiae* MNN4, in mannosylphosphorylation of N- and O-linked glycans," *Appl Environ Microbiol.*, 77(4):1187-1195, Epub Dec. 23, 2010.
Peberdy et al., "Protein secretion by fungi," *Applied Micology and Biotechnology, Agriculture and Food Production*, 1:73-114, 2001.
Penttilä et al., "Expression of two Trichoderma reesei endoglucanases in the yeast *Saccharomyces cerevisiae*," *Yeast.*, 3(3):175-185, Sep. 1987.
Potgieter et al., "Production of monoclonal antibodies by glycoengineered Pichia pastoris," *J Biotechnol.*, Feb. 23, 2009;139(4):318-325, Epub Dec. 27, 2008.
Rose, "Glycoside Hydrolase Family 38," CAZypedia [online], Feb. 2, 2010. Retrieved from the Internet: <URL: http://www.cazypedia.org/index.php/Glycoside_Hydrolase_Family_38>, 3 pages.
Seffernick et al., "Melamine deaminase and atrazine chlorohydrolase: 98 percent identical but functionally different," *J Bacteriol.*, 183(8):2405-2410, Apr. 2001.
Swennen et al., "Folding proteome of Yarrowia lipolytica targeting with uracil permease mutants," *J Proteome Res.*, 9(12):6169-6179, Epub Nov. 12, 2010.
Swiss Protein Accession No. P15291, Nov. 30, 2010, 9 pages.
Swiss Protein Accession No. P26572, Nov. 30, 2010, 4 pages.
Swiss Protein Accession No. P38069, Nov. 30, 2010, 3 pages.
Swiss Protein Accession No. Q09326, Nov. 30, 2010, 3 pages.
Swiss Protein Accession No. Q24451, Nov. 30, 2010, 12 pages.
Tiels et al., "A bacterial glycosidase enables mannose-6-phosphate modification and improved cellular uptake of yeast-produced recombinant human lysosomal enzymes," *Nat Biotechnol.*, 30(12):1225-1231, Epub Nov. 18, 2012.
van den Elsen et al., "Structure of Golgi alpha-mannosidase II: a target for inhibition of growth and metastasis of cancer cells," *EMBO J.*, 20(12):3008-3017, Jun. 15, 2001.
Van Hove et al., "High-level production of recombinant human lysosomal acid alpha-glucosidase in Chinese hamster ovary cells which targets to heart muscle and corrects glycogen accumulation in fibroblasts from patients with Pompe disease," *Proc Natl Acad Sci U S A.*, 93(1):65-70, Jan. 9, 1996.
Vervecken et al., "Modification of the N-glycosylation pathway to produce homogeneous, human-like glycans using GlycoSwitch plasmids," *Methods Mol Biol.*, 389:119-138, 2007.
Whisstock and Lesk, "Prediction of protein function from protein sequence and structure," *Q Rev Biophys.*, 36(3):307-340, Aug. 2003.
Witkowski et al. "Conversion of a beta-ketoacyl synthase to a malonyl decarboxylase by replacement of the active-site cysteine with glutamine," *Biochemistry*, 38(36):11643-11650, Sep. 7, 1999.
Wu et al., Asparagine-linked glycosylational modifications in yeast, *Cell Engineering*, 3:215-232, 2002.
YALI0A16819g YALI0A16819p[Yarrowia lipolytica CLIB122] Gene ID: 2906333, created on Jul. 24, 2004, 2 pages.
YALI0C10135g YALI0C10135p[Yarrowia lipolytica CLIB122] Gene ID: 7009445, created on Oct. 29, 2008, 2 pages.
YALI0D10835g YALI0D10835p[Yarrowia lipolytica CLIB122] Gene ID: 2910442, created on Jul. 24, 2004, 2 pages.
YALI0E10175g YALI0E10175p[Yarrowia lipolytica CLIB122] Gene ID: 2912589, created on Jul. 28, 2004, 2 pages.
YALI0E20823g YALI0E20823p[Yarrowia lipolytica CLIB122] Gene ID: 2911836, created on Jul. 28, 2004, 2 pages.
YALI0E22374g YALI0E22374p[Yarrowia lipolytica CLIB122] Gene ID: 2912981, created on Jul. 28, 2004, 2 pages.
YALI0E24981g YALI0E24981p[Yarrowia lipolytica CLIB122 Gene ID: 2912672, created on Jul. 28, 2004, 2 pages.
YALI0E34331g YALI0E34331p[Yarrowia lipolytica CLIB122] Gene ID: 2912367, created on Jul. 28, 2004, 2 pages.
Yao et al., "Degradation of HSA-AX15(R13K) when expressed in Pichia pastoris can be reduced via the disruption of YPS1 gene in this yeast," *J Biotechnol.*, Jan. 15, 2009;139(2):131-136. Epub Oct. 8, 2008.
Zhu et al., "Glycoengineered acid alpha-glucosidase with improved efficacy at correcting the metabolic aberrations and motor function deficits in a mouse model of Pompe disease," *Mol Ther.*, 17(6):954-963, Epub Mar. 10, 2009.
Ekici et al., "Unconventional serine proteases: variations on the catalytic Ser/His/Asp triad configuration," *Protein Sci.*, 17(12):2023-2037, Epub Sep. 29, 2008.
Floudas, "Computational methods in protein structure prediction," Biotechnology and Bioengineering, 97(2): 207-213, Jun. 1, 2007.
Hedstrom, "Serine protease mechanism and specificity," *Chem Rev.*, 102(12):4501-4524, Dec. 2002.
Jaafar et al., "Isolation of the MNN9 gene of Yarrowia lipolytica (YlMNN9) and phenotype analysis of a mutant ylmnn9 Delta strain," *Yeast*, 20(7):633-644, May 2003.
Liang et al., "The crystal structures of two cuticle-degrading proteases from nematophagous fungi and their contribution to infection against nematodes," *FASEB J.*, 24(5):1391-1400, Epub Dec. 9, 2009.
Lobsanov et al., "Structure of Penicillium citrinum alpha 1,2-mannosidase reveals the basis for differences in specificity of the endoplasmic reticulum and Golgi class I enzymes," *J Biol Chem.*, 277(7):5620-5630, Epub Nov. 19, 2001.
Morya et al., "In silico characterization of alkaline proteases from different species of Aspergillus," *Appl Biochem Biotechnol.*, 166(1):243-257, Epub Nov. 10, 2011.
Perona and Craik et al., "Structural basis of substrate specificity in the serine proteases," *Protein Sci.*, 4(3):337-360, Mar. 1995.
Rawlings and Barrett, "Evolutionary families of peptidases," *Biochem J.*, 290 ( Pt 1):205-218, Feb. 15, 1993.
Siezen et al., "Subtilases: the superfamily of subtilisin-like serine proteases," *Protein Sci.*, 6(3):501-523, Mar. 1997.
Wright et al., "Structure of subtilisin BPN' at 2.5 angstrom resolution," *Nature*, 221(5177):235-242, Jan. 18, 1969.
Zhu et al., "Mechanistic insights into a Ca2+-dependent family of alpha-mannosidases in a human gut symbiont," Nat. Chem. Biol., 6(2):125-132. Supplementary Information, 25 pages. Epub Dec. 27, 2009, 2010.
GenBank Accession No. AA034683, "mi41c04.r1 Soares mouse embryo NbME13.5 14.5 Mus musculus cDNA clone IMAGE:466086 5-, mRNA sequence," Aug. 23, 1996, 2 pages.
NCBI Reference Sequence: XP_502492.1, "YALI0D06589p [Yarrowia lipolytica CLIB122]," 2 pages, Oct. 29, 2008.
NCBI Reference Sequence: XP_502939.1, "YALI0D17424p [Yarrowia lipolytica CLIB122]," 2 pages, Oct. 29, 2008.
Nett et al., "A combinatorial genetic library approach to target heterologous glycosylation enzymes to the endoplasmic reticulum or the Golgi apparatus of Pichia pastoris," *Yeast.*, 28(3):237-252, Epub Jan. 6, 2011.
UniProtKB/Swiss-Prot: P01588, "Erythropoietin precursor (Epoetin)," Jul. 21, 1986, 7 pages.
UniProtKB/Swiss-Prot: P04062, "Glucosylceramidase precursor (Beta-glucocerebrosidase) (Acid beta-glucosidase) (D-glucosyl-N-acylsphingosine glucohydrolase) (Alglucerase) (Imiglucerase)," Nov. 1, 1986, 31 pages.
U.S. Appl. No. 14/773,234, filed Sep. 4, 2015, Vervecken.

(56) References Cited

OTHER PUBLICATIONS

U.S. Appl. No. 14/981,123, filed Dec. 28, 2015, Vervecken.
U.S. Appl. No. 15/087,201, filed Mar. 31, 2016, Piens.
Database Geneseq, "*Aspergillus oryzae* alkaline protease, SEQ ID 1.", retrieved from EBI accession No. GSP: ARW11112, Database accession No. ARW11112, 1 page, Aug. 7, 2008.
Garcia-Gómez et al., "Advantages of a proteolytic extract by *Aspergillus oryzae* from fish flour over a commercial proteolytic preparation," Food Chemistry, 112(3):604-608, Feb. 1, 2009.
Kim et al., "Functional characterization of the Hansenula polymorpha HOC1, OCH1, and OCR1 genes as members of the yeast OCH1 mannosyltransferase family involved in protein glycosylation," J Biol Chem., 281(10):6261-6272, Epub Jan. 10, 2006.
Moreland et al., "Species-specific differences in the processing of acid α-glucosidase are due to the amino acid identity at position 201," Gene, 491(1):25-30, Jan. 1, 2012.

\* cited by examiner

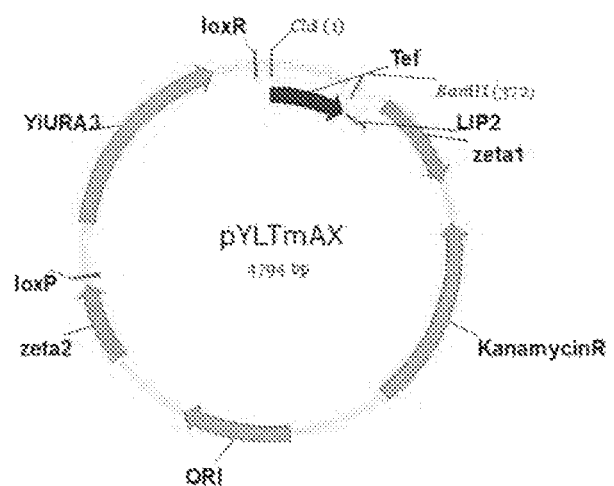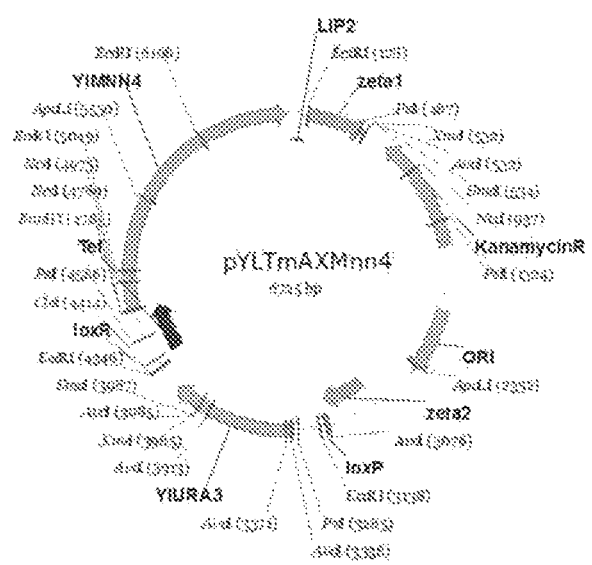
FIG. 1

```
ATGAGACGACCACGACTCGCCCTGCTCGCCGCGGGCTCGCGCTCGCCGTCGCACCGGG
CACGCTGCTGCCCGTCGCCGCGGGCGCCGCCCCGCCGACGAGGGCACCGTCACCGCCG
CCGCGGGCGACGACCTCACGCTCGAGGTCAACCCGTTCGTCGGCACCGAGAGCGAGGGC
AACGCCTACCCGGGCGCGACCGTGCCGTTCGGCATGGTCCAGCTCAGCCCGGACAACAC
GAACTCCTACGCCTCGACGTCGTACAGCACGAACGCGGGGCGCGTGTGGGCTTCAGCC
ACCGGCACGTGAACAGCGCGGGCTGCCCCGCGGCGGGCGAGCTGCTCGTCACGCCGGAC
ACGAGCGCGACCCCGCGCACGTCGCGCTCCTTCATCGCCATCAAGGACCAGAAGAGCAC
CGAGCGCGTCGGCCGGGTTCTACGAGGTGACCCTCGCGAACGACGTGCACGCCGAGC
TCACCGCGACCACGCGCGTCGGCGCGCACCGCTACACGTTCCCCGCCTCGACGACGTCG
CACCTGTCGTTCAACGTGGGCCAGACCCTGCGCGACGCCGGCGCGAGCTCGGTGACGTG
GGTCGACGACCGCACGCTCGAGGGCTGGGTCGACAACGGCGGCTTCTGCGGCGGCACGC
CGGACAAGCAGCGGTACTTCTTCAGCGCGACGTTCGACCGCCCGGTCGCGTCGAGCGGC
ACGTGGGGGACCGATGCGCGCTACGTCGCGGGCTCCACGACGAGCGAGGTCGCGGGCGG
CAACAACGGCGCCGTCGCGGTGTTCGACACCACGACCGACCGCGACGTCGAGGTGAGCG
TGGGCGTGTCCTTCGTGAGCGTCGACGGCGCGCGCGCCAACCGCGAGGCCGAGGCCACC
GACGAGGGCGGGCAGGTCGCGTTCGACACCGTGCGTGAGGACGCCCGCGACGCGTGGAA
CGCGGAGCTGGGCCGTGCCCCGATCGACGCGTCGCCCGACCAGCGCCGGATCTTCTACA
CCCAGCTCTACAAGACGCTGCTGTCCCCGACGATCGCAGCGACGTCGACGGCCGGTAC
CGCGGCATGGACCTCGAGGTCCACCAGGCCGACGGCTGGGACTACTACCAGAACTTCTC
GCTCTGGGACACGTACCGCACGCAGGCGACGCTGCACGCCCTCCTGCTGCCCGAGCGCG
CGCAGGACATCGTGCGCTCGATGTACCAGCACCGCGTCGAGGGCGGCTGGCTGCCGCGC
TGGTCCCTCGGTGCACTGGAGACCAACATCATGGCGGGCGACCCCGTCACGCCGTGGCT
CGCGGAGAACTTCGCGCTCGGCACCGTCCCCGACGACATCGCGGACGAGCTGTGGGACT
ACCTCGTCGAGAACGCCACGACGACCCCGCCGGACGACGTCGCGTCCGTCGGGCGGCGC
AGCACCGAGTTCTACGCCGAGCACGGCCACGTGCCGTTCTACCCCGAGAACGAGGGCGG
CCTCGGCGGCCAGTTCGAGGAGTACCGCCACGGCGGCTCGGCGACGCTCGAGCTCGCGC
TCGCCGACGCGAGCCTCGGCGCTGCGGCCGAGCGCACGGGTCGCGAGGGCGGCCAGGCG
TTCCTCGACAAGGGTCGCAACTGGCGCAACCTCTGGAACCCGGACGTCGAGCTCTCGGG
TGGCTTCCAGGGCATGGTCAACGCGAAGCGCCCGACGGGCGAGTTCGTCACGCTGCCCG
AGCTGACGGACGTCACGCGCTCGGCTTCCACGAGGGCGTGCCGTGGCAGTACCAGTGG
ATCGTGCCGCAGGACGTCACGGGCCTCCAGGAGGTCATGGGCGGCGAGGACGGCTTCGT
CGAGCGTCTCGACTACTACTTCGACCAGCCGGCGCTCGCCGCGAACCCCGGCGTCTCGC
CGAGCACGTGGGCCAAGGGCGGCAGCTCGTACTACACGACCATCCGCTACAACCCGGGC
AACGAGCCGACGATCATGAACGCGTGGCTCTACGGCTACGTGGGCCAGCCGTGGAAGAC
GAACGACGTCCTCGCCGCGAACCTCAACCGCTTCCCGGACACCCCGGGCGGCGGCGTCG
GGAACGACGACCTCGGCACGCTTGCCGCCTGGTACGTCATGGCGTCGCTCGGGTTCGAG
CCCGTCATGCCGGGCTCGGGGATCCTCGCGCTCAACGCGCCGAAGGTGCAGGCCGCGAC
GCTCACGACCGATGCCGGGGCGACGCTGCGCATCGACGCGGCGGGCGCGAACGAGAAGC
TCCCGAGCTACGTCGCCGGCCTGGAGGTCGACGGCTCGCGCACACCGCCGCGTGGCTC
GACGTCGCGGCGCTGCAGGACGGCGGCACGCTCGACTTCGACCTGTCCGGCACGAGCGC
GGGCCTCACGTGGGGCACCGGCGCGGCCGACCGCATCCCGTCGGTCTCCGCCGTCGCCC
CGCCCGCGCCGGTCGAGGTCGAGGCGAGCGCGCGCTGCCTCGGCGGCCGGGCGTTCGTC
GCGGTCCGCGCGACCAGCACGGCCGACGCGCCGGTGGACGTGACTCTCACGACGCCGTT
```

FIG. 8A-1

CGGCGAGCGGACGGTCCGGCACGTGCAGCCGGGCAGGASCGCCTACCAGTCGTTCACGA
CGCGCACGACGTCCGTCGAGGCCGGGACGGCGACCGTCACGGTCGTCGCCGCGGACGGC
ACGACGTCGACGGTCGACGCGGCGTACGAGGCGCTGGCCTGCGGC (SEQ ID NO:6)

FIG. 8A-2

MRRPRLALLAAGLALAVAPGTLLPVAAGAAPADEGTVTAAAGDDLTLEVNPFVGTESEG
NAYPGATVPFGMVQLSPDNTNSYASTSYSTNAGRVWGFSHRHVNSAGCPAAGELLVTPD
TSATPRTSRSFIAIKDQKSTEPASAGFYEVTLANDVHAELTATTRVGAHRYTFPASTTS
HLSFNVGQTLRDAGASSVTWVDDRTLEGWVDNGGFCGGTPDKQRYFFSATFDRPVASSG
TWGTDARYVAGSTTSEVAGGNNGAVAVFDTTTDKDVEVSVGVSFVSVDGARANREAEAT
DEGGQVAFDTVREEAPDAWNAELGRAAIDASPDQRRIFYTQLYKTLLSPTIGSDVDGRY
RGMDLEVHQADGWDYYQNFSLWDTYRTQATLHALLLPERAQDIVRSMYQHRVEGGWLPR
WSLGALETNIMAGDPVTPWLAENFALGTVPDDIADELWDYLVENATTPPDDVASVGRR
STEFYAEHGHVPFYPENEGGLGGQFEEYRHGGSATLELALADASLGAAAERTGREGGQA
FLDKGRNWRNLWNPDVELSGGFQGMVNAKRPTGEFVTLPELTDVTRSGFHEGVPWQYQW
MVPQDVTGLQEVMGGEDGFVERLDYYFDQPALAANPGVSPSTWAKGGSSYYTTIRYNPG
NEPTIMNAWLYGYVGQPWKTNDVLAANLNRFFDTPGGGVGNDDLGTLAAWYVMASLGFE
PVMPGSGILALNAPKVQAATLTTDAGATLRIDAAGANEKLPSYVAGLEVDGVAHTAAWL
DVAALQDGGTLDFDLSGTSAGLTWGTGAADRIPSVSAVAPPAPVEVEASARCLGGRAFV
AVPAPSPADAPVDVTLPTPFGERTVRHVQPGRSAYQSFTTRTTSVEAGTATVTVVAADG
TTSTVDAAYEALACG (SEQ ID NO:7)

FIG. 8B

```
GTGAGCCTCGCGCTCCCGCTGGCGGCGTACGCGGCGCCCGGGATCGGGGCGTCGCCCGC
GACCGCGCCGGGACGGAGGCAGCGACGGGGTCCGATGCCGCCGCCGTCGACGGCCCGC
TGGTCGACTACGTCAACCCGTTCATCGGGACCAAGGACGACGGCAACACCTACCCGGGC
GCTGCCGTGCCGTTCGGCATGGTGCAACTCTCGCCGGACAACGGCCACAACGTCGGGTA
CGACTACGACCGCACGTCGGTGCGCGGGTTCTCGCTCGTGCACCTGTCCGGCGTCGGCT
GCGGCCTCGGCGGTCCGCTCCCGACCCTGCCGACGACGGGCGCGATCACCTCGACCGAC
TACGGCCAGTACGCGCTCGGTTTCTCGCACGACGACGAGGAGGCCTCGCCGGGGTACTA
CCGCGTGGGTCTCCAGGCGCCGGCGGGCACGATCGAGGCCGAGCTCACCGCGACCGAGC
GCACGGGCGTCCAGCGGTACACGTTCCCCGCGACGGCGCAGGCCAACGTCCTGCTCAAC
GCCGGCCAGGCGCTCAACCGGGTGACGGAGTCCGACGTGCGCGTCGTGGACGACCGCAC
GGTCGAGACGCGCATCACCGTCCGCGGCTTCTGCCAGGACACCGAGCCGCAGACGATCT
GGACCCGCACGACCCTCGACCGGCCGTTCGTCGCGCACGGCACGTGGGACGGCCAGGTC
GTCACCGCGGGCGCGGACGCCGCGTCCGGCGGCGAGGGCCGTCGCGGCGCGTACGTCAC
GTTCGACACGACCGGCGGCGACCTCGACGTCGAGGCCGTCACCGCGATGAGCTACGTGG
GCGCCGACGGCGCCGCGGCGAACCTCGCCGCGGAGGCCGGCACGTTCGACGCCGTGCAC
GACGCCGCGCGCTCGGCCTGGGAGGAGCGGCTCGGCCTCGTGCGGGTCGCGCAGGGCGA
CCCGGACGACCTGCGCACCTTCTACTCCTCGCTCTACCGCAGCTTCCTCGCGCCGAACG
TCGGCTCCGACGTCGACGGGCGCTACCGCGGCTGGGACCAGGAGGTCCACGCCGCGGAA
CCGGACTTCACCTACTACCAGAACTACTCGCTCTGGGACACGTACCGCACCCAGCAGCA
GCTCCTGTACCTGCTCGCGCCCGACGAGTCGGCCGACATGGCGCTCTCGCTCGTGCGCC
AGGGCCAGCAGGGCGGGTGGCTCCCGCGCTGGGGCTACGGCACGGTCGAGACGAACATC
ATGACCGGCGACCCGGCGACGCCGTTCCTCGTCAGCGCCTGGCGCCAGGGCCTGCTCGC
GGGCCACGAGGAGGAGGCGTACGCGGTCCTGAGGGAGAACGCCGACGGCGTCCCGCCCG
CCGACTCGCCCTTCAACGGGCGCGCGGCGAACGTCGAGTACCTGCGCGACGGGTTCGTC
CCGCACGAGCCGGCGCGCTCGGGCAAGCCCGGCGACTACGACCTCCAGCACGGCGCCTC
GGCGACCATGGAGTACGCCCTCGCCGACGCGATGCTCTCGACCATGGCGCGCGGCCTCG
GCCACGACGAGGACGCCGACCGGTACGCCGCCGCGGCCAGAGCTACCGCAACGTGTTC
GACCCGCGCACGGGCAACTTCCGGGCGCGTAACGGGACGGCTTCTTCGTGGGCGACGC
GGACCCCGCGCACTCCGACGGGTTCCACGAGGGCACGGCGGTGCAGTACCAGTGGCTCG
TGCCCCAGGACGTGCCGGGCCTGTTCGACCTCATGGGCGGCACCGACGCCGCGGTCGAC
CGCCTCGATGCGTTCTTCGCGTACGACGAGCTCGTCGCCGACCCCCGCACGTCGCGAG
CGAGGTGTGGGTCAACGGCACGTACGACTACTACGGCTGGGAGACCTACAACCCGAACA
ACGAGCCCAACCTCCATGCGCCGTACGTCTACCTGTGGACCGGGCAGCCCTGGAAGACG
ACGGACGTCGTGCGCGCCGCGTCGACCCTCTTCACCGACGGCCCCGACGGCGTCACGGG
CAACGACGACCTCGGCACGATGTCCGCGTGGCACGTGCTGTCGTCGATCGGCGTGTACC
CGATCGTGCCGGGCGCCGATCTGTGGGCCTGACGACGCCGCTCTTCGACGACGTGACG
ATCACGCTCGACCCGGAGGTCTTCGGTCGGGACTCCCTGCGCCTCACGGCGGACGGCGT
CGCGCCCGACACGCACTACACGCAGTCCGTGTCGCTCGGCGGCGAGCCGCTCGATCGCG
CCTGGGTCACGGGCGACGAGCTCACCGCGGCCGGCACGCTCGACGTGACCGTCGGCACC
GAGCCGTCCGCGTGGGCGACCGACCCGCGGCCTCGCCGGGCGCCGTCGTGCCTGCGGA
CGGCACGGTCGAGCGCCTGTTCGTCGGCGCGACGCCGCGGCAGCCGGTCCTCGCCCCGG
GCGGGCGGACCGAGGTCGCAGTCCAGGTCGTCGCCCAGGGCGCGGGGACGTCCAGCGGG
ACGCTCGAGGTGACGTCCGACGGCGCGGTCACCGCGACGACCGACCTCGCCGAGTGGAC
CGCCGAGTCCGACGGCCTGCCGGCCACGGTCGAGGGCACGGTGACGATCGAGGCTCCCG
CCGACGCCGAGCCGGGTCTGCACACGGTGCCGCTCGTCGTGCGCGACGCCGCGGGGACC
```

FIG. 9A-1

```
GAGGCGGTCCGCGAGGTCTCGGTCGTCGTGTCCGGGGAGTCGTGGATCGCCGACGCGTT
CGACAACGTCGGCATCGGCGACGCCGGGGCGGCCAACGCGAACCTCGACGGCTCGGGCG
CCTACCTCCTGCGCGACCTGCTCGCGGACCTCGGCGCCGTCCAGGGCCTGGAGCTCACC
GTGCCGGGCACGGACCTCACCTACACGCTCGGGGCCCCGCGGGCGGGCGCGCCCGACAA
CGTCGCCGCGAGCGGCGAGGTCCTCGAGGTGCCCGAGCACCTGCGCTCGGCCCGCCACC
TCTCGGTGGTCGGGACGAGCACGCACGGCACGCACGGGGCGGCCTCGTCCTCGGGTTC
GCCGACGGCTCGTCGCAGACCGTCGACGTGCGCCTCAGCGACTGGTGCACGGGCTCGCC
CGAGCCCGGCAACATCACGGTCGCGAAGGCCGGGGCGCGCGGCGACCGCGAGAACGTGC
AGAAGATCGGCTGCGGCCTCTACGCCACCGCGCCCGTCGCGATCCCCGAGGGCAAGGTC
CTGACGTCGGTCACGCTGCCGAGCGACGAGCGGTTCCACGTGTTCGCGATCGCGACCGA
CGCGACGGGGGACGTCCCCGCGCCGCAGGTCGAGGTCACGGCGCAGGCCCGCTGCCTCG
GCGGCAAGGCGTTCGTCGCGGTGCGCGCGGCTCAACACGGGCGAGCAGCCCGCCGCGATC
GAGCTCGCGACCCCGTACGGCTCCAAGCTCTTCGGTGACGTCGCTCCCGGGGCGAACGC
GTACCAGTCGTTCGCCACCCGCGCCGCCGCCGTCGAGGCGGGCGAGGTCACGGTGACCG
TGACGACGCCCGACGGCGAGCCCCAGCAGGTCACGGCCGCGTACGACGCCGCCGCCTGC
TCC (SEQ ID NO:8)
```

FIG. 9A-2

VSLALPLAAYAAPGIGASPATAAGTEAATGSDAAAVDGPLVDYVNPFIGTKDDGNTYPG
AAVPFGMVQLSPDNGHNVGYDYDRTSVRGFSLVHLSGVGCGLGGPLPTLPTTGAITSTD
YGQYALGFSHDDEEASPGYYRVGLQAPAGTIEAELTATERTGVQRYTFPATAQANVLLN
AGQALNRVTESDVRVVDDRTVETRITVRGFCQDTEPQTIWTRTTFDRPFVAHGTWDGQV
VTAGADAASGGEGRRGAYVTFDTTGGDLDVEAVTAMSYVGADGAAANLAAEAGTFDAVH
DAARSAWEERLGLVRVAQGDPDDLPTFYSSLYRSFLAPNVGSDVDGRYRGWDQEVHAAE
PDFTYYQNYSLWDTYRTQQQLLYLLAPDESADMALSLVRQGQQGGWLPRWGYGTVETNI
MTGDPATPFLVSAWRQGLLAGHEEEAYAVLRENADGVPPADSFFNGRAANVEYLRDGFV
PHEPARSGKPGDYDLQHGASATMEYALADAMLSTMARGLGHDEDADRYAARGQSYRNVF
DPRTGNFRARNADGFFVGDADPARSDGFHEGTAVQYQWLVPQDVPGLFDLMGGTDAAVD
RLDAFFAYDELVADPPHVASEVWVNGTYDYYGWETYNPNNEPNLHAFYVYLWTGQFWKT
TDVVRAASTLFTDGPDGVTGNDDLGTMSAWHVLSSIGVYPIVPGADLWGLTTPLFDDVT
ITLDPEVFGRDSLRLTADGVAPDTHYTQSVSLGGEPLDRAWVTGDELTAAGTLDVTVGT
EPSAWATDPAASPGAVVPADGTVERLFVGATPRQPVLAPGGRTEVAVQVVAQGAGTSSG
TLEVTSDGAVTATTDLARWTAESDGLPATVEGTVTIEAPADAEPGLHTVRLVVRDAAGT
EAVREVSVVSGESWIADAFDNVGIGDAGAANANLDGSGAYLLRDLLADLGAVQGLELT
VPGTDLTYTLGAPRAGAPDNVAASGEVLEVPEHLRSARHLSVVGTSTHGTHGGGLVLGF
ADGSSQTVDVRLSDWCTGSPEPGNITVAKAGARGDRENVQKIGCGLYATAPVAIPEGKV
LTSVTLPSDERFHVFAIATDATGDVPAPQVEVTAQARCLGGKAFVAVRALNTGEQPAAI
ELATPYGSKLFGDVAPGANAYQSFATRAAAVEAGEVTVTVTTPDGEPQQVTAAYDAAAC
S

FIG. 9B

```
GTGCGGCGCTCCGTCGCGGCGCTCTCTGCCACGGCGGTCCTGGCCGCCGGACTCTCGAT
CGCGCCCGCCGTCGGGCTCGCGGTCCCGGCGGTCGCGGCCGCACCCGACCTCGTTGAGG
ACCCCGTCTCCTTCGTCGACCCGTTCGTCGGGACCGGCCAGGCGACGGGCGTCGTCGGG
GAGATCAACAACTTCCCCGGGCCGTCGATGCCGTTCGGCATGATGCAGCTCTCGCCCGA
CACCCAGGTCTCCGTGGGCAACGGCGACAAGGCGTACGCGGGCTACCGCTACTCGCACC
AGGCGATCCGCGGCTTCTCCATGACGCACGCGGCCGCCGGGTGCTGGATCTTCGGCGAC
GTCCCGATCCTCCCCGTGACGGGCGACGTCGGGCAGTACCCGTGGGACCGCAAGGAGGC
GTTCAGCCACGACGCGGAGAGCGCCGAGGTCGGCCGGTACGCGGTCACGCTCCAGTCGT
CGGGGATCGATGCGGAGGTGTCGGCCGCGACCCGCTCGGGCGGACTGACGTTCGACTAC
CCCGAGGGCGGTGCCGCGTCGCAGGTGATCGTCAACGCCGCGGGCTCGCTCGCGAGCGT
GCGCAACGCGACGGTCGAGGTCGAGGACGCGCGCACGGTCACCGGCTCGGTGACGAGCG
GCGGGTTCTGCGGCAAGAACAACACGCACACGACGTACTTCGCGATCGAGCTCGACCAG
GACGCGCAGGCGTTCGGCACGTGGCAGGGCTCGACCGTCTCGCCCGGCGACCCGTCGGC
CGACGGCAACGGCGCGGGCGCGTGGCTCACCTTCGCGCCCGGCGCGACGGTGCACGCGA
AGGTCGGCATGTCCTACGTGAGCGTCGAGGGCGCGCGCGCCAACCTCGCGGCCGAGATC
CCGGGCTTCGACTTCGACGCCGTCCGGGACGCCAACCGCGCCGCCTGGTCCGACCTGCT
CGGCAAGGTCCGCGTCGCGGGCAGGACGCCGACGACCTCACCATGTTCTACACGTCGC
TCTACCACTCGCTGCTGCACCCGAACACGTTCACCGACGTGGACGGCCGGTACGTCGGG
TTCGACGGGGAGATCCACCAGGCCCCCGAGGGGCACGAGCGGTACGCGAACTTCTCCGA
CTGGGACACGTACCGGTCGCTCGGCGCGCTCCAGGCGCTGCTGGCGCCCGACCAGGCGT
CGGACATGGCGCAGTCGCTCGTCGAGGTCGCCGACCAGTCCGGCTGGCTGCCGCGCTGG
CCCGTCGCGAACCAGCACACGGGCCAGATGACCGGTGACTCCTCGGTGCCGCTCATCGC
GAGCATGTACGCGTTCGGGCGCGCGACTTCGACGCGGAGTCGGCGCTCGCGCACATGG
TCAAGGGTGCGACGAGCGCCGCCCCGACCGCGAACGGCTACGTGCAGCGGCGCGGGATC
GAGACGTACCTCGAGCGCGGCTACGCGCCCCAGACCGAGGAGTTCCGGGGCGACCACCG
CGTCGTCGGCGCGTCGATCACGCTCGAGTGGTCGATCGCCGACTTCGCGATCGGGCAGC
TCGCGGCCGCGCTCGGCCAGGACGACGTCGCCACCGAGTACGCCGCCCGCGGCCAGTGG
TGGCAGAACGTCCACGACCCCGTGACCCGCACGGCGGGCGCCGGAACGACGACGGCAC
GTTCGTGCGGTCGCAGGGCGGCGGCGGGTTCGGGCAGGAGGCTTCGACGAGGGCAACG
CCGAGCAGTACACGTGGCTCGTGCCGCAGAACGTCGCGGGGCTCACCGACGCGCTCGGC
GGGCGTGAGGCCGTCGCGGAGCGGCTCGATGCCTTCACGGTGCAGCACAACGCCGGCCC
GAACGAGCCGTACCTGTGGATCGGCAACGAGCCGAACTTCGGCGTCCCGTGGCTGTACG
ACTACGTGGGCCAGCCGTGGCGGACGAGCGAGCTCGTGGACGAGCTTACGTCCACGCTG
TTCCGGCCCGAGCCGAACGGCAAGCCCGGCAACGACGACCTCGGCGCCCAGGCCGGCTG
GTACGTGTGGGCCGCGATGGGCCTGTACCCCACCACGCCGGGCACGGACGTGCTCGCGC
TCAACGCGCCGCGCTTCGACCGCGTCGTGGTCGACCTCGGCGAGGGCGACACCCTCGAC
CTGCGCGCCCCCGGCGCCTCGACCGGCGCCCGCTACATCAGCGGCGTCACCATCGACGG
CGCAGCCTGGGACGGGACCTCCCTGCCCGCGCCACGTCGCGCACGACGGCGGCGTCGTCG
AGCTCGCGATGTCGACCGCACGCGACACGACGTGGGGGACCGCAGCCGAGGACGCCCCG
CCGTCGTGGCGCGACGGCGAGTCCGCCGTGGTCGCCGCCGCGGACCCGGGCCTCGTGAC
GGTCGCCCCCGGCGGGACCGCCGACGCGTCGGTGGCCGTGCAGCTCTTCGGCGCCGACG
CCGCCGACGTGCGCGTCGCGGTCGACGCGCCCGGGGCATCGGGGTCGGTGAGCCCGCG
CTCGTCGACGACGGCTCGGGCCACCTCACCGGGACGGTCCCCGTCCAGGTGGGTGCCGG
CGTCGCGTCCGGCTACCACGACGCGCGCCTCGTGCTCTCGGCCGGGACGACGACGTCG
AGGTGCCCCTCACCGTCCTCGTCGCCGCGCCCGGGTCGCTCGTTGCGGCCTACGACACG
```

FIG. 10A-1

```
GTCGGCACTGCGCCCGAGGCGAACCGCGGCGTCGGGAACTTCGACGCGGCCGGCAACTC
GTTCTCGCGCGAGGCGCTCGCCCGACGCGGGTCTCACGCCCGGGTCGGCGCACGACGTCG
ACGGCCTGGCGTTCACGTGGCCGTCCTCACCCGTGGGGCGCCCGGACTCGGTCACGCTC
ACCGGCGAGACCGTGCGGCTCGACGCGCCGACGAGCCGGCTCGCGTTCGTGGGCGCCGC
GACCGACGGGACCCATCGCGGGACCGCGGTCGTGACGTTCGACGACGGCAGCACCGCGA
CCACGACGATCGGCTTCGGCGACTGGGTGCTGCCGAGCGCGGACGGCTCGCCGGTCGAG
GGCAACTCGGTCGTCGCGCAGATGAACCGGCGCAACGGCGACAAGGACAGCGCGTTCGT
GTTCGCCACCGCCCGTACACCGCGCCCGAGGACCGCCGCGTGGTCGCGGTGAGGTTCC
CCGACGTCGACGACCTGCACGTCTTTGCGATCGCGACCGAGCCGGCCGCGGACGTGCAC
CTCGTGGACGTGACGGTCTCCCTGCGCTGCCTCGCCGGGACCCCGTACGTGGCGGTGCG
CGCGGCGAACGTCTCCGCCGGGGCCGTCGACGTCGACCTCACGACGGGCGTGGGCTCGC
GGTCCTTCACGGCCGTCGCCCCGGCGCCAACGCCTACCAGTCGTTCGCCGCCCGCGGC
GCGACCGGGAACGTCGACGTCACCGTCACGGCCACGGGGGAGGAGGGGACGCAGACGGT
CGCGCGGACCGTCGTCGTCCCGCGCTGCTCC (SEQ ID NO:10)
```

FIG. 10A-2

VRRSVAALSATAVLAAGLSIAPAVGLAVPAVAAAPDLVEDFVSFVDPFVGTGQATGVVG
EINNFPGPSMPFGMMQLSPDTQVSVGNGDKAYAGYRYSHQAIRGFSMTHAAAGCWIFGD
VPILPVTGDVGQYPWDRKEAFSHDAESAEVGRYAVTLQSSGIDAEVSAATRSGGLTFDY
PEGGAASQVIVNAAGSLASVRNATVEVEDARTVTGSVTSGGFCGKNNTHTTYFAIELDQ
DAQAFGTWQGSTVSPGDFSADGNGAGAWLTFAPGATVHAKVGMSYVSVEGARANLAAEI
PGFDFDAVRDANRAAWSDLLGKVRVAGQDADDLTMFYTSLYHSLLIPNTFTDVDGRYVG
FDGEIHQAPEGHERYANFSDWDTYRSLGALQALLAPDQASDMAQSLVEVADQSGWLPRW
PVANQHTGQMTGDSSVPLIASMYAFGARDFDAESALAHMVKGATSAAPTANGYVQRRGI
ETYLERGYAPQTEEFRGDHRVVGASITLEWSIADFAIGQLAAALGQDDVATEYAARGQW
WQNVHDPVTRTAGARNDDGTFVRSQSGGGFGQEGFDEGNAEQYTWLVPQNVAGLTDALG
GREAVAERLDAFTVQHNAGPNEPYLWIGNEPNFGVPWLYDYVGQPWRTSELVDELTSTL
FRPEPNGKFGNDDLGAQAGWYVWAAMGLYPTTPGTDVLALNAPRFDRVVDLGEGDTLD
LRAPGASTGARYISGVTIDGAAWDGTSLPRHVAHDGGVVELAMSTARDTTWGTAAEDAP
PSWRDGESAVVAAADPGLVTVAPGGTADASVAVQLFGADAADVRVAVDAPGGIGVGEPA
LVDDGSGHLTGTVPVQVGAGVASGYHDARLVLSAGDDDVEVPLTVLVAAPGSLVAAYDT
VGTAPEANRGVGNFDAAGNSFSREALADAGLTPGSAHDVDGLAFTWPSSPVGRPDSVTL
TGETVRLDAPTSRLAFVGAATDGTHRGTAVVTFDDGSTATTTIGFGDWVLPSADGSPVE
GNSVVAQMNRRNGDKDSAFVFATAPYTAPEDRRVVAVRFPDVDDLHVFAIATEPAADVH
LVDVTVSLRCLAGTPYVAVRAANVSAGAVDVDLTTGVGSRSFTAVAPGANAYQSFAARG
ATGNVDTVTATGESGTQTVARTVVVPRCS (SEQ ID NO:11)

FIG. 10B

ATGACCAGACCACTCCCGCCCGGACGCGCGGTCGCGCGGTCCGGCAGCGGCCGCGCCCG
GCCCCTCGGCCTCGTGCTCGCCGCCGCACTCGCCGTCCCGCTCGGGGTGCCTCTCGCGG
CCCCGCGGGAGCCCTCGCTGCCGCGCCCGCCGCGGCCGCCGAGCCCGGCGACTTCTCG
TCCTCGTTCGAGTCCGGCGACCCGGCCGCGCTGCCCACCACCGTGGCGGAGCGCGACGG
CGCGCCCTGGCAGGCGAACGTCGGCTCGTTCACGGCCGGCCTGCCCGGGAGCGTCCTCG
GGCAGCTGAAGGGCGTCACGGCGAGCGCGCAGAACCTGCCCAACGAGGGCGCGGCGAAC
CTCGCCGACGGCAGCTCGGGCACCAAGTGGCTCGCCGTTCGCGTCGACCGGCTGGGTCCG
GTACGAGTTCGCCGAGCCCGTCTCGTTCGTCGCGTACACGATGACCTCCGGCGACGACG
CCGCCGGTCGCGACCCGAAGACCTGGACGGTCGAGGGGTCGAACGACGGGTCCACGTGG
GCCGCGCTCGACCGCCGGACGGACGAGGACTTCCCGAACCGCCAGCAGACGCGCACGTT
CGAGCTCGAGGCGCCCACCGCGGCGTACACGTACCTGCGCCTCAACGTCACGGCGAACT
CGGGCGACTCCATCGTCCAGCTCGCCGGGTGGGACCTCTCGGCCGACCTGAGCGCCGGC
CCGTCCGCGGCCCCCATGACGACGAAGGTCGGCACCGGCCGCGCGTCAGCTTCACCAA
CAAGGCGGGCGTCGGGTTCTCCGGCCTGCACTCGCTCCGGTACGACGGCTCGCACCTCG
CCGACGGCGAGACGTACGCGACGAACGTGCTCTACGACGACGTGGACGTCGTCGTCGGC
GAGGACACGCGCCTGAGCTACACGATCTTCCCCGAGCTGCTCGACGATCTGCAGTACCC
GTCGACGTACGCGGCGGTGGACGTCCTGTTCACCGACGGGACCTACCTGTCCGACCTCG
GCGCGCGACGCGCACGAGACGGTCGCGACCGCGCAGGCGCAGGGCGAGGGCAAGATC
CTCTACGCCGACCAGTGGAACTCGGTGCGGGTCGACCTCGGCGACGTCGCCGAGGGCAA
GACCGTGGACCAGGTGCTGCTCGGGTACGACAACCCGGGCGGTCACGCCGGGACGAAGT
TCGCGGGCTGGCTCGACGACGTCGAGATCACGGCGGAGCCGGCCACGATCGACGGGTCG
AGCCTCGCCAACTACGTGGACACGCGCCGCGGCACGCTCGCGTCGGGCAGCTTCTCGCG
CGGGAACAACATCCCCGCGACGGCGACGCTCGAACGGGTTCAACTTCTGGACGCCGTACA
CGAACGCCTCCTCGCAGAGCTGGCTGTACGAGTACCACAAGGCCAACAACGCCAACAAC
AAGCCCGTCCTCCAGGGCTTCGGGATCTCGCACGAGCCGAGCCCGTGGATGGGCGACCG
CAACCAGCTGACGTTCCTCCCGTCGACGGCGTCGGGGACGCCCGACGCCACGCTCTCGA
CGCGCGGCCTCGAGTTCGACCACGCGGACGAGACGGCGCGGCCGGACTACTACGGGGTC
ACGTTCACCAACGGGTCCGCGATCGAGGCGACGCCCACCGACCACGGCGCGGTGCTCCG
CTTCAGCTACCCCGGAGCCAAGGGCCACGTGCTCGTGGACAAGGTGGACGGCTCCTCCA
AGCTCACGTACGACCAGGCCACGGGCACGATCTCCGGCTGGGTCGAGAACGGCTCGGGC
CTGTCCGTGGGCCGCACGCGCATGTTCGTCGCCGGCACCTCGACCGTAGTCCGACGGC
GGTCGGGACGGCGGCGGGCAACCGTGCGGACGCGCGCTTCGCGACGTTCGAGACGTCGT
CCGACAAGACGGTCGAGCTGCGCGTCGCGACGTCGTTCATCAGCCTCGACCAGGCGCGC
AAGAACCTCGACCTGGAGGTGACGGGCAAGACCTTCACGGAGGTCAAGGCCGCCGCCGC
GCAGGCGTGGAACGACCGCCTGGGGGTCATCGAGGTCGAGGGCGCGAGCGAGGACCAGC
TCGTCACGCTGTACTCGAACCTCTACCGCCTCAACCTGTACCCGAACTCGCAGTTCGAG
AACACGGGCACGGCGCAGGAGCCGGTGTACAGGTACGCGAGCCCGGTCTCCGCGACCAC
GGGCTCCGCGACGGACACGCAGACCAACGCGAAGATCGTCGACGGCAAGATCTACGTGA
ACAACGGGTTCTGGGACACGTACCGCACGGCCTGGCCGGCGTACTCGCTCCTCTACCCG
GAGCTCGCGGCCGAGCTGGTCGACGGGTTCGTCCAGCAGTACGCGACGGCGGCTGGAT
CGCGCGCTGGTCCTCGCCGGGCTACGCCGACCTCATGACGGGCACGAGCTCCGACGTGG
CGTTCGCCGACGCGTACCTCAAGGGCTCGCTCCCCACGGGCACGGCGCTCGAGGCGTAC
GACGCCGCGCTGCGCAACGCGACCGTCGCGCCGCCGAGCAACGCCGTGGGCCGCAAGGG
CCTGCAGACCTCGCCGTTCCTCGGGTTCACGCCGGAGTCCACGCACGAGTCCGTGTCGT

FIG. 11A-1

```
GGGGCCTGGAGGGCCTGGTCAACGACTTCGGCATCGGCAACATGGCCGCCGCCCTCGCG
GAGGACCCGGCGACGCCGGAGGAGCGCCGCGAGACGCTGCGCGAGGAGTCCGCGTACTT
CCTCGAGCGGGCCACGCACTACGTCGAGCTGTTCGACCCCGAGGTCGACTTCTTCGTGC
CGCGGCACGAGGACGGCACGTGGGCCGTCGACCCCGAGACGTACGACCCGGAGGCCTGG
GGCGGCGGGTACACCGAGACGAACGGCTGGAACTTCGCGTTCCACGCCCCGCAGGACGG
CCAGGGCCTCGCCAACCTCTACGGCGGCAAGCAGGGCCTCGAGGACAAGCTCGACGAGT
TCTTCTCCACGCCGGAGAAGGGCGCCGGCAACGGCGGCATCCACGAGCAGCGCGAGGCG
CGCGACGTCCGCATGGGCCAGTGGGGCATGAGCAACCAGGTGTCGCACCACATCCCGTG
GCTCTACGACGCCGCGGGCGCGCCGTCGAAGGCGCAGGAGAAGGTCCGCGAGGTCACCC
GCCGCCTGTTCGTGGGCAGCGAGATCGGCCAGGGCTACCCGGGCGACGAGGACAACGGC
GAGATGTCGTCGTGGTGGATCTTCGCCTCGCTCGGCTTCTACCCGCTCCAGGTCGGCTC
GGACCAGTACGCGGTCGGTTCGCCGCTGTTCGACAAGGCGACCGTGCACCTGCCGGACG
GCGACCTCGTCGTCAACGCCGAGAACAACTCGGTCGACAACCTCTACGTGCAGTCCCTC
GCGGTGGACGGCGAGGCCCGCACCTCGACGTCACTCTCCCAGGCGGACCTCTCGGGCGG
CACGACTCTGGACTTCGTCATGGGTCCGGAGCCGTCGGACTGGGGCACGGGCGAGGACG
ACGCGCCGCCGTCGCTCACCGAGGGCGACGAGCCCCGACGCCGGTGCAGGACGCGACG
ACCGCGGGCCTCGGCACCACCACCGTCGCCGACGGCGACGCCACCACGAGCGCCGCGGC
GCTCACGGACAACACGTCCGGGACGCGCACGACGTTCGCCACCACGACGCCGTCGATCA
CGTGGGCGGCAACGGCATCCGCCCGACCGTCGGGTCGTACACGCTGACCTCCGGGGCG
AGCGGGACGGCGTCACCGTCCGCATGGACTCTCGAGGGTTCCGACGACGGCGAGACGTG
GACGACGCTCGACGAGCGGTCCGGCGAGCAGTTCCGCTGGGCCCTGCAGACGCGGCCGT
TCACGGTCGCGGAGCCGACGGCGTTCGCGCGGTACCGGGTCACGGTCACCGCGACGTCG
GGCTCCGGCGCGCTGTCGCTCGCCGAGGTCGAGCTCCTCGCCGACCCGAAGGAGTCGGG
GGCCGAGGAGCTCACCCTCTCGGCCGCGCCGGACCGTGACGGCGTCACGGGCCGCGAGG
TCTCGGCTCGTTCGCGACCCTCACCGGGTCGAGGGCGACGTCGCGGCGCTCGACGTG
CAGGTCGCGTTCGGCGACGGCTCCGAGCCGGTCGCCGGGACGCTGCGGGCGGGCGCGTT
CGGCGGGTACGCGGTGGACGCCGCGCACACGTGGACCGCACCCGGCGTCTACCCCGTGA
CCGTCACGGTCTCGGGCGAGGGGATCGAGACCGTCTCGGCCTCCTCGTACGTCAGCGTC
TCGCTCCTGCCGAGGGCTCGCTGCTCGCCGCGTACGACAACGTCTGCATCGGCGACGC
CGGGACGACGGTCGGCTCCGTGCGACGGCCAGGGCGTGTTCTTCGACCGGGCGCAGCTCG
CGGCGAAGGGCTTCGTCCAGGGCGAGCGCGCGACGGTGCCGGCACGGACCTCGCGTTC
GACGTCCCGGCGGTCCCCGCCGGGCAGCCGGACAACGCCACGGGCGACGGGCAGACCAT
CGAGCTCGACGTCCCCGCGGACGCGGAGCAGCTCTCGGTGATCGGCACGGGCACGGAGA
AGAACCAGCAGGCCACCGGCACGCTGACCTTCGACGACGGCTCGACCCAGCCGATCGAC
CTGAGCTTCGGCGACTGGTCGGGCGCGGCCCGCAACCCCGTGTTCGGCAACATCCCCGT
CGCGGTGACGGACAGCCGCCTCCGCGGCGGCAGCCCGCAGACCGGCACCCCCGCCGCGT
TCTTCGCGACGGCGCCGATCACCCTCCCCGAGGGCAAGCGGCCCGTGAGCCTCACGCTC
CCGGACCAGCCGGGCGAGCTCTCGCGCGACGGCCGCATCCACGTGGTCGCGGTCGCGCA
CGACGGCACGTTCGCCGAGCACCCCGCGCTCGAGGTCACGGCCGCGGAGGGCGTGACGC
TCGCCGTCGGGCAGACCTCGGACGTGGCGCTCGCCCAGGTGGCGGGCGGCCGCGAGGGC
GCCGACCTCCGGCGGCGGTCACGTGGGCGACGGCTCCGACGTCGCGGCCGGCGCGGT
GACCGACGGGTCGGTCTCCGGCTCGCACGCCTACACGGCGGCCGGGACGTACACGGCGT
ACGTCGTGGTCGACGACGGCTGGACCAGCCAGGTGGTCGAGGTCCCCGTGACCGTGACC
GAGGCGGAGCCGGCCCTCGCCGTCGACGTCACGGTGAGCACACGCTGCCTCGCCGGCAA
GGCGTACGTCGCGGTCCGCGCCGAGAACGGCGAGGACGTGCCGCTCGCGATCCGGCTCG
TCACGCCGTTCGGCACCAAGGAGGTCGCGGCCGTCGCGCCGGGCGCCAACGCCTACCAG
TCGTTCGCGACGCGGGTCACGGCGGTCGAGGCCGGCACCGTCACCGTCGAGGCGACGCG
```

FIG. 11A-2

CGGCACCGGCGACGAGGAGGTGACGGCGTCGATCCAGGCCGACTACGCCGCCGTGACCT
GCGGC (SEQ ID NO:12)

FIG. 11A-3

MTRPLPPGRAVARSGSGRARPLGLVLAAALAVPLGVPLAAPAGALAAAPAAAAEPGDFS
SSFESGDPAALPTTVAERDGAPWQANVGSFTAGLPGSVLGQLKGVTASAQNLPNEGAAN
LADGSSGTKWLAFASTGWVRYEFAEPVSFVAYTMTSGDDAAGRDPKTWTVEGSNDGSTW
AALDRRTDEDFPNRQQTRTFELEAPTAAYTYLRLNVTANSGDSIVQLAGWDLSADLSAG
PSAAPMTTKVGTGPRVSFTNKAGVGFSGLHSLRYDGSHLADGETYATNVLYDDVDVVVG
EDTRLSYTIFPELLDDLQYPSTYAAVDVLFTDGTYLSDLGARDAHETVATAQAQGEGKI
LYADQWNSVRVDLGDVAEGKTVDQVLLGYDNPGGHAGTKFAGWLDDVEITAEPATIDGS
SLANYVDTRRGTLASGSFSRGNNIPATATPNGFNFWTPYTNASSQSWLYEYHKANNANN
KPVLQGFGISHEPSPWMGDRNQLTFLPSTASGTPDATLSTRGLEFDHADETARPDYYGV
TFTNGSAIEATPTDHGAVLRFSYPGAKGHVLVDKVDGSSKLTYDQATGTISGWVENGSG
LSVGRTRMFVAGTFDRSPTAVGTAAGNRADARFATFETSSDKTVELRVATSFISLDQAR
KNLDLEVTGKTFTEVKAAAAQAWNDRLGVIEVEGASEDQLVTLYSNLYRLNLYPNSQFE
NTGTAQEPVYRYASPVSATTGSATDTQTNAKIVDGKIYVNNGFWDTYRTAWPAYSLLYP
ELAAELVDGFVQQYRDGGWIARWSSPGYADLMTGTSSDVAFADAYLKGSLPTGTALEAY
DAALRNATVAPPSNAVGRKGLQTSPFLGFTPESTRESVSWGLEGLVNDFGIGNMAAALA
EDPATPEERRETLREEKSAYFLERATHYVELFDPEVDFFVPRHEDGTWAVDPETYDPEAW
GGGYTETNGWNFAFHAPQDGQGLANLYGGKQGLEDKLDEFFSTPEKGAGNGGIHEQREA
RDVRMGQWGMSNQVSHHIPWLYDAAGAPSKAQEKVREVTERLPVGSEIGQGYPGDEDNG
EMSSWWIFASLGFYPLQVGSQQYAVGSPLFDKATVHLPDGDLVVNAENNSVDNVYVQSL
AVDGEAPTSTSLSQADLSGGTTLDFVMGPEPSDWGTGEDDAFPSLTEGDEPPTPVQDAT
TAGLGPTTVADGDATTSAAALTDNTSGTRTTFATTTPSITWAGNGIRPTVGSYTLTSGA
SGTASPSAWTLEGSDDGETWTTLDERSGEQFRWALQTRPFTVAEPTAFARYRVTVTATS
GSGALSLAEVELLADPKESGAEELTLSAAPDRDGVTGREVSGSPATLTGVEGDVAALDV
QVAFGDGSEPVAGTLRAGAFGGYAVDAAHTWTAPGVYPVTVTSGEGIETVSASSYVSV
SLLREGSLLAAYDNVCIGDAGTTVGSCDGQGVFFDRAQLAAKGFVQGERATVPGTDLAF
DVPAVPAGQPDNATGDGQTIELDVPADAEQLSVIGTGTEKNQQATGTLTFDDGSTQPID
LSFGDWSGAARNPVFGNIPVAVTDSRLRGGSPQTGTPAAFFATAPITLPEGKRPVSLTL
PDQPGELSPDGRIHVVAVAHDGTFAEHPALEVTAAEGVTLAVGQTSDVALAQVAGGREG
ADLRAAVTWGDGSDVAAGAVTDGSVSGSHAYTAAGTYTAYVVVDDGWTSQVVEVPVTVT
EAEPALAVDVTVSTRCLAGKAYVAVRAENGEDVPLAIRLVTPFGTKEVAAVAPGANAYQ
SFATRVTAVEAGTVTVEATRGTGDEEVTASIQADYAAVTCG (SEQ ID NO:13)

FIGURE 11B

```
GCGCTCGCCGTCGTCGGCCTCGCGCCCGCGACCGCCGCGAGCGCCGCCCCGAGCCGCC
GTCGGCCGACTACGCGTCCCTGGTCGACGTCTTCGTCGGCACCGAGGGCGACTTCGGCA
ACGACATGCCCGCCGCGCAGGCGCCGAACGGCCTCGCGAAGGTCAACCCGCGCACGACC
CCGGGCCGCAACAACACCGGGTACGACTACGCGCAGTCGAAGATCTCGGGCTTCACGCA
CACCAACCTCGACGGGGTCGGGGGCTCCGGCGGCGGTGGTGACCTCCTCGTGGTGCCGA
CGTCCGGGTCGTACACGGCGCGCCCGGCACGGGCACGTACGCGCACCCGTTCTCGCAC
GACGACGAGGACGCCGGACCGGGCTTCTACTCCGTCGGGCTCGGCAACGTCGCGGGCAC
GGACGGCGCGATCACCGGCGCGCCGGGCACGATCGAGGCCGAGGTCGCGGCGGCCACGC
GCTCGGGCGTGCACCGCTACGCGTTCCCCGCGGGCTCGACGCCGAGCCTCGTCGTGGAC
CTCGAGACGAACAACACGAGCCGCCGGTCGTCCTCGGTGCAGGTCGAGACGCGCGCGGA
CGGCACCGTGGAGCTGTCCGGACAGGTCACGGGCTACTTCTACAACGCGGCCTACACGC
TGTACTACACCGCGCGCACGCTCCAGCCCGCGACGGTGCAGACGTGGGGCGACGACGAC
CGGCTCGTCGACGCCACGGCCCAGGACGGCGTCGACACCGGCGCGATCCTCACGTTCGA
CCCGGCGGACGCCGGGGAGATCGGGCTCCAGGTCACCCTGTCGCCGGTGAGCGTCGAGC
AGGCGCGGATCGACCAGCAGGTCGAGCTCGGCGACCTGTCGTTCGACGCGATCCGTGAC
CGCACCCGCGCGGAGTGGAACGCGACGCTCGGGCGGGTCGCGATCGACGCCTCGACGGC
GACGGACCCGACGGGCGAGCTCCAGCGGCTCTTCTACACGCACCTCTACCGCATGTTCG
CGATGCCGATGAACGCGACGAGCACCTCGGGCACGTACCGCGGCGTCGACGGGGCGGTG
CACGCCGCGCAGGGCTTCACGTACTACGACTCGTGGGCCACGTGGGACGACTTCCGCAA
GTTCTCCGTCATCGCGTACATCGACCCGGCGCTGTACCGGGACATGGTGCAGTCGCTGG
TCTACCTGTTCGCGGACGCCGAGGCGACGGGCACCGGCGGCGGCCTCGGCGGGTTCGTG
CACTCGGTCCCGACGGTGCGCTGGGAGCGGTCGTCGGTCGTGGTCGCGGACGCGATCGC
CAAGGGCTTCGACGGGTTCGACCGCCTCGACGAGGCGTACCCGGCGCTCCAGCGGCTCG
TCGGGCAGTACAGCGCGGACGAGCTCCGGCGCGGCTACGTGGCGGGCAACCCCGGCGCG
TCCGTGCAGCGCGGCTACGACCAGTACGGCCTGTCCGTGATCGCGGACGAGCTCGGCCT
GACCGAGGAGGCCGAGACGCTGCGCGAGCAGGCGTCGTGGCCGATCGAGAAGCTCACCA
AGCCGGGCGCGTGGACCGCCGCCGACGGCACGCAGGTCGGCCTCCTCACCCCGCGCGCC
GCGGACGGGTCGTGGCAGAGCGCCGACCACGCGAAGTTCGAGGCCGCCGGCCTCTACCA
GGGCACGCTCTGGCAGTACCACTGGTACGACGCGTACGACATGGACGCGCTCGTCGAGG
CGATGGGCGGCCACGAGGCGGCGCGCCTCGGCATGCGCCACATGTTCGGTGAGCACGCG
CCGGACGACGGCAAGGCCATGCTCCACTCGAACGCCAACGAGATCGACCTCCAGGCGCC
GTACCTCTTCAACTACACGGGCGAGCCGAGCCTCACGCAGAAGTGGGCGCGCGCGATCT
ACACGAAGGAGACCTGGAACCGGTACATCGCGACCGGCTCCTCCAGCGCCGTGCCGAGC
GGCGGCGGCGAGTTCACGCCGCCCTTGAAGACGAAGGTGTACCGGCTCGACCCCGCGG
GATGCTCCCACGATGGACAACGACGCGGGCACGATGTCGACGATGTTCGTCGCCGCGG
CCGTCGGGCTGTTCCCGGTGACCGCGGGCTCGTCCCAGTTCCAGGTCGGGTCGCCGTTC
TTCGACTCGACGACCATCACCTACGACGACGGCAGCGCCTTCACGGTCACGGCCGACGG
CGTCTCCGAGGACGCGTTCTACGTCCAGTCCGCGACGCTCGACGGCGCGACGTTCGGCA
ACACGTGGGTCGACTACGCCACCGTGGTCGGGGGAGCCGACCTCGCGTTCCGCATGGGC
GAGCAGCCGAGCGACTGGGGCACGGACACCGCGCCCGCGTTCTCGATGAGTACCGCGAC
CGACGAGCCGGCCGAGGGACCGCGCGTCAGCGCCGAACCGACCACCGTGCAGACCGGCG
ACGGCGGCGCGCTCGACGCGACCGTGACGCTCACGCTCGACGGCGCCCGCCTCGCCGCG
CCCGCCGGCACGGACCTCGTCACGAGCGGGGCGGCGAGCGTCGTCGGGCTGCCCGACGG
CGTCACGGCGGCCGTGACGGTCGCGTCGCCGACCGCGCTGACCGTCTCCCTGACGGGGA
CGGCGTCCGCCGACGCGCGCTTCTTCGTGCACCTGCGCGACGCCGCGCTCGCCGACGGC
```

FIG. 12A-1

```
GTCGCCGCGGCGTCGCTCCAGGGACAGGGCGTCTCGGTGCGCTCGCCCTGCGGCTGTC
CGTGGCGTCCGCCGAGCGCGACGCGCTCGCCGCGCTCGTCGACGACGCCGTGCTCGTGC
GGCACGGGAACTACTCCTCGGTGACGTTCGACCGGTTCTCCACCGCGCTGACGAAGGCG
CAGGAGGCCCTCGGCGACGAGGCCGCGACGAGCATCGCGCTGCGGTTCGCGGCCGACCG
GCTCGGTGCGGCGGCCGACGCGCTCGACCTCACGGGCGGCGGGTACCGCACGCTCGAGG
CCGAGCAGTCCGAGGCGTGGTCGGGCGGGGAGCTGAAGAACGAGGCGAACAGCTCGTCC
GGCAACCTCGGCGGCGTGCGCTCCGGGTCGTGGGTGCAGTACCGCGACATGACCTTCGA
GACCGCCGCGGGGACACCCCGCCGCGCTTCCTCACGGTCCGGTACGACACGAGCTTCG
CCCCGACGGACACGCCGAGCACGTGCGCGTGCACGCGGGCGACGTGAGCGGCCCTGTG
GTCGCGACCGTCGACCTGAAGGGCACGAGCGGCTGGGCAAGTACACCGAGGTCACGGC
GGAGCTCGGCGACGTGCAGGCGCTCGTCGACGCGCAGGTCGTCACGTTCGAGCTGCTCG
CGCCGTCCGGGCGGAGCTGGGTCGGCAACTTCGACTGGTTCCGGTTCAGCGCCGAGGAC
CCGGCTGCCCCAGGTCAGCCGGCGAGTCCCCGACGGTGACGATCGAGGCCGAGGACTG
GACCGCGAGCTCCGGTCGCGGGCTCAAGAAGGAGTCCTCGACGTGGACGAGCGGTCCGG
TGACGAACGTCGGCGGCACCGCGGACGGCGACTGGATCGCCTACGGCGAGGTCGACCTG
GGTGAGCTCCGCTCGGCGAGCTGTCGGTCCACTACGTGCACAACTCCAACCGGTCCGG
GAACAACTCCGCGCTGTCGGTGTACCTCGACGCGTTCGACCCGGCGAACCCGGGCGAGC
CGTTCGTCACCGTGCCGCTGCCGACGACCGGGTCGAGCTGGACCGCGGACGGGACCGCG
ACCGTCGTCCTGCCCGAGACGGTGCAGGGGACGCACGAGGTGTTCGTGCGCCTGTCGAC
CGAGCCGTACGCCGACCACCCGTACGTCGCGAACCTCGACAGCCTGACGTTCGCGCCGG
GCGGCCCGACGTCGGTCGTCGTCGAGTCCGAGGCCTGGACGTCGAACTCCGGCCGCGGG
CTGAAGAACGAGAGCTCGACGTGGACGAGCGGTCCGGTGACGAACGTCGGCGGCACCGC
GGACGGCGACTGGCTCGCCTACGGCGAGATCGACCTCGGCTCCGCCGCGCTCGACCAGC
TCTCGGTCCACTACGTGCACAACTCCAACCGGTCCGGGCGGAACTCCGCGCTGTCGGTG
TACCTCGACGCGTTCGACCCGGCGAACCCGGGCGAGCCGTTCGTCACCGTCCGCTGGC
CAACACCGGGTCGAGCTGGACGACGGACGGGACCGCCGTCGTCGACCTGCCGAGCACGG
TGCGCGGCAAGCACCAGGTGTGGGTGCGCCTGTCCACCGAGGCGTACGCCGACCACCCG
TACGTCGCCAACCTCGACAGCATGCGCTTCTTCACCGACGCGTACGACGTCGAGGTCCC
GCCGACCGACACCGCGGCGCTCGCGGCGGTGGTCGACGCGGCCGGGACGCCCGAGGCGG
AGATCGCGCGGTACGGCCGGATCGACGCGCGCGTCTTCACACGCGAGCTCGCGGCGGCA
CGGTCCGTGCTCGCCGACGCCGGCGCCACCCAGGCGCAGGCCGACGAGCGGGCGCGGCG
CCTCGGCCTGGCGACCGACCAGTTCGTGCCCGCCGAGCGCCGTCGGCTCGAGAACCTCG
TGGCGAGCGCCGAGGCCCTGACCGACGAGGGGTACAGCCCCGAGTCCTGGCAGGCCTTC
CGCACGGCTCTCGCCGCGGCGACCGGGACGCTCGACGACGCGGCGGCGTCGACGAGGC
GCTGCACGACGCGCGGCTCGCGCTCCAGGGCGCCGTCGACGCCTGGAGGAGCCGGCCG
ACGTCGTGCTCGTCGAGGTCGAGGTCAGCCCGCGCTGCCTCGCCGGCAAGCCCTACGTC
GCGGTCCGCGCGGTGAACGTCTCCGACGCGGCCGTCGACGTCGAGCTGGCGTCGTCACT
GGGCACGAGGTCGTTCGTCGGCGTCGCGCCGGGGGCGAGCGCGTACCAGTCGTTCGCCG
CGCGGTCCGCGACGGGCGACCTGGACGTCACCGTCACGGCGACGGGGGCGGACGGCACC
CAGACGGTCGAGCAGGTCGTCACCGTCCCGTCCTGCTCC (SEQ ID NO:14)
```

FIG. 12A-2

ALAVVGLAPATAASAAPEPPSADYASLVDVFVGTEGDFGNDMPAAQAPNGLAKVNPRTT
PGRNNTGYDYAQSKISGFTHTNLDGVGGSGGGGDLLVVPTSGSYTARPGTGTYAHPFSH
DDEDAGPGFYSVGLGNVAGTDGAITGAPGTIEAEVAAATRSGVHRYAFPAGSTPSLVVD
LETNNTSRPSSSVQVETRADGTVELSGQVTGYFYNAAYTLYYTARTLQPATVQTWGDDD
RLVDATAQDGVDTGAILTFDPADAGEIGLQVTLSPVSVEQARIDQQVELGDLSFDAIRD
RTRAEWNATLGRVAIDASTATDPTGELQRLFYTHLYPMFAMPMNATSTSGTYRGVDGAV
HAAQGFTYYDSWATWDDFRKFSVIAYIDPALYRDMVQSLVYLFADAEATGTGGGLGGFV
HSVPTVRWERSSVVVADAIAKGFDGFDRLDEAYPALQRLVGQYSADELRRGYVAGNPGA
SVQRGYDQYGLSVIADELGLTEEAETLREQASWPIEKLTKPGAWTAADGTQVGLLTPRA
ADGSWQSADHAKFEAAGLYQGTLWQYHWYDAYDMDALVEAMGGHEAARLGMRHMFGEHA
PDDGKAMLHSNANEIDLQAPYLFNYTGEPSLTQKWARAIYTKETWNRYIATGSSSAVPS
GGGEFTPPFLKTKVYRLDFRGMLPTMDNDAGTMSTMFVAAAVGLFPVTAGSSQFQVGSPP
FDSTTITYDDGSAFTVTADGVSEDAFYVQSATLDGATFGNTWVDYATVVGGADLAFRMG
EQPSDWGTDTAPAFSMSTAFDEPAEGPRVSAEPTTVQTGDGGALDATVLTLDGARLAA
PAGTDLVTSGAASVVGLPDGVTAAVTVASPTALTVSLTGTASADARFFVHLRDAALADG
VAAASLQGQGVSVRSPLRLSVASAERDALAALVDDAVLVRHGNYSSVTFDRFSTALFKA
QEALGDEAATSIALRFAADRLGAAADALDLTGGGYRTLEAEQSEAWSGGELKNEANSSS
GNLGGVRSGSWVQYRDMTFETAAGDTPPRFLTVRYDTSFAPTDTPSTVRHAGDVSGPV
VATVDLKGTSGWGKYTEVTAELGDVQALVDAQVVTFELLAPSGRSWVGNFDWFRFSAED
PAAPGQPGESPTVTIEAEDWTASSGRGLKKESSTWTSGPVTNVGGTADGDWIAYGEVDL
GELPLGELSVHYVHNSNRSGNNSALSVYLDAFDPANPGEPFVTVPLPTTGSSWTADGTA
TVVLPETVQGTHEVFVRLSTEPYADHPYVANLDSLTFAPGGPTSVVVESEAWTSNSGRG
LKNESSTWTSGPVTNVGGTADGDWLAYGEIDLGSAALDQLSVHYVHNSNRSGRNSALSV
YLDAFDPANPGEPFVTVPLANTGSSWTTDGTAVVDLPSTVRGKHQVWVRLSTEAYADHP
YVANLDSMRFFTDAYDVEVPPTDTAALAAVVDAAGTPEAEIARYGRIDARVFTRELAAA
RSVLADAGATQAQADERARRLGLATDQLVPAERRRLENLVASAEALTDEGYSPESWQAF
RTALAAATGTLDDAAASDEALHDARLALQGAVDALEEPADVVLVEVEVSPRCLAGKPYV
AVPAVNVSDAAVDVELASSLGTRSFVGVAPGASAYQSFAARSATGDLDVTVTATGADGT
QTVEQVVTVPSCS (SEQ ID NO:15)

FIG. 12B

```
APEPPSADYASLVDVFVGTEGDFGNDMPAAQAPNGLAKVNPRTTPGRNNTGYDYAQSKISGF
THTNLDGVGGSGGGGDLLVVPTSGSYTARPGTGTYAHPFSHDDEDAGPGFYSVGLGNVAGTD
GAITGAPGTIEAEVAAATRSGVHRYAFPAGSTPSLVVDLETDNTSRRSSSVQVETRADGTVE
LSGQVTGYFYNAAYTLYYTARTLQPATVQTWGDDDRLVDATAQDGVDTGAILTFDPADAGEI
GLQVTLSPVSVEQAKIDQQVELGDLSFDAIRDKTRAEWNATLGRVAIDASTATDPTGELQRL
FYTHLYRMFAMPMNATSTSGTYPGVDGAVHAAQGFTYYDSWATWDDFRKFSVIAYIDPALYR
DMVQSLVYLFADAEATGTGGGLGGFVHSVPTVRWERSSVVVADAIAKGFDGFDRLDEAYPAL
QRLVGQYSADELRRGYVAGNPGASVQRGYDQYGLSVIADELGLTEEAETLREQASWPIEKLT
KPGAWTAADGTQVGLLTPRAADGSWQSADHAKFEAAGLYQGTLWQYSWYDAYDMDALVEAMG
GREAARLGMRHMFGESAPDDGKAMLHSNANEIDLQAPYLFNYTGEPSLTQKWARAIYTKETW
NRYIATGSSSAVPSGGGEPTPPLKTKVYRLDPRGMLPTMDNDAGTMSTMFVAAAVGLFPVTA
GSSQFQVGSPFFDSTTITYDDGSAFTVTADGVSEDAFYVQSATLDGATFGNTWVDYATVVGG
ADLAFRMGEQPSDWGTDTAPAFSMSTATDEPAEGPRVSAEPTTVQTGDGGALDATVTLTLDG
ARLAAPAGTDLVTSGAASVVGLPDGVTAAVTVASPTALTVSLTGTASADARFFVHLRDAALA
DGVAAASLQGQGVSVRSPLRLSVASAERDALAALVDDAVLVRHGNYSSVTFDRFSTALTKAQ
EALGDEAATSIALRFAADRLGAAADALDLTGGGYRTLEAEQSEAWSGGELKNEANSSSGNLG
GVKSGSWVQYRDMTFETAAGDTPPRFLTVRYDTSFAPTDTPSTVRVHAGDVSGPVVATVDLK
GTSGWGKYTEVTAELGDVQALVDAQVVTFELLAPSGRSWVGNFDWFRFSAEDPAAPGQPGES
PTVTIEAEDWTASSGRGLKKESSTWTSGPVTNVGGTADGDWIAYGEVDLGELPLGELSVHYV
HNSNRSGNDSALSVYLDAFDPANPGEPFVTVPLPTTGSSWTADGTATVVLPETVQGTHEVFV
RLSTEPYADSPYVANLDSLTFAPGGPTSVVVESEAWTSNSGRGLKNESSTWTSGPVTNVGGT
ADGDWLAYGEIDLGSAALDQLSVHYVHNSNRSGRNSALSVYLDAFDPANPGEPFVTVPLANT
GSSWTTLGTAVVDLPSTVRGKHQVWVRLSTEAYADHPYVANLDSMRFFTDAYDVEVPPTDTA
ALAAVVDAAGTPEAEIARYGPIDARVFTRELAAARSVLADAGATQAQADERARRLGLATDQL
VPAERRRLENLVASAEALTDEGYSPESWQAFRTALAAATGTLDDAAASDEALHDARLALQGA
VDALEEPADVVLVEVEVSPRCLAGKPYVAVRAVNVSDAAVDVELASSLGTRSFVGVAPGASA
YQSFAARSATGDLDVTVTATGADGTQTVEQVVTVPSCS      (SEQ ID NO:50)
```

FIG. 12C

```
GCACCGGCAGATGAAGGCACCGTTACCGCAGCAGCCGGTGATGATCTGACCCTGGAAGTTAATCCGTTTGT
TGGCACCGAAAGCGAAGGTAATGCATATCCGGGTGCAACCGTTCCGTTTGGTATGGTTCAGCTGTCTCCGG
ATAATACCAATAGCTATGCCAGCACCAGCTATAGCACCAATGCAGGTGGTGTTTGGGGTTTTAGCCATCGT
CATGTTAATAGCGCAGGTTGTCCGGCAGCCGGTGAACTGCTGGTTACACCGGATACCAGCGCAACACCGCG
TACCAGCCGTAGCTTTATTGCCATCAAAGATCAGAAAAGCACCGAACGTGCAAGCGCAGGTTTTTATGAAG
TTACCCTGGCAAATGATGTTCATGCAGAACTGACCGCAACCACCCGTGTTGGTGCACATCGTTATACCTTT
CCGGCAAGCACCACCCTCATCTGAGCTTTAATGTTGGTCAGACCCTGCCGTGATGCCCGGTGCAAGCAGCGT
TACCTGGGTTGATGATCGTACACTGGAAGGTTGGGTTGATAATGGTGGTTTTTGTGGTGGTACACCGGATA
AACAGCGCTATTTTTTTACCGCAACCTTTGATCGTCCGGTTGCCAGCAGCGGTACATGGGGCACCGATGCA
CGTTATGTTGCAGGTAGCACCACCAGTGAAGTTGCCGGTGGTAATAATGGTGCAGTTGCCGTTTTTGATAC
CACCACCGATCGTGATGTTGAAGTTAGCGTTGGTGTTAGCTTTGTTAGCGTTGATGGTGCACGTGCAAATC
GTGAAGCCGAAGCAACCGATGAAGGTGGTCAGGTTGCATTTGATACCGTTCGTGAAGAAGCACGCGACGCC
TGGAATGCAGAACTGGGTCGTGCAGCAATTGATGCATCTCCGGATCAGCGTCGTATCTTTTATACCCAGCT
GTATAAAACCTGCTGAGCCCGACCATTGGTTCTGATGTTGATGGTCGTTATCGTGGTATGCATCTGGAAG
TTCATCAGGCAGATGGCTGGGATTATTATCAGAACTTTAGCCTGTGGGATACCTATCGTACCCAGGCAACC
CTGCATGCACTGCTGCTGCCGGAACGTGCACAGGATATTGTTCGTAGCATGTATCAGCATCGTGTTGAAGG
TGGTTGGCTGCCTCGTTGGTCTCTGGGTGCACTGGAAACCAATATCATGGCAGGCGATCCGGTTACCCGT
GGCTGGCAGAAAATTTTGCACTGGGCACCGTTCCGGATGATATTGCAGATGAACTGTGGGATTATCTGGTT
GAAAATGCAACCACCACCCCTCCGGATGATGTTGCCAGCGTTGGTCGTCGTAGCACCGAATTTTATGCCGA
ACATGGTCATGTTCCGTTTTATCCGGAAAACGAAGGTGGCCTGGGTGGTCAGTTTGAAGAATATCGTCATG
GTGGTAGCCGCAACCCTGGAACGTGGCACTGGCAGATGCAAGCCTGGGTGCCGCAGCAGAACGTACCGGTCGT
GAAGGTGGCCAGGCATTTCTGGATAAAGCTGCAATTGGCGTAATCTGTGGAATCCGGATGTTGAACTGAG
CGGTGGTTTTCAGGGTATGGTTAATGCAAAACGTCCGACCGGTGAATTTGTTACCCTGCCGGAACTGACCG
ATGTTACCCGTAGCGGTTTTCATGAAGGTGTTCCGTGGCAGTATCAGTGGATGGTTCCGCAGGATGTTACC
GGTCTGCAAGAAGTTATGGGAGGCGAAGATGGTTTTGTGGAACGCCTGGATTATTATTTTGATCAGCCTGC
ACTGGCAGCAAATCCGGGTGTTAGCCCGAGCACCTGGGCAAAAGGTGGTAGCAGCTATTATACCACCATTC
GCTATAATCCGGGTAATGAACCGACCATTATGAATGCATGGCTGTATGGTTATGTTGGTCAGCCGTGCAAA
ACCAATGATGTTCTGGCAGCCAATCTGAATCGTTTTCCGGATACACCGGGTGGTGGTGTTGGTAATGATGA
TCTGGGCACCCTGGCAGCATGGTATGTTATGGCCAGCCTGGGTTTTGAACCGGTTATGCCTGGTAGCGGTA
TTCTGGCACTGAATGCACCGAAAGTTCAGGCAGCAACCCTGACCACCGATGCCGGTGCCACCCTGCCGTATT
GATGCAGCCGGTGCAAATGAAAAACTGCCGAGCTATGTTCCCGGTCTGGAAGTTGATGGTGTTGCACATAC
CGCAGCATGGCTGGATGTTGCAGCACTGCAGGATGGTGGCACCCTGGATTTTGATCTGAGCGGTACAAGCG
CAGGTCTGACATGGGGTACAGTTGCAGCAGATCGTATTCCGAGCGTTAGCGCAGTTGCACCGCCTGCACCG
GTTGAAGTGGAAGCAAGCGCACGTTGTCTGGGTGGTCGTGCATTTGTTGCAGTTCGTGCAACCAGCACCCGC
AGATGCACCGGTGGATGTTACACTGACCACACCGTTTGGTGAACGTACCGTTCCGTCATGTTCAGCCTGGTC
GTAGCGCATATCAGAGCTTTACCACCCGTACCACCTCTGTTGAAGCAGGCACCGCAACCGTTACCGTTGTT
GCAGCAGATGGCACCACCTCAACCGTTGATGCAGCATATGAAGCACTGGCATGTGGTTAATAA (SEQ ID
NO:16)
```

FIG. 14

```
GCAGGCACCGAAGCAGCAACCGGTTCTGATGCAGCAGCAGTTGATGGTCCGCTGGTTGATTATGTGAATCC
GTTTATTGGCACCAAAGATGATGGTAATACCTATCCGGGTGCAGCAGTTCCGTTTGGTATGGTTCAGCTGT
CTCCGGATAATGGTCATAATGTGGCTATGATTATGATCGTACCAGCGTTCGTGGTTTTAGCCTGGTTCAT
CTGAGCGGTGTTGGTTGTGGTCTGGGTGGTCCGCTGCCGACACTGCGACCACCGGTGCAATTACCAGCAC
CGATTATGGTCAGTATGCACTGGGTTTTAGCCATGATGATGAAGAAGCATCTCCGGGTTATTATCGTGTTG
GTCTGCAGGCACCTGCAGGAACCATTGAAGCAGAACTGACCGCAACCGAACGTACCGGTGTTCAGCGTTAT
ACCTTTCCGGCAACCGCACAGCCAAATGTTCTGCTCAATGCAGGTCAGCCACTGAATCCTGTTACCGAATC
TGATGTTCGTGTTGTTGATGATCGTACCGTTGAAACCCGTATTACCGTGCGTGGTTTTTGTCAGGATACCG
AACCGCAGACCATTGGACCCGTACCACCTTTGATCGTCCGTTTGTTGCACATGGCACCTGGGATGGTCAG
GTTGTTACCGCAGGCGCAGATGCAGCAAGCGGTGGTGAAGGTCGTCGTGGTGCATATGTTACCTTTGATAC
AACCGGTGGTGATCTGGATGTTGAAGCAGTTACCGCAATGAGCTATGTTGGTGCAGATGGTGCAGCAGCAA
ATCTGGCAGCAGAAGCAGGCACCTTTGACGCAGTTCATGATGCAGCACGTAGCGCATGGGAAGAACGTCTG
GGTCTGGTTCGTGTTGCACAGGGTGATCCGGATGATCTGCGTACCTTTTATAGCAGCTGTATCGTAGCTT
TCTGGCACCGAATGTTGGTTCTGATGTGGATGGTCGTTATCGTGGTTGGGATCAGGAAGTTCACGCAGCAG
AACCGGATTTTACCTATTATCAGAATTATAGCCTGTGGGATACCTATCGTACCCAACAGCAACTGCTGTAT
CTGCTGGCACCGGATGAAAGCGCAGATATGGCACTGAGCCTGGTTCGTCAGGGTCAGCAGGGTGGTTGGCT
GCCTCGTTGGGGTTATGGTACAGTGGAAACCAATATTATGACCGGTGATCCGGCAACCCCGTTTCTGGTTA
GCGCATGGCGTCAGGGTCTGCTTGCAGGTCATGAAGAAGAAGCATACGCAGTCCTGCGTGAAAATGCAGAT
GGTGTTCCTCCGGCAGATAGCCCGTTTAATGGTCGTGCAGCCAATGTTGAATATCTGCGTGATGGTTTTGT
TCCGCATGGAACCGGCACGTAGCGGTAAACCGGGTGATTATGATCTGCAGCATGGTGCAAGCGCAACCATGG
AATATGCACTGGCAGATGCAATGCTGAGCACCATGGCACGTGGTCTGGGTCATGATGAAGATGCAGATCGT
TATGCAGCCCGTGGTCAGAGCTATCGTAATGTTTTTGATCCGCGTACCGGTAATTTCGTGCACGTAATGC
CGATGGTTTTTTGTTGGTGATGCAGATCCGGCACATTCTGATGGTTTTCATGAAGGCACCGCAGTTCAGT
ATCAGTGGCTGGTTCCGCAGGATGTTCCGGGTCTGTTTGATCTGATGGGTGGCACCGATGCAGCCGTTGAT
CGTCGGATGCATTTTTTGCCTATGATGAACTGGTTGCAGATCCTCCGCATGTTGCAAGCGAAGTTTGGGT
TAATGGCACCTATGATTATTATGGCTGGGAAACCTATAATCCGAATAATGAACCGAATCTGCATGCACCGT
ATGTTTATCTGTGGACCGGTCAGTCGTGGAAAACCACCGATGTTGTTCGTGCAGCAAGCACCCTGTTTACC
GATGGTCCGGATGGTGTTACCGGTAATGATGATCTGGGCACCATGAGCGCATGGCATGTTCTGTGAGCAGCAT
GGTGTTTATCCGATTGTTCCGGGTGCCGATCTGTGGGGTCTGACCACACCGGCTGTTTGATGATGTTACCA
TTACCCTGGACCCGGAAGTTTTTGGTCGTGATAGCCTGCGTCTGACCGCAGATGGTGTGGCACCGGATACC
CATTATACCCAGAGCGTTAGCCTGGGTGGTGAACCGCTGGATCGTGCATGGGTTACAGGTGATGAACTGAC
CGCTGCAGGCACCCTGGATGTTACCGTTGGCACCGAACCGAGCGCATGGGCAACCGATCCGGCAGCATCAC
CGGGTGCAGTTGTTCCGGCTGATGGCACCGTTGAACGTCTGTTTGTTGGTGCAACACCGCGTCAGCCGGTT
CTGGCACCGGGTGGTCGTACCGAAGTTGCAGTTCAGGTTGTTGCCCAGGGTGCAGGCACCTCTAGCGGCAC
CCTGGAAGTGACCTCTGATGGTGCAGTTACCGCCACCACCGATCTGGCAGAATGGACCGCAGAATCTGATG
GTCTGCCTGCCCACCGTTGAAGGAACCGTTACCATTGAAGCTCCGGCAGATGCCGAACCGGGTCTGCATACC
GTTCGTCTGGTTGTTCGTGATGCAGCCGGTACAGAAGCAGTTCGCGAAGTTACGCTTGTTGTTAGCGGTGA
AAGCTGGATTGCAGATGCCTTTGATAATGTGGGTATTGGTGATGCCGGTGCAGCAAATGCAAATCTGGATG
GTAGCGGTGCCTATCTGCTGCGTGATCTGGTGGCCGATCTGGGTGCAGTTCAGGGTCTGGAACTGACCGTT
CCGGGTACTGATCTGACCTATACCCTGGGTGCACCCGTGCTGGTGCACCGGATAATGTTGCAGCCAGCGG
TGAAGTTCTGGAAGTTCCGGACATCTGCGTAGCGCACGTCATCTGAGCGTTGTGGGCACCAGCACCCATG
GTACACATCGTGGTGGTCTGGTTCTGGGTTTTGCCGATGGTAGCAGCCAGACCGTTGATGTTCGTCTGAGC
GATTGGTGTACCGGTTCTCCGGAACCGGTAATATTACCGTTGCAAAAGCCGGTGCACGTGGTGATCGTGA
AAATGTGCAGAAAATTGGCTGTGGTCTGTATGCAACCGCACCGGTGGCAATTCCGGAAGGTAAAGTTCTGA
CCAGCGTTACCCTGCCGTCTGATGAACGTTTTCATGTGTTTGCAATTGCAACCGATGCAACCGGTGATGTT
CCGGCGCCAGGTTGAAGTTACCGCACAGCTCCGTTGTCTGGTGGTAAAGCATTTGTTGCAGTTCGTGC
ACTGAATACCGGTGAACAGCCTGCACCAATTGAACTGGCCAACCCGTATGGTAGCAAACTGTTTGGTGATG
TTGCTCCGGGTGCAAATGCATATCAGAGCTTTGCAACCCGTGTAGCAGCCGTTGAAGCCGGTGAAGTTACC
GTTACCCGTGACCACACCGGATGGTGAACCGCAGCAGGTTACCGCAGCATATGATGCAGCCGGCATGTAGCTA
ATAA (SEQ ID NO:17)
```

FIG. 15

```
GCAGGCACCGAAGCAGCAACCGGTTCTGATGCAGCAGCAGTTGATGGTCCGCTGGTTGATTATGTGAATCC
GTTTATTGGCACCAAAGATGATGGTAATACCTATCCGGGTGCAGCAGTTCCGTTTGGTATGGTTCAGCTGT
CTCCGGATAATGGTCATAATGTGGGCTATGATTATGATCGTACCAGCGTTCCTGGGTTTAGCCTGGTTCAT
CTGAGCGGTGTTGGTGTGCTCTGGGTGGTCCGCTGCCGACACTGCCGACCACCGGTGCAATTACCAGCAC
CGATTATGGTCAGTATGCACTGGGTTTTAGCCATGATGATGAAGAAGCATCTCCGGGTTATTATCGTGTTG
GTCTGCAGGCACCTGCAGGAACCATTGAAGCAGAACTGACCGCAACCGAACGTACCGGTGTTCAGCGTTAT
ACCTTTCCGGCAACCGCACAGGCAAATGTTCTGCTGAATGCAGGTCAGCCACTGAATCGTGTTACCGAATC
TGATGTTCGTGTTGTTGATGATCGTACCGTTGAAACCCGTATTACCGTGCGTGGTTTTTGTCAGGATACCG
AACCGCAGACCATTGGACCCGTACCACCTTTGATCGTCCGTTTGTTGCACATGGCACCTGGGATGGTCAG
GTTGTTACCGCAGGCGCAGATGCAGCAAGCGGTGGTGAAGGTCGTCGTGGTGCATATGTTACCTTTGATAC
AACCGGTGGTGATCTGGATGTTGAAGCAGTTACCGCAATGAGCTATGTTGGTGCAGATGGTGCAGCAGCAA
ATCTGGCAGCAGAAGCAGGCACCTTTGACGCAGTTCATGATGCAGCACGTAGCGCATGGGAAGAACGTCTG
GGTCTGGTTCGTGTTGCACAGGGTGATCCGGATGATCTGCGTACCTTTTATAGCAGCTGTATCGTAGCTT
TCTGGCACCGAATGTTGGTTCTGATGTGGATGGTCGTTATCGTGGTTGGGATCAGGAAGTTCACGCAGCAG
AACCGGATTTTAGCCTATTATCAGAATTATAGCCTGTGGGATACCTATCGTACCCAACAGCAACTGCTGTAT
CTGCTGGCACCGGATGAAAGCGCAGATATGGCACTGAGCCTGGTTCGTCAGGGTCAGCAGGGTGGTTGGCT
GCCTCGTTGGGGTTATGGTACAGTGGAAACCAATATTATGACCGGTGATCCGGCTAACCCCGTTTCTGGTTA
GCGCATGCCGTCAGGTCTGCTGGCAGGTCATGAAGAAGAAGCATACGCAGTCCTGCGTGAAAATGCAGAT
GGTGTTCCTCCGGCAGATAGCCCGTTTAATGGTCGTGCAGCCAATGTTGAATATTCCGTGATGGTTTTGT
TCCGCATGAACCGGCACGTAGCGGTAAACCGGTGATTATGATCTGCAGCATGGTGCAAGCGCAACCATGG
AATATGCACTGGCAGATGCAATGCTGAGCACCATGGCACCGTGGTCTGGGTCATGATGAAGATGCAGATCGT
TATGCAGCCCGTGGTCAGAGCTATCGTAATGTTTTTGATCCGCGTACCCGTAATTTTCGTGCACGTAATGC
CGATGGTTTTTTTGTTGGTGATGCAGATCCGGCACATTCTGATGGTTTTCATGAAGGCACCGCAGTTCAGT
ATCAGTGGCTGGTTCCGCAGGATGTTCCGGGTCTGTTTGATCTGATGGGTGGCACCGATGCAGCCGTTGAT
CGTCTGGATGCATTTTTGCCTATGATGAACTGGTTGCAGATCCTCCGCATGTGCAAGCGAAGTTTGGGT
TAATGGCACCTATGATTATTATGGCTGGAAACCTATAATCCGAATAATGAACCGAATCTGCATGCACCGT
ATGTTTATCTGTGGACCGGTCAGCCGTGGAAAACCACCGATGTTGTTCCTGCAGCAAGCACCCTGTTTACC
GATGGTCCGGATGGTGTTACCGGTAATGATGATCTGGGCACCATGAGCGGCATGGCATGTTCTGAGCAGCAT
TGGTGTTATCCGATTGTTCCGGGTGCCGATCTGTGGGGTCTGACCACACCGCTGTTTGATGATGTTACCA
TTACCCTGGACCCGGAAGTTTTTGGTCGTGATAGCCTGCGTCTGACCGCAGATGGTGTGGCACCGGATACC
CATTATACCCAGAGCGTTAGCCTGCGTGGTGAACCGCTGGATCGTGCATGGGTTACAGGTGATGAACTGAC
CGCTGCAGGCACCCTGGATGTTACCGTTGGCACCGAACCGAGCGCATGGGCAACTGATCCGGCAGCATCAC
CGGGTGCAGTTGTTCCGGCTGATGGCACCGTTGAACGTCTGTTTGTTGGTGCAACACCGCGTCAGCCGGTT
CTGGCACCGGGTGGTCGTACCGAAGTTGCAGTTCAGGTTGTTGCCCAGGGTGCAGGCACCTCTAGCGGCAC
CCTGGAAGTGACCTCTGATGGTGCAGTTACCGCCACCACCGATCTGGCAGAATGGACCGCAGAATCTGATG
GTCTGCCTGCCACCGTTGAAGGAACCGTTACCATTGAAGCTCCGGCAGATGCCGAACCGGGTCTGCATACC
GTTCGTCTGGTTGTTCCGTGATGCAGCCGGTACAGAAGCAGTTCGCGAAGTTAGCGTTCTTGTTAGCGGTGA
AAGCTGGATTGCAGATGCCTTTGATAATGTGGGTATTGGTGATGCCGGTGCAGCAAATGCAAATCTGGATG
GTAGCGGTGCCTATCTGCTGCGTGATCTGCTGGCCGATCTGGGTGCAGTTCAGGGTCTGGAACTGACCGTT
CCGGGTACTGATCTGACCTATACCCTGGGTGCACCGCGTGCTGGTGCACCGGATAATGTTGCAGCCAGCGG
TGAAGTTCTGGAAGTTCCGGAACATCTGCGTAGCGCACGTCATCTGAGCGTTCTGGGCACCAGCACCCATG
GTACACATGGTGGTCTGGTTCTGGGTTTTGCCGATGGTAGCAGCCAGACCGTTGATGTTCGTCTGAGC
GATTGGTGTACCGGTTCTCCGGAACCGGGTAATATTACCGTTGCAAAAGCCGGTGCACGTGGTGATCGTGA
AAATGTGCAGAAAATTGGCTGTGGTCTGTATGCAACCGGCACCGGTGGCAATTCCGGAAGGTAAAGTTCTGA
CCAGCGTTACCCTGCCGTCTGATGAACGTTTTCATGTGTTTGCAATTGCAACCGATGCAACCGGTGATGTT
CCGGCACCGCAGGTTGAAGTTACCGCACAGGCTCGTTGTCTGGGTGGTAAAGCATTTGTTGCAGTTCGTGC
ACTGAATACCGGTGAACAGCCTGCAGCAATTGAACTGGCAACCCCGTATGGTAGCAAACTGTTTGGTGATG
TTGCTCCGGGTGCAAATGCATATCAGAGCTTTGCAACCCGTGCAGCAGCCGTTGAAGCCGGTGAAGTTACC
GTTACCGTGACCACACCGGATGGTCAACCGCAGCAGGTTACCGCAGCATATGATGCAGCGGCATGTAGCTA
ATAA (SEQ ID NO:18)
```

```
GATGGCGTTACCGGTCGTGAAGTTAGCGGTTCTTTTGCAACCCTGACCGGTGTCGAAGGTGATGTTGCCGC
ACTGGATGTTCAGGTTGCATTTGGTGATGGTAGCGAACCGGTTGCAGGTACACTGCGTGCCGGTGCATTTG
GTGGTTATGCAGTTGATGCAGCACATACCTGGACCCGCACCGGGTGTTTATCCGGTTACCGTGACCGTTAGC
GGTGAAGGTATTGAAACCGTTAGCGCAAGCAGCTATGTTAGCGTTAGCCTGCTGCGTGAACGTTCTCTGCT
GGCAGCATATGATAATGTGTGCATTGGTGATGCAGGTACAACCGTTGGTTCTTGTGATGGTCAGGGCGTTT
TTTTTGATCGTGCACAGCTGGCAGCAAAAGGTTTTGTGCAGGGTGAACGTGCAACCGTTCCGGGTACAGAT
CTGGCATTTGATGTTCCGGCAGTTCCGGCTGGTCAGCCTGATAATGCAACCGGTGATGGTCAGACCATTGA
ACTGGATGTTCCGGCTGATGCAGAACAGCTGAGCGTTATTGGCACCGGCACCGAAAAAAATCAGCAGGCAA
CCGGTACACTGACCTTTGATGATGGTTCTACCCAGCCGATTGATCTGAGCTTTGGTGATTGGAGCGGTGCA
GCACGTAATCCGGTGTTTGGTAATATTCCGGTTGCAGTTACCGATAGCCGTCTGCGTGGTGGTTCTCCGCA
GACCGGTACACCGGCAGCATTTTTTGCCACCGCACCGATTACCCTGCCCGGAAGGTAAACGTCCGGTTAGCC
TGACCCTGCCGGATCAGCCTGGTGAACTGAGCCGTCATGGTCGTATTCATGTTGTTGCAGTTGCACATGAT
GGCACCTTTGCAGAACATCCTGCACTGGAAGTGACCGCAGCAGAAGGTGTTACCCTGGCAGTTGGTCAGAC
CTCAGATGTTGCACTGGCACAGGTTGCCGGTGGTCGTGAAGGTGCAGATCTGCGTGTTGCAGTTACCTGGG
GTGATGGTCTGATGTGGCAGCCGGTGCCGTTACCGATGGTAGCGTTAGCGGTAGCCATGCATATACCGCA
GCAGGCACCTATACCGCATATGTTGTTGTGGATGATGGTTGGACCAGCCAGGTTGTTGAAGTTCCGGTGAC
CGTTACAGAAGCCGAACCGGCACTGGCCGTTGATGTCACCGTTAGCACCCGTTGCCTGGCAGGTAAAGCAT
ATGTTGCAGTGCCGTGCAGAAAATGGTGAAGATGTTCCGCTGGCAATTCGTCTGGTTACCCCGTTTGGCACC
AAAGAAGTTGCAGCAGTTGCTCCCGGGAGCCAATGCATATCAGAGCTTTGCAACCCGTGTTACCGCAGTTGA
AGCAGGCACCGTTACCGTTGAAGCCACCCGTGGCACCGGTGATGAAGAAGTTACCGCCAGCATTCAGGCAG
ATTATGCAGCCGTTACCTGCGGTTAATAA (SEQ ID NO:19)
```

FIG. 17-2

```
GATATGCCTGCAGCACAGGCACCGAATGGTCTGGCAAAAGTTAATCCGCGTACCACACCGGGTCGTAATAA
TACCGGTTATGATTATGCCCAGAGCAAAATTAGCGGTTTTACCCATACCAATCTGGATGGTGTTGGTGGTA
GCGGTGGTGGTGGTGATCTGCTGGTTGTTCCGACCAGCCGGTAGCTATACCGCACGTCCGGGTACAGGCACC
TATGCACATCCGTTTAGCCATGATGATGAAGATGCAGGTCCGGGTTTTTATAGCGTTGGTCTGCGTAATGT
TGCAGGCACCGATGGTGCAATTACCGGTGCTCCGGGTACAATTGAAGCAGAAGTTGCAGCAGCAACCCGTA
GCGGTGTTCATGGTTATGCATTTCCGGCAGGTAGCACCCGGAGCCTGGTTGTTGATCTGGAAACCAATAAT
ACCAGCCGTCGTAGCCAGCAGCCGTTCAGGTTGAAACCCGTGCAGATGGCACCGTTGAACTGAGCGGTCAGGT
TACCGGCTATTTTATAATGCAGCCTATACCCTGTATTATACCGCACGCACCCTGCAGCCTGCAACCGTTC
AGACCTGGGGTGATGATGATCGTCTGGTTGATGCAACCGCACAGGATGGTGTTGATACCGGTGCAATTCTG
ACCTTTGATCCGGCAGATGCCGGTGAAATTGGTCTGCAGGTTACCCTGTCTCCGGTTAGCGTTGAACAGGC
ACGTATTGATCAGCAGGTTGAACTGGGTGATCTGAGCTTTGATGCAATTCCTGATCGTACCCGGTGCAGAAT
GGAATGCAACCCTGGGTCGTGTTGCAATTGATGCAAGCACCGCAACCGATCCGACCGGTGAACTGCAGCGT
CTGTTTATACCCATCTGTATCGCATGTTTGCAATGCCGATGAATGCAACCAGCACCAGCGGCACCTATCG
TGGTGTTGATGGTGCAGTTCATGCAGCACAGGGCTTTACCTATTATGATAGCTGGGCAACCTGGGATGATT
TTCGCAAATTTAGCGTGATTGCCTATATTGATCCGGCACTGTATCGTGATATGGTTCAGAGCCTGGTTTAC
CTGTTTGCAGATGCAGAAGCAACCGGTACAGGCGGTGGTCTGGGTGGTTTTGTTCATAGCGTTCCGACCGT
TCGTTGCGGAACGTAGCAGCGTTGTTGTTGCAGATGCAATTGCCAAAGGCTTTGATGGTTTTGATCGTCTGG
ATGAAGCATATCCGGCACTGCAGCGCCTGGTTGGTCAGTATACCGCAGATGAACTGCGTCGTGGTTATGTT
GCAGGTAATCCGGGTGCAAGCCGTTCAGCCTGGTTATGATCAGTATGGTCTGAGCGTTATTGCCGATGAACT
GGGTCTGACCGGAAGAAGCAGAAACCCTGCGCGAACAGGCAAGCTGGCCGATTGAAAAACTGACCAAACCGG
GTGCATGCACCGCAGCAGATGGTACACAGGTTGGTCTGCTGACACCGCGTGCAGCCGATGGTAGCTGGCAG
AGCGTAGATCATGCCAAATTTGAAGCAGCAGGTCTGTATAGCGCATTCTGTGGTAGTATCATTGGTATGA
TGCCTATGATATGGATGCACTGGTTGAAGCAATGGGTGGTCATGAAGCAGCCCGTCTGGGTATGCGTCATA
TGTTTGGTGAACATGCACCGGATGATGGTAAAGCAATGCTTGCATAGCCAATGCCAATGAAATTGATCTGCAG
GCACCGTACCTGTTTAATTATACCGGTGAACCGGACCCTGACCTAGAAATGGGCACGTGCAATTTATACCAA
AGAAACCTGGAATCGCTATATTGCAACCGGTAGCAGCTCTGCAGTTCCGTCAGGTGGTGGTGAATTTACAC
CTGCGCTGAAAACCAAAGTTTATGGTCTGGACCCTCGTGGTATGCTGCCGACCATGGATAATGATGCAGGT
ACAATGAGCACCATGTTTGTTGCAGCAGCCGTTGGTCTGTTTCCGGTTACCGCAGGTAGCAGCCAGTTTCA
GGTTGGTAGCCCTGTTTTTGATAGCACCACCATTAGCTATGATGATGGTAGCGCATTTACCGTTACCGCAG
ATGGTGTTAGCGAAGATGCCTTTTATGTTCAGAGCGCAACCCTGGATGGTGCAACCTTTGGTAATACCTGG
GGTGATTATGCAACCGTGTTGGTGGTGCAGATCTGGCATTTCGTATGGGTGAACAGCCGAGCGATGGGG
CACCGATACCGCACCGGCATTTAGCATGAGCACCGCCACCGATGAACCGGCAGAAGGTCCTCGCGTTAGCG
CAGAACCGACCACCGTGCAGACCGGTGATGGTGGTGCACTGGATGCAACCGTTACCCTGACACTGGATGGC
GCACGTCTGGCAGCACCGGCAGGTACAGATCTGGTTACCAGCGGTGCAGCAACGTTGTTGGTCTGCCGGA
TGGTGTTACCGCAGCAGTTACCGTTGCAAGCCCGACCGCACTGACCGTTAGCCTGACCGGCACCGGCATCAG
CAGATGCACGTTTTTTTGTGCATCTGGCTGATGCAGCACTGGTCGATGGTGTTGCAGCCGCAAGCCTGCAG
GGTCAGGGTGTTAGCGTTCGTTCTCCGCTGCGTGCTGAGCGTTGCAAGCGCAGAACGTGATGCACTGGCAGC
ACTGGTTGATGACGCCGTTCTGGTTCGTCATGCTAATTAAGCAGCGTTACCTTTGATCGTTTTAGCACCG
CTCTGACAAAAGCACAGGAAGCACTGGGCGACGAAGCAGCAACCAGCATTGCACTGCGTTTGCAGCAGAT
CGTCTGGGTGCAGCAGCAGATGCACTGGATCTGACCGGTGGTGGTTATCGTACCCTGGAAGCAGAACAGAG
CGAAGCATGGTCTGGTGCTGAACTGAAAAATGAAGCCAATAGCAGCAGCGGTAATCTGGGTGGTGTTCGTA
GCGGTAGCTGGGTTCAGTATCGCGATATGACCTTTGAAACCGCAGCCGGTGATACACCTCCGCGTTTTCTG
ACCGTTCGTTATGATACCAGCTTTGCACCGACCGATACCCCGAGCACCCTTCGTGTTCATGCCGGTGATGT
TTCTGGTCCGGTTGTTGCAACCGTTGATCTGAAAGGCACCAGCGGTTGGGGTAAATATACCGAAGTTACCG
CAGAACTGGGTGATGTTCAGGGCCCTGGTTGATGCCCAGGTTGTTACCTTTGAACTGCTGGCACCGAGCGGT
CGTAGCTGGGTTGGTAATTTTGATTGGTTTCGCTTTAGCGCAGAAGATCCGGCAGCACCGGGTCAGCCTGG
TGAAAGCCCGACCGTTACCATTGAAGCCGAAGATTGGACCGCAAGCAGCGGTCGTGGTCTGAAAAAAGAAA
GCAGCACCTGGACCAGCGGTCCGGTGACCAATGTTGGTGGTACAGCAGATGGTGATTGGATTGCCTATGGT
GAAGTTGATCTGGGTGAACTGCCGCTGGGCGAACTGAGCGGTCGTTCATTATGTGCATAATAGCAATCGCAGCGG
TAATAATACCGCACTGTAGCGTTTATCTGGATGCATTTGATCCGGCTAATCCGGGTGAACCGTTTGTTACCG
TTCCGCTGCCGACCACCGGTAGCAGTTGGACCGGCAGATGGCACAGCCATCGTTGTTCTGCCGGAAACCGTG
CAGGGCACCCATGAAGTTTTTGTTCGTCTGAGCACCGAACCGTATGCAGATCATCCCGTATGTTGCAAATCT
GGATAGCCTGACCTTTGCACCGGGTGGTCCGACCAGCGTTGTGGTTGAAAGCGAAGCCTGGACCAGCAATT
CTGGTCGTGGCCTGAAAAATGAATCTTCTACCTGGACCTTTGGTCCGGTTACAAATGTGGGTGGCACCGCT
```

FIG. 18-1

```
GATGGCGATTGGCTGGCATATGGCGAAATTGATCTGGGCAGCGCAGCACTGGATCAGCTGTCTGTGCATTA
TGTTCATAATTCTAATCGCTCTGGTCGTAATTCTGCACTGTCTGTGTATCTGGATGCCTTTGATCCGGCAA
ATCCGGGTGAACCGTTTGTGACAGTGCCGCTGGCAAATACCGGTAGCTCTTGGACCACCGATGGTACTGCA
GTTGTGGATCTGCCGTCTACCGTTCGTGGTAAACATCAGGTTTGGGTTCGTCTGTCTACCGAAGCATATGC
CGATCATCCGTATGTGGCCAATCTGGATTCTATGCGCTTTTTTACCGATGCATATGATGTTGAAGTTCCTC
CGACCGATACAGCAGCACTGGCAGCCGTTGTTGATGCAGCAGGTACACCGGAAGCAGAAATTGCACGTTAT
GGTCGTATTGATGCCCGTGTTTTTACCCGTGAACTGGCAGCAGCACGTAGCGTTCTGGCCGATGCCGGTGC
AACACAGGCACAGGCAGATGAACGTGCTCGTCGTCTGGGTCTGGCAACCGATCAGCTGGTTCCGGCAGAAC
GTCGTCGTCTGGAAAATCTGGTTGCCAGCGCAGAAGCACTGACCGACGAAGGTTATTCTCCGGAAAGCTGG
CAGGCATTTCGTACCGCACTGGCTGCTGCAACCGGCACCCTGGATGATGCAGCAGCATCTGATGAAGCACT
GCATGATGCACGTCTGGCGCTGCAGGGTGCAGTTGATGCACTGGAAGAACCGGCAGATGTTGTTCTGGTTG
AAGTTGAAGTTTCTCCGCGTTGTCTGGCAGGTAAACCGTATGTTGCCGTTCGTGCAGTTAATGTTTCTGAT
GCAGCCGTTGATGTTGAACTGGCAAGCTCTCTGGGCACCCGTAGCTTTGTTGGTGTGGCACCGGGTGCGAG
CGCATATCAGAGCTTTGCAGCCCGTAGCGCAACCGGTGATCTGGATGTTACCGTGACCGCAACCGGTGCAG
ATGGTACTCAGACCGTTGAACAGGTTGTGACCGTTCCGAGCTGTAGCTAATAA  (SEQ ID NO:20)
```

FIG. 18-2

ATGAAGCTTTCCACCATCCTCTTCACAGCCTGCGCTACCCTGGCCCTGGACAACGGCCTGGCCCGAACCCC
CACCATGGGCTGGCTGCACTGGGAGCGATTCATGTGTAACCTGGACTGTCAGGAAGAGCCCGACTCTTGTA
TCTGAGAAGCTGTTCATGGAAATGGCCGAGCTGATGGTGTCTGAGGGCTGGAAGGATGCCGGCTACGAG
TACCTGTGTATCGACGACTGTTGGATGGCCCCCCACCGAGACTCTGAGGGCCGACTCCAGGCCGACCCCCA
GCGATTCCCCCACGGCATCCGACAGCTCGCCAACTACGTGCACTCTAAGGGCCTGAAGCTGGGCATCTACG
CCGACGTGGGCAACAAGACCTGTGCCGGCTTCCCCCGGCTCTTTGGCTACTACGACATCGACGCCCAGACC
TTCGCCGACTGGGGCGTGGACCTGCTGAAGTTCGACGGCTGTTACTGTGACTCTCTCGAGAACCTGGCCGA
CGGCTACAAGCACATGTCTCTGGCCCTGAACCGAACCGGCTGATCTATCGTGTACTCTTGTGAGTGGCCCC
TGTACATGTGGCCCTTCCAGAAGCCCAACTACACCGAGATCCGACAGTACTGTAACCACTGGCGAAAACTTC
GCCGACATCGACGACTCGTGGAAGTCTATCAAGTCTATTCTGGACTGGACCTCTTTCAACCAGGAGCGAAT
CGTCGACGTCGCCGGACCCGGCGGATGGAACGACCCCGACATGCTGGTGATCGGCAACTTCGGCCTGTCTT
GGACCAGCACGGTGACCCAGATGGCCCTGTGGGCTATCATGGCTGCTCCCTGTTCATGTCTAACGACTTG
CGACACATCCTCTCCCCAGGCCAAGGCCCTGCTCCAGGACAAGGACGTGATCGCCATCAACGACGACCCCT
GGGCAAGCAGGGCTACCAGCTCCGACAGGGCGACAACTTCGAGCTGTGGGAGCGACCCCTGTCTGGCCTGG
CCTGGGCCGTGGCCATGATCAACCGACAGGAGATCGGCGGACCCCGATCTTACACCACCGCCGTGGCCTCC
CTGGGAAAGGGCGTGGCCTGTAACCCGGCCTGTTTCATCACCCAGCTCCTGCCCGTGAAGCGAAAGCTGGG
ATTCTACGAGTGGACCTCTCGACTGCGATCTCACATCAACCCCACCGGCACCGTGCTGCTCCAGCTCGAGA
ACACCGTGCAGATGTCTCTGAAGGACCTGCTGACGCGTGAACAAAAACTCATCTCAGAAGAGGATCTGAAT
AGCGCCGTCGACCATCATCATCATCATCAT (SEQ ID NO:22)

FIG. 26A

MKLSTILFTACATLALDNGLARTPTMGWLAWERFMCNLDCQEEPDSCISEKLFMEMAELNVSEGWKDAGYE
YLCIDDCWMAPQRDSEGRLQADPQRFPEGIPQLANYVHSKGLKLGIYADVGNKTCAGFPGSFGYYDIDAQT
FADWGVDLLKFDGCYCDSLENLADGYKHMSLALNRTGKSIVYSCEWPLYMWPFQKPNYTEIPQYCNHWRNF
ADIDDSWKSIKSILDWTSFNQERIVDVAGPGGWNDPDMLVIGNFGLSWNQQVTQMALWAIMAAPLFMSNDL
RHISPQAKALLQDKDVIAINQDPLGKQGYQLRQGDNFEVWERPLSGLAWAVAMINRQEIGGPRSYTIAVAG
LGKGVACNPACFITQLLPVKRKLGFYEWTSRLRSHINPTGTVLLQLENTMQMSLKDLL<u>TREQKLISEEDLW
SAVDHHHHHH</u> (SEQ ID NO:23)

FIG. 26B

ATGAAGCTTTCCACCATCCTCTTCACAGCCTGCGCTACCCTGGCTGCCGCCCAGCAGGGAGCCT
CTCGACCCGGACCCCGAGATGCCCAGGCTCACCCCGGACGACCTCGAGCTGTGCCCACCCAGTGTG
ACGTGCCCCCCAACTCTCGATTCGACTGTGCCCCGACAAGGCCATCACCCAGGAGCAGTGCGAGG
CCCGAGGCTGTTGTTACATCCCCGCTAAGCAGGGCCTGCAGGGCGCTCAGATGGGCCAGCCCTGGT
GTTTCTTCCCCCCCTCTTACCCCTCCTACAAGCTGGAGAACCTGTCCTCTTCGGAGATGGGCTACAC
CGCCACCCTGACCCGAACCACCCCCACCTTTTTCCCCAAGGACATCCTGACCCTGCGACTGGACGTG
ATGATGGAGACCGAGAACCGACTGCACTTCACCATCAAGGACCCCGCCAACCGACGATACGAGGT
GCCCCTGGAGACCCCCCACGTGCACTCTCGAGCCCCTTCCCCCCTGTACTCTGTGGAGTTCTCTGAG
GAGCCCTTCGGCGTGATCGTGCGACGACAGCTGGACGGCCGAGTGCTGCTGAACACCACCGTGGCC
CCCCTGTTCTTCGCCGACCAGTTCCTGCAGCTGTCTACCTCTCTGCCCTCTCAGTACATCACCGGCCT
GGCCGAGCACCTGTCCCCCCTGATGCTGTCCACCTCTTGGACTCGAATCACCCTGTGGAACCGAGA
CCTGGCCCCCACCCCGGTGCCAACCTGTACGGCTCTCACCCCTTCTACCTGGCCCTGGAGGACGGC
GGCTCTGCCCACGGCGTGTTTCTGCTGAACTCTAACGCCATGGACGTGGTGCTGCAGCCCTCTCCCG
CCCTGTCTTGGCGATCTACCGGCGGCATCCTGGACGTGTACATCTTCCTGGGCCCTGAGCCCAAGTC
TGTGGTCCAGCAGTACCTGGACGTGGTCGGATACCCCTTCATGCCCCCCTACTGGGGCCTGGGCTTC
CACCTGTGTGTCGATGGGCTACTCTTCTACCGCCATCACCCGACAGGTGGTGGAGAACATGACCCGA
GCCCACTTCCCCCTGGACGTGCAATGGAACGACCTGGACTACATGGACTCTCGACGAGACTTCACC
TTCAACAAGGACGGCTTCCGAGACTTCCCCGCCATGGTCCAGGAGCTGCACCAGGGAGGACGACG
ATACATGATGATCGTGGACCCCGCCATCTCTTCTTCCGGACCCGCCGGATCTTACCGACCCTACGAC
GAGGGCCTGCGACGAGGCGTGTTCATCACCAACGAGACCGGCCAGCCCCTGATCGGCAAGGTGTG
GCCCGGCTCTACCGCCTTCCCCGACTTCACCAACCCCACCGCCCTGGCTTGGTGGAGGACATGGT
GGCCGAGTTCCACGACCAGGTGCCCTTCGACGGCATGTGGATCGACATGAACGAGCCCTCTAACTT
CATCCGAGGCTCTGAGGACGGCTGTCCCAACAACGAGCTGGAGAACCCCCCCTACGTGCCCGGCGT
GGTGGGCGGAACCCTGCAGGCCGCCACCATCTGTGCCTCTTCGCACCAGTTTCTGTCTACCCACTAC
AACCTGCACAACCTGTACGGACTGACCGAGGCCATTGCCTCTCACCGAGCCCTGGTGAAGGCCCGA
GGCACCCGACCCTTCGTGATCTCTCGATCTACCTTCGCCGGCCACGGCCGATACGCCGGACACTGG
ACCGGCGATGTGTGGTCCTCTTGGGAGCAGCTGGCCTCTTCTGTGCCCGAGATCCTGCAGTTCAACC
TGCTGGGCGTGCCCCTGGTGGGCGCCGACGTGTGTGGCTTCCTGGGCAACACCTCTGAGGAGCTGT
GTGTTCGATGGACCCAGCTCCGGCGCCTTCTACCCTTTCATGCGAAACCACAACTCCCTGCTGTCTCT
GCCCCAGGAGCCCTACTCGTTCTCTGAGCCCGCTCAGCAGGCCATGCGAAAGGCTCTGACCCTGCG
ATACGCCCTGCTGCCCCACCTGTACACCCTGTTCCACCAGGCCCACGTGGCTGGAGAGACCGTGGC
CCGACCCCTGTTCCTGGAGTTCCCCTAAGGACTCTTCTACCTGGACCGTGGACCATCAGCTGCTGTGG
GGCGAGGCCCTCCTGATCACCCCCGTGCTGCAGGCCGGCAAGGCTGAGGTGACCGGCTACTTCCCT
CTGGGCACCTGGTACGACCTGCAGACCGTGCCTGTGGAGGCCCTGGGATCTCTGCCCCCTCCTCCCG
CCGCTCCCCGAGAGCCCGCCATCCACTCTGAGGGCCAGTGGGTGACCCTGCCCGCTCCCCTGGACA
CCATCAACGTGCACCTGCGAGCCGGCTACATCATCCCTCTGCAGGGACCCGGCCTGACCACCACCG
AGTCTCGACAGCAGCCCATGGCCCTGGCCGTGGCTCTGACCAAGGGCGGAGAGGCCCGAGGCGAG
CTGTTCTGGGACGATGGCGAGTCTCTGGAGGTGCTGGAGCGAGGCGCCTACACCCAGGTGATCTTT
CTGGCCCCGAAACAACACCATCGTGAACGAGCTGGTGCGAGTGACCTCTGAGGTCGCTGGTCTGCAG
CTCCAGAAGGTGACCGTTCCTGGCCGTGGCCACCGCTCCCCAGCAGGTCCTGTCTAACGGCGTGCCC
GTGTCTAACTTCACCTACTCTCCCGACACCAAGGTGCTGGACATCTGTGTGTCTCTGCTGATGGGCG
AGCAGTTCCTGGTGTCTTGGTGTTAAC (SEQ ID NO:24)

FIG. 27A

MKLSTILFTACATLAAAQQGASRPGPRDAQAHPGRPRAVPTQCDVPPNSRFDCAPDK
AITQEQCEARGCCYIPAKQGLQGAQMGQPWCFPPPSYPSYKLENLSSSEMGYTATLTRT
TPTFFPKDILTLRLDVMMETENRLBFTIKDPANRRYEVPLETPHVHSRAPSPLYSVEFSE
EPFGVIVRRQLDGRVLLNTTVAPLFFADQFLQLSTSLPSQYITGLAEHLSPLMLSTSWTR
ITLWNRDLAPTPGANLYQSHPFYLALEDGGSAHGVFLLNSNAMDVVLQPSPALSWRST
GGILDVYIFLGPEPKSVVQQYLDVVGYPFMPPYWGLGFHLCRWGYSSTAITRQVVENM
TRAHFPLDVQWNDLDYMDSRRDFTFNKDGFRDFPAMVQELHQGGRRYMMIVDPAISS
SGPAGSYRPYDEGLRRGVFITNETGQPLIGKVWPGSTAFPDFTNPTALAWWEDMVAEP
HDQVPFDGMWIDMNEPSNFIRGSEDGCPNNELENPPYVPGVVGGTLQAATICASSHQF
LSTHYNLHNLYGLTEAIASHRALVKARGTRPFVISRSTFAGHGRYAGHWTGDVWSSWE
QLASSVPEILQFNLLGVPLVGADVCGFLGNTSEELCVRWTQLGAFYPFMRNHNSLLSLP
QEPYSFSEPAQQAMRKALTLRYALLPHLYTLFHQAHVAGETVARPLFLEFPKDSSTWT
VDHQLLWGEALLITPVLQAGKAEVTGYFPLGTWYDLQTVPVEALGSLPPPPAAPREPAI
HSEGQWVTLPAPLDTINVHLRAGYIIPLQGPGLTTTESRQQPMALAVALTKGGEARGEL
FWDDGESLEVLERGAYTQVIFLARNNTIVNELVRVTSEGAGLQLQKVTVLGVATAPQQ
VLSNGVPVSNFTYSPDTKVLDICVSLLMGEQFLVSWC* (SEQ ID NO:25)

FIG. 27B

Numbering for equivalent residues in SEQ ID NO:50 is given in parenthesis

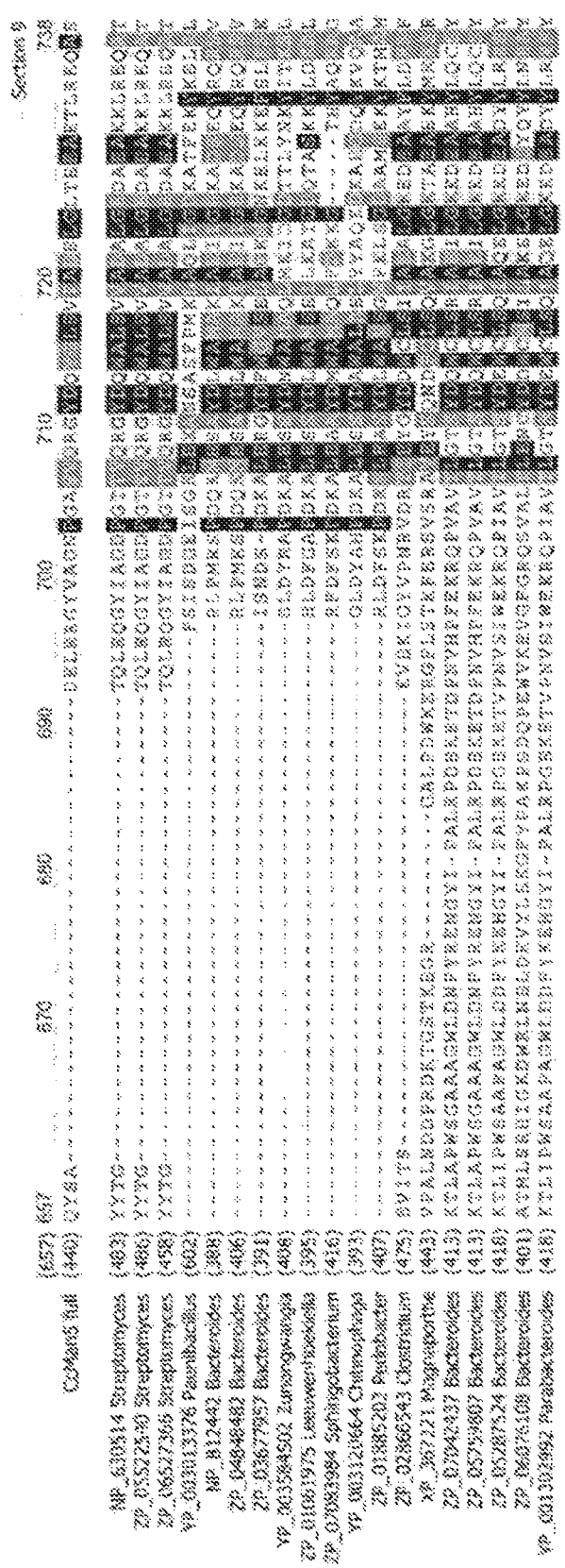
FIG. 32.9

```
ATOM   5859  N   GLY B  21       8.798  41.888 151.532  1.00  6.14      B   N
ATOM   5860  CA  GLY B  21       7.349  41.901 151.577  1.00  6.87      B   C
ATOM   5861  C   GLY B  21       6.718  40.662 150.976  1.00  7.36      B   C
ATOM   5862  O   GLY B  21       7.111  39.536 151.272  1.00  7.83      B   O
ATOM   5863  N   ASP B  22       5.749  40.896 150.115  1.00  6.37      B   N
ATOM   5864  CA  ASP B  22       5.019  39.846 149.439  1.00  6.61      B   C
ATOM   5865  CB  ASP B  22       3.516  40.156 149.545  1.00  6.75      B   C
ATOM   5866  CG  ASP B  22       2.645  38.964 149.165  1.00  8.00      B   C
ATOM   5867  OD1 ASP B  22       3.121  37.817 149.252  1.00  8.66      B   O
ATOM   5868  OD2 ASP B  22       1.479  39.168 148.781  1.00 10.69      B   O
ATOM   5869  C   ASP B  22       5.471  39.814 147.976  1.00  6.58      B   C
ATOM   5870  O   ASP B  22       4.647  39.899 147.070  1.00  6.88      B   O
ATOM   5871  N   PHE B  23       6.785  39.719 147.753  1.00  5.72      B   N
ATOM   5872  CA  PHE B  23       7.350  39.730 146.400  1.00  5.51      B   C
ATOM   5873  CB  PHE B  23       8.139  41.020 146.136  1.00  5.56      B   C
ATOM   5874  CG  PHE B  23       7.315  42.266 146.256  1.00  6.38      B   C
ATOM   5875  CD1 PHE B  23       7.127  42.875 147.497  1.00  7.33      B   C
ATOM   5876  CE1 PHE B  23       6.344  44.032 147.621  1.00  6.32      B   C
ATOM   5877  CZ  PHE B  23       5.755  44.584 146.490  1.00  7.38      B   C
ATOM   5878  CE2 PHE B  23       5.943  43.979 145.235  1.00  7.39      B   C
ATOM   5879  CD2 PHE B  23       6.713  42.834 145.132  1.00  7.45      B   C
ATOM   5880  C   PHE B  23       8.243  38.517 146.175  1.00  5.47      B   C
ATOM   5881  O   PHE B  23       9.345  38.640 145.613  1.00  5.14      B   O
ATOM   5882  N   GLY B  24       7.750  37.349 146.600  1.00  4.56      B   N
ATOM   5883  CA  GLY B  24       8.458  36.090 146.362  1.00  4.07      B   C
ATOM   5884  C   GLY B  24       8.397  35.090 147.493  1.00  3.76      B   C
ATOM   5885  O   GLY B  24       8.310  33.871 147.263  1.00  4.04      B   O
ATOM   5886  N   ASN B  25       8.467  35.594 148.734  1.00  2.92      B   N
ATOM   5887  CA  ASN B  25       8.571  34.746 149.915  1.00  2.81      B   C
ATOM   5888  CB  ASN B  25       7.253  34.007 150.179  1.00  3.39      B   C
ATOM   5889  CG  ASN B  25       6.227  34.911 150.842  1.00  3.87      B   C
ATOM   5890  OD1 ASN B  25       6.476  35.461 151.917  1.00  6.16      B   O
ATOM   5891  ND2 ASN B  25       5.090  35.098 150.199  1.00  5.31      B   N
ATOM   5892  C   ASN B  25       9.804  33.823 149.943  1.00  2.73      B   C
ATOM   5893  O   ASN B  25       9.747  32.691 150.423  1.00  2.49      B   O
ATOM   5894  N   ASP B  26      10.924  34.343 149.450  1.00  3.00      B   N
ATOM   5895  CA  ASP B  26      12.206  33.663 149.535  1.00  3.13      B   C
ATOM   5896  CB  ASP B  26      13.975  33.839 148.235  1.00  3.67      B   C
ATOM   5897  CG  ASP B  26      12.481  32.904 147.140  1.00  4.56      B   C
ATOM   5898  OD1 ASP B  26      12.308  31.693 147.408  1.00  6.75      B   O
ATOM   5899  OD2 ASP B  26      12.281  33.385 146.007  1.00  5.43      B   O
ATOM   5900  C   ASP B  26      13.041  34.166 150.702  1.00  3.37      B   C
ATOM   5901  O   ASP B  26      12.747  35.212 151.278  1.00  3.44      B   O
ATOM   6036  N   GLY B  46       7.869  42.739 161.557  1.00  5.19      B   N
ATOM   6037  CA  GLY B  46       7.346  42.212 160.323  1.00  4.86      B   C
ATOM   6038  C   GLY B  46       8.311  41.184 159.770  1.00  5.18      B   C
ATOM   6039  O   GLY B  46       9.481  41.143 160.175  1.00  5.13      B   O
ATOM   6040  N   ARG B  47       7.818  40.352 158.848  1.00  5.25      B   N
ATOM   6041  CA  ARG B  47       8.581  39.247 158.248  1.00  4.58      B   C
ATOM   6042  CB  ARG B  47       8.650  38.046 159.210  1.00  4.70      B   C
ATOM   6043  CG  ARG B  47       7.282  37.403 159.599  1.00  5.20      B   C
ATOM   6044  CD  ARG B  47       7.495  36.267 160.596  1.00  6.03      B   C
ATOM   6045  NE  ARG B  47       6.339  35.388 160.817  1.00  5.27      B   N
ATOM   6046  CZ  ARG B  47       5.957  34.374 160.030  1.00  7.87      B   C
ATOM   6047  NH1 ARG B  47       6.586  34.104 158.889  1.00  6.65      B   N
ATOM   6048  NH2 ARG B  47       4.910  33.627 160.378  1.00  6.18      B   N
ATOM   6049  C   ARG B  47       7.861  38.854 156.975  1.00  4.46      B   C
ATOM   6050  O   ARG B  47       6.656  39.134 156.837  1.00  3.68      B   O
ATOM   6051  N   ASN B  48       8.584  38.257 156.029  1.00  4.25      B   N
ATOM   6052  CA  ASN B  48       7.898  37.485 154.983  1.00  4.09      B   C
ATOM   6053  CB  ASN B  48       8.627  37.525 153.605  1.00  3.81      B   C
ATOM   6054  CG  ASN B  48       9.824  36.572 153.502  1.00  3.63      B   C
ATOM   6055  OD1 ASN B  48      10.131  35.864 154.455  1.00  4.51      B   O
ATOM   6056  ND2 ASN B  48      10.441  36.556 152.325  1.00  2.00      B   N
ATOM   6057  C   ASN B  48       7.626  36.082 155.535  1.00  4.15      B   C
ATOM   6058  O   ASN B  48       7.938  35.813 156.710  1.00  4.08      B   O
```

FIG. 33-1

```
ATOM   6059  N    ASN B  49       7.049  35.200 154.730  1.00  3.96           B  N
ATOM   6060  CA   ASN B  49       6.685  33.858 155.217  1.00  4.78           B  C
ATOM   6061  CB   ASN B  49       5.892  33.072 154.155  1.00  4.58           B  C
ATOM   6062  CG   ASN B  49       4.528  33.683 153.864  1.00  6.22           B  C
ATOM   6063  OD1  ASN B  49       3.827  33.270 152.922  1.00  8.25           B  O
ATOM   6064  ND2  ASN B  49       4.151  34.685 154.655  1.00  4.90           B  N
ATOM   6065  C    ASN B  49       7.840  33.013 155.763  1.00  4.50           B  C
ATOM   6066  O    ASN B  49       7.632  32.168 156.622  1.00  5.46           B  O
ATOM   6067  N    THR B  50       9.054  33.243 155.273  1.00  5.02           B  N
ATOM   6068  CA   THR B  50      10.346  32.516 155.744  1.00  4.39           B  C
ATOM   6069  CB   THR B  50      11.413  32.651 154.749  1.00  4.34           B  C
ATOM   6070  OG1  THR B  50      11.883  34.011 154.743  1.00  3.44           B  O
ATOM   6071  CG2  THR B  50      10.950  32.254 153.325  1.00  4.57           B  C
ATOM   6072  C    THR B  50      10.745  33.031 157.096  1.00  4.84           B  C
ATOM   6073  O    THR B  50      11.450  32.306 157.804  1.00  4.84           B  O
ATOM   6074  N    GLY B  51      10.432  34.293 157.416  1.00  4.48           B  N
ATOM   6075  CA   GLY B  51      10.802  34.910 158.707  1.00  4.48           B  C
ATOM   6076  C    GLY B  51      11.560  36.232 158.553  1.00  5.18           B  C
ATOM   6077  O    GLY B  51      11.863  36.918 159.542  1.00  5.14           B  O
ATOM   6200  N    LEU B  67      10.876  26.584 154.563  1.00  4.37           B  N
ATOM   6201  CA   LEU B  67      10.335  26.238 153.272  1.00  4.24           B  C
ATOM   6202  CB   LEU B  67       8.858  25.822 153.413  1.00  3.74           B  C
ATOM   6203  CG   LEU B  67       8.558  24.462 154.063  1.00  2.90           B  C
ATOM   6204  CD1  LEU B  67       7.076  24.167 154.019  1.00  2.92           B  C
ATOM   6205  CD2  LEU B  67       9.351  23.328 153.400  1.00  2.00           B  C
ATOM   6206  C    LEU B  67      10.436  27.457 152.371  1.00  4.38           B  C
ATOM   6207  O    LEU B  67       9.926  28.517 152.720  1.00  4.30           B  O
ATOM   6208  N    ASP B  68      11.070  27.282 151.216  1.00  4.40           B  N
ATOM   6209  CA   ASP B  68      11.312  28.351 150.252  1.00  4.81           B  C
ATOM   6210  CB   ASP B  68      12.398  27.937 149.254  1.00  4.70           B  C
ATOM   6211  CG   ASP B  68      13.677  27.503 149.932  1.00  5.37           B  C
ATOM   6212  OD1  ASP B  68      13.702  26.364 150.444  1.00  4.55           B  O
ATOM   6313  OD2  ASP B  68      14.636  28.300 149.964  1.00  5.37           B  O
ATOM   6214  C    ASP B  68      10.079  28.727 149.459  1.00  4.93           B  C
ATOM   6215  O    ASP B  68       9.469  27.878 148.818  1.00  5.94           B  O
ATOM   6216  N    GLY B  69       9.733  30.005 149.507  1.00  5.17           B  N
ATOM   6217  CA   GLY B  69       8.769  30.598 148.558  1.00  4.56           B  C
ATOM   6218  C    GLY B  69       7.327  30.161 148.689  1.00  4.60           B  C
ATOM   6219  O    GLY B  69       6.573  30.236 147.713  1.00  4.30           B  O
ATOM   6220  N    VAL B  70       6.932  29.725 149.887  1.00  3.48           B  N
ATOM   6221  CA   VAL B  70       5.589  29.149 150.102  1.00  3.51           B  C
ATOM   6222  CB   VAL B  70       5.627  27.927 151.053  1.00  3.54           B  C
ATOM   6223  CG1  VAL B  70       6.419  26.772 150.442  1.00  3.34           B  C
ATOM   6224  CG2  VAL B  70       6.209  28.314 152.422  1.00  2.91           B  C
ATOM   6225  C    VAL B  70       4.609  30.183 150.644  1.00  3.44           B  C
ATOM   6226  O    VAL B  70       5.033  31.257 151.119  1.00  3.41           B  O
ATOM   6227  N    GLY B  71       3.317  29.856 150.590  1.00  3.21           B  N
ATOM   6228  CA   GLY B  71       2.243  30.766 151.033  1.00  4.39           B  C
ATOM   6229  C    GLY B  71       1.896  30.610 152.517  1.00  5.23           B  C
ATOM   6230  O    GLY B  71       2.732  30.168 153.313  1.00  5.01           B  O
ATOM   6231  N    GLY B  72       0.653  30.950 152.869  1.00  5.67           B  N
ATOM   6232  CA   GLY B  72       0.155  30.889 154.256  1.00  5.93           B  C
ATOM   6233  C    GLY B  72       0.949  31.862 155.107  1.00  6.07           B  C
ATOM   6234  O    GLY B  72       1.165  33.016 154.692  1.00  6.64           B  O
ATOM   6235  N    SER B  73       1.390  31.404 156.282  1.00  5.79           B  N
ATOM   6236  CA   SER B  73       2.360  32.159 157.086  1.00  5.71           B  C
ATOM   6237  CB   SER B  73       1.884  32.320 158.534  1.00  5.72           B  C
ATOM   6238  OG   SER B  73       1.572  31.062 159.111  1.00  5.04           B  O
ATOM   6239  C    SER B  73       3.751  31.512 157.055  1.00  5.79           B  C
ATOM   6240  O    SER B  73       4.631  31.864 157.855  1.00  5.53           B  O
ATOM   6241  N    GLY B  74       3.943  30.560 156.136  1.00  5.50           B  N
ATOM   6242  CA   GLY B  74       5.232  29.886 155.962  1.00  4.98           B  C
ATOM   6243  C    GLY B  74       5.389  28.660 156.834  1.00  4.36           B  C
ATOM   6244  O    GLY B  74       4.702  28.512 157.834  1.00  4.36           B  O
ATOM   6245  N    GLY B  75       6.284  27.765 156.443  1.00  4.59           B  N
ATOM   6246  CA   GLY B  75       6.527  26.565 157.216  1.00  4.40           B  C
```

FIG. 33-2

```
ATOM   6247  C    GLY B  75       7.889  26.594 157.880  1.00  4.18           B  C
ATOM   6248  O    GLY B  75       8.717  27.435 157.575  1.00  4.41           B  O
ATOM   6249  N    GLY B  76       8.116  25.653 158.788  1.00  4.82           B  N
ATOM   6250  CA   GLY B  76       9.371  25.580 159.508  1.00  4.57           B  C
ATOM   6251  C    GLY B  76       9.475  26.759 160.434  1.00  4.29           B  C
ATOM   6252  O    GLY B  76       8.504  27.108 161.114  1.00  4.51           B  O
ATOM   6253  N    GLY B  77      10.647  27.390 160.433  1.00  3.80           B  N
ATOM   6254  CA   GLY B  77      10.953  28.443 161.386  1.00  3.39           B  C
ATOM   6255  C    GLY B  77      11.241  27.958 162.792  1.00  3.21           B  C
ATOM   6256  O    GLY B  77      11.099  28.729 163.743  1.00  3.66           B  O
ATOM   7082  N    TYR B 194       3.643  22.233 162.238  1.00  3.12           B  N
ATOM   7083  CA   TYR B 194       2.613  21.951 161.250  1.00  3.30           B  C
ATOM   7084  CB   TYR B 194       1.229  21.842 161.911  1.00  3.34           B  C
ATOM   7085  CG   TYR B 194       0.110  21.512 160.948  1.00  3.71           B  C
ATOM   7086  CD1  TYR B 194      -0.461  22.504 160.135  1.00  4.84           B  C
ATOM   7087  CE1  TYR B 194      -1.490  22.204 159.240  1.00  6.19           B  C
ATOM   7088  CZ   TYR B 194      -1.954  20.908 159.146  1.00  4.77           B  C
ATOM   7089  OH   TYR B 194      -2.964  20.602 158.255  1.00  6.66           B  O
ATOM   7090  CE2  TYR B 194      -1.400  19.908 159.936  1.00  5.56           B  C
ATOM   7091  CD2  TYR B 194      -0.370  20.213 160.817  1.00  2.00           B  C
ATOM   7092  C    TYR B 194       2.618  23.039 160.183  1.00  3.39           B  C
ATOM   7093  O    TYR B 194       2.833  24.217 160.484  1.00  2.89           B  O
ATOM   7094  N    PHE B 195       2.402  22.634 158.934  1.00  3.57           B  N
ATOM   7095  CA   PHE B 195       2.176  23.583 157.852  1.00  4.28           B  C
ATOM   7096  CB   PHE B 195       3.496  24.128 157.273  1.00  3.41           B  C
ATOM   7097  CG   PHE B 195       3.307  25.061 156.101  1.00  2.84           B  C
ATOM   7098  CD1  PHE B 195       2.857  26.368 156.296  1.00  2.00           B  C
ATOM   7099  CE1  PHE B 195       2.688  27.240 155.214  1.00  2.78           B  C
ATOM   7100  CZ   PHE B 195       2.970  26.810 153.920  1.00  2.01           B  C
ATOM   7101  CE2  PHE B 195       3.431  25.487 153.713  1.00  3.28           B  C
ATOM   7102  CD2  PHE B 195       3.588  24.636 154.801  1.00  2.14           B  C
ATOM   7103  C    PHE B 195       1.340  22.977 156.739  1.00  4.75           B  C
ATOM   7104  O    PHE B 195       1.700  21.949 156.158  1.00  4.94           B  O
ATOM   7105  N    TYR B 196       0.234  23.655 156.460  1.00  6.22           B  N
ATOM   7106  CA   TYR B 196      -0.598  23.431 155.296  1.00  7.19           B  C
ATOM   7107  CB   TYR B 196       0.228  23.437 153.995  1.00  7.83           B  C
ATOM   7108  CG   TYR B 196      -0.616  23.795 152.800  1.00 10.54           B  C
ATOM   7109  CD1  TYR B 196      -1.022  25.116 152.596  1.00 12.24           B  C
ATOM   7110  CE1  TYR B 196      -1.824  25.468 151.513  1.00 15.08           B  C
ATOM   7111  CZ   TYR B 196      -2.237  24.487 150.613  1.00 16.10           B  C
ATOM   7112  OH   TYR B 196      -3.015  24.861 149.550  1.00 19.44           B  O
ATOM   7113  CE2  TYR B 196      -1.840  23.147 150.800  1.00 15.05           B  C
ATOM   7114  CD2  TYR B 196      -1.038  22.812 151.890  1.00 11.35           B  C
ATOM   7115  C    TYR B 196      -1.432  22.161 155.434  1.00  7.32           B  C
ATOM   7116  O    TYR B 196      -2.593  22.244 155.848  1.00  8.08           B  O
ATOM   7117  N    ASN B 197      -0.848  21.010 155.111  1.00  6.91           B  N
ATOM   7118  CA   ASN B 197      -1.587  19.737 155.148  1.00  7.00           B  C
ATOM   7119  CB   ASN B 197      -1.448  19.010 153.804  1.00  6.93           B  C
ATOM   7120  CG   ASN B 197      -2.381  19.573 152.756  1.00  8.25           B  C
ATOM   7121  OD1  ASN B 197      -3.492  19.991 153.063  1.00  6.81           B  O
ATOM   7122  ND2  ASN B 197      -1.932  19.577 151.499  1.00  9.68           B  N
ATOM   7123  C    ASN B 197      -1.097  18.779 156.242  1.00  6.55           B  C
ATOM   7124  O    ASN B 197      -1.841  17.875 156.589  1.00  6.69           B  O
ATOM   7125  N    ALA B 198       0.104  18.977 156.793  1.00  5.68           B  N
ATOM   7126  CA   ALA B 198       0.738  17.907 157.606  1.00  5.17           B  C
ATOM   7127  CB   ALA B 198       1.519  16.952 156.715  1.00  3.39           B  C
ATOM   7128  C    ALA B 198       1.644  18.391 158.727  1.00  4.90           B  C
ATOM   7129  O    ALA B 198       2.316  19.416 158.594  1.00  5.24           B  O
ATOM   8311  N    ALA B 352       5.634  20.319 147.023  1.00  5.44           B  N
ATOM   8312  CA   ALA B 352       4.594  21.317 146.769  1.00  6.09           B  C
ATOM   8313  CB   ALA B 352       5.135  22.730 146.962  1.00  5.99           B  C
ATOM   8314  C    ALA B 352       4.223  21.089 145.329  1.00  6.35           B  C
ATOM   8315  O    ALA B 352       4.288  21.990 144.503  1.00  6.13           B  O
ATOM   8316  N    THR B 353       3.821  19.855 145.044  1.00  7.15           B  N
ATOM   8317  CA   THR B 353       3.818  19.350 143.690  1.00  7.57           B  C
ATOM   8318  CB   THR B 353       3.887  17.837 143.696  1.00  7.65           B  C
```

FIG. 33-3

| | | | | | | | | | | |
|---|---|---|---|---|---|---|---|---|---|---|
| ATOM | 8319 | OG1 | THR | B | 353 | 4.943 | 17.447 | 144.680 | 1.00 | 8.17 | B | O |
| ATOM | 8320 | CG2 | THR | B | 353 | 4.184 | 17.295 | 142.296 | 1.00 | 6.93 | B | C |
| ATOM | 8321 | C | THR | B | 353 | 2.656 | 19.914 | 142.859 | 1.00 | 8.28 | B | C |
| ATOM | 8322 | O | THR | B | 353 | 3.750 | 19.993 | 141.631 | 1.00 | 8.21 | B | O |
| ATOM | 8323 | N | TRP | B | 354 | 1.881 | 20.325 | 143.531 | 1.00 | 8.91 | B | N |
| ATOM | 8324 | CA | TRP | B | 354 | 0.511 | 21.060 | 142.861 | 1.00 | 10.38 | B | C |
| ATOM | 8325 | CB | TRP | B | 354 | -0.559 | 21.535 | 143.859 | 1.00 | 10.88 | B | C |
| ATOM | 8326 | CG | TRP | B | 354 | -1.795 | 22.053 | 143.189 | 1.00 | 13.77 | B | C |
| ATOM | 8327 | CD1 | TRP | B | 354 | -2.904 | 21.331 | 142.861 | 1.00 | 15.75 | B | C |
| ATOM | 8328 | NE1 | TRP | B | 354 | -3.829 | 22.131 | 142.242 | 1.00 | 18.84 | B | N |
| ATOM | 8329 | CE2 | TRP | B | 354 | -3.338 | 23.407 | 142.172 | 1.00 | 19.33 | B | C |
| ATOM | 8330 | CD2 | TRP | B | 354 | -2.050 | 23.396 | 142.753 | 1.00 | 17.76 | B | C |
| ATOM | 8331 | CE3 | TRP | B | 354 | -1.317 | 24.588 | 142.806 | 1.00 | 19.35 | B | C |
| ATOM | 8332 | CZ3 | TRP | B | 354 | -1.887 | 25.751 | 142.273 | 1.00 | 22.00 | B | C |
| ATOM | 8333 | CH2 | TRP | B | 354 | -3.175 | 25.730 | 141.696 | 1.00 | 22.73 | B | C |
| ATOM | 8334 | CZ2 | TRP | B | 354 | -3.914 | 24.569 | 141.634 | 1.00 | 22.09 | B | C |
| ATOM | 8335 | C | TRP | B | 354 | 1.082 | 22.248 | 142.090 | 1.00 | 9.94 | B | C |
| ATOM | 8336 | O | TRP | B | 354 | 0.679 | 22.498 | 140.957 | 1.00 | 10.17 | B | O |
| ATOM | 8337 | N | ASP | B | 355 | 2.027 | 22.961 | 142.708 | 1.00 | 9.68 | B | N |
| ATOM | 8338 | CA | ASP | B | 355 | 2.607 | 24.171 | 142.126 | 1.00 | 9.25 | B | C |
| ATOM | 8339 | CB | ASP | B | 355 | 3.020 | 25.161 | 143.224 | 1.00 | 9.39 | B | C |
| ATOM | 8340 | CG | ASP | B | 355 | 1.920 | 25.410 | 144.250 | 1.00 | 11.18 | B | C |
| ATOM | 8341 | OD1 | ASP | B | 355 | 2.026 | 24.884 | 145.380 | 1.00 | 12.17 | B | O |
| ATOM | 8342 | OD2 | ASP | B | 355 | 0.957 | 26.138 | 143.927 | 1.00 | 14.96 | B | O |
| ATOM | 8343 | C | ASP | B | 355 | 3.832 | 23.883 | 141.261 | 1.00 | 8.63 | B | C |
| ATOM | 8344 | O | ASP | B | 355 | 4.010 | 24.505 | 140.198 | 1.00 | 8.49 | B | O |
| ATOM | 8345 | N | ASP | B | 356 | 4.679 | 22.961 | 141.721 | 1.00 | 7.73 | B | N |
| ATOM | 8346 | CA | ASP | B | 356 | 6.027 | 22.821 | 141.162 | 1.00 | 7.97 | B | C |
| ATOM | 8347 | CB | ASP | B | 356 | 7.084 | 22.835 | 142.282 | 1.00 | 8.30 | B | C |
| ATOM | 8348 | CG | ASP | B | 356 | 7.193 | 21.517 | 143.028 | 1.00 | 10.67 | B | C |
| ATOM | 8349 | OD1 | ASP | B | 356 | 6.378 | 20.590 | 142.800 | 1.00 | 12.81 | B | O |
| ATOM | 8350 | OD2 | ASP | B | 356 | 8.130 | 21.405 | 143.856 | 1.00 | 13.11 | B | O |
| ATOM | 8351 | C | ASP | B | 356 | 6.290 | 21.648 | 140.235 | 1.00 | 6.85 | B | C |
| ATOM | 8352 | O | ASP | B | 356 | 7.432 | 21.434 | 139.843 | 1.00 | 6.23 | B | O |
| ATOM | 8702 | N | THR | B | 403 | 6.656 | 20.211 | 154.931 | 1.00 | 2.24 | B | N |
| ATOM | 8703 | CA | THR | B | 403 | 6.223 | 19.841 | 153.605 | 1.00 | 2.00 | B | C |
| ATOM | 8704 | CB | THR | B | 403 | 6.095 | 18.282 | 153.520 | 1.00 | 2.05 | B | C |
| ATOM | 8705 | OG1 | THR | B | 403 | 5.760 | 17.892 | 152.198 | 1.00 | 3.15 | B | O |
| ATOM | 8706 | CG2 | THR | B | 403 | 5.030 | 17.770 | 154.453 | 1.00 | 2.00 | B | C |
| ATOM | 8707 | C | THR | B | 403 | 4.913 | 20.578 | 153.289 | 1.00 | 2.00 | B | C |
| ATOM | 8708 | O | THR | B | 403 | 4.316 | 21.193 | 154.178 | 1.00 | 2.00 | B | O |
| ATOM | 8709 | N | VAL | B | 404 | 4.491 | 20.536 | 152.026 | 1.00 | 2.00 | B | N |
| ATOM | 8710 | CA | VAL | B | 404 | 3.295 | 21.247 | 151.583 | 1.00 | 2.03 | B | C |
| ATOM | 8711 | CB | VAL | B | 404 | 3.633 | 22.358 | 150.571 | 1.00 | 2.00 | B | C |
| ATOM | 8712 | CG1 | VAL | B | 404 | 2.406 | 23.239 | 150.320 | 1.00 | 2.00 | B | C |
| ATOM | 8713 | CG2 | VAL | B | 404 | 4.800 | 23.187 | 151.064 | 1.00 | 2.00 | B | C |
| ATOM | 8714 | C | VAL | B | 404 | 2.175 | 20.345 | 151.023 | 1.00 | 2.65 | B | C |
| ATOM | 8715 | O | VAL | B | 404 | 1.193 | 20.118 | 151.702 | 1.00 | 2.92 | B | O |
| ATOM | 8716 | N | ARG | B | 405 | 2.332 | 19.834 | 149.803 | 1.00 | 3.29 | B | N |
| ATOM | 8717 | CA | ARG | B | 405 | 1.236 | 19.105 | 149.134 | 1.00 | 3.66 | B | C |
| ATOM | 8718 | CB | ARG | B | 405 | 0.170 | 20.101 | 148.633 | 1.00 | 3.90 | B | C |
| ATOM | 8719 | CG | ARG | B | 405 | 0.641 | 20.982 | 147.480 | 1.00 | 3.00 | B | C |
| ATOM | 8720 | CD | ARG | B | 405 | -0.271 | 22.201 | 147.301 | 1.00 | 2.92 | B | C |
| ATOM | 8721 | NE | ARG | B | 405 | -1.643 | 21.828 | 146.974 | 1.00 | 3.88 | B | N |
| ATOM | 8722 | CZ | ARG | B | 405 | -2.594 | 22.709 | 146.644 | 1.00 | 5.53 | B | C |
| ATOM | 8723 | NH1 | ARG | B | 405 | -2.324 | 24.001 | 146.580 | 1.00 | 5.29 | B | N |
| ATOM | 8724 | NH2 | ARG | B | 405 | -3.812 | 22.271 | 146.379 | 1.00 | 6.58 | B | N |
| ATOM | 8725 | C | ARG | B | 405 | 1.717 | 18.221 | 147.981 | 1.00 | 3.69 | B | C |
| ATOM | 8726 | O | ARG | B | 405 | 2.837 | 18.353 | 147.494 | 1.00 | 3.54 | B | O |
| ATOM | 8727 | N | TRP | B | 406 | 0.861 | 17.315 | 147.540 | 1.00 | 4.26 | B | N |
| ATOM | 8728 | CA | TRP | B | 406 | 1.343 | 16.193 | 146.726 | 1.00 | 4.40 | B | C |
| ATOM | 8729 | CB | TRP | B | 406 | 1.380 | 14.930 | 147.575 | 1.00 | 4.23 | B | C |
| ATOM | 8730 | CG | TRP | B | 406 | 2.088 | 15.094 | 148.872 | 1.00 | 4.31 | B | C |
| ATOM | 8731 | CD1 | TRP | B | 406 | 3.417 | 14.922 | 149.110 | 1.00 | 4.94 | B | C |
| ATOM | 8732 | NE1 | TRP | B | 406 | 3.696 | 15.167 | 150.429 | 1.00 | 5.82 | B | N |
| ATOM | 8733 | CE2 | TRP | B | 406 | 2.537 | 15.516 | 151.067 | 1.00 | 4.54 | B | C |

FIG. 33-4

```
ATOM   8734  CD2 TRP B 406       1.800  16.472 150.112  1.00  4.03    B  C
ATOM   8735  CE3 TRP B 406       0.192  15.805 150.507  1.00  2.57    B  C
ATOM   8736  CZ3 TRP B 406      -0.024  16.148 151.840  1.00  4.33    B  C
ATOM   8737  CH2 TRP B 406       1.032  16.167 152.764  1.00  4.13    B  C
ATOM   8738  CZ2 TRP B 406       2.316  15.859 152.397  1.00  3.80    B  C
ATOM   8739  C   TRP B 406       0.565  15.933 145.433  1.00  4.65    B  C
ATOM   9696  N   GLY B 533     -15.847  27.725 140.342  1.00  9.53    B  N
ATOM   9697  CA  GLY B 533     -15.211  26.855 141.335  1.00  9.25    B  C
ATOM   9698  C   GLY B 533     -13.795  26.691 141.187  1.00  8.71    B  C
ATOM   9699  O   GLY B 533     -13.098  25.875 141.683  1.00  8.16    B  O
ATOM   9700  N   LEU B 534     -13.099  27.477 140.293  1.00  8.58    B  N
ATOM   9701  CA  LEU B 534     -11.653  27.398 140.006  1.00  8.07    B  C
ATOM   9702  CB  LEU B 534     -11.286  28.145 138.724  1.00  7.63    B  C
ATOM   9703  CG  LEU B 534     -11.866  27.619 137.420  1.00  6.93    B  C
ATOM   9704  CD1 LEU B 534     -11.597  28.602 136.307  1.00  3.89    B  C
ATOM   9705  CD2 LEU B 534     -11.303  26.245 137.079  1.00  7.25    B  C
ATOM   9706  C   LEU B 534     -10.747  27.869 141.134  1.00  8.88    B  C
ATOM   9707  O   LEU B 534     -11.033  28.870 141.822  1.00  7.62    B  O
ATOM   9708  N   TYR B 535      -9.637  27.152 141.288  1.00  9.49    B  N
ATOM   9709  CA  TYR B 535      -8.638  27.486 142.280  1.00 10.81    B  C
ATOM   9710  CB  TYR B 535      -8.010  26.197 142.861  1.00 11.89    B  C
ATOM   9711  CG  TYR B 535      -8.753  25.749 144.106  1.00 16.97    B  C
ATOM   9712  CD1 TYR B 535      -8.130  25.772 145.361  1.00 20.37    B  C
ATOM   9713  CE1 TYR B 535      -8.832  25.389 146.520  1.00 23.75    B  C
ATOM   9714  CZ  TYR B 535     -10.184  25.009 146.424  1.00 23.62    B  C
ATOM   9715  OH  TYR B 535     -10.865  24.649 147.562  1.00 24.62    B  O
ATOM   9716  CE2 TYR B 535     -10.827  24.987 145.193  1.00 22.59    B  C
ATOM   9717  CD2 TYR B 535     -10.111  25.365 144.038  1.00 20.58    B  C
ATOM   9718  C   TYR B 535      -7.604  28.447 141.703  1.00 10.16    B  C
ATOM   9719  O   TYR B 535      -6.865  28.094 140.801  1.00 10.24    B  O
ATOM   9720  N   GLN B 536      -7.600  29.677 142.211  1.00  9.98    B  N
ATOM   9721  CA  GLN B 536      -6.568  30.681 141.905  1.00 10.33    B  C
ATOM   9722  CB  GLN B 536      -5.234  30.334 142.598  1.00 10.30    B  C
ATOM   9723  CG  GLN B 536      -5.313  30.141 144.128  1.00 13.24    B  C
ATOM   9724  CD  GLN B 536      -3.939  29.900 144.772  1.00 16.30    B  C
ATOM   9725  OE1 GLN B 536      -2.909  29.886 144.095  1.00 17.97    B  O
ATOM   9726  NE2 GLN B 536      -3.929  29.725 146.091  1.00 18.13    B  N
ATOM   9727  C   GLN B 536      -6.337  30.936 140.402  1.00 10.03    B  C
ATOM   9728  O   GLN B 536      -5.217  31.217 139.967  1.00 10.11    B  O
ATOM   9729  N   GLY B 537      -7.397  30.850 139.608  1.00 10.06    B  N
ATOM   9730  CA  GLY B 537      -7.264  31.159 138.187  1.00  8.79    B  C
ATOM   9731  C   GLY B 537      -8.584  31.268 137.454  1.00  8.30    B  C
ATOM   9732  O   GLY B 537      -9.659  31.075 138.037  1.00  7.71    B  O
ATOM  10119  N   ASN B 586       1.158  35.774 134.842  1.00  4.61    B  N
ATOM  10120  CA  ASN B 586       2.561  35.487 135.130  1.00  4.87    B  C
ATOM  10121  CB  ASN B 586       3.446  36.671 134.695  1.00  4.94    B  C
ATOM  10122  CG  ASN B 586       3.354  36.954 133.194  1.00  4.99    B  C
ATOM  10123  OD1 ASN B 586       2.930  38.041 132.796  1.00  8.76    B  O
ATOM  10124  ND2 ASN B 586       3.754  36.017 132.371  1.00  4.46    B  N
ATOM  10125  C   ASN B 586       2.791  35.182 136.618  1.00  5.09    B  C
ATOM  10126  O   ASN B 586       3.852  34.691 136.997  1.00  3.71    B  O
ATOM  10127  N   ALA B 587       1.777  35.465 137.446  1.00  5.34    B  N
ATOM  10128  CA  ALA B 587       1.917  35.442 138.923  1.00  6.16    B  C
ATOM  10129  CB  ALA B 587       1.006  36.491 139.546  1.00  5.10    B  C
ATOM  10130  C   ALA B 587       1.686  34.108 139.636  1.00  6.83    B  C
ATOM  10131  O   ALA B 587       2.084  33.957 140.784  1.00  6.45    B  O
ATOM  10132  N   ASN B 588       0.997  33.179 138.977  1.00  8.41    B  N
ATOM  10133  CA  ASN B 588       0.684  31.857 139.540  1.00  9.70    B  C
ATOM  10134  CB  ASN B 588      -0.790  31.765 139.954  1.00 10.13    B  C
ATOM  10135  CG  ASN B 588      -1.026  30.782 141.077  1.00 12.36    B  C
ATOM  10136  OD1 ASN B 588      -0.090  30.198 141.622  1.00 15.20    B  O
ATOM  10137  ND2 ASN B 588      -2.286  30.513 141.418  1.00 15.01    B  N
ATOM  10138  C   ASN B 588       1.027  30.786 138.509  1.00 10.25    B  C
ATOM  10139  O   ASN B 588       1.296  31.109 137.356  1.00 10.70    B  O
ATOM  10140  N   GLU B 589       1.014  29.523 138.913  1.00 10.86    B  N
ATOM  10141  CA  GLU B 589       1.574  28.445 138.079  1.00 11.52    B  C
```

FIG. 33-5

```
ATOM  10142  CB   GLU B 589      2.198  27.370 138.976  1.00 11.45      B  C
ATOM  10143  CG   GLU B 589      3.501  27.805 139.630  1.00  9.96      B  C
ATOM  10144  CD   GLU B 589      3.311  28.386 141.028  1.00 10.68      B  C
ATOM  10145  OE1  GLU B 589      2.146  28.629 141.434  1.00 10.43      B  O
ATOM  10146  OE2  GLU B 589      4.335  28.606 141.722  1.00  8.00      B  O
ATOM  10147  C    GLU B 589      0.608  27.804 137.071  1.00 11.76      B  C
ATOM  10148  O    GLU B 589      1.027  27.008 136.207  1.00 11.79      B  O
ATOM  10149  N    ILE B 590     -0.670  28.170 137.171  1.00 11.86      B  N
ATOM  10150  CA   ILE B 590     -1.724  27.523 136.394  1.00 11.76      B  C
ATOM  10151  CB   ILE B 590     -3.097  28.106 136.760  1.00 11.88      B  C
ATOM  10152  CG1  ILE B 590     -3.531  27.471 138.085  1.00 12.53      B  C
ATOM  10153  CD1  ILE B 590     -4.228  28.396 138.985  1.00 13.66      B  C
ATOM  10154  CG2  ILE B 590     -4.143  27.847 135.665  1.00 12.30      B  C
ATOM  10155  C    ILE B 590     -1.461  27.444 134.877  1.00 11.77      B  C
ATOM  10156  O    ILE B 590     -1.563  26.362 134.286  1.00 11.66      B  O
ATOM  10444  CA   ILE B 624     -2.166  38.601 140.777  1.00  6.95      B  C
ATOM  10445  CB   ILE B 624     -3.394  39.529 142.009  1.00  7.43      B  C
ATOM  10446  CG1  ILE B 624     -3.881  39.873 142.189  1.00  6.21      B  C
ATOM  10447  CD1  ILE B 624     -4.256  40.384 143.613  1.00  6.93      B  C
ATOM  10448  CG2  ILE B 624     -1.889  40.820 141.848  1.00  6.38      B  C
ATOM  10449  C    ILE B 624     -2.529  37.158 141.097  1.00  8.00      B  C
ATOM  10450  O    ILE B 624     -3.395  36.597 140.423  1.00  7.71      B  O
ATOM  10451  N    ALA B 625     -1.676  36.566 142.107  1.00  8.28      B  N
ATOM  10452  CA   ALA B 625     -2.036  35.146 142.429  1.00  9.17      B  C
ATOM  10453  CB   ALA B 625     -0.672  34.532 142.890  1.00  8.73      B  C
ATOM  10454  C    ALA B 625     -3.131  34.846 143.476  1.00  9.67      B  C
ATOM  10455  O    ALA B 625     -3.305  33.688 143.871  1.00  9.55      B  O
ATOM  10456  N    THR B 626     -3.813  35.889 143.941  1.00 10.19      B  N
ATOM  10457  CA   THR B 626     -4.883  35.743 144.940  1.00  9.61      B  C
ATOM  10458  CB   THR B 626     -4.311  35.718 146.381  1.00 10.06      B  C
ATOM  10459  OG1  THR B 626     -5.328  35.323 147.300  1.00  9.01      B  O
ATOM  10460  CG2  THR B 626     -3.722  37.088 146.791  1.00 10.40      B  C
ATOM  10461  C    THR B 626     -5.830  36.882 144.760  1.00  9.89      B  C
ATOM  10462  O    THR B 626     -5.682  37.753 143.914  1.00  9.41      B  O
ATOM  10463  N    GLY B 627     -6.954  36.880 145.563  1.00 10.02      B  N
ATOM  10464  CA   GLY B 627     -8.057  37.828 145.428  1.00 11.00      B  C
ATOM  10465  C    GLY B 627     -7.684  39.294 145.557  1.00 12.06      B  C
ATOM  10466  O    GLY B 627     -8.185  40.135 144.815  1.00 13.64      B  O
ATOM  10467  N    SER B 628     -6.793  39.604 146.489  1.00 13.03      B  N
ATOM  10468  CA   SER B 628     -6.410  40.988 146.753  1.00 14.00      B  C
ATOM  10469  CB   SER B 628     -7.482  41.550 147.614  1.00 14.26      B  C
ATOM  10470  OG   SER B 628     -7.266  43.039 147.549  1.00 15.26      B  O
ATOM  10471  C    SER B 628     -5.047  41.111 147.452  1.00 14.28      B  C
ATOM  10472  O    SER B 628     -4.640  40.217 148.191  1.00 14.61      B  O
ATOM  10473  N    SER B 629     -4.362  42.239 147.219  1.00 14.43      B  N
ATOM  10474  CA   SER B 629     -3.095  42.511 147.827  1.00 14.96      B  C
ATOM  10475  CB   SER B 629     -1.950  42.366 146.779  1.00 14.81      B  C
ATOM  10476  OG   SER B 629     -0.708  42.826 147.280  1.00 15.07      B  O
ATOM  10477  C    SER B 629     -2.997  43.923 148.390  1.00 15.25      B  C
ATOM  10478  O    SER B 629     -3.433  44.866 147.747  1.00 15.02      B  O
ATOM  10680  N    PRO B 657      4.050  41.388 143.073  1.00  6.53      B  N
ATOM  10681  CA   PRO B 657      3.402  41.236 144.385  1.00  6.71      B  C
ATOM  10682  CB   PRO B 657      2.633  42.551 144.560  1.00  6.75      B  C
ATOM  10683  CG   PRO B 657      2.497  43.125 143.179  1.00  6.81      B  C
ATOM  10684  CD   PRO B 657      3.695  42.650 142.401  1.00  6.66      B  C
ATOM  10685  C    PRO B 657      2.446  40.037 144.343  1.00  7.09      B  C
ATOM  10686  O    PRO B 657      1.785  39.823 143.317  1.00  7.21      B  O
ATOM  10687  N    THR B 658      2.382  39.270 145.438  1.00  6.82      B  N
ATOM  10688  CA   THR B 658      1.659  37.972 145.528  1.00  7.41      B  C
ATOM  10689  CB   THR B 658      0.160  38.025 145.092  1.00  7.22      B  C
ATOM  10690  OG1  THR B 658      0.091  38.108 143.663  1.00  8.46      B  O
ATOM  10691  CG2  THR B 658     -0.562  39.183 145.720  1.00  7.56      B  C
ATOM  10692  C    THR B 658      2.281  36.761 144.802  1.00  6.95      B  C
ATOM  10693  O    THR B 658      1.850  35.614 145.012  1.00  7.00      B  O
ATOM  10694  N    MET B 659      3.266  37.002 143.944  1.00  6.43      B  N
ATOM  10695  CA   MET B 659      3.892  35.925 143.184  1.00  5.95      B  C
```

FIG. 33-6

```
ATOM  10696  CB   MET B 659       4.588  36.511 141.944  1.00  5.41           B  C
ATOM  10697  CG   MET B 659       5.187  35.490 140.977  1.00  5.34           B  C
ATOM  10698  SD   MET B 659       5.754  36.339 139.483  1.00  5.63           B  S
ATOM  10699  CE   MET B 659       6.973  35.196 138.813  1.00  4.33           B  C
ATOM  10700  C    MET B 659       4.865  35.073 144.034  1.00  5.78           B  C
ATOM  10701  O    MET B 659       6.092  35.284 144.006  1.00  6.02           B  O
ATOM  10702  N    ASP B 660       4.227  34.118 144.791  1.00  4.92           B  N
ATOM  10703  CA   ASP B 660       5.190  33.199 145.543  1.00  4.96           B  C
ATOM  10704  CB   ASP B 660       4.357  32.285 146.424  1.00  5.01           B  C
ATOM  10705  CG   ASP B 660       3.584  33.032 147.473  1.00  6.04           B  C
ATOM  10706  OD1  ASP B 660       4.035  34.111 147.913  1.00  7.34           B  O
ATOM  10707  OD2  ASP B 660       2.522  32.524 147.864  1.00  7.88           B  O
ATOM  10708  C    ASP B 660       6.037  32.337 144.596  1.00  4.93           B  C
ATOM  10709  O    ASP B 660       5.508  31.791 143.621  1.00  4.69           B  O
ATOM  10710  N    ASN B 661       7.340  32.240 144.873  1.00  4.84           B  N
ATOM  10711  CA   ASN B 661       8.255  31.368 144.118  1.00  5.08           B  C
ATOM  10712  CB   ASN B 661       9.694  31.455 144.681  1.00  5.10           B  C
ATOM  10713  CG   ASN B 661      10.780  31.140 143.629  1.00  6.08           B  C
ATOM  10714  OD1  ASN B 661      10.526  30.495 142.608  1.00  5.96           B  O
ATOM  10715  ND2  ASN B 661      11.992  31.636 143.872  1.00  6.67           B  N
ATOM  10716  C    ASN B 661       7.761  29.903 144.132  1.00  5.04           B  C
ATOM  10717  O    ASN B 661       7.831  29.211 143.113  1.00  4.57           B  O
ATOM  10718  N    ASP B 662       7.240  29.473 145.287  1.00  4.48           B  N
ATOM  10719  CA   ASP B 662       6.702  28.114 145.513  1.00  4.85           B  C
ATOM  10720  CB   ASP B 662       5.483  27.819 144.630  1.00  5.02           B  C
ATOM  10721  CG   ASP B 662       4.285  28.656 144.983  1.00  5.82           B  C
ATOM  10722  OD1  ASP B 662       3.900  28.697 146.173  1.00  7.25           B  O
ATOM  10723  OD2  ASP B 662       3.726  29.259 144.068  1.00  5.44           B  O
ATOM  10724  C    ASP B 662       7.733  27.009 145.398  1.00  4.49           B  C
ATOM  10725  O    ASP B 662       7.726  26.335 144.268  1.00  4.33           B  O
ATOM  10726  N    ALA B 663       8.587  26.804 146.304  1.00  4.58           B  N
ATOM  10727  CA   ALA B 663       9.647  25.783 146.215  1.00  5.19           B  C
ATOM  10728  CB   ALA B 663       9.032  24.354 146.294  1.00  4.88           B  C
ATOM  10729  C    ALA B 663      10.523  25.941 144.958  1.00  5.61           B  C
ATOM  10730  O    ALA B 663      10.951  24.953 144.355  1.00  6.58           B  O
ATOM  10731  N    GLY B 664      10.798  27.191 144.580  1.00  6.10           B  N
ATOM  10732  CA   GLY B 664      11.674  27.503 143.453  1.00  5.63           B  C
ATOM  10733  C    GLY B 664      11.067  27.352 142.068  1.00  5.88           B  C
ATOM  10734  O    GLY B 664      11.783  27.416 141.077  1.00  6.30           B  O
ATOM  12383  CA   CA  C    6      1.503  30.134 143.317  1.00 32.32           C  CA
ATOM  11905  O    HOH C    7      2.949  31.974 142.705  1.00  3.45           C  O
ATOM  12345  O    HOH C    8      1.937  29.983 147.278  1.00 20.75           C  O
ATOM  12381  O    HOH C    9      0.607  31.785 144.943  1.00 23.64           C  O
ATOM  12380  O    HOH C   10      0.075  28.500 144.774  1.00 23.09           C  O
ATOM  12403  O3   GOL E    1      2.366  27.082 149.806  1.00 23.71           E  O
ATOM  12404  C3   GOL E    1      0.966  27.273 149.833  1.00 24.21           E  C
ATOM  12405  C2   GOL E    1      0.495  27.587 148.416  1.00 22.96           E  C
ATOM  12406  O2   GOL E    1     -0.173  28.816 148.396  1.00 22.95           E  O
ATOM  12407  C1   GOL E    1     -0.470  26.521 147.940  1.00 23.83           E  C
ATOM  12408  O1   GOL E    1      0.108  25.826 146.867  1.00 22.02           E  O
END
```

FIG. 33-7

```
CRYST1   82.202   91.158  234.523  90.00  90.00  90.00 P 2 2 21
SCALE1      0.012165  0.000000  0.000000        0.00000
SCALE2     -0.000000  0.010970  0.000000        0.00000
SCALE3      0.000000 -0.000000  0.004454        0.00000
ATOM      2  CA  ALA A   7      74.405  12.350  86.541  1.00 19.71      A  C
ATOM      7  CA  ASP A   8      72.571  11.287  83.330  1.00 16.72      A  C
ATOM     15  CA  TYR A   9      68.912  11.738  84.261  1.00 12.13      A  C
ATOM     27  CA  ALA A  10      68.003  12.081  80.575  1.00  8.97      A  C
ATOM     32  CA  SER A  11      68.548   8.297  80.172  1.00  8.34      A  C
ATOM     38  CA  LEU A  12      66.749   7.661  82.703  1.00  6.43      A  C
ATOM     46  CA  VAL A  13      63.113   9.638  80.736  1.00  5.75      A  C
ATOM     53  CA  ASP A  14      60.886   7.538  78.450  1.00  6.27      A  C
ATOM     61  CA  VAL A  15      59.534  10.004  75.643  1.00  4.66      A  C
ATOM     68  CA  PHE A  16      57.177   7.311  74.498  1.00  3.87      A  C
ATOM     79  CA  VAL A  17      55.121   7.160  77.667  1.00  3.47      A  C
ATOM     86  CA  GLY A  18      51.656   8.454  76.610  1.00  3.67      A  C
ATOM     90  CA  THR A  19      52.191   8.387  72.991  1.00  3.13      A  C
ATOM     97  CA  GLU A  20      49.720   5.556  72.200  1.00  4.27      A  C
ATOM    106  CA  GLY A  21      46.188   6.265  70.980  1.00  5.40      A  C
ATOM    110  CA  ASP A  22      43.990   8.104  73.483  1.00  5.27      A  C
ATOM    118  CA  PHE A  23      46.225   7.338  76.520  1.00  4.39      A  C
ATOM    129  CA  GLY A  24      47.673  10.774  77.312  1.00  3.08      A  C
ATOM    133  CA  ASN A  25      48.095  12.630  73.991  1.00  2.47      A  C
ATOM    141  CA  ASP A  26      51.797  13.270  74.588  1.00  3.20      A  C
ATOM    149  CA  MET A  27      54.647  13.334  71.981  1.00  3.36      A  C
ATOM    157  CA  PRO A  28      57.941  11.662  71.502  1.00  3.20      A  C
ATOM    164  CA  ALA A  29      59.066  14.935  69.784  1.00  3.06      A  C
ATOM    169  CA  ALA A  30      62.625  16.198  70.105  1.00  3.69      A  C
ATOM    174  CA  GLN A  31      62.423  19.283  72.321  1.00  5.14      A  C
ATOM    183  CA  ALA A  32      64.432  21.430  74.735  1.00  4.55      A  C
ATOM    188  CA  PRO A  33      63.094  22.317  78.204  1.00  4.64      A  C
ATOM    195  CA  ASN A  34      60.021  24.568  77.625  1.00  4.19      A  C
ATOM    203  CA  GLY A  35      60.994  24.689  73.959  1.00  3.44      A  C
ATOM    207  CA  LEU A  36      59.041  26.309  71.169  1.00  3.34      A  C
ATOM    215  CA  ALA A  37      60.477  23.938  68.541  1.00  3.52      A  C
ATOM    220  CA  LYS A  38      58.932  20.498  68.910  1.00  3.01      A  C
ATOM    229  CA  VAL A  39      60.209  18.174  66.213  1.00  2.00      A  C
ATOM    236  CA  ASN A  40      57.543  15.463  66.213  1.00  2.24      A  C
ATOM    244  CA  PRO A  41      57.420  12.468  63.910  1.00  3.24      A  C
ATOM    251  CA  ARG A  42      53.989  13.144  62.244  1.00  4.43      A  C
ATOM    262  CA  THR A  43      52.366   8.720  62.032  1.00  5.82      A  C
ATOM    269  CA  THR A  44      49.941   7.692  59.271  1.00  7.54      A  C
ATOM    276  CA  PRO A  45      47.070   6.985  58.732  1.00  7.64      A  C
ATOM    283  CA  GLY A  46      46.363   7.283  62.482  1.00  5.22      A  C
ATOM    287  CA  ARG A  47      47.876   9.677  65.005  1.00  4.33      A  C
ATOM    298  CA  ASN A  48      47.297  10.971  68.487  1.00  2.87      A  C
ATOM    306  CA  ASN A  49      46.469  14.686  68.971  1.00  3.59      A  C
ATOM    314  CA  THR A  50      50.174  15.553  68.695  1.00  2.96      A  C
ATOM    321  CA  GLY A  51      50.582  13.739  65.384  1.00  2.16      A  C
ATOM    325  CA  TYR A  52      52.147  10.463  66.622  1.00  2.75      A  C
ATOM    337  CA  ASP A  53      50.289   7.308  67.663  1.00  3.03      A  C
ATOM    345  CA  TYR A  54      52.612   4.563  69.034  1.00  3.42      A  C
ATOM    357  CA  ALA A  55      50.295   1.835  67.698  1.00  3.80      A  C
ATOM    362  CA  GLN A  56      50.932   2.905  64.064  1.00  4.22      A  C
ATOM    371  CA  SER A  57      53.533   1.527  61.658  1.00  6.71      A  C
ATOM    377  CA  LYS A  58      54.031   4.328  59.145  1.00  6.64      A  C
ATOM    385  CA  ILE A  59      55.576   7.777  59.431  1.00  6.57      A  C
ATOM    394  CA  SER A  60      55.344  10.584  56.904  1.00  4.00      A  C
ATOM    400  CA  GLY A  61      57.749  13.214  58.346  1.00  3.12      A  C
ATOM    404  CA  PHE A  62      58.483  15.778  61.088  1.00  4.01      A  C
ATOM    415  CA  THR A  63      56.355  18.741  62.306  1.00  3.06      A  C
ATOM    422  CA  HIS A  64      57.952  21.581  64.185  1.00  2.46      A  C
ATOM    432  CA  THR A  65      55.187  23.059  66.356  1.00  2.07      A  C
ATOM    439  CA  ASN A  66      52.932  21.418  68.894  1.00  2.86      A  C
ATOM    447  CA  LEU A  67      51.019  21.341  72.178  1.00  3.42      A  C
ATOM    455  CA  ASP A  68      51.591  18.692  74.851  1.00  2.88      A  C
```

FIG. 34-1

```
ATOM    463  CA   GLY A  69      48.598   16.584   76.017  1.00   3.16      A    C
ATOM    467  CA   VAL A  70      45.743   18.719   74.687  1.00   2.95      A    C
ATOM    474  CA   GLY A  71      42.319   17.506   73.447  1.00   4.24      A    C
ATOM    478  CA   GLY A  72      40.310   18.076   70.238  1.00   5.07      A    C
ATOM    482  CA   SER A  73      42.497   16.981   67.319  1.00   5.30      A    C
ATOM    488  CA   GLY A  74      45.570   18.547   68.860  1.00   4.44      A    C
ATOM    492  CA   GLY A  75      47.211   22.012   68.196  1.00   4.03      A    C
ATOM    496  CA   GLY A  76      50.230   23.149   66.192  1.00   3.47      A    C
ATOM    500  CA   GLY A  77      51.645   20.417   63.910  1.00   2.77      A    C
ATOM    504  CA   ASP A  78      53.003   23.083   61.502  1.00   3.19      A    C
ATOM    512  CA   LEU A  79      55.816   22.729   58.975  1.00   3.46      A    C
ATOM    520  CA   LEU A  80      55.960   19.099   57.867  1.00   3.19      A    C
ATOM    528  CA   VAL A  81      59.330   17.935   56.541  1.00   2.39      A    C
ATOM    535  CA   VAL A  82      59.151   14.633   54.633  1.00   2.66      A    C
ATOM    542  CA   PRO A  83      62.241   12.791   53.307  1.00   3.10      A    C
ATOM    549  CA   THR A  84      61.709   10.950   50.007  1.00   3.64      A    C
ATOM    556  CA   SER A  85      63.546    9.484   47.006  1.00   3.93      A    C
ATOM    562  CA   GLY A  86      60.474   10.171   44.894  1.00   4.58      A    C
ATOM    566  CA   SER A  87      59.775   13.000   42.432  1.00   6.80      A    C
ATOM    572  CA   TYR A  88      56.783   15.353   42.023  1.00   6.34      A    C
ATOM    584  CA   THR A  89      55.168   17.278   39.133  1.00   6.35      A    C
ATOM    591  CA   ALA A  90      52.313   18.731   41.257  1.00   5.37      A    C
ATOM    596  CA   ARG A  91      51.505   19.377   44.932  1.00   5.13      A    C
ATOM    607  CA   PRO A  92      52.147   16.058   46.755  1.00   5.88      A    C
ATOM    614  CA   GLY A  93      49.327   13.739   47.757  1.00   6.88      A    C
ATOM    618  CA   THR A  94      49.802   13.201   51.509  1.00   7.19      A    C
ATOM    625  CA   GLY A  95      49.477    9.410   51.104  1.00   6.49      A    C
ATOM    629  CA   THR A  96      52.770    9.459   49.173  1.00   4.50      A    C
ATOM    636  CA   TYR A  97      54.650   10.619   52.300  1.00   3.46      A    C
ATOM    643  CA   ALA A  98      54.035    7.311   54.100  1.00   3.39      A    C
ATOM    653  CA   HIS A  99      57.136    5.240   55.089  1.00   4.47      A    C
ATOM    663  CA   PRO A 100      57.203    1.916   56.975  1.00   5.44      A    C
ATOM    670  CA   PHE A 101      58.803    2.128   60.401  1.00   5.59      A    C
ATOM    681  CA   SER A 102      59.416   -0.191   63.342  1.00   7.19      A    C
ATOM    687  CA   HIS A 103      59.895    0.563   67.048  1.00   6.56      A    C
ATOM    697  CA   ASP A 104      62.859   -1.852   66.789  1.00  10.39      A    C
ATOM    705  CA   ASP A 105      64.517    0.789   64.587  1.00  10.01      A    C
ATOM    713  CA   GLU A 106      63.589    3.886   66.611  1.00   9.26      A    C
ATOM    722  CA   ASP A 107      65.354    5.697   69.473  1.00   9.20      A    C
ATOM    730  CA   ALA A 108      64.818    8.899   71.371  1.00   5.45      A    C
ATOM    735  CA   GLY A 109      65.127   10.798   74.597  1.00   4.60      A    C
ATOM    739  CA   PRO A 110      65.502   14.365   75.896  1.00   3.95      A    C
ATOM    746  CA   GLY A 111      66.404   15.609   72.933  1.00   4.36      A    C
ATOM    750  CA   PHE A 112      66.407   13.997   70.163  1.00   4.28      A    C
ATOM    761  CA   TYR A 113      64.446   11.529   68.079  1.00   5.36      A    C
ATOM    773  CA   SER A 114      65.729    8.957   65.540  1.00   5.75      A    C
ATOM    779  CA   VAL A 115      64.016    6.387   63.260  1.00   4.53      A    C
ATOM    786  CA   GLY A 116      64.781    4.199   60.259  1.00   5.51      A    C
ATOM    790  CA   LEU A 117      62.194    4.893   57.576  1.00   5.77      A    C
ATOM    798  CA   GLY A 118      61.496    2.539   54.687  1.00   6.00      A    C
ATOM    802  CA   ASN A 119      62.614    4.169   51.445  1.00   5.77      A    C
ATOM    810  CA   VAL A 120      59.965    5.458   49.014  1.00   5.26      A    C
ATOM    817  CA   ALA A 121      60.384    6.350   45.306  1.00   6.56      A    C
ATOM    822  CA   GLY A 122      58.455    6.925   42.071  1.00   6.12      A    C
ATOM    826  CA   THR A 123      56.572    9.913   40.635  1.00   7.50      A    C
ATOM    833  CA   ASP A 124      53.644   11.573   42.245  1.00   7.71      A    C
ATOM    841  CA   GLY A 125      50.654    9.176   43.087  1.00   7.97      A    C
ATOM    845  CA   ALA A 126      52.803    6.284   41.903  1.00   8.07      A    C
ATOM    850  CA   ILE A 127      55.283    6.769   44.795  1.00   8.60      A    C
ATOM    858  CA   THR A 128      55.591    3.528   46.766  1.00   9.40      A    C
ATOM    865  CA   GLY A 129      58.010    1.444   48.876  1.00   9.09      A    C
ATOM    869  CA   ALA A 130      61.528    1.221   47.442  1.00   8.74      A    C
ATOM    874  CA   PRO A 131      64.650   -0.773   48.532  1.00   9.45      A    C
ATOM    881  CA   GLY A 132      66.719    0.579   51.405  1.00   9.13      A    C
ATOM    885  CA   THR A 133      66.380    2.820   54.435  1.00   8.85      A    C
ATOM    892  CA   ILE A 134      66.150    6.548   55.030  1.00   7.14      A    C
```

FIG. 34-2

```
ATOM    900  CA  GLU A 135      67.868   6.967  58.400  1.00  7.03      A    C
ATOM    909  CA  ALA A 136      66.326  10.008  60.046  1.00  5.25      A    C
ATOM    914  CA  GLU A 137      67.736  11.833  63.043  1.00  3.46      A    C
ATOM    923  CA  VAL A 138      66.270  15.029  64.552  1.00  2.00      A    C
ATOM    930  CA  ALA A 139      67.283  17.116  67.586  1.00  2.00      A    C
ATOM    935  CA  ALA A 140      66.021  20.401  69.089  1.00  3.39      A    C
ATOM    940  CA  ALA A 141      67.192  23.587  70.725  1.00  5.41      A    C
ATOM    945  CA  THR A 142      64.774  26.112  73.324  1.00  3.98      A    C
ATOM    952  CA  ARG A 143      63.747  27.685  69.007  1.00  3.05      A    C
ATOM    963  CA  SER A 144      65.330  25.253  66.475  1.00  3.15      A    C
ATOM    969  CA  GLY A 145      64.814  21.832  64.969  1.00  3.61      A    C
ATOM    973  CA  VAL A 146      67.745  20.138  63.259  1.00  3.66      A    C
ATOM    980  CA  HIS A 147      67.601  17.212  60.859  1.00  4.27      A    C
ATOM    990  CA  ARG A 148      70.193  14.697  59.628  1.00  5.28      A    C
ATOM   1001  CA  TYR A 149      69.133  12.182  56.930  1.00  5.88      A    C
ATOM   1013  CA  ALA A 150      70.978   9.286  55.295  1.00  6.54      A    C
ATOM   1018  CA  PHE A 151      69.444   8.138  51.980  1.00  6.34      A    C
ATOM   1029  CA  PRO A 152      70.329   4.881  50.196  1.00  8.11      A    C
ATOM   1036  CA  ALA A 153      73.284   5.138  47.799  1.00  9.27      A    C
ATOM   1041  CA  GLY A 154      72.114   6.062  44.300  1.00  9.43      A    C
ATOM   1045  CA  SER A 155      69.016   7.860  45.553  1.00  8.94      A    C
ATOM   1051  CA  THR A 156      68.111  11.379  44.480  1.00  5.81      A    C
ATOM   1058  CA  PRO A 157      67.363  12.771  47.997  1.00  5.54      A    C
ATOM   1065  CA  SER A 158      64.501  15.181  48.463  1.00  5.58      A    C
ATOM   1071  CA  LEU A 159      62.767  16.902  51.348  1.00  4.75      A    C
ATOM   1079  CA  VAL A 160      59.189  18.092  50.985  1.00  3.15      A    C
ATOM   1086  CA  VAL A 161      58.408  21.099  53.170  1.00  2.91      A    C
ATOM   1093  CA  ASP A 162      54.597  21.003  53.529  1.00  2.92      A    C
ATOM   1101  CA  LEU A 163      53.165  24.242  54.913  1.00  4.33      A    C
ATOM   1109  CA  GLU A 164      49.518  23.196  54.922  1.00  4.22      A    C
ATOM   1118  CA  THR A 165      49.840  20.473  57.636  1.00  3.09      A    C
ATOM   1125  CA  ASN A 166      48.201  21.399  60.948  1.00  3.13      A    C
ATOM   1133  CA  ASN A 167      46.701  19.356  63.804  1.00  3.44      A    C
ATOM   1141  CA  THR A 168      43.479  21.366  63.648  1.00  4.11      A    C
ATOM   1148  CA  SER A 169      43.334  24.170  61.980  1.00  2.77      A    C
ATOM   1154  CA  ARG A 170      45.644  25.892  58.648  1.00  3.20      A    C
ATOM   1165  CA  ARG A 171      44.592  29.537  58.189  1.00  2.85      A    C
ATOM   1176  CA  SER A 172      47.387  30.959  56.027  1.00  2.36      A    C
ATOM   1182  CA  SER A 173      50.993  30.215  55.065  1.00  3.42      A    C
ATOM   1188  CA  SER A 174      53.645  31.585  52.935  1.00  4.21      A    C
ATOM   1194  CA  VAL A 175      57.213  30.528  51.618  1.00  4.87      A    C
ATOM   1201  CA  GLN A 176      60.036  32.533  50.060  1.00  7.10      A    C
ATOM   1210  CA  VAL A 177      63.000  30.700  48.499  1.00  8.23      A    C
ATOM   1217  CA  GLU A 178      66.645  31.960  48.440  1.00 10.90      A    C
ATOM   1226  CA  THR A 179      69.583  30.187  46.804  1.00  9.85      A    C
ATOM   1233  CA  ARG A 180      72.927  31.368  48.203  1.00 10.39      A    C
ATOM   1244  CA  ALA A 181      76.419  31.485  46.632  1.00 11.40      A    C
ATOM   1249  CA  ASP A 182      77.367  28.014  47.948  1.00 11.35      A    C
ATOM   1257  CA  GLY A 183      74.201  26.531  46.431  1.00  9.02      A    C
ATOM   1261  CA  THR A 184      72.333  25.942  49.733  1.00  6.71      A    C
ATOM   1268  CA  VAL A 185      68.670  26.993  50.031  1.00  5.35      A    C
ATOM   1275  CA  GLU A 186      66.959  29.077  52.696  1.00  5.35      A    C
ATOM   1284  CA  LEU A 187      63.146  29.005  52.987  1.00  3.46      A    C
ATOM   1292  CA  SER A 188      61.169  31.481  55.086  1.00  2.87      A    C
ATOM   1298  CA  GLY A 189      57.690  32.795  55.787  1.00  2.92      A    C
ATOM   1302  CA  GLN A 190      54.605  32.417  58.223  1.00  2.71      A    C
ATOM   1311  CA  VAL A 191      52.276  29.832  59.268  1.00  2.84      A    C
ATOM   1318  CA  THR A 192      48.954  30.793  60.850  1.00  3.69      A    C
ATOM   1325  CA  GLY A 193      46.998  28.053  62.583  1.00  3.21      A    C
ATOM   1329  CA  TYR A 194      44.116  27.767  64.995  1.00  3.16      A    C
ATOM   1341  CA  PHE A 195      43.413  25.739  68.120  1.00  3.26      A    C
ATOM   1352  CA  TYR A 196      40.408  25.930  70.460  1.00  3.84      A    C
ATOM   1364  CA  ASN A 197      39.874  29.693  71.045  1.00  4.26      A    C
ATOM   1372  CA  ALA A 198      42.510  31.491  69.033  1.00  3.45      A    C
ATOM   1377  CA  ALA A 199      44.567  31.753  65.914  1.00  3.47      A    C
ATOM   1382  CA  TYR A 200      48.369  32.096  66.243  1.00  2.36      A    C
```

FIG. 34-3

```
ATOM   1394  CA  THR A 201      51.191  33.045  63.858  1.00  2.69           A    C
ATOM   1401  CA  LEU A 202      54.816  31.843  63.819  1.00  2.11           A    C
ATOM   1409  CA  TYR A 203      57.621  32.892  61.467  1.00  2.45           A    C
ATOM   1421  CA  TYR A 204      60.210  30.396  60.264  1.00  2.82           A    C
ATOM   1433  CA  THR A 205      63.573  30.086  58.500  1.00  2.58           A    C
ATOM   1440  CA  ALA A 206      64.904  26.723  57.213  1.00  4.47           A    C
ATOM   1445  CA  ARG A 207      68.253  26.305  55.508  1.00  5.09           A    C
ATOM   1456  CA  THR A 208      69.773  23.209  53.912  1.00  4.88           A    C
ATOM   1463  CA  LEU A 209      73.404  23.419  54.694  1.00  5.26           A    C
ATOM   1471  CA  GLN A 210      73.983  20.900  51.175  1.00  6.01           A    C
ATOM   1480  CA  PRO A 211      73.274  22.391  47.732  1.00  6.91           A    C
ATOM   1487  CA  ALA A 212      69.689  21.962  46.560  1.00  7.18           A    C
ATOM   1492  CA  THR A 213      67.307  23.100  43.847  1.00  5.83           A    C
ATOM   1499  CA  VAL A 214      63.724  23.957  44.710  1.00  5.43           A    C
ATOM   1506  CA  GLN A 215      60.146  24.166  43.470  1.00  5.10           A    C
ATOM   1515  CA  THR A 216      57.130  25.576  45.286  1.00  4.16           A    C
ATOM   1522  CA  TRP A 217      53.372  25.146  45.243  1.00  3.72           A    C
ATOM   1536  CA  GLY A 218      50.356  27.288  46.105  1.00  3.16           A    C
ATOM   1540  CA  ASP A 219      46.696  26.736  46.322  1.00  3.69           A    C
ATOM   1548  CA  ASP A 220      46.180  25.735  42.659  1.00  3.99           A    C
ATOM   1556  CA  ASP A 221      48.330  22.647  43.374  1.00  5.99           A    C
ATOM   1564  CA  ARG A 222      50.800  23.609  40.598  1.00  6.95           A    C
ATOM   1575  CA  LEU A 223      54.426  22.727  41.314  1.00  6.51           A    C
ATOM   1583  CA  VAL A 224      56.418  25.552  39.779  1.00  7.29           A    C
ATOM   1590  CA  ASP A 225      59.828  27.203  39.538  1.00  8.47           A    C
ATOM   1598  CA  ALA A 226      58.537  30.421  41.281  1.00  8.13           A    C
ATOM   1603  CA  THR A 227      60.445  31.383  44.417  1.00  7.82           A    C
ATOM   1610  CA  ALA A 228      57.480  32.859  46.386  1.00  7.30           A    C
ATOM   1615  CA  GLN A 229      54.054  31.642  47.513  1.00  5.21           A    C
ATOM   1624  CA  ASP A 230      51.457  33.169  49.802  1.00  5.36           A    C
ATOM   1632  CA  GLY A 231      48.063  31.590  50.521  1.00  3.52           A    C
ATOM   1636  CA  VAL A 232      46.718  28.704  52.595  1.00  2.62           A    C
ATOM   1643  CA  ASP A 233      48.105  25.470  51.111  1.00  3.49           A    C
ATOM   1651  CA  THR A 234      51.701  26.281  50.149  1.00  3.46           A    C
ATOM   1658  CA  GLY A 235      54.937  24.312  50.148  1.00  3.13           A    C
ATOM   1662  CA  ALA A 236      58.416  23.735  48.763  1.00  3.15           A    C
ATOM   1667  CA  ILE A 237      60.286  20.673  47.495  1.00  3.80           A    C
ATOM   1675  CA  LEU A 238      64.059  20.549  47.934  1.00  4.57           A    C
ATOM   1683  CA  THR A 239      66.059  18.244  45.649  1.00  6.16           A    C
ATOM   1690  CA  PHE A 240      69.681  17.296  46.371  1.00  8.00           A    C
ATOM   1701  CA  ASP A 241      72.537  15.737  44.401  1.00 10.79           A    C
ATOM   1709  CA  PRO A 242      72.834  11.907  44.637  1.00 10.26           A    C
ATOM   1716  CA  ALA A 243      76.443  12.489  45.768  1.00  9.54           A    C
ATOM   1721  CA  ASP A 244      75.082  13.939  49.047  1.00  9.68           A    C
ATOM   1729  CA  ALA A 245      72.792  10.984  49.778  1.00  9.01           A    C
ATOM   1734  CA  GLY A 246      75.008   9.953  52.749  1.00  8.32           A    C
ATOM   1738  CA  GLU A 247      74.244  13.241  54.603  1.00  8.02           A    C
ATOM   1747  CA  ILE A 248      71.325  15.626  54.100  1.00  6.42           A    C
ATOM   1755  CA  GLY A 249      71.023  18.320  56.806  1.00  5.33           A    C
ATOM   1759  CA  LEU A 250      68.338  20.392  57.577  1.00  3.68           A    C
ATOM   1767  CA  GLN A 251      67.982  23.542  60.272  1.00  3.91           A    C
ATOM   1776  CA  VAL A 252      64.613  25.109  61.086  1.00  4.45           A    C
ATOM   1783  CA  THR A 253      64.148  28.007  63.522  1.00  4.13           A    C
ATOM   1790  CA  LEU A 254      60.850  29.555  64.744  1.00  3.15           A    C
ATOM   1798  CA  SER A 255      60.066  33.075  65.957  1.00  3.13           A    C
ATOM   1804  CA  PRO A 256      56.835  34.755  67.030  1.00  2.33           A    C
ATOM   1811  CA  VAL A 257      58.462  38.034  65.945  1.00  2.47           A    C
ATOM   1818  CA  SER A 258      59.667  37.831  62.318  1.00  3.37           A    C
ATOM   1824  CA  VAL A 259      61.516  35.892  59.699  1.00  3.32           A    C
ATOM   1831  CA  GLU A 260      64.595  38.024  60.217  1.00  4.54           A    C
ATOM   1840  CA  GLN A 261      64.385  37.533  63.976  1.00  2.88           A    C
ATOM   1849  CA  ALA A 262      64.235  33.748  63.289  1.00  3.15           A    C
ATOM   1854  CA  ARG A 263      67.445  34.085  61.196  1.00  4.21           A    C
ATOM   1865  CA  ILE A 264      69.210  35.928  64.012  1.00  4.33           A    C
ATOM   1873  CA  ASP A 265      67.932  33.358  66.544  1.00  4.14           A    C
ATOM   1881  CA  GLN A 266      69.289  30.623  64.311  1.00  6.08           A    C
```

FIG. 34-4

```
ATOM   1890  CA   GLN A 267      72.772   32.164   64.108  1.00   9.62       A    C
ATOM   1899  CA   VAL A 268      72.748   32.711   67.907  1.00   8.96       A    C
ATOM   1906  CA   GLU A 269      71.365   29.282   68.615  1.00   8.04       A    C
ATOM   1915  CA   LEU A 270      73.089   27.043   66.271  1.00   8.55       A    C
ATOM   1923  CA   GLY A 271      76.001   29.052   64.802  1.00  10.23       A    C
ATOM   1927  CA   ASP A 272      78.321   26.600   63.009  1.00  10.69       A    C
ATOM   1935  CA   LEU A 273      77.764   23.840   65.566  1.00   8.02       A    C
ATOM   1943  CA   SER A 274      77.383   20.316   64.224  1.00   5.99       A    C
ATOM   1949  CA   PHE A 275      74.219   18.210   64.582  1.00   4.80       A    C
ATOM   1960  CA   ASP A 276      75.912   16.069   67.289  1.00   5.78       A    C
ATOM   1968  CA   ALA A 277      76.925   19.139   69.337  1.00   5.08       A    C
ATOM   1973  CA   ILE A 278      73.442   20.669   69.150  1.00   5.84       A    C
ATOM   1981  CA   ARG A 279      71.924   17.315   70.206  1.00   6.83       A    C
ATOM   1992  CA   ASP A 280      74.549   16.902   72.944  1.00   7.77       A    C
ATOM   2000  CA   ARG A 281      74.023   20.429   74.293  1.00   7.74       A    C
ATOM   2011  CA   THR A 282      70.270   19.953   74.599  1.00   6.38       A    C
ATOM   2018  CA   ARG A 283      70.839   16.638   76.431  1.00   5.81       A    C
ATOM   2029  CA   ALA A 284      73.047   18.504   78.940  1.00   5.99       A    C
ATOM   2034  CA   GLU A 285      70.461   21.247   79.310  1.00   6.57       A    C
ATOM   2043  CA   TRP A 286      67.904   18.490   80.139  1.00   5.67       A    C
ATOM   2057  CA   ASN A 287      70.291   16.909   82.648  1.00   8.00       A    C
ATOM   2065  CA   ALA A 288      70.657   20.275   84.422  1.00   8.86       A    C
ATOM   2070  CA   THR A 289      66.862   20.740   84.464  1.00   7.09       A    C
ATOM   2077  CA   LEU A 290      66.138   17.180   85.630  1.00   6.19       A    C
ATOM   2085  CA   GLY A 291      69.085   17.378   88.069  1.00   6.65       A    C
ATOM   2089  CA   ARG A 292      67.121   19.931   90.104  1.00   6.77       A    C
ATOM   2100  CA   VAL A 293      65.530   16.844   91.707  1.00   8.09       A    C
ATOM   2107  CA   ALA A 294      67.845   14.070   92.912  1.00  10.40       A    C
ATOM   2112  CA   ILE A 295      66.318   10.811   94.046  1.00  13.23       A    C
ATOM   2120  CA   ASP A 296      67.534    7.879   96.131  1.00  14.69       A    C
ATOM   2128  CA   ALA A 297      65.001    5.043   95.685  1.00  13.88       A    C
ATOM   2133  CA   SER A 298      65.612    1.701   97.456  1.00  11.58       A    C
ATOM   2139  CA   THR A 299      64.657   -1.726   96.152  1.00   9.13       A    C
ATOM   2146  CA   ALA A 300      61.955   -1.728   98.846  1.00   7.00       A    C
ATOM   2151  CA   THR A 301      59.955    1.150   97.314  1.00   6.08       A    C
ATOM   2158  CA   ASP A 302      61.022    0.632   93.655  1.00   6.93       A    C
ATOM   2166  CA   PRO A 303      62.048   -3.016   93.116  1.00   7.98       A    C
ATOM   2173  CA   THR A 304      62.107   -2.745   89.277  1.00   8.90       A    C
ATOM   2180  CA   GLY A 305      63.438    0.816   88.893  1.00   8.26       A    C
ATOM   2184  CA   GLU A 306      60.285    1.808   86.935  1.00   8.98       A    C
ATOM   2193  CA   LEU A 307      59.007    4.206   89.571  1.00   6.57       A    C
ATOM   2201  CA   GLN A 308      62.236    6.260   89.308  1.00   7.75       A    C
ATOM   2210  CA   ARG A 309      61.928    6.228   85.486  1.00   7.83       A    C
ATOM   2221  CA   LEU A 310      58.276    7.253   85.828  1.00   6.95       A    C
ATOM   2229  CA   PHE A 311      59.288   10.140   88.071  1.00   5.21       A    C
ATOM   2240  CA   TYR A 312      61.933   11.475   85.641  1.00   4.28       A    C
ATOM   2252  CA   THR A 313      59.676   10.962   82.611  1.00   3.87       A    C
ATOM   2259  CA   HIS A 314      56.982   13.080   84.288  1.00   4.29       A    C
ATOM   2269  CA   LEU A 315      59.599   15.636   85.519  1.00   3.00       A    C
ATOM   2277  CA   TYR A 316      60.512   15.912   81.637  1.00   2.15       A    C
ATOM   2289  CA   ARG A 317      56.827   16.467   80.909  1.00   3.71       A    C
ATOM   2300  CA   MET A 318      56.497   19.172   83.611  1.00   6.35       A    C
ATOM   2308  CA   PHE A 319      58.967   21.419   81.712  1.00   7.83       A    C
ATOM   2319  CA   ALA A 320      57.045   21.807   78.404  1.00   7.53       A    C
ATOM   2324  CA   MET A 321      54.323   24.487   78.650  1.00   6.18       A    C
ATOM   2332  CA   PRO A 322      54.063   27.434   78.638  1.00   5.02       A    C
ATOM   2339  CA   MET A 323      56.762   27.568   75.935  1.00   4.44       A    C
ATOM   2347  CA   ASN A 324      59.593   30.069   75.619  1.00   3.49       A    C
ATOM   2355  CA   ALA A 325      57.989   32.716   73.341  1.00   2.49       A    C
ATOM   2360  CA   THR A 326      61.012   35.098   73.515  1.00   2.79       A    C
ATOM   2367  CA   SER A 327      63.597   35.861   76.819  1.00   3.68       A    C
ATOM   2373  CA   THR A 328      67.381   35.744   71.383  1.00   4.17       A    C
ATOM   2380  CA   SER A 329      67.191   39.550   71.284  1.00   4.95       A    C
ATOM   2386  CA   GLY A 330      64.860   39.602   74.337  1.00   4.52       A    C
ATOM   2390  CA   THR A 331      61.681   40.533   72.420  1.00   2.64       A    C
ATOM   2397  CA   TYR A 332      58.212   38.956   72.097  1.00   2.99       A    C
```

FIG. 34-5

```
ATOM   2409  CA   ARG A 333      55.039  39.623  70.103  1.00   4.36      A    C
ATOM   2420  CA   GLY A 334      52.050  40.974  71.967  1.00   4.85      A    C
ATOM   2424  CA   VAL A 335      48.352  40.362  71.328  1.00   5.79      A    C
ATOM   2431  CA   ASP A 336      48.362  43.923  69.904  1.00   8.91      A    C
ATOM   2439  CA   GLY A 337      50.391  42.488  67.010  1.00   8.05      A    C
ATOM   2443  CA   ALA A 338      53.464  44.524  67.878  1.00   7.17      A    C
ATOM   2448  CA   VAL A 339      56.967  43.729  69.093  1.00   6.49      A    C
ATOM   2455  CA   HIS A 340      57.792  44.405  72.780  1.00   8.62      A    C
ATOM   2465  CA   ALA A 341      60.735  44.008  75.137  1.00   9.13      A    C
ATOM   2470  CA   ALA A 342      60.679  41.217  77.711  1.00  11.07      A    C
ATOM   2475  CA   GLN A 343      63.952  43.339  79.907  1.00  14.61      A    C
ATOM   2484  CA   GLY A 344      64.997  41.352  82.439  1.00  14.36      A    C
ATOM   2488  CA   PHE A 345      62.907  38.172  82.163  1.00  11.18      A    C
ATOM   2499  CA   THR A 346      61.913  35.493  79.671  1.00   8.35      A    C
ATOM   2506  CA   TYR A 347      58.429  35.786  78.204  1.00   5.52      A    C
ATOM   2518  CA   TYR A 348      56.503  32.511  78.127  1.00   4.55      A    C
ATOM   2530  CA   ASP A 349      53.244  31.880  76.254  1.00   3.32      A    C
ATOM   2538  CA   SER A 350      50.780  29.020  75.499  1.00   3.95      A    C
ATOM   2544  CA   TRP A 351      48.175  28.588  78.184  1.00   3.88      A    C
ATOM   2558  CA   ALA A 352      45.515  26.000  79.064  1.00   3.29      A    C
ATOM   2563  CA   THR A 353      44.865  27.385  82.495  1.00   3.82      A    C
ATOM   2570  CA   TRP A 354      41.278  26.050  82.947  1.00   4.26      A    C
ATOM   2584  CA   ASP A 355      42.871  23.556  82.994  1.00   4.99      A    C
ATOM   2592  CA   ASP A 356      46.325  23.205  84.330  1.00   5.97      A    C
ATOM   2600  CA   PHE A 357      46.209  25.899  87.012  1.00   5.02      A    C
ATOM   2611  CA   ARG A 358      47.433  23.675  89.886  1.00   4.11      A    C
ATOM   2622  CA   LYS A 359      50.623  22.752  87.999  1.00   2.82      A    C
ATOM   2631  CA   PHE A 360      52.171  26.201  88.467  1.00   2.32      A    C
ATOM   2643  CA   SER A 361      52.098  25.888  92.261  1.00   2.68      A    C
ATOM   2648  CA   VAL A 362      54.293  22.814  91.937  1.00   3.61      A    C
ATOM   2655  CA   ILE A 363      56.639  24.444  89.399  1.00   3.43      A    C
ATOM   2663  CA   ALA A 364      57.066  27.142  92.096  1.00   3.80      A    C
ATOM   2668  CA   TYR A 365      58.855  24.692  94.414  1.00   4.70      A    C
ATOM   2680  CA   ILE A 366      59.869  22.863  91.729  1.00   6.01      A    C
ATOM   2688  CA   ASP A 367      63.106  25.836  89.627  1.00   5.57      A    C
ATOM   2696  CA   PRO A 368      61.134  29.124  91.362  1.00   3.96      A    C
ATOM   2703  CA   ALA A 369      62.922  31.367  88.734  1.00   3.74      A    C
ATOM   2708  CA   LEU A 370      61.088  29.740  85.833  1.00   3.88      A    C
ATOM   2716  CA   TYR A 371      57.894  30.009  87.729  1.00   4.80      A    C
ATOM   2728  CA   ARG A 372      58.430  33.689  88.384  1.00   5.45      A    C
ATOM   2739  CA   ASP A 373      59.035  34.310  84.651  1.00   6.19      A    C
ATOM   2747  CA   MET A 374      55.843  32.441  83.776  1.00   3.88      A    C
ATOM   2755  CA   VAL A 375      53.730  34.523  86.171  1.00   2.79      A    C
ATOM   2762  CA   GLN A 376      55.358  37.744  84.962  1.00   3.18      A    C
ATOM   2771  CA   SER A 377      54.574  36.606  81.413  1.00   3.14      A    C
ATOM   2777  CA   LEU A 378      50.953  35.908  82.336  1.00   3.14      A    C
ATOM   2785  CA   VAL A 379      50.799  39.454  83.766  1.00   3.57      A    C
ATOM   2792  CA   TYR A 380      52.193  40.950  80.508  1.00   4.06      A    C
ATOM   2804  CA   LEU A 381      49.694  38.961  78.456  1.00   4.18      A    C
ATOM   2812  CA   PHE A 382      46.697  40.475  80.286  1.00   4.57      A    C
ATOM   2823  CA   ALA A 383      48.397  43.881  80.475  1.00   6.03      A    C
ATOM   2828  CA   ASP A 384      48.684  43.708  76.664  1.00   7.44      A    C
ATOM   2836  CA   ALA A 385      44.974  43.882  76.223  1.00   9.01      A    C
ATOM   2841  CA   GLU A 386      44.193  45.935  78.362  1.00  10.91      A    C
ATOM   2850  CA   ALA A 387      46.670  48.106  76.365  1.00  12.41      A    C
ATOM   2855  CA   THR A 388      44.776  47.471  73.087  1.00  13.68      A    C
ATOM   2862  CA   GLY A 389      41.944  49.514  74.624  1.00  14.39      A    C
ATOM   2866  CA   THR A 390      39.452  47.191  72.889  1.00  15.63      A    C
ATOM   2873  CA   GLY A 391      38.019  45.522  76.019  1.00  14.99      A    C
ATOM   2877  CA   GLY A 392      37.896  42.282  73.993  1.00  13.79      A    C
ATOM   2881  CA   GLY A 393      38.759  38.874  75.470  1.00  11.07      A    C
ATOM   2885  CA   LEU A 394      42.017  37.084  74.740  1.00   7.81      A    C
ATOM   2893  CA   GLY A 395      40.143  34.863  72.238  1.00   7.24      A    C
ATOM   2897  CA   GLY A 396      39.767  37.812  69.847  1.00   7.80      A    C
ATOM   2901  CA   PHE A 397      43.479  38.330  69.213  1.00   7.11      A    C
ATOM   2912  CA   VAL A 398      46.038  36.458  67.145  1.00   5.79      A    C
```

FIG. 34-6

```
ATOM   2919  CA  HIS A 399      48.446  34.799  69.624  1.00  3.71      A    C
ATOM   2929  CA  SER A 400      52.295  34.594  69.802  1.00  3.42      A    C
ATOM   2935  CA  VAL A 401      52.383  30.703  69.819  1.00  2.51      A    C
ATOM   2942  CA  PRO A 402      49.744  27.945  69.645  1.00  3.03      A    C
ATOM   2949  CA  THR A 403      47.621  28.327  72.753  1.00  2.63      A    C
ATOM   2956  CA  VAL A 404      44.423  27.083  74.389  1.00  2.59      A    C
ATOM   2963  CA  ARG A 405      42.502  28.941  77.121  1.00  2.87      A    C
ATOM   2974  CA  TRP A 406      43.027  31.341  80.033  1.00  3.31      A    C
ATOM   2988  CA  GLU A 407      40.430  30.754  82.763  1.00  4.40      A    C
ATOM   2997  CA  ARG A 408      41.610  30.579  86.344  1.00  3.53      A    C
ATOM   3008  CA  SER A 409      44.708  32.938  85.445  1.00  3.56      A    C
ATOM   3014  CA  SER A 410      43.670  35.101  88.463  1.00  4.17      A    C
ATOM   3020  CA  VAL A 411      44.366  32.099  90.707  1.00  3.23      A    C
ATOM   3027  CA  VAL A 412      47.816  31.532  89.197  1.00  2.11      A    C
ATOM   3034  CA  VAL A 413      48.819  35.209  89.648  1.00  2.29      A    C
ATOM   3041  CA  ALA A 414      47.478  35.051  93.214  1.00  2.19      A    C
ATOM   3046  CA  ASP A 415      49.593  31.906  93.728  1.00  3.52      A    C
ATOM   3054  CA  ALA A 416      52.816  33.913  93.216  1.00  3.54      A    C
ATOM   3059  CA  ILE A 417      51.560  36.792  95.351  1.00  4.96      A    C
ATOM   3067  CA  ALA A 418      50.526  34.493  98.238  1.00  7.10      A    C
ATOM   3072  CA  LYS A 419      53.976  32.864  97.904  1.00  7.37      A    C
ATOM   3081  CA  GLY A 420      55.694  36.259  98.483  1.00  8.91      A    C
ATOM   3085  CA  PHE A 421      56.789  37.036  94.914  1.00  9.86      A    C
ATOM   3095  CA  ASP A 422      56.741  40.741  94.170  1.00 13.61      A    C
ATOM   3104  CA  GLY A 423      57.809  43.423  91.676  1.00 13.34      A    C
ATOM   3108  CA  PHE A 424      55.491  43.086  88.966  1.00 11.76      A    C
ATOM   3119  CA  ASP A 425      55.749  44.833  86.387  1.00 13.47      A    C
ATOM   3127  CA  ARG A 426      52.408  45.949  84.848  1.00 10.18      A    C
ATOM   3138  CA  LEU A 427      50.173  44.147  87.370  1.00  9.19      A    C
ATOM   3146  CA  ASP A 428      48.058  47.323  87.663  1.00 10.66      A    C
ATOM   3154  CA  GLU A 429      47.378  47.038  83.880  1.00 10.07      A    C
ATOM   3163  CA  ALA A 430      46.738  43.286  83.995  1.00  8.16      A    C
ATOM   3168  CA  TYR A 431      44.031  43.690  86.747  1.00  8.35      A    C
ATOM   3180  CA  PRO A 432      41.138  45.159  84.775  1.00  8.05      A    C
ATOM   3187  CA  ALA A 433      41.670  42.554  82.030  1.00  7.78      A    C
ATOM   3192  CA  LEU A 434      41.696  39.872  84.724  1.00  7.39      A    C
ATOM   3200  CA  GLN A 435      38.424  41.359  86.060  1.00  9.52      A    C
ATOM   3209  CA  ARG A 436      36.760  41.034  82.610  1.00  8.83      A    C
ATOM   3220  CA  LEU A 437      38.067  37.458  82.349  1.00  8.34      A    C
ATOM   3228  CA  VAL A 438      36.448  36.553  85.664  1.00  9.83      A    C
ATOM   3235  CA  GLY A 439      33.227  38.399  84.746  1.00  9.87      A    C
ATOM   3239  CA  GLN A 440      30.557  39.769  87.076  1.00 11.48      A    C
ATOM   3248  CA  TYR A 441      27.387  38.162  88.403  1.00  9.33      A    C
ATOM   3260  CA  SER A 442      24.326  39.771  86.747  1.00  9.01      A    C
ATOM   3266  CA  ALA A 443      21.930  41.944  88.804  1.00 10.00      A    C
ATOM   3271  CA  ASP A 444      19.645  38.962  89.504  1.00 11.36      A    C
ATOM   3279  CA  GLU A 445      22.683  36.814  90.345  1.00 10.65      A    C
ATOM   3288  CA  LEU A 446      24.057  39.420  92.752  1.00 12.13      A    C
ATOM   3296  CA  ARG A 447      20.688  39.484  94.519  1.00 14.84      A    C
ATOM   3307  CA  ARG A 448      20.411  35.689  94.956  1.00 13.37      A    C
ATOM   3318  CA  GLY A 449      24.148  34.933  95.289  1.00 11.12      A    C
ATOM   3322  CA  TYR A 450      24.570  32.356  92.478  1.00 11.01      A    C
ATOM   3334  CA  VAL A 451      24.024  31.514  88.794  1.00 10.44      A    C
ATOM   3341  CA  ALA A 452      20.597  29.813  88.469  1.00 11.06      A    C
ATOM   3346  CA  GLY A 453      20.832  26.118  87.493  1.00 10.92      A    C
ATOM   3350  CA  ASN A 454      24.597  26.415  86.920  1.00  9.68      A    C
ATOM   3358  CA  PRO A 455      26.517  25.184  90.002  1.00  9.01      A    C
ATOM   3365  CA  GLY A 456      29.710  24.813  87.923  1.00  7.30      A    C
ATOM   3369  CA  ALA A 457      29.902  28.429  86.804  1.00  5.98      A    C
ATOM   3374  CA  SER A 458      29.216  29.530  90.428  1.00  5.00      A    C
ATOM   3380  CA  VAL A 459      32.021  27.538  92.097  1.00  3.77      A    C
ATOM   3387  CA  GLN A 460      34.377  28.579  89.297  1.00  3.69      A    C
ATOM   3396  CA  ARG A 461      33.738  32.298  89.725  1.00  3.05      A    C
ATOM   3407  CA  GLY A 462      34.143  31.742  93.464  1.00  2.45      A    C
ATOM   3411  CA  TYR A 463      37.707  30.519  92.994  1.00  3.51      A    C
ATOM   3423  CA  ASP A 464      38.419  33.243  90.372  1.00  3.80      A    C
```

FIG. 34-7

```
ATOM   3431  CA  GLN A 465      37.202  35.909  92.790  1.00   4.82           A    C
ATOM   3440  CA  TYR A 466      39.300  34.526  95.621  1.00   5.23           A    C
ATOM   3452  CA  GLY A 467      42.325  34.871  93.265  1.00   5.67           A    C
ATOM   3456  CA  LEU A 468      41.385  38.365  92.150  1.00   6.17           A    C
ATOM   3464  CA  SER A 469      40.991  39.304  95.828  1.00   5.97           A    C
ATOM   3470  CA  VAL A 470      44.682  38.455  95.482  1.00   6.48           A    C
ATOM   3477  CA  ILE A 471      45.705  40.579  93.461  1.00   6.17           A    C
ATOM   3485  CA  ALA A 472      43.411  43.420  94.600  1.00   8.07           A    C
ATOM   3490  CA  ASP A 473      45.060  43.606  98.080  1.00  10.08           A    C
ATOM   3498  CA  GLU A 474      48.496  43.569  96.443  1.00  10.69           A    C
ATOM   3507  CA  LEU A 475      47.508  46.603  94.342  1.00  11.15           A    C
ATOM   3515  CA  GLY A 476      46.177  48.346  97.453  1.00  13.34           A    C
ATOM   3519  CA  LEU A 477      42.538  48.006  96.344  1.00  15.39           A    C
ATOM   3527  CA  THR A 478      41.434  47.034  99.867  1.00  17.62           A    C
ATOM   3534  CA  GLU A 479      37.723  47.742  99.394  1.00  18.74           A    C
ATOM   3543  CA  GLU A 480      37.595  45.763  96.110  1.00  16.33           A    C
ATOM   3552  CA  ALA A 481      39.372  42.864  97.813  1.00  13.75           A    C
ATOM   3557  CA  GLU A 482      36.715  42.720 100.596  1.00  14.63           A    C
ATOM   3566  CA  THR A 483      33.842  42.673  98.101  1.00  12.95           A    C
ATOM   3573  CA  LEU A 484      35.614  39.932  96.121  1.00  11.73           A    C
ATOM   3581  CA  ARG A 485      36.127  37.758  99.233  1.00  11.05           A    C
ATOM   3592  CA  GLU A 486      32.458  38.265 100.146  1.00  10.61           A    C
ATOM   3601  CA  GLN A 487      31.331  37.147  96.664  1.00   8.60           A    C
ATOM   3610  CA  ALA A 488      33.786  34.225  95.759  1.00   6.52           A    C
ATOM   3615  CA  SER A 489      32.029  32.893  99.875  1.00   7.12           A    C
ATOM   3621  CA  TRP A 490      28.661  33.726  98.010  1.00   7.33           A    C
ATOM   3635  CA  PRO A 491      28.980  29.421  96.072  1.00   6.73           A    C
ATOM   3642  CA  ILE A 492      29.746  27.439  99.257  1.00   8.58           A    C
ATOM   3650  CA  GLU A 493      27.034  29.091 101.368  1.00  11.10           A    C
ATOM   3659  CA  LYS A 494      24.283  29.217  98.744  1.00  10.38           A    C
ATOM   3668  CA  LEU A 495      24.772  25.993  96.727  1.00   8.08           A    C
ATOM   3676  CA  THR A 496      25.642  23.390  99.397  1.00   9.94           A    C
ATOM   3683  CA  LYS A 497      22.269  21.696  99.874  1.00  10.32           A    C
ATOM   3692  CA  PRO A 498      21.844  20.282 103.387  1.00   9.82           A    C
ATOM   3699  CA  GLY A 499      21.074  16.559 103.567  1.00  10.14           A    C
ATOM   3703  CA  ALA A 500      21.838  16.042  99.846  1.00  10.83           A    C
ATOM   3708  CA  TRP A 501      23.386  12.728 100.863  1.00  11.71           A    C
ATOM   3722  CA  THR A 502      23.581  10.696 104.006  1.00  12.62           A    C
ATOM   3729  CA  ALA A 503      25.365   8.647 105.597  1.00  13.78           A    C
ATOM   3734  CA  ALA A 504      24.951   4.994 106.737  1.00  15.02           A    C
ATOM   3739  CA  ASP A 505      24.357   6.130 110.325  1.00  14.83           A    C
ATOM   3747  CA  GLY A 506      21.856   8.861 109.305  1.00  12.52           A    C
ATOM   3751  CA  THR A 507      24.298  11.810 109.343  1.00  10.12           A    C
ATOM   3758  CA  GLN A 508      23.119  14.588 106.989  1.00   8.56           A    C
ATOM   3767  CA  VAL A 509      25.765  15.604 104.451  1.00   6.31           A    C
ATOM   3774  CA  GLY A 510      25.468  18.758 102.362  1.00   5.03           A    C
ATOM   3778  CA  LEU A 511      26.594  18.750  98.733  1.00   4.48           A    C
ATOM   3786  CA  LEU A 512      26.894  21.130  95.793  1.00   5.45           A    C
ATOM   3794  CA  THR A 513      23.470  21.012  94.071  1.00   7.09           A    C
ATOM   3801  CA  PRO A 514      21.941  23.109  91.250  1.00   7.88           A    C
ATOM   3808  CA  ARG A 515      19.517  25.737  92.573  1.00   9.63           A    C
ATOM   3819  CA  ALA A 516      16.670  27.438  90.743  1.00  11.40           A    C
ATOM   3824  CA  ALA A 517      16.291  31.213  90.509  1.00  13.83           A    C
ATOM   3829  CA  ASP A 518      13.518  31.125  93.261  1.00  16.58           A    C
ATOM   3837  CA  GLY A 519      15.865  29.277  95.648  1.00  16.47           A    C
ATOM   3841  CA  SER A 520      14.292  25.852  95.063  1.00  15.99           A    C
ATOM   3847  CA  TRP A 521      16.785  23.089  94.870  1.00  13.14           A    C
ATOM   3861  CA  GLN A 522      16.876  21.329  91.494  1.00  12.01           A    C
ATOM   3870  CA  SER A 523      16.780  17.550  91.127  1.00  12.74           A    C
ATOM   3876  CA  ALA A 524      20.170  15.972  90.267  1.00  11.18           A    C
ATOM   3881  CA  ASP A 525      23.087  12.671  90.488  1.00   8.84           A    C
ATOM   3889  CA  HIS A 526      25.271  13.887  92.225  1.00   6.57           A    C
ATOM   3899  CA  ALA A 527      27.293  11.003  90.717  1.00   6.14           A    C
ATOM   3904  CA  LYS A 528      26.151  11.481  87.106  1.00   7.50           A    C
ATOM   3913  CA  PHE A 529      28.818  12.767  84.690  1.00   7.13           A    C
ATOM   3924  CA  GLU A 530      27.867  16.202  83.304  1.00   7.31           A    C
```

FIG. 34-8

```
ATOM  3933  CA  ALA A 531   24.633  16.513  85.106  1.00   8.44  A  C
ATOM  3938  CA  ALA A 532   23.397  20.032  86.170  1.00   7.77  A  C
ATOM  3943  CA  GLY A 533   25.194  21.889  83.332  1.00   6.76  A  C
ATOM  3947  CA  LEU A 534   28.619  20.734  84.578  1.00   5.97  A  C
ATOM  3955  CA  TYR A 535   31.682  20.411  82.372  1.00   8.46  A  C
ATOM  3967  CA  GLN A 536   33.627  17.123  82.410  1.00   6.34  A  C
ATOM  3976  CA  GLY A 537   32.521  16.050  85.901  1.00   4.04  A  C
ATOM  3980  CA  THR A 538   29.936  16.281  88.564  1.00   3.50  A  C
ATOM  3987  CA  LEU A 539   28.500  17.232  91.498  1.00   3.71  A  C
ATOM  3995  CA  TRP A 540   30.500  15.072  93.986  1.00   3.80  A  C
ATOM  4009  CA  GLN A 541   33.680  16.012  92.073  1.00   3.42  A  C
ATOM  4018  CA  TYR A 542   32.808  19.714  91.708  1.00   4.03  A  C
ATOM  4030  CA  HIS A 543   31.606  19.795  95.352  1.00   4.44  A  C
ATOM  4040  CA  TRP A 544   35.221  20.315  96.537  1.00   4.40  A  C
ATOM  4054  CA  TYR A 545   36.045  23.019  93.950  1.00   4.18  A  C
ATOM  4066  CA  ASP A 546   36.276  26.024  96.237  1.00   5.25  A  C
ATOM  4074  CA  ALA A 547   39.546  24.793  97.671  1.00   5.51  A  C
ATOM  4079  CA  TYR A 548   40.358  28.217  99.183  1.00   6.10  A  C
ATOM  4091  CA  ASP A 549   37.753  27.586 101.917  1.00   6.22  A  C
ATOM  4099  CA  MET A 550   37.554  24.017 103.177  1.00   6.61  A  C
ATOM  4107  CA  ASP A 551   36.549  25.382 106.586  1.00   8.26  A  C
ATOM  4115  CA  ALA A 552   33.422  27.067 105.225  1.00   7.80  A  C
ATOM  4120  CA  LEU A 553   32.600  24.021 103.038  1.00   7.77  A  C
ATOM  4128  CA  VAL A 554   32.983  21.675 106.066  1.00   8.48  A  C
ATOM  4135  CA  GLU A 555   30.421  23.906 107.886  1.00  10.05  A  C
ATOM  4144  CA  ALA A 556   28.101  24.172 104.863  1.00   8.14  A  C
ATOM  4149  CA  MET A 557   28.262  20.355 104.586  1.00   7.75  A  C
ATOM  4157  CA  GLY A 558   26.833  20.080 108.112  1.00   7.77  A  C
ATOM  4161  CA  GLY A 559   29.595  19.989 110.230  1.00   8.36  A  C
ATOM  4165  CA  HIS A 560   33.086  17.891 110.775  1.00  10.24  A  C
ATOM  4175  CA  GLU A 561   31.498  14.448 111.036  1.00  10.61  A  C
ATOM  4184  CA  ALA A 562   29.420  15.118 107.900  1.00   9.17  A  C
ATOM  4189  CA  ALA A 563   32.594  16.099 105.943  1.00   7.47  A  C
ATOM  4194  CA  ARG A 564   34.534  13.129 107.304  1.00   6.15  A  C
ATOM  4205  CA  LEU A 565   31.813  10.683 106.236  1.00   5.27  A  C
ATOM  4213  CA  GLY A 566   31.408  12.469 102.857  1.00   4.45  A  C
ATOM  4217  CA  MET A 567   35.136  12.086 102.137  1.00   5.05  A  C
ATOM  4225  CA  ARG A 568   35.000   8.412 103.020  1.00   6.55  A  C
ATOM  4236  CA  HIS A 569   31.985   7.943 100.689  1.00   7.31  A  C
ATOM  4246  CA  MET A 570   33.786   9.924  97.906  1.00   7.92  A  C
ATOM  4254  CA  PHE A 571   36.388   7.150  97.840  1.00   7.04  A  C
ATOM  4265  CA  GLY A 572   34.056   4.168  98.426  1.00   8.17  A  C
ATOM  4269  CA  GLU A 573   35.790   3.316 101.736  1.00  10.14  A  C
ATOM  4278  CA  HIS A 574   32.693   1.377 102.888  1.00  11.27  A  C
ATOM  4288  CA  ALA A 575   32.914  -0.845  99.770  1.00  11.91  A  C
ATOM  4293  CA  PRO A 576   36.615  -1.198  98.736  1.00  13.14  A  C
ATOM  4300  CA  ASP A 577   35.933  -3.909  96.131  1.00  13.69  A  C
ATOM  4308  CA  ASP A 578   33.994  -2.108  94.404  1.00  12.41  A  C
ATOM  4316  CA  GLY A 579   34.247  -0.897  91.423  1.00  11.12  A  C
ATOM  4320  CA  LYS A 580   30.905   1.748  91.259  1.00  11.21  A  C
ATOM  4329  CA  ALA A 581   31.370   3.276  94.757  1.00   8.19  A  C
ATOM  4334  CA  MET A 582   34.356   5.303  93.506  1.00   5.86  A  C
ATOM  4342  CA  LEU A 583   33.022   8.889  93.198  1.00   4.23  A  C
ATOM  4350  CA  HIS A 584   36.434  10.466  92.671  1.00   3.37  A  C
ATOM  4360  CA  SER A 585   37.816  10.665  89.126  1.00   3.12  A  C
ATOM  4366  CA  ASN A 586   41.508  10.091  88.353  1.00   3.90  A  C
ATOM  4374  CA  ALA A 587   41.103  10.824  84.638  1.00   5.72  A  C
ATOM  4379  CA  ASN A 588   40.425  14.577  84.853  1.00   7.03  A  C
ATOM  4387  CA  GLU A 589   41.649  17.614  86.824  1.00   7.17  A  C
ATOM  4396  CA  ILE A 590   38.295  18.647  88.338  1.00   7.24  A  C
ATOM  4404  CA  ASP A 591   38.863  16.848  91.650  1.00   7.24  A  C
ATOM  4412  CA  LEU A 592   42.668  16.431  91.471  1.00   6.70  A  C
ATOM  4420  CA  GLN A 593   42.981  17.626  95.053  1.00   4.59  A  C
ATOM  4429  CA  ALA A 594   40.356  15.206  96.428  1.00   4.71  A  C
ATOM  4434  CA  PRO A 595   42.784  12.503  97.633  1.00   5.03  A  C
ATOM  4441  CA  TYR A 596   44.506  15.069  99.845  1.00   6.02  A  C
```

FIG. 34-9

```
ATOM   4453  CA   LEU A 597     41.304   16.226  101.591  1.00   4.94        A    C
ATOM   4461  CA   PHE A 598     41.417   13.474  104.213  1.00   5.47        A    C
ATOM   4472  CA   ASN A 599     44.037   15.684  105.929  1.00   6.53        A    C
ATOM   4480  CA   TYR A 600     41.176   18.148  106.491  1.00   7.92        A    C
ATOM   4492  CA   THR A 601     38.801   15.556  107.938  1.00   9.25        A    C
ATOM   4499  CA   GLY A 602     41.334   14.393  110.555  1.00   9.27        A    C
ATOM   4503  CA   GLU A 603     42.359   11.247  108.634  1.00   8.63        A    C
ATOM   4512  CA   PRO A 604     45.534   11.962  107.132  1.00   7.11        A    C
ATOM   4519  CA   SER A 605     46.475    8.224  106.915  1.00   5.46        A    C
ATOM   4525  CA   LEU A 606     43.781    7.926  104.201  1.00   4.96        A    C
ATOM   4533  CA   THR A 607     45.390   10.729  102.175  1.00   4.57        A    C
ATOM   4540  CA   GLN A 608     48.682    8.824  102.393  1.00   5.02        A    C
ATOM   4549  CA   LYS A 609     47.008    5.602  101.265  1.00   5.44        A    C
ATOM   4558  CA   TRP A 610     45.214    7.268   98.331  1.00   5.42        A    C
ATOM   4572  CA   ALA A 611     48.211    9.266   97.205  1.00   6.31        A    C
ATOM   4577  CA   ARG A 612     50.436    6.184   97.093  1.00   5.71        A    C
ATOM   4588  CA   ALA A 613     47.643    4.974   95.492  1.00   4.20        A    C
ATOM   4593  CA   ILE A 614     46.445    6.379   92.691  1.00   4.67        A    C
ATOM   4601  CA   TYR A 615     49.973    7.212   91.557  1.00   4.85        A    C
ATOM   4613  CA   THR A 616     51.897    3.963   92.071  1.00   4.62        A    C
ATOM   4620  CA   LYS A 617     49.365    1.088   92.368  1.00   6.36        A    C
ATOM   4629  CA   GLU A 618     46.132   -0.236   90.829  1.00   7.91        A    C
ATOM   4638  CA   THR A 619     42.939    1.583   91.795  1.00   6.88        A    C
ATOM   4645  CA   TRP A 620     39.227    1.357   91.008  1.00   7.46        A    C
ATOM   4659  CA   ASN A 621     38.296    3.692   88.170  1.00   6.73        A    C
ATOM   4667  CA   ARG A 622     34.663    4.574   87.576  1.00   4.87        A    C
ATOM   4678  CA   TYR A 623     35.087    7.709   85.473  1.00   5.03        A    C
ATOM   4690  CA   ILE A 624     36.716    8.661   82.149  1.00   5.64        A    C
ATOM   4698  CA   ALA A 625     37.316   12.291   81.127  1.00   6.35        A    C
ATOM   4703  CA   THR A 626     34.590   13.516   78.473  1.00   6.19        A    C
ATOM   4710  CA   GLY A 627     31.208   10.937   77.589  1.00   5.93        A    C
ATOM   4714  CA   SER A 628     32.592    7.840   75.913  1.00   7.00        A    C
ATOM   4720  CA   SER A 629     35.720    6.302   74.355  1.00   9.77        A    C
ATOM   4726  CA   SER A 630     36.292    3.632   71.688  1.00  11.33        A    C
ATOM   4733  CA   ALA A 631     39.492    2.767   73.559  1.00  10.90        A    C
ATOM   4737  CA   VAL A 632     37.659    1.102   76.492  1.00   8.53        A    C
ATOM   4744  CA   PRO A 633     34.094   -0.107   77.097  1.00   7.28        A    C
ATOM   4751  CA   SER A 634     33.472    3.099   78.345  1.00   5.04        A    C
ATOM   4757  CA   GLY A 635     29.414    3.345   78.326  1.00   4.96        A    C
ATOM   4761  CA   GLY A 636     27.832    8.244   80.176  1.00   6.17        A    C
ATOM   4765  CA   GLY A 637     31.304    9.416   81.298  1.00   5.99        A    C
ATOM   4769  CA   GLU A 638     32.099    6.071   82.923  1.00   5.01        A    C
ATOM   4778  CA   PHE A 639     34.199    2.868   82.500  1.00   4.24        A    C
ATOM   4789  CA   THR A 640     31.342    0.261   81.956  1.00   5.80        A    C
ATOM   4796  CA   PRO A 641     32.109   -1.741   83.969  1.00   6.76        A    C
ATOM   4803  CA   PRO A 642     34.393    0.103   86.417  1.00   9.12        A    C
ATOM   4810  CA   LEU A 643     38.016   -0.971   85.969  1.00   9.82        A    C
ATOM   4818  CA   LYS A 644     40.825   -1.805   88.435  1.00  11.06        A    C
ATOM   4827  CA   THR A 645     43.998   -0.565   86.793  1.00   8.37        A    C
ATOM   4834  CA   LYS A 646     47.067    1.537   87.273  1.00   7.54        A    C
ATOM   4843  CA   VAL A 647     46.307    5.272   86.488  1.00   5.75        A    C
ATOM   4850  CA   TYR A 648     49.922    5.935   85.527  1.00   5.56        A    C
ATOM   4862  CA   ARG A 649     51.964    3.328   83.533  1.00   7.76        A    C
ATOM   4873  CA   LEU A 650     55.512    3.322   82.177  1.00   6.76        A    C
ATOM   4881  CA   ASP A 651     54.026    2.407   78.809  1.00   6.42        A    C
ATOM   4889  CA   PRO A 652     53.043    4.126   75.570  1.00   5.92        A    C
ATOM   4896  CA   ARG A 653     49.549    3.680   77.020  1.00   4.60        A    C
ATOM   4907  CA   GLY A 654     50.724    6.058   79.774  1.00   4.89        A    C
ATOM   4911  CA   MET A 655     47.517    7.356   81.356  1.00   4.93        A    C
ATOM   4919  CA   LEU A 656     43.963    6.075   81.567  1.00   3.04        A    C
ATOM   4927  CA   PRO A 657     42.105    6.134   78.251  1.00   3.10        A    C
ATOM   4934  CA   THR A 658     40.764    9.734   77.676  1.00   3.53        A    C
ATOM   4941  CA   MET A 659     43.088   11.046   80.398  1.00   3.65        A    C
ATOM   4949  CA   ASP A 660     44.895   13.859   78.555  1.00   3.95        A    C
ATOM   4957  CA   ASN A 661     48.031   15.161   80.276  1.00   3.15        A    C
ATOM   4965  CA   ASP A 662     46.843   18.761   79.522  1.00   2.87        A    C
```

FIG. 34-10

```
ATOM  4973  CA  ALA A 663   50.075  20.739  79.098  1.00  3.12   A  C
ATOM  4978  CA  GLY A 664   51.894  18.459  81.548  1.00  2.70   A  C
ATOM  4982  CA  THR A 665   49.328  18.721  84.376  1.00  2.81   A  C
ATOM  4989  CA  MET A 666   48.910  14.993  85.026  1.00  2.55   A  C
ATOM  4997  CA  SER A 667   52.753  14.620  84.837  1.00  2.87   A  C
ATOM  5003  CA  THR A 668   53.193  17.554  87.294  1.00  3.50   A  C
ATOM  5010  CA  MET A 669   50.719  16.032  89.771  1.00  2.90   A  C
ATOM  5018  CA  PHE A 670   52.751  12.810  89.639  1.00  2.90   A  C
ATOM  5029  CA  VAL A 671   55.921  14.716  90.519  1.00  3.29   A  C
ATOM  5036  CA  ALA A 672   54.049  16.446  93.385  1.00  3.04   A  C
ATOM  5041  CA  ALA A 673   53.740  13.136  94.733  1.00  3.21   A  C
ATOM  5046  CA  ALA A 674   56.289  11.665  94.548  1.00  4.16   A  C
ATOM  5051  CA  VAL A 675   57.770  14.572  95.510  1.00  3.68   A  C
ATOM  5058  CA  GLY A 676   54.729  14.329  96.773  1.00  3.81   A  C
ATOM  5062  CA  LEU A 677   53.626  17.976  96.689  1.00  3.63   A  C
ATOM  5070  CA  PHE A 678   50.401  18.865  96.910  1.00  4.98   A  C
ATOM  5081  CA  PRO A 679   48.736  22.236  96.308  1.00  4.89   A  C
ATOM  5088  CA  VAL A 680   45.131  21.802  97.449  1.00  3.54   A  C
ATOM  5095  CA  THR A 681   44.815  25.594  97.517  1.00  3.01   A  C
ATOM  5102  CA  ALA A 682   46.410  27.062  94.421  1.00  2.78   A  C
ATOM  5107  CA  GLY A 683   46.558  30.790  95.067  1.00  4.10   A  C
ATOM  5111  CA  SER A 684   47.895  30.234  98.585  1.00  5.30   A  C
ATOM  5117  CA  SER A 685   51.390  29.528  99.913  1.00  6.30   A  C
ATOM  5123  CA  GLN A 686   50.476  26.083 101.310  1.00  5.66   A  C
ATOM  5132  CA  PHE A 687   51.101  22.447 100.320  1.00  5.37   A  C
ATOM  5143  CA  GLN A 688   49.438  19.356 101.748  1.00  4.94   A  C
ATOM  5152  CA  VAL A 689   51.517  16.390 102.936  1.00  5.79   A  C
ATOM  5159  CA  GLY A 690   50.928  13.088 101.117  1.00  6.69   A  C
ATOM  5163  CA  SER A 691   52.974   9.889 100.906  1.00  7.27   A  C
ATOM  5169  CA  PRO A 692   56.528  10.626  99.669  1.00  6.85   A  C
ATOM  5176  CA  PHE A 693   57.581   7.765  97.347  1.00  6.34   A  C
ATOM  5187  CA  PHE A 694   61.346   7.747  97.796  1.00  6.87   A  C
ATOM  5198  CA  ASP A 695   63.891   7.202 100.575  1.00  7.56   A  C
ATOM  5206  CA  SER A 696   65.365  10.532  99.830  1.00  6.91   A  C
ATOM  5212  CA  THR A 697   64.278  13.400  97.424  1.00  7.09   A  C
ATOM  5219  CA  THR A 698   66.465  16.572  97.123  1.00  7.46   A  C
ATOM  5226  CA  ILE A 699   65.459  19.752  95.308  1.00  6.95   A  C
ATOM  5234  CA  THR A 700   68.553  21.914  94.670  1.00  8.40   A  C
ATOM  5241  CA  TYR A 701   67.913  25.630  94.091  1.00  9.41   A  C
ATOM  5253  CA  ASP A 702   69.971  28.028  91.946  1.00 11.48   A  C
ATOM  5261  CA  ASP A 703   72.068  29.199  94.915  1.00 13.97   A  C
ATOM  5269  CA  GLY A 704   73.018  25.617  95.847  1.00 13.70   A  C
ATOM  5273  CA  SER A 705   70.765  25.419  98.907  1.00 12.46   A  C
ATOM  5279  CA  ALA A 706   68.419  22.383  98.854  1.00 10.18   A  C
ATOM  5284  CA  PHE A 707   65.052  21.131 100.137  1.00  7.55   A  C
ATOM  5295  CA  THR A 708   65.351  17.581 101.387  1.00  7.30   A  C
ATOM  5302  CA  VAL A 709   62.397  15.352 102.091  1.00  7.65   A  C
ATOM  5309  CA  THR A 710   63.206  11.874 103.424  1.00  8.06   A  C
ATOM  5316  CA  ALA A 711   60.926   8.889 103.973  1.00  8.76   A  C
ATOM  5321  CA  ASP A 712   62.785   6.541 106.270  1.00 10.03   A  C
ATOM  5329  CA  GLY A 713   61.790   2.931 105.687  1.00  7.18   A  C
ATOM  5333  CA  VAL A 714   59.420   3.754 103.770  1.00  5.21   A  C
ATOM  5340  CA  SER A 715   58.461   0.754 100.621  1.00  5.75   A  C
ATOM  5346  CA  GLU A 716   55.621  -0.434  98.399  1.00  7.40   A  C
ATOM  5355  CA  ASP A 717   53.911  -1.492 101.619  1.00  7.77   A  C
ATOM  5363  CA  ALA A 718   55.257   1.143 103.993  1.00  5.28   A  C
ATOM  5368  CA  PHE A 719   53.472   4.224 102.665  1.00  3.86   A  C
ATOM  5379  CA  TYR A 720   51.935   5.573 105.926  1.00  5.07   A  C
ATOM  5391  CA  VAL A 721   53.647   8.305 107.943  1.00  6.16   A  C
ATOM  5398  CA  GLN A 722   54.378   7.196 111.544  1.00  8.68   A  C
ATOM  5407  CA  SER A 723   56.107  10.362 112.750  1.00  9.44   A  C
ATOM  5413  CA  ALA A 724   57.936  13.385 111.311  1.00  8.65   A  C
ATOM  5418  CA  THR A 725   60.561  16.054 112.006  1.00  8.30   A  C
ATOM  5425  CA  LEU A 726   61.170  19.486 110.467  1.00  8.74   A  C
ATOM  5433  CA  ASP A 727   64.804  20.662 110.723  1.00  9.93   A  C
ATOM  5441  CA  GLY A 728   65.330  18.182 113.597  1.00 11.60   A  C
```

FIG. 34-11

```
ATOM   5445  CA   ALA A 729      62.241  19.122 115.636  1.00 11.25           A    C
ATOM   5450  CA   THR A 730      58.993  17.157 116.102  1.00 10.67           A    C
ATOM   5457  CA   PHE A 731      56.579  18.066 113.320  1.00  9.05           A    C
ATOM   5468  CA   GLY A 732      52.846  17.319 113.474  1.00  8.76           A    C
ATOM   5472  CA   ASN A 733      51.196  19.402 110.742  1.00  8.99           A    C
ATOM   5480  CA   THR A 734      49.869  17.843 107.528  1.00  9.35           A    C
ATOM   5487  CA   TRP A 735      50.725  20.969 105.477  1.00  8.91           A    C
ATOM   5501  CA   VAL A 736      53.901  22.986 104.955  1.00  8.70           A    C
ATOM   5508  CA   ASP A 737      54.483  26.555 103.781  1.00  8.20           A    C
ATOM   5516  CA   TYR A 738      56.186  27.338 100.476  1.00  6.61           A    C
ATOM   5528  CA   ALA A 739      58.753  29.437 102.391  1.00  6.41           A    C
ATOM   5533  CA   THR A 740      59.787  26.356 104.396  1.00  7.06           A    C
ATOM   5540  CA   VAL A 741      60.397  24.354 101.242  1.00  6.62           A    C
ATOM   5547  CA   VAL A 742      63.422  26.857  99.172  1.00  7.73           A    C
ATOM   5554  CA   GLY A 743      64.172  27.894 102.414  1.00  9.90           A    C
ATOM   5558  CA   GLY A 744      65.997  24.543 102.207  1.00  9.66           A    C
ATOM   5562  CA   ALA A 745      64.348  22.686 105.078  1.00  9.46           A    C
ATOM   5567  CA   ASP A 746      64.950  19.052 106.107  1.00  9.46           A    C
ATOM   5575  CA   LEU A 747      61.574  17.315 106.252  1.00  7.98           A    C
ATOM   5583  CA   ALA A 748      62.092  13.775 107.535  1.00  8.59           A    C
ATOM   5588  CA   PHE A 749      59.312  11.203 107.659  1.00  9.99           A    C
ATOM   5599  CA   ARG A 750      59.238   7.807 109.398  1.00 11.09           A    C
ATOM   5610  CA   MET A 751      57.231   5.392 107.265  1.00  8.36           A    C
ATOM   5618  CA   GLY A 752      55.426   2.175 108.214  1.00  8.95           A    C
ATOM   5622  CA   GLU A 753      53.025  -0.439 106.937  1.00 10.36           A    C
ATOM   5631  CA   GLN A 754      50.077   0.533 109.170  1.00 10.20           A    C
ATOM   5640  CA   PRO A 755      48.069   3.743 109.500  1.00  9.59           A    C
ATOM   5647  CA   SER A 756      49.021   5.965 112.430  1.00 10.96           A    C
ATOM   5653  CA   ASP A 757      47.455   8.970 114.180  1.00 12.39           A    C
ATOM   5661  CA   TRP A 758      50.369  11.238 113.073  1.00 11.54           A    C
ATOM   5675  CA   GLY A 759      49.073  14.673 112.067  1.00 12.17           A    C
ATOM   5679  CA   THR A 760      45.608  14.275 113.614  1.00 12.83           A    C
ATOM   5686  CA   ASP A 761      46.374  17.270 115.851  1.00 13.13           A    C
ATOM   5694  CA   THR A 762      47.486  19.473 112.939  1.00 10.45           A    C
ATOM   5701  CA   ALA A 763      47.395  23.279 113.157  1.00  9.30           A    C
ATOM   5706  CA   PRO A 764      44.545  24.274 110.760  1.00  8.86           A    C
ATOM   5713  CA   ALA A 765      45.404  24.788 107.092  1.00  8.11           A    C
ATOM   5718  CA   PHE A 766      44.495  27.881 105.084  1.00  9.09           A    C
ATOM   5729  CA   SER A 767      40.845  28.777 104.581  1.00  9.56           A    C
ATOM   5735  CA   MET A 768      39.792  32.266 103.433  1.00 11.12           A    C
ATOM   5743  CA   SER A 769      37.000  32.591 106.061  1.00 14.28           A    C
ATOM   5749  CA   THR A 770      39.217  31.636 109.046  1.00 17.50           A    C
ATOM   5756  CA   ALA A 771      42.527  33.224 107.955  1.00 19.68           A    C
ATOM   5761  CA   ASP B   8      33.160  32.500 141.172  1.00 18.72           B    C
ATOM   5769  CA   TYR B   9      29.570  31.506 140.394  1.00 14.20           B    C
ATOM   5781  CA   ALA B  10      28.423  31.895 143.925  1.00 10.68           B    C
ATOM   5786  CA   SER B  11      29.320  35.514 143.693  1.00 10.07           B    C
ATOM   5792  CA   LEU B  12      26.696  36.062 140.938  1.00  8.36           B    C
ATOM   5800  CA   VAL B  13      23.923  34.801 143.242  1.00  6.94           B    C
ATOM   5807  CA   ASP B  14      21.680  37.475 145.013  1.00  6.81           B    C
ATOM   5815  CA   VAL B  15      20.179  35.726 147.955  1.00  4.17           B    C
ATOM   5822  CA   PHE B  16      18.230  38.889 148.802  1.00  3.40           B    C
ATOM   5833  CA   VAL B  17      16.289  38.686 145.547  1.00  3.53           B    C
ATOM   5840  CA   GLY B  18      12.666  38.026 146.520  1.00  4.03           B    C
ATOM   5844  CA   THR B  19      13.196  38.689 150.262  1.00  5.26           B    C
ATOM   5851  CA   GLU B  20      10.979  41.797 150.516  1.00  5.53           B    C
ATOM   5860  CA   GLY B  21       7.349  41.901 151.577  1.00  6.87           B    C
ATOM   5864  CA   ASP B  22       5.019  39.846 149.439  1.00  6.61           B    C
ATOM   5872  CA   PHE B  23       7.350  39.730 146.400  1.00  5.51           B    C
ATOM   5883  CA   GLY B  24       8.458  36.090 146.363  1.00  4.07           B    C
ATOM   5887  CA   ASN B  25       8.571  34.746 149.915  1.00  2.81           B    C
ATOM   5895  CA   ASP B  26      12.206  33.663 149.535  1.00  3.13           B    C
ATOM   5903  CA   MET B  27      14.936  33.714 152.197  1.00  4.16           B    C
ATOM   5911  CA   PRO B  28      18.531  35.061 152.473  1.00  3.52           B    C
ATOM   5918  CA   ALA B  29      19.101  32.077 154.801  1.00  2.82           B    C
ATOM   5923  CA   ALA B  30      22.436  30.302 154.790  1.00  2.98           B    C
```

FIG. 34-12

```
ATOM   5928  CA  GLN B  31      21.896  26.852 153.161  1.00  4.61           B    C
ATOM   5937  CA  ALA B  32      23.671  24.106 151.121  1.00  5.14           B    C
ATOM   5942  CA  PRO B  33      22.380  22.821 147.805  1.00  6.54           B    C
ATOM   5949  CA  ASN B  34      18.900  21.202 148.694  1.00  5.61           B    C
ATOM   5957  CA  GLY B  35      19.876  21.616 152.349  1.00  4.62           B    C
ATOM   5961  CA  LEU B  36      17.780  20.633 155.336  1.00  5.14           B    C
ATOM   5969  CA  ALA B  37      19.361  23.239 157.533  1.00  3.87           B    C
ATOM   5974  CA  LYS B  38      18.219  26.746 156.507  1.00  3.49           B    C
ATOM   5983  CA  VAL B  39      19.767  29.259 158.883  1.00  3.32           B    C
ATOM   5990  CA  ASN B  40      17.444  32.226 158.346  1.00  3.32           B    C
ATOM   5998  CA  PRO B  41      17.676  35.552 160.107  1.00  3.73           B    C
ATOM   6005  CA  ARG B  42      14.314  36.534 161.600  1.00  3.05           B    C
ATOM   6016  CA  THR B  43      13.161  40.161 161.230  1.00  2.80           B    C
ATOM   6023  CA  THR B  44      10.738  41.938 163.588  1.00  5.21           B    C
ATOM   6030  CA  PRO B  45       8.030  43.161 163.977  1.00  6.45           B    C
ATOM   6037  CA  GLY B  46       7.346  42.212 160.323  1.00  4.86           B    C
ATOM   6041  CA  ARG B  47       8.581  39.247 158.248  1.00  4.58           B    C
ATOM   6052  CA  ASN B  48       7.898  37.485 154.983  1.00  4.09           B    C
ATOM   6060  CA  ASN B  49       6.685  33.858 155.217  1.00  4.78           B    C
ATOM   6068  CA  THR B  50      10.246  32.516 155.744  1.00  4.39           B    C
ATOM   6075  CA  GLY B  51      10.802  34.910 158.707  1.00  4.48           B    C
ATOM   6079  CA  TYR B  52      12.693  37.754 157.012  1.00  5.15           B    C
ATOM   6091  CA  ASP B  53      11.399  40.842 155.301  1.00  5.15           B    C
ATOM   6099  CA  TYR B  54      14.064  43.028 153.656  1.00  5.43           B    C
ATOM   6111  CA  ALA B  55      11.984  46.169 154.374  1.00  5.97           B    C
ATOM   6116  CA  GLN B  56      12.446  45.769 158.155  1.00  6.73           B    C
ATOM   6125  CA  SER B  57      15.268  47.086 160.349  1.00  7.18           B    C
ATOM   6131  CA  LYS B  58      15.306  44.770 163.351  1.00  4.81           B    C
ATOM   6140  CA  ILE B  59      16.408  41.138 163.680  1.00  4.41           B    C
ATOM   6148  CA  SER B  60      15.847  38.827 166.673  1.00  4.63           B    C
ATOM   6154  CA  GLY B  61      17.915  35.758 165.791  1.00  3.36           B    C
ATOM   6158  CA  PHE B  62      18.276  32.810 163.426  1.00  3.48           B    C
ATOM   6169  CA  THR B  63      15.870  29.935 162.748  1.00  3.46           B    C
ATOM   6176  CA  HIS B  64      17.063  26.876 161.377  1.00  3.52           B    C
ATOM   6186  CA  THR B  65      14.187  25.010 159.402  1.00  4.13           B    C
ATOM   6193  CA  ASN B  66      12.141  26.467 156.576  1.00  4.29           B    C
ATOM   6201  CA  LEU B  67      10.335  26.226 153.272  1.00  4.24           B    C
ATOM   6209  CA  ASP B  68      11.312  28.351 150.252  1.00  4.81           B    C
ATOM   6217  CA  GLY B  69       8.769  30.598 148.558  1.00  4.56           B    C
ATOM   6221  CA  VAL B  70       5.589  29.149 150.102  1.00  3.51           B    C
ATOM   6228  CA  GLY B  71       2.243  30.766 151.033  1.00  4.39           B    C
ATOM   6232  CA  GLY B  72       0.165  30.889 154.256  1.00  5.93           B    C
ATOM   6236  CA  SER B  73       2.360  32.159 157.086  1.00  5.71           B    C
ATOM   6242  CA  GLY B  74       5.232  29.886 155.962  1.00  4.98           B    C
ATOM   6246  CA  GLY B  75       6.827  26.565 157.216  1.00  4.40           B    C
ATOM   6250  CA  GLY B  76       9.371  25.580 159.505  1.00  4.57           B    C
ATOM   6254  CA  GLY B  77      10.953  28.443 161.386  1.00  3.39           B    C
ATOM   6258  CA  ASP B  78      11.986  26.048 164.188  1.00  3.33           B    C
ATOM   6266  CA  LEU B  79      14.886  26.547 166.612  1.00  5.32           B    C
ATOM   6274  CA  LEU B  80      15.348  30.284 167.110  1.00  5.08           B    C
ATOM   6282  CA  VAL B  81      18.851  31.213 168.309  1.00  4.86           B    C
ATOM   6289  CA  VAL B  82      19.084  34.745 169.745  1.00  5.18           B    C
ATOM   6296  CA  PRO B  83      22.375  36.414 170.798  1.00  5.18           B    C
ATOM   6303  CA  THR B  84      22.055  38.823 173.750  1.00  4.92           B    C
ATOM   6310  CA  SER B  85      24.059  40.445 176.538  1.00  3.51           B    C
ATOM   6316  CA  GLY B  86      20.865  40.604 178.572  1.00  3.93           B    C
ATOM   6320  CA  SER B  87      19.752  38.579 181.582  1.00  5.25           B    C
ATOM   6326  CA  TYR B  88      16.498  36.653 182.221  1.00  5.05           B    C
ATOM   6338  CA  THR B  89      14.650  35.335 185.336  1.00  5.80           B    C
ATOM   6345  CA  ALA B  90      11.608  33.987 183.443  1.00  4.94           B    C
ATOM   6350  CA  ARG B  91      10.687  32.820 179.933  1.00  5.95           B    C
ATOM   6361  CA  PRO B  92      11.913  35.587 177.603  1.00  5.93           B    C
ATOM   6368  CA  GLY B  93       9.414  38.047 176.166  1.00  5.97           B    C
ATOM   6372  CA  THR B  94       9.767  37.813 172.371  1.00  6.48           B    C
ATOM   6379  CA  GLY B  95      10.124  41.588 172.055  1.00  4.67           B    C
ATOM   6383  CA  THR B  96      13.359  41.564 174.059  1.00  4.82           B    C
```

FIG. 34-13

```
ATOM   6396  CA  TYR B  97      15.098  39.637 171.228  1.00  4.32           B   C
ATOM   6402  CA  ALA B  98      15.015  42.620 168.846  1.00  4.26           B   C
ATOM   6407  CA  HIS B  99      18.311  44.130 167.648  1.00  4.45           B   C
ATOM   6417  CA  PRO B 100      18.684  47.027 165.199  1.00  4.56           B   C
ATOM   6424  CA  PHE B 101      20.304  46.145 161.878  1.00  5.62           B   C
ATOM   6435  CA  SER B 102      21.236  47.834 158.588  1.00  6.73           B   C
ATOM   6441  CA  HIS B 103      21.603  46.324 155.111  1.00  7.29           B   C
ATOM   6451  CA  ASP B 104      24.879  48.336 155.037  1.00  9.91           B   C
ATOM   6459  CA  ASP B 105      26.290  45.946 157.703  1.00 10.20           B   C
ATOM   6467  CA  GLU B 106      24.917  42.703 156.229  1.00  9.23           B   C
ATOM   6476  CA  ASP B 107      26.499  40.286 153.765  1.00  9.46           B   C
ATOM   6484  CA  ALA B 108      25.243  36.970 152.370  1.00  6.84           B   C
ATOM   6489  CA  GLY B 109      25.559  34.488 149.524  1.00  4.80           B   C
ATOM   6493  CA  PRO B 110      25.491  30.714 148.861  1.00  4.09           B   C
ATOM   6500  CA  GLY B 111      26.276  29.034 152.198  1.00  4.03           B   C
ATOM   6504  CA  PHE B 112      26.451  32.010 154.507  1.00  4.63           B   C
ATOM   6515  CA  TYR B 113      24.841  35.051 156.062  1.00  4.43           B   C
ATOM   6527  CA  SER B 114      26.381  37.783 158.200  1.00  5.09           B   C
ATOM   6533  CA  VAL B 115      24.962  40.865 159.954  1.00  4.89           B   C
ATOM   6540  CA  GLY B 116      25.874  43.467 162.573  1.00  6.35           B   C
ATOM   6544  CA  LEU B 117      23.215  43.437 165.294  1.00  6.43           B   C
ATOM   6552  CA  GLY B 118      22.939  46.299 167.802  1.00  6.20           B   C
ATOM   6556  CA  ASN B 119      23.960  44.928 171.238  1.00  5.86           B   C
ATOM   6564  CA  VAL B 120      21.162  44.472 173.803  1.00  4.83           B   C
ATOM   6571  CA  ALA B 121      21.260  44.132 177.613  1.00  4.23           B   C
ATOM   6576  CA  GLY B 122      19.365  44.559 180.893  1.00  4.36           B   C
ATOM   6580  CA  THR B 123      16.919  42.174 182.582  1.00  5.43           B   C
ATOM   6587  CA  ASP B 124      13.711  40.546 181.298  1.00  5.91           B   C
ATOM   6595  CA  GLY B 125      11.132  43.006 179.823  1.00  6.02           B   C
ATOM   6599  CA  ALA B 126      13.463  45.973 180.415  1.00  5.90           B   C
ATOM   6604  CA  ILE B 127      16.092  44.620 177.976  1.00  5.52           B   C
ATOM   6612  CA  THR B 128      17.063  47.192 175.369  1.00  4.75           B   C
ATOM   6619  CA  GLY B 129      19.991  48.703 173.407  1.00  4.79           B   C
ATOM   6623  CA  ALA B 130      23.437  48.378 175.037  1.00  5.28           B   C
ATOM   6628  CA  PRO B 131      26.932  49.536 173.894  1.00  5.84           B   C
ATOM   6635  CA  GLY B 132      28.389  48.225 170.633  1.00  5.70           B   C
ATOM   6639  CA  THR B 133      27.548  45.592 168.062  1.00  6.06           B   C
ATOM   6646  CA  ILE B 134      27.013  41.848 168.174  1.00  7.11           B   C
ATOM   6654  CA  GLU B 135      28.833  40.654 165.045  1.00  8.84           B   C
ATOM   6663  CA  ALA B 136      26.820  37.651 163.802  1.00  6.19           B   C
ATOM   6668  CA  GLU B 137      27.966  35.088 161.226  1.00  4.63           B   C
ATOM   6677  CA  VAL B 138      26.200  31.897 160.196  1.00  3.25           B   C
ATOM   6684  CA  ALA B 139      26.905  29.212 157.622  1.00  3.25           B   C
ATOM   6689  CA  ALA B 140      25.244  25.933 156.657  1.00  4.37           B   C
ATOM   6694  CA  ALA B 141      26.177  22.444 155.558  1.00  5.98           B   C
ATOM   6699  CA  THR B 142      23.483  19.964 154.381  1.00  4.34           B   C
ATOM   6705  CA  ARG B 143      22.140  19.123 157.865  1.00  4.38           B   C
ATOM   6717  CA  SER B 144      23.954  21.728 159.957  1.00  4.49           B   C
ATOM   6723  CA  GLY B 145      23.839  25.419 160.895  1.00  5.05           B   C
ATOM   6727  CA  VAL B 146      26.994  26.868 162.414  1.00  4.62           B   C
ATOM   6734  CA  HIS B 147      27.242  30.186 164.272  1.00  4.38           B   C
ATOM   6744  CA  ARG B 148      30.103  32.540 165.208  1.00  4.25           B   C
ATOM   6755  CA  TYR B 149      29.335  35.704 167.264  1.00  4.46           B   C
ATOM   6767  CA  ALA B 150      31.522  38.561 168.553  1.00  5.60           B   C
ATOM   6772  CA  PHE B 151      30.094  40.472 171.553  1.00  6.42           B   C
ATOM   6783  CA  PRO B 152      31.380  43.820 172.738  1.00  8.35           B   C
ATOM   6790  CA  ALA B 153      34.133  43.586 175.369  1.00  8.99           B   C
ATOM   6795  CA  GLY B 154      32.667  43.385 178.865  1.00  8.42           B   C
ATOM   6799  CA  SER B 155      29.390  41.759 177.743  1.00  8.54           B   C
ATOM   6805  CA  THR B 156      28.171  38.643 179.484  1.00  7.06           B   C
ATOM   6812  CA  PRO B 157      27.319  36.804 176.247  1.00  7.08           B   C
ATOM   6819  CA  SER B 158      24.232  34.650 176.044  1.00  6.71           B   C
ATOM   6825  CA  LEU B 159      22.370  32.582 173.502  1.00  4.87           B   C
ATOM   6833  CA  VAL B 160      18.646  31.941 173.847  1.00  3.09           B   C
ATOM   6840  CA  VAL B 161      17.419  28.777 172.147  1.00  3.34           B   C
ATOM   6847  CA  ASP B 162      13.682  29.337 171.720  1.00  4.07           B   C
```

FIG. 34-14

```
ATOM   6855  CA   LEU B 163      11.876  26.065 170.870  1.00   3.79      B    C
ATOM   6863  CA   GLU B 164       8.402  27.636 170.688  1.00   4.18      B    C
ATOM   6872  CA   THR B 165       9.046  29.648 167.474  1.00   2.64      B    C
ATOM   6879  CA   ASN B 166       7.417  29.351 164.312  1.00   2.42      B    C
ATOM   6887  CA   ASN B 167       6.159  30.090 161.193  1.00   2.44      B    C
ATOM   6895  CA   THR B 168       2.700  28.469 161.520  1.00   2.77      B    C
ATOM   6902  CA   SER B 169       2.191  26.088 164.470  1.00   3.44      B    C
ATOM   6908  CA   ARG B 170       4.367  24.663 167.209  1.00   3.61      B    C
ATOM   6919  CA   ARG B 171       2.777  21.329 168.092  1.00   4.09      B    C
ATOM   6930  CA   SER B 172       5.367  20.136 170.618  1.00   3.92      B    C
ATOM   6936  CA   SER B 173       9.026  20.436 171.605  1.00   4.52      B    C
ATOM   6942  CA   SER B 174      11.644  19.095 174.010  1.00   5.26      B    C
ATOM   6948  CA   VAL B 175      15.144  19.964 175.194  1.00   7.61      B    C
ATOM   6955  CA   GLN B 176      17.707  17.943 177.116  1.00   9.87      B    C
ATOM   6964  CA   VAL B 177      20.827  19.575 178.479  1.00  10.75      B    C
ATOM   6971  CA   GLU B 178      24.266  17.972 178.853  1.00  11.75      B    C
ATOM   6980  CA   THR B 179      27.408  19.621 180.271  1.00  10.76      B    C
ATOM   6987  CA   ARG B 180      30.637  17.869 179.161  1.00  11.07      B    C
ATOM   6998  CA   ALA B 181      34.052  17.533 180.867  1.00  12.32      B    C
ATOM   7003  CA   ASP B 182      35.476  20.584 179.023  1.00  11.74      B    C
ATOM   7011  CA   GLY B 183      32.508  22.707 180.228  1.00   9.15      B    C
ATOM   7015  CA   THR B 184      30.755  22.961 176.837  1.00   5.80      B    C
ATOM   7022  CA   VAL B 185      27.013  23.306 176.541  1.00   5.32      B    C
ATOM   7029  CA   GLU B 186      24.991  20.053 174.245  1.00   6.37      B    C
ATOM   7038  CA   LEU B 187      21.225  20.551 173.801  1.00   5.44      B    C
ATOM   7046  CA   SER B 188      19.138  17.900 172.108  1.00   4.09      B    C
ATOM   7052  CA   GLY B 189      15.468  17.973 171.486  1.00   3.12      B    C
ATOM   7056  CA   GLN B 190      12.682  17.382 168.938  1.00   2.37      B    C
ATOM   7065  CA   VAL B 191      10.502  19.973 167.357  1.00   2.26      B    C
ATOM   7072  CA   THR B 192       7.128  19.112 165.863  1.00   2.53      B    C
ATOM   7079  CA   GLY B 193       5.491  21.715 163.683  1.00   2.57      B    C
ATOM   7083  CA   TYR B 194       2.613  21.953 161.250  1.00   3.30      B    C
ATOM   7095  CA   PHE B 195       2.176  23.583 157.852  1.00   4.28      B    C
ATOM   7106  CA   TYR B 196      -0.598  23.421 155.296  1.00   7.19      B    C
ATOM   7118  CA   ASN B 197      -1.557  19.737 155.149  1.00   7.00      B    C
ATOM   7126  CA   ALA B 198       0.738  17.907 157.606  1.00   5.17      B    C
ATOM   7131  CA   ALA B 199       2.648  17.834 160.876  1.00   4.90      B    C
ATOM   7136  CA   TYR B 200       6.409  17.069 160.789  1.00   4.22      B    C
ATOM   7148  CA   THR B 201       9.101  16.185 163.362  1.00   5.31      B    C
ATOM   7155  CA   LEU B 202      12.799  16.977 163.328  1.00   3.48      B    C
ATOM   7163  CA   TYR B 203      15.415  15.973 165.896  1.00   3.48      B    C
ATOM   7175  CA   TYR B 204      18.277  18.294 166.724  1.00   4.54      B    C
ATOM   7187  CA   THR B 205      21.584  18.494 168.504  1.00   5.64      B    C
ATOM   7194  CA   ALA B 206      23.308  21.765 169.341  1.00   5.72      B    C
ATOM   7199  CA   ARG B 207      26.654  22.253 170.998  1.00   5.49      B    C
ATOM   7210  CA   THR B 208      28.691  25.232 172.226  1.00   4.80      B    C
ATOM   7217  CA   LEU B 209      32.264  25.598 171.305  1.00   4.71      B    C
ATOM   7225  CA   GLN B 210      33.041  27.516 174.554  1.00   6.35      B    C
ATOM   7234  CA   PRO B 211      32.110  26.663 178.148  1.00   7.67      B    C
ATOM   7241  CA   ALA B 212      28.543  27.611 179.143  1.00   7.25      B    C
ATOM   7246  CA   THR B 213      26.099  27.434 182.004  1.00   7.17      B    C
ATOM   7253  CA   VAL B 214      22.470  26.720 181.121  1.00   6.69      B    C
ATOM   7260  CA   GLN B 215      18.911  27.268 182.283  1.00   6.38      B    C
ATOM   7269  CA   THR B 216      15.794  25.836 180.631  1.00   4.98      B    C
ATOM   7276  CA   TRP B 217      12.111  26.703 180.466  1.00   3.54      B    C
ATOM   7290  CA   GLY B 218       8.884  24.866 180.016  1.00   5.63      B    C
ATOM   7294  CA   ASP B 219       5.244  25.649 179.622  1.00   8.12      B    C
ATOM   7302  CA   ASP B 220       4.977  27.146 183.127  1.00  12.50      B    C
ATOM   7310  CA   ASP B 221       7.168  30.093 181.953  1.00  12.91      B    C
ATOM   7318  CA   ARG B 222       9.634  29.500 184.787  1.00  11.75      B    C
ATOM   7329  CA   LEU B 223      13.374  29.633 184.047  1.00   9.26      B    C
ATOM   7337  CA   VAL B 224      15.093  26.886 186.002  1.00   9.70      B    C
ATOM   7344  CA   ASP B 225      18.254  24.870 186.542  1.00   9.71      B    C
ATOM   7352  CA   ALA B 226      16.446  21.645 185.479  1.00   8.94      B    C
ATOM   7357  CA   THR B 227      18.172  19.922 182.585  1.00   8.94      B    C
ATOM   7364  CA   ALA B 228      15.027  18.498 180.872  1.00   8.41      B    C
```

FIG. 34-15

```
ATOM   7369  CA   GLN B 229      11.887  19.991 179.343  1.00   7.11           B    C
ATOM   7378  CA   ASP B 230       9.154  18.361 177.262  1.00   7.62           B    C
ATOM   7386  CA   GLY B 231       5.982  20.180 176.272  1.00   6.49           B    C
ATOM   7390  CA   VAL B 232       5.019  22.814 173.687  1.00   3.91           B    C
ATOM   7397  CA   ASP B 233       6.717  26.124 174.666  1.00   3.59           B    C
ATOM   7405  CA   THR B 234      10.207  25.219 175.870  1.00   3.22           B    C
ATOM   7412  CA   GLY B 235      13.760  26.456 175.485  1.00   2.52           B    C
ATOM   7416  CA   ALA B 236      17.165  27.054 176.932  1.00   2.01           B    C
ATOM   7421  CA   ILE B 237      19.409  30.014 177.730  1.00   2.63           B    C
ATOM   7429  CA   LEU B 238      23.188  29.544 177.393  1.00   3.80           B    C
ATOM   7437  CA   THR B 239      25.439  31.941 179.352  1.00   5.81           B    C
ATOM   7444  CA   PHE B 240      29.137  32.391 178.663  1.00   7.71           B    C
ATOM   7455  CA   ASP B 241      32.053  34.026 180.461  1.00  10.49           B    C
ATOM   7463  CA   PRO B 242      32.976  37.585 179.419  1.00  10.21           B    C
ATOM   7470  CA   ALA B 243      36.482  36.270 178.652  1.00  10.56           B    C
ATOM   7475  CA   ASP B 244      34.898  34.545 175.608  1.00  10.23           B    C
ATOM   7483  CA   ALA B 245      32.993  37.584 174.265  1.00   9.19           B    C
ATOM   7488  CA   GLY B 246      35.260  37.861 171.199  1.00   9.07           B    C
ATOM   7492  CA   GLU B 247      34.117  34.471 169.883  1.00   8.40           B    C
ATOM   7501  CA   ILE B 248      30.976  32.504 170.743  1.00   6.36           B    C
ATOM   7509  CA   GLY B 249      30.419  29.317 168.700  1.00   5.26           B    C
ATOM   7513  CA   LEU B 250      27.365  27.148 168.128  1.00   4.75           B    C
ATOM   7521  CA   GLN B 251      26.729  24.080 165.940  1.00   4.54           B    C
ATOM   7530  CA   VAL B 252      23.221  22.815 165.229  1.00   4.09           B    C
ATOM   7537  CA   THR B 253      22.517  19.573 163.382  1.00   3.14           B    C
ATOM   7544  CA   LEU B 254      19.085  18.325 162.254  1.00   3.66           B    C
ATOM   7552  CA   SER B 255      17.710  14.818 161.568  1.00   3.72           B    C
ATOM   7558  CA   PRO B 256      14.350  13.322 160.581  1.00   3.90           B    C
ATOM   7565  CA   VAL B 257      15.675  10.122 162.247  1.00   4.49           B    C
ATOM   7572  CA   SER B 258      16.553  10.685 165.919  1.00   5.09           B    C
ATOM   7578  CA   VAL B 259      18.811  12.681 168.270  1.00   6.85           B    C
ATOM   7585  CA   GLU B 260      21.309   9.841 168.225  1.00   8.56           B    C
ATOM   7594  CA   GLN B 261      21.425  10.162 164.416  1.00   7.14           B    C
ATOM   7603  CA   ALA B 262      21.764  13.965 164.573  1.00   6.00           B    C
ATOM   7608  CA   ARG B 263      24.840  13.567 166.780  1.00   6.59           B    C
ATOM   7619  CA   ILE B 264      26.315  11.008 164.363  1.00   7.36           B    C
ATOM   7627  CA   ASP B 265      25.571  13.292 161.370  1.00   6.50           B    C
ATOM   7635  CA   GLN B 266      27.201  16.188 163.205  1.00   7.37           B    C
ATOM   7644  CA   GLN B 267      30.403  14.178 163.786  1.00  11.20           B    C
ATOM   7653  CA   VAL B 268      30.481  13.075 160.124  1.00  10.88           B    C
ATOM   7660  CA   GLU B 269      29.430  16.369 158.505  1.00  11.16           B    C
ATOM   7669  CA   LEU B 270      31.314  18.882 160.704  1.00  10.96           B    C
ATOM   7677  CA   GLY B 271      33.869  16.943 162.740  1.00  11.80           B    C
ATOM   7681  CA   ASP B 272      36.639  19.186 164.002  1.00  11.87           B    C
ATOM   7689  CA   LEU B 273      36.374  21.606 161.059  1.00   9.30           B    C
ATOM   7697  CA   SER B 274      36.585  25.316 161.684  1.00   8.10           B    C
ATOM   7703  CA   PHE B 275      33.652  27.729 161.001  1.00   7.57           B    C
ATOM   7714  CA   ASP B 276      35.633  29.291 158.049  1.00   9.11           B    C
ATOM   7722  CA   ALA B 277      36.286  25.679 156.588  1.00   8.17           B    C
ATOM   7727  CA   ILE B 278      32.607  24.690 155.805  1.00   6.31           B    C
ATOM   7735  CA   ARG B 279      31.510  27.935 155.180  1.00   7.50           B    C
ATOM   7746  CA   ASP B 280      34.193  27.585 152.447  1.00   8.14           B    C
ATOM   7754  CA   ARG B 281      33.248  23.952 151.718  1.00   7.53           B    C
ATOM   7765  CA   THR B 282      29.590  24.914 151.207  1.00   7.03           B    C
ATOM   7772  CA   ARG B 283      30.749  27.748 148.908  1.00   8.06           B    C
ATOM   7783  CA   ALA B 284      32.685  25.192 146.803  1.00   7.18           B    C
ATOM   7788  CA   GLU B 285      29.647  22.838 146.826  1.00   8.04           B    C
ATOM   7797  CA   TRP B 286      27.513  25.684 145.409  1.00   6.44           B    C
ATOM   7811  CA   ASN B 287      30.194  26.541 142.822  1.00   7.77           B    C
ATOM   7819  CA   ALA B 288      30.163  23.844 141.765  1.00   8.01           B    C
ATOM   7824  CA   THR B 289      26.340  22.924 141.481  1.00   7.57           B    C
ATOM   7831  CA   LEU B 290      25.928  26.258 139.687  1.00   6.68           B    C
ATOM   7839  CA   GLY B 291      28.992  25.412 137.486  1.00   8.30           B    C
ATOM   7843  CA   ARG B 292      26.832  22.721 135.807  1.00   8.97           B    C
ATOM   7854  CA   VAL B 293      25.594  25.636 133.725  1.00  10.54           B    C
ATOM   7861  CA   ALA B 294      28.121  27.918 132.046  1.00  12.46           B    C
```

FIG. 34-16

```
ATOM   7866  CA   ILE  B  295      26.911  31.025 130.202  1.00 15.01           B    C
ATOM   7874  CA   ASP  B  296      28.503  33.444 127.743  1.00 16.68           B    C
ATOM   7882  CA   ALA  B  297      26.492  36.686 127.506  1.00 16.02           B    C
ATOM   7887  CA   SER  B  298      27.400  39.653 125.271  1.00 15.26           B    C
ATOM   7893  CA   THR  B  299      26.636  43.276 126.121  1.00 14.42           B    C
ATOM   7900  CA   ALA  B  300      24.046  43.110 123.336  1.00 11.48           B    C
ATOM   7905  CA   THR  B  301      21.783  40.582 125.103  1.00  9.84           B    C
ATOM   7912  CA   ASP  B  302      22.704  41.538 128.706  1.00  9.77           B    C
ATOM   7920  CA   PRO  B  303      23.868  45.197 128.715  1.00 10.54           B    C
ATOM   7927  CA   THR  B  304      23.489  45.589 132.512  1.00 11.07           B    C
ATOM   7934  CA   GLY  B  305      24.761  42.194 133.524  1.00 11.11           B    C
ATOM   7938  CA   GLU  B  306      21.483  41.714 135.433  1.00 10.64           B    C
ATOM   7947  CA   LEU  B  307      20.268  38.736 133.293  1.00 10.30           B    C
ATOM   7955  CA   GLN  B  308      23.365  36.685 134.127  1.00 10.19           B    C
ATOM   7964  CA   ARG  B  309      22.914  37.469 137.835  1.00  8.46           B    C
ATOM   7975  CA   LEU  B  310      19.207  36.600 137.644  1.00  6.90           B    C
ATOM   7983  CA   PHE  B  311      20.109  33.341 135.894  1.00  5.42           B    C
ATOM   7994  CA   TYR  B  312      22.509  32.208 138.679  1.00  4.65           B    C
ATOM   8006  CA   THR  B  313      20.288  33.567 141.446  1.00  3.72           B    C
ATOM   8013  CA   HIS  B  314      17.411  31.465 140.078  1.00  3.77           B    C
ATOM   8023  CA   LEU  B  315      19.597  28.434 139.419  1.00  4.98           B    C
ATOM   8031  CA   TYR  B  316      20.467  28.753 143.144  1.00  4.55           B    C
ATOM   8043  CA   ARG  B  317      16.731  28.839 144.007  1.00  5.20           B    C
ATOM   8054  CA   MET  B  318      16.085  25.817 141.789  1.00  7.54           B    C
ATOM   8062  CA   PHE  B  319      18.175  23.558 144.063  1.00  8.02           B    C
ATOM   8073  CA   ALA  B  320      16.316  24.249 147.345  1.00  7.35           B    C
ATOM   8078  CA   MET  B  321      13.403  21.781 147.467  1.00  5.88           B    C
ATOM   8086  CA   PRO  B  322      12.863  18.952 147.903  1.00  4.25           B    C
ATOM   8093  CA   MET  B  323      15.380  18.850 150.769  1.00  3.69           B    C
ATOM   8101  CA   ASN  B  324      17.944  16.177 151.447  1.00  3.38           B    C
ATOM   8109  CA   ALA  B  325      16.107  14.133 154.077  1.00  3.72           B    C
ATOM   8114  CA   THR  B  326      18.714  11.357 154.443  1.00  3.39           B    C
ATOM   8121  CA   SER  B  327      21.071  10.805 157.383  1.00  4.75           B    C
ATOM   8127  CA   THR  B  328      24.861  10.478 156.953  1.00  5.56           B    C
ATOM   8134  CA   SER  B  329      24.175   6.783 157.673  1.00  5.03           B    C
ATOM   8140  CA   GLY  B  330      21.990   6.586 154.509  1.00  5.56           B    C
ATOM   8144  CA   THR  B  331      18.681   6.308 156.385  1.00  4.67           B    C
ATOM   8151  CA   TYR  B  332      15.380   8.194 156.221  1.00  4.08           B    C
ATOM   8163  CA   ARG  B  333      12.110   8.234 158.156  1.00  5.90           B    C
ATOM   8174  CA   GLY  B  334       8.940   7.045 156.393  1.00  7.33           B    C
ATOM   8178  CA   VAL  B  335       5.362   8.276 156.776  1.00  9.86           B    C
ATOM   8185  CA   ASP  B  336       4.715   4.745 156.108  1.00 11.83           B    C
ATOM   8193  CA   GLY  B  337       6.473   5.889 161.292  1.00 12.67           B    C
ATOM   8197  CA   ALA  B  338       9.546   3.713 160.784  1.00 10.29           B    C
ATOM   8202  CA   VAL  B  339      13.181   4.400 159.827  1.00  8.36           B    C
ATOM   8209  CA   HIS  B  340      14.277   2.783 156.523  1.00  8.22           B    C
ATOM   8219  CA   ALA  B  341      17.345   2.466 154.295  1.00  9.30           B    C
ATOM   8224  CA   ALA  B  342      17.738   4.699 151.232  1.00 10.96           B    C
ATOM   8229  CA   GLN  B  343      19.736   1.973 149.549  1.00 14.92           B    C
ATOM   8238  CA   GLY  B  344      22.061   3.243 146.798  1.00 14.18           B    C
ATOM   8242  CA   PHE  B  345      20.330   6.658 146.470  1.00  9.94           B    C
ATOM   8253  CA   THR  B  346      19.663   9.851 148.454  1.00  5.70           B    C
ATOM   8260  CA   TYR  B  347      16.132  10.341 149.769  1.00  3.08           B    C
ATOM   8272  CA   TYR  B  348      14.568  13.786 149.336  1.00  2.49           B    C
ATOM   8284  CA   ASP  B  349      11.394  15.091 150.938  1.00  3.40           B    C
ATOM   8292  CA   SER  B  350       9.337  18.340 151.066  1.00  3.13           B    C
ATOM   8298  CA   TRP  B  351       6.904  18.558 148.223  1.00  3.44           B    C
ATOM   8312  CA   ALA  B  352       4.594  21.317 148.769  1.00  6.09           B    C
ATOM   8317  CA   THR  B  353       3.818  19.352 143.690  1.00  7.57           B    C
ATOM   8324  CA   TRP  B  354       0.511  21.060 142.861  1.00 10.28           B    C
ATOM   8338  CA   ASP  B  355       2.607  24.171 142.126  1.00  9.25           B    C
ATOM   8346  CA   ASP  B  356       6.027  22.831 141.162  1.00  7.97           B    C
ATOM   8354  CA   PHE  B  357       5.476  19.675 139.069  1.00  5.45           B    C
ATOM   8365  CA   ARG  B  358       7.086  31.219 135.923  1.00  4.54           B    C
ATOM   8376  CA   LYS  B  359      10.204  22.174 137.907  1.00  3.86           B    C
ATOM   8385  CA   PHE  B  360      11.251  18.513 137.948  1.00  3.85           B    C
```

FIG. 34-17

```
ATOM   8396  CA  SER B 361      11.230  18.254 134.132  1.00   4.19      B    C
ATOM   8402  CA  VAL B 362      13.848  21.051 134.057  1.00   4.66      B    C
ATOM   8409  CA  ILE B 363      15.981  19.656 136.859  1.00   3.60      B    C
ATOM   8417  CA  ALA B 364      15.986  16.487 134.724  1.00   4.12      B    C
ATOM   8422  CA  TYR B 365      18.152  18.190 132.040  1.00   5.46      B    C
ATOM   8434  CA  ILE B 366      20.412  20.182 134.397  1.00   6.51      B    C
ATOM   8442  CA  ASP B 367      21.232  17.532 137.055  1.00   6.76      B    C
ATOM   8450  CA  PRO B 368      19.936  14.178 135.858  1.00   6.15      B    C
ATOM   8457  CA  ALA B 369      21.273  13.238 138.895  1.00   5.16      B    C
ATOM   8462  CA  LEU B 370      19.595  14.581 141.391  1.00   5.66      B    C
ATOM   8470  CA  TYR B 371      16.368  14.393 139.413  1.00   5.00      B    C
ATOM   8482  CA  ARG B 372      16.537  10.538 139.507  1.00   6.13      B    C
ATOM   8493  CA  ASP B 373      16.991  10.482 143.321  1.00   4.65      B    C
ATOM   8501  CA  MET B 374      14.069  12.884 143.690  1.00   3.74      B    C
ATOM   8509  CA  VAL B 375      11.706  10.681 141.648  1.00   3.94      B    C
ATOM   8516  CA  GLN B 376      12.653   7.548 143.481  1.00   3.66      B    C
ATOM   8525  CA  SER B 377      13.139   9.421 146.732  1.00   3.93      B    C
ATOM   8531  CA  LEU B 378       8.564  10.288 145.559  1.00   4.51      B    C
ATOM   8539  CA  VAL B 379       8.064   6.634 144.704  1.00   3.56      B    C
ATOM   8545  CA  TYR B 380       9.204   5.663 148.259  1.00   4.22      B    C
ATOM   8558  CA  LEU B 381       6.969   8.247 149.897  1.00   3.49      B    C
ATOM   8566  CA  PHE B 382       3.836   6.774 148.265  1.00   3.82      B    C
ATOM   8577  CA  ALA B 383       5.141   3.221 148.777  1.00   4.94      B    C
ATOM   8582  CA  ASP B 384       5.471   3.935 152.503  1.00   6.79      B    C
ATOM   8590  CA  ALA B 385       1.923   5.413 152.611  1.00   9.08      B    C
ATOM   8595  CA  GLU B 386       0.765   2.141 150.976  1.00  10.89      B    C
ATOM   8604  CA  ALA B 387       2.810   0.119 153.498  1.00  13.19      B    C
ATOM   8609  CA  THR B 388       0.740   1.552 156.446  1.00  15.38      B    C
ATOM   8616  CA  GLY B 389      -2.271  -0.495 155.224  1.00  15.84      B    C
ATOM   8620  CA  THR B 390      -4.587   2.321 156.337  1.00  14.91      B    C
ATOM   8627  CA  GLY B 391      -5.415   3.543 152.829  1.00  12.96      B    C
ATOM   8631  CA  GLY B 392      -5.069   7.090 154.245  1.00  10.55      B    C
ATOM   8635  CA  GLY B 393      -3.986  10.168 152.254  1.00   8.29      B    C
ATOM   8639  CA  LEU B 394      -0.516  11.579 152.818  1.00   6.39      B    C
ATOM   8647  CA  GLY B 395      -1.926  14.514 154.938  1.00   6.51      B    C
ATOM   8651  CA  GLY B 396      -2.978  13.076 157.705  1.00   7.77      B    C
ATOM   8655  CA  PHE B 397       0.603  11.030 158.585  1.00   7.05      B    C
ATOM   8666  CA  VAL B 398       3.457  12.825 160.317  1.00   6.28      B    C
ATOM   8673  CA  HIS B 399       6.082  13.832 157.779  1.00   4.37      B    C
ATOM   8683  CA  SER B 400       9.868  13.714 158.080  1.00   4.62      B    C
ATOM   8689  CA  VAL B 401      10.519  17.328 157.074  1.00   3.81      B    C
ATOM   8696  CA  PRO B 402       8.279  20.398 156.732  1.00   2.81      B    C
ATOM   8703  CA  THR B 403       6.233  19.841 153.605  1.00   2.00      B    C
ATOM   8710  CA  VAL B 404       3.295  21.247 151.582  1.00   2.02      B    C
ATOM   8717  CA  ARG B 405       1.236  19.105 149.134  1.00   3.66      B    C
ATOM   8728  CA  TRP B 406       1.343  16.193 146.726  1.00   4.40      B    C
ATOM   8742  CA  GLU B 407      -1.154  16.632 143.859  1.00   4.95      B    C
ATOM   8751  CA  ARG B 408       0.354  16.656 140.358  1.00   4.63      B    C
ATOM   8762  CA  SER B 409       2.805  13.445 141.798  1.00   4.41      B    C
ATOM   8768  CA  SER B 410       1.577  10.955 139.158  1.00   5.65      B    C
ATOM   8774  CA  VAL B 411       2.871  13.412 136.534  1.00   4.55      B    C
ATOM   8781  CA  VAL B 412       6.352  13.733 138.090  1.00   3.62      B    C
ATOM   8788  CA  VAL B 413       6.857   9.945 138.202  1.00   3.87      B    C
ATOM   8795  CA  ALA B 414       5.438   9.358 134.653  1.00   5.13      B    C
ATOM   8800  CA  ASP B 415       7.928  12.368 133.664  1.00   4.82      B    C
ATOM   8808  CA  ALA B 416      10.908  10.154 134.613  1.00   4.44      B    C
ATOM   8813  CA  ILE B 417       9.427   7.020 132.987  1.00   5.16      B    C
ATOM   8821  CA  ALA B 418       8.712   8.909 129.732  1.00   6.23      B    C
ATOM   8826  CA  LYS B 419      12.303  10.194 129.851  1.00   8.29      B    C
ATOM   8835  CA  GLY B 420      13.794   6.696 129.923  1.00  10.82      B    C
ATOM   8839  CA  PHE B 421      14.569   6.285 133.624  1.00  11.95      B    C
ATOM   8850  CA  ASP B 422      13.949   2.885 135.136  1.00  14.46      B    C
ATOM   8858  CA  GLY B 423      14.815   0.654 138.084  1.00  14.15      B    C
ATOM   8862  CA  PHE B 424      12.489   2.574 140.366  1.00  12.52      B    C
ATOM   8873  CA  ASP B 425      12.381   0.289 143.387  1.00  12.13      B    C
ATOM   8881  CA  ARG B 426       8.874  -0.058 144.898  1.00   9.62      B    C
```

FIG. 34-18

```
ATOM   8892  CA  LEU B 427       6.950   1.477 141.964  1.00  9.74      B    C
ATOM   8900  CA  ASP B 428       4.503  -1.436 142.300  1.00 11.74      B    C
ATOM   8908  CA  GLU B 429       3.837  -0.485 145.942  1.00 10.85      B    C
ATOM   8917  CA  ALA B 430       3.557   3.228 145.139  1.00  9.56      B    C
ATOM   8922  CA  TYR B 431       0.970   2.649 142.393  1.00  9.69      B    C
ATOM   8934  CA  PRO B 432      -2.178   2.019 144.553  1.00  8.88      B    C
ATOM   8941  CA  ALA B 433      -1.368   5.086 146.736  1.00  7.60      B    C
ATOM   8946  CA  LEU B 434      -0.914   7.129 143.556  1.00  7.98      B    C
ATOM   8954  CA  GLN B 435      -4.332   5.893 142.378  1.00  9.79      B    C
ATOM   8963  CA  ARG B 436      -5.876   6.985 145.714  1.00  8.63      B    C
ATOM   8974  CA  LEU B 437      -4.175  10.398 145.345  1.00  8.82      B    C
ATOM   8982  CA  VAL B 438      -5.651  10.832 141.863  1.00 10.73      B    C
ATOM   8989  CA  GLY B 439      -9.074   9.520 142.973  1.00 11.53      B    C
ATOM   8993  CA  GLN B 440     -11.952   7.945 141.034  1.00 13.71      B    C
ATOM   9002  CA  TYR B 441     -14.865   9.454 139.124  1.00 12.01      B    C
ATOM   9014  CA  SER B 442     -18.189   8.549 140.760  1.00 12.74      B    C
ATOM   9020  CA  ALA B 443     -20.666   6.339 138.839  1.00 12.68      B    C
ATOM   9025  CA  ASP B 444     -22.553   9.434 137.697  1.00 12.59      B    C
ATOM   9033  CA  GLU B 445     -19.307  11.199 136.788  1.00 10.37      B    C
ATOM   9042  CA  LEU B 446     -18.282   8.164 134.766  1.00 10.75      B    C
ATOM   9050  CA  ARG B 447     -21.517   8.211 132.730  1.00 12.18      B    C
ATOM   9061  CA  ARG B 448     -21.331  11.954 131.904  1.00 11.28      B    C
ATOM   9072  CA  GLY B 449     -17.521  12.199 131.769  1.00  9.56      B    C
ATOM   9076  CA  TYR B 450     -16.840  15.171 134.104  1.00  8.69      B    C
ATOM   9088  CA  VAL B 451     -17.362  16.664 137.586  1.00  8.42      B    C
ATOM   9095  CA  ALA B 452     -20.609  18.655 137.398  1.00  9.63      B    C
ATOM   9100  CA  GLY B 453     -19.943  22.350 137.910  1.00  9.76      B    C
ATOM   9104  CA  ASN B 454     -16.242  21.775 138.624  1.00  8.50      B    C
ATOM   9112  CA  PRO B 455     -14.156  22.194 135.439  1.00  8.33      B    C
ATOM   9119  CA  GLY B 456     -11.107  22.756 137.693  1.00  8.02      B    C
ATOM   9123  CA  ALA B 457     -11.159  19.292 139.280  1.00  6.90      B    C
ATOM   9128  CA  SER B 458     -11.963  17.688 135.889  1.00  6.05      B    C
ATOM   9134  CA  VAL B 459      -8.939  18.989 133.896  1.00  5.70      B    C
ATOM   9141  CA  GLN B 460      -6.681  18.365 136.882  1.00  5.79      B    C
ATOM   9150  CA  ARG B 461      -7.804  14.732 137.121  1.00  6.42      B    C
ATOM   9161  CA  GLY B 462      -7.221  14.406 133.370  1.00  5.35      B    C
ATOM   9165  CA  TYR B 463      -3.539  15.278 133.771  1.00  5.04      B    C
ATOM   9177  CA  ASP B 464      -3.270  13.035 136.851  1.00  5.57      B    C
ATOM   9185  CA  GLN B 465      -4.804  10.198 134.841  1.00  5.78      B    C
ATOM   9194  CA  TYR B 466      -2.483  10.769 131.919  1.00  6.49      B    C
ATOM   9206  CA  GLY B 467       0.439  10.511 134.547  1.00  5.94      B    C
ATOM   9210  CA  LEU B 468      -1.027   7.423 136.006  1.00  7.08      B    C
ATOM   9218  CA  SER B 469      -1.447   5.806 132.563  1.00  7.35      B    C
ATOM   9224  CA  VAL B 470       2.324   6.119 131.916  1.00  7.31      B    C
ATOM   9231  CA  ILE B 471       3.054   4.452 135.299  1.00  7.55      B    C
ATOM   9239  CA  ALA B 472       0.432   1.758 134.635  1.00  8.69      B    C
ATOM   9244  CA  ASP B 473       2.077   0.765 131.318  1.00 10.11      B    C
ATOM   9252  CA  GLU B 474       5.524   0.684 132.942  1.00 11.08      B    C
ATOM   9261  CA  LEU B 475       4.081  -1.770 135.471  1.00 10.77      B    C
ATOM   9269  CA  GLY B 476       2.557  -3.863 132.643  1.00 12.28      B    C
ATOM   9273  CA  LEU B 477      -1.005  -2.946 133.703  1.00 14.48      B    C
ATOM   9281  CA  THR B 478      -1.957  -2.607 130.034  1.00 17.13      B    C
ATOM   9288  CA  GLU B 479      -5.736  -3.506 130.474  1.00 18.35      B    C
ATOM   9297  CA  GLU B 480      -5.722   0.045 133.355  1.00 15.71      B    C
ATOM   9306  CA  ALA B 481      -3.447   2.289 131.256  1.00 13.30      B    C
ATOM   9311  CA  GLU B 482      -5.993   2.198 128.387  1.00 13.38      B    C
ATOM   9320  CA  THR B 483      -8.838   3.007 130.776  1.00 11.91      B    C
ATOM   9327  CA  LEU B 484      -6.802   5.857 132.279  1.00  9.11      B    C
ATOM   9335  CA  ARG B 485      -6.030   7.235 128.765  1.00  8.25      B    C
ATOM   9346  CA  GLU B 486      -9.735   7.030 127.831  1.00  8.59      B    C
ATOM   9355  CA  GLN B 487     -10.721   8.982 130.961  1.00  7.84      B    C
ATOM   9364  CA  ALA B 488      -7.917  11.568 130.491  1.00  6.39      B    C
ATOM   9369  CA  SER B 489      -9.413  12.554 127.143  1.00  6.88      B    C
ATOM   9375  CA  TRP B 490     -12.765  13.388 128.798  1.00  7.07      B    C
ATOM   9389  CA  PRO B 491     -13.065  16.904 130.180  1.00  7.75      B    C
ATOM   9396  CA  ILE B 492     -11.068  18.232 126.748  1.00 10.03      B    C
```

FIG. 34-19

```
ATOM   9404  CA   GLU B 493     -13.896  16.510 124.906  1.00 12.06      B    C
ATOM   9413  CA   LYS B 494     -16.671  17.061 127.437  1.00 10.91      B    C
ATOM   9422  CA   LEU B 495     -15.887  20.513 128.833  1.00  9.26      B    C
ATOM   9430  CA   THR B 496     -14.827  22.544 125.800  1.00  9.84      B    C
ATOM   9437  CA   LYS B 497     -17.372  24.524 124.878  1.00 10.36      B    C
ATOM   9446  CA   PRO B 498     -18.062  25.503 121.171  1.00 10.16      B    C
ATOM   9453  CA   GLY B 499     -18.441  29.251 120.587  1.00 11.73      B    C
ATOM   9457  CA   ALA B 500     -17.533  30.238 124.159  1.00 12.89      B    C
ATOM   9462  CA   TRP B 501     -15.979  33.120 122.622  1.00 13.33      B    C
ATOM   9475  CA   THR B 502     -16.087  34.739 119.196  1.00 14.82      B    C
ATOM   9483  CA   ALA B 503     -13.072  36.086 117.234  1.00 17.18      B    C
ATOM   9488  CA   ALA B 504     -12.857  39.344 115.232  1.00 19.86      B    C
ATOM   9493  CA   ASP B 505     -13.256  36.963 112.234  1.00 21.28      B    C
ATOM   9501  CA   GLY B 506     -16.585  35.755 113.609  1.00 20.03      B    C
ATOM   9505  CA   THR B 507     -14.731  32.439 114.087  1.00 18.03      B    C
ATOM   9512  CA   GLN B 508     -16.251  30.532 117.010  1.00 15.34      B    C
ATOM   9521  CA   VAL B 509     -13.708  29.336 119.570  1.00 11.34      B    C
ATOM   9528  CA   GLY B 510     -14.366  26.537 122.049  1.00  9.07      B    C
ATOM   9532  CA   LEU B 511     -13.137  27.026 125.631  1.00  7.86      B    C
ATOM   9540  CA   LEU B 512     -13.319  25.124 128.921  1.00  7.01      B    C
ATOM   9548  CA   THR B 513     -16.601  25.890 130.550  1.00  8.85      B    C
ATOM   9555  CA   PRO B 514     -18.393  24.554 133.677  1.00 10.28      B    C
ATOM   9562  CA   ARG B 515     -21.081  22.039 132.717  1.00 12.26      B    C
ATOM   9573  CA   ALA B 516     -24.111  20.973 134.766  1.00 13.16      B    C
ATOM   9578  CA   ALA B 517     -24.951  17.342 135.666  1.00 14.35      B    C
ATOM   9583  CA   ASP B 518     -27.642  17.167 132.923  1.00 16.53      B    C
ATOM   9591  CA   GLY B 519     -25.191  18.281 130.210  1.00 16.33      B    C
ATOM   9595  CA   SER B 520     -26.240  21.945 129.971  1.00 15.96      B    C
ATOM   9601  CA   TRP B 521     -23.959  24.648 130.008  1.00 15.21      B    C
ATOM   9615  CA   GLN B 522     -23.432  26.929 133.060  1.00 15.39      B    C
ATOM   9624  CA   SER B 523     -22.733  30.599 132.427  1.00 15.49      B    C
ATOM   9630  CA   ALA B 524     -19.406  32.190 133.361  1.00 13.08      B    C
ATOM   9635  CA   ASP B 525     -16.958  34.949 132.667  1.00 10.42      B    C
ATOM   9643  CA   HIS B 526     -13.996  33.026 131.216  1.00  9.11      B    C
ATOM   9653  CA   ALA B 527     -11.679  35.887 132.307  1.00  9.10      B    C
ATOM   9658  CA   LYS B 528     -12.918  36.154 135.899  1.00 10.32      B    C
ATOM   9667  CA   PHE B 529     -10.563  35.052 138.686  1.00  8.73      B    C
ATOM   9678  CA   GLU B 530     -11.981  32.036 140.571  1.00  8.70      B    C
ATOM   9687  CA   ALA B 531     -15.175  31.800 138.513  1.00  9.23      B    C
ATOM   9692  CA   ALA B 532     -16.810  28.339 138.183  1.00 10.09      B    C
ATOM   9697  CA   GLY B 533     -15.211  26.855 141.335  1.00  9.25      B    C
ATOM   9701  CA   LEU B 534     -11.553  27.388 140.006  1.00  8.07      B    C
ATOM   9709  CA   TYR B 535      -8.638  27.496 142.280  1.00 10.81      B    C
ATOM   9721  CA   GLN B 536      -6.568  30.581 141.905  1.00 10.33      B    C
ATOM   9730  CA   GLY B 537      -7.264  31.159 138.187  1.00  8.79      B    C
ATOM   9734  CA   THR B 538      -9.626  31.771 135.278  1.00  7.44      B    C
ATOM   9741  CA   LEU B 539     -11.154  29.505 132.643  1.00  8.31      B    C
ATOM   9749  CA   TRP B 540      -8.976  31.006 129.900  1.00  6.79      B    C
ATOM   9763  CA   GLN B 541      -6.091  30.062 132.087  1.00  5.72      B    C
ATOM   9772  CA   TYR B 542      -7.247  26.567 133.014  1.00  6.07      B    C
ATOM   9784  CA   HIS B 543      -8.336  25.987 129.378  1.00  6.44      B    C
ATOM   9794  CA   TRP B 544      -4.804  24.912 128.489  1.00  5.93      B    C
ATOM   9808  CA   TYR B 545      -4.279  22.715 131.546  1.00  4.79      B    C
ATOM   9820  CA   ASP B 546      -4.407  19.324 129.817  1.00  4.56      B    C
ATOM   9828  CA   ALA B 547      -0.984  19.835 128.277  1.00  5.44      B    C
ATOM   9833  CA   TYR B 548      -0.609  16.142 127.393  1.00  6.08      B    C
ATOM   9845  CA   ASP B 549      -3.092  16.487 124.510  1.00  5.83      B    C
ATOM   9853  CA   MET B 550      -2.830  19.820 122.688  1.00  7.27      B    C
ATOM   9861  CA   ASP B 551      -3.867  18.042 119.495  1.00  9.92      B    C
ATOM   9869  CA   ALA B 552      -7.181  17.034 121.101  1.00  9.29      B    C
ATOM   9874  CA   LEU B 553      -7.610  20.544 122.602  1.00  8.74      B    C
ATOM   9882  CA   VAL B 554      -6.969  22.270 119.291  1.00  9.28      B    C
ATOM   9889  CA   GLU B 555      -9.660  20.056 117.696  1.00 10.79      B    C
ATOM   9898  CA   ALA B 556     -12.151  20.721 120.539  1.00  8.98      B    C
ATOM   9903  CA   MET B 557     -11.629  24.480 120.201  1.00  9.27      B    C
ATOM   9911  CA   GLY B 558     -12.831  24.096 116.592  1.00 11.18      B    C
```

FIG. 34-20

```
ATOM   9915 CA  GLY B 559      -9.648  23.449 114.651  1.00 12.57           B    C
ATOM   9919 CA  HIS B 560      -6.240  24.925 113.907  1.00 13.76           B    C
ATOM   9929 CA  GLU B 561      -7.665  28.397 113.047  1.00 13.40           B    C
ATOM   9938 CA  ALA B 562      -9.852  28.561 116.156  1.00 11.93           B    C
ATOM   9943 CA  ALA B 563      -6.829  27.744 118.342  1.00 11.17           B    C
ATOM   9948 CA  ARG B 564      -4.548  30.202 116.523  1.00 10.14           B    C
ATOM   9959 CA  LEU B 565      -6.933  33.167 117.193  1.00  9.78           B    C
ATOM   9967 CA  GLY B 566      -7.517  31.781 120.726  1.00  8.93           B    C
ATOM   9971 CA  MET B 567      -3.792  31.948 121.520  1.00  9.45           B    C
ATOM   9979 CA  ARG B 568      -3.398  35.497 120.126  1.00  9.92           B    C
ATOM   9990 CA  HIS B 569      -6.452  36.639 122.170  1.00  9.91           B    C
ATOM  10000 CA  MET B 570      -4.961  34.969 125.270  1.00 10.22           B    C
ATOM  10008 CA  PHE B 571      -1.992  37.376 124.985  1.00  9.43           B    C
ATOM  10019 CA  GLY B 572      -3.956  40.469 123.877  1.00 11.08           B    C
ATOM  10023 CA  GLU B 573      -2.196  40.540 120.476  1.00 13.30           B    C
ATOM  10032 CA  HIS B 574      -5.029  42.598 118.931  1.00 14.86           B    C
ATOM  10042 CA  ALA B 575      -4.622  45.304 121.645  1.00 15.90           B    C
ATOM  10047 CA  PRO B 576      -0.972  45.390 122.696  1.00 17.21           B    C
ATOM  10054 CA  ASP B 577      -1.328  48.595 124.695  1.00 18.80           B    C
ATOM  10062 CA  ASP B 578      -4.243  47.440 126.680  1.00 16.37           B    C
ATOM  10070 CA  GLY B 579      -3.447  45.773 129.999  1.00 14.31           B    C
ATOM  10074 CA  LYS B 580      -6.893  44.273 130.536  1.00 14.35           B    C
ATOM  10083 CA  ALA B 581      -6.401  42.289 127.289  1.00 11.55           B    C
ATOM  10088 CA  MET B 582      -3.732  40.150 128.992  1.00  9.08           B    C
ATOM  10096 CA  LEU B 583      -5.611  36.913 129.818  1.00  6.75           B    C
ATOM  10104 CA  HIS B 584      -2.406  35.966 130.755  1.00  5.26           B    C
ATOM  10114 CA  SER B 585      -1.183  35.314 134.331  1.00  5.08           B    C
ATOM  10120 CA  ASN B 586       2.561  35.487 135.130  1.00  4.87           B    C
ATOM  10128 CA  ALA B 587       1.917  35.442 138.923  1.00  6.16           B    C
ATOM  10133 CA  ASN B 588       0.684  31.857 139.540  1.00  6.70           B    C
ATOM  10141 CA  GLU B 589       1.574  28.445 138.079  1.00 11.52           B    C
ATOM  10150 CA  ILE B 590      -1.724  27.523 136.394  1.00 11.76           B    C
ATOM  10158 CA  ASP B 591      -0.787  28.589 132.835  1.00 11.65           B    C
ATOM  10166 CA  LEU B 592       3.036  28.784 133.060  1.00 10.00           B    C
ATOM  10174 CA  GLN B 593       3.220  26.855 129.797  1.00  7.99           B    C
ATOM  10183 CA  ALA B 594       0.955  29.258 127.891  1.00  7.42           B    C
ATOM  10188 CA  PRO B 595       3.697  31.434 126.264  1.00  6.47           B    C
ATOM  10195 CA  TYR B 596       5.040  28.300 124.524  1.00  5.99           B    C
ATOM  10207 CA  LEU B 597       1.684  27.269 123.043  1.00  5.41           B    C
ATOM  10215 CA  PHE B 598       2.175  29.492 119.962  1.00  6.82           B    C
ATOM  10226 CA  ASN B 599       4.570  26.728 118.788  1.00  7.99           B    C
ATOM  10234 CA  TYR B 600       1.469  24.494 118.559  1.00  8.95           B    C
ATOM  10246 CA  THR B 601      -0.592  27.029 116.565  1.00  9.34           B    C
ATOM  10253 CA  GLY B 602       2.026  27.493 113.815  1.00  9.48           B    C
ATOM  10257 CA  GLU B 603       3.299  30.812 115.139  1.00  9.51           B    C
ATOM  10266 CA  PRO B 604       6.593  29.991 116.946  1.00  8.50           B    C
ATOM  10273 CA  SER B 605       7.845  33.576 116.478  1.00  7.57           B    C
ATOM  10279 CA  LEU B 606       5.226  34.638 119.060  1.00  7.18           B    C
ATOM  10287 CA  THR B 607       6.454  32.030 121.578  1.00  5.66           B    C
ATOM  10294 CA  GLN B 608       9.959  33.487 121.141  1.00  5.96           B    C
ATOM  10303 CA  LYS B 609       8.701  37.059 121.593  1.00  6.51           B    C
ATOM  10312 CA  TRP B 610       6.714  36.241 124.769  1.00  7.00           B    C
ATOM  10326 CA  ALA B 611       9.360  33.957 126.314  1.00  7.18           B    C
ATOM  10331 CA  ARG B 612      11.852  36.768 125.860  1.00  7.07           B    C
ATOM  10342 CA  ALA B 613       9.502  39.547 127.021  1.00  7.16           B    C
ATOM  10347 CA  ILE B 614       8.036  37.923 130.160  1.00  7.15           B    C
ATOM  10355 CA  TYR B 615      11.442  37.037 131.633  1.00  8.13           B    C
ATOM  10367 CA  THR B 616      13.573  39.966 130.409  1.00  8.81           B    C
ATOM  10374 CA  LYS B 617      11.308  42.977 129.716  1.00  9.89           B    C
ATOM  10383 CA  GLU B 618       8.290  44.801 130.976  1.00 10.62           B    C
ATOM  10392 CA  THR B 619       4.925  43.183 130.129  1.00 10.85           B    C
ATOM  10399 CA  TRP B 620       1.277  43.848 130.780  1.00 10.87           B    C
ATOM  10413 CA  ASN B 621       0.104  42.242 133.955  1.00  8.54           B    C
ATOM  10421 CA  ARG B 622      -3.614  41.858 134.675  1.00  6.42           B    C
ATOM  10432 CA  TYR B 623      -3.638  39.093 137.312  1.00  6.84           B    C
ATOM  10444 CA  ILE B 624      -2.156  38.601 140.777  1.00  6.95           B    C
```

FIG. 34-21

```
ATOM  10452  CA  ALA B 625      -2.036  36.146 142.429  1.00  9.17           B C
ATOM  10457  CA  THR B 626      -4.883  35.743 144.940  1.00  9.61           B C
ATOM  10464  CA  GLY B 627      -8.057  37.828 145.428  1.00 11.00           B C
ATOM  10468  CA  SER B 628      -6.410  40.988 146.753  1.00 14.00           B C
ATOM  10474  CA  SER B 629      -3.055  42.511 147.827  1.00 14.96           B C
ATOM  10480  CA  SER B 630      -2.186  45.392 150.152  1.00 15.87           B C
ATOM  10486  CA  ALA B 631       1.099  45.793 148.230  1.00 15.19           B C
ATOM  10491  CA  VAL B 632      -0.451  46.993 144.954  1.00 12.68           B C
ATOM  10498  CA  PRO B 633      -3.837  48.543 144.078  1.00 11.90           B C
ATOM  10505  CA  SER B 634      -5.790  45.403 143.232  1.00 10.24           B C
ATOM  10511  CA  GLY B 635      -9.047  43.424 143.555  1.00 10.87           B C
ATOM  10515  CA  GLY B 636     -10.965  40.434 142.243  1.00 11.37           B C
ATOM  10519  CA  GLY B 637      -7.618  38.717 141.514  1.00 10.74           B C
ATOM  10523  CA  GLU B 638      -6.354  41.552 139.331  1.00 10.06           B C
ATOM  10532  CA  PHE B 639      -4.034  44.542 139.288  1.00 10.96           B C
ATOM  10543  CA  THR B 640      -6.497  47.479 139.174  1.00 13.37           B C
ATOM  10550  CA  PRO B 641      -5.496  48.960 136.843  1.00 14.12           B C
ATOM  10557  CA  PRO B 642      -3.275  46.456 134.964  1.00 13.72           B C
ATOM  10564  CA  LEU B 643       0.396  47.404 135.238  1.00 14.65           B C
ATOM  10572  CA  LYS B 644       3.137  47.317 132.691  1.00 13.96           B C
ATOM  10581  CA  THR B 645       6.095  45.936 134.647  1.00 11.78           B C
ATOM  10588  CA  LYS B 646       8.969  43.450 134.688  1.00 11.14           B C
ATOM  10597  CA  VAL B 647       7.800  40.166 136.218  1.00  8.36           B C
ATOM  10604  CA  TYR B 648      11.303  39.198 137.406  1.00  7.74           B C
ATOM  10616  CA  ARG B 649      13.591  41.824 139.020  1.00  9.04           B C
ATOM  10627  CA  LEU B 650      17.093  41.707 140.433  1.00  7.53           B C
ATOM  10635  CA  ASP B 651      15.807  43.347 143.621  1.00  5.17           B C
ATOM  10643  CA  PRO B 652      14.545  42.350 147.055  1.00  5.40           B C
ATOM  10650  CA  ARG B 653      11.139  42.853 145.381  1.00  6.53           B C
ATOM  10661  CA  GLY B 654      12.108  40.059 142.996  1.00  6.41           B C
ATOM  10665  CA  MET B 655       8.705  38.795 141.823  1.00  6.72           B C
ATOM  10673  CA  LEU B 656       5.334  40.460 141.196  1.00  6.70           B C
ATOM  10681  CA  PRO B 657       3.402  41.236 144.385  1.00  6.71           B C
ATOM  10688  CA  THR B 658       1.659  37.972 145.528  1.00  7.41           B C
ATOM  10695  CA  MET B 659       3.892  35.925 143.184  1.00  5.95           B C
ATOM  10703  CA  ASP B 660       5.190  33.199 145.543  1.00  4.96           B C
ATOM  10711  CA  ASN B 661       8.255  31.368 144.118  1.00  5.08           B C
ATOM  10719  CA  ASP B 662       6.702  28.114 145.513  1.00  4.85           B C
ATOM  10727  CA  ALA B 663       9.647  25.783 146.215  1.00  5.19           B C
ATOM  10732  CA  GLY B 664      11.674  27.503 143.453  1.00  5.63           B C
ATOM  10736  CA  THR B 665       9.108  26.987 140.680  1.00  6.11           B C
ATOM  10743  CA  MET B 666       9.161  30.568 139.404  1.00  7.32           B C
ATOM  10751  CA  SER B 667      12.973  30.544 139.595  1.00  7.14           B C
ATOM  10757  CA  THR B 668      13.107  27.187 137.738  1.00  8.41           B C
ATOM  10764  CA  MET B 669      10.894  28.674 134.975  1.00  8.61           B C
ATOM  10772  CA  PHE B 670      13.293  31.613 134.474  1.00  5.87           B C
ATOM  10783  CA  VAL B 671      15.332  29.234 134.165  1.00  5.19           B C
ATOM  10790  CA  ALA B 672      14.275  27.232 131.532  1.00  5.77           B C
ATOM  10795  CA  ALA B 673      13.327  30.366 129.576  1.00  6.53           B C
ATOM  10800  CA  ALA B 674      17.004  31.392 129.691  1.00  6.52           B C
ATOM  10808  CA  VAL B 675      18.093  27.945 128.278  1.00  6.08           B C
ATOM  10812  CA  GLY B 676      15.236  28.143 125.757  1.00  5.59           B C
ATOM  10816  CA  LEU B 677      13.801  24.680 126.537  1.00  4.36           B C
ATOM  10824  CA  PHE B 678      10.456  24.513 128.310  1.00  4.27           B C
ATOM  10835  CA  PRO B 679       8.476  21.443 129.468  1.00  4.23           B C
ATOM  10842  CA  VAL B 680       4.935  22.169 128.193  1.00  4.71           B C
ATOM  10849  CA  THR B 681       4.133  18.524 128.725  1.00  4.02           B C
ATOM  10856  CA  ALA B 682       5.534  17.401 132.029  1.00  2.99           B C
ATOM  10861  CA  GLY B 683       5.162  13.611 132.013  1.00  4.05           B C
ATOM  10865  CA  SER B 684       6.552  13.443 128.463  1.00  5.13           B C
ATOM  10871  CA  SER B 685      10.143  13.369 127.150  1.00  6.66           B C
ATOM  10877  CA  GLN B 686       9.863  16.641 125.200  1.00  6.38           B C
ATOM  10886  CA  PHE B 687      10.738  20.344 125.639  1.00  5.59           B C
ATOM  10897  CA  GLN B 688       9.427  23.232 123.520  1.00  6.03           B C
ATOM  10906  CA  VAL B 689      11.793  25.796 122.043  1.00  6.55           B C
ATOM  10913  CA  GLY B 690      11.579  29.419 123.274  1.00  7.04           B C
```

FIG. 34-22

```
ATOM  10917  CA  SER B 691    14.106  32.286 122.899  1.00  7.79    B  C
ATOM  10923  CA  PRO B 692    17.484  31.426 124.531  1.00  7.84    B  C
ATOM  10930  CA  PHE B 693    18.864  34.550 126.227  1.00  7.82    B  C
ATOM  10941  CA  PHE B 694    23.594  34.664 125.890  1.00  7.33    B  C
ATOM  10952  CA  ASP B 695    25.205  33.655 123.125  1.00  9.43    B  C
ATOM  10960  CA  SER B 696    26.210  30.332 124.574  1.00  9.32    B  C
ATOM  10966  CA  THR B 697    24.781  28.206 127.383  1.00  8.98    B  C
ATOM  10973  CA  THR B 698    26.586  24.967 128.241  1.00  8.91    B  C
ATOM  10980  CA  ILE B 699    25.297  22.278 130.616  1.00  9.45    B  C
ATOM  10988  CA  THR B 700    28.086  19.908 131.647  1.00 10.12    B  C
ATOM  10995  CA  TYR B 701    27.061  16.493 132.887  1.00  9.88    B  C
ATOM  11007  CA  ASP B 702    29.712  14.246 135.442  1.00 11.45    B  C
ATOM  11015  CA  ASP B 703    30.657  12.267 132.819  1.00 13.40    B  C
ATOM  11023  CA  GLY B 704    32.161  15.461 131.345  1.00 11.98    B  C
ATOM  11027  CA  SER B 705    29.921  15.485 128.268  1.00 10.92    B  C
ATOM  11033  CA  ALA B 706    27.994  18.613 127.584  1.00 10.52    B  C
ATOM  11038  CA  PHE B 707    24.798  20.036 125.938  1.00  9.26    B  C
ATOM  11049  CA  THR B 708    25.464  23.375 124.241  1.00  8.98    B  C
ATOM  11056  CA  VAL B 709    22.737  25.748 123.064  1.00  9.09    B  C
ATOM  11063  CA  THR B 710    24.043  28.747 121.128  1.00 11.17    B  C
ATOM  11070  CA  ALA B 711    23.134  31.834 120.050  1.00 13.24    B  C
ATOM  11075  CA  ASP B 712    24.141  33.564 117.322  1.00 14.25    B  C
ATOM  11083  CA  GLY B 713    23.732  37.334 117.271  1.00 12.57    B  C
ATOM  11087  CA  VAL B 714    21.303  37.259 120.194  1.00 12.10    B  C
ATOM  11094  CA  SER B 715    20.477  40.687 121.622  1.00 11.79    B  C
ATOM  11100  CA  GLU B 716    17.633  42.447 123.438  1.00 13.43    B  C
ATOM  11109  CA  ASP B 717    16.112  43.108 119.987  1.00 12.74    B  C
ATOM  11117  CA  ALA B 718    17.337  39.953 118.227  1.00 11.10    B  C
ATOM  11122  CA  PHE B 719    15.169  37.456 120.135  1.00 10.51    B  C
ATOM  11133  CA  TYR B 720    13.602  35.772 117.045  1.00 10.60    B  C
ATOM  11145  CA  VAL B 721    14.971  32.509 115.687  1.00  9.51    B  C
ATOM  11152  CA  GLN B 722    15.866  32.757 111.949  1.00  9.69    B  C
ATOM  11161  CA  SER B 723    17.260  29.236 111.377  1.00 10.67    B  C
ATOM  11167  CA  ALA B 724    18.749  26.372 113.367  1.00 10.44    B  C
ATOM  11172  CA  THR B 725    21.057  23.385 113.295  1.00 10.19    B  C
ATOM  11179  CA  LEU B 726    21.285  20.299 115.497  1.00  9.79    B  C
ATOM  11187  CA  ASP B 727    24.740  18.682 115.470  1.00 10.78    B  C
ATOM  11195  CA  GLY B 728    25.486  20.471 112.168  1.00  9.59    B  C
ATOM  11199  CA  ALA B 729    22.291  19.355 110.407  1.00  9.37    B  C
ATOM  11204  CA  THR B 730    19.314  21.561 109.437  1.00  9.54    B  C
ATOM  11211  CA  PHE B 731    16.911  21.620 112.380  1.00  9.46    B  C
ATOM  11222  CA  GLY B 732    13.291  22.799 111.894  1.00 10.01    B  C
ATOM  11226  CA  ASN B 733    11.337  21.345 114.625  1.00 10.28    B  C
ATOM  11234  CA  THR B 734     9.967  23.567 117.612  1.00 10.95    B  C
ATOM  11241  CA  TRP B 735    10.620  20.889 120.262  1.00  9.83    B  C
ATOM  11255  CA  VAL B 736    13.910  18.634 121.295  1.00  9.57    B  C
ATOM  11262  CA  ASP B 737    13.581  15.277 123.044  1.00  9.41    B  C
ATOM  11270  CA  TYR B 738    15.214  14.889 126.458  1.00  7.09    B  C
ATOM  11282  CA  ALA B 739    17.544  12.232 125.051  1.00  6.73    B  C
ATOM  11287  CA  THR B 740    19.020  14.795 122.576  1.00  6.66    B  C
ATOM  11294  CA  VAL B 741    19.805  17.297 125.352  1.00  6.54    B  C
ATOM  11301  CA  VAL B 742    21.387  14.908 127.847  1.00  6.53    B  C
ATOM  11308  CA  GLY B 743    23.160  13.136 124.986  1.00  8.60    B  C
ATOM  11312  CA  GLY B 744    25.256  16.293 124.535  1.00  8.96    B  C
ATOM  11316  CA  ALA B 745    23.948  17.869 121.301  1.00  8.77    B  C
ATOM  11321  CA  ASP B 746    24.946  21.245 119.824  1.00  9.39    B  C
ATOM  11329  CA  LEU B 747    21.727  23.156 119.256  1.00  9.30    B  C
ATOM  11337  CA  ALA B 748    23.723  26.298 117.347  1.00  9.57    B  C
ATOM  11342  CA  PHE B 749    20.245  29.087 116.636  1.00  9.42    B  C
ATOM  11353  CA  ARG B 750    20.864  32.051 114.353  1.00 10.76    B  C
ATOM  11364  CA  MET B 751    18.965  35.015 115.906  1.00 10.21    B  C
ATOM  11372  CA  GLY B 752    17.672  38.240 114.387  1.00 12.06    B  C
ATOM  11376  CA  GLU B 753    15.318  41.247 114.999  1.00 14.15    B  C
ATOM  11385  CA  GLN B 754    12.309  40.094 112.932  1.00 15.06    B  C
ATOM  11394  CA  PRO B 755     9.930  37.094 113.128  1.00 14.14    B  C
ATOM  11401  CA  SER B 756    10.685  34.248 110.709  1.00 14.80    B  C
```

FIG. 34-23

```
ATOM  11407  CA   ASP B 757       8.804  31.176 109.465  1.00 14.96      B    C
ATOM  11415  CA   TRP B 758      11.407  28.912 111.150  1.00 13.21      B    C
ATOM  11429  CA   GLY B 759       9.689  25.918 112.773  1.00 13.37      B    C
ATOM  11433  CA   THR B 760       6.357  26.434 111.014  1.00 13.94      B    C
ATOM  11440  CA   ASP B 761       6.914  23.023 109.382  1.00 13.96      B    C
ATOM  11448  CA   THR B 762       7.829  21.295 112.640  1.00 10.47      B    C
ATOM  11455  CA   ALA B 763       7.173  17.563 113.052  1.00  9.77      B    C
ATOM  11460  CA   PRO B 764       4.213  17.436 115.464  1.00  9.45      B    C
ATOM  11467  CA   ALA B 765       4.950  17.568 119.216  1.00  7.60      B    C
ATOM  11472  CA   PHE B 766       3.648  14.939 121.659  1.00  7.84      B    C
ATOM  11483  CA   SER B 767      -0.100  14.561 122.179  1.00  8.05      B    C
ATOM  11489  CA   MET B 768      -1.670  11.546 123.865  1.00 10.37      B    C
ATOM  11497  CA   SER B 769      -4.411  11.138 121.212  1.00 13.56      B    C
ATOM  11503  CA   THR B 770      -1.982  11.233 118.242  1.00 17.85      B    C
ATOM  11510  CA   ALA B 771       0.792   9.094 119.762  1.00 20.44      B    C
ATOM  12382  CA   CA  C   1      41.435  16.915  81.268  1.00 30.05      C   CA
ATOM  12383  CA   CA  C   6       1.503  30.134 143.317  1.00 32.32      C   CA
END
```

HYDROLYSIS OF MANNOSE-1-PHOSPHO-6-MANNOSE LINKAGE TO PHOSPHO-6-MANNOSE

CROSS-REFERENCE TO RELATED APPLICATIONS

This application is a U.S. national phase application, and claims priority, of International Patent Application No. PCT/IB2010/002589, filed Sep.29, 2010, which claims priority to U.S. Provisional Application No. 61/246,847, filed on Sep.29, 2009. The disclosures International Application No. PCT/IB2010/002589and U.S. Provisional Application No. 61/246,846 are incorporated by reference in their entirety.

TECHNICAL FIELD

The invention relates to methods of hydrolyzing mannose-1-phospho-6-mannose linkages on glycoproteins, and more particularly, to using a mannosidase to hydrolyze mannose-1-phospho-6-mannose linkages to uncap the phospho-6-mannose residues on the glycoprotein.

BACKGROUND

High performance expression systems are required to produce most biopharmaceuticals (e.g., recombinant proteins) currently under development. The biological activity of many of these biopharmaceuticals is dependent on their post-translational modification (e.g., phosphorylation or glycosylation). A yeast-based expression system combines the ease of genetic manipulation and fermentation of a microbial organism with the capability to secrete and to modify proteins. However, recombinant glycoproteins produced in yeast cells exhibit mainly heterogeneous high-mannose and hyper-mannose glycan structures, which can be detrimental to protein function, downstream processing, and subsequent therapeutic use, particularly where glycosylation plays a biologically significant role.

U.S. application Ser. No. 12/062,469 is incorporated by reference in its entirety.

SUMMARY

The present invention is based, at least in part, on the discovery of a mannosidase that is capable of hydrolyzing mannose-1-phospho-6-mannose linkages on glycoproteins. As such, the mannosidase can be used to obtain glycoproteins containing uncapped terminal mannose-6-phosphate residues. In vitro and in vivo methods of obtaining such glycoproteins are described herein. Genetically engineered cells can be used in the methods to produce target molecules having uncapped terminal mannose-6-phosphate residues.

In one aspect, this document features a method for uncapping a mannose-6-phosphate residue on an oligosaccharide. The method includes providing the oligosaccharide having a mannose-1-phospho-6-mannose linkage; and contacting the oligosaccharide with a mannosidase capable of hydrolyzing the mannose-1-phospho-6-mannose linkage to phospho-6-mannose. The contacting step can be performed using a purified mannosidase, a recombinant mannosidase, a cell lysate containing the recombinant mannosidase, or a fungal cell containing the recombinant mannosidase. The mannosidase can include a targeting sequence. The oligosaccharide can be attached to a protein (e.g., a human protein expressed in a fungal organism).

In another aspect, this document features a method of producing a target protein having terminal phospho-6-mannose residues. The method includes providing a fungal cell genetically engineered to include a nucleic acid encoding a mannosidase, the mannosidase capable of hydrolyzing a mannose-1-phospho-6-mannose linkage to phospho-6-mannose; and introducing into the cell a nucleic acid encoding a target protein, wherein the cell produces the target protein comprising the terminal phospho-6-mannose residues.

This document also features a method of producing a target protein having terminal phospho-6-mannose residues in a fungal organism. The method includes providing a fungal cell genetically engineered to include a nucleic acid encoding a mannosidase capable of hydrolyzing a mannose-1-phospho-6-mannose linkage to phospho-6-mannose, wherein the fungal cell further includes a nucleic acid encoding a target protein; and isolating the target protein having the terminal phospho-6-mannose residues. The fungal cell further can include a nucleic acid encoding a polypeptide capable of promoting mannosyl phosphorylation and/or can be genetically engineered to be deficient in OCH1 activity.

This document also features an isolated fungal cell genetically engineered to produce glycoproteins comprising terminal phospho-6-mannose residues. The fungal cell includes a nucleic acid encoding a mannosidase, wherein expression of the mannosidase in the fungal cell produces glycoproteins comprising the terminal phospho-6-mannose residues. The fungal cell further can include a nucleic acid encoding a target glycoprotein protein.

In another aspect, this document features a substantially pure culture of *Yarrowia lipolytica*, *Pichia pastoris*, *Hansenula polymorpha*, *Arxula adeninivorans*, *Pichia methanolica*, *Oogataea minuta*, or *Aspergillus niger* cells, a substantial number of which are genetically engineered to produce glycoproteins comprising a terminal phospho-6-mannose residue, the cells comprising a nucleic acid encoding a mannosidase capable of hydrolyzing a mannose-1-phospho-6-mannose linkage to phospho-6-mannose.

In any of the embodiments described herein, the fungal organism can be *Yarrowia lipolytica* or *Arxula adeninivorans*. The fungal organism can be a methylotrophic yeast such as *Pichia pastoris*, *Pichia methanolica*, *Oogataea minuta*, or *Hansenula polymorpha*. The fungal organism can be a filamentous fungus (e.g., a filamentous fungus selected from the group consisting of *Aspergillus caesiellus*, *Aspergillus candidus*, *Aspergillus carneus*, *Aspergillus clavatus*, *Aspergillus deflectus*, *Aspergillus flavus*, *Aspergillus fumigatus*, *Aspergillus glaucus*, *Aspergillus nidulans*, *Aspergillus niger*, *Aspergillus ochraceus*, *Aspergillus oryzae*, *Aspergillus parasiticus*, *Aspergillus penicilloides*, *Aspergillus restrictus*, *Aspergillus sojae*, *Aspergillus sydowi*, *Aspergillus tamari*, *Aspergillus terreus*, *Aspergillus ustus*, and *Aspergillus versicolor*).

In any of embodiments described herein, the protein can be a pathogen protein, a lysosomal protein, a growth factor, a cytokine, a chemokine, an antibody or antigen-binding fragment thereof, or a fusion protein. The lysosomal protein can be a lysosomal enzyme (e.g., a lysosomal enzyme associated with a lysosomal storage disorder (LSD) such as acid alpha glucosidase or alpha galactosidase). The LSD can be Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia. For example, the LSD can be Pompe disease or Fabry's disease.

In any of the embodiments described herein, for the mannosidase, the three dimensional protein coordinates of the atoms in the amino acid side chains located in the minimal catalytic center fall within 1.5 Å deviation of the coordinates of the equivalent atoms in FIG. 33.

In any of the embodiments described herein, the mannosidase can include an amino acid sequence having at least 90% identity (e.g., at least 95% or 98% identity) to the amino acid sequence set forth in residues 1 to 774 of SEQ ID NO:50 or to the amino acid sequence set forth in SEQ ID NO:50.

In any of the embodiments described herein, the mannosidase can include an amino acid sequence having (i) a GVGXXGXGG motif, where X is Gly, Ala, Ser, Thr, or Cys; (ii) a VRXE motif, where X is any amino acid other than Pro; (iii) an $X_1$YQG$X_2$ motif, where $X_1$ is Leu, Ile, Val, Ala, Phe, Tyr or Met, and $X_2$ is Thr, Ser, or Asn; or (iv) a GDXGN motif, where X can be any amino acid other than Pro.

In any of the embodiments described herein, the mannosidase can be a *C. cellulans, Streptomyces coelicolor,* or *Streptomyces lividans* mannosidase.

In any of the embodiments described herein, the fungal cell further can include a nucleic acid encoding a polypeptide capable of promoting mannosyl phosphorylation (e.g., a MNN4 polypeptide such as *Yarrowia lipolytica, S. cerevisiae, Ogataea minuta, Pichia pastoris,* or *C. albicans* polypeptide) and/or can be genetically engineered to be deficient in OCH1 activity. For example, the polypeptide capable of promoting mannosyl phosphorylation can be a *P. pastoris* PNO1 polypeptide.

In any of the embodiments described herein, the mannosidase can include a secretion signal and/or a targeting signal to target the mannosidase to an intracellular compartment. The target protein and the mannosidase can be cosecreted.

This document also features an isolated glycoprotein that includes terminal phospho-6-mannose residues, wherein the protein is produced by the methods described herein.

In yet another aspect, this document features a composition that includes a glycoprotein, wherein at least 47% of the N-glycans on the glycoprotein have terminal phospho-6-mannose residues. For example, at least 50%, 75%, 80%, 85%, or 90% of the N-glycans on the glycoprotein can have terminal phospho-6-mannose residues.

This document also features an isolated nucleic acid that includes a nucleotide sequence set forth in SEQ ID NO:6, SEQ ID NO:8, SEQ ID NO:10, SEQ ID NO:12, or SEQ ID NO:14, or a nucleotide sequence that is at least 90% identical to SEQ ID NO:6, SEQ ID NO:8, SEQ ID NO:10, SEQ ID NO:12, SEQ ID NO:14, or SEQ ID NO:20. This document also features a vector that includes a promoter operably linked to such a nucleic acid, wherein the nucleic acid encodes a mannosidase. The nucleic acid further can include a secretion signal or targeting sequence to target the mannosidase to an intracellular compartment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS7

FIG. 1 is a schematic of the pYLTmAX and pYLTmAX-Mnn4 constructs.

Figure 3:
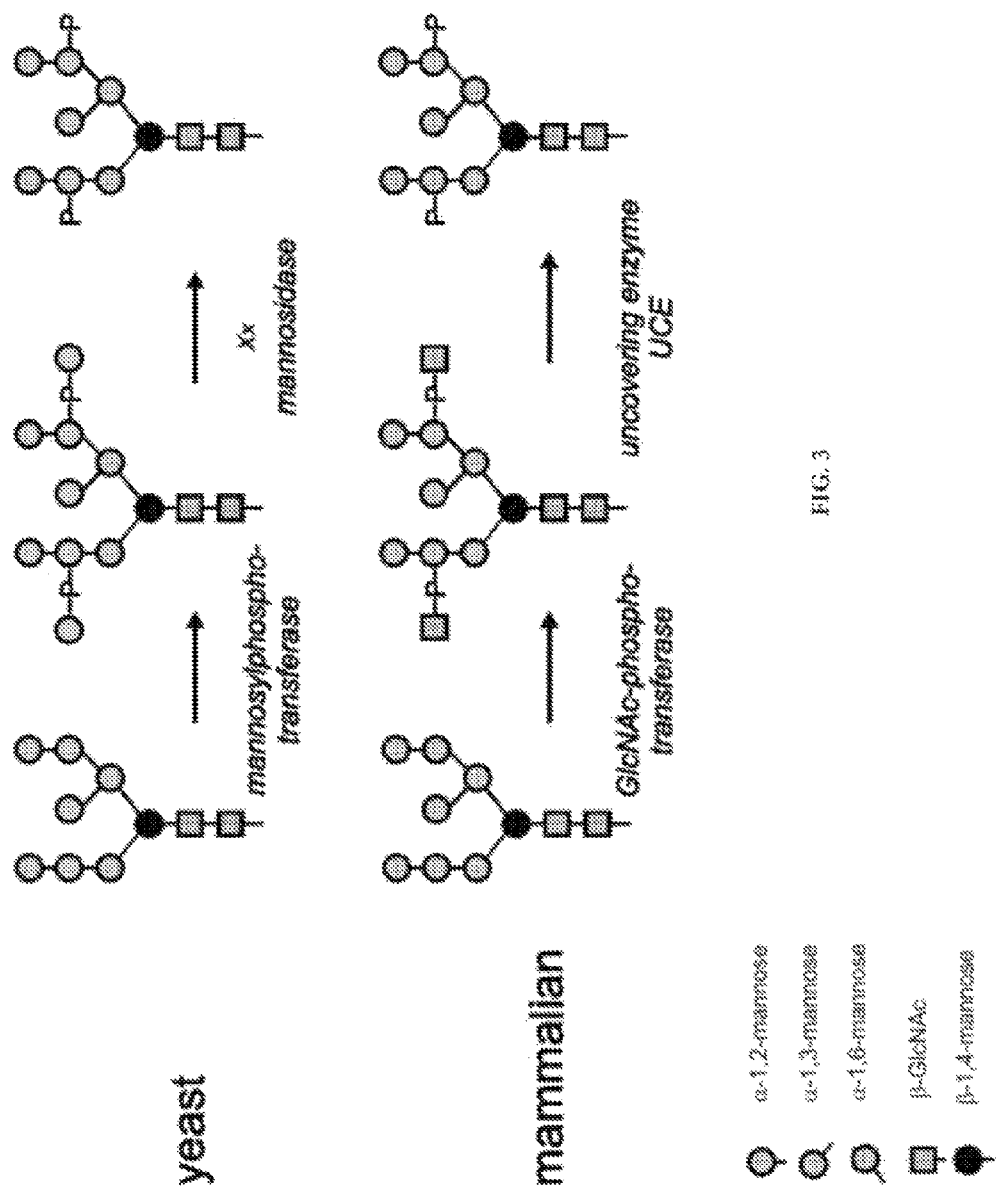

FIG. 3 is a schematic of mammalian and yeast glycan phosphorylation pathways. The mammalian glycan phosphorylation pathway involves addition of a phospho-GlcNAc catalyzed by GlcNAc-phosphotransferase to $Man_8GlcNAc_2$ glycans followed by decapping of the GlcNAc to expose the phosphate by an uncovering enzyme. In contrast, yeast glycan phosphorylation involves addition of a phospho-mannose to $Man_8GlcNAc_2$ glycans, but no endogenous enzyme is present to uncap the mannose to expose the phosphate.

Figure 4:
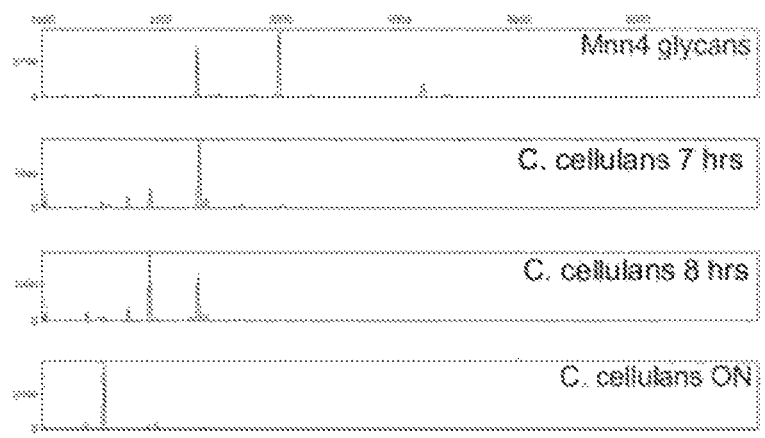

FIG. 4 is a series of electroferograms depicting N-glycans derived from strain MTLY60Δoch1+Hp4dMnn4+TEFMnn4 treated for different time frames (7 hrs, 8 hrs, or overnight (ON)) with supernatants from *C. cellulans* medium.

Figure 5:
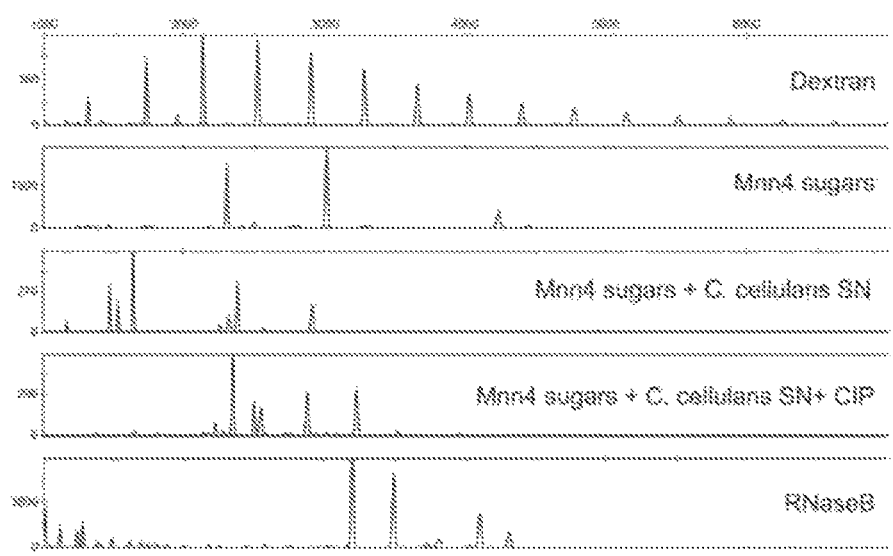

FIG. 5 is a series of electroferograms depicting N-glycans derived from an MNN4 overexpressing strain treated with *C. cellulans* supernatant (SN) with and without phosphatase (CIP) incubation.

Figure 6:
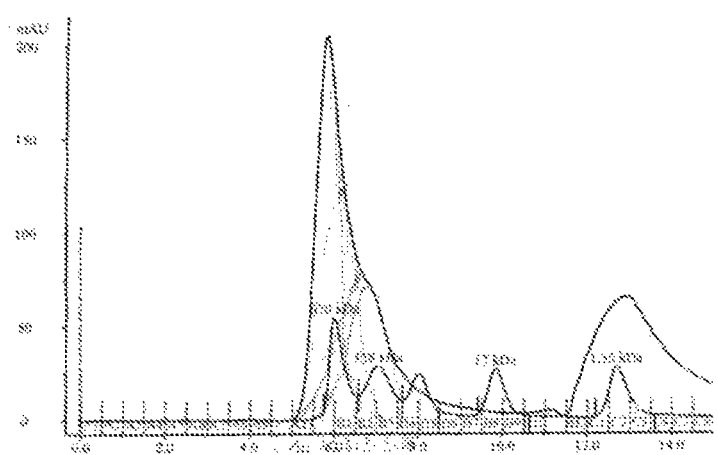

FIG. 6 is a graph of the absorbance units (mAU) of elution fractions at the indicated MW. Each elution fraction contained ~500 µl.

Figure 7:
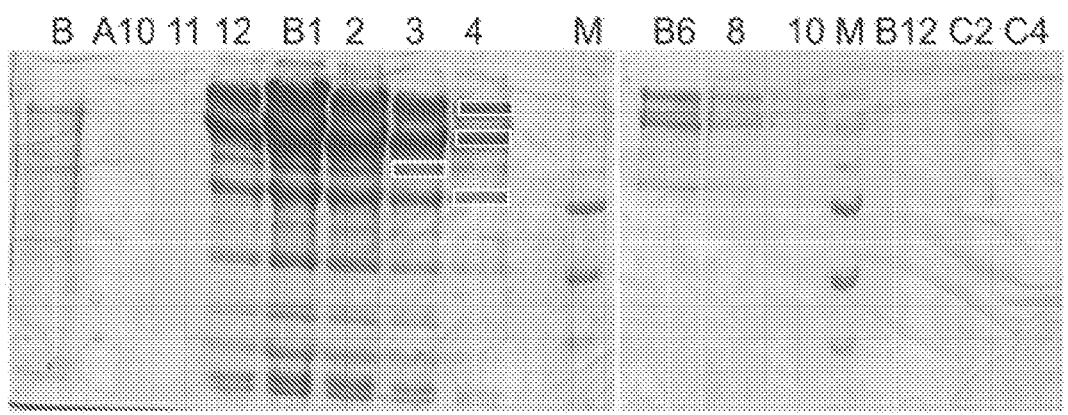

FIG. 7 is a representation of a SDS-polyacrylamide gel after electrophoresis of elution fractions from silica-based gel filtration (250 µl of each fraction was DOC/TCA precipitated). The boxed bands were cut out for peptide mass fingerprinting and de novo sequencing using tandem mass spectrometry (MS/MS).

FIG. 8A is the nucleotide sequence (SEQ ID NO:6) encoding CcMan1 (i.e., mannosidase candidate 1 from *C. Cellulans*) (on contig 1003), which was identified in the MS/MS de novo sequencing. FIG. 8B is the amino acid sequence (SEQ ID NO:7) of CcMan 1, including the signal sequence (in bold). The predicted molecular weight of the CcMan 1 polypeptide without the signal sequence is 92.6 kDa.

FIG. 9A is the nucleotide sequence (SEQ ID NO:8) encoding CcMan2 (on contig 774) and FIG. 9B is the amino acid sequence of CcMan2 (SEQ ID NO:9) with signal sequence (in bold). The predicted molecular weight of the CcMan2 polypeptide without the signal sequence is 121.6 kDa.

Figures 3, 32:
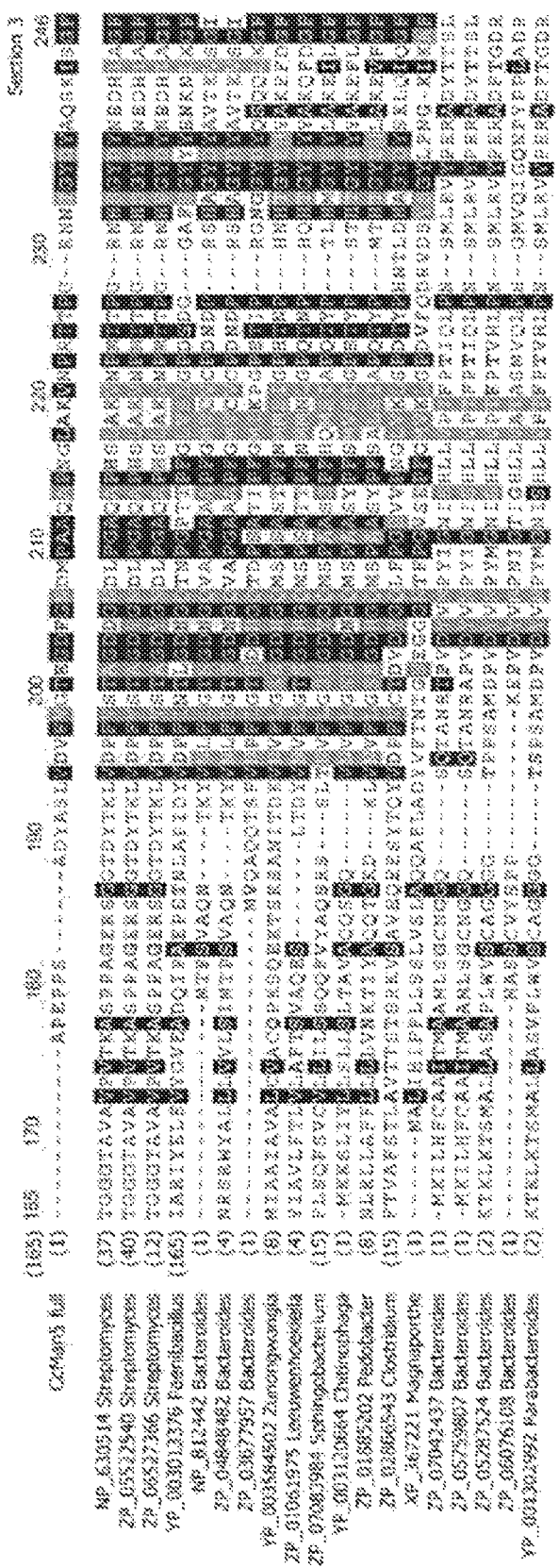
Figures 4, 32:
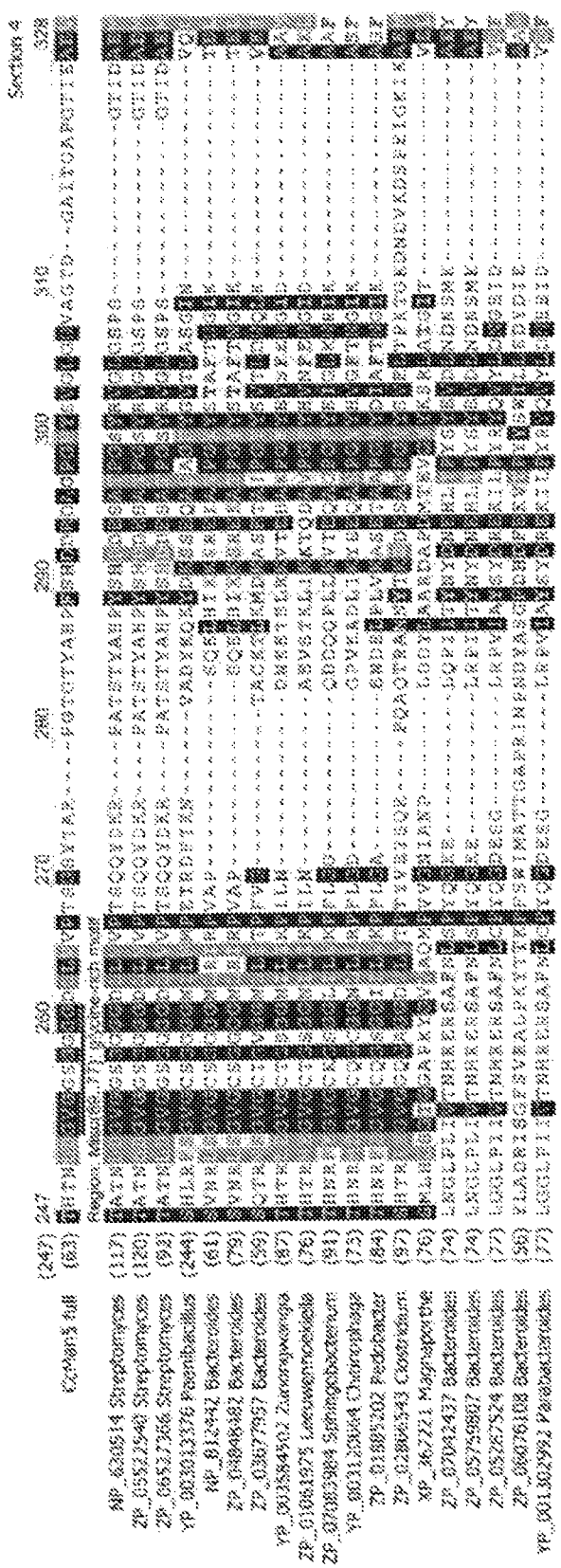
Figures 8, 32:
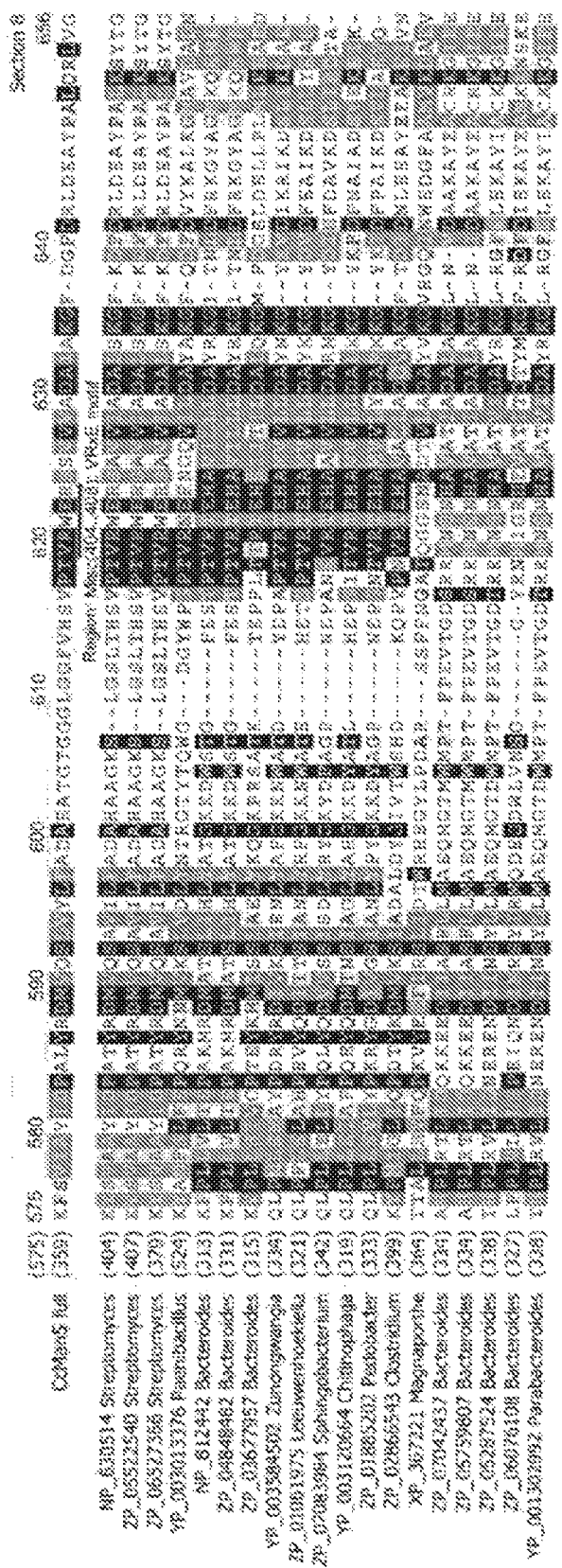
Figures 10, 32:
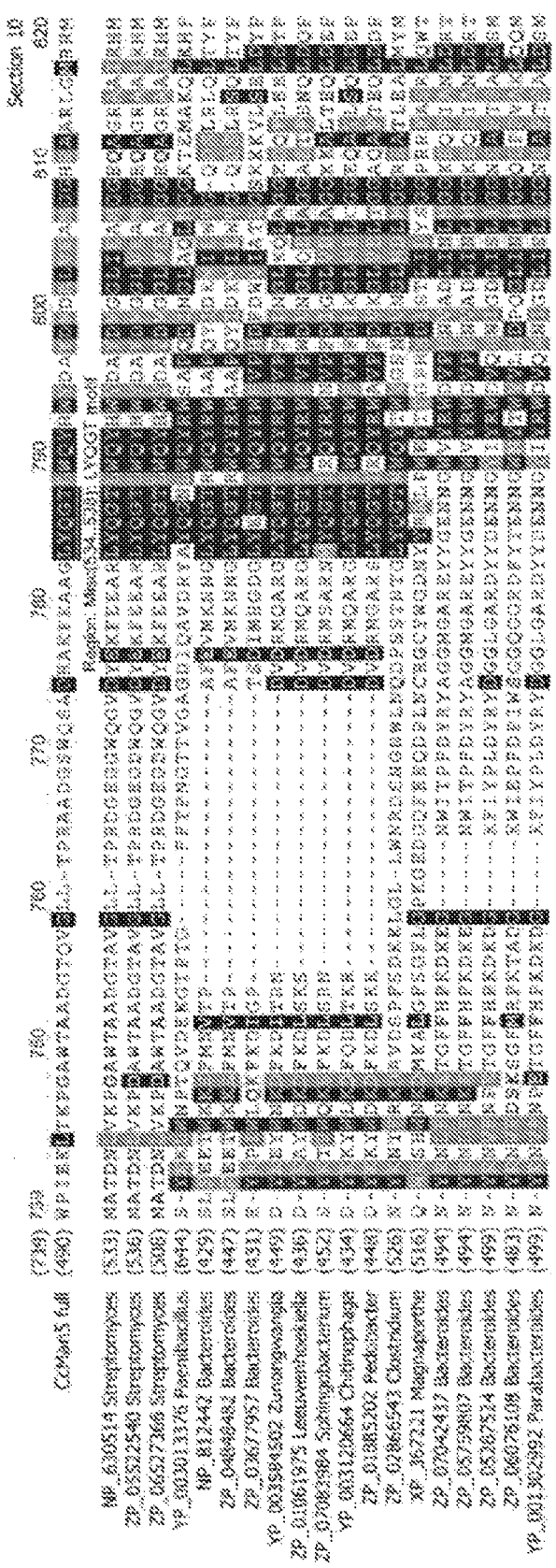

FIG. 10A is the nucleotide sequence (SEQ ID NO:10) encoding CcMan3 (on contig 774) and FIG. 10 B is the amino acid sequence of CcMan3 (SEQ ID NO:11) with signal sequence (in bold). The predicted molecular weight of the CcMan3 polypeptide without the signal sequence is 116 kDa.

FIG. 11A is the nucleotide sequence (SEQ ID NO:12) encoding CcMan4 (on contig 1237) and FIG. 11B is the amino acid sequence of CcMan4 (SEQ ID NO:13) with signal sequence (in bold). The predicted molecular weight of the CcMan4 polypeptide without the signal sequence is 184 kDa.

Figures 12, 32:
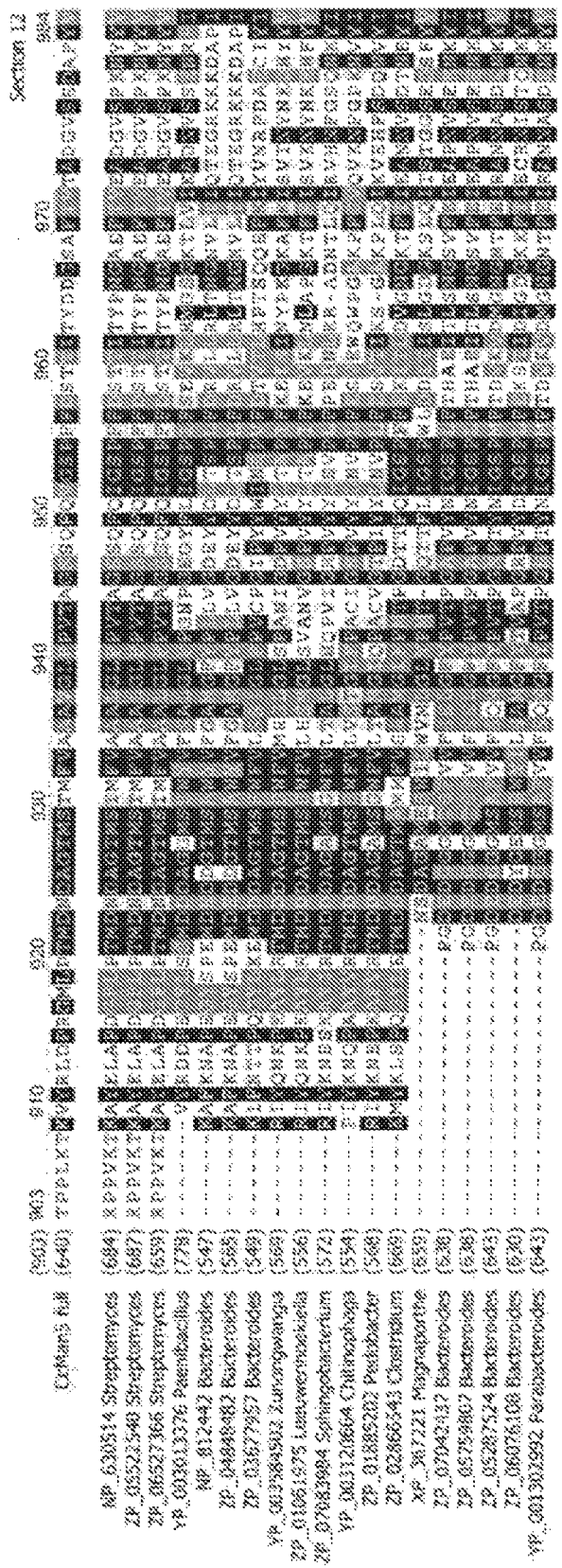
Figures 13, 32:
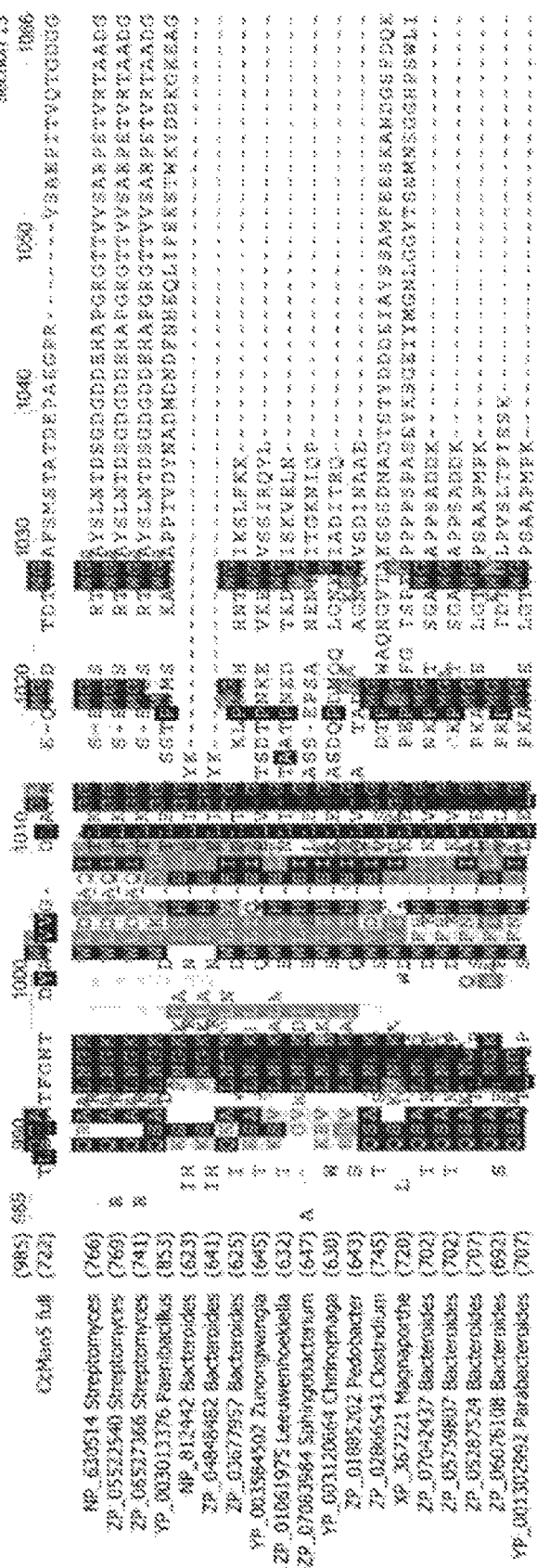
Figures 20, 32:
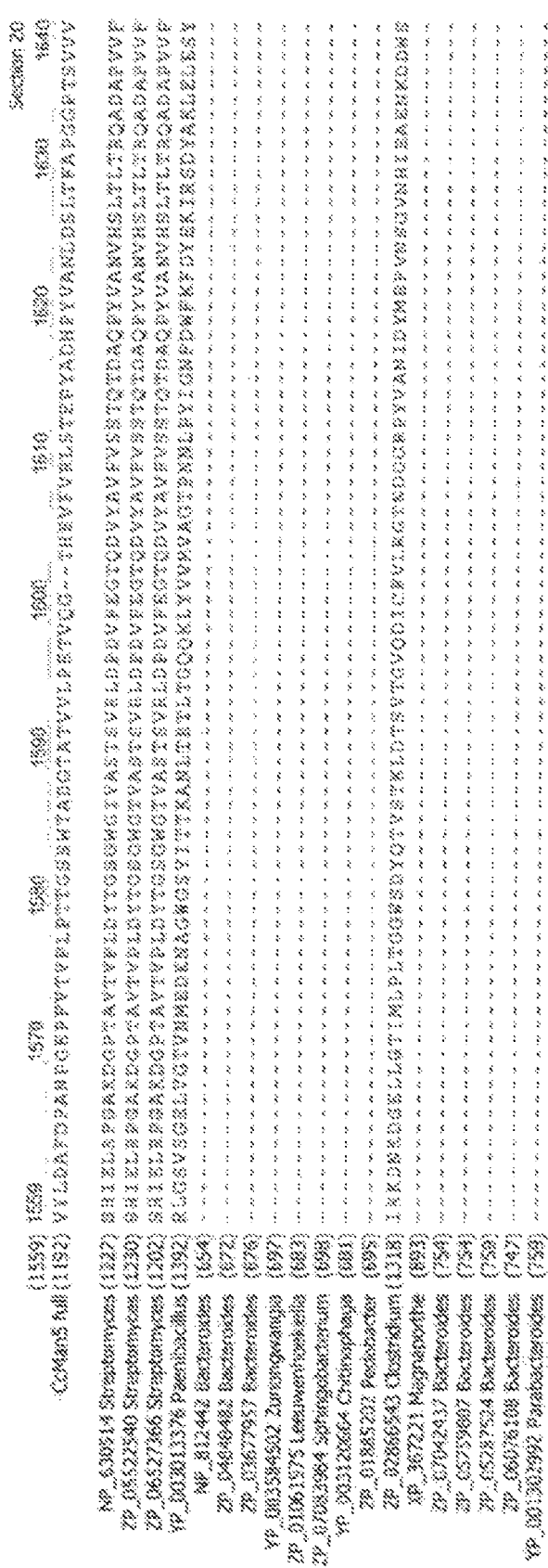

FIG. 12A is the nucleotide sequence (SEQ ID NO:14) encoding CcMan5 (on contig 896). FIG. 12B is the amino acid sequence of CcMan5 with signal sequence (in bold) (SEQ ID NO:15) and FIG. 12C is the amino acid sequence of CcMan5 without signal sequence (SEQ ID NO:50). The predicted molecular weight of the CcMan5 polypeptide without the signal sequence is 173 kDa.

Figure 13:
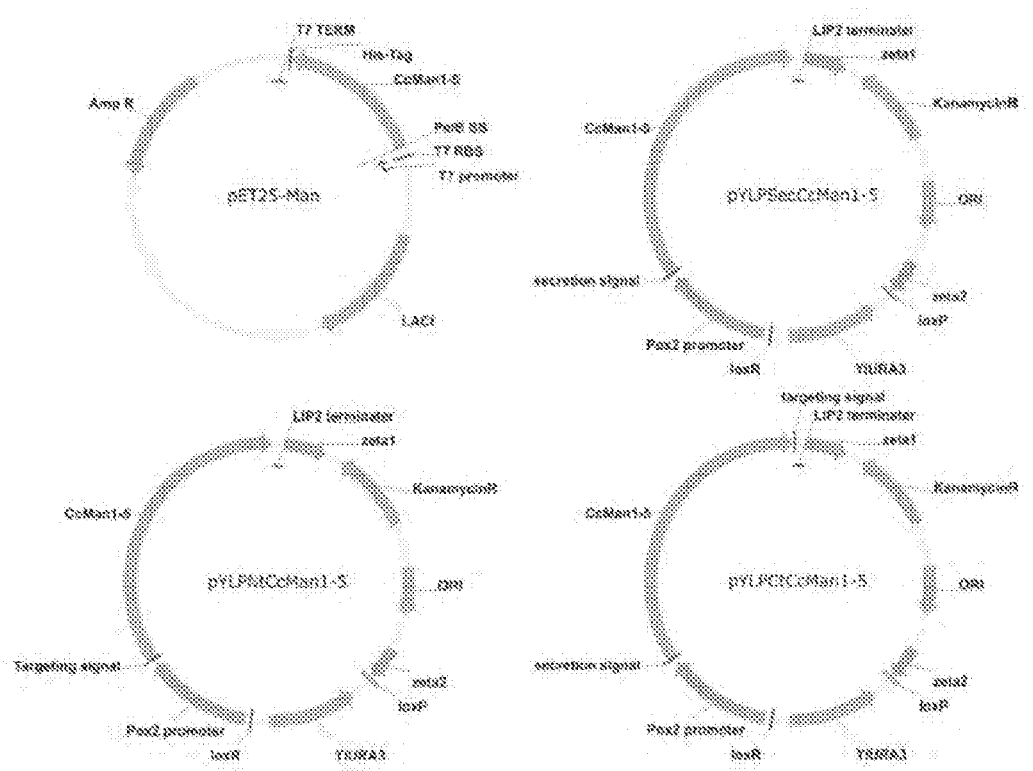

FIG. 13 contains examples of expression plasmids for the expression of CcMan1-5 in the periplasm of *E. coli* (pET25-Man), as secreted proteins in *Yarrowia lipolytica* (pYLP-SecCcMan1-5), as proteins targeted to the secretory pathway of *Yarrowia lipolytica*, tagged to the N-terminus (pYLPNtCcMan1-5) or tagged to the C-terminus (pYLPCtCcMan1-5).

FIG. 14 is the nucleotide sequence of CcMan1 that has been codon optimized for expression in *E. coli* (SEQ ID NO:16).

FIG. 15 is the nucleotide sequence of CcMan2 that has been codon optimized for expression *E. coli* (SEQ ID NO:17).

FIG. 16 is the nucleotide sequence of CcMan3 that has been codon optimized for expression in *E. coli* (SEQ ID NO:18).

FIG. 17 is the nucleotide sequence of CcMan4 that has been codon optimized for expression in *E. coli* (SEQ ID NO:19).

FIG. 18 is the nucleotide sequence of CcMan5 that has been codon optimized for expression in *E. coli* (SEQ ID NO:20).

Figure 19:
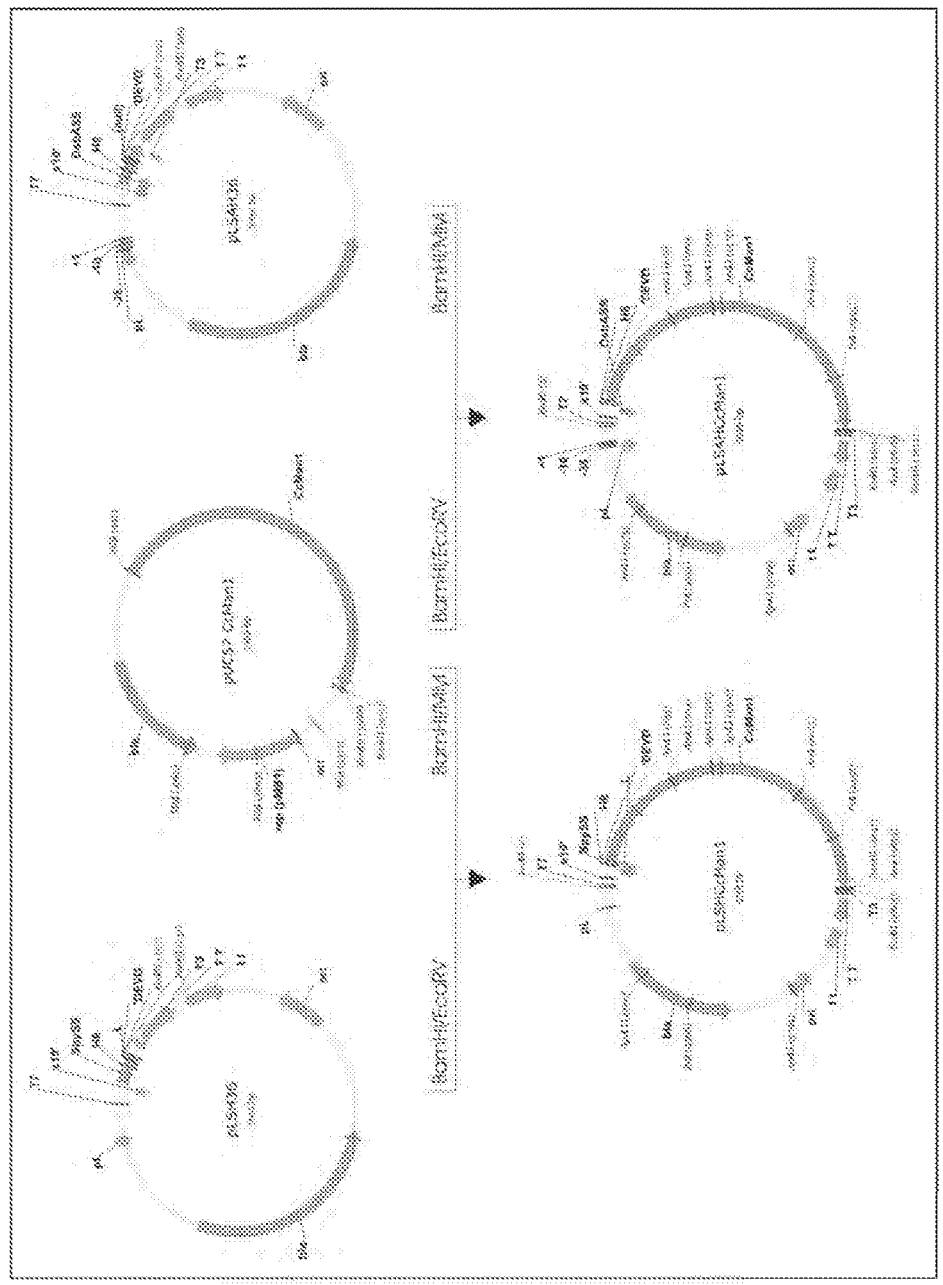

FIG. 19 is a schematic of the pLSAH36 and pLSH36 vectors and the cloning strategy for introducing the *C. cellulans* genes into the vectors.

Figure 20:
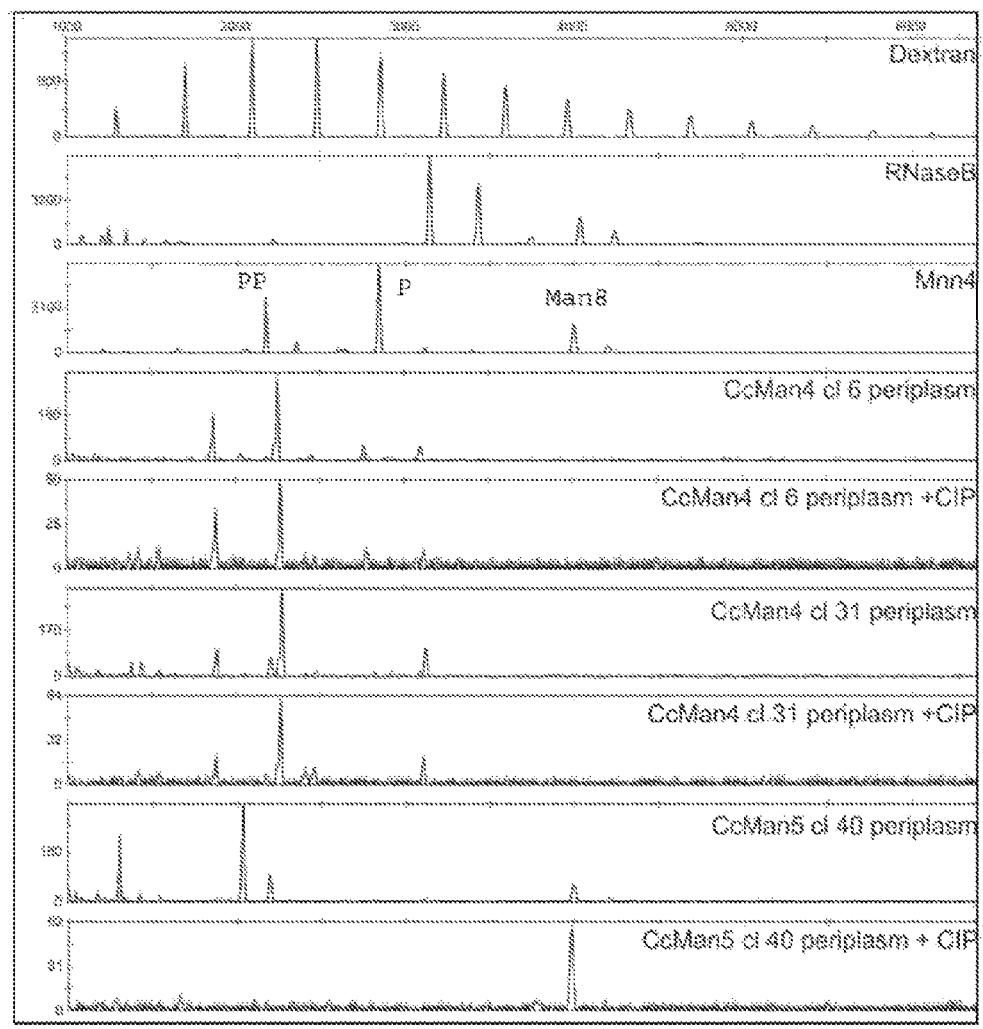

FIG. 20 is a series of electroferograms depicting analysis of the periplasmic fraction of CcMan4 and CcMan5 expressing *E. coli* cells. Analysis was performed using DNA sequencer-assisted, fluorophore-assisted carbohydrate electrophoresis (DSA-FACE). The first and second panels represent the dextran ladder and the sugars from RNaseB, respectively. The third panel is the untreated Mnn4 sugars with "P" corresponding to the mono mannophosphorylated $Man_8GlcNAc_2$ peak, "PP" corresponding to the double mannophosphorylated $Man_8GlcNAc_2$ peak, and "Man8" corresponding to the $Man_8GlcNAc_2$ peak. Panels 4 to 9 are the results obtained with Mnn4 glycans incubated with the indicated periplasm, with or without a subsequent calf intestinal phosphatase (CIP) digest.

Figure 21:
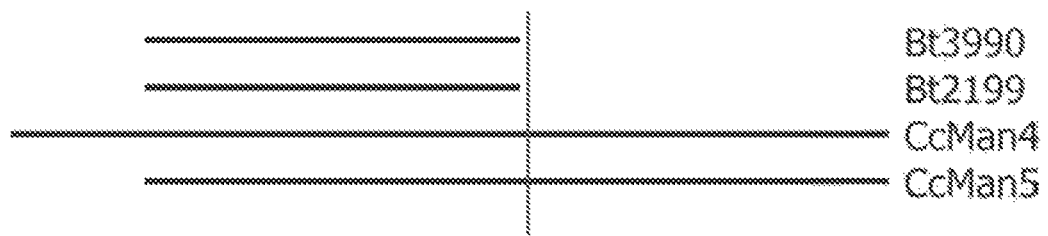

FIG. 21 is a schematic alignment of CcMan4 (1759 AA) and CcMan5 (1650 AA) with Bt3990 (744 AA) and Bt2199 (739 AA) mannosidases described in Zhu et al., *Nat. Chem. Biol.*, 6(2):125-32. Epub 2009 Dec. 27 (2010).

Figure 22:
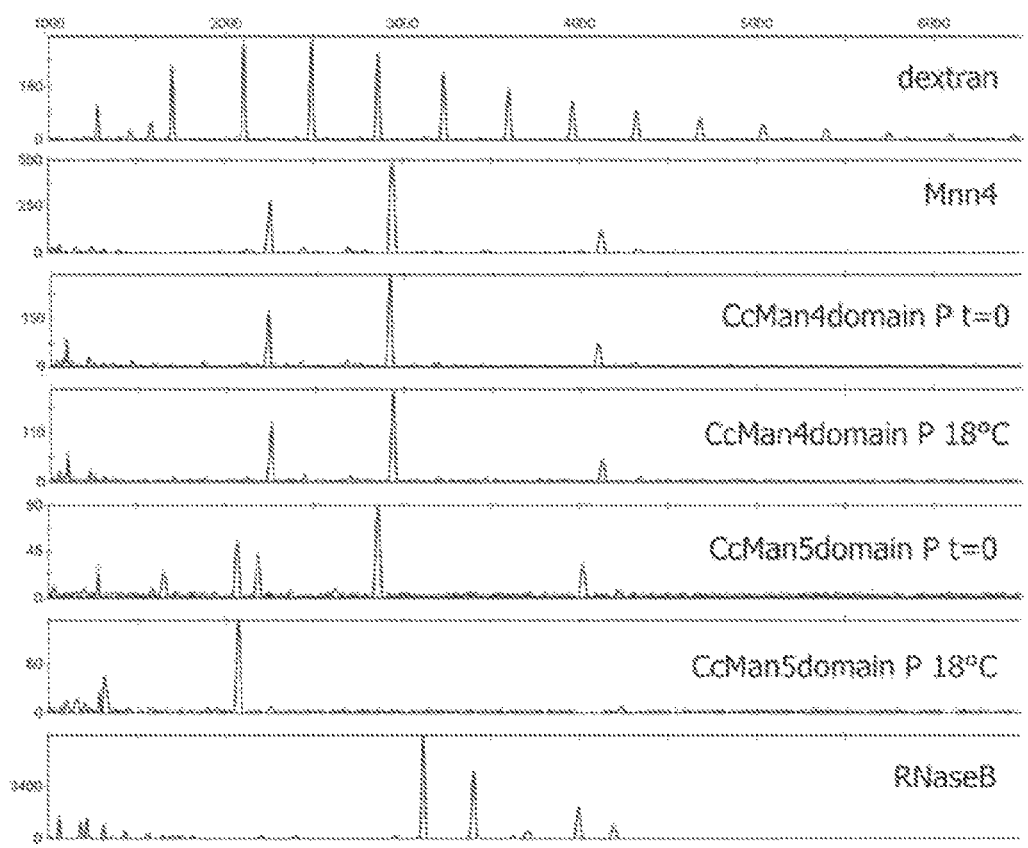

FIG. 22 is a series of electroferograms depicting the analysis of the CcMan4 and CcMan5 enzymes obtained from expressing *E. coli* cells. Analysis was performed using DSA-FACE using MNN4 overexpressing strain derived glycans (referred to as MNN4 glycans or MNN4 sugars) as a substrate. The first panel represents the dextran ladder and the second panel represents the untreated Mnn4 sugars. In the third through sixth panels, the sugars were incubated with the CcMan4domain periplasmic fraction not induced, induced overnight at 18° C. with IPTG, the CcMan5domain periplasmic fraction not induced, and induced overnight at 18° C. with IPTG, respectively. The last panel represents the sugars from RNaseB.

Figure 23:

FIG. 23 is a ribbon representation of $CcMan5_{1-774}$. $CcMan5_{1-744}$ consists of a N-terminal β-sandwich domain (residues 8-271; light gray), an α-helical linker (residues 272-290; black) and a (αα)6 barrel domain (residues 291-771; dark gray). The catalytic Ca2+ is shown as a sphere.

Figure 24:
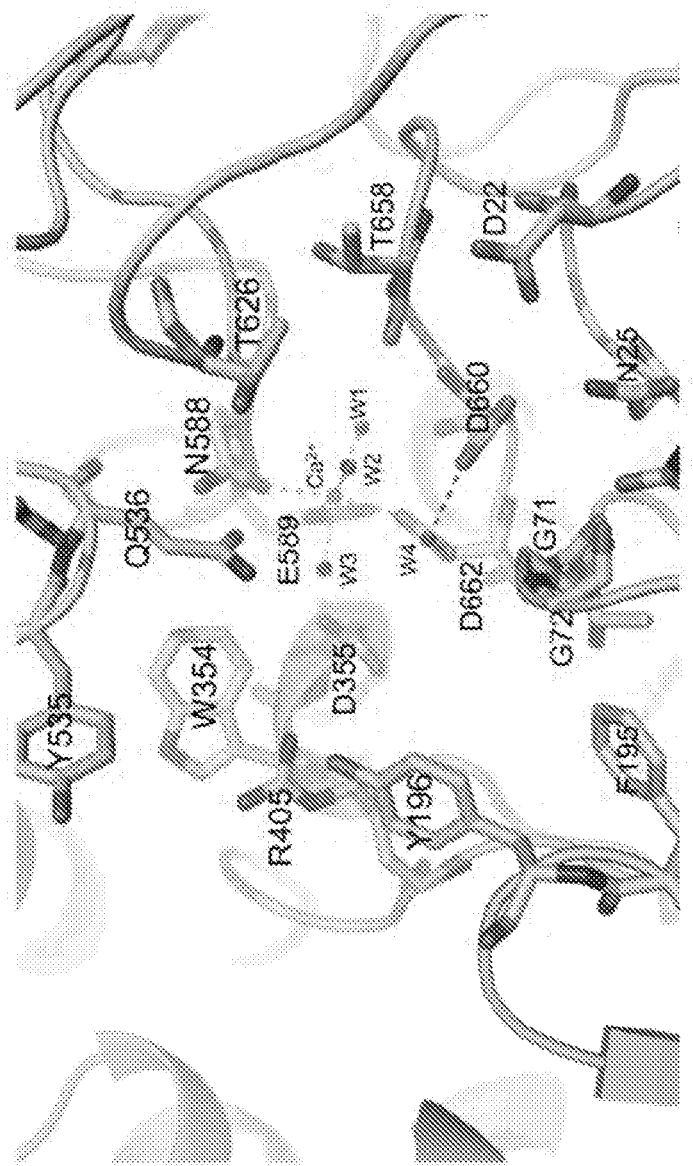

FIG. 24 is a ribbon representation of the $CcMan5_{1-774}$ protein backbone with side chains lining the substrate binding site shown in stick representation. Carbon, oxygen and nitrogen atoms are colored light gray, gray, and dark gray, respectively The $Ca^{2+}$ ion and waters W1, W2, W3 and W4 in the catalytic center are shown as spheres.

Figure 25:
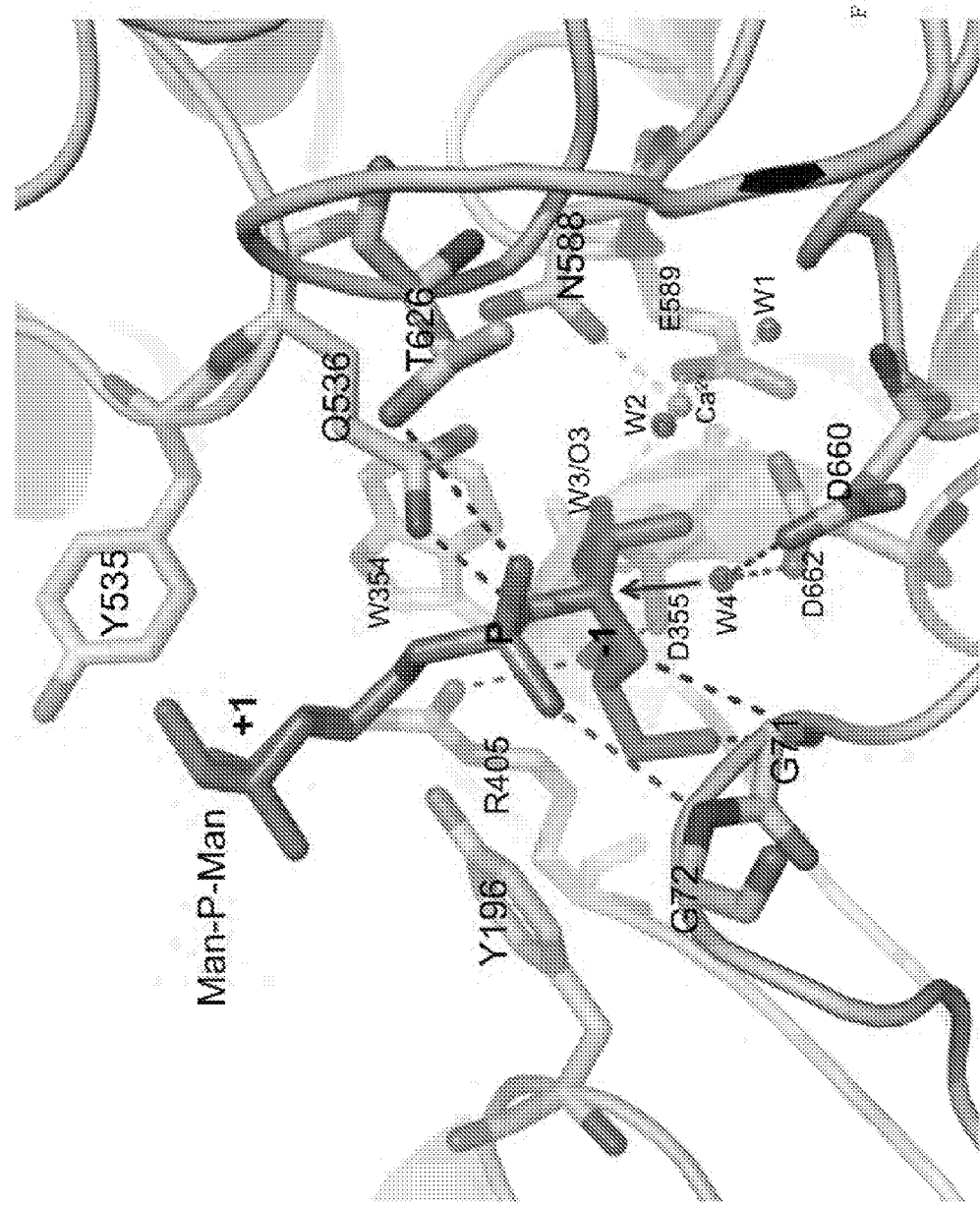

FIG. 25 is a ribbon representation of the $CcMan5_{1-774}$ protein backbone with side chains lining the substrate binding site and the modeled position of mannose-1-phospho-6-mannose (labeled Man-P-Man) shown in stick representation. Carbon, oxygen and nitrogen atoms are coloured light gray, gray, and dark gray, respectively. The Ca2+ ion and water molecules W1, W2, W3 and W4 in the catalytic center are shown as spheres (for comparison, the positions of W2 and W3 which will be displaced by the substrate O2 and O3 hydroxyl groups are still shown). Yellow, red and black dashed lines indicate coordination bonds with Ca2+, H-bonds with the proposed nucleophilic water (W4) and H-binds with the −1 site mannose and phosphate, respectively. The −1 site mannose is modeled in its ground state chair conformation. During catalysis, its O2 hydroxyl will occupy a position nearer that seen for W2, in the equatorial coordination plane of Ca2+ ion, thereby leading to a distortion to a half-chair conformation in the mannose −1 ring and facilitating in line attack of the nucleophilic water (W4) on the C1 carbon (arrow).

FIG. 26A is the *Y. lipolytica* codon optimized nucleotide sequence encoding α-GalactosidaseA with lip2 pre sequence in bold and the Myc His tag underlined (SEQ ID NO:22). FIG. 26B is the amino acid sequence of α-GalactosidaseA with lip2 pre sequence in bold and the Myc His tag underlined (SEQ ID NO:23).

FIG. 27A is the codon optimized nucleotide sequence of human alpha glucosidase (GAA) with lip2 pre sequence in bold (SEQ ID NO:24). FIG. 27B is the amino acid sequence of human GAA with lip2 pre sequence in bold (SEQ ID NO:25), where the * represents the stop codon.

Figure 28:
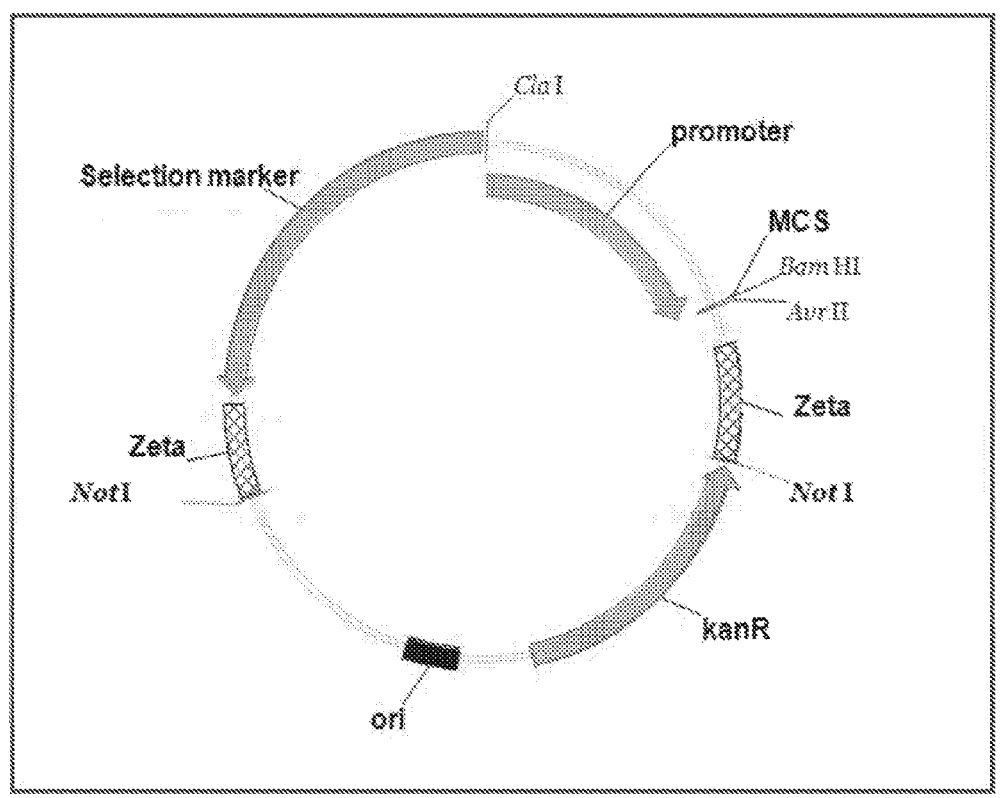

FIG. 28 is a schematic of a *Y. lipolytica* expression vector used for cloning of huGAA.

Figure 29:
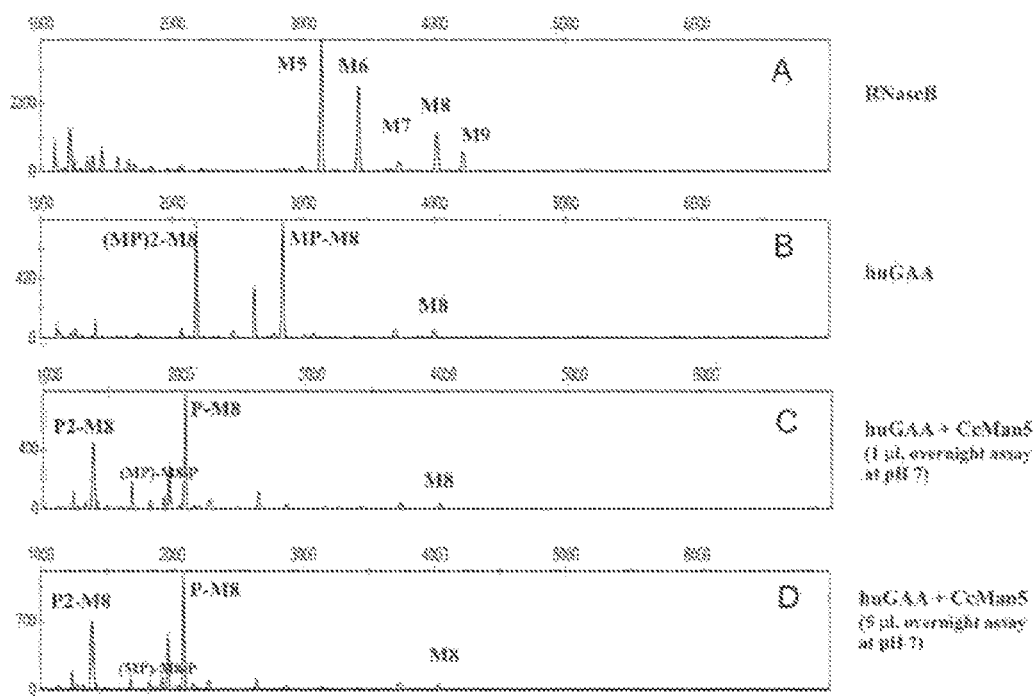

FIG. 29 is a series of electroferograms depicting analysis of treatment of huGAA with CcMan5 derived from the periplasmic fraction of *E. coli* cells. Analysis was performed using DSA-FACE.

Figure 30:
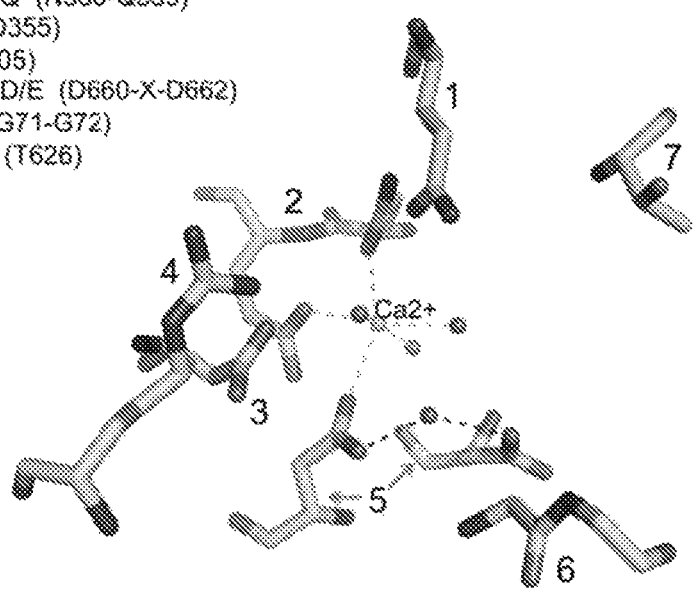

FIG. 30 is a depiction of the minimal catalytic center of CcMan5. The numbering of equivalent residues in SEQ ID NO:50 is given in parenthesis. 1: Q (Q536); 2: N/D-E/Q (N588-Q589); 3: D/E (D355); 4: R(R405); 5: D/E-X-D/E (D660-X-D662); 6: G-G (G71-G72); and 7: T/S/G (T626).

Figures 2, 31:
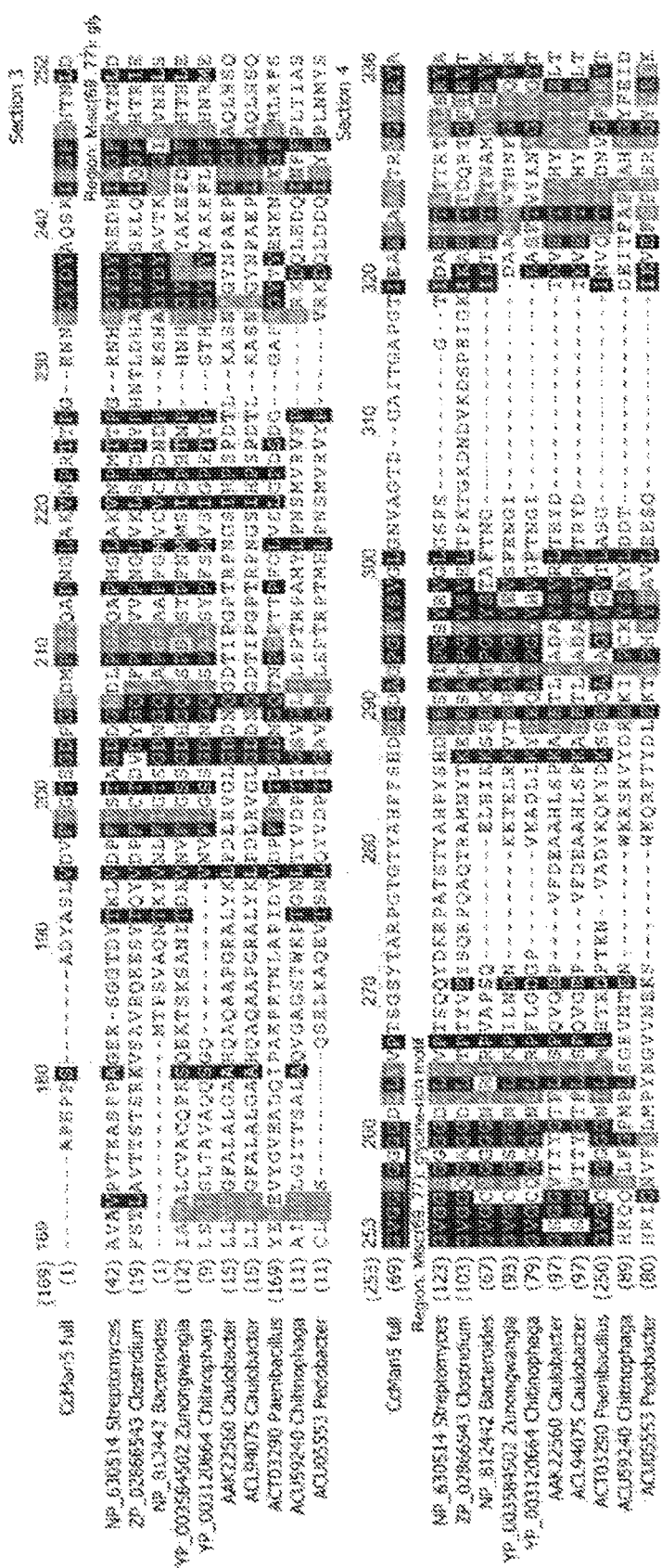
Figures 5, 31:
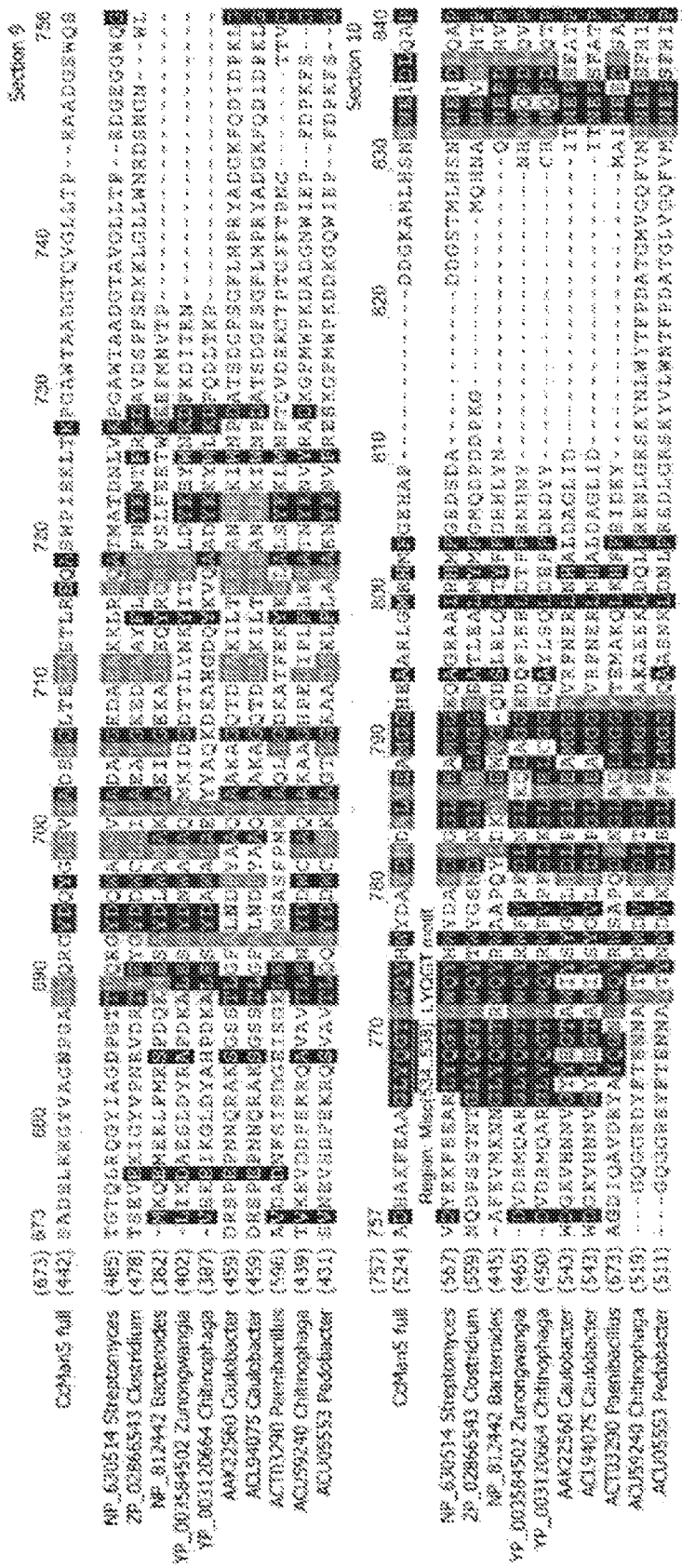

FIG. 31 is an alignment of the amino acid sequence of CcMan5 (SEQ ID NO:50, the amino acid sequence set forth in SEQ ID NO:15 without the signal peptide) and 10 of its homologs using MUSCLE (MUltiple Sequence Comparison by Log-Expectation). NP_630514 *Streptomyces*, SEQ ID NO:26; ZP_02866543 *Clostridium*, SEQ ID NO:27; NP_812442 *Bacteroides*, SEQ ID NO:28; YP_003584502 *Zunongwangia*, SEQ ID NO:29; YP_003120664 *Chitin-*

*ophaga*, SEQ ID NO:30; AAK22560 *Caulobacter*, SEQ ID NO:31; ACL94075 *Caulobacter*, SEQ ID NO:32; ACT03290 *Paenibacillus*, SEQ ID NO:33; ACU59240 *Chitinophaga*, SEQ ID NO:34; ACU05553 *Pedobacter*, SEQ ID NO:35.

FIG. 32 is an alignment of the amino acid sequence of CcMan5 (SEQ ID NO:50) and 19 of its homologs using MUSCLE. *Streptomyces* NP_630514, SEQ ID NO:26; *Streptomyces* ZP_02866543, SEQ ID NO:36, ZP_06527366 *Streptomyces*, SEQ ID NO:37; YP_003013376 *Paenibacillus*, SEQ ID NO:38; NP_812442 *Bacteroides*, SEQ ID NO:28; ZP_04848482 *Bacteroides*, SEQ ID NO:39; ZP_03677957 *Bacteroides*, SEQ ID NO:40; YP_003584502 *Zunongwangia*, SEQ ID NO:29; ZP_01061975 *Leeuwenhoekiella*, SEQ ID NO:41; ZP_07083984 *Sphingobacterium*, SEQ ID NO:42; YP_003120664 *Chitinophaga*, SEQ ID NO:30; ZP_01885202 *Pedobacter*, SEQ ID NO:43; ZP_02866543 *Clostridium*, SEQ ID NO:27; XP_367221 *Magnaporthe*, SEQ ID NO:44; ZP_07042437 *Bacteroides*, SEQ ID NO:45; ZP_05759807 *Bacteroides*, SEQ ID NO:46; ZP_05287524 *Bacteroides*, SEQ ID NO:47; ZP_06076108 *Bacteroides*, SEQ ID NO:48; YP_001302992 *Parabacteroides*, SEQ ID NO:49.

FIG. 33 contains the structural coordinates of the residues surrounding the active site of CcMan5$_{1-774}$.

FIG. 34 contains the protein C alpha atoms and the catalytic Ca2+ atoms of the two CcMan5$_{1-774}$ molecules in the asymmetric unit in PDB entry 2xsg and describes the overall fold of the protein.

DETAILED DESCRIPTION

In general, this document provides methods and materials for hydrolyzing mannose-1-phospho-6-mannose linkages on glycoproteins to produce target molecules (e.g., target proteins) having uncapped phospho-6-mannose (M6P) residues. The methods and materials described herein are particularly useful for producing agents for treating patients with lysosomal storage disorders (LSDs), a diverse group of hereditary metabolic disorders characterized by the accumulation of storage products in the lysosomes due to impaired activity of catabolic enzymes involved in their degradation. The build-up of storage products leads to cell dysfunction and progressive clinical manifestations. Deficiencies in catabolic enzymes can be corrected by enzyme replacement therapy (ERT), provided that the administered enzyme can be targeted to the lysosomes of the diseased cells. Lysosomal enzymes typically are glycoproteins that are synthesized in the endoplasmic reticulum (ER), transported via the secretory pathway to the Golgi, and then recruited to the lysosomes. One way in which lysosomal enzymes are delivered to the lysosome is via a cation-dependent (CD) mannose 6-phosphate receptor (MPR). M6P terminal glycans are recognized in the trans-Golgi network (TGN) by two MPRs that mediate the sorting of lysosomal enzymes from the secretory pathway and deliver the enzyme to the lysosome. Using the methods and materials described herein, a microbial based production process can be used to obtain therapeutic proteins with uncapped M6P glycans, which can be delivered to lysosomes by exploiting the same M6P dependent pathway. Thus, the methods and materials described herein are useful for preparing glycoproteins for the treatment of metabolic disorders such as LSDs.

Mannosidases

This document provides isolated nucleic acids encoding mannosidase polypeptides capable of hydrolyzing terminal mannose-1-phospho-6-mannose linkages on oligosaccharides, as well as isolated mannosidases capable of hydrolyzing terminal mannose-1-phospho-6-mannose linkages on oligosaccharides. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

"Polypeptide" and "protein" are used interchangeably herein and mean any peptide-linked chain of amino acids, regardless of length or post-translational modification. Typically, a polypeptide described herein (e.g., a mannosidase or a target protein having uncapped M6P residues) is isolated when it constitutes at least 60%, by weight, of the total protein in a preparation, e.g., 60% of the total protein in a sample. In some embodiments, a polypeptide described herein consists of at least 75%, at least 90%, or at least 99%, by weight, of the total protein in a preparation.

An "isolated nucleic acid" refers to a nucleic acid that is separated from other nucleic acid molecules that are present in a naturally-occurring genome, including nucleic acids that normally flank one or both sides of the nucleic acid in a naturally-occurring genome (e.g., a yeast genome). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The term "exogenous" as used herein with reference to nucleic acid and a particular host cell refers to any nucleic acid that does not occur in (and cannot be obtained from) that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast.

A nucleic acid encoding a mannosidase can have at least 70% sequence identity (e.g., at least 80%, 85%, 90%, 95%, 97%, 98%, 99%, or 100% sequence identity) to a nucleotide sequence set forth in SEQ ID NO:6, SEQ ID NO:8, SEQ ID NO:10, SEQ ID NO:12, or SEQ ID NO:14. In some embodiments, nucleic acids described herein can encode mannosidase polypeptides that have at least 70% (e.g., at least 75, 80, 85, 90, 95, 99, or 100 percent) identity to an amino acid sequence set forth in SEQ ID NOs: 7, 9, 11, 13, 15, 50. For example, a nucleic acid can encode a mannosidase having at least 90% (e.g., at least 95 or 98%) identity to the amino acid sequence set forth in SEQ ID NO:15 or SEQ ID NO:50, or a portion thereof. For example, a nucleic acid can encode a mannosidase having at least 90% identity to amino acid residues 1 to 774 of SEQ ID NO:50. The percent identity between a particular amino acid sequence and the amino acid sequence set forth in SEQ ID NO:7, SEQ ID NO:9, SEQ ID NO:11, SEQ ID NO:13, SEQ ID NO:15, or SEQ ID NO:50 is determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length mannosidase polypeptide amino acid sequence followed by multiplying the resulting value by 100. For example, an amino acid sequence that has 700 matches when aligned with the sequence set forth in SEQ ID NO:7 is 77.8 percent identical to the sequence set forth in SEQ ID NO:7 (i.e., 700÷900*100=77.8).

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given mannosidase polypeptide can be modified such that optimal expression in a particular species (e.g., bacteria or fungus) is obtained, using appropriate codon bias tables for that species. For example, the nucleic acids set forth in SEQ ID NO:6, SEQ ID NO:8, SEQ ID NO:10, SEQ ID NO:12, or SEQ ID NO:14 can be codon optimized for *E. coli* expression as set forth in FIGS. 14-18 (see SEQ ID NOs:16-20).

Hybridization also can be used to assess homology between two nucleic acid sequences. A nucleic acid sequence described herein, or a fragment or variant thereof, can be used as a hybridization probe according to standard hybridization techniques. The hybridization of a probe of interest (e.g., a probe containing a portion of a CcMan5 nucleotide sequence) to DNA or RNA from a test source is an indication of the presence of DNA or RNA (e.g., a CcMan5 nucleotide sequence) corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

Mannosidase polypeptides capable of hydrolyzing terminal mannose-1-phospho-6-mannose linkages on oligosaccharides also can be identified based on the three dimensional structure described herein for a portion of a mannosidase from *C. cellulans* (residues 1 to 774 of SEQ ID NO:50, also referred to as $CcMan5_{1-774}$). The three dimensional structure can be determined by, for example, X-ray diffraction of a crystal of $CcMan5_{1-774}$. Structural coordinates of $CcMan5_{1-774}$ (e.g., the coordinates of $CcMan5_{1-774}$ deposited with the Protein Data Bank (world wide web at PDB.org under PDB ID No. 2xs), the coordinates set forth in FIG. 33 for the catalytic center of CcMan5, or the coordinates set forth in FIG. 34 for the protein C alpha atoms and the catalytic Ca2+ atoms of the two $CcMan5_{1-774}$ molecules in the asymmetric unit in PDB entry 2xsg) are useful for a number of applications, including, but not limited to, the characterization of a three dimensional structure of a mannosidase capable of hydrolyzing terminal mannose-1-phospho-6-mannose linkages on oligosaccharides, as well as the visualization, identification and characterization of regions of the mannosidase that are involved in acceptance of mannose-6-phosphate-alpha, 1-mannose (hereafter referred to as Man-P-Man) as a substrate, and conferring its ability to hydrolyse Man-P-Man to produce a terminal phospho-6-mannose. "Structural coordinates" are the Cartesian coordinates corresponding to an atom's spatial relationship to other atoms in a molecule or molecular complex. Structural coordinates can be obtained using x-ray crystallography techniques or NMR techniques, or can be derived using molecular replacement analysis or homology modeling. Various software programs allow for the graphical representation of a set of structural coordinates to obtain a three dimensional representation of a molecule or molecular complex. The structural coordinates of the structures described herein can be modified from the original set provided in FIG. 33 or FIG. 34 by mathematical manipulation, such as by inversion or integer additions or subtractions. As such, it is recognized that the structural coordinates of the present invention are relative, and are in no way specifically limited by the actual x, y, z coordinates of FIG. 33 or FIG. 34.

As set forth in Example 8, the structure of CcMan5$_{1-774}$ consists of two domains, an N-terminal β-sandwich domain (residues 8 to 271 of SEQ ID NO:50) and a C-terminal (αα)6 barrel domain (residues 291 to 771 of SEQ ID NO:50), connected via an α-helical linker (residues 272 to 290 of SEQ ID NO:50). The interface between both domains gives shape to a shallow cavity that harbors a conserved catalytic Ca$^{2+}$ ion and gives shape to the −1 substrate binding site (nomenclature as described by Davies et al., *Biochem. J.* 321:557-9 (1997)) and the catalytic center. Residues 22, 25, 71, 72, 195, 196, 354, 405, 535, 536, 588, 589, 626, 658, 660, and 662 of SEQ ID NO: 50 form the substrate binding site.

The three dimensional structure of CcMan5$_{1-774}$ can be characterized in part, or all, using the structural coordinates of PDB ID No. 2xs, or an extract of which that is presented in FIG. 33, comprising the residues surrounding the active site of CcMan5$_{1-774}$, or an extract of which that is presented in FIG. 34, comprising the protein C alpha atoms and the catalytic Ca2+ atoms of the two CcMan5$_{1-774}$ molecules in the asymmetric unit in PDB entry 2xsg, and describing the overall fold of the protein. For example, the three-dimensional structure of CcMan5$_{1-774}$ can be characterized by the structural coordinates of amino acid residues 7 to 771 according to PDB ID No. 2xs, ±a root mean square deviation from the conserved backbone atoms of said amino acids of not more than 2 Å. In some embodiments, the three dimensional structure of CcMan5$_{1-774}$ comprises the complete structural coordinates of the amino acids according to PDB ID No. 2xs, ±a root mean square deviation from the conserved backbone atoms of said amino acids of not more than 2 Å (e.g., not more than 1.5 Å, 1.0 Å or 0.5 Å). As used herein, "root mean square deviation" is the square root of the arithmetic mean of the squares of the deviations from the mean, and is a way of expressing deviation or variation from the structural coordinates described herein. The present disclosure includes all embodiments comprising conservative substitutions of the noted amino acid residues resulting in same structural coordinates within the stated root mean square deviation.

The structural coordinates provided herein can be used to characterize a three dimensional structure of a mannosidase polypeptide. From such a structure, substrate binding sites, for example, can be computationally visualized, identified and characterized based on the surface structure of the molecule, surface charge, steric arrangement, the presence of reactive amino acids, regions of hydrophobicity or hydrophilicity, etc.

In order to use the structural coordinates generated for a structure described herein as set forth in FIG. 33, FIG. 34, or PDB ID No. 2xs, the relevant coordinates can be displayed as, or converted to, a three dimensional shape or graphical representation. Software programs are commercially available that are capable of generating three dimensional graphical representations of molecules or portions thereof from a set of structural coordinates. Examples of commercially available software programs include, without limitation, the following: GRID (Oxford University, Oxford, UK); MCSS (Molecular Simulations, San Diego, Calif.); AUTODOCK (Scripps Research Institute, La Jolla, Calif.); DOCK (University of California, San Francisco, Calif.); Flo99 (Thistlesoft, Morris Township, N.J.); Ludi (Molecular Simulations, San Diego, Calif.); QUANTA (Molecular Simulations, San Diego, Calif.); Insight (Molecular Simulations, San Diego, Calif.); SYBYL (TRIPOS, Inc., St. Louis. MO); and LEAPFROG (TRIPOS, Inc., St. Louis, Mo.).

The structural coordinates described herein can be used with standard homology modeling techniques in order to determine the unknown three-dimensional structure of a molecule or molecular complex. Homology modeling involves constructing a model of an unknown structure using structural coordinates of one or more related protein molecules, molecular complexes or parts thereof. Homology modeling can be conducted by fitting common or homologous portions of the protein whose three dimensional structure is to be solved to the three dimensional structure of homologous structural elements in the known molecule, specifically using the relevant (i.e., homologous) structural coordinates provided by FIGS. 33 and 34 herein. Homology may be determined using amino acid sequence identity, homologous secondary structure elements, and/or homologous tertiary folds. Homology modeling can include rebuilding part or all of a three dimensional structure with replacement of amino acids (or other components) by those of the related structure to be solved. Accordingly, a three dimensional structure for the unknown molecule may be generated using the three dimensional structure of CcMan5$_{1-774}$ described herein, and refined using a number of techniques well known in the art.

Based on the three dimensional structure described herein, substitutions can be made in some of the atoms or side groups of CcMan5$_{1-774}$ or other mannosidases in order to improve or modify its selectivity. For example, CcMan5 contains a non-acidic residue at positions 536 and 588, which may allow the mannosidase to tolerate the phosphate linkage to the anomeric oxygen in Man-P-Man substrates. As such, corresponding residues in other mannosidases can be changed to non-acidic residues to increase the ability of the mannosidase to accept Man-P-Man substrates.

Other mannosidase polypeptide candidates suitable for use herein can be identified by analysis of nucleotide and polypeptide sequence alignments. For example, performing a query on a database of nucleotide or polypeptide sequences can identify homologs and/or orthologs of mannosidase polypeptides. Sequence analysis can involve BLAST, Reciprocal BLAST, or PSI-BLAST analysis of nonredundant databases using known mannosidase amino acid sequences. Those polypeptides in the database that have greater than 40% sequence identity can be identified as candidates for further evaluation for suitability as a mannosidase polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains suspected of being present in mannosidases capable of hydrolyzing terminal mannose-1-phospho-6-mannose linkages, e.g., one or more (e.g., 1, 2, 3, 4 or more) conserved domains or functional regions (e.g., substrate binding cavity). Such domains can include a glycine-rich motif GVGXXGXGG, where X is Gly, Ser, Thr, Val, Ala, Cys or Gln (or other amino acid with a small side chain). This motif is found at residues 69-77 of SEQ ID NO:50. This region makes a loop that provides essential hydrogen bonds to the −1 mannose and phosphate-binding subsite in the active site of the enzyme.

Another example of a conserved motif includes a VRXE motif, where Arg (R) makes a hydrogen bond to the −1 ring and possibly the +1 ring, Glu (E) is in a salt bridge to this R residue, probably shaping this motif; and X is Trp or any of the 20 amino acids except Pro. This motif is found at residues 404-407 of SEQ ID NO:50.

A suitable motif also can be an $X_1YQGX_2$ motif, where $X_1$ can be Leu, Ile, Val Ala, Phe, Tyr or Met, and $X_2$ can be Thr, Ser or Asn. This motif is found at residues 534-538 of SEQ ID NO:50. The Gln (Q) in this motif is important as an E is present in mannosidases that do not have the ability to hydrolyze terminal mannose-1-phospho-6-mannose linkages on oligosaccharides. The Tyr (Y) in this motif also is thought to be important for the +1 site formation.

In addition, a region defined by residues 22, 25, 71, 72, 195, 196, 354, 405, 535, 536, 588, 589, 626, 658, 660, and 662 of SEQ ID NO:50 forms the substrate binding cavity of CcMan5. As a minimal requirement, G71, G72, D355, R405, Q536, N588, Q589, T626, D660, D662 form the catalytic center, where N588, Q589 and D660 are involved in coordinating the catalytic Ca2+ ion, D662 and D660 are involved in activating the nucleophilic water, Q536 stabilizes the anomeric oxygen during the transition state and G71, G71, D355, R405 and T626 are involved in substrate binding at the −1 site. See FIG. 30 for a representation of this minimal catalytic center. As such, a mannosidase can be selected as a candidate mannosidase capable of hydrolyzing terminal mannose-1-phospho-6-mannose linkages when the three dimensional protein coordinates of the atoms in the amino acid side chains located in the minimal catalytic center (e.g., as set forth in FIG. 30) fall within 1.5 Å deviation of the coordinates of the equivalent atoms in FIG. 33.

A conserved motif also can be a GDXGN motif in the N-terminal domain of the protein, where X can be any amino acid except P. This motif is found at residues 21-25 of SEQ ID NO:50 and forms part of the substrate binding pocket of the enzyme as shown in FIG. 24. In particular, the side chains of the D and N line the substrate binding cavity and may shape an alternative subpocket to bind the +1 mannose.

As set forth in Example 14, performing a query on a database of polypeptide sequences identified homologs of CcMan5 in the following organisms: *Streptomyces coelicolor* (GenBank Accession No. NP_630514), *Streptomyces lividans* (GenBank Accession No. ZP_05522540); *Streptomyces lividans* (GenBank Accession No. ZP_06527366); *Clostridium spiroforme* (GenBank Accession No. ZP_02866543), *Bacteroides thetaiotaomicron* (GenBank Accession No. NP_812442), *Zunongwangia profunda* (GenBank Accession No. YP_003584502); *Chitinophaga pinensis* (GenBank Accession No. YP_003120664); *Paenibacillus* sp (GenBank Accession No. YP_003013376); *Bacteroides* sp. (GenBank Accession No. ZP_04848482); *Bacteroides cellulosilyticus* (GenBank Accession No. ZP_03677957); *Leeuwenhoekiella blandensis* (GenBank Accession No. ZP_01061975); *Sphingobacterium spiritivorum* (GenBank Accession No. ZP_07083984); and *Pedobacter* sp. (GenBank Accession No. ZP_01885202). The mannosidases from *Streptomyces coelicolor* and *Streptomyces lividans* are similar (66% sequence identity to the CcMan5 GH92 domain, with 501 identities over 765 aligned residues by BLASTP), not only in the above motifs but also in many the loops of the three dimensional structure.

Isolated nucleic acid molecules encoding mannosidase polypeptides can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

This document also provides (i) biologically active variants and (ii) biologically active fragments or biologically active variants thereof, of the mannosidases described herein. Biologically active variants of mannosidases can contain additions, deletions, or substitutions relative to the sequences set forth in SEQ ID NOs: 7, 9, 11, 13, 15, or 50. Proteins with substitutions will generally have not more than 50 (e.g., not more than one, two, three, four, five, six, seven, eight, nine, ten, 12, 15, 20, 25, 30, 35, 40, or 50) conservative amino acid substitutions. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics. The sequence alignments set forth in FIGS. 31 and 32 provide numerous examples of amino acid substitutions that can be made.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include fusion proteins containing: (a) a mannosidase set forth in SEQ ID NOs: 7, 9, 11, 13, or 15, or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences also can be proteins useful as diagnostic or detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH useful, e.g., in eliciting an immune response for antibody generation) or endoplasmic reticulum or Golgi apparatus retention signals. Heterologous sequences can be of varying length and in some cases can be a longer sequences than the full-length target proteins to which the heterologous sequences are attached.

Biologically active fragments or biologically active variants of the mannosidases have at least 40% (e.g., at least: 50%; 60%; 70%; 75%; 80%; 85%; 90%; 95%; 97%; 98%; 99%; 99.5%, or 100% or even greater) of the mannosidase activity (e.g., uncapping of M6P residues) of the wild-type, full-length, mature protein. For example, a biologically active fragment of a mannosidase can contain residues 1 to 774 of SEQ ID NO:50.

The mannosidases described herein can be used to produce molecules (e.g., target proteins) having uncapped terminal phospho-6-mannose (M6P) residues. The methods can be performed in vitro or in vivo.

In Vitro Methods of Uncapping M6P Residues

A mannosidase described herein can be recombinantly produced and used in vitro to uncap terminal M6P residues on oligosaccharides. To recombinantly produce a mannosidase, a vector is used that contains a promoter operably linked to nucleic acid encoding a mannosidase polypeptide. As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be separate from a promoter sequence and can be, e.g., within an intronic region of a gene or 3' to the coding region of the gene.

As used herein, "operably linked" means incorporated into a genetic construct (e.g., vector) so that expression control sequences effectively control expression of a coding sequence of interest.

Expression vectors can be introduced into host cells (e.g., by transformation or transfection) for expression of the encoded polypeptide, which then can be purified. Expression systems that can be used for small or large scale production of mannosidase polypeptides include, without limitation, microorganisms such as bacteria (e.g., E. coli) transformed with recombinant bacteriophage DNA, plasmid DNA, or cosmid DNA expression vectors containing the nucleic acid molecules, and fungal (e.g., S. cerevisiae, Yarrowia lipolytica, Arxula adeninivorans, Pichia pastoris, Hansenula polymorpha, or Aspergillus) transformed with recombinant fungal expression vectors containing the nucleic acid molecules. Useful expression systems also include insect cell systems infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors (e.g., Ti plasmid) containing the nucleic acid molecules. Mannosidase polypeptides also can be produced using mammalian expression systems, which include cells (e.g., immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids described herein.

Typically, recombinant mannosidase polypeptides are tagged with a heterologous amino acid sequence such FLAG, polyhistidine (e.g., hexahistidine), hemagluttanin (HA), glutathione-S-transferase (GST), or maltose-binding protein (MBP) to aid in purifying the protein. Other methods for purifying proteins include chromatographic techniques such as ion exchange, hydrophobic and reverse phase, size exclusion, affinity, hydrophobic charge-induction chromatography, and the like (see, e.g., Scopes, Protein Purification: Principles and Practice, third edition, Springer-Verlag, New York (1993); Burton and Harding, J. Chromatogr. A 814: 71-81 (1998)).

To produce molecules having uncapped terminal M6P residues in vitro, a target molecule containing a mannose-1-phospho-6 mannose linkage is contacted under suitable conditions with a purified mannosidase or a cell lysate containing a recombinantly produced mannosidase. The cell lysate can be from any genetically engineered cell, including a fungal cell, a plant cell, or animal cell. Non-limiting examples of animal cells include nematode, insect, plant, bird, reptile, and mammals such as a mouse, rat, rabbit, hamster, gerbil, dog, cat, goat, pig, cow, horse, whale, monkey, or human. Upon contacting the target molecule (e.g., an oligosaccharide or glycoprotein) with the purified mannosidase or cell lysate, the mannosidase hydrolyzes the mannose-1-phospho-6 mannose linkage and produces a target molecule having one or more uncapped terminal M6P residues. The methods described in Example 2 can be used to determine if the terminal M6P residues have been uncapped. Following processing by the mannosidase, the target molecule having uncapped terminal M6P residues can be isolated.

Suitable methods for obtaining cell lysates that preserve the activity or integrity of the mannosidase activity in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like.

In some embodiments, a cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) *J. Biol. Chem.* 266(7):4329-4333; Moreau et al. (1991) *J. Biol. Chem.* 266(7):4322-4328; Rexach et al. (1991) *J. Cell Biol.* 114(2):219-229; and Paulik et al. (1999) *Arch. Biochem. Biophys.* 367(2):265-273.

Target molecules, as used herein, refer to any molecule containing terminal mannose-1-phospho-6 mannose linkages or any molecule, when expressed in a cell of fungal origin, that contains mannose-1-phospho-6 mannose linkages. Suitable target proteins include pathogen proteins such as tetanus toxoid or diptheria toxoid; viral surface proteins such as cytomegalovirus (CMV) glycoproteins B, H and gCIII, human immunodeficiency virus 1 (HIV-1) envelope glycoproteins, Rous sarcoma virus (RSV) envelope glycoproteins, herpes simplex virus (HSV) envelope glycoproteins, Epstein Barr virus (EBV) envelope glycoproteins, varicella-zoster virus (VZV) envelope glycoproteins, human papilloma virus (HPV) envelope glycoproteins, Influenza virus glycoproteins, and Hepatitis family surface antigen; lysosomal proteins (e.g., acid alpha glucosidase, alpha galatosidase, glucocerebrosidase, cerebrosidase, or galactocerebrosidase); insulin; glucagons; growth factors; cytokines; chemokines; and antibodies or fragments thereof. Growth factors include, e.g., vascular endothelial growth factor (VEGF), Insulin-like growth factor (IGF), bone morphogenic protein (BMP), Granulocyte-colony stimulating factor (G-CSF), Granulocyte-macrophage colony stimulating factor (GM-CSF), Nerve growth factor (NGF); a Neurotrophin, Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), Epidermal growth factor (EGF), Hepatocyte growth factor (HGF). Cytokines include, for example, interleukins such as IL-1 to IL-33 (e.g., IL-1, IL-2, IL-3, IL-4, IL-5, IL-6, IL-7, IL-8, IL-9, IL-10, IL-12, IL-13, or IL-15)). Chemokines include, e.g., I-309, TCA-3, MCP-1, MIP-1α, MIP-1β, RANTES, C10, MRP-2, MARC, MCP-3, MCP-2, MRP-2, CCF18, MIP-1γ, Eotaxin, MCP-5, MCP-4, NCC-1, Ckβ10, HCC-1, Leukotactin-1, LEC, NCC-4, TARC, PARC, or Eotaxin-2. Also included are tumor glycoproteins (e.g., tumor-associated antigens), for example, carcinoembryonic antigen (CEA), human mucins, HER-2/neu, and prostate-specific antigen (PSA) [Henderson and Finn, *Advances in Immunology*, 62, pp. 217-56 (1996)].

In some embodiments, the target protein can be one associated with a lysosomal storage disorder, which target proteins include, e.g., acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuraminidase, phosphotransferase, acid lipase, acid ceramidase, sphingomyelinase, thioesterase, cathepsin K, and lipoprotein lipase.

In some embodiments, the target proteins are fusion proteins in which the target protein is fused to another polypeptide sequence, or to a polymer, a carrier, an adjuvant, an immunotoxin, or a detectable (e.g., fluorescent, luminescent, or radioactive) moiety. For example, a target protein can be joined to a polymer such as polyethyleneglycol to increase the molecular weight of small proteins and/or increase circulation residence time.

In Vivo Methods of Uncapping M6P Residues

Genetically engineered cells described herein can be used to produce target molecules containing uncapped M6P residues. For example, a cell based method can include the steps of introducing into a fungal cell genetically engineered to include a nucleic acid encoding a mannosidase, a nucleic acid encoding a target molecule, wherein the cell produces the target molecule containing uncapped terminal M6P residues. In some embodiments, the nucleic acids encoding the mannosidase and target molecule contain a secretion sequence such that the mannosidase and target molecule are co-secreted.

Genetically engineered cells described herein contain a nucleic acid encoding a mannosidase and are useful for producing one or more target molecules having uncapped terminal M6P residues. Cells suitable for in vivo production of uncapped M6P residues can be of fungal origin, including *Yarrowia lipolytica*, *Arxula adeninivorans*, methylotrophic yeast (such as a methylotrophic yeast of the genus *Candida*, *Hansenula*, *Oogataea*, *Pichia* or *Torulopsis*) or filamentous fungi of the genus *Aspergillus*, *Trichoderma*, *Neurospora*, *Fusarium*, or *Chrysosporium*. Exemplary fungal species include, without limitation, *Pichia anomala*, *Pichia bovis*, *Pichia canadensis*, *Pichia carsonii*, *Pichia farinose*, *Pichia fermentans*, *Pichia fluxuum*, *Pichia membranaefaciens*, *Pichia membranaefaciens*, *Candida valida*, *Candida albicans*, *Candida ascalaphidarum*, *Candida amphixiae*, *Candida Antarctica*, *Candida atlantica*, *Candida atmospha-erica*, *Candida blattae*, *Candida carpophila*, *Candida cerambycidarum*, *Candida chauliodes*, *Candida corydalis*, *Candida dosseyi*, *Candida dubliniensis*, *Candida ergatensis*, *Candida fructus*, *Candida glabrata*, *Candida fermentati*, *Candida guilliermondii*, *Candida haemulonii*, *Candida insectamens*, *Candida insectorum*, *Candida intermedia*, *Candida jeffresii*, *Candida kefyr*, *Candida krusei*, *Candida lusitaniae*, *Candida lyxosophila*, *Candida maltosa*, *Candida* membranifaciens, Candida milleri, Candida oleophila, Candida oregonensis, Candida parapsilosis, Candida quercitrusa, Candida shehatea, Candida temnochilae, Candida tenuis, Candida tropicalis, Candida tsuchiyae, Candida sinolaborantium, Candida sojae, Candida viswanathii, Candida utilis, Oogataea minuta, Pichia membranaefaciens, Pichia silvestris, Pichia membranaefaciens, Pichia chodati, Pichia membranaefaciens, Pichia menbranaefaciens, Pichia minuscule, Pichia pastoris, Pichia pseudopolymorpha, Pichia quercuum, Pichia robertsii, Pichia saitoi, Pichia silvestrisi, Pichia strasburgensis, Pichia terricola, Pichia vanriji, Pseudozyma Antarctica, Rhodosporidium toruloides, Rhodotorula glutinis, Saccharomyces bayanus, Saccharomyces bayanus, Saccharomyces momdshuricus, Saccharomyces uvarum, Saccharomyces bayanus, Saccharomyces cerevisiae, Saccharomyces bisporus, Saccharomyces chevalieri, Saccharomyces delbrueckii, Saccharomyces exiguous, Saccharomyces fermentati, Saccharomyces fragilis, Saccharomyces marxianus, Saccharomyces mellis, Saccharomyces rosei, Saccharomyces rouxii, Saccharomyces uvarum, Saccharomyces willianus, Saccharomycodes ludwigii, Saccharomycopsis capsularis, Saccharomycopsis fibuligera, Saccharomycopsis fibuligera, Endomyces hordei, Endomycopsis fobuligera, Saturnispora saitoi, Schizosaccharomyces octosporus, Schizosaccharomyces pombe, Schwanniomyces occidentalis, Torulaspora delbrueckii, Torulaspora delbrueckii, Saccharomyces dairensis, Torulaspora delbrueckii, Torulaspora fermentati, Saccharomyces fermentati, Torulaspora delbrueckii, Torulaspora rosei, Saccharomyces rosei, Torulaspora delbrueckii, Saccharomyces rosei, Torulaspora delbrueckii, Saccharomyces delbrueckii, Torulaspora delbrueckii, Saccharomyces delbrueckii, Zygosaccharomyces mongolicus, Dorulaspora globosa, Debaryomyces globosus, Torulopsis globosa, Trichosporon cutaneum, Trigonopsis variabilis, Williopsis californica, Williopsis saturnus, Zygosaccharomyces bisporus, Zygosaccharomyces bisporus, Debaryomyces disporua, Saccharomyces bisporas, Zygosaccharomyces bisporus, Saccharomyces bisporus, Zygosaccharomyces mellis, Zygosaccharomyces priorianus, Zygosaccharomyces rouxiim, Zygosaccharomyces rouxii, Zygosaccharomyces barkeri, Saccharomyces rouxii, Zygosaccharomyces rouxii, Zygosaccharomyces major, Saccharomyces rousii, Pichia anomala, Pichia bovis, Pichia Canadensis, Pichia carsonii, Pichia farinose, Pichia fermentans, Pichia fluxuum, Pichia membranaefaciens, Pichia pseudopolymorpha, Pichia quercuum, Pichia robertsii, Pseudozyma Antarctica, Rhodosporidium toruloides, Rhodosporidium toruloides, Rhodotorula glutinis, Saccharomyces bayanus, Saccharomyces bayanus, Saccharomyces bisporus, Saccharomyces cerevisiae, Saccharomyces chevalieri, Saccharomyces delbrueckii, Saccharomyces fermentati, Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis, or Zygosaccharomyces rouxii. Exemplary filamentous fungi include various species of Aspergillus including, but not limited to, Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus, or Aspergillus versicolor. Such cells, prior to the genetic engineering as specified herein, can be obtained from a variety of commercial sources and research resource facilities, such as, for example, the American Type Culture Collection (Rockville, Md.). Target molecules include proteins such as any of the target proteins described herein (see above).

Genetic engineering of a cell can include, in addition to an exogenous nucleic acid encoding a mannosidase, one or more genetic modifications such as: (i) deletion of an endogenous gene encoding an Outer CHain elongation (OCH1) protein; (ii) introduction of a recombinant nucleic acid encoding a polypeptide capable of promoting mannosyl phosphorylation (e.g, a MNN4 polypeptide from Yarrowia lipolytica, S. cerevisiae, Ogataea minuta, Pichia pastoris, or C. albicans, or PNO1 polypeptide from P. pastoris) to increasing phosphorylation of mannose residues; (iii) introduction or expression of an RNA molecule that interferes with the functional expression of an OCH1 protein; (iv) introduction of a recombinant nucleic acid encoding a wild-type (e.g., endogenous or exogenous) protein having a N-glycosylation activity (i.e., expressing a protein having an N-glycosylation activity); (v) introduction of a recombinant nucleic acid encoding a target molecule described above; or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., by site-directed mutagenesis or homologous recombination) or can be introduced randomly (for example, cells can be chemically mutagenized as described in, e.g., Newman and Ferro-Novick (1987) *J. Cell Biol.* 105(4):1587.

Genetic modifications described herein can result in one or more of (i) an increase in one or more activities in the genetically modified cell, (ii) a decrease in one or more activities in the genetically modified cell, or (iii) a change in the localization or intracellular distribution of one or more activities in the genetically modified cell. It is understood that an increase in the amount of a particular activity (e.g., promoting mannosyl phosphorylation) can be due to overexpressing one or more proteins capable of promoting mannosyl phosphorylation, an increase in copy number of an endogenous gene (e.g., gene duplication), or an alteration in the promoter or enhancer of an endogenous gene that stimulates an increase in expression of the protein encoded by the gene. A decrease in one or more particular activities can be due to overexpression of a mutant form (e.g., a dominant negative form), introduction or expression of one or more interfering RNA molecules that reduce the expression of one or more proteins having a particular activity, or deletion of one or more endogenous genes that encode a protein having the particular activity.

To disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis. A selectable marker can be removed from the genome of the host cell by, e.g., Cre-loxP systems (see below).

Alternatively, a gene replacement vector can be constructed in such a way as to include a portion of the gene to be disrupted, which portion is devoid of any endogenous gene promoter sequence and encodes none or an inactive fragment of the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression vectors can be autonomous or integrative. A recombinant nucleic acid (e.g., one encoding a mannosidase) can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362). Expression vectors can also include an autonomous replication sequence (ARS). For example, U.S. Pat. No. 4,837,148 describes autonomous replication sequences which provide a suitable means for maintaining plasmids in *Pichia pastoris*.

Integrative vectors are disclosed, e.g., in U.S. Pat. No. 4,882,279. Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding a protein having N-glycosylation activity) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., *Yarrowia lipolytica, Arxula adeninivorans, P. pastoris*, or other suitable fungal species) promoter, which enables them to be expressed in fungal cells. Suitable yeast promoters include, e.g., ADC1, TPI1, ADH2, hp4d, PDX, and Gal10 (see, e.g., Guarente et al. (1982) *Proc. Natl. Acad. Sci. USA* 79(23):7410) promoters. Additional suitable promoters are described in, e.g., Zhu and Zhang (1999) *Bioinformatics* 15(7-8):608-611 and U.S. Pat. No. 6,265,185.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

It is understood that other genetically engineered modifications can also be conditional. For example, a gene can be conditionally deleted using, e.g., a site-specific DNA recombinase such as the Cre-loxP system (see, e.g., Gossen et al. (2002) *Ann. Rev. Genetics* 36:153-173 and U.S. Application Publication No. 20060014264).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreekrishna et al. (1987) *Gene* 59:115, the disclosures of each of which are incorporated herein by reference in their entirety. Electroporation and PEG1000 whole cell transformation procedures may also be used, as described by Cregg and Russel, Methods in Molecular Biology: Pichia Protocols, Chapter 3, Humana Press, Totowa, N.J., pp. 27-39 (1998).

Transformed fungal cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*) as described above. The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

In some embodiments, the genetically engineered fungal cell lacks the OCH1 gene or gene products (e.g., mRNA or protein) thereof, and is deficient in OCH1 activity. In some embodiments, the genetically engineered cell expresses a polypeptide capable of promoting mannosyl phosphorylation (e.g., a MNN4 polypeptide from *Yarrowia lipolytica, S. cerevisiae, Ogataea minuta, Pichia pastoris,* or *C. albicans,* or a PNO1 polypeptide from *P. pastoris*). For example, the fungal cell can express a MNN4 polypeptide from *Y. lipolytica* (Genbank® Acccession Nos: XM_503217, Genolevures Ref: YALI0D24101g). In some embodiments, the genetically engineered cell is deficient in OCH1 activity and expresses a polypeptide capable of promoting mannosyl phosphorylation.

Following uncapping of the M6P residues, the target molecule can be isolated. In some embodiments, the target molecule is maintained within the yeast cell and released upon cell lysis. In some embodiments, the target molecule is secreted into the culture medium via a mechanism provided by a coding sequence (either native to the exogenous nucleic acid or engineered into the expression vector), which directs secretion of the molecule from the cell. The presence of the uncapped target molecule in the cell lysate or culture medium can be verified by a variety of standard protocols for detecting the presence of the molecule. For example, where the altered target molecule is a protein, such protocols can include, but are not limited to, immunoblotting or radioimmunoprecipitation with an antibody specific for the altered target protein (or the target protein itself), binding of a ligand specific for the altered target protein (or the target protein itself), or testing for a specific enzyme activity of the altered target protein (or the target protein itself).

In the target molecules produced using the methods described herein, at least 47% (e.g., at least 50, 55, 60, 65, 70, 75, 80, 85, or 90%) of the N-glycans on the glycoprotein have terminal phospho-6-mannose residues. The percentage of N-glycans having terminal phospho-6-mannose residues can be estimated from the peak areas in the DSA-FACE electropherograms. See Example 13.

In some embodiments, following isolation, the uncapped target molecule can be attached to a heterologous moiety, e.g., using enzymatic or chemical means. A "heterologous moiety" refers to any constituent that is joined (e.g., covalently or non-covalently) to the altered target molecule, which constituent is different from a constituent originally present on the altered target molecule. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

Methods for detecting glycosylation of a target molecule include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Optionally, isolated mannoproteins can be further treated with one or more enzymes to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) *Glycobiology* 11(4):275-281 and Freire et al. (2006) *Bioconjug. Chem.* 17(2):559-564.

Cultures of Engineered Cells

This document also provides a substantially pure culture of any of the genetically engineered cells described herein. As used herein, a "substantially pure culture" of a genetically engineered cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Metabolic Disorders

Molecules having uncapped terminal M6P residues can be used to treat a variety of metabolic disorders. A metabolic disorder is one that affects the production of energy within individual human (or animal) cells. Most metabolic disorders are genetic, though some can be "acquired" as a result of diet, toxins, infections, etc. Genetic metabolic disorders are also known as inborn errors of metabolism. In general, the genetic metabolic disorders are caused by genetic defects that result in missing or improperly constructed enzymes necessary for some step in the metabolic process of the cell. The largest classes of metabolic disorders are disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism disorders of mitochondrial function, disorders of peroxisomal function, and lysosomal storage disorders (LSDs).

Examples of metabolic disorders that can be treated through the administration of one or more molecules having uncapped terminal M6P residues (or pharmaceutical compositions of the same) can include hereditary hemochromatosis, oculocutaneous albinism, protein C deficiency, type I hereditary angioedema, congenital sucrase-isomaltase deficiency, Crigler-Najjar type II, Laron syndrome, hereditary Myeloperoxidase, primary hypothyroidism, congenital long QT syndrome, tyroxine binding globulin deficiency, familial hypercholesterolemia, familial chylomicronemia, abeta-lipoproteinema, low plasma lipoprotein A levels, hereditary emphysema with liver injury, congenital hypothyroidism, osteogenesis imperfecta, hereditary hypofibrinogenemia, alpha-1 antichymotrypsin deficiency, nephrogenic diabetes insipidus, neurohypophyseal diabetes insipidus, adenosine deaminase deficiency, Pelizaeus Merzbacher disease, von Willebrand disease type IIA, combined factors V and VIII deficiency, spondylo-epiphyseal dysplasia tarda, choroideremia, I cell disease, Batten disease, ataxia telangiectasias, ADPKD-autosomal dominant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adreno-leukodystrophy, Scott syndrome, Hermansky-Pudlak syndrome types 1 and 2, Zellweger syndrome, rhizomelic chondrodysplasia puncta, autosomal recessive primary hyperoxaluria, Mohr Tranebjaerg syndrome, spinal and bullar muscular atrophy, primary ciliary diskenesia (Kartagener's syndrome), giantism and acromegaly, galactorrhea, Addison's disease, adrenal virilism, Cushing's syndrome, ketoacidosis, primary or secondary aldosteronism, Miller Dieker syndrome, lissencephaly, motor neuron disease, Usher's syndrome, Wiskott-Aldrich syndrome, Optiz syndrome, Huntington's disease, hereditary pancreatitis, anti-phospholipid syndrome, overlap connective tissue disease, Sjögren's syndrome, stiff-man syndrome, Brugada syndrome, congenital nephritic syndrome of the Finnish type, Dubin-Johnson syndrome, X-linked hypophosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharidosis type IV, hereditary familial amyloidosis of Finish, Anderson disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented retinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. In addition, metabolic disorders can also include lysosomal storage disorders such as, but not limited to, Fabry disease, mucopolysaccharidosis I, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis (types II ,III, and IV), cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

Symptoms of a metabolic disorder are numerous and diverse and can include one or more of, e.g., anemia, fatigue, bruising easily, low blood platelets, liver enlargement, spleen enlargement, skeletal weakening, lung impairment, infections (e.g., chest infections or pneumonias), kidney impairment, progressive brain damage, seizures, extra thick meconium, coughing, wheezing, excess saliva or mucous production, shortness of breath, abdominal pain, occluded bowel or gut, fertility problems, polyps in the nose, clubbing of the finger/toe nails and skin, pain in the hands or feet, angiokeratoma, decreased perspiration, corneal and lenticular opacities, cataracts, mitral valve prolapse and/or regurgitation, cardiomegaly, temperature intolerance, difficulty walking, difficulty swallowing, progressive vision loss, progressive hearing loss, hypotonia, macroglossia, areflexia, lower back pain, sleep apnea, orthopnea, somnolence, lordosis, or scoliosis. It is understood that due to the diverse nature of the defective or absent proteins and the resulting disease phenotypes (e.g., symptomatic presentation of a metabolic disorder), a given disorder will generally present only symptoms characteristic to that particular disorder. For example, a patient with Fabry disease can present a particular subset of the above-mentioned symptoms such as, but not limited to, temperature intolerance, corneal whirling, pain, skin rashes, nausea, or dirarrhea. A patient with Gaucher syndrome can present with splenomegaly, cirrhosis, convulsions, hypertonia, apnea, osteoporosis, or skin discoloration.

In addition to the administration of one or more uncapped molecules described herein, a metabolic disorder can also be treated by proper nutrition and vitamins (e.g., cofactor therapy), physical therapy, and pain medications.

Depending on the specific nature of a given metabolic disorder, a patient can present these symptoms at any age. In many cases, symptoms can present in childhood or in early adulthood. For example, symptoms of Fabry disease can present at an early age, e.g., at 10 or 11 years of age.

As used herein, a subject "at risk of developing a metabolic disorder" is a subject that has a predisposition to develop a disorder, i.e., a genetic predisposition to develop metabolic disorder as a result of a mutation in a enzyme such as acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuromimidase, phosphotransferase, acid lipase, acid ceramidase, sphinogmyelinase, thioesterase, cathepsin K, or lipoprotein lipase. Clearly, subjects "at risk of developing a metabolic disorder" are not all the subjects within a species of interest.

A subject "suspected of having a disorder" is one having one or more symptoms of a metabolic disorder such as any of those described herein.

Pharmaceutical Compositions and Methods of Treatment

A target molecule having uncapped M6P residues can be incorporated into a pharmaceutical composition containing a therapeutically effective amount of the molecule and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing molecules with uncapped M6P residues can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted altered N-glycosylation molecule production cells). See, e.g., U.S. Pat. Nos. 4,407,957, 5,798,113, and 5,800,828. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984); microencapsulation (see, e.g., U.S. Pat. Nos. 4,352,883; 4,353,888; and 5,084,350); continuous release polymer implants (see, e.g., Sabel, U.S. Pat. No. 4,883,666); macroencapsulation (see, e.g., U.S. Pat. Nos. 5,284,761, 5,158,881, 4,976,859 and 4,968,733 and published PCT patent applications WO92/19195, WO 95/05452); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

A molecule having uncapped M6P residues suitable for topical administration can be administered to a mammal (e.g., a human patient) as, e.g., a cream, a spray, a foam, a gel, an ointment, a salve, or a dry rub. A dry rub can be rehydrated at the site of administration. Such molecules can also be infused directly into (e.g., soaked into and dried) a bandage, gauze, or patch, which can then be applied topically. Such molecules can also be maintained in a semi-liquid, gelled, or fully-liquid state in a bandage, gauze, or patch for topical administration (see, e.g., U.S. Pat. No. 4,307,717).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a molecule having uncapped M6P residues can be first administered at different dosing regimens. The unit dose and regimen depend on factors that include, e.g., the species of mammal, its immune status, the body weight of the mammal. Typically, levels of a such a molecule in a tissue can be monitored using appropriate screening assays as part of a clinical testing procedure, e.g., to determine the efficacy of a given treatment regimen.

The frequency of dosing for a molecule having uncapped M6P residues is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such molecules or pharmaceutical compositions thereof can be determined by known pharmaceutical procedures in, for example, cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the ED50 with little or no toxicity. The dosage may vary within this range depending upon the dosage form employed and the route of administration utilized. For a pharmaceutical composition used as described herein (e.g., for treating a metabolic disorder in a subject), the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of a molecule having uncapped M6P residues is an amount of the molecule that is capable of producing a medically desirable result (e.g., amelioration of one or more symptoms of a metabolic disorder) in a treated subject. A therapeutically effective amount (i.e., an effective dosage) can includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

A molecule or pharmaceutical composition thereof described herein can be administered to a subject as a combination therapy with another treatment, e.g., a treatment for a metabolic disorder (e.g., a lysosomal storage disorder). For example, the combination therapy can include administering to the subject (e.g., a human patient) one or more additional agents that provide a therapeutic benefit to the subject who has, or is at risk of developing, (or suspected of having) a metabolic disorder (e.g., a lysosomal storage disorder). Thus, the compound or pharmaceutical composition and the one or more additional agents can be administered at the same time. Alternatively, the molecule can be administered first and the one or more additional agents administered second, or vice versa.

It will be appreciated that in instances where a previous therapy is particularly toxic (e.g., a treatment for a metabolic disorder with significant side-effect profiles), administration of a molecule described herein can be used to offset and/or lessen the amount of the previously therapy to a level sufficient to give the same or improved therapeutic benefit, but without the toxicity.

Any of the pharmaceutical compositions described herein can be included in a container, pack, or dispenser together with instructions for administration.

The following are examples of the practice of the invention. They are not to be construed as limiting the scope of the invention in any way.

EXAMPLES

Example 1

Figure 2:
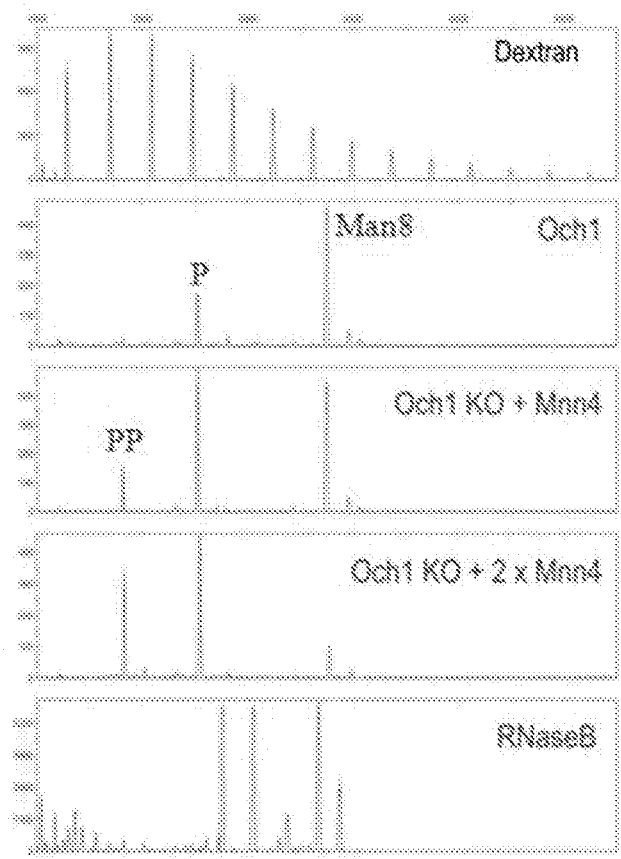
FIG. 2 is a series of electroferograms depicting sugar analysis of MTLY60Δoch1 (1 wild type copy of Mnn4), MTLY60Δoch1+Hp4dMnn4 (1WT+1 extra copy of Mnn4) and MTLY60Δoch1+Hp4dMnn4+TEFMnn4. P represents the monophosphorylated peak, PP represents the diphosphorylated peak, and Man8 represents the $Man_8GlcNAc_2$ peak.

Creation of a *Yarrowia lipolytica* Strain with a Higher Degree of Phosphorylated N-Glycans To upregulate the phosphorylation of glycans in *Y. lipolytica*, strain MTLY60 was transformed with 2 extra copies of the MNN4 gene, each in a separate expression vector. The MNN4 gene is involved in increasing glycan phosphorylation in yeast. FIG. 1 contains a schematic of the pYLTmAX plasmid into which the MNN4 gene was cloned to produce pYLTmAXMnn4, which contains the MNN4 open reading frame under control of the TEF promoter. A strain was made that contains two extra copies of the MNN4 gene, one under control of the hp4d promoter and one under control of the TEF1 promoter. N-glycans were prepared from strain MTLY60Δoch1 (1 wild type copy of MNN4), strain MTLY60Δoch1+Hp4dMNN4 (1WT+1 extra copy of MNN4) and strain MTLY60Δoch1+Hp4dMNN4+TEF-MNN4 (1WT+2 extra copies of Mnn4) and assayed by DNA sequencer-assisted (DSA), fluorophore-assisted carbohydrate electrophoresis (FACE). See, Callewaert et al., *Glycobiology* 11(4):275-281 (2001). Based on the results in FIG. 2, it can be deduced that the mono phosphorylated peak is upregulated in the strain with 1 extra copy and that a peak of double phosphorylation appears. In the strain with 2 extra copies, the double phosphorylated peak was much higher and the peak of neutral $Man_8GlcNAc_2$ sugars was much lower.

Example 2

Identification of a Mannosidase Activity that can Uncap the Capping Mannose Residue Present on Phosphorylated Glycans of Fungal Origin The phosphorylation of sugars by yeast and filamentous fungi results in a mannose-phospho-mannose di-ester linkage (FIG. 3). To obtain a structure where the phosphate is in a mono-ester linkage, a mannosidase is required that is able to hydrolyze the mannose-phosphate linkage, leaving the phosphate attached to the 6 position of a mannose of the high mannose glycan structure. Chiba et al., *Glycobiology*, 12(12):821-8 (2002) indicate that a mannosidase from a *Cellulomonas* species is capable of decapping the mannose. However, Chiba et al. only partially purified the mannosidase protein and could not identify the gene encoding the protein.

A *Cellulosimicrobium cellulans* (also known as *Oerskovia xanthineolytica* and *Arthrobacter luteus*) isolate was obtained from the LMG bacteria collection and tested for production of mannosidase activity. The bacteria were grown at 30° C. and in mannan containing medium to secrete the mannosidase in the medium. Bacterial supernatants (SN) were obtained from the cultures and tested for the desired mannosidase activity by incubating the SN with isolated N-glycans derived from the MNN4 overexpressing strain described in Example 1. After incubation, the glycans were assayed by DSA-FACE (FIG. 4).

After treatment with the SN, glycans gain an additional charge and migrate faster in the electric field and shift to the left hand side of the electroferogram. If these fast-running structures are indeed phosphomonoester-substituted high mannose glycans, they would be larger in size than the neutral products running at the same position. Treatment of such glycans with a phosphatase would result in neutral oligosaccharides that run much slower. As shown in FIG. 5, treatment with calf intestine phosphatase (CIP) resulted in the peaks displaying lower electrophoretic mobility, proving that the phosphates are terminal and that the mannose was decapped.

Example 3

Partial Purification and Further Identification of a Mannosidase

To purify the mannosidase, *C. cellulans* was grown in 1 L of medium B (Bagiyan et al., *Eur. J. Biochem.* 249(1): 286-92 (1997)) or medium A (Chiba et al., 2002, supra). See Table 1. Thereafter, the medium was precipitated with 40% and 80% ammonium sulphate and the samples were analysed by SDS-PAGE. The ammonium sulphate fractions were dialyzed against 20 mM Na-phosphate buffer pH 6.5 with 1 mM CaCl$_2$, and then tested for activity on oligosaccharides derived from a MNN4 overexpressing strain (Example 1).

TABLE 1

Medium components

| Medium A (1 liter) | Medium B (1 liter) |
|---|---|
| 2 g mannan | 2 g mannan |
| 0.5 g (NH$_4$)$_2$SO$_4$ | 2 g (NH$_4$)$_2$SO$_4$ |
| 0.4 g MgSO$_4$•7H$_2$O | 0.02 g MgSO$_4$•7H$_2$O |
| 20 mg FeSO$_4$•7H$_2$O | 1 mg FeSO$_4$•7H$_2$O |
| 60 mg CaCl$_2$•2H$_2$O | 1 g yeast extract |
| 1 g yeast extract | 4.2 g KOH |
| 7.54 g K$_2$HPO$_4$ | 14 g KH$_2$PO$_4$ |
| 2.32 g KH$_2$PO$_4$ | |

Both cultivation conditions resulted in the production of the uncapping activity. Only the 40% ammonium sulphate fraction derived from medium B showed activity, whereas all fractions of the medium A supernatant displayed activity.

The 40% ammonium sulphate sample derived from the medium A cultivation was further purified over a silica-based gel filtration column (FIG. 6). This resulted in a peak with a shoulder around 670 kDa.

All elution fractions were incubated with oligosaccharides derived from a MNN4 overexpressing *Yarrowia lipolytica* strain (described in Example 1) (with or without a following CIP-digest) to test for the phosphate uncapping activity. The decapping and mannosidase activity was observed in all of the samples. Samples were also analyzed on SDS-PAGE (FIG. 7), which showed not just one protein band, but several protein bands. Several bands were cut out from the gel and portions of their sequence analyzed by de novo peptide sequencing using Mass Spectrometry.

The de novo sequencing results revealed several peptide sequences, whichwere compared against the sequences in the non redundant database using BLAST. Peptides with homology to the following proteins were identified: a phosphodiesterase, a hypothetical protein, a putative alpha-1,2 mannosidase (identified peptides shown in Table 2) (homology to a mannosidase from *Magnetospirillum*), and an aminopeptidase Y. The phosphodiesterase was a possible candidate, but here only 2 of the 6 peptides gave a hit. The mannosidase also was a candidate with 3/5 and 5/5 hits for 2 different mannosidases.

TABLE 2

Peptide Sequences

| Peptide Sequence | SEQ ID NO |
|---|---|
| SAYQSFTTR | 1 |
| VWGFSHR | 2 |
| VEGGWLPR | 3 |
| TQGNNFALLLPER | 4 |
| DVHAELTAMAR | 5 |

Example 4

Identification of Mannosidases with the Desired Sequence Based on Whole Genome Sequencing To identify the mannosidase gene coding for the desired activity, the genome of *C. cellulans* was sequenced using a Titanium 454 sequencing (Eurofins MWG Operon). Due to the high GC content, the sequencing was only partial (1.96 Mbases) and of poor quality (with only a low average contig size). The high GC content of the genome that causes loop formation during the emulsion PCR (emPCR), resulting in deletions and very short sequences.

This problem was overcome using new sequencing chemistry for the emPCR that was made available in beta testing by Roche. This gave a much improved sequence (4.7 Mbases), allowing the identification of 5 mannosidase genes belonging to glycosyl hydrolase family 92, one of which (CcMan1, SEQ ID NO:6) corresponds to the sequence from which the peptides described in Example 3 were obtained. No mannosidases from family 38 or 47 were found. The start codon of each of CcMan1-CcMan4 was predicted by Meta-GeneAnnotator (see the world wide web at metagene.cb.k.u-tokyo.ac.jp/metagene/) and compared to Blast results with known genes. The start codon of CcMan5 could not be predicted since it is missing from the sequence. The signal sequence of each gene was predicted with signal P (see the world wide web at cbs.dtu.dk/services/SignalP/) by two methods (neural networks and hidden markov models).

FIGS. 8-12 contain the nucleotide and encoded amino acid sequences of the 5 mannosidase genes from *C. cellulans*.

Example 5

Heterologous Expression of Mannosidase for In Vitro or In Vivo Mannose Decapping In order to allow decapping of the yeast type phosphorylation by the mannosidase, it has to be expressed either heterologously in a different host or in the same fungal host from which the protein for therapeutic use is expressed. In the latter case it can be co-secreted or targeted to an intracellular compartment (e.g., Golgi apparatus or endoplasmic reticulum). This can be accomplished by cloning the gene (be it codon optimised for the target host or not) operably linked after a promoter in an expression vector. The mannosidase can be tagged with an epitope tag to allow easy detection and purification or expressed as such. It can be secreted in the periplasm of a bacterial cell or expressed intracellularly. In case of expression in the fungal host, the sequence can contain a secretion signal or a targeting signal to target the protein to an intracellular compartment or both. Table 3 contains a list of secretion and targeting signals for expression in fungal organisms. Examples of such expression vectors are presented in FIG. 13.

TABLE 3

Secretion and targeting signals for expression in fungal organisms

| | Golgi targeting signal | |
|---|---|---|
| Secretion signals | N-terminal | C-terminal |
| LIP2 prepro | MNN2 | KEX2 |
| LIP2 pre | MNN4 | |
| S.c. α mating factor | MNN6 | |
| XPR2 prepro | MNN1 | |
| XPR2 pre | MNN9 | |
| | OCH1 | |
| | SEC12 | |
| | KRE2 | |

The CcMan1-Man5 genes were codon optimized for expression in *E. coli*. See FIGS. 14-18 for the codon optimized sequences. Table 4 contains the length of each codon optimized nucleotide sequence and the predicted molecular weight of each polypeptide without the signal sequence.

TABLE 4

Codon Optimized Genes

|  | Length (bp) | SEQ ID NO | Size (kDa) of encoded product |
|---|---|---|---|
| CcMan1 | 2613 | 16 | 92.6 |
| CcMan2 | 3483 | 17 | 121.6 |
| CcMan3 | 3363 | 18 | 116 |
| CcMan4 | 5283 | 19 | 184 |
| CcMan5 | 4956 | 20 | 173 |

Example 6

Cloning and Activity of C. Cellulans Glycosyl Hydrolase (GH) Family 92 Enzymes

The CcMan1-CcMan5 codon optimized nucleic acids were cloned into *E. coli* vectors pLSH36, which contains a Spy signal sequence, and/or pLSAH36, which contains a DsbA signal sequence for periplasmic expression. Both pLSH36 and pLSAH36 result in the encoded polypeptide having a polyhistidine tag and a murine caspase-3 site, which can be used for the removal of the His6-tag during purification. FIG. 19 contains a schematic of the pLSH36 and pLSAH36 vectors as well as the cloning strategy for introducing the *C. cellulans* GH92 genes into the vectors. After cloning, the different mannosidases were transformed into *E. coli* BL21+pICa2 expression strain. The transformed strains were grown to an optical density (OD) of 0.5 to 1 and induced with 1 mM isopropyl β-D-1-thiogalactopyranoside (IPTG). Different cell fractions (medium, periplasm, soluble and insoluble fraction) were isolated and analyzed by SDS PAGE and Western blotting with an anti-His6 antibody. For CcMan1, CcMan2, and CcMan3, expression was detected in all fractions. For CcMan4 and CcMan5, expression was the highest in the soluble fraction, but some expression also was detected in the other fractions.

To determine the activity of the CcMan1-CcMan5 proteins, activity tests were performed using methylumbelliferyl alpha mannoside (MUM) as set forth in Chiba et al., 2002, supra. For CcMan1 and CcMan2, the medium and periplasm samples were able to hydrolyze MUM weakly, whereas CcMan3 and CcMan5 were not able to hydrolyze MUM. The soluble fraction of CcMan4 gave the highest fluorescent signal, indicating that CcMan4 is the only mannosidase with α1,2-mannosidase activity.

All medium and periplasmic samples of the 5 different *C. cellulans* mannosidases also were tested on sugars derived from the MNN4 overexpressing strain of Example 1 (referred to herein as MNN4 sugars) to see if they were able to degrade the sugars and uncap the mannose of the mannose-6-phosphate. The sugars were incubated overnight and analysed by DNA sequencer-assisted, fluorophore-assisted carbohydrate electrophoresis (DSA-FACE). The sugar profiles of the medium samples could not be analyzed due to fluorophoric molecules in the medium presentation resulting in irrelevant peaks in the electroferogram. The sugar profiles of the periplasm of CcMan1, CcMan2 and CcMan3 showed neither degradation nor decapping, CcMan4 showed degradation, and CcMan5 showed decapping activity (FIG. 20). A CIP-digest on the decapped sugars confirmed the decapping activity of CcMan5 as the dephosphorylated peaks moved to neutral Man8.

The active mannosidases CcMan4 and CcMan5 were aligned with Bt3990 (744 AA) and Bt2199 (739 AA), family 92 mannosidases with known structure (see Zhu et al., *Nat. Chem. Biol.,* 6(2):125-32. Epub 2009 Dec. 27 (2010)). See FIG. 21. Since only the first part of CcMan4 and CcMan5 aligned with Bt3990 and Bt2199, and because they are large proteins, it was decided to clone the first domain of each protein separately and test the activity. CcMan4domain (1-3357 bp, i.e., nucleotides 1-3357 of SEQ ID NO:20) and CcMan5domain (1-2322 bp, i.e., nucleotides 1-2322 of SEQ ID NO:20) were cloned into the pLSAH36 *E. coli* expression vector. See, FIG. 19 for a schematic of the pLSAH36 cloning vector. The expression vectors were transformed into the *E. coli* BL21+pICa2 expression strain, which was grown to an OD of 0.5 to 1, and induced with 1 mM IPTG. Different cell fractions (medium, periplasm, soluble and insoluble fraction) were isolated and analyzed by SDS PAGE and Western blotting with an anti-His6 antibody. Expression was detected in all 4 cell fractions.

The activity of the domains was tested on Mnn4 sugars. Hereto, the periplasmic fraction of each of the CcMan4domain and CcMan5domain was incubated in the presence of Mnn4 sugars (FIG. 22) and analyzed by DSA-FACE. This experiment showed that the CcMan4domain lost its mannosidase activity since no degradation could be detected (FIG. 22, panel 4). In contrast, the CcMan5domain kept its uncapping activity (FIG. 22, panel 6).

Example 7

Production and Purification of CcMan5 and its Family 92 Homologous Domain

The recombinant CCman5 (nucleotides 1-4995 of SEQ ID NO:20 and CCMan5 domain (nucleotides 1-2322 of SEQ ID NO:20) were expressed in *E. coli* strain BL21codon+pICA2 that were transformed with the expression vectors pLSAH-CcMan5 and pLSAHCcMan5 domain. Expression was induced by IPTG under control of a λpL-promotor (see WO 98/48025 and WO 04/074488). See Example 6 and FIG. 19 for a descriptionof pLSAH. The transformed bacteria were grown in Luria Bertani (LB) medium supplemented with ampicillin (100 μg/ml) and kanamycin (50 μg/ml) overnight at 28° C. before 1/100 inoculation in a 20 liter fermenter provided with LB medium supplemented with ampicillin (100 μg/ml) and 1% glycerol. The initial stirring and airflow was 200 rpm and 1.5 l/min., respectively, and was automatically adapted to keep the pO$_2$ at 30%. The temperature was kept at 28° C. The cells were grown to an optical density of $A_{600\ nm}$=1.0, transferred at 20° C., and expression was induced by addition of 1 mM IPTG overnight. Cells were then harvested and frozen at −20° C. After thawing, the cells were gently resuspended at a concentration of 3 ml/g in 50 mM NaH$_2$PO$_4$ pH 8.0, 300 mM NaCl, 1 mM PMSF and 10 μg/ml DNaseI. The periplasmic fraction was prepared by stirring the cell suspension for 1 h at 4° C. and was isolated by centrifugation at 18,000×g for 30 min. All steps were conducted at 4° C. The clear supernatant was applied to a 20 ml Ni-Sepharose 6 FF column (GE Healthcare), equilibrated with 20 mM NaH$_2$PO$_4$ pH 7.4, 300 mM NaCl, 20 mM imidazole, 0.1% CHAPS. The column was eluted with 20 mM NaH$_2$PO$_4$ pH 7.4, 20 mM NaCl, 400 mM imidazole, 0.1% CHAPS after an extra wash step with 50 mM of imidazole in the same buffer. The elution fraction was diluted 1/10 with 20 mM Tris pH 8.0, 0.1% CHAPS and loaded on an 14 ml Source 15Q column (GE Healthcare) to remove contaminants. After equilibration, the protein of interest was eluted by a linear gradient over 10 column volumes of NaCl from 0 to 1 M in 20 mM Tris, 0.1% CHAPS. The CcMan5 and CcMan5 domain containing fractions were further injected on a HiLoad 26/60 Superdex 200 prep grade with PBS as running solution. The obtained fractions were analyzed by SDS-PAGE and western blotting with an anti-His6 antibody. Finally, the concentration was determined using the BCA assay (Pierce). The purified yield for the full-length CcMan5 protein was 5.7 mg, and for the CcMan5 family 92 domain, it was 110 mg from these 20 L fermentations, showing that the family 92 domain alone can be produced and purified in higher yield. The activity of the purified CcMan5 domain was tested on the Mnn4 isolated sugars as set forth in Example 6. A decapped sugar profile was obtained.

Example 8

Structure of CcMan5Domain

CcMan5$_{1-774}$ (residues 1 to 774 of SEQ ID NO:50, encoded by nucleotides 1-2322 of SEQ ID NO:20; corresponding to the mature protein after removal its natural leader sequence) was expressed in *E. coli* BL21 (DE3) periplasm as a fusion product starting with an N-terminal 6×His tag followed by a 9 amino acid linker (VGPGS-DEVD, SEQ ID NO:21) after the DsbA leader sequence. Cells were cultured in M9 medium containing 100 µg/ml of kanamycin and 100 µg/ml ampicillin at 28 C. At an $OD_{600}$ of 0.4, CcMan5$_{1-774}$ expression was induced by addition of 1 mM IPTG and the culture was further grown overnight at 18° C. Cells from the overnight culture were harvested by centrifugation, washed and incubated for 20 min at 4° C. with buffer containing 20 mM Tris/HCl pH 8.0, 20% sucrose, 5 mM EDTA, and 0.1 mg/ml lysozyme to make spheroplasts. Periplasmic proteins were isolated from spheroplasts by centrifugation at 20,000×g for 20 min. CcMan5$_{1-774}$ was purified from the periplasmic extract by metal ion affinity chromatography (HisTrap HP, GE Healthcare, loading under a buffer containing 50 mM Tris-HCl pH 8.0, 150 mM NaCl, and eluted using an imidazole gradient up to 400 mM), ion exchange chromatography (HiTrap Q FF, GE Healthcare, buffer: 20 mM Tris-HCl pH 8.0, 40 mM NaCl and a NaCl gradient up to 1 M) and hydrophobic interaction chromatography (HiTrap Phenyl HP, GE Healthcare, loading buffer: 20 mM Tris-HCl pH 8.0, 10 mM NaCl, 1 M $(NH_4)_2SO_4$ and eluted using a $(NH_4)_2SO_4$ gradient up to 0 mM).

Purified CcMan5$_{1-774}$ was concentrated to 130 mg/ml in 10 mM Tris-HCl pH 8.0, 10 mM NaCl and plate-like crystals (0.2×0.07×0.01 mm³) were grown by vapor diffusion using a crystallization solution containing 0.2 M Na fluoride, 0.1 M Bis-Tris propane pH 7.5 and 20% PEG 3350. Crystals were briefly transferred into a cryoprotecting solution containing the crystallization solution supplemented with 10% (v/v) glycerol and flash-cooled in liquid nitrogen. Single crystal diffraction data were collected at 100 K at the PXIII beamline at the Swiss Light Source (SLS, Villigen, Swiss) and beamline BM30A at the European Synchrotron Radiation Facility (ESRF, Grenoble, France). The structure of CcMan5$_{1-774}$ was solved using a KAuCl4-soaked crystal for the calculation of experimental phases from a SAD experiment at 11.958 keV, corresponding to the Au L-III absorption edge. FIG. 33 contains the structural coordinates of the catalytic center. The CcMan5 model built from the experimental phases was refined by maximum likelihood methods against 2 Å resolution data collected on a native crystal to a final R- and freeR-factor of 19.3 and 23.9%, respectively. The final model contains 2 CcMan5$_{1-774}$ molecules per asymmetric unit (residues 8 to 771), comprising 11.513 protein atoms, 860 solvent atoms, 2 $Ca^{2+}$ ions and 1 bistris-propane and glycerol molecule each.

Based on sequence similarity, CcMan5 falls within family 92 of glycosyl hydrolases (GH92), which are defined as exo-acting alpha-mannosidases. The X-ray structures for two GH92 family members with α1,2-mannosidase activity are available: Bt3990 and Bt2199 (PDB access codes 2WVX and 2WVY, respectively). The overall fold seen from the CcMan5$_{1-774}$ structure solved here, and deposited as PDB entry 2xsg, corresponds well with that seen in both Bt3990 and Bt2199, with r.m.s.d (root mean standard deviation) values of 1.99 Å and 2.12 Å over 624 and 621 matched Cα atoms, respectively. CcMan5$_{1-774}$ consists of two domains, an N-terminal β-sandwich domain (residues 8 to 271) and a C-terminal (αα)6 barrel domain (residues 291 to 771), connected via an α-helical linker (residues 272 to 290). The interface between both domains gives shape to a shallow cavity that harbors a conserved catalytic $Ca^{2+}$ ion and gives shape to the −1 substrate binding site (nomenclature: Davies et al., *Biochem. J.* 321:557-9 (1997)) and the catalytic center (FIGS. 23 and 24).

GH92 family glycosyl hydrolases are $Ca^{2+}$-dependent alpha-mannosidases that catalyse glycosidic bond hydrolysis through a single displacement mechanism, leading to inversion of the anomeric configuration in the released mannose (Zhu et. al., 2010, supra). In CcMan5$_{1-774}$, the catalytic $Ca^{2+}$ is octahedrally coordinated via the carbonyl oxygen of Asn 588, a carboxyl oxygen of Glu589 and Asp662 each, and three water molecules (W1, W2, W3—see FIG. 23) that lie in the equatorial coordination plane. An additional water molecule (W4) is present near the catalytic center, bound to the carboxyl groups of the conserved pair Asp 660 and Asp 662. The substrate binding cavity surrounding the catalytic $Ca^{2+}$ is lined by the residues Asn 588, Gln 589, Thr 626, Thr 658, Asp 22, Asn 25, Gly 71, Gly 72, Phe 195, Tyr 196, Arg 405, Trp 354, Tyr 535, and Gln536 (FIG. 23).

CcMan5 sets itself apart from other alpha-mannosidases in the GH92 family because of its unique ability to accept mannose-alpha-1-phospho-6-mannose (Man-P-Man) as a substrate and a lack of alpha-1,2-, alpha-1,3-, alpha-1,4- or alpha-1,6-mannosidase activity. In order to obtain insight in the discriminating residues in the CcMan5 active site that give rise to this unique substrate specificity, Man-P-Man was modeled into the CcMan5$_{1-774}$ active site of molecule B of the asymmetric unit (FIG. 25). Positioning of the −1 mannose was based on the gross binding conformation observed in Bt3990 and guided by the positions of two water molecules (W2 and W3) and a glycerol molecule present in the apo active site. In this way, the O2, O3, O4 and O6 hydroxyl groups of the −1 mannose take equivalent positions to those observed for the water molecules W2, W3 and the O1 and O3 hydroxyl groups of the glycerol molecule, respectively. Thus, the mannose-1 O2 and O3 hydroxyl group position in the equatorial plane of the actohedral $Ca^{2+}$ coordination sphere. O3 makes an additional hydrogen bond to the Asp 355 carboxyl group. The latter is further provides a H-bond to the O4 hydroxyl, which also comes within H-bonding distance of the Arg 405 guanidinium group. The O6 hydroxyl and O5 oxygen can be involved in H-bonding with the Gly 71 amide. For modeling, the −1 mannose was retained in its ground state chair conformation. As observed for Bt3990, positioning of the O2 hydroxyl group to come into idealized coordination with $Ca^{2+}$ will lead to a distortion of the sugar ring to a half chair conformation (see FIG. 25). This is in line with the general acceptance that a distortion of the sugar ring during catalysis is required for the nucleophilic substitution at the acetal center in α-mannosides in order to break the 1,2-diaxial interaction of the incoming nucleophile with the O2 hydroxyl (Vocadlo et al., Curr. Opin. Chem. Biol. 12:539-55 (2008)). The obtained model for substrate binding in the −1 site further shows that water molecule W4 lies in a good position to act as nucleophile for in line attack on the acetal carbon. W4 is in H-bond interaction with the carboxyl groups of Asp 660 and Asp 662, which are conserved throughout GH92 enzymes and are proposed to form the base catalyst(s) for activation of the nucleophile. Therefore, the modeled substrate binding at the −1 site and the position of catalytic residues and nucleophile are consistent with the mechanistic requirements for nucleophilic substitution with inversion of the anomeric center in the released mannose. As discussed above, CcMan5 distinguishes itself by the ability to bind and hydrolyse Man-P-Man. The obtained model for Man-P-Man binding to the CcMan5 active site now provides a rationale for these observations. In known GH92 family members, the anomeric oxygen making the glycosidic bond, is in electrostatic interaction with the carboxyl group of a conserved glutamic acid residue (Glu 533 in Bt3990). The glutamic acid residue has been shown to serve as catalytic acid, stabilizing the transition intermediate by binding the anomeric oxygen and protonating the leaving group (Zhu et. al., 2010, supra). In CcMan5, the equivalent residue to Bt3990 Glu 533 is mutated to glutamine, which is not able to serve as a proton donor and therefore explains the loss-of-function in CcMan5 for hydrolysis of mannobiosides. In Man-P-Man substrates, however, the phosphate bound to the anomeric oxygen constitutes a much stronger leaving group that would not require an acid catalyst to protonate the anomeric oxygen, explaining why enzymes like CcMan5 can retain catalytic activity for Man-P-Man substrates. Concomitant with substitution of the catalytic acid, the equivalent of Glu 585 in Bt3990 is replaced by Thr in CcMan5 (Thr 626). In Bt3990, Glu 585 interacts with Glu 533 and has been suggested to regulate the latter's $pK_a$ and/or play a role in binding the leaving group in 2-linked mannosides (Zhu et. al., 2010, supra).

It appears that mutation to non-acidic residues in the Gln 536 and Thr 626 pair alleviates part of the negative electrostatic potential in the binding site, thereby tolerating the phosphate linkage to the anomeric oxygen in Man-P-Man substrates. In CcMan5, the modeled phosphate binding site (P in FIG. 25) is shaped by Thr 626 and the amide of Gly 72, both of which appear able to donate a H-bond to the non-glycosidic oxygens in the phosphate.

Finally, based on the modeled binding of Man-p-Man in the $CcMan5_{1-774}$ active site, the reducing end mannose comes in the vicinity of two tyrosine residues, Tyr 535 and Tyr 196, suggesting the latter to residues form part of the +1 mannose binding site. Both residues lay at the edge of a shallow cleft that could be involved in further interactions with glycans at the reducing end of the glycan tree.

Example 9

Expression of αGalactosidaseA in *Y. Lipolytica*

A nucleic acid encoding human α-GalactosidaseA, without pre and pro sequence, was synthesized with codon optimization for *Y. lipolytica* and addition of a Myc-His tag. The obtained sequence was cloned in frame after the pre sequence of the lip2 gene. The nucleotide sequence of the codon optimized nucleotide sequence (SEQ ID NO:22) is set forth in FIG. 26A; amino acid sequence (SEQ ID NO:23) is presented in FIG. 26B.

*Y. lipolytica* MTLY60 with 2 extra copies of MNN4 and one copy of α-GalactosidaseA was induced in a larger culture to purify over a Ni-NTA column. Thus, they were grown in YTG and induced in oleic acid medium in 2×225 ml (2 L shake flask) during 48 hours. The culture was centrifuged, followed by filtration of the medium over a 0.22 μm filter. The filtered medium was desalted on a sephadex G25 XK50/100 column (GE Healthcare) to 20 mM $NaH_2PO_4$ pH 7.4, 0.5 M NaCl, 20 mM imidazole to remove non-protein disturbing contaminants before purification on Ni-sepharose 6 FF. The desalted protein fraction was loaded on a 4.3 ml Ni-sepharose 6 FF column (GE Healthcare), equilibrated with 20 mM $NaH_2PO_4$ pH 7.4, 0.5 M NaCl, 20 mM imidazole, washed with 50 mM imidazole in the same buffer and eluted with 20 mM $NaH_2PO_4$ pH 7.4, 20 mM NaCl, 400 mM imidazole. Samples 3-10 and 36-49 after the Ni-sepharose column were analysed on SDS-PAGE and Western blotting using an anti-His6 antibody. A protein band of around 50 kDa and of 65 kDa was present on coomassie in samples 40 and 41 was revealed by Coomassie blue staining of the SDS-PAGE gel. In the western blot, only a band of 50 kDa was detected and is most likely the α-GalactosidaseA. The estimated yield of the purified α-GalactosidaseA was 100-125 μg/L culture medium.

The purified sample was used to determine the type of sugars on the recombinant α-GalactosidaseA. The sugars were removed in solution and afterwards labelled with APTS. After cleaning the sample by gel filtration, the sugars were analyzed on DSA-FACE. The expected sugars, the mono mannophosphorylated $Man_8GlcNAc_2$ peak (P) and the double mannophosphorylated $Man_8GlcNAc_2$ peak (PP) were present as major peaks.

Example 10

Expression of Human Alpha Glucosidase in *Y. Lipolytica*

*Y. lipolytica* strain OXYY1589 was constructed that contained three copies of the human alpha glucosidase (also known as acid alpha glucosidase (GAA) or acid maltase EC3.2.1.3) and two copies of the *Y. lipolytica* MNN4 gene. The genotype of strain OXY1589 is as follows:
MatA, leu2-958, ura3-302, xpr2-322,
gut2-744, ade2-844
POX2-Lip2pre-huGAA:URA3Ex::zeta
POX2-Lip2pre-huGAA:LEU2Ex::zeta
POX2-Lip2pre-hGM-CSF: GUTEx::zeta
Y1MNN4-POX2-hp4d-YLMNN4:ADE2::PT targeted All transformations were carried out according to well established protocols with modifications for the different selective markers. In all cases (unless otherwise specified), a huGAA integration fragment has been obtained by NotI restriction digestion in order to remove the kanamycin resistance gene from the expression plasmids. The resulting fragments were all separated by agarose gel electrophoresis followed by Qiagen column purification of the correct huGAA fragment. Strain OXYY1589 was constructed by first cloning human GAA (huGAA) into a *Y. lipolytica* expression vector and constructing a *Y. lipolytica* MNN4 tandem expression vector. Three stable integrative transformations then were performed in order to obtain the final huGAA production strain OXYY1589.

*Y. Lipolytica* Codon Optimized huGAA Expression Vector: The nucleotide sequence encoding the 110 kDA human GAA (huGAA) precursor was chemically synthesized and codon optimized for *Y. lipolytica* expression. In the synthetic construct, the pre- and the pro-huGAA signal peptides were eliminated such that the protein starts at amino acid 57. The synthetic ORF of huGAA (FIG. 27A) is fused in frame at the 5' end to the 3' end of the *Y. lipolytica* LIP2 signal sequence (pre), followed by the coding sequence of two Xxx-Ala cleavage sites and flanked by BamHI and AvrII restriction sites for cloning in expression vector. The construct is under the control of the inducible POX2 promoter. The complete amino acid sequence of the fusion construct is shown on FIG. 27B.

A general scheme of an expression vector is presented in FIG. 28. The bacterial moiety is derived from the plasmid pHSS6, and comprises a bacterial origin of replication (ori) and the kanamycin-resistant gene conferring resistance to kanamycin (KanR). The integration cassette comprises a) the selection marker for transformation to *Yarrowia lipolytica* (URA3; LEU2; GUT2), b) the expression cassette composed of a promoter, c) a multiple cloning site (MCS) to insert huGAA in frame with signal sequence and d) the terminator of the LIP2 gene. The integration cassette is flanked by zeta sequences for stable non-homologous integration into the *Y. lipolytica* genome. Two NotI restriction sites enable the isolation of the expression cassette before transformation. Plasmids pRAN034, pRAN036 and OXYP183 have been used to generate huGAA expression vectors pRAN058, pRAN059 and pRAN060, respectively, containing URA3, LEU2 and GUT2 transformation markers, respectively.

Tandem Y1MNN4 Expression Vector: The Y1MNN4 gene was cloned under control of the inducible pPOX2 promoter and the (semi)constitutive hp4d promoter. These two expression cassettes of Y1MNN4 were subcloned in one vector as a tandem construct carrying flanking regions (PT) of the ADE2 gene for targeted integration into the ADE2 locus of the genome and the ADE2 gene as a selection marker.

Intermediate Strain OXYY1569: The first transformation was a co-transformation of the expression cassette purified from pRAN058 and pRAN059 vectors using URA3 and LEU2 marker to produce intermediate recombinant strain OXYY1569. OXYY1569 carries two expression constructs of huGAA under control of the pPOX2 promoter randomly integrated in the genome of strain G014.

OXYY1569 was selected as follows. PCR screening of genomic DNA was performed in order to confirm the integration of the foreign huGAA DNA into the genome of *Y. lipolytica*. Primers were designed to amplify a fragment of 2552 bp from huGAA nucleotide sequence. Southern blot analysis of the genomic DNA also was performed in order to confirm the integration of at least 2 copies of huGAA DNA. In particular, genomic DNA from OXYY1569 clones were digested with Hind III and probed with huGAA DIG labeled specific probe.

In order to select a clone secreting high levels of huGAA, several randomly selected clones that were identified as positive in the PCR screening and Southern blot were grown in shake flasks under POX2 inducing conditions according to a standard procedure. In all cases, the culture supernatant was collected 72 h post-induction and screened in a standard Western blot and enzyme activity assay analysis. N-Glycan analysis of OXYY1569 indicated the predominant structure in OXYY1569 is $Man_8GlcNAc_2$.

Intermediate Strain OXYY1584: Recombinant strain OXYY1569 was transformed in order to integrate two copies of the *Y. lipolytica* MNN4 gene into its genome to produce OXYY1584. The transformation was performed with a SacII/XmaI derived expression cassette excised from plasmid OXYP1479B. The expression cassette was designed for targeted integration into the ADE2 locus of *Y. lipolytica* genome. The recombinant strain was selected after Southern blotting and glycan analysis to evaluate the strain behavior with respect to the increased phosphorylation. Genomic DNA of several arbitrary chosen transformants was SpeI digested and probed with MNN4 specific DIG labeled probe. Correct targeted integration of MNN4 expression cassette into the ADE2 locus of *Y. lipolytica* genome should give 4207 bp and 5683 bp bands. Southern blot positive clones were grown in a standard shake flask procedure. N-glycan analysis of secreted proteins was performed in order to select the intermediate clone OXYY1584. Compared to the parent stain OXXY1569, the predominant structures after MNN4 over-expression are $Man_8GlcNAc_2$ $(PMan)_1$ and $Man_8GlcNAc_2$ $(PMan)_2$.

Production Strain OXYY1589:- To generate the final prototrophic production strain OXYY1589, a third copy of huGAA was integrated into the genome of recombinant OXYY1584 strain. The transformation was performed with Not I excised expression cassette from pRAN069. Transformants were first screened by PCR on gDNA for presence of the additional copy of huGAA. To evaluate huGAA production arbitrary selected PCR positive clones were further analyzed for expression after a standard shake flask cultivation. The clone expressing the highest level of huGAA (OXYY1589) was chosen after Western blot analysis and enzymatic activity assay. It also was reconfirmed that the conversion levels of M8 to MP2-M8 and MP-M8 N-glycans was not influenced by the presence of the additional huGAA expression cassette.

Example 11

Fed Batch Cultivation of Strain OXYY1589

To produce huGAA from strain OXYY1589 (Example 10), a fed batch process was established using a 10 L stirred tank, with a working volume of 6-8 liters. The process was divided in two phases:

1) Batch growth on glucose for biomass formation
2) Product formation by induction with help of a limited oleic acid feed. Typically the batch phase was about 20 hours (h) and the production phase approximately 72 hours. At the end of the process, the culture broth was centrifuged and the supernatant was collected. The supernatant was used as starting material for the purification of the GAA (see Example 12).

The following parameters were controlled during the fermentation. Aeration was maintained at a constant value of 1.5 vvm air (volume per volume per minute). Dissolved oxygen (DO) was initially kept at 30%. The stirring was increased from 600 to 1200 rpm depending on the DO levels. Once it reached the maximum of 1200 rpm, this speed was kept constant and the DO-setpoint was set to 10%. To maintain 10% DO, oxygen was spiked into the reactor with a maximal percentage of 50%. Foam evolution was controlled by a foam probe. In case of foam detection, antifoam was added to the bioreactor. The pH was controlled by adding 14% (v/v) ammonia (base) or 10% phosphoric acid to maintain a constant value of pH 6.8. The temperature was kept constant at 28° C. throughout the whole process.

Biomass was monitored by measurement of optical density at 600 nm (OD600). The samples were diluted 2-1000 times in distilled water to obtain values in the linear range of the spectrophotometer. Product formation was detected by Western blot analysis and specific enzymatic activity tests.

Example 12

Purification of Recombinant huGAA (rhGAA)

The supernatant after cultivation (see Example 11) was clarified via depth filtration. The resulting material was then concentrated 20 times via TFF and diafiltered against 20 mM sodium phosphate pH 6 and 100 mM NaCl on a 10 kDa MWCO membrane (Millipore).

Purification of rhGAA was start by adding ammonium sulphate up to a concentration of 1 M. After centrifugation, the supernatant was loaded on a Toyopearl-Phenyl 650M (Tosoh Biosciences) packed XK16/40 column. A linear gradient from 1 to 0 M ammonium sulphate was applied for elution. Those fractions that contain rhGAA were then pooled and subjected to a buffer exchange into 10 mM BIS-TRIS pH 6. Further purification was achieved via anion exchange chromatography on a source 30Q packed Tricorn 10/50 or XK25/20 column (GE Healthcare) using a linear salt gradient from 0 to 1 M NaCl. The resulting GAA-containing fractions were then concentrated before loading onto a final Hiload 16/60 superdex 200 gel filtration column (GE Healthcare) that was pre-equilibrated with 50 mM sodium phosphate pH 6 and 200 mM NaCl. Fractions were selected on the basis of specific activity and purity on Coomassie-stained SDS-PAGE gels and then combined and concentrated to a final concentration of 5-10 mg/ml. Protein concentration was done on 15 ml Amicon Ultra centrifugal devices (Millipore) with a MWCO of 10 kDa.

The reactions for the qualitative screening for rhGAA were started by adding the reaction buffer consisting of 0.35 mM 4-MUG, 0.1% BSA and 100 mM sodium acetate pH 4 in a 10:1 or 20:1 volume proportion to 10 or 5 µl of elution fraction. All reactions were done in 96-well flat-bottom microtiter plates. After an incubation period of 30 minutes to 1 hour at 37° C., an equal volume of 100 mM glycine pH11 was added to stop the reaction and the release of the fluorogenic reaction product 4-methylumbelliferone was observed under UV-light. Specific activities (units/mg protein) were determined using a colorimetric assay with the synthetic substrate p-nitrophenyl-α-D-glucopyranoside (PNPG) that measures the enzymatic release of the yellow coloured p-nitrophenolate reaction product. The reactions were started by mixing 10 µl of enzyme solution and 90 µl of substrate reaction buffer (2 mM PNPG in 150 mM citrate-phosphate buffer pH4, 1% BSA) in reaction wells of a microtiterplate and were subsequently incubated at 37° C. After 1 to 2 hours an equal volume of stop buffer, 10% sodium carbonate pH 12, was added to quench the reaction and bring the released p-nitrophenol (PNP) in its ionized state. Background-corrected absorbances and p-nitrophenolate standards were measured at a wavelength of 405 nm and specific activities were calculated. Protein concentrations were determined with the bicinchoninic acid (BCA) method. One unit was defined as the amount of enzyme that catalyzes the conversion of 1 nmol of PNPG to 1 nmol PNP and D-glucose per min at 37° C. at a final substrate concentration of 2 mM in a citrate-phosphate buffer, pH 4.0.

Example 13

Phosphate Uncapping Activity of Heterologously Expressed CcMan5 on Glycoproteins Expressed in a Y. Lipolytica Strain with a Higher Degree of Phosphorylated N-Glucans The huGAA was expressed in Y. lipolytica strain OXYY1589 to yield a glycoprotein with a high degree of phosphorylated N-glycan structures (see Example 10). The huGAA was purified as described in Example 12.

CcMan5 (1 and 5 µl respectively at a concentration of 70 µg/ml) was added to a solution of 4 µg huGAA in 100 mM HEPES buffer pH 7.0 with 2 mM $CaCl_2$. The 20 µl reaction mixture was incubated overnight at room temperature. The N-glycans were released with PNGaseF, labelled with APTS and subsequently analysed on DSA-FACE, essentially as described in Laroy W. et al., *Nature Protocols*, 1: 397-405 (2006). The N-glycan profiles before and after CcMan5 treatment are shown in FIG. 29. The N-glycan mixture released from purified huGAA is mainly composed of ManP-Man8GlcNAc$_2$ and (ManP)2-Man8GlcNAc$_2$ (FIG. 29, panel B). A peak running slightly faster than ManP-Man8GlcNAc$_2$ can be assigned to ManP-Man7GlcNAc$_2$. Only very minor amounts of Man$_8$GlcNAc$_2$ and Man$_7$GlcNAc$_2$ are present. After incubation of huGAA with CcMan5 the conversion of ManP-Man8GlcNAc$_2$ and (ManP)2-Man8GlcNAc$_2$ to P-Man8GlcNAc$_2$ and P2-Man8GlcNAc$_2$ respectively is observed (FIG. 29, panel C and D). The peak in the electropherogram running between P-Man8GlcNAc$_2$ and P2-Man8GlcNAc$_2$ corresponds to the partially uncapped bi-phosphorylated (ManP) 2-Man8GlcNAc$_2$ with a phosphodiester- and a phosphomonoester-linkage present ((MP)-M8-P in FIG. 29, panel C and D). This product is further hydrolyzed to the fully uncapped P2-Man8GlcNAc$_2$ when using a higher concentration of CcMan5 or a longer incubation time.

The percentage of phosphorylated N-glycans versus neutral N-glycans was estimated from measuring the peak areas in the DSA-FACE electropherograms (FIG. 29). The figures related to the area under the curve are presented for the different N-glycans present on huGAA before (Panel B) and after CcMan5 treatment (Panel D). In huGAA (Panel B), (ManP)2-Man8GlcNAc$_2$ (11597), ManP-Man6GlcNAc$_2$ (1261), ManP-Man7GlcNAc$_2$ (5901), ManP-Man8GlcNAc$_2$ (15576), Man6GlcNAc$_2$ (680), Man7GlcNAc$_2$ (1716), Man8GlcNAc$_2$ (1572) were present. Approximately 90% of the N-glycans on recombinant huGAA were composed of mannose-phosphate containing structures.

After an overnight treatment of recombinant huGAA with CcMan5 (Panel D), P2-Man8GlcNAc$_2$ (16182), (ManP)P-Man8GlcNAc$_2$ (1997), P-Man7GlcNAc$_2$ (8254), P-Man8GlcNAc$_2$ (17893), ManP-Man6GlcNAc$_2$ (500), ManP-Man7GlcNAc$_2$ (2495), ManP-Man8GlcNAc$_2$ (1326), Man6GlcNAc$_2$ (1097), Man7GlcNAc$_2$ (2143), Man8GlcNAc$_2$ (1599) were present. The N-glycans released from huGAA were composed of 83% uncapped phosphorylated structures, 8% is still mannose-phosphate capped and 9% neutral N-glycans are present. The percentage of uncapped phosphorylated structures can be increased when using a higher concentration of CcMan5 or a longer incubation time.

Example 14

Identification of Homologs Likely to have Uncapping Activity

To identify other GH92 family members with similar predicted catalytic site topology and functionality, curated GH92 family members, as mined from the world wide web at cazy.org/GH92_all.html, were analyzed as were the top 500 hits obtained by Blastp search with the CcMan5 domain sequence on the Non Redundant Protein Sequences database at NCBI. Subsequently, these 392 sequences were used as the input for the multiple sequence alignment package MUSCLE (MUltiple Sequence Comparison by Log-Expectation), which also ranks the sequences in order of 'phylogenetic' distance (from closest related to furthest related).

Based on the curated GH92 family members from the Cazy database, MUSCLE alignment of all GH92 protein sequences (392) and the CcMan5 domain sequence identified the following as the closest homologs of CcMan5:

Streptomyces coelicolor CAA18915 (GenBank Accession No. NP_630514)
Clostridium spiroforme (GenBank Accession No. ZP_02866543)
Bacteroides thetaiotaomicron AAO78636 (GenBank Accession No. NP_812442)
Zunongwangia profunda ADF52306 (GenBank Accession No. YP_003584502)
Chitinophaga pinensis ACU58463 (GenBank Accession No. YP_003120664)

Their sequences and those of the next 5 closest homologs are aligned in FIG. 31.

Based on MUSCLE alignment of the 500 best scoring blastp protein hits versus the CcMan5 domain, the following were considered the closest homologs of CcMan5

Streptomyces coelicolor (GenBank Accession No. NP_630514)
Streptomyces lividans (GenBank Accession No. ZP_05522540)
Streptomyces lividans (GenBank Accession No. ZP_06527366)
Paenibacillus sp (GenBank Accession No. YP_003013376)
Bacteroides thetaiotaomicron (GenBank Accession No. NP_812442)
Bacteroides sp. (GenBank Accession No. ZP_04848482)
Bacteroides cellulosilyticus (GenBank Accession No. ZP_03677957)
Zunongwangia profunda (GenBank Accession No. YP_003584502)
Leeuwenhoekiella blandensis (GenBank Accession No. ZP_01061975)
Sphingobacterium spiritivorum (GenBank Accession No. ZP_07083984)
Chitinophaga pinensis (GenBank Accession No. YP_003120664)
Pedobacter sp. (GenBank Accession No. ZP_01885202)
Clostridium spiroforme (GenBank Accession No. ZP_02866543)

Alignment of these and the 5 next-best homologs can be found in FIG. 32. All 5 best hits from the annotated GH92 database are also found in these 13 best hits from the Blast search on the entire sequence database.

The top 5 hits in FIG. 31 and the top 13 hits in FIG. 32 uniquely share the following three motifs, which were shown in the crystal structure of Example 8 to be different from the alpha-1,2-mannosidase GH92 family members of which the structure was reported in Zhu et. al., 2010, supra.

1) a glycine-rich motif GVGxxGxGG, with each X being G, S, T, V, A, C or Q (small side chains), numbering of crystal structure residues of CcMan5 domain: 69-77. This region makes a loop that provides essential hydrogen bonds to the −1 and phosphate-binding subsite in the active site of the enzyme.

2) a VRxE motif. The R makes a hydrogen bond to the −1 ring and possibly the +1 ring. E is in a salt bridge to this R residue, probably shaping this motif. x is W in the closest-related subfamily (top 3 homologs to CcMan5), or could be any of the 20 amino acids except P. This motif is found at residues 404-407 of SEQ ID NO:50.

3) a LYQGT motif, containing the Q which is an E in the mannosidases (proton donor), and which contains Y535, which is important for the +1 site formation. In some of the sequences, the L is A or Y and could reasonably be expected to also be I, V, A, F or M, and in some of them the T is N and can be expected to also tolerate S. Two Caulobacter sequences have an E instead of Q and would thus be predicted not to work on phosphorylated glycans.

4) a GDXGN motif. The D and N make part of the substrate binding cavity and may shape an alternative sub-pocket to bind the +1 mannose. X can be any amino acid other than P. This motif is found at residues 21-25 of SEQ ID NO:50.

Based on the above bioinformatics workflow and motif search based on the structure, it is thus possible to filter the GH92 sequences present in the non-redundant proteins sequence database (currently containing over 1220 sequences) for those rare family members that are good candidates for having the same substrate specificity to CcMan5, i.e., to be capable of uncapping Man-6-Pi-Man structures. In particular, the 3 sequences from Streptomyces coelicolor and Streptomyces lividans are similar to CcMan5, not only in the above motifs but also in many of the loops of the structure.

A search with Hidden Markov Models based on the sequence elements unique to CcMan5 and its closest homologs, reveals no further GH92 sequences which contain all of these elements, strongly indicating that no such GH92 members have obtained these elements through convergent evolution (these are the ones that would not be top-ranked in multiple-sequence alignments).

Example 15

The Presence of Phosphate Uncapping Activity in GH92 Glycosidases from Bacteroides thetaiotaomicron An enzymatic analysis of 23 family GH92 α-mannosidases from Bacteroides thetaiotaomicron has been reported by Zhu, Y. et al, 2010, supra. Enzymes with α1,2-, α1,4-, α1,3- or α1,6-mannosidase activity are present in this group of enzymes, although some variants display very low activity. The three-dimensional structure of two α-1,2 mannosidases (Bt3990 and Bt2199) allowed to identify key amino-acid residues which seem to be a signature motif for α-1,2-mannosidase activity, i.e. His584-Glu585 and Trp99 in Bt3990. The activity on phosphorylated N-glycans (MNN4 sugars described in Example 1) of three GH92 enzymes from B. thetaiotaomicron, Bt3530 (Genbank nr AAO78636.1), Bt3965 (Genbank nr AAO79070.1) and Bt3994 (Genbank nr AAO79099.1) was tested. These enzymes display low α1,4-mannosidase activity and lack the His-Glu and Pro-Trp motif.

Bt3530, Bt3965 and Bt3994 were expressed in *E. coli* and purified as described in Zhu et al, 2010, supra. Samples (1 µl enzyme at a concentration of 0.1 mg/ml) were incubated with 7 µl APTS-labeled MNN4 sugars dissolved in 10 mM HEPES buffer pH 7.0 with 2 mM $CaCl_2$ in an overnight assay at room temperature. A control assay with CcMan5 was included. To confirm the presence of a terminal phosphate the reaction mixture was incubated with CIP. An N-glycan preparation containing $Man8GlcNAc_2$ (M8) and the monophosphorylated $ManP-Man8GlcNAc_2$ (MP-M8) was used as substrate. No uncapping activity for Bt3530, Bt3965 and Bt3994 was detected under the above assay conditions. No shift in electrophoretic mobility of the peaks was observed compared to the CcMan5 control reaction (appearance of fast running P-M8 peak), followed by CIP treatment (disappearance of P-M8).

In an additional experiment, 1 µl of enzyme, i.e. Bt3530 (0.1 mg/ml), Bt3965 (4.75 mg/ml) and Bt3994 (1.37 mg/ml) respectively, was incubated with MNN4 N-glycans at pH 7.0 (10 mM HEPES buffer pH 7.0 with 2 mM $CaCl_2$) and at pH 5.0 (10 mM Ammonium Acetate pH 5.0 with 2 mM $CaCl_2$) during 60 hours at room temperature. Very minor α1,2-mannosidase activity was observed with Bt3530 at pH 7.0, as a small $Man5GlcNAc_2$ (M5) peak appears in the electropherogram. At pH 5.0, on the other hand, no α1,2-mannosidase activity is present, but a fast running peak at the left hand side of the electropherogram appears. This peak has the same electrophoretic mobility as $P-Man8GlcNAc_2$ (P-M8) and the terminal phosphate is hydrolyzed after incubation with CIP. CcMan5 (used at same concentration as Bt3530) is fully uncapping $ManP-Man8GlcNAc_2$ within 20 hours incubation at room temperature and at pH 7.0; therefore the observed activity of Bt3530 is rather low. After purification, the Bt3530 sample slowly precipitates when stored at 4° C. in 20 mM TRIS buffer, pH 8.0 with 300 mM NaCl. Therefore it is possible that instability of the Bt3530 protein influences the activity under the assay conditions used. Bt3965, which was used at a 40 times higher concentration, gave a similar result as Bt3530 at pH 7.0 (Panel G and H) and pH 5.0 (Panel I and J). No activity at all was observed with Bt3994 under the same reaction conditions (Panel K till N).

From these experiments can be concluded that phosphate uncapping activity is only a minor side activity of two of the three *B. thetaiotaomicron* GH 92 enzymes tested on MNN4 sugars.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for uncapping a mannose-6-phosphate residue on an oligosaccharide, said method comprising
   a) providing said oligosaccharide having a mannose-1-phospho-6-mannose linkage; and
   b) contacting said oligosaccharide with a mannosidase capable of hydrolyzing said mannose-1-phospho-6-mannose residue to phospho-6-mannose, wherein said mannosidase is a member of glycosyl hydrolase family 92, wherein said mannosidase comprises an amino acid sequence having at least 95% identity to residues 1 to 774 of SEQ ID NO:50 or at least 98% identity to SEQ ID NO:50.

2. The method of claim 1, wherein said mannosidase comprises an amino acid sequence having at least 98% identity to residues 1 to 774 of SEQ ID NO:50.

3. The method of claim 1, wherein said amino acid sequence comprises residues 1-774 of SEQ ID NO:50 or SEQ ID NO:50.

4. The method of claim 3, wherein said amino acid sequence further comprises, N-terminal of residues 1-774 of SEQ ID NO:50 or of SEQ ID NO:50, residues 1-15 of SEQ ID NO:15.

5. The method of claim 1, wherein for said mannosidase, the three dimensional protein coordinates of the atoms in the amino acid side chains located in the minimal catalytic center fall within 1.5 Å deviation of the coordinates of the equivalent atoms in FIG. 33.

6. The method of claim 1, wherein said mannosidase comprises an amino acid sequence having (i) a GVGXXGXGG motif, where X is Gly, Ala, Ser, Thr, or Cys; (ii) a VRXE motif, where X is any amino acid other than Pro; (iii) an $X_1YQGX_2$ motif, where $X_1$ is Leu, Ile, Val, Ala, Phe, Tyr or Met, and $X_2$ is Thr, Ser, or Asn; or (iv) GDXGN, where X can be any amino acid other than Pro.

7. The method of claim 1, wherein said contacting step is performed using a purified mannosidase, a recombinant mannosidase, a cell lysate containing said recombinant mannosidase, or a fungal cell containing said recombinant mannosidase.

8. The method of claim 1, wherein said oligosaccharide is attached to a protein.

9. The method of claim 8, wherein said protein is a human protein expressed in a fungal organism.

10. The method of claim 9, wherein said fungal organism is *Yarrowia lipolytica* or *Arxula adeninivorans*.

11. The method of claim 9, wherein said fungal organism is a methylotrophic yeast.

12. The method of claim 11, wherein said methylotrophic yeast is *Pichia pastoris*, *Pichia methanolica*, *Oogataea minuta*, or *Hansenula polymorpha*.

13. The method of claim 9, wherein said fungal organism is a filamentous fungus.

14. The method of claim 13, wherein said filamentous fungus is selected from the group consisting of *Aspergillus caesiellus*, *Aspergillus candidus*, *Aspergillus carneus*, *Aspergillus clavatus*, *Aspergillus deflectus*, *Aspergillus flavus*, *Aspergillus fumigatus*, *Aspergillus glaucus*, *Aspergillus nidulans*, *Aspergillus niger*, *Aspergillus ochraceus*, *Aspergillus oryzae*, *Aspergillus parasiticus*, *Aspergillus penicilloides*, *Aspergillus restrictus*, *Aspergillus sojae*, *Aspergillus sydowi*, *Aspergillus tamari*, *Aspergillus terreus*, *Aspergillus ustus*, and *Aspergillus versicolor*.

15. The method of claim 8, wherein said protein is a pathogen protein, a lysosomal protein, a growth factor, a cytokine, a chemokine, an antibody or antigen-binding fragment thereof, or a fusion protein.

16. The method of claim 15, wherein said lysosomal protein is a lysosomal enzyme.

17. The method of claim 16, wherein said lysosomal enzyme is associated with a lysosomal storage disorder (LSD).

18. The method of claim 17, wherein said LSD is Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

19. The method of claim 17, wherein said LSD is Pompe disease or Fabry's disease.

20. The method of claim 1, wherein said mannosidase comprises a targeting signal to target said mannosidase to an intracellular compartment.

21. The method of claim 1, wherein the mannosidase is:
   (a) a deletion variant that is the polypeptide consisting of residues 1 to 774 of SEQ ID NO:50 or consisting of SEQ ID NO:50, but lacks up to ten amino acid segments, each segment consisting of one or two amino acids; or
   (b) a substitution variant that is:
      (i) the polypeptide consisting of residues 1 to 774 of SEQ ID NO:50 or consisting of SEQ ID NO:50; or
      (ii) the variant of (a);
      but with no more than 10 conservative substitutions.

* * * * *

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Ser Ala Tyr Gln Ser Phe Thr Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide

<400> SEQUENCE: 2

Val Trp Gly Phe Ser His Arg
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Val Glu Gly Gly Trp Leu Pro Arg
1               5
```

<210> SEQ ID NO 4
<211> LENGTH: 13
<212> TYPE: PRT
<213> ORGANISM: Artificial Sequence
<220> FEATURE:
<223> OTHER INFORMATION: synthetic peptide

<400> SEQUENCE: 4

Thr Gln Gly Asn Asn Phe Ala Leu Leu Leu Pro Glu Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Asp Val His Ala Glu Leu Thr Ala Met Ala Arg
1               5                   10

<210> SEQ ID NO 6
<211> LENGTH: 2700
<212> TYPE: DNA
<213> ORGANISM: Cellulosimicrobium cellulans

<400> SEQUENCE: 6

| | | | | | |
|---|---|---|---|---|---|
| atgagacgac | cacgactcgc | cctgctcgcc | gcggggctcg | cgctcgccgt | cgcaccgggc | 60 |
| acgctgctgc | ccgtcgccgc | gggcgccgcc | ccgccgacg | agggcaccgt | caccgccgcc | 120 |
| gcgggcgacg | acctcacgct | cgaggtcaac | ccgttcgtcg | gcaccgagag | cgagggcaac | 180 |
| gcctacccgg | gcgcgaccgt | gccgttcggc | atggtccagc | tcagcccgga | caacacgaac | 240 |
| tcctacgcct | cgacgtcgta | cagcacgaac | gcggggcgcg | tgtggggctt | cagccaccgg | 300 |
| cacgtgaaca | gcgcgggctg | ccccgcggcg | ggcgagctgc | tcgtcacgcc | ggacacgagc | 360 |
| gcgaccccgc | gcacgtcgcg | ctccttcatc | gccatcaagg | accagaagag | caccgagcgc | 420 |
| gcgtcggccg | ggttctacga | ggtgaccctc | gcgaacgacg | tgcacgccga | gctcaccgcg | 480 |
| accacgcgcg | tcggcgcgca | ccgctacacg | ttccccgcct | cgacgacgtc | gcacctgtcg | 540 |
| ttcaacgtgg | gccagaccct | gcgcgacgcc | ggcgcgagct | cggtgacgtg | ggtcgacgac | 600 |
| cgcacgctcg | agggctgggt | cgacaacggc | ggcttctgcg | gcggcacgcc | ggacaagcag | 660 |
| cggtacttct | tcagcgcgac | gttcgaccgc | ccggtcgcgt | cgagcggcac | gtgggggacc | 720 |
| gatgcgcgct | acgtcgcggg | ctccacgacg | agcgaggtcg | cgggcggcaa | caacggcgcc | 780 |
| gtcgcggtgt | cgacaccac | gaccgaccgc | gacgtcgagg | tgagcgtggg | cgtgtccttc | 840 |
| gtgagcgtcg | acggcgcgcg | cgccaaccgc | gaggccgagg | ccaccgacga | gggcgggcag | 900 |
| gtcgcgttcg | acaccgtgcg | tgaggaggcc | cgcgacgcgt | ggaacgcgga | gctgggccgt | 960 |
| gccgcgatcg | acgcgtcgcc | cgaccagcgc | cggatcttct | acacccagct | ctacaagacg | 1020 |
| ctgctgtccc | cgacgatcgg | cagcgacgtc | gacggccggt | accgcggcat | ggacctcgag | 1080 |
| gtccaccagg | ccgacggctg | ggactactac | cagaacttct | cgctctggga | cacgtaccgc | 1140 |
| acgcaggcga | cgctgcacgc | cctcctgctg | cccgagcgcg | cgcaggacat | cgtgcgctcg | 1200 |
| atgtaccagc | accgcgtcga | gggcggctgg | ctgccgcgct | ggtccctcgg | tgcactggag | 1260 |
| accaacatca | tggcgggcga | ccccgtcacg | ccgtggctcg | cggagaactt | cgcgctcggc | 1320 |
| accgtccccg | acgacatcgc | ggacgagctg | tgggactacc | tcgtcgagaa | cgccacgacg | 1380 |

```
acccccgccgg acgacgtcgc gtccgtcggg cggcgcagca ccgagttcta cgccgagcac   1440
ggccacgtgc cgttctaccc cgagaacgag ggcggcctcg gcggccagtt cgaggagtac   1500
cgccacggcg gctcggcgac gctcgagctc gcgctcgccg acgcgagcct cggcgctgcg   1560
gccgagcgca cgggtcgcga gggcggccag gcgttcctcg acaagggtcg caactggcgc   1620
aacctctgga acccggacgt cgagctctcg ggtggcttcc agggcatggt caacgcgaag   1680
cgcccgacgg gcgagttcgt cacgctgccc gagctgacgg acgtcacgcg ctccggcttc   1740
cacgagggcg tgccgtggca gtaccagtgg atggtgccgc aggacgtcac gggcctccag   1800
gaggtcatgg gcggcgagga cggcttcgtc gagcgtctcg actactactt cgaccagccg   1860
gcgctcgccg cgaaccccgg cgtctcgccg agcacgtggg ccaagggcgg cagctcgtac   1920
tacacgacca tccgctacaa ccccgggcaac gagccgacga tcatgaacgc gtggctctac   1980
ggctacgtgg ccagccgtg gaagacgaac gacgtcctcg ccgcgaacct caaccgcttc   2040
ccggacaccc cgggcggcgg cgtcgggaac gacgacctcg gcacgcttgc cgcctggtac   2100
gtcatggcgt cgctcgggtt cgagcccgtc atgccgggct cggggatcct cgcgctcaac   2160
gcgccgaagg tgcaggccgc gacgctcacg accgatgccg gggcgacgct gcgcatcgac   2220
gcggcgggcg cgaacgagaa gctcccgagc tacgtcgccg gcctggaggt cgacggcgtc   2280
gcgcacaccg ccgcgtggct cgacgtcgcg gcgctgcagg acggcggcac gctcgacttc   2340
gacctgtccg gcacgagcgc gggcctcacg tggggcaccg gcgcggccga ccgcatcccg   2400
tcggtctccg ccgtcgcccc gccgcgcgcc gtcgaggtcg aggcgagcgc gcgctgcctc   2460
ggcggccggg cgttcgtcgc ggtccgcgcg accagcacgg ccgacgcgcc ggtggacgtg   2520
actctcacga cgccgttcgg cgagcggacg gtccggcacg tgcagccggg caggagcgcc   2580
taccagtcgt tcacgacgcg cacgacgtcc gtcgaggccg gacggcgac cgtcacggtc   2640 gtcgccgcgg acggcacgac gtcgacggtc gacgcggcgt acgaggcgct ggcctgcggc   2700
```

<210> SEQ ID NO 7
<211> LENGTH: 900
<212> TYPE: PRT
<213> ORGANISM: Cellulosimicrobium cellulans

<400> SEQUENCE: 7

```
Met Arg Arg Pro Arg Leu Ala Leu Leu Ala Ala Gly Leu Ala Leu Ala
 1               5                  10                  15

Val Ala Pro Gly Thr Leu Leu Pro Val Ala Ala Gly Ala Ala Pro Ala
            20                  25                  30

Asp Glu Gly Thr Val Thr Ala Ala Ala Gly Asp Asp Leu Thr Leu Glu
        35                  40                  45

Val Asn Pro Phe Val Gly Thr Glu Ser Glu Gly Asn Ala Tyr Pro Gly
    50                  55                  60

Ala Thr Val Pro Phe Gly Met Val Gln Leu Ser Pro Asp Asn Thr Asn
65                  70                  75                  80

Ser Tyr Ala Ser Thr Ser Tyr Ser Thr Asn Ala Gly Arg Val Trp Gly
                85                  90                  95

Phe Ser His Arg His Val Asn Ser Ala Gly Cys Pro Ala Ala Gly Glu
            100                 105                 110

Leu Leu Val Thr Pro Asp Thr Ser Ala Thr Pro Arg Thr Ser Arg Ser
        115                 120                 125

Phe Ile Ala Ile Lys Asp Gln Lys Ser Thr Glu Arg Ala Ser Ala Gly
    130                 135                 140
```

```
Phe Tyr Glu Val Thr Leu Ala Asn Asp Val His Ala Glu Leu Thr Ala
145                 150                 155                 160
Thr Thr Arg Val Gly Ala His Arg Tyr Thr Phe Pro Ala Ser Thr Thr
            165                 170                 175
Ser His Leu Ser Phe Asn Val Gly Gln Thr Leu Arg Asp Ala Gly Ala
        180                 185                 190
Ser Ser Val Thr Trp Val Asp Asp Arg Thr Leu Glu Gly Trp Val Asp
    195                 200                 205
Asn Gly Gly Phe Cys Gly Gly Thr Pro Asp Lys Gln Arg Tyr Phe Phe
210                 215                 220
Ser Ala Thr Phe Asp Arg Pro Val Ala Ser Gly Thr Trp Gly Thr
225                 230                 235                 240
Asp Ala Arg Tyr Val Ala Gly Ser Thr Thr Ser Glu Val Ala Gly Gly
                245                 250                 255
Asn Asn Gly Ala Val Ala Val Phe Asp Thr Thr Thr Asp Arg Asp Val
            260                 265                 270
Glu Val Ser Val Gly Val Ser Phe Val Ser Val Asp Gly Ala Arg Ala
        275                 280                 285
Asn Arg Glu Ala Glu Ala Thr Asp Glu Gly Gly Gln Val Ala Phe Asp
    290                 295                 300
Thr Val Arg Glu Glu Ala Arg Asp Ala Trp Asn Ala Glu Leu Gly Arg
305                 310                 315                 320
Ala Ala Ile Asp Ala Ser Pro Asp Gln Arg Ile Phe Tyr Thr Gln
                325                 330                 335
Leu Tyr Lys Thr Leu Leu Ser Pro Thr Ile Gly Ser Asp Val Asp Gly
            340                 345                 350
Arg Tyr Arg Gly Met Asp Leu Glu Val His Gln Ala Asp Gly Trp Asp
        355                 360                 365
Tyr Tyr Gln Asn Phe Ser Leu Trp Asp Thr Tyr Arg Thr Gln Ala Thr
    370                 375                 380
Leu His Ala Leu Leu Pro Glu Arg Ala Gln Asp Ile Val Arg Ser
385                 390                 395                 400
Met Tyr Gln His Arg Val Glu Gly Gly Trp Leu Pro Arg Trp Ser Leu
                405                 410                 415
Gly Ala Leu Glu Thr Asn Ile Met Ala Gly Asp Pro Val Thr Pro Trp
            420                 425                 430
Leu Ala Glu Asn Phe Ala Leu Gly Thr Val Pro Asp Asp Ile Ala Asp
        435                 440                 445
Glu Leu Trp Asp Tyr Leu Val Glu Asn Ala Thr Thr Pro Pro Asp
    450                 455                 460
Asp Val Ala Ser Val Gly Arg Arg Ser Thr Glu Phe Tyr Ala Glu His
465                 470                 475                 480
Gly His Val Pro Phe Tyr Pro Glu Asn Glu Gly Leu Gly Gly Gln
                485                 490                 495
Phe Glu Glu Tyr Arg His Gly Gly Ser Ala Thr Leu Glu Leu Ala Leu
            500                 505                 510
Ala Asp Ala Ser Leu Gly Ala Ala Ala Glu Arg Thr Gly Arg Glu Gly
        515                 520                 525
Gly Gln Ala Phe Leu Asp Lys Gly Arg Asn Trp Arg Asn Leu Trp Asn
    530                 535                 540
Pro Asp Val Glu Leu Ser Gly Gly Phe Gln Gly Met Val Asn Ala Lys
545                 550                 555                 560
Arg Pro Thr Gly Glu Phe Val Thr Leu Pro Glu Leu Thr Asp Val Thr
```

```
                    565                 570                 575
Arg Ser Gly Phe His Glu Gly Val Pro Trp Gln Tyr Gln Trp Met Val
                580                 585                 590

Pro Gln Asp Val Thr Gly Leu Gln Glu Val Met Gly Gly Glu Asp Gly
            595                 600                 605

Phe Val Glu Arg Leu Asp Tyr Tyr Phe Asp Gln Pro Ala Leu Ala Ala
        610                 615                 620

Asn Pro Gly Val Ser Pro Ser Thr Trp Ala Lys Gly Gly Ser Ser Tyr
625                 630                 635                 640

Tyr Thr Thr Ile Arg Tyr Asn Pro Gly Asn Glu Pro Thr Ile Met Asn
                645                 650                 655

Ala Trp Leu Tyr Gly Tyr Val Gly Gln Pro Trp Lys Thr Asn Asp Val
                660                 665                 670

Leu Ala Ala Asn Leu Asn Arg Phe Pro Asp Thr Pro Gly Gly Gly Val
            675                 680                 685

Gly Asn Asp Asp Leu Gly Thr Leu Ala Ala Trp Tyr Val Met Ala Ser
        690                 695                 700

Leu Gly Phe Glu Pro Val Met Pro Gly Ser Gly Ile Leu Ala Leu Asn
705                 710                 715                 720

Ala Pro Lys Val Gln Ala Ala Thr Leu Thr Thr Asp Ala Gly Ala Thr
                725                 730                 735

Leu Arg Ile Asp Ala Ala Gly Ala Asn Glu Lys Leu Pro Ser Tyr Val
                740                 745                 750

Ala Gly Leu Glu Val Asp Gly Val Ala His Thr Ala Ala Trp Leu Asp
            755                 760                 765

Val Ala Ala Leu Gln Asp Gly Gly Thr Leu Asp Phe Asp Leu Ser Gly
770                 775                 780

Thr Ser Ala Gly Leu Thr Trp Gly Thr Gly Ala Ala Asp Arg Ile Pro
785                 790                 795                 800

Ser Val Ser Ala Val Ala Pro Pro Ala Pro Val Glu Val Glu Ala Ser
                805                 810                 815

Ala Arg Cys Leu Gly Gly Arg Ala Phe Val Ala Val Arg Ala Thr Ser
            820                 825                 830

Thr Ala Asp Ala Pro Val Asp Val Thr Leu Thr Thr Pro Phe Gly Glu
        835                 840                 845

Arg Thr Val Arg His Val Gln Pro Gly Arg Ser Ala Tyr Gln Ser Phe
        850                 855                 860

Thr Thr Arg Thr Thr Ser Val Glu Ala Gly Thr Ala Thr Val Thr Val
865                 870                 875                 880

Val Ala Ala Asp Gly Thr Thr Ser Thr Val Asp Ala Ala Tyr Glu Ala
                885                 890                 895

Leu Ala Cys Gly
            900

<210> SEQ ID NO 8
<211> LENGTH: 3543
<212> TYPE: DNA
<213> ORGANISM: Cellulosimicrobium cellulans

<400> SEQUENCE: 8
gtgagcctcg cgctcccgct ggcggcgtac gcggcgcccg ggatcggggc gtcgcccgcg      60
accgccgccg ggacggaggc agcgacgggg tccgatgccg ccgccgtcga cggcccgctg     120
gtcgactacg tcaacccgtt catcgggacc aaggacgacg caacaccta cccgggcgct     180
```

```
gccgtgccgt tcggcatggt gcaactctcg ccggacaacg gccacaacgt cgggtacgac     240
tacgaccgca cgtcggtgcg cgggttctcg ctcgtgcacc tgtccggcgt cggctgcggc     300
ctcggcggtc cgctcccgac cctgccgacg acgggcgcga tcacctcgac cgactacggc     360
cagtacgcgc tcggtttctc gcacgacgac gaggaggcct cgccgggta ctaccgcgtg      420 ggtctccagg cgccggcggg cacgatcgag gccgagctca ccgcgaccga gcgcacgggc     480
gtccagcggt acacgttccc cgcgacggcg caggccaacg tcctgctcaa cgccggccag     540
gcgctcaacc gggtgacgga gtccgacgtg cgcgtcgtgg acgaccgcac ggtcgagacg     600
cgcatcaccg tccgcggctt ctgccaggac accgagccgc agacgatctg gacccgcacg     660
accttcgacc ggccgttcgt cgcgcacggc acgtgggacg gccaggtcgt caccgcgggc     720
gcggacgccg cgtccggcgg cgagggccgt cgcggcgcgt acgtcacgtt cgacacgacc     780
ggcggcgacc tcgacgtcga ggccgtcacc gcgatgagct acgtgggcgc cgacggcgcc     840
gcggcgaacc tcgccgcgga ggccggcacg ttcgacgccg tgcacgacgc cgcgcgctcg     900
gcctgggagg agcggctcgg cctcgtgcgg gtcgcgcagg gcgacccgga cgacctgcgc     960
accttctact cctcgctcta ccgcagcttc ctcgcgccga acgtcggctc cgacgtcgac     1020
gggcgctacc gcggctggga ccaggaggtc cacgccgcgg aaccggactt cacctactac     1080
cagaactact cgctctggga cacgtaccgc acccagcagc agctcctgta cctgctcgcg     1140
cccgacgagt cggccgacat ggcgctctcg ctcgtgcgcc agggccagca gggcgggtgg     1200
ctcccgcgct ggggctacgg cacggtcgag acgaacatca tgaccggcga cccggcgacg     1260
ccgttcctcg tcagcgcctg gcgccagggc ctgctcgcgg gccacgagga ggaggcgtac     1320
gcggtcctga gggagaacgc cgacggcgtc ccgcccgccg actcgcccct taacgggcgc     1380
gcggcgaacg tcgagtacct gcgcgacggg ttcgtcccgc acgagccggc gcgctcgggc     1440
aagcccggcg actacgacct ccagcacggc gcctcggcga ccatggagta cgccctcgcc     1500
gacgcgatgc tctcgaccat ggcgcgcggc ctcggccacg acgaggacgc cgaccggtac     1560
gccgcccgcg gccagagcta ccgcaacgtg ttcgacccgc gcacgggcaa cttccgggcg     1620
cgtaacgcgg acggcttctt cgtgggcgac gcggaccccg cgcactccga cgggttccac     1680
gagggcacgg cggtgcagta ccagtggctc gtgccccagg acgtgccggg cctgttcgac     1740
ctcatgggcg gcaccgacgc cgcggtcgac cgcctcgatg cgttcttcgc gtacgacgag     1800
ctcgtcgccg acccccgca cgtcgcgagc gaggtgtggg tcaacggcac gtacgactac     1860
tacggctggg agacctacaa cccgaacaac gagcccaacc tccatgcgcc gtacgtctac     1920
ctgtggaccg ggcagccctg gaagacgacg gacgtcgtgc gcgccgcgtc gaccctcttc     1980
accgacggcc ccgacggcgt cacgggcaac gacgacctcg gcacgatgtc cgcgtggcac     2040
gtgctgtcgt cgatcggcgt gtacccgatc gtgccgggcg ccgatctgtg gggcctgacg     2100
acgccgctct tcgacgacgt gacgatcacg ctcgacccgg aggtcttcgg tcgggactcc     2160
ctgcgcctca cggcggacgg cgtcgcgccc gacacgcact acacgcagtc cgtgtcgctc     2220
ggcggcgagc cgctcgatcg cgcctgggtc acgggcgacg agctcaccgc ggccggcacg     2280
ctcgacgtga ccgtcggcac cgagccgtcc gcgtgggcga ccgaccccgc ggcctcgccg     2340
ggcgccgtcg tgcctgcgga cggcacggtc gagcgcctgt tcgtcggcgc gacgccgcgg     2400
cagccggtcc tcgcccccggg cggcggacc gaggtcgcag tccaggtcgt cgcccagggc     2460
gcggggacgt ccagcgggac gctcgaggtg acgtccgacg gcgcggtcac cgcgacgacc     2520
gacctcgccg agtggaccgc cgagtccgac ggcctgccgg ccacggtcga gggcacggtg     2580
```

-continued

```
acgatcgagg ctcccgccga cgccgagccg ggtctgcaca cggtgcggct cgtcgtgcgc    2640
gacgccgcgg ggaccgaggc ggtccgcgag gtctcggtcg tcgtgtccgg ggagtcgtgg    2700
atcgccgacg cgttcgacaa cgtcggcatc ggcgacgccg gggcggccaa cgcgaacctc    2760
gacggctcgg gcgcctacct cctgcgcgac ctgctcgcgg acctcggcgc cgtccagggc    2820
ctggagctca ccgtgccggg cacggacctc acctacacgc tcggggcccc gcgggcgggc    2880
gcgcccgaca acgtcgccgc gagcggcgag gtcctcgagg tgcccgagca cctgcgctcg    2940
gcccgccacc tctcggtggt cgggacgagc acgcacggca cgcacggggg cggcctcgtc    3000
ctcgggttcg ccgacggctc gtcgcagacc gtcgacgtgc gcctcagcga ctggtgcacg    3060
ggctcgcccg agcccggcaa catcacggtc gcgaaggccg gggcgcgcgg cgaccgcgag    3120
aacgtgcaga gatcggctg cggcctctac gccaccgcgc ccgtcgcgat ccccgagggc    3180
aaggtcctga cgtcggtcac gctgccgagc gacgagcggt tccacgtgtt cgcgatcgcg    3240
accgacgcga cggggacgt ccccgcgccg caggtcgagg tcacggcgca ggcccgctgc    3300
ctcggcggca aggcgttcgt cgcggtgcgc gcgctcaaca cgggcgagca gcccgccgcg    3360
atcgagctcg cgaccccgta cggctccaag ctcttcggtg acgtcgctcc cggggcgaac    3420
gcgtaccagt cgttcgccac ccgcgccgcc gccgtcgagg cgggcgaggt cacggtgacc    3480
gtgacgacgc ccgacggcga gccccagcag gtcacggccg cgtacgacgc cgccgcctgc    3540
tcc                                                                 3543
```

<210> SEQ ID NO 9
<211> LENGTH: 1181
<212> TYPE: PRT
<213> ORGANISM: Cellulosimicrobium cellulans

<400> SEQUENCE: 9

| Val | Ser | Leu | Ala | Leu | Pro | Leu | Ala | Ala | Tyr | Ala | Ala | Pro | Gly | Ile | Gly |
|---|---|---|---|---|---|---|---|---|---|---|---|---|---|---|---|
| 1 | | | | 5 | | | | | 10 | | | | | 15 | |

Ala Ser Pro Ala Thr Ala Ala Gly Thr Glu Ala Ala Thr Gly Ser Asp
                20                  25                  30

Ala Ala Ala Val Asp Gly Pro Leu Val Asp Tyr Val Asn Pro Phe Ile
            35                  40                  45

Gly Thr Lys Asp Asp Gly Asn Thr Tyr Pro Gly Ala Ala Val Pro Phe
        50                  55                  60

Gly Met Val Gln Leu Ser Pro Asp Asn Gly His Asn Val Gly Tyr Asp
    65                  70                  75                  80

Tyr Asp Arg Thr Ser Val Arg Gly Phe Ser Leu Val His Leu Ser Gly
                    85                  90                  95

Val Gly Cys Gly Leu Gly Gly Pro Leu Pro Thr Leu Pro Thr Thr Gly
                100                 105                 110

Ala Ile Thr Ser Thr Asp Tyr Gly Gln Tyr Ala Leu Gly Phe Ser His
            115                 120                 125

Asp Asp Glu Glu Ala Ser Pro Gly Tyr Tyr Arg Val Gly Leu Gln Ala
        130                 135                 140

Pro Ala Gly Thr Ile Glu Ala Glu Leu Thr Ala Thr Glu Arg Thr Gly
    145                 150                 155                 160

Val Gln Arg Tyr Thr Phe Pro Ala Thr Ala Gln Ala Asn Val Leu Leu
                    165                 170                 175

Asn Ala Gly Gln Ala Leu Asn Arg Val Thr Glu Ser Asp Val Arg Val
                180                 185                 190

Val Asp Asp Arg Thr Val Glu Thr Arg Ile Thr Val Arg Gly Phe Cys
            195                 200                 205

Gln Asp Thr Glu Pro Gln Thr Ile Trp Thr Arg Thr Thr Phe Asp Arg
    210                 215                 220

Pro Phe Val Ala His Gly Thr Trp Asp Gly Gln Val Val Thr Ala Gly
225                 230                 235                 240

Ala Asp Ala Ala Ser Gly Gly Glu Gly Arg Arg Gly Ala Tyr Val Thr
                245                 250                 255

Phe Asp Thr Thr Gly Gly Asp Leu Asp Val Glu Ala Val Thr Ala Met
            260                 265                 270

Ser Tyr Val Gly Ala Asp Gly Ala Ala Asn Leu Ala Ala Glu Ala
    275                 280                 285

Gly Thr Phe Asp Ala Val His Asp Ala Ala Arg Ser Ala Trp Glu Glu
    290                 295                 300

Arg Leu Gly Leu Val Arg Val Ala Gln Gly Asp Pro Asp Asp Leu Arg
305                 310                 315                 320

Thr Phe Tyr Ser Ser Leu Tyr Arg Ser Phe Leu Ala Pro Asn Val Gly
                325                 330                 335

Ser Asp Val Asp Gly Arg Tyr Arg Gly Trp Asp Gln Glu Val His Ala
            340                 345                 350

Ala Glu Pro Asp Phe Thr Tyr Tyr Gln Asn Tyr Ser Leu Trp Asp Thr
        355                 360                 365

Tyr Arg Thr Gln Gln Gln Leu Leu Tyr Leu Leu Ala Pro Asp Glu Ser
    370                 375                 380

Ala Asp Met Ala Leu Ser Leu Val Arg Gln Gly Gln Gln Gly Gly Trp
385                 390                 395                 400

Leu Pro Arg Trp Gly Tyr Gly Thr Val Glu Thr Asn Ile Met Thr Gly
                405                 410                 415

Asp Pro Ala Thr Pro Phe Leu Val Ser Ala Trp Arg Gln Gly Leu Leu
            420                 425                 430

Ala Gly His Glu Glu Ala Tyr Ala Val Leu Arg Glu Asn Ala Asp
        435                 440                 445

Gly Val Pro Pro Ala Asp Ser Pro Phe Asn Gly Arg Ala Ala Asn Val
450                 455                 460

Glu Tyr Leu Arg Asp Gly Phe Val Pro His Glu Pro Ala Arg Ser Gly
465                 470                 475                 480

Lys Pro Gly Asp Tyr Asp Leu Gln His Gly Ala Ser Ala Thr Met Glu
                485                 490                 495

Tyr Ala Leu Ala Asp Ala Met Leu Ser Thr Met Ala Arg Gly Leu Gly
            500                 505                 510

His Asp Glu Asp Ala Asp Arg Tyr Ala Ala Arg Gly Gln Ser Tyr Arg
        515                 520                 525

Asn Val Phe Asp Pro Arg Thr Gly Asn Phe Arg Ala Arg Asn Ala Asp
    530                 535                 540

Gly Phe Phe Val Gly Asp Ala Asp Pro Ala His Ser Asp Gly Phe His
545                 550                 555                 560

Glu Gly Thr Ala Val Gln Tyr Gln Trp Leu Val Pro Gln Asp Val Pro
                565                 570                 575

Gly Leu Phe Asp Leu Met Gly Gly Thr Asp Ala Ala Val Asp Arg Leu
            580                 585                 590

Asp Ala Phe Phe Ala Tyr Asp Glu Leu Val Ala Asp Pro Pro His Val
        595                 600                 605

Ala Ser Glu Val Trp Val Asn Gly Thr Tyr Asp Tyr Tyr Gly Trp Glu

```
              610                 615                 620
Thr Tyr Asn Pro Asn Asn Glu Pro Asn Leu His Ala Pro Tyr Val Tyr
625                 630                 635                 640

Leu Trp Thr Gly Gln Pro Trp Lys Thr Thr Asp Val Val Arg Ala Ala
                    645                 650                 655

Ser Thr Leu Phe Thr Asp Gly Pro Asp Gly Val Thr Gly Asn Asp Asp
                    660                 665                 670

Leu Gly Thr Met Ser Ala Trp His Val Leu Ser Ser Ile Gly Val Tyr
                675                 680                 685

Pro Ile Val Pro Gly Ala Asp Leu Trp Gly Leu Thr Thr Pro Leu Phe
690                 695                 700

Asp Asp Val Thr Ile Thr Leu Asp Pro Glu Val Phe Gly Arg Asp Ser
705                 710                 715                 720

Leu Arg Leu Thr Ala Asp Gly Val Ala Pro Asp Thr His Tyr Thr Gln
                    725                 730                 735

Ser Val Ser Leu Gly Gly Glu Pro Leu Asp Arg Ala Trp Val Thr Gly
                740                 745                 750

Asp Glu Leu Thr Ala Ala Gly Thr Leu Asp Val Thr Val Gly Thr Glu
            755                 760                 765

Pro Ser Ala Trp Ala Thr Asp Pro Ala Ala Ser Pro Gly Ala Val Val
770                 775                 780

Pro Ala Asp Gly Thr Val Glu Arg Leu Phe Val Gly Ala Thr Pro Arg
785                 790                 795                 800

Gln Pro Val Leu Ala Pro Gly Arg Thr Glu Val Ala Val Gln Val
                805                 810                 815

Val Ala Gln Gly Ala Gly Thr Ser Ser Gly Thr Leu Glu Val Thr Ser
                820                 825                 830

Asp Gly Ala Val Thr Ala Thr Thr Asp Leu Ala Glu Trp Thr Ala Glu
            835                 840                 845

Ser Asp Gly Leu Pro Ala Thr Val Glu Gly Thr Val Thr Ile Glu Ala
        850                 855                 860

Pro Ala Asp Ala Glu Pro Gly Leu His Thr Val Arg Leu Val Val Arg
865                 870                 875                 880

Asp Ala Ala Gly Thr Glu Ala Val Arg Glu Val Ser Val Val Ser
                885                 890                 895

Gly Glu Ser Trp Ile Ala Asp Ala Phe Asp Asn Val Gly Ile Gly Asp
                900                 905                 910

Ala Gly Ala Ala Asn Ala Asn Leu Asp Gly Ser Gly Ala Tyr Leu Leu
            915                 920                 925

Arg Asp Leu Leu Ala Asp Leu Gly Ala Val Gln Gly Leu Glu Leu Thr
930                 935                 940

Val Pro Gly Thr Asp Leu Thr Tyr Thr Leu Gly Ala Pro Arg Ala Gly
945                 950                 955                 960

Ala Pro Asp Asn Val Ala Ala Ser Gly Glu Val Leu Glu Val Pro Glu
                965                 970                 975

His Leu Arg Ser Ala Arg His Leu Ser Val Val Gly Thr Ser Thr His
            980                 985                 990

Gly Thr His Gly Gly Leu Val Leu Gly Phe Ala Asp Gly Ser Ser
        995                 1000                1005

Gln Thr Val Asp Val Arg Leu Ser Asp Trp Cys Thr Gly Ser Pro Glu
    1010                1015                1020

Pro Gly Asn Ile Thr Val Ala Lys Ala Gly Ala Arg Gly Asp Arg Glu
1025                1030                1035                1040
```

Asn Val Gln Lys Ile Gly Cys Gly Leu Tyr Ala Thr Ala Pro Val Ala
                1045                1050                1055

Ile Pro Glu Gly Lys Val Leu Thr Ser Val Thr Leu Pro Ser Asp Glu
                1060                1065                1070

Arg Phe His Val Phe Ala Ile Ala Thr Asp Ala Thr Gly Asp Val Pro
            1075                1080                1085

Ala Pro Gln Val Glu Val Thr Ala Gln Ala Arg Cys Leu Gly Gly Lys
    1090                1095                1100

Ala Phe Val Ala Val Arg Ala Leu Asn Thr Gly Glu Gln Pro Ala Ala
1105                1110                1115                1120

Ile Glu Leu Ala Thr Pro Tyr Gly Ser Lys Leu Phe Gly Asp Val Ala
                1125                1130                1135

Pro Gly Ala Asn Ala Tyr Gln Ser Phe Ala Thr Arg Ala Ala Ala Val
            1140                1145                1150

Glu Ala Gly Glu Val Thr Val Thr Val Thr Pro Asp Gly Glu Pro
        1155                1160                1165

Gln Gln Val Thr Ala Ala Tyr Asp Ala Ala Ala Cys Ser
    1170                1175                1180

<210> SEQ ID NO 10
<211> LENGTH: 3453
<212> TYPE: DNA
<213> ORGANISM: Cellulosimicrobium cellulans

<400> SEQUENCE: 10
gtgcggcgct ccgtcgcggc gctctctgcc acggcggtcc tggccgccgg actctcgatc      60
gcgcccgccg tcgggctcgc ggtcccggcg gtcgcggccg cacccgacct cgttgaggac     120
cccgtctcct tcgtcgaccc gttcgtcggg accggccagg cgacgggcgt cgtcggggag     180
atcaacaact ccccggggcc gtcgatgccg ttcggcatga tgcagctctc gcccgacacc     240
caggtctccg tgggcaacgg cgacaaggcg tacgcgggct accgctactc gcaccaggcg     300
atccgcggct tctccatgac gcacgcggcc gccggtgctg gatcttcgg cgacgtcccg     360 atcctccccg tgacgggcga cgtcgggcag taccgtgggg accgcaagga ggcgttcagc     420
cacgacgcgg agagcgccga ggtcggccgg tacgcggtca cgctccagtc gtcggggatc     480
gatgcggagg tgtcggccgc gacccgctcg ggcggactga cgttcgacta ccccgagggc     540
ggtgccgcgt cgcaggtgat cgtcaacgcc gcgggctcgc tcgcgagcgt gcgcaacgcg     600
acggtcgagg tcgaggacgc gcgcacggtc accggctcgg tgacgagcgg cgggttctgc     660
ggcaagaaca acacgcacac gacgtacttc gcgatcgagc tcgaccagga cgcgcaggcg     720
ttcggcacgt ggcagggctc gaccgtctcg cccggcgacc cgtcggccga cggcaacggc     780
gcgggcgcgt ggctcacctt cgcgcccggc gcgacggtgc acgcgaaggt cggcatgtcc     840
tacgtgagcg tcgagggcgc gcgcgccaac ctcgcggccg agatcccggg cttcgacttc     900
gacgccgtcc gggacgccaa ccgcgccgcc tggtccgacc tgctcggcaa ggtccgcgtc     960
gcggggcagg acgccgacga cctcaccatg ttctacacgt cgctctacca ctcgctgctg    1020
cacccgaaca cgttcaccga cgtggacggc cggtacgtcg ggttcgacgg ggagatccac    1080 caggccccg aggggcacga gcggtacgcg aacttctccg actgggacac gtaccggtcg    1140
ctcggcgcgc tccaggcgct gctggcgccc gaccaggcgt cggacatggc gcagtcgctc    1200
gtcgaggtcg ccgaccagtc cggctggctg ccgcgctggc cgtcgcgaa ccagcacacg    1260 ggccagatga ccggtgactc ctcggtgccg ctcatcgcga gcatgtacgc gttcggggcg    1320

```
cgcgacttcg acgcggagtc ggcgctcgcg cacatggtca agggtgcgac gagcgccgcc    1380
ccgaccgcga acggctacgt gcagcggcgc gggatcgaga cgtacctcga gcgcggctac    1440
gcgccccaga ccgaggagtt ccggggcgac caccgcgtcg tcggcgcgtc gatcacgctc    1500
gagtggtcga tcgccgactt cgcgatcggg cagctcgcgg ccgcgctcgg ccaggacgac    1560
gtcgccaccg agtacgccgc ccgcggccag tggtggcaga acgtccacga ccccgtgacc    1620
cgcacggcgg gcgcccggaa cgacgacggc acgttcgtgc ggtcgcaggg cggcggcggg    1680
ttcgggcagg agggcttcga cgagggcaac gccgagcagt acacgtggct cgtgccgcag    1740
aacgtcgcgg ggctcaccga cgcgctcggc gggcgtgagg ccgtcgcgga gcggctcgat    1800
gccttcacgg tgcagcacaa cgccggcccg aacgagccgt acctgtggat cggcaacgag    1860
ccgaacttcg gcgtcccgtg gctgtacgac tacgtgggcc agccgtggcg gacgagcgag    1920
ctcgtggacg agcttacgtc cacgctgttc cggcccgagc cgaacggcaa gcccggcaac    1980
gacgacctcg gcgcccaggc cggctggtac gtgtgggccg cgatgggcct gtaccccacc    2040
acgccgggca cggacgtgct cgcgctcaac gcgccgcgct tcgaccgcgt cgtggtcgac    2100
ctcggcgagg gcgacaccct cgacctgcgc gcccccggcg cctcgaccgg cgcccgctac    2160
atcagcggcg tcaccatcga cggcgcagcc tgggacggga cctccctgcc gcgccacgtc    2220
gcgcacgacg gcgcgtcgt cgagctcgcg atgtcgaccg cacgcgacac gacgtggggg    2280
accgcagccg aggacgcccc gccgtcgtgg cgcgacggcg agtccgccgt ggtcgccgcc    2340
gcggacccgg gcctcgtgac ggtcgcccc ggcgggaccg ccgacgcgtc ggtggccgtg    2400
cagctcttcg gcgccgacgc cgccgacgtg cgcgtcgcgg tcgacgcgcc cggggcatc    2460 ggggtcggtg agcccgcgct cgtcgacgac ggctcgggcc acctcaccgg gacggtcccc    2520
gtccaggtgg gtgccggcgt cgcgtccggc taccacgacg cgcgcctcgt gctctcggcc    2580
ggggacgacg acgtcgaggt gccctcacc gtcctcgtcg ccgcgcccgg gtcgctcgtt    2640
gcggcctacg acacggtcgg cactgcgccc gaggcgaacc gcggcgtcgg gaacttcgac    2700
gcggccggca actcgttctc gcgcgaggcg ctcgccgacg cgggtctcac gcccgggtcg    2760
gcgcacgacg tcgacggcct ggcgttcacg tggccgtcct cacccgtggg gcgccccggac    2820 tcggtcacgc tcaccggcga gaccgtgcgg ctcgacgcgc cgacgagccg gctcgcgttc    2880
gtgggcgccg cgaccgacgg gacccatcgc gggaccgcgg tcgtgacgtt cgacgacggc    2940
agcaccgcga ccacgacgat cggcttcggc gactgggtgc tgccgagcgc ggacggctcg    3000
ccggtcgagg gcaactcggt cgtcgcgcag atgaaccggc gcaacggcga caaggacagc    3060
gcgttcgtgt tcgccaccgc cccgtacacc gcgcccgagg accgccgcgt ggtcgcggtg    3120
aggttccccg acgtcgacga cctgcacgtc tttgcgatcg cgaccgagcc ggccgcggac    3180
gtgcacctcg tggacgtgac ggtctccctg cgctgcctcg ccgggacccc gtacgtggcg    3240 gtgcgcgcg cgaacgtctc cgccggggcc gtcgacgtcg acctcacgac gggcgtgggc    3300
tcgcggtcct tcacggccgt cgccccccggc gccaacgcct accagtcgtt cgccgcccgc    3360
ggcgcgaccg ggaacgtcga cgtcaccgtc acggccacgg gggaggaggg gacgcagacg    3420
gtcgcgcgga ccgtcgtcgt cccgcgctgc tcc                                3453
```

<210> SEQ ID NO 11
<211> LENGTH: 1151
<212> TYPE: PRT
<213> ORGANISM: Cellulosimicrobium cellulans

<400> SEQUENCE: 11

```
Val Arg Arg Ser Val Ala Ala Leu Ser Ala Thr Ala Val Leu Ala Ala
 1               5                  10                  15

Gly Leu Ser Ile Ala Pro Ala Val Gly Leu Ala Val Pro Ala Val Ala
             20                  25                  30

Ala Ala Pro Asp Leu Val Glu Asp Pro Val Ser Phe Val Asp Pro Phe
         35                  40                  45

Val Gly Thr Gly Gln Ala Thr Gly Val Val Gly Glu Ile Asn Asn Phe
 50                  55                  60

Pro Gly Pro Ser Met Pro Phe Gly Met Met Gln Leu Ser Pro Asp Thr
 65                  70                  75                  80

Gln Val Ser Val Gly Asn Gly Asp Lys Ala Tyr Ala Gly Tyr Arg Tyr
                 85                  90                  95

Ser His Gln Ala Ile Arg Gly Phe Ser Met Thr His Ala Ala Ala Gly
                100                 105                 110

Cys Trp Ile Phe Gly Asp Val Pro Ile Leu Pro Val Thr Gly Asp Val
            115                 120                 125

Gly Gln Tyr Pro Trp Asp Arg Lys Glu Ala Phe Ser His Asp Ala Glu
130                 135                 140

Ser Ala Glu Val Gly Arg Tyr Ala Val Thr Leu Gln Ser Ser Gly Ile
145                 150                 155                 160

Asp Ala Glu Val Ser Ala Ala Thr Arg Ser Gly Gly Leu Thr Phe Asp
                165                 170                 175

Tyr Pro Glu Gly Gly Ala Ala Ser Gln Val Ile Val Asn Ala Ala Gly
            180                 185                 190

Ser Leu Ala Ser Val Arg Asn Ala Thr Val Glu Val Glu Asp Ala Arg
        195                 200                 205

Thr Val Thr Gly Ser Val Thr Ser Gly Gly Phe Cys Gly Lys Asn Asn
210                 215                 220

Thr His Thr Thr Tyr Phe Ala Ile Glu Leu Asp Gln Asp Ala Gln Ala
225                 230                 235                 240

Phe Gly Thr Trp Gln Gly Ser Thr Val Ser Pro Gly Asp Pro Ser Ala
                245                 250                 255

Asp Gly Asn Gly Ala Gly Ala Trp Leu Thr Phe Ala Pro Gly Ala Thr
            260                 265                 270

Val His Ala Lys Val Gly Met Ser Tyr Val Ser Val Glu Gly Ala Arg
        275                 280                 285

Ala Asn Leu Ala Ala Glu Ile Pro Gly Phe Asp Phe Asp Ala Val Arg
    290                 295                 300

Asp Ala Asn Arg Ala Ala Trp Ser Asp Leu Leu Gly Lys Val Arg Val
305                 310                 315                 320

Ala Gly Gln Asp Ala Asp Asp Leu Thr Met Phe Tyr Thr Ser Leu Tyr
                325                 330                 335

His Ser Leu Leu His Pro Asn Thr Phe Thr Asp Val Asp Gly Arg Tyr
            340                 345                 350

Val Gly Phe Asp Gly Glu Ile His Gln Ala Pro Glu Gly His Glu Arg
        355                 360                 365

Tyr Ala Asn Phe Ser Asp Trp Asp Thr Tyr Arg Ser Leu Gly Ala Leu
    370                 375                 380

Gln Ala Leu Leu Ala Pro Asp Gln Ala Ser Asp Met Ala Gln Ser Leu
385                 390                 395                 400

Val Glu Val Ala Asp Gln Ser Gly Trp Leu Pro Arg Trp Pro Val Ala
                405                 410                 415
```

-continued

Asn Gln His Thr Gly Gln Met Thr Gly Asp Ser Ser Val Pro Leu Ile
            420                 425                 430

Ala Ser Met Tyr Ala Phe Gly Ala Arg Asp Phe Asp Ala Glu Ser Ala
        435                 440                 445

Leu Ala His Met Val Lys Gly Ala Thr Ser Ala Ala Pro Thr Ala Asn
    450                 455                 460

Gly Tyr Val Gln Arg Arg Gly Ile Glu Thr Tyr Leu Glu Arg Gly Tyr
465                 470                 475                 480

Ala Pro Gln Thr Glu Glu Phe Arg Gly Asp His Arg Val Val Gly Ala
                485                 490                 495

Ser Ile Thr Leu Glu Trp Ser Ile Ala Asp Phe Ala Ile Gly Gln Leu
            500                 505                 510

Ala Ala Ala Leu Gly Gln Asp Val Ala Thr Glu Tyr Ala Ala Arg
        515                 520                 525

Gly Gln Trp Trp Gln Asn Val His Asp Pro Val Thr Arg Thr Ala Gly
    530                 535                 540

Ala Arg Asn Asp Asp Gly Thr Phe Val Arg Ser Gln Gly Gly Gly Gly
545                 550                 555                 560

Phe Gly Gln Glu Gly Phe Asp Glu Gly Asn Ala Glu Gln Tyr Thr Trp
                565                 570                 575

Leu Val Pro Gln Asn Val Ala Gly Leu Thr Asp Ala Leu Gly Gly Arg
            580                 585                 590

Glu Ala Val Ala Glu Arg Leu Asp Ala Phe Thr Val Gln His Asn Ala
        595                 600                 605

Gly Pro Asn Glu Pro Tyr Leu Trp Ile Gly Asn Glu Pro Asn Phe Gly
    610                 615                 620

Val Pro Trp Leu Tyr Asp Tyr Val Gly Gln Pro Trp Arg Thr Ser Glu
625                 630                 635                 640

Leu Val Asp Glu Leu Thr Ser Thr Leu Phe Arg Pro Glu Pro Asn Gly
                645                 650                 655

Lys Pro Gly Asn Asp Asp Leu Gly Ala Gln Ala Gly Trp Tyr Val Trp
            660                 665                 670

Ala Ala Met Gly Leu Tyr Pro Thr Thr Pro Gly Thr Asp Val Leu Ala
        675                 680                 685

Leu Asn Ala Pro Arg Phe Asp Arg Val Val Val Asp Leu Gly Glu Gly
    690                 695                 700

Asp Thr Leu Asp Leu Arg Ala Pro Gly Ala Ser Thr Gly Ala Arg Tyr
705                 710                 715                 720

Ile Ser Gly Val Thr Ile Asp Gly Ala Ala Trp Asp Gly Thr Ser Leu
                725                 730                 735

Pro Arg His Val Ala His Asp Gly Gly Val Val Glu Leu Ala Met Ser
            740                 745                 750

Thr Ala Arg Asp Thr Thr Trp Gly Thr Ala Ala Glu Asp Ala Pro Pro
        755                 760                 765

Ser Trp Arg Asp Gly Glu Ser Ala Val Val Ala Ala Asp Pro Gly
    770                 775                 780

Leu Val Thr Val Ala Pro Gly Gly Thr Ala Asp Ala Ser Val Ala Val
785                 790                 795                 800

Gln Leu Phe Gly Ala Asp Ala Ala Asp Val Arg Val Ala Val Asp Ala
                805                 810                 815

Pro Gly Gly Ile Gly Val Gly Glu Pro Ala Leu Val Asp Asp Gly Ser
            820                 825                 830

Gly His Leu Thr Gly Thr Val Pro Val Gln Val Gly Gly Val Ala
         835                 840                 845

Ser Gly Tyr His Asp Ala Arg Leu Val Leu Ser Ala Gly Asp Asp
    850                 855                 860

Val Glu Val Pro Leu Thr Val Leu Val Ala Ala Pro Gly Ser Leu Val
865                 870                 875                 880

Ala Ala Tyr Asp Thr Val Gly Thr Ala Pro Glu Ala Asn Arg Gly Val
                885                 890                 895

Gly Asn Phe Asp Ala Ala Gly Asn Ser Phe Ser Arg Glu Leu Ala
            900                 905                 910

Asp Ala Gly Leu Thr Pro Gly Ser Ala His Asp Val Asp Gly Leu Ala
                915                 920                 925

Phe Thr Trp Pro Ser Ser Pro Val Gly Arg Pro Asp Ser Val Thr Leu
            930                 935                 940

Thr Gly Glu Thr Val Arg Leu Asp Ala Pro Thr Ser Arg Leu Ala Phe
945                 950                 955                 960

Val Gly Ala Ala Thr Asp Gly Thr His Arg Gly Thr Ala Val Val Thr
                965                 970                 975

Phe Asp Asp Gly Ser Thr Ala Thr Thr Thr Ile Gly Phe Gly Asp Trp
            980                 985                 990

Val Leu Pro Ser Ala Asp Gly Ser Pro Val Glu Gly Asn Ser Val Val
            995                 1000                1005

Ala Gln Met Asn Arg Arg Asn Gly Asp Lys Asp Ser Ala Phe Val Phe
            1010                1015                1020

Ala Thr Ala Pro Tyr Thr Ala Pro Glu Asp Arg Arg Val Val Ala Val
1025                1030                1035                1040

Arg Phe Pro Asp Val Asp Asp Leu His Val Phe Ala Ile Ala Thr Glu
            1045                1050                1055

Pro Ala Ala Asp Val His Leu Val Asp Val Thr Val Ser Leu Arg Cys
            1060                1065                1070

Leu Ala Gly Thr Pro Tyr Val Ala Val Arg Ala Ala Asn Val Ser Ala
            1075                1080                1085

Gly Ala Val Asp Val Asp Leu Thr Thr Gly Val Gly Ser Arg Ser Phe
            1090                1095                1100

Thr Ala Val Ala Pro Gly Ala Asn Ala Tyr Gln Ser Phe Ala Ala Arg
1105                1110                1115                1120

Gly Ala Thr Gly Asn Val Asp Val Thr Val Thr Ala Thr Gly Glu Glu
            1125                1130                1135

Gly Thr Gln Thr Val Ala Arg Thr Val Val Val Pro Arg Cys Ser
            1140                1145                1150

<210> SEQ ID NO 12
<211> LENGTH: 5433
<212> TYPE: DNA
<213> ORGANISM: Cellulosimicrobium cellulans

<400> SEQUENCE: 12
atgaccagac cactcccgcc cggacgcgcg gtcgcgcggt ccggcagcgg ccgcgcccgg     60
cccctcggcc tcgtgctcgc cgccgcactc gccgtcccgc tcggggtgcc tctcgcggcc    120
cccgcgggag ccctcgctgc cgcgcccgcc gcggccgccg agcccggcga cttctcgtcc    180
tcgttcgagt ccggcgaccc ggccgcgctg cccaccaccg tggcggagcg cgacggcgcg    240
ccctggcagg cgaacgtcgg ctcgttcacg gccggcctgc ccgggagcgt cctcgggcag    300
ctgaagggcg tcacggcgag cgcgcagaac ctgcccaacg agggcgcggc gaacctcgcc    360

| | |
|---|---|
| gacggcagct cgggcaccaa gtggctcgcg ttcgcgtcga ccggctgggt ccggtacgag | 420 |
| ttcgccgagc ccgtctcgtt cgtcgcgtac acgatgacct ccggcgacga cgccgccggt | 480 |
| cgcgacccga agacctggac ggtcgagggg tcgaacgacg ggtccacgtg ggccgcgctc | 540 |
| gaccgccgga cggacgagga cttcccgaac cgccagcaga cgcgcacgtt cgagctcgag | 600 |
| gcgcccaccg cggcgtacac gtacctgcgc ctcaacgtca cggcgaactc gggcgactcc | 660 |
| atcgtccagc tcgccgggtg ggacctctcg gccgacctga gcgccggccc gtccgcggcc | 720 |
| cccatgacga cgaaggtcgg caccgggccg cgcgtcagct tcaccaacaa ggcgggcgtc | 780 |
| gggttctccg gcctgcactc gctccggtac gacggctcgc acctcgccga cggcgagacg | 840 |
| tacgcgacga acgtgctcta cgacgacgtg gacgtcgtcg tcggcgagga cacgcgcctg | 900 |
| agctacacga tcttccccga gctgctcgac gatctgcagt acccgtcgac gtacgcggcg | 960 |
| gtggacgtcc tgttcaccga cgggacctac ctgtccgacc tcggcgcgcg cgacgcgcac | 1020 |
| gagacggtcg cgaccgcgca ggcgcagggc gagggcaaga tcctctacgc cgaccagtgg | 1080 |
| aactcggtgc gggtcgacct cggcgacgtc gccgagggca agaccgtgga ccaggtgctg | 1140 |
| ctcgggtacg acaacccggg cggtcacgcc gggacgaagt tcgcgggctg gctcgacgac | 1200 |
| gtcgagatca cggcggagcc ggccacgatc gacgggtcga gcctcgccaa ctacgtggac | 1260 |
| acggccgcg gcacgctcgc gtcgggcagc ttctcgcgcg ggaacaacat ccccgcgacg | 1320 |
| gcgacgccga acgggttcaa cttctggacg ccgtacacga acgcctcctc gcagagctgg | 1380 |
| ctgtacgagt accacaaggc caacaacgcc aacaacaagc ccgtcctcca gggcttcggg | 1440 |
| atctcgcacg agccgagccc gtggatgggc gaccgcaacc agctgacgtt cctcccgtcg | 1500 |
| acggcgtcgg ggacgcccga cgccacgctc tcgacgcgcg gcctcgagtt cgaccacgcg | 1560 |
| gacgagacgg cgcggccgga ctactacggg gtcacgttca ccaacgggtc cgcgatcgag | 1620 |
| gcgacgccca ccgaccacgg cgcggtgctc cgcttcagct accccggagc caagggccac | 1680 |
| gtgctcgtgg acaaggtgga cggctcctcc aagctcacgt acgaccaggc cacgggcacg | 1740 |
| atctccggct gggtcgagaa cggctcgggc ctgtccgtgg gccgcacgcg catgttcgtc | 1800 |
| gccggcacct tcgaccgtag tccgacggcg gtcgggacgg cggcgggcaa ccgtgcggac | 1860 |
| gcgcgcttcg cgacgttcga gacgtcgtcc gacaagacgg tcgagctgcg cgtcgcgacg | 1920 |
| tcgttcatca gcctcgacca ggcgcgcaag aacctcgacc tggaggtgac gggcaagacc | 1980 |
| ttcacggagg tcaaggccgc cgccgcgcag gcgtggaacg accgcctggg ggtcatcgag | 2040 |
| gtcgagggcg cgagcgagga ccagctcgtc acgctgtact cgaacctcta ccgcctcaac | 2100 |
| ctgtacccga actcgcagtt cgagaacacg ggcacggcgc aggagccggt gtacaggtac | 2160 |
| gcgagcccgg tctccgcgac cacgggctcc gcgacggaca cgcagaccaa cgcgaagatc | 2220 |
| gtcgacggca agatctacgt gaacaacggg ttctgggaca cgtaccgcac ggcctggccg | 2280 |
| gcgtactcgc tcctctaccc ggagctcgcg ccgagctgg tcgacgggtt cgtccagcag | 2340 |
| taccgcgacg gcggctggat cgcgcgctgg tcctcgccgg gctacgccga cctcatgacg | 2400 |
| ggcacgagct ccgacgtggc gttcgccgac gcgtacctca agggctcgct ccccacgggc | 2460 |
| acggcgctcg aggcgtacga cgccgcgctg cgcaacgcga ccgtcgcgcc gccgagcaac | 2520 |
| gccgtgggcc gcaagggcct gcagacctcg ccgttcctcg ggttcacgcc ggagtccacg | 2580 |
| cacgagtcca tgtcgtgggg cctggagggc ctggtcaacg acttcggcat cggcaacatg | 2640 |
| gccgccgccc tcgcggagga cccggcgacg ccggaggagc gccgcgagac gctgcgcgag | 2700 |

```
gagtccgcgt acttcctcga gcgggccacg cactacgtcg agctgttcga ccccgaggtc    2760
gacttcttcg tgccgcggca cgaggacggc acgtgggccg tcgacccga cgtacgac      2820 ccggaggcct ggggcggcgg gtacaccgag acgaacggct ggaacttcgc gttccacgcc    2880
ccgcaggacg ccagggcct cgccaacctc tacggcggca agcagggcct cgaggacaag     2940
ctcgacgagt tcttctccac gccggagaag ggcgccggca acggcggcat ccacgagcag    3000
cgcgaggcgc gcgacgtccg catgggccag tggggcatga gcaaccaggt gtcgcaccac   3060
atcccgtggc tctacgacgc cgcgggcgcg ccgtcgaagg cgcaggagaa ggtccgcgag    3120
gtcacccgcc gcctgttcgt gggcagcgag atcggccagg gctacccggg cgacgaggac   3180
aacggcgaga tgtcgtcgtg gtggatcttc gcctcgctcg gcttctaccc gctccaggtc   3240
ggctcggacc agtacgcggt cggttcgccg ctgttcgaca aggcgaccgt gcacctgccg    3300
gacggcgacc tcgtcgtcaa cgccgagaac aactcggtcg acaacgtcta cgtgcagtcc   3360
ctcgcggtgg acggcgaggc ccgcacctcg acgtcactct cccaggcgga cctctcgggc   3420
ggcacgactc tggacttcgt catgggtccg gagccgtcgg actggggcac gggcgaggac   3480
gacgcgccgc cgtcgctcac cgagggcgac gagcccccga cgccggtgca ggacgcgacg    3540
accgcgggcc tcggcaccac caccgtcgcc gacggcgacg ccaccacgag cgccgcggcg    3600
ctcacggaca acacgtccgg gacgcgcacg acgttcgcca ccacgacgcc gtcgatcacg    3660
tgggcgggca acggcatccg cccgaccgtc gggtcgtaca cgctgacctc cggggcgagc    3720
gggacggcgt caccgtccgc atggactctc gagggttccg acgacggcga cgtggacg    3780 acgctcgacg agcggtccgg cgagcagttc cgctgggccc tgcagacgcg gccgttcacg   3840
gtcgcggagc cgacggcgtt cgcgcggtac cgggtcacgg tcaccgcgac gtcgggctcc   3900
ggcgcgctgt cgctcgccga ggtcgagctc ctcgccgacc cgaaggagtc gggggccgag   3960
gagctcaccc tctcggccgc gccggaccgt gacggcgtca cgggccgcga ggtctcgggc   4020
tcgttcgcga ccctcaccgg ggtcgagggc gacgtcgcgg cgctcgacgt gcaggtcgcg   4080
ttcggcgacg gctccgagcc ggtcgccggg acgctgcggg cgggcgcgtt cggcgggtac    4140
gcggtggacc ccgcgcacac gtggaccgca cccggcgtct accccgtgac cgtcacggtc   4200
tcgggcgagg ggatcgagac cgtctcggcc tcctcgtacg tcagcgtctc gctcctgcgc   4260
gagggctcgc tgctcgccgc gtacgacaac gtctgcatcg gcgacgccgg gacgacggtc   4320
ggctcgtgcg acggccaggg cgtgttcttc gaccgggcgc agctcgcggc gaagggcttc    4380
gtccagggcg agcgcgcgac ggtgccggc acggacctcg cgttcgacgt cccggcggtc   4440
cccgccgggc agccggacaa cgccacgggc gacgggcaga ccatcgagct cgacgtcccc   4500
gcggacgcgg agcagctctc ggtgatcggc acggcacgg agaagaacca gcaggccacc   4560
ggcacgctga ccttcgacga cggctcgacc cagccgatcg acctgagctt cggcgactgg   4620
tcgggcgcgg cccgcaaccc cgtgttcggc aacatccccg tcgcggtgac ggacagccgc   4680
ctccgcggcg gcagcccgca gaccggcacc cccgccgcgt tcttcgcgac ggcgccgatc   4740
accctccccg agggcaagcg gcccgtgagc ctcacgctcc cggaccagcc gggcgagctc   4800
tcgcgcgacg gccgcatcca cgtggtcgcg gtcgcgcacg acggcacgtt cgccgagcac   4860
cccgcgctcg aggtcacggc cgcggagggc gtgacgctcg ccgtcgggca gacctcggac   4920
gtggcgctcg cccaggtggc ggggccgcg gagggcgccg acctccgggc ggcggtcacg   4980
tggggcgacg gctccgacgt cgcggccggc gcggtgaccg acgggtcggt ctccggctcg    5040
cacgcctaca cggcggccgg gacgtacacg gcgtacgtcg tggtcgacga cggctggacc   5100
```

```
agccaggtgg tcgaggtccc cgtgaccgtg accgaggcgg agccggccct cgccgtcgac    5160
gtcacggtga gcacacgctg cctcgccggc aaggcgtacg tcgcggtccg cgccgagaac    5220
ggcgaggacg tgccgctcgc gatccggctc gtcacgccgt tcggcaccaa ggaggtcgcg    5280
gccgtcgcgc cgggcgccaa cgcctaccag tcgttcgcga cgcgggtcac ggcggtcgag    5340
gccggcaccg tcaccgtcga ggcgacgcgc ggcaccggcg acgaggaggt gacggcgtcg    5400
atccaggccg actacgccgc cgtgacctgc ggc                                 5433
```

<210> SEQ ID NO 13
<211> LENGTH: 1811
<212> TYPE: PRT
<213> ORGANISM: Cellulosimicrobium cellulans

<400> SEQUENCE: 13

```
Met Thr Arg Pro Leu Pro Gly Arg Ala Val Ala Arg Ser Gly Ser
 1               5                  10                  15

Gly Arg Ala Arg Pro Leu Gly Leu Val Leu Ala Ala Leu Ala Val
                20                  25                  30

Pro Leu Gly Val Pro Leu Ala Ala Pro Ala Gly Ala Leu Ala Ala
                35                  40                  45

Pro Ala Ala Ala Glu Pro Gly Asp Phe Ser Ser Phe Glu Ser
         50                  55                  60

Gly Asp Pro Ala Ala Leu Pro Thr Thr Val Ala Glu Arg Asp Gly Ala
 65                  70                  75                  80

Pro Trp Gln Ala Asn Val Gly Ser Phe Thr Ala Gly Leu Pro Gly Ser
                85                  90                  95

Val Leu Gly Gln Leu Lys Gly Val Thr Ala Ser Ala Gln Asn Leu Pro
            100                 105                 110

Asn Glu Gly Ala Ala Asn Leu Ala Asp Gly Ser Ser Gly Thr Lys Trp
            115                 120                 125

Leu Ala Phe Ala Ser Thr Gly Trp Val Arg Tyr Glu Phe Ala Glu Pro
        130                 135                 140

Val Ser Phe Val Ala Tyr Thr Met Thr Ser Gly Asp Asp Ala Ala Gly
145                 150                 155                 160

Arg Asp Pro Lys Thr Trp Thr Val Glu Gly Ser Asn Asp Gly Ser Thr
                165                 170                 175

Trp Ala Ala Leu Asp Arg Arg Thr Asp Glu Asp Phe Pro Asn Arg Gln
            180                 185                 190

Gln Thr Arg Thr Phe Glu Leu Glu Ala Pro Thr Ala Ala Tyr Thr Tyr
        195                 200                 205

Leu Arg Leu Asn Val Thr Ala Asn Ser Gly Asp Ser Ile Val Gln Leu
    210                 215                 220

Ala Gly Trp Asp Leu Ser Ala Asp Leu Ser Ala Gly Pro Ser Ala Ala
225                 230                 235                 240

Pro Met Thr Thr Lys Val Gly Thr Gly Pro Arg Val Ser Phe Thr Asn
                245                 250                 255

Lys Ala Gly Val Gly Phe Ser Gly Leu His Ser Leu Arg Tyr Asp Gly
            260                 265                 270

Ser His Leu Ala Asp Gly Glu Thr Tyr Ala Thr Asn Val Leu Tyr Asp
        275                 280                 285

Asp Val Asp Val Val Gly Glu Asp Thr Arg Leu Ser Tyr Thr Ile
    290                 295                 300

Phe Pro Glu Leu Leu Asp Asp Leu Gln Tyr Pro Ser Thr Tyr Ala Ala
```

```
              305                 310                 315                 320
Val Asp Val Leu Phe Thr Asp Gly Thr Tyr Leu Ser Asp Leu Gly Ala
                    325                 330                 335

Arg Asp Ala His Glu Thr Val Ala Thr Ala Gln Ala Gln Gly Glu Gly
                    340                 345                 350

Lys Ile Leu Tyr Ala Asp Gln Trp Asn Ser Val Arg Val Asp Leu Gly
                    355                 360                 365

Asp Val Ala Glu Gly Lys Thr Val Asp Gln Val Leu Leu Gly Tyr Asp
        370                 375                 380

Asn Pro Gly Gly His Ala Gly Thr Lys Phe Ala Gly Trp Leu Asp Asp
385                 390                 395                 400

Val Glu Ile Thr Ala Glu Pro Ala Thr Ile Asp Gly Ser Ser Leu Ala
                    405                 410                 415

Asn Tyr Val Asp Thr Arg Arg Gly Thr Leu Ala Ser Gly Ser Phe Ser
                    420                 425                 430

Arg Gly Asn Asn Ile Pro Ala Thr Ala Thr Pro Asn Gly Phe Asn Phe
                435                 440                 445

Trp Thr Pro Tyr Thr Asn Ala Ser Ser Gln Ser Trp Leu Tyr Glu Tyr
        450                 455                 460

His Lys Ala Asn Asn Ala Asn Asn Lys Pro Val Leu Gln Gly Phe Gly
465                 470                 475                 480

Ile Ser His Glu Pro Ser Pro Trp Met Gly Asp Arg Asn Gln Leu Thr
                    485                 490                 495

Phe Leu Pro Ser Thr Ala Ser Gly Thr Pro Asp Ala Thr Leu Ser Thr
                500                 505                 510

Arg Gly Leu Glu Phe Asp His Ala Asp Glu Thr Ala Arg Pro Asp Tyr
            515                 520                 525

Tyr Gly Val Thr Phe Thr Asn Gly Ser Ala Ile Glu Ala Thr Pro Thr
        530                 535                 540

Asp His Gly Ala Val Leu Arg Phe Ser Tyr Pro Gly Ala Lys Gly His
545                 550                 555                 560

Val Leu Val Asp Lys Val Asp Gly Ser Ser Lys Leu Thr Tyr Asp Gln
                    565                 570                 575

Ala Thr Gly Thr Ile Ser Gly Trp Val Glu Asn Gly Ser Gly Leu Ser
                    580                 585                 590

Val Gly Arg Thr Arg Met Phe Val Ala Gly Thr Phe Asp Arg Ser Pro
            595                 600                 605

Thr Ala Val Gly Thr Ala Ala Gly Asn Arg Ala Asp Ala Arg Phe Ala
610                 615                 620

Thr Phe Glu Thr Ser Ser Asp Lys Thr Val Glu Leu Arg Val Ala Thr
625                 630                 635                 640

Ser Phe Ile Ser Leu Asp Gln Ala Arg Lys Asn Leu Asp Leu Glu Val
                    645                 650                 655

Thr Gly Lys Thr Phe Thr Glu Val Lys Ala Ala Ala Gln Ala Trp
                    660                 665                 670

Asn Asp Arg Leu Gly Val Ile Glu Val Glu Gly Ala Ser Glu Asp Gln
            675                 680                 685

Leu Val Thr Leu Tyr Ser Asn Leu Tyr Arg Leu Asn Leu Tyr Pro Asn
        690                 695                 700

Ser Gln Phe Glu Asn Thr Gly Thr Ala Gln Glu Pro Val Tyr Arg Tyr
705                 710                 715                 720

Ala Ser Pro Val Ser Ala Thr Thr Gly Ser Ala Thr Asp Thr Gln Thr
                    725                 730                 735
```

```
Asn Ala Lys Ile Val Asp Gly Lys Ile Tyr Val Asn Asn Gly Phe Trp
            740                 745                 750

Asp Thr Tyr Arg Thr Ala Trp Pro Ala Tyr Ser Leu Leu Tyr Pro Glu
            755                 760                 765

Leu Ala Ala Glu Leu Val Asp Gly Phe Val Gln Gln Tyr Arg Asp Gly
            770                 775                 780

Gly Trp Ile Ala Arg Trp Ser Ser Pro Gly Tyr Ala Asp Leu Met Thr
785                 790                 795                 800

Gly Thr Ser Ser Asp Val Ala Phe Ala Asp Ala Tyr Leu Lys Gly Ser
                805                 810                 815

Leu Pro Thr Gly Thr Ala Leu Glu Ala Tyr Asp Ala Ala Leu Arg Asn
            820                 825                 830

Ala Thr Val Ala Pro Pro Ser Asn Ala Val Gly Arg Lys Gly Leu Gln
            835                 840                 845

Thr Ser Pro Phe Leu Gly Phe Thr Pro Glu Ser Thr His Glu Ser Val
            850                 855                 860

Ser Trp Gly Leu Glu Gly Leu Val Asn Asp Phe Gly Ile Gly Asn Met
865                 870                 875                 880

Ala Ala Ala Leu Ala Glu Asp Pro Ala Thr Pro Glu Glu Arg Arg Glu
                885                 890                 895

Thr Leu Arg Glu Glu Ser Ala Tyr Phe Leu Glu Arg Ala Thr His Tyr
            900                 905                 910

Val Glu Leu Phe Asp Pro Glu Val Asp Phe Phe Val Pro Arg His Glu
            915                 920                 925

Asp Gly Thr Trp Ala Val Asp Pro Glu Thr Tyr Asp Pro Glu Ala Trp
            930                 935                 940

Gly Gly Gly Tyr Thr Glu Thr Asn Gly Trp Asn Phe Ala Phe His Ala
945                 950                 955                 960

Pro Gln Asp Gly Gln Gly Leu Ala Asn Leu Tyr Gly Gly Lys Gln Gly
                965                 970                 975

Leu Glu Asp Lys Leu Asp Glu Phe Phe Ser Thr Pro Glu Lys Gly Ala
            980                 985                 990

Gly Asn Gly Gly Ile His Glu Gln Arg Glu Ala Arg Asp Val Arg Met
            995                 1000                1005

Gly Gln Trp Gly Met Ser Asn Gln Val Ser His His Ile Pro Trp Leu
            1010                1015                1020

Tyr Asp Ala Ala Gly Ala Pro Ser Lys Ala Gln Glu Lys Val Arg Glu
1025                1030                1035                1040

Val Thr Arg Arg Leu Phe Val Gly Ser Glu Ile Gly Gln Gly Tyr Pro
            1045                1050                1055

Gly Asp Glu Asp Asn Gly Glu Met Ser Ser Trp Trp Ile Phe Ala Ser
            1060                1065                1070

Leu Gly Phe Tyr Pro Leu Gln Val Gly Ser Asp Gln Tyr Ala Val Gly
            1075                1080                1085

Ser Pro Leu Phe Asp Lys Ala Thr Val His Leu Pro Asp Gly Asp Leu
            1090                1095                1100

Val Val Asn Ala Glu Asn Asn Ser Val Asp Asn Val Tyr Val Gln Ser
1105                1110                1115                1120

Leu Ala Val Asp Gly Glu Ala Arg Thr Ser Thr Ser Leu Ser Gln Ala
            1125                1130                1135

Asp Leu Ser Gly Gly Thr Thr Leu Asp Phe Val Met Gly Pro Glu Pro
            1140                1145                1150
```

-continued

Ser Asp Trp Gly Thr Gly Glu Asp Ala Pro Ser Leu Thr Glu
    1155                1160                1165

Gly Asp Glu Pro Pro Thr Pro Val Gln Asp Ala Thr Thr Ala Gly Leu
    1170                1175                1180

Gly Thr Thr Thr Val Ala Asp Gly Asp Ala Thr Thr Ser Ala Ala Ala
1185                1190                1195                1200

Leu Thr Asp Asn Thr Ser Gly Thr Arg Thr Thr Phe Ala Thr Thr Thr
        1205                1210                1215

Pro Ser Ile Thr Trp Ala Gly Asn Gly Ile Arg Pro Thr Val Gly Ser
        1220                1225                1230

Tyr Thr Leu Thr Ser Gly Ala Ser Gly Thr Ala Ser Pro Ser Ala Trp
        1235                1240                1245

Thr Leu Glu Gly Ser Asp Asp Gly Glu Thr Trp Thr Thr Leu Asp Glu
        1250                1255                1260

Arg Ser Gly Glu Gln Phe Arg Trp Ala Leu Gln Thr Arg Pro Phe Thr
1265                1270                1275                1280

Val Ala Glu Pro Thr Ala Phe Ala Arg Tyr Arg Val Thr Val Thr Ala
        1285                1290                1295

Thr Ser Gly Ser Gly Ala Leu Ser Leu Ala Glu Val Glu Leu Leu Ala
        1300                1305                1310

Asp Pro Lys Glu Ser Gly Ala Glu Glu Leu Thr Leu Ser Ala Ala Pro
        1315                1320                1325

Asp Arg Asp Gly Val Thr Gly Arg Glu Val Ser Gly Ser Phe Ala Thr
        1330                1335                1340

Leu Thr Gly Val Glu Gly Asp Val Ala Ala Leu Asp Val Gln Val Ala
1345                1350                1355                1360

Phe Gly Asp Gly Ser Glu Pro Val Ala Gly Thr Leu Arg Ala Gly Ala
        1365                1370                1375

Phe Gly Gly Tyr Ala Val Asp Ala Ala His Thr Trp Thr Ala Pro Gly
        1380                1385                1390

Val Tyr Pro Val Thr Val Thr Val Ser Gly Glu Gly Ile Glu Thr Val
        1395                1400                1405

Ser Ala Ser Ser Tyr Val Ser Val Ser Leu Leu Arg Glu Gly Ser Leu
        1410                1415                1420

Leu Ala Ala Tyr Asp Asn Val Cys Ile Gly Asp Ala Gly Thr Thr Val
1425                1430                1435                1440

Gly Ser Cys Asp Gly Gln Gly Val Phe Phe Asp Arg Ala Gln Leu Ala
        1445                1450                1455

Ala Lys Gly Phe Val Gln Gly Glu Arg Ala Thr Val Pro Gly Thr Asp
        1460                1465                1470

Leu Ala Phe Asp Val Pro Ala Val Pro Ala Gly Gln Pro Asp Asn Ala
        1475                1480                1485

Thr Gly Asp Gly Gln Thr Ile Glu Leu Asp Val Pro Ala Asp Ala Glu
        1490                1495                1500

Gln Leu Ser Val Ile Gly Thr Gly Thr Glu Lys Asn Gln Gln Ala Thr
1505                1510                1515                1520

Gly Thr Leu Thr Phe Asp Asp Gly Ser Thr Gln Pro Ile Asp Leu Ser
        1525                1530                1535

Phe Gly Asp Trp Ser Gly Ala Ala Arg Asn Pro Val Phe Gly Asn Ile
        1540                1545                1550

Pro Val Ala Val Thr Asp Ser Arg Leu Arg Gly Gly Ser Pro Gln Thr
        1555                1560                1565

Gly Thr Pro Ala Ala Phe Phe Ala Thr Ala Pro Ile Thr Leu Pro Glu

```
                1570             1575             1580
Gly Lys Arg Pro Val Ser Leu Thr Leu Pro Asp Gln Pro Gly Glu Leu
1585             1590             1595             1600

Ser Arg Asp Gly Arg Ile His Val Val Ala Val Ala His Asp Gly Thr
            1605             1610             1615

Phe Ala Glu His Pro Ala Leu Glu Val Thr Ala Ala Glu Gly Val Thr
            1620             1625             1630

Leu Ala Val Gly Gln Thr Ser Asp Val Ala Leu Ala Gln Val Ala Gly
        1635             1640             1645

Gly Arg Glu Gly Ala Asp Leu Arg Ala Ala Val Thr Trp Gly Asp Gly
        1650             1655             1660

Ser Asp Val Ala Ala Gly Ala Val Thr Asp Gly Ser Val Ser Gly Ser
1665             1670             1675             1680

His Ala Tyr Thr Ala Ala Gly Thr Tyr Thr Ala Tyr Val Val Val Asp
            1685             1690             1695

Asp Gly Trp Thr Ser Gln Val Val Glu Val Pro Val Thr Val Thr Glu
            1700             1705             1710

Ala Glu Pro Ala Leu Ala Val Asp Val Thr Val Ser Thr Arg Cys Leu
            1715             1720             1725

Ala Gly Lys Ala Tyr Val Ala Val Arg Ala Glu Asn Gly Glu Asp Val
        1730             1735             1740

Pro Leu Ala Ile Arg Leu Val Thr Pro Phe Gly Thr Lys Glu Val Ala
1745             1750             1755             1760

Ala Val Ala Pro Gly Ala Asn Ala Tyr Gln Ser Phe Ala Thr Arg Val
            1765             1770             1775

Thr Ala Val Glu Ala Gly Thr Val Thr Val Glu Ala Thr Arg Gly Thr
            1780             1785             1790

Gly Asp Glu Glu Val Thr Ala Ser Ile Gln Ala Asp Tyr Ala Ala Val
            1795             1800             1805

Thr Cys Gly
    1810

<210> SEQ ID NO 14
<211> LENGTH: 4995
<212> TYPE: DNA
<213> ORGANISM: Cellulosimicrobium cellulans

<400> SEQUENCE: 14
gcgctcgccg tcgtcggcct cgcgcccgcg accgccgcga gcgccgcccc cgagccgccg      60
tcggccgact acgcgtccct ggtcgacgtc ttcgtcggca ccgagggcga cttcggcaac     120
gacatgcccg ccgcgcaggc gccgaacggc ctcgcgaagg tcaacccgcg cacgaccccg     180
ggccgcaaca acaccgggta cgactacgcg cagtcgaaga tctcgggctt cacgcacacc     240
aacctcgacg gggtcggggg ctccggcggc ggtggtgacc tcctcgtggt gccgacgtcc     300
gggtcgtaca cggcgcgccc cggcacgggc acgtacgcgc accgttctc gcacgacgac     360
gaggacgccg accgggcttc tactccgtcg ggctcggca acgtcgcggg cacggacggc     420
gcgatcaccg gcgcgccggg cacgatcgag gccgaggtcg cggcggccac gcgctcgggc     480
gtgcaccgct acgcgttccc gcgggcctcg acgccgagcc tcgtcgtgga cctcgagacg     540
aacaacacga gccgccggtc gtcctcggtg caggtcgaga cgcgcgcgga cggcaccgtg     600
gagctgtccg acaggtcac gggctacttc tacaacgcgg cctacacgct gtactacacc     660
gcgcgcacgc tccagcccgc gacggtgcag acgtggggcg acgacgaccg gctcgtcgac     720
```

```
gccacggccc aggacggcgt cgacaccggc gcgatcctca cgttcgaccc ggcggacgcc      780
ggggagatcg ggctccaggt caccctgtcg ccggtgagcg tcgagcaggc gcggatcgac      840
cagcaggtcg agctcggcga cctgtcgttc gacgcgatcc gtgaccgcac ccgcgcggag      900
tggaacgcga cgctcgggcg ggtcgcgatc gacgcctcga cggcgacgga cccgacgggc      960
gagctccagc ggctcttcta cacgcacctc taccgcatgt tcgcgatgcc gatgaacgcg     1020
acgagcacct cgggcacgta ccgcggcgtc gacggggcgg tgcacgccgc gcagggcttc     1080
acgtactacg actcgtgggc cacgtgggac gacttccgca agttctccgt catcgcgtac     1140
atcgacccgg cgctgtaccg ggacatggtg cagtcgctgg tctacctgtt cgcggacgcc     1200
gaggcgacgg gcaccggcgg cggcctcggc gggttcgtgc actcggtccc gacggtgcgc     1260
tgggagcggt cgtcggtcgt ggtcgcggac gcgatcgcca agggcttcga cgggttcgac     1320
cgcctcgacg aggcgtaccc ggcgctccag cggctcgtcg ggcagtacag cgcggacgag     1380
ctccggcgcg gctacgtggc gggcaacccc ggcgcgtccg tgcagcgcgg ctacgaccag     1440
tacggcctgt ccgtgatcgc ggacgagctc ggcctgaccg aggaggccga dacgctgcgc     1500
gagcaggcgt cgtggccgat cgagaagctc accaagccgg gcgcgtggac cgccgccgac     1560
ggcacgcagg tcggcctcct cacccccgcg ccgcggacg gtcgtggca gagcgccgac     1620 cacgcgaagt tcgaggccgc cggcctctac cagggcacgc tctggcagta ccactggtac     1680
gacgcgtacg acatggacgc gctcgtcgag gcgatgggcg ccacgaggc ggcgcgcctc     1740 ggcatgcgcc acatgttcgg tgagcacgcg ccggacgacg gcaaggccat gctccactcg     1800
aacgccaacg agatcgacct ccaggcgccg tacctcttca actacacggg cgagccgagc     1860
ctcacgcaga agtgggcgcg cgcgatctac acgaaggaga cctggaaccg gtacatcgcg     1920
accggctcct ccagcgccgt gccgagcggc ggcggcgagt tcacgccgcc cttgaagacg     1980
aaggtgtacc ggctcgaccc ccgcgggatg ctccccacga tggacaacga cgcgggcacg     2040
atgtcgacga tgttcgtcgc gcgcggccgtc gggctgttcc cggtgaccgc gggctcgtcc     2100
cagttccagg tcgggtcgcc gttcttcgac tcgacgacca tcacctacga cgacggcagc     2160
gccttcacgg tcacggccga cggcgtctcc gaggacgcgt tctacgtcca gtccgcgacg     2220
ctcgacggcg cgacgttcgg caacacgtgg gtcgactacg ccaccgtggt cgggggagcc     2280
gacctcgcgt tccgcatggg cgagcagccg agcgactggg gcacggacac cgcgcccgcg     2340
ttctcgatga gtaccgcgac cgacgagccg gccgagggac cgcgcgtcag cgccgaaccg     2400
accaccgtgc agaccggcga cggcggcgcg ctcgacgcga ccgtgacgct cacgctcgac     2460
ggcgcccgcc tcgccgcgcc cgccggcacg gacctcgtca cgagcggggc ggcgagcgtc     2520
gtcgggctgc ccgacggcgt cacggcgcc gtgacggtcg cgtcgccgac cgcgctgacc     2580
gtctccctga cggggacggc gtccgccgac gcgcgcttct tcgtgcacct gcgcgacgcc     2640
gcgctcgccg acggcgtcgc cgcggcgtcg ctccagggac agggcgtctc ggtgcgctcg     2700
cccctgcggc tgtccgtggc gtccgccgag cgcgacgcgc tcgccgcgct cgtcgacgac     2760
gccgtgctcg tgcggcacgg gaactactcc tcggtgacgt tcgaccggtt ctccaccgcg     2820
ctgacgaagg cgcaggaggc cctcggtgac gaggccgcga cgagcatcgc gctgcggttc     2880
gcggccgacc ggctcggtgc ggcggccgac gcgctcgacc tcacgggcgg cgggtaccgc     2940
acgctcgagg ccgagcagtc cgaggcgtgg tcgggcgggg agctgaagaa cgaggcgaac     3000
agctcgtccg gcaacctcgg cggcgtgcgc tccgggtcgt gggtgcagta ccgcgacatg     3060
accttcgaga ccgccgccgg ggacacccg ccgcgcttcc tcacggtccg gtacgacacg     3120
```

```
agcttcgccc cgacggacac gccgagcacc gtgcgcgtgc acgcgggcga cgtgagcggc    3180
cctgtggtcg cgaccgtcga cctgaagggc acgagcggct ggggcaagta caccgaggtc    3240
acggcggagc tcggcgacgt gcaggcgctc gtcgacgcgc aggtcgtcac gttcgagctg    3300
ctcgcgccgt ccggcggag ctgggtcggc aacttcgact ggttccggtt cagcgccgag    3360
gacccggctg ccccaggtca gccgggcgag tccccgacgg tgacgatcga ggccgaggac    3420
tggaccgcga gctccggtcg cgggctcaag aaggagtcct cgacgtggac gagcggtccg    3480
gtgacgaacg tcggcggcac cgcggacggc gactggatcg cctacggcga ggtcgacctg    3540
ggtgagctcc cgctcggcga gctgtcggtc cactacgtgc acaactccaa ccggtccggg    3600
aacaactccg cgctgtcggt gtacctcgac gcgttcgacc cggcgaaccc gggcgagccg    3660
ttcgtcaccg tgccgctgcc gacgaccggg tcgagctgga ccgcggacgg gaccgcgacc    3720
gtcgtcctgc ccgagacggt gcaggggacg cacgaggtgt cgtgcgcct gtcgaccgag    3780
ccgtacgccg accacccgta cgtcgcgaac ctcgacagcc tgacgttcgc gccggggcgg    3840
ccgacgtcgg tcgtcgtcga gtccgaggcc tggacgtcga actccggccg cgggctgaag    3900
aacgagagct cgacgtggac gagcggtccg gtgacgaacg tcggcggcac cgcggacggc    3960
gactggctcg cctacggcga gatcgacctc ggctccgccg cgctcgacca gctctcggtc    4020
cactacgtgc acaactccaa ccggtccggg cggaactccg cgctgtcggt gtacctcgac    4080
gcgttcgacc cggcgaaccc gggcgagccg ttcgtcaccg tcccgctggc caacaccggg    4140
tcgagctgga cgacggacgg gaccgccgtc gtcgacctgc cgagcacggt gcgcggcaag    4200
caccaggtgt gggtgcgcct gtccaccgag gcgtacgccg accacccgta cgtcgccaac    4260
ctcgacagca tgcgcttctt caccgacgcg tacgacgtcg aggtcccgcc gaccgacacc    4320
gcggcgctcg cggcggtggt cgacgcggcc gggacgcccg aggcggagat cgcgcggtac    4380
ggccggatcg acgcgcgcgt cttcacacgc gagctcgcgg cggcacgtc cgtgctcgcc    4440
gacgccggcg ccacccaggc gcaggccgac gagcgggcgc ggcgcctcgg cctggcgacc    4500
gaccagctcg tgcccgccga gcgccgtcgg ctcgagaacc tcgtggcgag cgccgaggcc    4560
ctgaccgacg agggtacag ccccgagtcc tggcaggcct tccgcacggc tctcgccgcg    4620
gcgaccggga cgctcgacga cgcggcggcg tccgacgagg cgctgcacga cgcgcggctc    4680
gcgctccagg gcgccgtcga cgccctggag gagccggccg acgtcgtgct cgtcgaggtc    4740
gaggtcagcc cgcgctgcct cgccggcaag ccctacgtcg cggtccgcgc ggtgaacgtc    4800
tccgacgcgc ccgtcgacgt cgagctggcg tcgtcactgg cacgaggtc gttcgtcggc    4860
gtcgcgccgg gggcgagcgc gtaccagtcg ttcgccgcgc ggtccgcgac gggcgacctg    4920
gacgtcaccg tcacggcgac gggggcggac ggcacccaga cggtcgagca ggtcgtcacc    4980
gtcccgtcct gctcc                                                    4995
```

<210> SEQ ID NO 15
<211> LENGTH: 1665
<212> TYPE: PRT
<213> ORGANISM: Cellulosimicrobium cellulans

<400> SEQUENCE: 15

Ala Leu Ala Val Val Gly Leu Ala Pro Ala Thr Ala Ala Ser Ala Ala
1               5                   10                  15

Pro Glu Pro Pro Ser Ala Asp Tyr Ala Ser Leu Val Asp Val Phe Val
            20                  25                  30

```
Gly Thr Glu Gly Asp Phe Gly Asn Asp Met Pro Ala Ala Gln Ala Pro
            35                  40                  45

Asn Gly Leu Ala Lys Val Asn Pro Arg Thr Thr Pro Gly Arg Asn Asn
 50                  55                  60

Thr Gly Tyr Asp Tyr Ala Gln Ser Lys Ile Ser Gly Phe Thr His Thr
 65                  70                  75                  80

Asn Leu Asp Gly Val Gly Ser Gly Gly Gly Asp Leu Leu Val
                 85                  90                  95

Val Pro Thr Ser Gly Ser Tyr Thr Ala Arg Pro Gly Thr Gly Thr Tyr
                100                 105                 110

Ala His Pro Phe Ser His Asp Asp Glu Asp Ala Gly Pro Gly Phe Tyr
                115                 120                 125

Ser Val Gly Leu Gly Asn Val Ala Gly Thr Asp Gly Ala Ile Thr Gly
        130                 135                 140

Ala Pro Gly Thr Ile Glu Ala Glu Val Ala Ala Ala Thr Arg Ser Gly
145                 150                 155                 160

Val His Arg Tyr Ala Phe Pro Ala Gly Ser Thr Pro Ser Leu Val Val
                165                 170                 175

Asp Leu Glu Thr Asn Asn Thr Ser Arg Arg Ser Ser Ser Val Gln Val
                180                 185                 190

Glu Thr Arg Ala Asp Gly Thr Val Glu Leu Ser Gly Gln Val Thr Gly
        195                 200                 205

Tyr Phe Tyr Asn Ala Ala Tyr Thr Leu Tyr Tyr Thr Ala Arg Thr Leu
        210                 215                 220

Gln Pro Ala Thr Val Gln Thr Trp Gly Asp Asp Asp Arg Leu Val Asp
225                 230                 235                 240

Ala Thr Ala Gln Asp Gly Val Asp Thr Gly Ala Ile Leu Thr Phe Asp
                245                 250                 255

Pro Ala Asp Ala Gly Glu Ile Gly Leu Gln Val Thr Leu Ser Pro Val
                260                 265                 270

Ser Val Glu Gln Ala Arg Ile Asp Gln Gln Val Glu Leu Gly Asp Leu
        275                 280                 285

Ser Phe Asp Ala Ile Arg Asp Arg Thr Arg Ala Glu Trp Asn Ala Thr
        290                 295                 300

Leu Gly Arg Val Ala Ile Asp Ala Ser Thr Ala Thr Asp Pro Thr Gly
305                 310                 315                 320

Glu Leu Gln Arg Leu Phe Tyr Thr His Leu Tyr Arg Met Phe Ala Met
                325                 330                 335

Pro Met Asn Ala Thr Ser Thr Ser Gly Thr Tyr Arg Gly Val Asp Gly
                340                 345                 350

Ala Val His Ala Ala Gln Gly Phe Thr Tyr Tyr Asp Ser Trp Ala Thr
        355                 360                 365

Trp Asp Asp Phe Arg Lys Phe Ser Val Ile Ala Tyr Ile Asp Pro Ala
        370                 375                 380

Leu Tyr Arg Asp Met Val Gln Ser Leu Val Tyr Leu Phe Ala Asp Ala
385                 390                 395                 400

Glu Ala Thr Gly Thr Gly Gly Leu Gly Gly Phe Val His Ser Val
                405                 410                 415

Pro Thr Val Arg Trp Glu Arg Ser Val Val Ala Asp Ala Ile
                420                 425                 430

Ala Lys Gly Phe Asp Gly Phe Asp Arg Leu Asp Glu Ala Tyr Pro Ala
                435                 440                 445

Leu Gln Arg Leu Val Gly Gln Tyr Ser Ala Asp Glu Leu Arg Arg Gly
```

```
            450             455             460
Tyr Val Ala Gly Asn Pro Gly Ala Ser Val Gln Arg Gly Tyr Asp Gln
465                 470                 475                 480

Tyr Gly Leu Ser Val Ile Ala Asp Glu Leu Gly Leu Thr Glu Glu Ala
                485                 490                 495

Glu Thr Leu Arg Glu Gln Ala Ser Trp Pro Ile Glu Lys Leu Thr Lys
                500                 505                 510

Pro Gly Ala Trp Thr Ala Ala Asp Gly Thr Gln Val Gly Leu Leu Thr
                515                 520                 525

Pro Arg Ala Ala Asp Gly Ser Trp Gln Ser Ala Asp His Ala Lys Phe
                530                 535                 540

Glu Ala Ala Gly Leu Tyr Gln Gly Thr Leu Trp Gln Tyr His Trp Tyr
545                 550                 555                 560

Asp Ala Tyr Asp Met Asp Ala Leu Val Glu Ala Met Gly Gly His Glu
                565                 570                 575

Ala Ala Arg Leu Gly Met Arg His Met Phe Gly Glu His Ala Pro Asp
                580                 585                 590

Asp Gly Lys Ala Met Leu His Ser Asn Ala Asn Glu Ile Asp Leu Gln
                595                 600                 605

Ala Pro Tyr Leu Phe Asn Tyr Thr Gly Glu Pro Ser Leu Thr Gln Lys
                610                 615                 620

Trp Ala Arg Ala Ile Tyr Thr Lys Glu Thr Trp Asn Arg Tyr Ile Ala
625                 630                 635                 640

Thr Gly Ser Ser Ser Ala Val Pro Ser Gly Gly Glu Phe Thr Pro
                645                 650                 655

Pro Leu Lys Thr Lys Val Tyr Arg Leu Asp Pro Arg Gly Met Leu Pro
                660                 665                 670

Thr Met Asp Asn Asp Ala Gly Thr Met Ser Thr Met Phe Val Ala Ala
                675                 680                 685

Ala Val Gly Leu Phe Pro Val Thr Ala Gly Ser Ser Gln Phe Gln Val
                690                 695                 700

Gly Ser Pro Phe Phe Asp Ser Thr Thr Ile Thr Tyr Asp Asp Gly Ser
705                 710                 715                 720

Ala Phe Thr Val Thr Ala Asp Gly Val Ser Glu Asp Ala Phe Tyr Val
                725                 730                 735

Gln Ser Ala Thr Leu Asp Gly Ala Thr Phe Gly Asn Thr Trp Val Asp
                740                 745                 750

Tyr Ala Thr Val Val Gly Gly Ala Asp Leu Ala Phe Arg Met Gly Glu
                755                 760                 765

Gln Pro Ser Asp Trp Gly Thr Asp Thr Ala Pro Ala Phe Ser Met Ser
                770                 775                 780

Thr Ala Thr Asp Glu Pro Ala Glu Gly Pro Arg Val Ser Ala Glu Pro
785                 790                 795                 800

Thr Thr Val Gln Thr Gly Asp Gly Gly Ala Leu Asp Ala Thr Val Thr
                805                 810                 815

Leu Thr Leu Asp Gly Ala Arg Leu Ala Ala Pro Ala Gly Thr Asp Leu
                820                 825                 830

Val Thr Ser Gly Ala Ala Ser Val Val Gly Leu Pro Asp Gly Val Thr
                835                 840                 845

Ala Ala Val Thr Val Ala Ser Pro Thr Ala Leu Thr Val Ser Leu Thr
                850                 855                 860

Gly Thr Ala Ser Ala Asp Ala Arg Phe Phe Val His Leu Arg Asp Ala
865                 870                 875                 880
```

```
Ala Leu Ala Asp Gly Val Ala Ala Ser Leu Gln Gly Gln Gly Val
                885                 890                 895

Ser Val Arg Ser Pro Leu Arg Leu Ser Val Ala Ser Ala Glu Arg Asp
            900                 905                 910

Ala Leu Ala Ala Leu Val Asp Asp Ala Val Leu Val Arg His Gly Asn
            915                 920                 925

Tyr Ser Ser Val Thr Phe Asp Arg Phe Ser Thr Ala Leu Thr Lys Ala
            930                 935                 940

Gln Glu Ala Leu Gly Asp Glu Ala Ala Thr Ser Ile Ala Leu Arg Phe
945                 950                 955                 960

Ala Ala Asp Arg Leu Gly Ala Ala Asp Ala Leu Asp Leu Thr Gly
            965                 970                 975

Gly Gly Tyr Arg Thr Leu Glu Ala Glu Gln Ser Glu Ala Trp Ser Gly
            980                 985                 990

Gly Glu Leu Lys Asn Glu Ala Asn Ser Ser Gly Asn Leu Gly Gly
            995                 1000                1005

Val Arg Ser Gly Ser Trp Val Gln Tyr Arg Asp Met Thr Phe Glu Thr
            1010                1015                1020

Ala Ala Gly Asp Thr Pro Pro Arg Phe Leu Thr Val Arg Tyr Asp Thr
1025                1030                1035                1040

Ser Phe Ala Pro Thr Asp Thr Pro Ser Thr Val Arg Val His Ala Gly
            1045                1050                1055

Asp Val Ser Gly Pro Val Val Ala Thr Val Asp Leu Lys Gly Thr Ser
            1060                1065                1070

Gly Trp Gly Lys Tyr Thr Glu Val Thr Ala Glu Leu Gly Asp Val Gln
            1075                1080                1085

Ala Leu Val Asp Ala Gln Val Val Thr Phe Glu Leu Leu Ala Pro Ser
            1090                1095                1100

Gly Arg Ser Trp Val Gly Asn Phe Asp Trp Phe Arg Phe Ser Ala Glu
1105                1110                1115                1120

Asp Pro Ala Ala Pro Gly Gln Pro Gly Glu Ser Pro Thr Val Thr Ile
            1125                1130                1135

Glu Ala Glu Asp Trp Thr Ala Ser Ser Gly Arg Gly Leu Lys Lys Glu
            1140                1145                1150

Ser Ser Thr Trp Thr Ser Gly Pro Val Thr Asn Val Gly Gly Thr Ala
            1155                1160                1165

Asp Gly Asp Trp Ile Ala Tyr Gly Glu Val Asp Leu Gly Glu Leu Pro
            1170                1175                1180

Leu Gly Glu Leu Ser Val His Tyr Val His Asn Ser Asn Arg Ser Gly
1185                1190                1195                1200

Asn Asn Ser Ala Leu Ser Val Tyr Leu Asp Ala Phe Asp Pro Ala Asn
            1205                1210                1215

Pro Gly Glu Pro Phe Val Thr Val Pro Leu Pro Thr Thr Gly Ser Ser
            1220                1225                1230

Trp Thr Ala Asp Gly Thr Ala Thr Val Val Leu Pro Glu Thr Val Gln
            1235                1240                1245

Gly Thr His Glu Val Phe Val Arg Leu Ser Thr Glu Pro Tyr Ala Asp
            1250                1255                1260

His Pro Tyr Val Ala Asn Leu Asp Ser Leu Thr Phe Ala Pro Gly Gly
1265                1270                1275                1280

Pro Thr Ser Val Val Val Glu Ser Glu Ala Trp Thr Ser Asn Ser Gly
            1285                1290                1295
```

Arg Gly Leu Lys Asn Glu Ser Ser Thr Trp Thr Ser Gly Pro Val Thr
            1300                1305                1310

Asn Val Gly Gly Thr Ala Asp Gly Asp Trp Leu Ala Tyr Gly Glu Ile
        1315                1320                1325

Asp Leu Gly Ser Ala Ala Leu Asp Gln Leu Ser Val His Tyr Val His
        1330                1335                1340

Asn Ser Asn Arg Ser Gly Arg Asn Ser Ala Leu Ser Val Tyr Leu Asp
1345                1350                1355                1360

Ala Phe Asp Pro Ala Asn Pro Gly Glu Pro Phe Val Thr Val Pro Leu
                1365                1370                1375

Ala Asn Thr Gly Ser Ser Trp Thr Thr Asp Gly Thr Ala Val Val Asp
            1380                1385                1390

Leu Pro Ser Thr Val Arg Gly Lys His Gln Val Trp Val Arg Leu Ser
        1395                1400                1405

Thr Glu Ala Tyr Ala Asp His Pro Tyr Val Ala Asn Leu Asp Ser Met
    1410                1415                1420

Arg Phe Phe Thr Asp Ala Tyr Asp Val Glu Val Pro Pro Thr Asp Thr
1425                1430                1435                1440

Ala Ala Leu Ala Ala Val Val Asp Ala Ala Gly Thr Pro Glu Ala Glu
                1445                1450                1455

Ile Ala Arg Tyr Gly Arg Ile Asp Ala Arg Val Phe Thr Arg Glu Leu
            1460                1465                1470

Ala Ala Ala Arg Ser Val Leu Ala Asp Ala Gly Ala Thr Gln Ala Gln
        1475                1480                1485

Ala Asp Glu Arg Ala Arg Arg Leu Gly Leu Ala Thr Asp Gln Leu Val
    1490                1495                1500

Pro Ala Glu Arg Arg Leu Glu Asn Leu Val Ala Ser Ala Glu Ala
1505                1510                1515                1520

Leu Thr Asp Glu Gly Tyr Ser Pro Glu Ser Trp Gln Ala Phe Arg Thr
                1525                1530                1535

Ala Leu Ala Ala Ala Thr Gly Thr Leu Asp Asp Ala Ala Ala Ser Asp
            1540                1545                1550

Glu Ala Leu His Asp Ala Arg Leu Ala Leu Gln Gly Ala Val Asp Ala
        1555                1560                1565

Leu Glu Glu Pro Ala Asp Val Val Leu Val Glu Val Glu Val Ser Pro
    1570                1575                1580

Arg Cys Leu Ala Gly Lys Pro Tyr Val Ala Val Arg Ala Val Asn Val
1585                1590                1595                1600

Ser Asp Ala Ala Val Asp Val Glu Leu Ala Ser Ser Leu Gly Thr Arg
                1605                1610                1615

Ser Phe Val Gly Val Ala Pro Gly Ala Ser Ala Tyr Gln Ser Phe Ala
            1620                1625                1630

Ala Arg Ser Ala Thr Gly Asp Leu Asp Val Thr Val Thr Ala Thr Gly
        1635                1640                1645

Ala Asp Gly Thr Gln Thr Val Glu Gln Val Val Thr Val Pro Ser Cys
    1650                1655                1660

Ser
1665

<210> SEQ ID NO 16
<211> LENGTH: 2619
<212> TYPE: DNA
<213> ORGANISM: Artificial Sequence
<220> FEATURE:
<223> OTHER INFORMATION: synthetic polynucleotide

<400> SEQUENCE: 16

```
gcaccggcag atgaaggcac cgttaccgca gcagccggtg atgatctgac cctggaagtt      60
aatccgtttg ttggcaccga aagcgaaggt aatgcatatc cgggtgcaac cgttccgttt     120
ggtatggttc agctgtctcc ggataatacc aatagctatg ccagcaccag ctatagcacc     180
aatgcaggtc gtgtttgggg ttttagccat cgtcatgtta atagcgcagg ttgtccggca     240
gccggtgaac tgctggttac accggatacc agcgcaacac cgcgtaccag ccgtagcttt     300
attgccatca aagatcagaa aagcaccgaa cgtgcaagcg caggttttta tgaagttacc     360
ctggcaaatg atgttcatgc agaactgacc gcaaccaccc gtgttggtgc acatcgttat     420
accttccgg caagcaccac ctctcatctg agctttaatg ttggtcagac cctgcgtgat     480
gccggtgcaa gcagcgttac ctgggttgat gatcgtacac tggaaggttg ggttgataat     540
ggtggttttt gtggtggtac accggataaa cagcgctatt ttttagcgc aacctttgat     600
cgtccggttg ccagcagcgg tacatggggc accgatgcac gttatgttgc aggtagcacc     660
accagtgaag ttgccggtgg taataatggt gcagttgccg ttttgatac caccaccgat     720
cgtgatgttg aagttagcgt tggtgttagc tttgttagcg ttgatggtgc acgtgcaaat     780
cgtgaagccg aagcaaccga tgaaggtggt caggttgcat ttgataccgt tcgtgaagaa     840
gcacgcgacg cctggaatgc agaactgggc cgtgcagcaa ttgatgcatc tccggatcag     900
cgtcgtatct tttatacca gctgtataaa accctgctga gcccgaccat tggttctgat     960
gttgatggtc gttatcgtgg tatggatctg gaagttcatc aggcagatgg ctgggattat    1020
tatcagaact ttagcctgtg ggatacctat cgtacccagg caaccctgca tgcactgctg    1080
ctgccggaac gtgcacagga tattgttcgt agcatgtatc agcatcgtgt gaaggtggt    1140
tggctgcctc gttggtctct gggtgcactg gaaaccaata tcatggcagg cgatccggtt    1200
acccgtggc tggcagaaaa ttttgcactg gcaccgttc ggatgatat tgcagatgaa    1260
ctgtgggatt atctggttga aaatgcaacc accacccctc cggatgatgt tgccagcgtt    1320
ggtcgtcgta gcaccgaatt ttatgccgaa catggtcatg ttccgtttta tccggaaaac    1380
gaaggtggcc tgggtggtca gtttgaagaa tatcgtcatg gtggtagcgc aaccctggaa    1440
ctggcactgg cagatgcaag cctgggtgcc gcagcagaac gtaccggtcg tgaaggtggc    1500
caggcatttc tggataaagg tcgcaattgg cgtaatctgt ggaatccgga tgttgaactg    1560
agcggtggtt ttcagggtat ggttaatgca aaacgtccga ccggtgaatt tgttaccctg    1620
ccggaactga ccgatgttac ccgtagcggt tttcatgaag tgttccgtg gcagtatcag    1680
tggatggttc cgcaggatgt taccggtctg caagaagtta tgggaggcga agatggtttt    1740
gtggaacgcc tggattatta ttttgatcag cctgcactgg cagcaaatcc gggtgttagc    1800
ccgagcacct gggcaaaagg tggtagcagc tattataccca ccattcgcta taatccgggt    1860
aatgaaccga ccattatgaa tgcatggctg tatggttatg ttggtcagcc gtggaaaacc    1920
aatgatgttc tggcagccaa tctgaatcgt tttccggata caccgggtgg tggtgttggt    1980
aatgatgatc tgggcaccct ggcagcatgg tatgttatgg ccagcctggg ttttgaaccg    2040
gttatgcctg gtagcggtat tctggcactg aatgcaccga aagttcaggc agcaaccctg    2100
accaccgatg ccggtgccac cctgcgtatt gatgcagccg gtgcaaatga aaaactgccg    2160
agctatgttg ccggtctgga agttgatggt gttgcacata ccgcagcatg gctggatgtt    2220
gcagcactgc aggatggtgg caccctggat tttgatctga gcggtacaag cgcaggtctg    2280
```

| | |
|---|---:|
| acatggggta caggtgcagc agatcgtatt ccgagcgtta gcgcagttgc accgcctgca | 2340 |
| ccggttgaag tggaagcaag cgcacgttgt ctgggtggtc gtgcatttgt tgcagttcgt | 2400 |
| gcaaccagca ccgcagatgc accggtggat gttacactga ccacaccgtt tggtgaacgt | 2460 |
| accgttcgtc atgttcagcc tggtcgtagc gcatatcaga gctttaccac ccgtaccacc | 2520 |
| tctgttgaag caggcaccgc aaccgttacc gttgttgcag cagatggcac cacctcaacc | 2580 |
| gttgatgcag catatgaagc actggcatgt ggttaataa | 2619 |

<210> SEQ ID NO 17
<211> LENGTH: 3483
<212> TYPE: DNA
<213> ORGANISM: Artificial Sequence
<220> FEATURE:
<223> OTHER INFORMATION: synthetic polynucleotide

<400> SEQUENCE: 17

| | |
|---|---:|
| gcaggcaccg aagcagcaac cggttctgat gcagcagcag ttgatggtcc gctggttgat | 60 |
| tatgtgaatc cgtttattgg caccaaagat gatggtaata cctatccggg tgcagcagtt | 120 |
| ccgtttggta tggttcagct gtctccggat aatggtcata atgtgggcta tgattatgat | 180 |
| cgtaccagcg ttcgtggttt tagcctggtt catctgagcg tgttggttg tggtctgggt | 240 |
| ggtccgctgc cgacactgcc gaccaccggt gcaattacca gcaccgatta tggtcagtat | 300 |
| gcactgggtt ttagccatga tgatgaagaa gcatctccgg ttattatcg tgttggtctg | 360 |
| caggcacctg caggaaccat tgaagcagaa ctgaccgcaa ccgaacgtac cggtgttcag | 420 |
| cgttatacct ttccggcaac cgcacaggca atgttctgc tgaatgcagg tcaggcactg | 480 |
| aatcgtgtta ccgaatctga tgttcgtgtt gttgatgatc gtaccgttga aacccgtatt | 540 |
| accgtgcgtg ttttttgtca ggataccgaa ccgcagacca tttggacccg taccaccttt | 600 |
| gatcgtccgt ttgttgcaca tggcacctgg gatggtcagg ttgttaccgc aggcgcagat | 660 |
| gcagcaagcg gtggtgaagg tcgtcgtggt gcatatgtta cctttgatac aaccggtggt | 720 |
| gatctggatg ttgaagcagt taccgcaatg agctatgttg gtgcagatgg tgcagcagca | 780 |
| aatctggcag cagaagcagg caccttgac gcagttcatg atgcagcacg tagcgcatgg | 840 |
| gaagaacgtc tgggtctggt tcgtgttgca cagggtgatc cggatgatct gcgtaccttt | 900 |
| tatagcagcc tgtatcgtag ctttctggca ccgaatgttg ttctgatgt ggatggtcgt | 960 |
| tatcgtggtt gggatcagga agttcacgca gcagaaccgg attttaccta ttatcagaat | 1020 |
| tatagcctgt gggatacccta tcgtacccaa cagcaactgc tgtatctgct ggcaccggat | 1080 |
| gaaagcgcag atatggcact gagcctggtt cgtcagggtc agcagggtgg ttggctgcct | 1140 |
| cgttgggggtt atggtacagt ggaaaccaat attatgaccg tgatccggc aaccccgttt | 1200 |
| ctggttagcg catggcgtca gggtctgctg gcaggtcatg aagaagaagc atacgcagtc | 1260 |
| ctgcgtgaaa atgcagatgg tgttcctccg gcagatagcc cgtttaatgg tcgtgcagcc | 1320 |
| aatgttgaat atctgcgtga tggttttgtt ccgcatgaac cggcacgtag cggtaaaccg | 1380 |
| ggtgattatg atctgcagca tggtgcaagc gcaaccatgg aatatgcact ggcagatgca | 1440 |
| atgctgagca ccatggcacg tggtctgggt catgatgaag atgcagatcg ttatgcagcc | 1500 |
| cgtggtcaga gctatcgtaa tgttttttgat ccgcgtaccg taattttcg tgcacgtaat | 1560 |
| gccgatggtt tttttgttgg tgatgcagat ccggcacatt ctgatggttt tcatgaaggc | 1620 |
| accgcagttc agtatcagtg gctggttccg caggatgttc cgggtctgtt tgatctgatg | 1680 |
| ggtggcaccg atgcagccgt tgatcgtctg gatgcatttt ttgcctatga tgaactggtt | 1740 |

```
gcagatcctc cgcatgttgc aagcgaagtt tgggttaatg gcacctatga ttattatggc    1800
tgggaaacct ataatccgaa taatgaaccg aatctgcatg caccgtatgt ttatctgtgg    1860
accggtcagc cgtggaaaac caccgatgtt gttcgtgcag caagcaccct gtttaccgat    1920
ggtccggatg tgttaccgg taatgatgat ctgggcacca tgagcgcatg gcatgttctg    1980
agcagcattg gtgtttatcc gattgttccg ggtgccgatc tgtggggtct gaccacaccg    2040
ctgtttgatg atgttaccat taccctggac ccggaagttt ttggtcgtga tagcctgcgt    2100
ctgaccgcag atggtgtggc accggatacc cattataccc agagcgttag cctgggtggt    2160
gaaccgctgg atcgtgcatg ggttacaggt gatgaactga ccgctgcagg caccctggat    2220
gttaccgttg gcaccgaacc gagcgcatgg gcaaccgatc cggcagcatc accgggtgca    2280
gttgttccgg ctgatggcac cgttaacgt ctgtttgttg gtgcaacacc gcgtcagccg    2340
gttctggcac cgggtggtcg taccgaagtt gcagttcagg ttgttgccca gggtgcaggc    2400
acctctagcg gcaccctgga agtgacctct gatggtgcag ttaccgccac caccgatctg    2460
gcagaatgga ccgcagaatc tgatggtctg cctgccaccg ttgaaggaac cgttaccatt    2520
gaagctccgg cagatgccga accgggtctg cataccgttc gtctggttgt tcgtgatgca    2580
gccggtacag aagcagttcg cgaagttagc gttgttgtta gcggtgaaag ctggattgca    2640
gatgcctttg ataatgtggg tattggtgat gccggtgcag caaatgcaaa tctgatggt    2700 agcggtgcct atctgctgcg tgatctgctg gccgatctgg gtgcagttca gggtctggaa    2760
ctgaccgttc cgggtactga tctgacctat accctgggtg caccgcgtgc tggtgcaccg    2820
gataatgttg cagccagcgg tgaagttctg gaagttccgg aacatctgcg tagcgcacgt    2880
catctgagcg ttgtgggcac cagcacccat ggtacacatg gtggtggtct ggttctgggt    2940
tttgccgatg gtagcagcca gaccgttgat gttcgtctga gcgattggtg taccggttct    3000
ccggaaccgg gtaatattac cgttgcaaaa gccggtgcac gtggtgatcg tgaaaatgtg    3060
cagaaaattg gctgtggtct gtatgcaacc gcaccggtgg caattccgga aggtaaagtt    3120
ctgaccagcg ttaccctgcc gtctgatgaa cgttttcatg tgtttgcaat tgcaaccgat    3180
gcaaccggtg atgttccggc accgcaggtt gaagttaccg cacaggctcg ttgtctgggt    3240
ggtaaagcat tgttgcagt tcgtgcactg aataccggtg aacagcctgc agcaattgaa    3300
ctggcaaccc cgtatggtag caaactgttt ggtgatgttg ctccgggtgc aaatgcatat    3360
cagagctttg caaccgtgc agcagccgtt gaagccggtg aagttaccgt taccgtgacc    3420
acaccggatg tgaaccgca gcaggttacc gcagcatatg atgcagcggc atgtagctaa    3480
taa                                                                   3483
```

<210> SEQ ID NO 18
<211> LENGTH: 3483
<212> TYPE: DNA
<213> ORGANISM: Artificial Sequence
<220> FEATURE:
<223> OTHER INFORMATION: synthetic polynucleotide

<400> SEQUENCE: 18

```
gcaggcaccg aagcagcaac cggttctgat gcagcagcag ttgatggtcc gctggttgat      60
tatgtgaatc cgtttattgg caccaaagat gatggtaata cctatccggg tgcagcagtt     120
ccgtttggta tggttcagct gtctccggat aatggtcata atgtgggcta tgattatgat     180
cgtaccagcg ttcgtggttt tagcctggtt catctgagcg tgttggttg tggtctgggt     240
```

```
ggtccgctgc cgacactgcc gaccaccggt gcaattacca gcaccgatta tggtcagtat    300
gcactgggtt ttagccatga tgatgaagaa gcatctccgg gttattatcg tgttggtctg    360
caggcacctg caggaaccat tgaagcagaa ctgaccgcaa ccgaacgtac cggtgttcag    420
cgttatacct ttccggcaac cgcacaggca atgttctgc tgaatgcagg tcaggcactg    480
aatcgtgtta ccgaatctga tgttcgtgtt gttgatgatc gtaccgttga aacccgtatt    540
accgtgcgtg ttttttgtca ggataccgaa ccgcagacca tttggacccg taccaccttt    600
gatcgtccgt ttgttgcaca tggcacctgg gatggtcagg ttgttaccgc aggcgcagat    660
gcagcaagcg tggtgaagg tcgtcgtggt gcatatgtta cctttgatac aaccggtggt    720
gatctggatg ttgaagcagt taccgcaatg agctatgttg gtgcagatgg tgcagcagca    780
aatctggcag cagaagcagg cacctttgac gcagttcatg atgcagcacg tagcgcatgg    840
gaagaacgtc tgggtctggt tcgtgttgca cagggtgatc cggatgatct gcgtaccttt    900
tatagcagcc tgtatcgtag ctttctggca ccgaatgttg gttctgatgt ggatggtcgt    960
tatcgtggtt gggatcagga agttcacgca gcagaaccgg attttaccta ttatcagaat   1020
tatagcctgt gggataccta tcgtacccaa cagcaactgc tgtatctgct ggcaccggat   1080
gaaagcgcag atatggcact gagcctggtt cgtcagggtc agcagggtgg ttggctgcct   1140
cgttggggtt atggtacagt ggaaaccaat attatgaccg tgatccggc aaccccgttt   1200
ctggttagcg catggcgtca gggtctgctg gcaggtcatg aagaagaagc atacgcagtc   1260
ctgcgtgaaa atgcagatgg tgttcctccg gcagatagcc cgtttaatgg tcgtgcagcc   1320
aatgttgaat atctgcgtga tggttttgtt ccgcatgaac cggcacgtag cggtaaaccg   1380
ggtgattatg atctgcagca tggtgcaagc gcaaccatgg aatatgcact ggcagatgca   1440
atgctgagca ccatggcacg tggtctgggt catgatgaag atgcagatcg ttatgcagcc   1500
cgtggtcaga gctatcgtaa tgttttttgat ccgcgtaccg gtaattttcg tgcacgtaat   1560
gccgatggtt ttttttgttgg tgatgcagat ccggcacatt ctgatggttt tcatgaaggc   1620
accgcagttc agtatcagtg gctggttccg caggatgttc cgggtctgtt tgatctgatg   1680
ggtggcaccg atgcagccgt tgatcgtctg gatgcattt ttgcctatga tgaactggtt   1740
gcagatcctc cgcatgttgc aagcgaagtt tgggttaatg gcacctatga ttattatggc   1800
tgggaaacct ataatccgaa taatgaaccg aatctgcatg caccgtatgt ttatctgtgg   1860
accggtcagc cgtggaaaac caccgatgtt gttcgtgcag caagcaccct gtttaccgat   1920
ggtccggatg tgttaccgg taatgatgat ctgggcacca tgagcgcatg gcatgttctg   1980
agcagcattg tgtttatcc gattgttccg ggtgccgatc tgtggggtct gaccacaccg   2040
ctgtttgatg atgttaccat taccctggac ccggaagttt ttggtcgtga tagcctgcgt   2100
ctgaccgcag atggtgtggc accggatacc cattataccc agagcgttag cctgggtggt   2160
gaaccgctgg atcgtgcatg ggttacaggt gatgaactga ccgctgcagg caccctggat   2220
gttaccgttg gcaccgaacc gagcgcatgg gcaaccgatc cggcagcatc accgggtgca   2280
gttgttccgg ctgatggcac cgttgaacgt ctgtttgttg gtgcaacacc gcgtcagccg   2340
gttctggcac cggtggtcg taccgaagtt gcagttcagg ttgttgccca gggtgcaggc   2400
acctctagcg gcaccctgga agtgacctct gatggtgcag ttaccgccac caccgatctg   2460
gcagaatgga ccgcagaatc tgatggtctg cctgccaccg ttgaaggaac cgttaccatt   2520
gaagctccgg cagatgccga accgggtctg cataccgttc gtctggttgt tcgtgatgca   2580
gccggtacag aagcagttcg cgaagttagc gttgttgtta gcggtgaaag ctggattgca   2640
```

```
gatgcctttg ataatgtggg tattggtgat gccggtgcag caaatgcaaa tctggatggt    2700
agcggtgcct atctgctgcg tgatctgctg gccgatctgg gtgcagttca gggtctggaa    2760
ctgaccgttc cgggtactga tctgacctat accctgggtg caccgcgtgc tggtgcaccg    2820
gataatgttg cagccagcgg tgaagttctg gaagttccgg aacatctgcg tagcgcacgt    2880
catctgagcg ttgtgggcac cagcacccat ggtacacatg gtggtggtct ggttctgggt    2940
tttgccgatg gtagcagcca gaccgttgat gttcgtctga gcgattggtg taccggttct    3000
ccggaaccgg gtaatattac cgttgcaaaa gccggtgcac gtggtgatcg tgaaaatgtg    3060
cagaaaattg gctgtggtct gtatgcaacc gcaccggtgg caattccgga aggtaaagtt    3120
ctgaccagcg ttaccctgcc gtctgatgaa cgttttcatg tgtttgcaat gcaaccgat     3180 gcaaccggta tgttccggc accgcaggtt gaagttaccg cacaggctcg ttgtctgggt     3240
ggtaaagcat ttgttgcagt tcgtgcactg aataccggtg aacagcctgc agcaattgaa    3300
ctggcaaccc cgtatggtag caaactgttt ggtgatgttg ctccgggtgc aaatgcatat    3360
cagagctttg caaccgtgc agcagccgtt gaagccggtg aagttaccgt taccgtgacc    3420
acaccggatg gtgaaccgca gcaggttacc gcagcatatg atgcagcggc atgtagctaa    3480
taa                                                                  3483

<210> SEQ ID NO 19
<211> LENGTH: 5283
<212> TYPE: DNA
<213> ORGANISM: Artificial Sequence
<220> FEATURE:
<223> OTHER INFORMATION: synthetic polynucleotide

<400> SEQUENCE: 19
gcagaaccgg gtgattttag cagcagcttt gaatctggcg atccggcagc actgccgacc      60
accgttgcag aacgtgatgg tgcaccgtgg caggcaaatg ttggtagctt taccgcaggt     120
ctgcctggta gcgttctggg tcagctgaaa ggtgttaccg caagcgcaca gaatctgccg     180
aatgaaggtg cagcaaatct ggcagatggt agcagcggca ccaaatggct ggcatttgca     240
agcaccggtt gggttcgtta tgaatttgca gaaccggtta gctttgttgc ataccatg      300 accagcggtg atgatgccgc aggtcgtgat ccgaaaacct ggaccgttga aggtagcaat     360
gatggttcta cctgggcagc actggatcgt cgtaccgatg aagattttcc gaatcgtcag     420
cagacccgta cctttgaact ggaagcaccg accgcagcat ataccatct gcgtctgaat      480 gttaccgcaa atagcggtga tagcattgtt cagctggcag ttgggatct gagcgcagat      540 ctgtctgcag gtccgagcgc agcaccgatg accaccaaag ttggcaccgg tccgcgtgtt    600
agctttacca ataaagccgg tgttggtttt agcggtctgc atagcctgcg ttatgatggt    660
agccatctgg ccgatggtga aacctatgca accaatgtgc tgtatgatga tgttgatgtt    720
gtggttggtg aagatacccg tctgagctat accattttc cggaactgct ggatgatctg    780
cagtatccga gcacctatgc agcagttgat gttctgttta ccgatggcac ctatctgagc    840
gatctgggtg cacgtgatgc acatgaaacc gttgcaaccg cacaggcaca gggtgaaggt    900
aaaattctgt atgccgatca gtggaatagc gttcgtgttg atctgggtga tgttgcagaa    960
ggtaaaaccg ttgatcaggt tctgctgggt tatgataatc cgggtggtca tgcaggcacc    1020
aaatttgcag ttggctgga tgatgttgaa attaccgcag aaccggcaac cattgatggt    1080
agctcactgg caaattatgt tgatacccgt cgtggcaccc tggcaagcgg tagctttagc    1140
```

```
cgtggtaata atattccggc aaccgcaacc ccgaatggtt ttaattttg gaccccgtat    1200 accaatgcaa gcagccagag ctggctgtat gaatatcata aagccaataa tgcgaataat    1260
aaaccggttc tgcagggttt tggtattagc catgaaccga gcccgtggat gggtgatcgt    1320
aatcagctga cctttctgcc gagcaccgca agcggtacac cggatgcaac cctgagcacc    1380
cgtggtctgg aatttgatca tgcagatgaa accgcacgtc cggattatta tggtgtgacc    1440
tttaccaatg gtagcgcaat tgaagcaacc ccgaccgatc atggtgcagt tctgcgtttt    1500
agctatccgg gtgcaaaagg tcatgttctg gtggataaag ttgatggtag cagtaaactg    1560
acctatgatc aggcaaccgg caccattagc ggttgggttg aaaatggtag cggtctgagc    1620
gttggtcgta cccgtatgtt tgttgcaggc acctttgatc gtagcccgac cgcagttggc    1680
acagcagcag gtaatcgtgc agatgcacgt tttgcaacct ttgaaaccag cagcgataaa    1740
accgtggaac tgcgtgttgc aaccagcttt attagcctgg atcaggcacg taaaaatctg    1800
gatctggaag ttaccggtaa aacctttacc gaagttaaag cagcagcagc acaggcatgg    1860
aatgatcgtc tgggtgttat tgaagttgaa ggtgcaagcg aagatcagct ggttaccctg    1920
tatagcaatc tgtatcgcct gaatctgtat ccgaatagcc agtttgaaaa taccggcacc    1980
gcacaggaac cggtttatcg ttacgcatct ccggttagcg caaccaccgg tagcgcaacc    2040
gatacccaga ccaatgccaa aattgtggat ggcaaaattt atgtgaataa tggcttttgg    2100
gataccatcg gtaccgcatg gcctgcatat agcctgctgt atccggaact ggcagcagaa    2160
ctggttgatg gtttgttca gcagtatcgt gatggtggtt ggattgcacg ttggagcagt    2220
ccgggttatg cagatctgat gaccggtaca agctctgatg ttgcatttgc agatgcctat    2280
ctgaaaggta gcctgccgac cggtacagca ctggaagcat atgatgcagc actgcgtaat    2340
gcaaccgttg cacctccgag caatgcagtt ggtcgtaaag gtctgcagac aagcccgttt    2400
ctgggtttta caccggaaag cacccatgaa agcgttagct ggggtctgga aggtctggtt    2460
aatgattttg gcattggcaa tatggctgca gcactggcag aagatccggc aacaccggaa    2520
gaacgtcgtg aaaccctgcg tgaagaaagc gcatattttc tggaacgtgc cacccattat    2580
gttgaactgt ttgatccgga agtggatttt tttgttccgc gtcatgaaga tggtacatgg    2640
gcagttgatc cggaaaccta tgatccggaa gcatggggtg gtggttatac cgaaaccaat    2700
ggctggaatt ttgcatttca tgcaccgcag gatggtcagg gtctggcaaa tctgtatggt    2760
ggtaaacagg gtctggaaga taaactggat gaattttta gcacaccgga aaaaggtgca    2820
ggtaatggtg gtattcatga acagcgtgaa gcacgtgatg ttcgtatggg tcagtggggt    2880
atgagcaatc aggttagcca tcatattccg tggctgtatg atgcagccgg tgctccgagc    2940
aaagcacagg aaaaagttcg cgaagttacc cgtcgtctgt tgttggtag cgaaattggt    3000 cagggttatc cgggtgatga agataatggt gaaatgtcct cctggtggat ttttgcaagc    3060
ctgggttttt atccgctgca ggttggtagc gatcagtatg cagttggttc ccgctgtttt    3120
gataaagcaa ccgttcatct gccggatggt gatctggttg ttaatgccga aaataatagc    3180
gtggataatg tgtatgttca gagcctggca gttgatggtg aagcacgtac cagcaccagc    3240
ctgagccagg cagatctgag cggtggcacc accctggatt tgttatggg tccggaaccg    3300 agcgattggg gcaccggtga agatgatgca cctccgtcac tgaccgaagg tgatgaacct    3360
ccgacaccgg ttcaggatgc aaccaccgca ggcctgggca ccaccaccgt tgccgatggt    3420
gatgccacca cctctgcagc agccctgacc gataatacca gcggcacccg taccaccttt    3480
gcaaccacca ccccgagcat tacatgggca ggtaatggca ttcgtccgac cgttggtagc    3540
```

| | |
|---|---|
| tataccctga cctctggtgc aagcggcacc gcaagcccgt ctgcatggac cctggaaggt | 3600 |
| tctgatgatg gcgaaacctg gaccacactg gatgaacgta gcggtgaaca gtttcgttgg | 3660 |
| gcactgcaga cccgtccgtt taccgttgcc gaaccgaccg catttgcacg ttatcgtgtt | 3720 |
| accgttaccg caaccagcgg ttctggtgca ctgagcctgg cagaagttga actgctggca | 3780 |
| gatccgaaag aaagcggtgc agaagaactg accctgtctg cagcaccgga tcgtgatggc | 3840 |
| gttaccggtc gtgaagttag cggttctttt gcaaccctga ccggtgttga aggtgatgtt | 3900 |
| gccgcactgg atgttcaggt tgcatttggt gatggtagcg aaccggttgc aggtacactg | 3960 |
| cgtgccggtc catttggtgg ttatgcagtt gatgcagcac atacctggac cgcaccgggt | 4020 |
| gtttatccgg ttaccgtgac cgttagcggt gaaggtattg aaaccgttag cgcaagcagc | 4080 |
| tatgttagcg ttagcctgct gcgtgaaggt tctctgctgg cagcatatga taatgtgtgc | 4140 |
| attggtgatg caggtacaac cgttggttct tgtgatggtc agggcgtttt ttttgatcgt | 4200 |
| gcacagctgg cagcaaaagg ttttgtgcag ggtgaacgtg caaccgttcc gggtacagat | 4260 |
| ctggcatttg atgttccggc agttccggct ggtcagcctg ataatgcaac cggtgatggt | 4320 |
| cagaccattg aactggatgt tccggctgat gcagaacagc tgagcgttat ggcaccggc | 4380 |
| accgaaaaaa atcagcaggc aaccggtaca ctgacctttg atgatggttc tacccagccg | 4440 |
| attgatctga ctttggtga ttggagcggt gcagcacgta tccggtgtt tggtaatatt | 4500 |
| ccggttgcag ttaccgatag ccgtctgcgt ggtggttctc cgcagaccgg tacaccggca | 4560 |
| gcattttttg ccaccgcacc gattaccctg ccggaaggta aacgtccggt tagcctgacc | 4620 |
| ctgccggatc agcctggtga actgagccgt gatggtcgta ttcatgttgt tgcagttgca | 4680 |
| catgatggca cctttgcaga acatcctgca ctggaagtga ccgcagcaga aggtgttacc | 4740 |
| ctggcagttg gtcagacctc agatgttgca ctggcacagg ttgccggtgg tcgtgaaggt | 4800 |
| gcagatctgc gtgccgcagt tacctggggt gatggttctg atgtggcagc cggtgccgtt | 4860 |
| accgatggta gcgttagcgg tagccatgca tataccgcag caggcaccta taccgcatat | 4920 |
| gttgttgtgg atgatggttg gaccagccag gttgttgaag ttccggtgac cgttacagaa | 4980 |
| gccgaaccgg cactggccgt tgatgtcacc gttagcaccc gttgcctggc aggtaaagca | 5040 |
| tatgttgcag tgcgtgcaga aaatggtgaa gatgttccgc tggcaattcg tctggttacc | 5100 |
| ccgtttggca ccaaagaagt tgcagcagtt gctccgggag ccaatgcata tcagagcttt | 5160 |
| gcaacccgtg ttaccgcagt tgaagcaggc accgttaccg ttgaagccac ccgtggcacc | 5220 |
| ggtgatgaag aagttaccgc cagcattcag gcagattatg cagccgttac ctgcggttaa | 5280 |
| taa | 5283 |

<210> SEQ ID NO 20
<211> LENGTH: 4881
<212> TYPE: DNA
<213> ORGANISM: Artificial Sequence
<220> FEATURE:
<223> OTHER INFORMATION: synthetic polynucleotide

<400> SEQUENCE: 20

| | |
|---|---|
| gatatgcctg cagcacaggc accgaatggt ctggcaaaag ttaatccgcg taccacaccg | 60 |
| ggtcgtaata taccggtta tgattatgcc cagagcaaaa ttagcggttt tacccatacc | 120 |
| aatctggatg tgttggtgg tagcggtggt ggtggtgatc tgctggttgt tccgaccagc | 180 |
| ggtagctata ccgcacgtcc gggtacaggc acctatgcac atccgtttag ccatgatgat | 240 |

```
gaagatgcag gtccgggttt ttatagcgtt ggtctgggta atgttgcagg caccgatggt    300
gcaattaccg gtgctccggg tacaattgaa gcagaagttg cagcagcaac ccgtagcggt    360
gttcatcgtt atgcatttcc ggcaggtagc accccgagcc tggttgttga tctggaaacc    420
aataatacca gccgtcgtag cagcagcgtt caggttgaaa cccgtgcaga tggcaccgtt    480
gaactgagcg gtcaggttac cggctatttt tataatgcag cctatacccc gtattatacc    540
gcacgcaccc tgcagcctgc aaccgttcag acctggggtg atgatgatcg tctggttgat    600
gcaaccgcac aggatggtgt tgataccggt gcaattctga cctttgatcc ggcagatgcc    660
ggtgaaattg gtctgcaggt taccctgtct ccggttagcg ttgaacaggc acgtattgat    720
cagcaggttg aactgggtga tctgagcttt gatgcaattc gtgatcgtac ccgtgcagaa    780
tggaatgcaa ccctgggtcg tgttgcaatt gatgcaagca ccgcaaccga tccgaccggt    840
gaactgcagc gtctgttttta tacccatctg tatcgcatgt ttgcaatgcc gatgaatgca    900
accagcacca gcggcaccta tcgtggtgtt gatggtgcag ttcatgcagc acagggcttt    960
acctattatg atagctgggc aacctgggat gattttcgca aatttagcgt gattgcctat   1020
attgatccgg cactgtatcg tgatatggtt cagagcctgg tttacctgtt gcagatgca   1080 gaagcaaccg tacaggcgg tggtctgggt ggttttgttc atagcgttcc gaccgttcgt   1140
tgggaacgta gcagcgttgt tgttgcagat gcaattgcca aaggctttga tggttttgat   1200
cgtctggatg aagcatatcc ggcactgcag cgcctggttg gtcagtatag cgcagatgaa   1260
ctgcgtcgtg gttatgttgc aggtaatccg ggtgcaagcg ttcagcgtgg ttatgatcag   1320
tatggtctga gcgttattgc cgatgaactg ggtctgaccg aagaagcaga aaccctgcgc   1380
gaacaggcaa gctggccgat tgaaaaactg accaaaccgg gtgcatggac cgcagcagat   1440
ggtacacagg ttggtctgct gacaccgcgt gcagccgatg gtagctggca gagcgcagat   1500
catgccaaat ttgaagcagc aggtctgtat cagggcaccc tgtggcagta tcattggtat   1560
gatgcctatg atatggatgc actggttgaa gcaatgggtg tcatgaagc agcccgtctg   1620 ggtatgcgtc atatgtttgg tgaacatgca ccggatgatg gtaaagcaat gctgcatagc   1680
aatgccaatg aaattgatct gcaggcaccg tacctgttta attataccgg tgaaccgagc   1740
ctgacccaga atgggcacg tgcaattta accaaagaaa cctggaatcg ctatattgca   1800
accggtagca gctctgcagt tccgtcaggt ggtggtgaat ttacacctcc gctgaaaacc   1860
aaagtttatc gtctggaccc tcgtggtatg ctgccgacca tggataatga tgcaggtaca   1920
atgagcacca tgtttgttgc agcagccgtt ggtctgtttc cggttaccgc aggtagcagc   1980
cagtttcagg ttggtagccc gtttttgat agcaccacca ttacctatga tgatggtagc   2040
gcatttaccg ttaccgcaga tggtgttagc gaagatgcct tttatgttca gagcgcaacc   2100
ctggatggtg caacctttgg taatacctgg gttgattatg caaccgttgt tggtggtgca   2160
gatctggcat ttcgtatggg tgaacagccg agcgattggg gcaccgatac cgcaccggca   2220
tttagcatga gcaccgccac cgatgaaccg gcagaaggtc ctcgcgttag cgcagaaccg   2280
accaccgtgc agaccggtga tggtggtgca ctggatgcaa ccgttaccct gacactggat   2340
ggcgcacgtc tggcagcacc ggcaggtaca gatctggtta ccagcggtgc agcaagcgtt   2400
gttggtctgc cggatggtgt taccgcagca gttaccgttg caagcccgac cgcactgacc   2460
gttagcctga ccggcaccgc atcagcagat gcacgttttt ttgtgcatct gcgtgatgca   2520
gcactggccg atggtgttgc agccgcaagc ctgcagggtc agggtgttag cgttcgttct   2580
ccgctgcgtc tgagcgttgc aagcgcagaa cgtgatgcac tggcagcact ggttgatgat   2640
```

```
gccgttctgg ttcgtcatgg taattatagc agcgttacct ttgatcgttt tagcaccgct    2700
ctgacaaaag cacaggaagc actgggcgac gaagcagcaa ccagcattgc actgcgtttt    2760
gcagcagatc gtctgggtgc agcagcagat gcactggatc tgaccggtgg tggttatcgt    2820
accctggaag cagaacagag cgaagcatgg tctggtggtg aactgaaaaa tgaagccaat    2880
agcagcagcg gtaatctggg tggtgttcgt agcggtagct gggttcagta tcgcgatatg    2940
acctttgaaa ccgcagccgg tgatacacct ccgcgttttc tgaccgttcg ttatgatacc    3000
agctttgcac cgaccgatac cccgagcacc gttcgtgttc atgccggtga tgtttctggt    3060
ccggttgttg caaccgttga tctgaaaggc accagcggtt ggggtaaata taccgaagtt    3120
accgcagaac tgggtgatgt tcaggccctg gttgatgccc aggttgttac ctttgaactg    3180
ctggcaccga gcggtcgtag ctgggttggt aattttgatt ggtttcgctt tagcgcagaa    3240
gatccggcag caccgggtca gcctggtgaa agcccgaccg ttaccattga agccgaagat    3300
tggaccgcaa gcagcggtcg tggtctgaaa aaagaaagca gcacctggac cagcggtccg    3360
gtgaccaatg ttggtggtac agcagatggt gattggattg cctatggtga agttgatctg    3420
ggtgaactgc cgctgggcga actgagcgtt cattatgtgc ataatagcaa tcgcagcggt    3480
aataatagcg cactgagcgt ttatctggat gcatttgatc cggctaatcc gggtgaaccg    3540
tttgttaccg ttccgctgcc gaccaccggt agcagttgga ccgcagatgg cacagccacc    3600
gttgttctgc cggaaaccgt gcagggcacc catgaagttt ttgttcgtct gagcaccgaa    3660
ccgtatgcag atcatccgta tgttgcaaat ctggatagcc tgaccttgc accgggtggt    3720 ccgaccagcg ttgtggttga aagcgaagcc tggaccagca attctggtcg tggcctgaaa    3780
aatgaatctt ctacctggac ctctggtccg gttacaaatg tgggtggcac cgctgatggc    3840
gattggctgg catatggcga aattgatctg ggcagcgcag cactggatca gctgtctgtg    3900
cattatgttc ataattctaa tcgctctggt cgtaattctg cactgtctgt gtatctggat    3960
gcctttgatc cggcaaatcc gggtgaaccg tttgtgacag tgccgctggc aaataccggt    4020
agctcttgga ccaccgatgg tactgcagtt gtggatctgc cgtctaccgt tcgtggtaaa    4080
catcaggttt gggttcgtct gtctaccgaa gcatatgccg atcatccgta tgtggccaat    4140
ctggattcta tgcgcttttt taccgatgca tatgatgttg aagttcctcc gaccgataca    4200
gcagcactgg cagccgttgt tgatgcagca ggtacaccgg aagcagaaat tgcacgttat    4260
ggtcgtattg atgcccgtgt ttttacccgt gaactggcag cagcacgtag cgttctggcc    4320
gatgccggtg caacacaggc acaggcagat gaacgtgctc gtcgtctggg tctggcaacc    4380
gatcagctgg ttccggcaga acgtcgtcgt ctggaaaatc tggttgccag cgcagaagca    4440
ctgaccgacg aaggttattc tccggaaagc tggcaggcat tcgtaccgc actggctgct    4500 gcaaccggca ccctggatga tgcagcagca tctgatgaag cactgcatga tgcacgtctg    4560
gcgctgcagg gtgcagttga tgcactggaa gaaccggcag atgttgttct ggttgaagtt    4620
gaagtttctc cgcgttgtct ggcaggtaaa ccgtatgttg ccgttcgtgc agttaatgtt    4680
tctgatgcag ccgttgatgt tgaactggca agctctctgg caccccgtag ctttgttggt    4740
gtggcaccgg gtgcgagcgc atatcagagc tttcagcccc gtagcgcaac cggtgatctg    4800
gatgttaccg tgaccgcaac cggtgcagat ggtactcaga ccgttgaaca ggttgtgacc    4860
gttccgagct gtagctaata a                                              4881
```

<210> SEQ ID NO 21

<211> LENGTH: 9
<212> TYPE: PRT
<213> ORGANISM: Artificial Sequence
<220> FEATURE:
<223> OTHER INFORMATION: synthetic peptide

<400> SEQUENCE: 21

Val Gly Pro Gly Ser Asp Glu Val Asp
1               5

<210> SEQ ID NO 22
<211> LENGTH: 1308
<212> TYPE: DNA
<213> ORGANISM: Artificial Sequence
<220> FEATURE:
<223> OTHER INFORMATION: synthetic polynucleotide

<400> SEQUENCE: 22

```
atgaagcttt ccaccatcct cttcacagcc tgcgctaccc tggccctgga caacggcctg      60
gcccgaaccc ccaccatggg ctggctgcac tgggagcgat tcatgtgtaa cctggactgt     120
caggaagagc ccgactcttg tatctctgag aagctgttca tggaaatggc cgagctgatg     180
gtgtctgagg ctggaaggac cgccggctac gagtacctgt gtatcgacga ctgttggatg     240
gccccccagc gagactctga ggccgactc caggccgacc cccagcgatt cccccacggc     300
atccgacagc tcgccaacta cgtgcactct aagggcctga agctgggcat ctacgccgac     360
gtgggcaaca gacctgtgc cggcttcccc ggctctttcg gctactacga catcgacgcc     420
cagaccttcg ccgactgggg cgtggacctg ctgaagttcg acggctgtta ctgtgactct     480
ctcgagaacc tggccgacgg ctacaagcac atgtctctgg ccctgaaccg aaccggccga     540
tctatcgtgt actcttgtga gtggcccctg tacatgtggc ccttccagaa gcccaactac     600
accgagatcc gacagtactg taaccactgg cgaaacttcg ccgacatcga cgactcgtgg     660
aagtctatca gtctattct ggactggacc tctttcaacc aggagcgaat cgtcgacgtc     720
gccggacccg gcggatggaa cgaccccgac atgctggtga tcggcaactt cggcctgtct     780
tggaaccagc aggtgaccca gatggccctg tgggctatca tggctgcccc cctgttcatg     840
tctaacgacc tgcgacacat ctctccccag gccaaggccc tgctcaggga caaggacgtg     900
atcgccatca accaggaccc cctgggcaag cagggctacc agctccgaca gggcgacaac     960
ttcgaggtgt gggagcgacc cctgtctggc ctggcctggg ccgtggccat gatcaaccga    1020
caggagatcg gcggaccccg atcttacacc atcgccgtgg cctccctggg aaagggcgtg    1080
gcctgtaacc ccgcctgttt catcacccag ctcctgcccg tgaagcgaaa gctgggattc    1140
tacgagtgga cctctcgact gcgatctcac atcaaccca ccggcaccgt gctgctccag    1200
ctcgagaaca ccatgcagat gtctctgaag gacctgctga cgcgtgaaca aaaactcatc    1260
tcagaagagg atctgaatag cgccgtcgac catcatcatc atcatcat               1308
```

<210> SEQ ID NO 23
<211> LENGTH: 436
<212> TYPE: PRT
<213> ORGANISM: Artificial Sequence
<220> FEATURE:
<223> OTHER INFORMATION: synthetic polypeptide

<400> SEQUENCE: 23

Met Lys Leu Ser Thr Ile Leu Phe Thr Ala Cys Ala Thr Leu Ala Leu
1               5                   10                  15

Asp Asn Gly Leu Ala Arg Thr Pro Thr Met Gly Trp Leu His Trp Glu

```
            20              25              30
Arg Phe Met Cys Asn Leu Asp Cys Gln Glu Pro Asp Ser Cys Ile
         35              40              45
Ser Glu Lys Leu Phe Met Glu Met Ala Glu Leu Met Val Ser Glu Gly
 50              55              60
Trp Lys Asp Ala Gly Tyr Glu Tyr Leu Cys Ile Asp Asp Cys Trp Met
 65              70              75              80
Ala Pro Gln Arg Asp Ser Glu Gly Arg Leu Gln Ala Asp Pro Gln Arg
             85              90              95
Phe Pro His Gly Ile Arg Gln Leu Ala Asn Tyr Val His Ser Lys Gly
             100             105             110
Leu Lys Leu Gly Ile Tyr Ala Asp Val Gly Asn Lys Thr Cys Ala Gly
             115             120             125
Phe Pro Gly Ser Phe Gly Tyr Tyr Asp Ile Asp Ala Gln Thr Phe Ala
             130             135             140
Asp Trp Gly Val Asp Leu Leu Lys Phe Asp Gly Cys Tyr Cys Asp Ser
 145             150             155             160
Leu Glu Asn Leu Ala Asp Gly Tyr Lys His Met Ser Leu Ala Leu Asn
             165             170             175
Arg Thr Gly Arg Ser Ile Val Tyr Ser Cys Glu Trp Pro Leu Tyr Met
             180             185             190
Trp Pro Phe Gln Lys Pro Asn Tyr Thr Glu Ile Arg Gln Tyr Cys Asn
             195             200             205
His Trp Arg Asn Phe Ala Asp Ile Asp Asp Ser Trp Lys Ser Ile Lys
             210             215             220
Ser Ile Leu Asp Trp Thr Ser Phe Asn Gln Glu Arg Ile Val Asp Val
 225             230             235             240
Ala Gly Pro Gly Gly Trp Asn Asp Pro Asp Met Leu Val Ile Gly Asn
             245             250             255
Phe Gly Leu Ser Trp Asn Gln Gln Val Thr Gln Met Ala Leu Trp Ala
             260             265             270
Ile Met Ala Ala Pro Leu Phe Met Ser Asn Asp Leu Arg His Ile Ser
             275             280             285
Pro Gln Ala Lys Ala Leu Leu Gln Asp Lys Asp Val Ile Ala Ile Asn
             290             295             300
Gln Asp Pro Leu Gly Lys Gln Gly Tyr Gln Leu Arg Gln Gly Asp Asn
 305             310             315             320
Phe Glu Val Trp Glu Arg Pro Leu Ser Gly Leu Ala Trp Ala Val Ala
             325             330             335
Met Ile Asn Arg Gln Glu Ile Gly Gly Pro Arg Ser Tyr Thr Ile Ala
             340             345             350
Val Ala Ser Leu Gly Lys Gly Val Ala Cys Asn Pro Ala Cys Phe Ile
             355             360             365
Thr Gln Leu Leu Pro Val Lys Arg Lys Leu Gly Phe Tyr Glu Trp Thr
             370             375             380
Ser Arg Leu Arg Ser His Ile Asn Pro Thr Gly Thr Val Leu Leu Gln
 385             390             395             400
Leu Glu Asn Thr Met Gln Met Ser Leu Lys Asp Leu Thr Arg Glu
             405             410             415
Gln Lys Leu Ile Ser Glu Glu Asp Leu Asn Ser Ala Val Asp His His
             420             425             430
His His His His
             435
```

<210> SEQ ID NO 24
<211> LENGTH: 2743
<212> TYPE: DNA
<213> ORGANISM: Artificial Sequence
<220> FEATURE:
<223> OTHER INFORMATION: synthetic polynucleotide

<400> SEQUENCE: 24

```
atgaagcttt ccaccatcct cttcacagcc tgcgctaccc tggctgccgc ccagcaggga      60
gcctctcgac ccggaccccg agatgccag gctcaccccg gacgacctcg agctgtgccc     120
acccagtgtg acgtgccccc caactctcga ttcgactgtg cccccgacaa ggccatcacc     180
caggagcagt gcgaggcccg aggctgttgt tacatccccg ctaagcaggg cctgcagggc     240
gctcagatgg ccagccctg tgtttcttc ccccctctt accctcta caagctggag         300
aacctgtcct cttcggagat gggctacacc gccaccctga cccgaaccac ccccaccttt     360
ttccccaagg acatcctgac cctgcgactg acgtgatga tggagaccga gaaccgactg     420
cacttcacca tcaaggaccc cgccaaccga cgatacgagg tgcccctgga cccccccac     480
gtgcactctc gagccccttc ccccctgtac tctgtggagt ctctgaggac gcccttcggc     540
gtgatcgtgc gacgacagct ggacggccga gtgctgctga acaccaccgt ggccccctg     600
ttcttcgccg accagttcct gcagctgtct acctctctgc cctctcagta catcaccggc     660
ctggccgagc acctgtcccc cctgatgctg tccacctctt ggactcgaat caccctgtgg     720
aaccgagacc tggcccccac ccccggtgcc aacctgtacg gctctcaccc cttctacctg     780
gccctggagg acggcggctc tgcccacggc gtgtttctgc tgaactctaa cgccatggac     840
gtggtgctgc agccctctcc cgccctgtct tggcgatcta ccggcggcat cctggacgtg     900
tacatcttcc tgggccctga gccaagtct gtggtccagc agtacctgga cgtggtcgga     960
taccccttca tgccccccta ctggggcctg ggcttccacc tgtgtcgatg gggctactct    1020
tctaccgcca tcacccgaca ggtggtggag aacatgaccc gagcccactt cccctggac    1080
gtgcaatgga cgacctgga ctacatggac tctcgacgag acttcacctt caacaaggac    1140
ggcttccgag acttccccgc catggtccag gagctgcacc agggaggacg acgatacatg    1200
atgatcgtgg accccgccat ctcttcttcc ggacccgccg gatcttaccg accctacgac    1260
gagggcctgc gacgaggcgt gttcatcacc aacgagaccg ccagccccct gatcggcaag    1320
gtgtggcccg ctctaccgc cttccccgac ttcaccaacc ccaccgccct ggcttggtgg    1380
gaggacatgt tggccgagtt ccacgaccag gtgcccttcg acggcatgtg gatcgacatg    1440
aacgagccct ctaacttcat ccgaggctct gaggacggct gtcccaacaa cgagctggag    1500
aaccccccct acgtgcccgg cgtggtgggc ggaaccctgc aggccgccac catctgtgcc    1560
tcttcgcacc agtttctgtc tacccactac aacctgcaca acctgtacgg actgaccgag    1620
gccattgcct ctcaccgagc cctggtgaag gccgaggca cccgacccct cgtgatctct    1680
cgatctacct tcgccggcca cggccgatac gccggacact ggaccggcga tgtgtggtcc    1740
tcttgggagc agctgcctc ttctgtgccc gagatcctgc agttcaacct gctgggcgtg    1800
cccctggtgg gcgccgacgt gtgtggcttc ctgggcaaca cctctgagga gctgtgtgtt    1860
cgatggaccc agctcggcgc cttctaccct ttcatgcgaa accacaactc cctgctgtct    1920
ctgccccagg agccctactc gttctctgag cccgctcagc aggccatgcg aaaggctctg    1980
accctgcgat acgccctgct gccccacctg tacacctgt ccaccaggc ccacgtggct    2040
```

```
ggagagaccg tggcccgacc cctgttcctg gagttcccta aggactcttc tacctggacc 2100
gtggaccatc agctgctgtg gggcgaggcc ctcctgatca cccccgtgct gcaggccggc 2160
aaggctgagg tgaccggcta cttccctctg ggcacctggt acgacctgca gaccgtgcct 2220
```

```
gtggaggccc tgggatctct gccccctcct cccgccgctc cccgagagcc cgccatccac 2280
tctgagggcc agtgggtgac cctgcccgct cccctggaca ccatcaacgt gcacctgcga 2340
gccggctaca tcatccctct gcagggaccc ggcctgacca ccaccgagtc tcgacagcag 2400
cccatggccc tggccgtggc tctgaccaag ggcggagagg cccgaggcga gctgttctgg 2460
gacgatggcg agtctctgga ggtgctggag cgaggcgcct acacccaggt gatctttctg 2520
gcccgaaaca acaccatcgt gaacgagctg gtgcgagtga cctctgaggg cgctggtctg 2580
cagctccaga aggtgaccgt cctgggcgtg gccaccgctc cccagcaggt cctgtctaac 2640
ggcgtgcccg tgtctaactt cacctactct cccgacacca aggtgctgga catctgtgtg 2700
tctctgctga tgggcgagca gttcctggtg tcttggtgtt aac 2743
```

<210> SEQ ID NO 25
<211> LENGTH: 913
<212> TYPE: PRT
<213> ORGANISM: Artificial Sequence
<220> FEATURE:
<223> OTHER INFORMATION: synthetic polypeptide

<400> SEQUENCE: 25

```
Met Lys Leu Ser Thr Ile Leu Phe Thr Ala Cys Ala Thr Leu Ala Ala
1               5                   10                  15

Ala Gln Gln Gly Ala Ser Arg Pro Gly Pro Arg Asp Ala Gln Ala His
            20                  25                  30

Pro Gly Arg Pro Arg Ala Val Pro Thr Gln Cys Asp Val Pro Pro Asn
        35                  40                  45

Ser Arg Phe Asp Cys Ala Pro Asp Lys Ala Ile Thr Gln Glu Gln Cys
    50                  55                  60

Glu Ala Arg Gly Cys Cys Tyr Ile Pro Ala Lys Gln Gly Leu Gln Gly
65                  70                  75                  80

Ala Gln Met Gly Gln Pro Trp Cys Phe Phe Pro Pro Ser Tyr Pro Ser
                85                  90                  95

Tyr Lys Leu Glu Asn Leu Ser Ser Ser Glu Met Gly Tyr Thr Ala Thr
            100                 105                 110

Leu Thr Arg Thr Thr Pro Thr Phe Phe Pro Lys Asp Ile Leu Thr Leu
        115                 120                 125

Arg Leu Asp Val Met Met Glu Thr Glu Asn Arg Leu His Phe Thr Ile
    130                 135                 140

Lys Asp Pro Ala Asn Arg Arg Tyr Glu Val Pro Leu Glu Thr Pro His
145                 150                 155                 160

Val His Ser Arg Ala Pro Ser Pro Leu Tyr Ser Val Glu Phe Ser Glu
                165                 170                 175

Glu Pro Phe Gly Val Ile Val Arg Arg Gln Leu Asp Gly Arg Val Leu
            180                 185                 190

Leu Asn Thr Thr Val Ala Pro Leu Phe Phe Ala Asp Gln Phe Leu Gln
        195                 200                 205

Leu Ser Thr Ser Leu Pro Ser Gln Tyr Ile Thr Gly Leu Ala Glu His
    210                 215                 220

Leu Ser Pro Leu Met Leu Ser Thr Ser Trp Thr Arg Ile Thr Leu Trp
225                 230                 235                 240
```

```
Asn Arg Asp Leu Ala Pro Thr Pro Gly Ala Asn Leu Tyr Gly Ser His
                245                 250                 255

Pro Phe Tyr Leu Ala Leu Glu Asp Gly Ser Ala His Gly Val Phe
        260                 265                 270

Leu Leu Asn Ser Asn Ala Met Asp Val Val Leu Gln Pro Ser Pro Ala
            275                 280                 285

Leu Ser Trp Arg Ser Thr Gly Ile Leu Asp Val Tyr Ile Phe Leu
290                 295                 300

Gly Pro Glu Pro Lys Ser Val Val Gln Gln Tyr Leu Asp Val Val Gly
305                 310                 315                 320

Tyr Pro Phe Met Pro Pro Tyr Trp Gly Leu Gly Phe His Leu Cys Arg
                325                 330                 335

Trp Gly Tyr Ser Ser Thr Ala Ile Thr Arg Gln Val Val Glu Asn Met
                340                 345                 350

Thr Arg Ala His Phe Pro Leu Asp Val Gln Trp Asn Asp Leu Asp Tyr
                355                 360                 365

Met Asp Ser Arg Arg Asp Phe Thr Phe Asn Lys Asp Gly Phe Arg Asp
        370                 375                 380

Phe Pro Ala Met Val Gln Glu Leu His Gln Gly Gly Arg Arg Tyr Met
385                 390                 395                 400

Met Ile Val Asp Pro Ala Ile Ser Ser Gly Pro Ala Gly Ser Tyr
                405                 410                 415

Arg Pro Tyr Asp Glu Gly Leu Arg Arg Gly Val Phe Ile Thr Asn Glu
                420                 425                 430

Thr Gly Gln Pro Leu Ile Gly Lys Val Trp Pro Gly Ser Thr Ala Phe
        435                 440                 445

Pro Asp Phe Thr Asn Pro Thr Ala Leu Ala Trp Trp Glu Asp Met Val
        450                 455                 460

Ala Glu Phe His Asp Gln Val Pro Phe Asp Gly Met Trp Ile Asp Met
465                 470                 475                 480

Asn Glu Pro Ser Asn Phe Ile Arg Gly Ser Glu Asp Gly Cys Pro Asn
                485                 490                 495

Asn Glu Leu Glu Asn Pro Pro Tyr Val Pro Gly Val Val Gly Gly Thr
                500                 505                 510

Leu Gln Ala Ala Thr Ile Cys Ala Ser Ser His Gln Phe Leu Ser Thr
        515                 520                 525

His Tyr Asn Leu His Asn Leu Tyr Gly Leu Thr Glu Ala Ile Ala Ser
        530                 535                 540

His Arg Ala Leu Val Lys Ala Arg Gly Thr Arg Pro Phe Val Ile Ser
545                 550                 555                 560

Arg Ser Thr Phe Ala Gly His Gly Arg Tyr Ala Gly His Trp Thr Gly
                565                 570                 575

Asp Val Trp Ser Ser Trp Glu Gln Leu Ala Ser Ser Val Pro Glu Ile
            580                 585                 590

Leu Gln Phe Asn Leu Leu Gly Val Pro Leu Val Gly Ala Asp Val Cys
        595                 600                 605

Gly Phe Leu Gly Asn Thr Ser Glu Glu Leu Cys Val Arg Trp Thr Gln
        610                 615                 620

Leu Gly Ala Phe Tyr Pro Phe Met Arg Asn His Asn Ser Leu Leu Ser
625                 630                 635                 640

Leu Pro Gln Glu Pro Tyr Ser Phe Ser Glu Pro Ala Gln Gln Ala Met
                645                 650                 655

Arg Lys Ala Leu Thr Leu Arg Tyr Ala Leu Leu Pro His Leu Tyr Thr
```

```
                       660                 665                 670
Leu Phe His Gln Ala His Val Ala Gly Glu Thr Val Ala Arg Pro Leu
                675                 680                 685

Phe Leu Glu Phe Pro Lys Asp Ser Thr Trp Thr Val Asp His Gln
            690                 695                 700

Leu Leu Trp Gly Glu Ala Leu Leu Ile Thr Pro Val Leu Gln Ala Gly
705                 710                 715                 720

Lys Ala Glu Val Thr Gly Tyr Phe Pro Leu Gly Thr Trp Tyr Asp Leu
                725                 730                 735

Gln Thr Val Pro Val Glu Ala Leu Gly Ser Leu Pro Pro Pro Ala
            740                 745                 750

Ala Pro Arg Glu Pro Ala Ile His Ser Glu Gly Gln Trp Val Thr Leu
            755                 760                 765

Pro Ala Pro Leu Asp Thr Ile Asn Val His Leu Arg Ala Gly Tyr Ile
            770                 775                 780

Ile Pro Leu Gln Gly Pro Gly Leu Thr Thr Glu Ser Arg Gln Gln
785                 790                 795                 800

Pro Met Ala Leu Ala Val Ala Leu Thr Lys Gly Gly Glu Ala Arg Gly
                805                 810                 815

Glu Leu Phe Trp Asp Asp Gly Glu Ser Leu Glu Val Leu Glu Arg Gly
                820                 825                 830

Ala Tyr Thr Gln Val Ile Phe Leu Ala Arg Asn Asn Thr Ile Val Asn
                835                 840                 845

Glu Leu Val Arg Val Thr Ser Glu Gly Ala Gly Leu Gln Leu Gln Lys
            850                 855                 860

Val Thr Val Leu Gly Val Ala Thr Ala Pro Gln Gln Val Leu Ser Asn
865                 870                 875                 880

Gly Val Pro Val Ser Asn Phe Thr Tyr Ser Pro Asp Thr Lys Val Leu
                885                 890                 895

Asp Ile Cys Val Ser Leu Leu Met Gly Glu Gln Phe Leu Val Ser Trp
                900                 905                 910

Cys

<210> SEQ ID NO 26
<211> LENGTH: 2314
<212> TYPE: PRT
<213> ORGANISM: Streptomyces coelicolor

<400> SEQUENCE: 26

Met Pro Asp Arg Ser Lys Arg Pro Pro Ile Arg Ser Ser Pro Arg
1               5                   10                  15

Ala Ala Leu Arg Ala Thr Val Ala Ala Val Leu Ala Gly Ala Leu Gly
                20                  25                  30

Leu Ala Ala Leu Thr Gly Gly Gly Thr Ala Val Ala Val Pro Val Thr
            35                  40                  45

Lys Ala Ser Pro Pro Ala Gly Glu Arg Ser Gly Gly Thr Asp Tyr Thr
        50                  55                  60

Lys Leu Val Asp Pro Phe Val Ser Thr Ala Gly Asp Gly Asn Asp
65                  70                  75                  80

Leu Pro Gly Ala Gln Ala Pro His Ser Leu Ala Lys Val Asn Pro Met
                85                  90                  95

Thr Thr Pro Gly Arg Asn His Ser Gly Tyr Asp Tyr Asn Glu Asp His
            100                 105                 110

Ile Ala Gly Phe Thr Ala Thr Asn Leu Asp Gly Val Gly Gly Ser Gly
```

-continued

```
            115                 120                 125
Gly Gly Gly Asp Leu Leu Val Val Pro Thr Ser Gln Gln Tyr Asp Lys
130                 135                 140

Arg Pro Ala Thr Ser Thr Tyr Ala His Pro Tyr Ser His Asp Asp Glu
145                 150                 155                 160

Ser Ala Thr Pro Gly Ser Tyr Arg Val Gly Leu Gly Ser Pro Ser Gly
                165                 170                 175

Thr Ile Asp Ala Glu Met Thr Ala Thr Thr Arg Thr Ala Leu Glu Arg
            180                 185                 190

Tyr Ala Phe Pro Ala Lys Ala Arg Pro Gln Leu Val Leu Asp Leu Ala
        195                 200                 205

Asn Asn Phe Thr Ser Arg Thr Arg Ala Thr Leu Asp Ala Thr Arg Leu
    210                 215                 220

Lys Asp Gly Thr Thr Ala Ile Ser Gly Leu Val Ala Gly Ser Phe Asn
225                 230                 235                 240

Gly Ala Ser Tyr Arg Leu Tyr Tyr Tyr Ala Thr Thr Asn Val Pro Val
                245                 250                 255

Thr Ser Leu Arg Thr Trp Gly Asp Asp Gly Ala Leu Gly Asp Ala Thr
            260                 265                 270

Ala Arg Asp Gly Thr Asp Thr Gly Ala Val Leu Gly Phe Asp Pro Ala
        275                 280                 285

Asp Gly Asp Asp Val Glu Leu Arg Val Thr Leu Ser Pro Ile Ser Ala
    290                 295                 300

Glu Gln Ala Ala Thr Asp Gln His Glu Glu Val Ala Gly Arg Thr Phe
305                 310                 315                 320

Glu Glu Val Arg Ala Gln Thr Lys Ala Asp Trp Asn Arg Thr Leu Gly
                325                 330                 335

Ala Val Ala Val Lys Ala Ser Lys Lys Ala Asp Pro Asp Ser Thr Leu
            340                 345                 350

Thr Lys Gln Phe Tyr Thr His Leu Tyr Arg Met Tyr Ala Leu Pro Val
        355                 360                 365

Asn Ala Thr Ser Thr Ser Gly Thr Tyr Arg Gly Val Asp Gly Ala Val
    370                 375                 380

His Lys Ala Asn Gly Phe Thr Tyr Tyr Asp Gly Trp Ser Thr Trp Asp
385                 390                 395                 400

Asp Phe Arg Lys Tyr Ser Val Ala Ala Tyr Ile Asp Pro Ala Thr Tyr
                405                 410                 415

Arg Asp Met Val Gln Ser Ala Val Ile Leu Phe Ala Asp Ala His Ala
            420                 425                 430

Ala Gly Lys Ser Leu Gly Ser Leu Thr His Ser Val Pro Thr Val Arg
        435                 440                 445

Trp Glu Arg Ser Ala Val Val Ile Ala Asp Ala Leu Ser Lys Gly Phe
    450                 455                 460

Lys Asp Phe Asp Arg Leu Asp Glu Ala Tyr Pro Ala Leu Lys Ser Tyr
465                 470                 475                 480

Thr Gly Tyr Tyr Thr Gly Thr Gln Leu Arg Gln Gly Tyr Ile Ala Gly
                485                 490                 495

Asp Pro Gly Thr Thr Val Gln Arg Gly Tyr Asp Gln Trp Ala Leu Ser
            500                 505                 510

Val Val Ala Asp Ala Leu Gly Glu Asp Ala Glu Ala Lys Lys Leu Arg
        515                 520                 525

Glu Gln Ala Thr Met Ala Thr Asp Asn Leu Val Lys Pro Gly Ala Trp
530                 535                 540
```

```
Thr Ala Ala Asp Gly Thr Ala Val Gly Leu Leu Thr Pro Arg Asp Gly
545                 550                 555                 560

Glu Gly Gly Trp Gln Gly Val Asp Tyr Glu Lys Phe Glu Glu Ala Arg
            565                 570                 575

Leu Tyr Gln Gly Thr Leu Trp Gln Tyr His Trp Tyr Asp Ala Tyr Asp
                580                 585                 590

Met Gly Gly Leu Ile Glu Ala Met Gly Gly Glu Gln Ala Gly Arg Ala
            595                 600                 605

Ala Ile Arg His Met Phe Gly Glu Asp Ser Asp Ala Asp Asp Gly Ser
610                 615                 620

Thr Met Leu His Ser Asn Ala Asn Glu Ile Asp Leu Gln Ala Pro Tyr
625                 630                 635                 640

Leu Phe Asn Tyr Val Gly Glu Pro Ser Leu Thr Gln Lys Trp Val Arg
                645                 650                 655

Ala Ile Tyr Thr Gly Glu Thr Trp Asn Arg Tyr Ile Ala Thr Gly Ser
                660                 665                 670

Thr Asn Glu Ala Pro Ser Ser Gly Glu Phe Arg Pro Pro Val Lys
            675                 680                 685

Thr Lys Ala Tyr Glu Leu Ala Pro Asp Gly Phe Leu Pro Thr Met Asp
690                 695                 700

Asn Asp Ala Gly Thr Met Ser Thr Met Phe Val Ala Ala Ala Leu Gly
705                 710                 715                 720

Leu Phe Pro Val Thr Ala Gly Ser Ser Gln Phe Gln Ile Gly Ser Pro
                725                 730                 735

Phe Phe Asp Ser Thr Thr Ile Thr Tyr Pro Asn Gly Ala Glu Phe Thr
                740                 745                 750

Val Glu Ala Asp Gly Val Ser Pro Lys Asn Tyr Tyr Val Gln Arg Ala
                755                 760                 765

Ala Leu Asn Gly Lys Arg Phe Ser Asn Thr Trp Leu Asp Tyr Ala Gln
770                 775                 780

Ile Val Ala Gly Gly Thr Leu Lys Phe Asp Met Gly Ser Glu Pro Ser
785                 790                 795                 800

Ser Trp Gly Ala Arg Thr Glu Pro Ala Tyr Ser Leu Asn Thr Asp Ser
            805                 810                 815

Gly Asp Gly Asp Asp Glu His Ala Pro Gly Arg Gly Thr Thr Val Val
            820                 825                 830

Ser Ala Arg Pro Glu Thr Val Arg Thr Ala Ala Asp Gly Thr Val Asp
            835                 840                 845

Ala Ser Val Glu Leu Arg Leu Ser Gly Arg Ala Ser Phe Ala Ala Arg
            850                 855                 860

Lys Gly Thr Ser Leu Thr Arg Thr Gly Ala Ala Ser Val Thr Gly Leu
865                 870                 875                 880

Pro Asp Gly Val Thr Ala Asp Leu Arg Val Thr Gly Lys Arg Thr Ala
            885                 890                 895

Ser Leu Arg Leu Thr Gly Thr Thr Asp Ala Arg Phe Gly Ile
            900                 905                 910

Thr Phe Arg Asp Arg Ala Phe Pro His Gly Ile Pro Ala Ser Thr Val
            915                 920                 925

Thr Gly Thr Gly Val Ser Val Thr Asp Pro Leu Ile Val Ser Ala Ala
            930                 935                 940

Ala Val His Arg Gly Ser Leu Ala Ala Leu Val Asp Glu Ala Ser Leu
945                 950                 955                 960
```

-continued

Val Arg Glu Gly Asn Tyr Ser Asp Gly Ser Tyr Gly Ile Phe Arg Thr
            965                 970                 975

Ala Leu Glu Arg Ala Arg Thr Val Leu Ala Asp Ser Ala Ser Pro Thr
        980                 985                 990

Gly Thr Leu Met Ala Ala His Asp Ala Leu Arg Ser Ala Val Asp Ala
    995                 1000                1005

Leu Thr Leu Asp Glu Gly Gly Tyr Ala Val Leu Gln Ala Glu Asp Pro
1010                1015                1020

Asp Arg Met Glu Gly Pro Ser Leu Val Lys Glu Ala Tyr Tyr Ser Asp
1025                1030                1035                1040

Gly Asp Leu Gly Gly Val Thr Glu Gly Ala Trp Glu Gln Tyr Thr Asp
                1045                1050                1055

Leu Asp Phe Gly Gly Val Ala Pro Arg Ser Val Ser Val Arg Tyr Ala
            1060                1065                1070

Asn Ser Gln Ala Ala Ala Glu Pro Ser Ser Val Asp Ile His Ala
        1075                1080                1085

Gly Asp Ala Asp Gly Pro Val Val Ala Thr Val Ser Leu Pro Gly Thr
    1090                1095                1100

Gly Gly Trp Gln Tyr Tyr Thr Thr Val Arg Ala Ala Val Ser Asp Pro
1105                1110                1115                1120

Gln Ala Leu Leu Lys Ala Ser Ser Ala Thr Phe Val Phe His Ala Pro
                1125                1130                1135

Ser Gly Arg Gln Trp Val Ser Asn Phe Asp Trp Tyr Gln Phe Ser Pro
            1140                1145                1150

Glu Ala Ala Pro Ser Ser Ser Pro Ile Thr Thr Leu Ala Thr Leu Thr
        1155                1160                1165

Thr Ala Asn Thr Thr Ser Thr Gly Asp Gly Ser Leu Pro Leu Lys Val
    1170                1175                1180

Ser Gly Gly Val Phe Glu Asn Val Thr Asn Gly Ala Trp Ala Glu Trp
1185                1190                1195                1200

Arg Asp Thr Asp Leu Gly Asp Gly Ala Asp Thr Val Thr Val Ser Tyr
                1205                1210                1215

Asp Lys Pro Arg Ser Arg Ala Ala Ser Asp Ser His Ile Glu Leu Arg
            1220                1225                1230

Pro Gly Ala Lys Asp Gly Pro Thr Ala Val Thr Val Pro Leu Asp Tyr
        1235                1240                1245

Thr Gly Ser Gly Trp Gly Thr Val Ala Ser Thr Ser Val Arg Leu Asp
    1250                1255                1260

Pro Asp Val Phe Glu Gly Thr Gln Asp Val Tyr Ala Val Phe Val Ser
1265                1270                1275                1280

Ser Thr Gln Thr Asp Ala Gln Pro Tyr Val Ala Asn Val His Ser Leu
                1285                1290                1295

Thr Leu Thr Arg Gln Ala Asp Ala Pro Val Val Phe Asp Ala Thr Ala
            1300                1305                1310

Phe Glu Gly Ser Ser Gly Gly Gly Leu Lys Ser Glu Pro Ala Thr Trp
        1315                1320                1325

Ser Gly Ala Gly Ser Ala Thr Ser Leu Gly Gly Thr Tyr Asp Gly Ala
    1330                1335                1340

Trp Leu Asp Tyr Gly Asp Val Asp Phe Gly Asp Ser Pro Lys Asn Thr
1345                1350                1355                1360

Val Thr Leu Thr Tyr Val Asn Asn Ser Ala Arg Cys Gly Thr Gly Ser
                1365                1370                1375

Ala Val Gln Leu Tyr Leu Asp Ser Phe Asp Pro Asp Ala Pro Gly Thr

```
                1380                1385                1390
Pro Tyr Ala Thr Val Pro Leu Pro Val Thr Gly Ser Ser Trp Ser Ser
            1395                1400                1405
Gly Gly Thr Thr Ser Leu Thr Leu Pro Glu Ala Ile Thr Gly Thr His
        1410                1415                1420
Ala Val His Leu Arg Leu Thr Thr Asn Ala Asp Ser Ser His Pro Tyr
1425                1430                1435                1440
Val Ala Asn Leu Gly Gln Val Ala Phe Asp Arg Val Glu Ala Pro Ala
            1445                1450                1455
Gln Thr Asp Leu Ser Ala Leu Arg Lys Ala Ile Glu Gln Tyr Glu Gly
            1460                1465                1470
Leu Ser Glu Asp Ala Asp Arg Tyr Gly Thr Ile Asp Phe Gly Val Phe
            1475                1480                1485
Arg Arg Glu Leu Thr Ala Ala Arg Asp Leu Leu Gly Thr Glu Asp Ala
            1490                1495                1500
Thr Gln Leu Glu Ala Asp Leu Arg Thr Arg Ser Leu Thr Leu Ala Ala
1505                1510                1515                1520
Asn Gln Leu Val Pro Leu Pro Arg Leu Arg Leu Glu Ser Leu Val Ala
            1525                1530                1535
Thr Ala Ser Ala Leu Ala Asp Glu Arg Tyr Thr Asp Ala Ser Trp Lys
            1540                1545                1550
Ala Phe Thr Thr Ala Leu Thr Ala Ala Lys Thr Ala Leu Ala Asp Glu
            1555                1560                1565
Thr Ala Thr Asp Arg Thr Leu Thr Glu Arg Tyr Ala Ala Leu Asp Arg
            1570                1575                1580
Ala Arg Ser Ser Leu Thr Thr Lys Arg Arg Thr Val Pro Ala Ala Pro
1585                1590                1595                1600
Gly Ala Val Ser Ala Ala Pro Ser Gly Thr Ser Val Gln Val Thr Trp
            1605                1610                1615
Ser Ala Pro Glu Asp Asp Gly Gly Ser Pro Val Thr Gly Tyr Glu Ile
            1620                1625                1630
Thr Leu Ser Gly Gly Arg Gln Val Glu Ile Ala Asp Pro Asp Ser Arg
            1635                1640                1645
Ser Thr Val Phe Thr Arg Leu Lys Asp Gly Thr Ser Tyr Thr Ala Arg
            1650                1655                1660
Val Arg Ala Val Asn Ala Leu Gly Asp Ser Pro Trp Ser Ala Arg Thr
1665                1670                1675                1680
Gln Pro Ala Val Thr Gly Asp Asn Arg Pro Gln Thr Pro Thr Val Thr
            1685                1690                1695
Gly Val Val Thr Asp Gly Glu Arg Val Arg Val Asn Trp Arg Pro Ala
            1700                1705                1710
Gly Asp Gly Gly Phe Pro Val Val Gly Tyr Thr Val Ala Leu Asp Asp
            1715                1720                1725
Gly Thr Thr Ala His Val Pro Gly Thr Thr Ser Thr Ala Val Leu Thr
            1730                1735                1740
Ala Ala Gly Gly Ala Lys Ala His Thr Ala Thr Val Thr Ala Val Thr
1745                1750                1755                1760
Arg Ala Gly Ser Ser Asp Gly Ser Gly Ala Thr Val Ser Thr Ala Pro
            1765                1770                1775
Ala Thr Ser Thr Thr Ser Ala Thr Ser Ala Thr Ser Thr Gly Asp Pro
            1780                1785                1790
Ala Glu Tyr Glu Pro Ser Pro Phe Pro Gly Asp Thr Leu Asp Ala Thr
            1795                1800                1805
```

-continued

```
Tyr Ala Ser Asp Ala Trp Pro Glu Thr Gly Asp Gly Ser Asp Trp Phe
            1810                1815                1820

Thr His Leu Leu Ser Gly Phe Asp Asp Leu Gly Pro Ala Thr Leu Gly
1825                1830                1835                1840

Ala Asn Ser Glu Val Pro Ala Gly Thr Pro Leu Gly Ala Glu Asn Asp
                1845                1850                1855

Arg Ile Thr Val Ser Val Asn Asn Ala Ala Thr Gln Gln Val Asp
            1860                1865                1870

Arg Ala Glu Val Asp Ala Ser Asn Ser Ala Thr Val Thr Met Ala Asp
            1875                1880                1885

Gly Leu Gly Ser Arg Leu Gly Pro Leu Tyr Gly Glu Ala Leu Lys Glu
            1890                1895                1900

Gly Arg Leu Pro Lys Thr Ser Ala Leu Phe Ser Arg Val Asn Glu Asn
1905                1910                1915                1920

Leu Asp Thr His Asp Ala Ala Lys Asn His Tyr Gln Tyr Leu Arg Pro
                1925                1930                1935

Tyr Val Arg Leu Gly Phe Ala Gly Asp Gly Gly Ala Val Tyr Glu Ser
            1940                1945                1950

Gln Asp Ser Ser Tyr Ser Gly Leu Ala Gly Gln Gly Ser Tyr Pro Ser
            1955                1960                1965

Gly His Thr Tyr Gly Gly Tyr Glu Ala Gly Thr Ile Leu Ala Thr Leu
    1970                1975                1980

Leu Pro Asp Leu Ala Pro Ser Ile Leu Ala Arg Thr Ser Glu Tyr Gly
1985                1990                1995                2000

Asp Asn Arg Ile Val Leu Gly Phe His Tyr Pro Leu Asp Val Met Gly
                2005                2010                2015

Gly Arg Ile Thr Ala Gln Ala Thr Val Ala His Arg Trp Ala Asp Pro
            2020                2025                2030

Glu Phe Ala Lys Leu Leu Gly Gln Ala His Thr Glu Ile Glu Asn Val
            2035                2040                2045

Leu Leu Ala Arg Cys Glu Glu Glu Gly Tyr Gly Asp Thr Leu Thr Ala
    2050                2055                2060

Cys Ala Gly Asp Pro Tyr Ala Gly Leu Ser Thr Ala Gln Gln Val Asp
2065                2070                2075                2080

Arg Tyr Thr Gln Arg Leu Thr Tyr Gly Phe Ser Arg Thr Gly Glu Ala
                2085                2090                2095

Gly Gln Ala Leu Asp Ala Pro Ser Asp Ala Ala Leu Leu Ile Thr
            2100                2105                2110

Ala Phe Pro Asp Leu Thr Ala Glu Gln Arg Ala Gln Val Leu Glu Gln
            2115                2120                2125

Thr Ala Thr Asp Ser Gly Tyr Pro Leu Asp Leu Thr Gly Ser Gly Gly
            2130                2135                2140

Pro Gly Trp Gln Arg Ile Asn Leu Ala Ala Ala Met Ala Ala Asp Val
2145                2150                2155                2160

Val Val Asn Ala Asp Gly Ser Val Thr Val Thr Asn Phe Pro Asp Pro
                2165                2170                2175

Thr Ala Ala Ser Ala Ala Glu Ala Val Ala Ile Thr Val Gly Gly Val
            2180                2185                2190

Ala Leu Asp Gly Phe Asp Pro Asp Val Ser Thr Tyr Val Val Asp Trp
            2195                2200                2205

Pro Arg Asn Gly Gly Arg Ile Pro Ala Val Gly Ala Val Thr Ala Ala
            2210                2215                2220
```

-continued

Ser Gly Ala Arg Val Lys Val Thr Ser Gly Ser Ser Thr Val Ser Ser
2225                2230                2235                2240

Ser Gln Arg Gly Phe Ser Thr Arg Thr Leu Thr Val Thr Ser Ala Asp
            2245                2250                2255

Gly Glu Phe Thr Arg Thr Tyr Thr Val Gly Phe Arg Pro Val Glu Gln
                2260                2265                2270

His Pro His Arg Pro Gly Ala Leu Arg Asp Thr Gly Gly Gly Gly Thr
            2275                2280                2285

Ala Gly Gly Ser Ala Gly Gly Gly Asp Val Gly Gly Gly Leu Trp Ser
        2290                2295                2300

Pro Ala Arg Glu Trp Glu Leu Thr Val Asn
2305                2310

<210> SEQ ID NO 27
<211> LENGTH: 1984
<212> TYPE: PRT
<213> ORGANISM: Clostridium spiroforme

<400> SEQUENCE: 27

Met Asn Lys Lys Ile Asn Arg Leu Leu Lys Gly Ala Leu Ala Phe Thr
1               5                   10                  15

Val Ala Phe Ser Thr Leu Ala Val Thr Thr Ser Thr Ser Arg Lys Val
            20                  25                  30

Ser Ala Val Glu Gln Glu Glu Ser Tyr Thr Gln Tyr Val Asp Pro Phe
        35                  40                  45

Val Cys Thr Asp Val Asp Tyr Gly Gln Leu Phe Pro Gly Ser Val Val
    50                  55                  60

Pro Asn Gly Leu Val Lys Leu Ser Pro Asp Thr Tyr Pro His Asn Thr
65                  70                  75                  80

Leu Asp His Ala Gly Tyr Asp Tyr Ser Lys Leu Gln Ile Gln Gly Phe
                85                  90                  95

Ser His Thr Arg Ile Glu Gly Val Gly Gly Gln Gly Ala Gly Gly Asp
            100                 105                 110

Val Leu Val Thr Pro Thr Tyr Val Glu Tyr Ser Gln Arg Pro Gln Ala
        115                 120                 125

Gln Thr Arg Ala Met Asn Tyr Thr Lys Glu Asp Glu Ser Ala Lys Pro
    130                 135                 140

Gly Tyr Tyr Ser Val Glu Leu Thr Pro Lys Thr Gly Lys Asp Asn Asp
145                 150                 155                 160

Val Lys Asp Ser Pro Glu Ile Gly Lys Ile Lys Ala Glu Met Thr Thr
                165                 170                 175

Asp Gln Arg Thr Gly Phe His Arg Tyr Thr Phe Pro Glu Ala Gly Ser
            180                 185                 190

Val Asn Ile Ile Thr Asp Leu Asn Tyr Thr His Gly Thr Asp Ile
        195                 200                 205

Arg Asn Ala Tyr Val Asp Val Leu Glu Gln Ser Asp Thr Thr Thr Ala
    210                 215                 220

Ile Gly Gly Arg Phe Ser Gly Arg Asn Val Ser Gly Asn Gly Lys Tyr
225                 230                 235                 240

Thr Met Tyr Phe Tyr Met Glu Ser Lys Pro Ala Asn Ser Val Lys
                245                 250                 255

Thr Trp Asn Asp Thr Thr Leu Ser Asp Lys Thr Ser Gln Lys Gly Asn
            260                 265                 270

Asp Ile Gly Thr Ile Met Asn Phe Asp Val Lys Glu Asn Glu Glu Ile
        275                 280                 285

```
Gln Leu Lys Val Ser Ile Ser Pro Ile Ser Val Lys Gln Ala Lys Ile
            290                 295                 300

Asp Met His Asn Glu Ile Ser Asp Trp Asp Phe Asp Ala Ala Ala Ser
305                 310                 315                 320

Arg Ala Asp Lys Ala Trp Asn Asp Val Leu Ser Lys Val Arg Val Glu
                325                 330                 335

Ser Ser Lys Val Ser Asp Pro Thr Gly Glu Leu Lys Gln Leu Phe Tyr
                340                 345                 350

Thr His Leu Tyr His Met Phe Met Thr Pro Val Asn Ala Thr Ser Thr
            355                 360                 365

Ser Gly Thr Phe Arg Gly Thr Asp Gly Lys Ile His Glu Ala Asn Asp
        370                 375                 380

Tyr Ile His Tyr Asp Ser Trp Thr Leu Trp Asp Asp Tyr Arg Lys Tyr
385                 390                 395                 400

Pro Met Ile Gly Leu Ile Gln Pro Asp Thr Tyr Lys Asp Met Val Lys
                405                 410                 415

Ser Ile Ala Asp Ala Leu Asp Tyr Gly Ile Val Thr Trp Ser His Asp
                420                 425                 430

Lys Gln Pro Val Pro Asn Val Arg Thr Glu His Ala Val Ala Leu Leu
            435                 440                 445

Ala Asp Gly Val Ala Lys Gly Phe Thr Asp Ile Asp Asn Leu Glu Glu
450                 455                 460

Ala Tyr Glu Glu Ala Lys Glu Ile Val Asn Glu Val Ile Thr Ser Glu
465                 470                 475                 480

Val Glu Lys Ile Gly Tyr Val Pro Asn Arg Val Asp Arg Thr Ile Glu
                485                 490                 495

Tyr Gly Tyr Asp Asp Trp Cys Leu Ser Ile Ile Ala Glu Ala Leu Gly
            500                 505                 510

Lys Glu Asp Glu Ala Ala Tyr Phe Leu Asp Arg Ser Phe Asn Tyr Lys
            515                 520                 525

Asn Thr Phe Arg Lys Asp Ala Val Asp Ser Pro Phe Ser Asp Lys Lys
            530                 535                 540

Leu Gly Leu Leu Trp Asn Arg Asp Ser Asn Gly Asn Trp Leu Asn Gln
545                 550                 555                 560

Asp Pro Ser Ser Thr Asn Thr Gly Leu Tyr Gln Gly Thr Met Trp Gln
                565                 570                 575

Tyr Thr Trp Tyr Gly Ser Asn Asp Val Asn Gly Leu Met Asp Leu Met
            580                 585                 590

Gly Gly Arg Glu Ala Thr Leu Glu Ala Leu Met Tyr Met Phe Gly Met
        595                 600                 605

Gln Asp Pro Asp Pro Lys Gly Met Gln His Asn Ala Ala Asn Glu
            610                 615                 620

Val Glu Leu His Thr Pro Tyr Leu Phe Asn Phe Val Gly Arg Pro Asp
625                 630                 635                 640

Leu Thr Gln His Trp Val Arg Glu Ile Tyr Thr Arg Glu Thr Trp Asn
                645                 650                 655

Ser Asn Tyr Ala Ser Gly Thr Gln Thr Glu Lys Gln Lys Met Tyr Lys
                660                 665                 670

Leu Ser Pro Gln Gly Tyr Leu Glu Thr Met Asp Asp Ala Gly Thr
            675                 680                 685

Met Ala Met Met Phe Val Ser Ala Ala Met Gly Ile Phe Pro Met Thr
690                 695                 700
```

```
Pro Gly Asp Thr Thr Phe Gln Ile Gly Ser Pro Phe Phe Glu Lys Ile
705                 710                 715                 720

Thr Leu Asp Val Gly Asn Gly Lys Thr Phe Thr Ile Glu Ala Asn Asn
            725                 730                 735

Val Ser Asp Thr Asn Glu Tyr Ile Gln Ser Ala Thr Leu Asn Gly Lys
        740                 745                 750

Ser Phe Asp Arg Thr Trp Val Asp Tyr Ser Glu Ile Thr Arg Gly Gly
            755                 760                 765

Val Leu Ser Phe Glu Met Gly Asp Thr Pro Ser Ser Trp Ala Gln Asn
    770                 775                 780

Gly Val Thr Ala Lys Ser Ser Asp Asn Ala Asp Thr Ser Thr Tyr
785                 790                 795                 800

Asp Asp Asp Glu Ile Ala Tyr Ser Ser Ala Met Phe Glu Glu Ser Lys
                805                 810                 815

Ala Asn Asp Gly Ser Phe Asp Gln Lys Ile Thr Ile Thr Leu Lys Thr
                820                 825                 830

Lys Glu Phe Ala Gly Glu Ile Gly Glu Asp Leu Val Ala Thr Gly Lys
            835                 840                 845

Ile Asn Ile Thr Asn Ile Pro Glu Gly Leu Glu Ala Ser Ala Ile Lys
850                 855                 860

Thr Glu Ala Asn Lys Val Glu Val Ser Leu Asn Gly Lys Ala Lys Asn
865                 870                 875                 880

His Thr Leu Asn Asp Ser Ile Ser Asn Leu Thr Ile Glu Ile Thr Asp
                885                 890                 895

Gly Ala Thr Asn Glu Pro Ile Lys Asp Ser Ile Arg Lys Thr Lys Asp
                900                 905                 910

Asn Val Lys Val Met Phe Ile Asp Asn Gln Leu Thr Tyr Ser Gln Ser
            915                 920                 925

Glu Phe Lys Glu Ser Glu Ser Asp Asp Gly Ala Ile Leu Glu Thr Ser
    930                 935                 940

Thr Ile Thr Leu Thr Gly Asp Thr Thr Phe Ala Gly Glu Val Asn Glu
945                 950                 955                 960

Asp Phe Val Ala Thr Gly Lys Val Gln Ile Asn Asn Val Pro Glu Gly
                965                 970                 975

Leu Thr Val Lys Met Ile Lys Ile Asp Asp His Thr Ala Val Leu Ser
            980                 985                 990

Phe Glu Gly Lys Ala Val Asn Asn Asp Ala Asp Ala Glu Ile Glu Leu
    995                 1000                1005

Ala Phe Thr Asp Ser Ala Phe Asn Gly Ala Leu Ala Ser Glu Ile Gly
    1010                1015                1020

Gln Ser Ser Arg Gly Gly Met Thr Ala Leu Leu Leu Asp Phe Asp Tyr
1025                1030                1035                1040

Asp His Thr Ser Lys Leu Lys Arg Thr Met Ala Glu Ala Thr Tyr Ile
        1045                1050                1055

Asn Ala Ser Ala Tyr Thr Gln Ser Tyr Gln Ala Val Leu Asp Ala
        1060                1065                1070

Val Ala Lys Gly Gln Glu Leu Leu Asp Asn Lys Asn Ala Thr Ser Lys
    1075                1080                1085

Glu Ile Asp Leu Ala Ile Gly Asp Ile Asp Ala Gln Glu Gln Leu
    1090                1095                1100

Asp Ile Pro Arg Asp Gly Phe Ser Val Leu Gln Ala Glu Ser Ser Asp
1105                1110                1115                1120

Val Thr Ser Gly Gly Ser Leu Arg Val Glu Gly Ser Val Leu His Gly
```

```
                    1125            1130            1135
Thr Tyr Asp Gly Ala Trp Ile Arg Tyr Asp Ala Leu Asp Phe Asn Gly
                1140            1145            1150

Leu Ser Pro Lys Tyr Leu Glu Leu Arg Tyr Asp Asn Ala Ser Asn Arg
            1155            1160            1165

Cys Ala Ser Asp Ser His Leu Glu Val Arg Leu Asp Gly Val Asp Gly
        1170            1175            1180

Thr Leu Ile Gly Asp Ile Gln Leu Pro Ala Thr Gly Thr Ala Trp Gly
1185            1190            1195            1200

Ser Tyr Glu Thr Leu Gln Phe Glu Ile Ser Asn Pro Glu Leu Leu Asp
                1205            1210            1215

Gly Lys His Asp Val Tyr Phe Val Phe Lys Gly Thr Thr Glu Asp Ser
            1220            1225            1230

Lys Pro Tyr Val Ala Lys Val Asp Tyr Leu Gln Phe Lys Glu Thr Ala
        1235            1240            1245

Asp Ile Asp Ser Val Lys Leu Glu Ala Glu Lys Ser Asp Glu Asn Ser
    1250            1255            1260

Gly Asn Gly Leu Lys Asn Glu Ser Ile Asn Leu Gly Gly Thr Tyr Asp
1265            1270            1275            1280

Gly Ala Trp Ile Lys Tyr Asn Asn Val Asn Phe Asn Asn Leu Glu Ala
                1285            1290            1295

Asp Thr Ile Asn Val His Tyr Ser Thr Arg Val Asp Ala Cys Ala Leu
            1300            1305            1310

Asp Ala Arg Ile Glu Ile Arg Lys Asp Asn Lys Asp Gly Glu Leu Leu
        1315            1320            1325

Gly Thr Ile Met Leu Pro Leu Thr Gly Gly Trp Ser Asp Tyr Gln Thr
    1330            1335            1340

Val Ser Thr Lys Leu Asp Thr Ser Val Thr Gly Val Gln Asp Ile Cys
1345            1350            1355            1360

Phe Val Leu Arg Gly Thr Asn Asp Gly Gly Arg Pro Tyr Val Ala Asn
                1365            1370            1375

Ile Asp Tyr Met Glu Phe Val Asn Ser Gly Val Asn His Ile Glu Ala
            1380            1385            1390

Glu Asn Lys Asp Asp Trp Ser Gly Ala Glu Leu Lys Val Glu Asn Ser
        1395            1400            1405

Thr Asp Asn Thr Gly Lys Ser Leu Thr Asn Ile Gly Gly Ala Arg Asn
    1410            1415            1420

Asp Ala Trp Leu Arg Tyr Asn Gly Val Glu Phe Asn Gly Lys Thr Glu
1425            1430            1435            1440

Met Thr Val Arg Tyr Ser His Asn Pro Gly Thr Ala Gly Thr Asn Ser
                1445            1450            1455

Arg Ile Asp Val Tyr Leu Asp Asn Met Asp Gly Asn Pro Ile Gly Thr
            1460            1465            1470

Ile Asn Leu Pro Thr Thr Asn Gly Trp Ala Asn Tyr Thr Val Ile Arg
        1475            1480            1485

Glu Val Phe Asp Gln Glu Ile Thr Gly Ser His Asp Val Tyr Leu Lys
    1490            1495            1500

Leu His Thr Asp Gly Ser Gly Trp Val Ala Asn Phe Asp Trp Phe Glu
1505            1510            1515            1520

Phe Gly Glu Pro Ile Ala Asp Val Asp Lys Ser Gln Leu Gln Ala Lys
                1525            1530            1535

Tyr Asp Glu Asn Val Ala Leu Leu Gln Glu Tyr Asp Lys Tyr His Tyr
            1540            1545            1550
```

```
Val Gly Phe Asn Ile Phe Lys Asp Arg Leu Leu Thr Gly Ser Ala Val
        1555                1560                1565
Ile Asp Asn Gln Asn Ala Thr Ala Asn Asp Val Arg Ile Ala Ile Lys
        1570                1575                1580
Asp Ile Asp Asn Ala Leu Ala Ala Leu Gln Tyr Lys Ile Ala Phe Asp
1585                1590                1595                1600
Leu Asn Asp Tyr Val Val Gln Leu Glu Asn Ile Asn Glu Ala Asp Tyr
            1605                1610                1615
Thr Lys Asp Ser Tyr Ala Asn Leu Met Gln Ala Ile Glu Val Ala Lys
        1620                1625                1630
Ala Ile Pro Thr Asp Ser Glu Tyr Glu Val Phe Lys Asn Ala Tyr Asp
        1635                1640                1645
Gly Leu Val Asp Ala His Ser Lys Leu Thr Ala Leu Asn Arg Thr Ala
        1650                1655                1660
Leu Glu Glu Ile Ile Lys Gln Ala Glu Ala Ile Asp Leu Asp Leu Tyr
1665                1670                1675                1680
Lys Glu Glu Gly Lys Ala Glu Phe Lys Ala Ala Leu Glu Asn Ala Lys
            1685                1690                1695
Thr Val Tyr Glu Thr Val Ser Leu Thr Gln Ala Gln Val Asp Glu Ala
        1700                1705                1710
Val Ala Asn Leu Asp Gln Ala Ile Lys Ala Leu Lys Pro Ile Glu Thr
        1715                1720                1725
Asp Ser Val Asn Lys Val Ala Leu Lys Ile Ala Val Asp Leu Ala Asn
        1730                1735                1740
Ala Ile Thr Asp Glu Asp Leu Ala Asn Val Val Pro Ala Val Val Asp
1745                1750                1755                1760
Glu Phe Ile Ala Ala Arg Asp Glu Ala Asn Ala Val Tyr Asn Asp Val
            1765                1770                1775
Ser Ala Thr Gln Glu Glu Val Pro Arg Thr Phe Asp Arg Leu Ala Ser
        1780                1785                1790
Val Met Gln Lys Leu Glu Phe Phe Lys Gly Asp Lys Lys Ala Leu Lys
        1795                1800                1805
Ala Phe Ile Asp Lys Val Thr Gly Leu Asp Ser Ser Lys Tyr Thr Gln
        1810                1815                1820
Thr Thr Trp Thr Ala Phe Asp Lys Glu Leu Thr Glu Ala Ile Ala Val
1825                1830                1835                1840
Tyr Asn Asp Glu Asn Ala Met Gln Glu Glu Val Asn Thr Ala Tyr Ser
            1845                1850                1855
Glu Leu Val Thr Ala Phe Leu Asn Leu Arg Leu Ile Pro Asp Lys Ser
        1860                1865                1870
Leu Leu Glu Asp Leu Ile Asn Gln Ala Asn Gly Leu Asn Gly Ala Asn
        1875                1880                1885
Tyr Thr Lys Ala Thr Phe Asp Gly Leu Thr Lys Ala Leu Asp Glu Ala
        1890                1895                1900
Lys Ala Val Tyr Glu Asn Pro Asp Ala Thr Gln Lys Glu Val Pro Arg
1905                1910                1915                1920
Thr Lys Asp Val Leu Ala Lys Ala Ile Ala Gly Leu Gln Thr Val Thr
            1925                1930                1935
Thr Asp Asn Thr Val Ser Thr Pro Val Asn Asn Gly Asp Thr Thr Ala
            1940                1945                1950
Ser Val Lys Thr Gly Asp Glu Ser Leu Ala Gly Met Phe Ala Thr Ile
            1955                1960                1965
```

```
Ala Leu Leu Ser Ile Ala Gly Tyr Thr Ile Leu Lys Arg Lys Glu Asn
    1970                1975                1980

<210> SEQ ID NO 28
<211> LENGTH: 653
<212> TYPE: PRT
<213> ORGANISM: Bacteroides thetaiotaomicron

<400> SEQUENCE: 28

Met Thr Pro Ser Val Ala Gln Asn Thr Lys Tyr Val Asn Leu Phe Ile
  1               5                  10                  15

Gly Thr Ser Gly Asp Asn Gly Gln Val Ala Pro Gly Ala Ala Pro
             20                  25                  30

Phe Gly Met Val Cys Val Cys Pro Asp Asn Asp Pro Arg Ser His Ala
         35                  40                  45

Gly Tyr Asp Tyr Ala Val Thr Lys Val Ser Gly Ile Ser Val Asn Arg
 50                  55                  60

Leu Ser Gly Val Gly Cys Ser Gly Gly Gly Asn Leu Arg Ile Arg
 65                  70                  75                  80

Pro Val Ala Pro Ser Gln Glu Leu His Ile Lys Lys Ser Arg Glu Lys
                 85                  90                  95

Ala Thr Pro Gly Tyr Tyr Ser Thr Ala Phe Thr Asn Gly Ile Lys Thr
            100                 105                 110

Glu Leu Thr Ala Thr Asn Ala Met Ala Val Glu Arg Tyr Lys Phe Pro
        115                 120                 125

Arg Ser Leu Ser Ala Ala Leu Trp Ile Asp Phe Ala Ser Thr Phe Glu
    130                 135                 140

Asp Val Ala Thr Cys His Tyr Lys Arg Ile Ser Glu Thr Cys Ile Glu
145                 150                 155                 160

Gly Tyr Val Gln Ala Lys Asn Val Cys Gly His Gly Cys Tyr Lys Leu
                165                 170                 175

Tyr Phe Ser Leu Asn Thr Ser Gln Pro Phe Gln Leu Glu Gly Gln Lys
            180                 185                 190

Glu Thr Thr Ala Cys Leu Thr Phe Gly Lys Lys Val Arg Ser Val Glu
        195                 200                 205

Val Arg Ile Gly Leu Ser Ala Leu Ser Ser Glu Leu Ala Ser Trp Glu
    210                 215                 220

Cys Ala Arg Trp Glu Lys Met Asp Phe Glu Asp Val Lys Ser Arg Thr
225                 230                 235                 240

Ala Asp Gln Trp Glu Lys Gln Leu Ser Ala Ile Asp Val Lys Gly Gly
                245                 250                 255

Lys Lys Asp Asp Arg Val Ile Phe Tyr Thr Ser Leu Tyr Arg Thr Tyr
            260                 265                 270

Leu Ser Pro Ala Asp Val Ser Ser Pro Asp Gly Ala Tyr Leu Gly Thr
        275                 280                 285

Asp Gly Lys Val Tyr Ile Ser Glu Asp Phe Arg Tyr Tyr Ser Asn Trp
    290                 295                 300

Ser Leu Trp Asp Thr Phe Arg Thr Lys Phe Pro Leu Leu Val Leu Thr
305                 310                 315                 320

Glu Pro Ala Lys Met Arg Asp Met Ala Thr Ser Leu Ile His Leu Tyr
                325                 330                 335

Ala Thr Gly Lys Lys Asp Trp Ser Thr Gly Phe Glu Ser Thr Pro Thr
            340                 345                 350

Val Arg Thr Glu His Ala Val Ile Leu Leu Leu Asp Ala Tyr Arg Lys
        355                 360                 365
```

Gly Ile Thr Asn Leu Asp Phe Arg Lys Gly Tyr Ala Gly Met Lys Gln
                370                 375                 380

Glu Met Glu Arg Leu Pro Met Arg Ser Pro Asp Gln Lys Met Glu Ser
385                 390                 395                 400

Ala Tyr Asp Leu Trp Ala Met Ala Lys Ile Ala Glu Ile Ile Gly Glu
                405                 410                 415

Lys Ala Asp Ser Glu Gln Tyr Arg Gln Arg Ser Val Ser Leu Phe Glu
                420                 425                 430

Glu Thr Trp Lys Lys Glu Phe Met Asn Val Thr Pro Ala Phe Glu Val
                435                 440                 445

Met Lys Asn Asn Gly Leu Tyr Gln Gly Thr Arg Trp Gln Tyr Arg Trp
                450                 455                 460

Ala Ala Pro Gln Tyr Ile Asp Lys Met Ile Glu Trp Val Gly Gln Asp
465                 470                 475                 480

Ser Leu Arg Leu Gln Leu Thr Tyr Phe Phe Asp His His Leu Tyr Asn
                485                 490                 495

Gln Gly Asn Glu Pro Asp Ile His Val Pro Tyr Leu Phe Asn Arg Leu
                500                 505                 510

Gly Ala Pro Glu Lys Thr Gln Gln Ile Val Arg Ser Leu Met Thr Glu
                515                 520                 525

Pro Met Ile His Lys Tyr Gly Gly Asn Ser Glu Phe Lys Thr Pro Tyr
                530                 535                 540

Leu Gly Lys Ala Phe Lys Asn Ala Pro Glu Gly Tyr Ser Pro Glu Met
545                 550                 555                 560

Asp Glu Asp Asp Gly Thr Met Ser Ala Trp Tyr Val Phe Gly Ala Met
                565                 570                 575

Gly Phe Tyr Pro Leu Leu Val Gly Asp Glu Tyr Tyr Asp Leu Thr Ser
                580                 585                 590

Pro Leu Phe Asp Arg Val Leu Leu Arg Leu Thr Asn Gly Asn Val Leu
                595                 600                 605

Thr Ile Gln Thr Glu Gly Arg Lys Lys Asp Ala Pro Ile Lys Ser
                610                 615                 620

Ile His Phe Asn Gly Lys Lys Ile Ala Asp Tyr Arg Ile Ser His Asn
625                 630                 635                 640

Glu Leu Ile Lys Gly Gly Glu Leu Ile Tyr Asn Tyr Lys
                645                 650

<210> SEQ ID NO 29
<211> LENGTH: 696
<212> TYPE: PRT
<213> ORGANISM: Zunongwangia profunda

<400> SEQUENCE: 29

Met Thr Leu Ile Met Lys Arg Met Ile Ala Ala Ile Ala Val Ala Leu
1               5                   10                  15

Cys Val Ala Cys Gln Pro Lys Ser Gln Glu Lys Thr Ser Lys Ser Ala
                20                  25                  30

Asn Ile Thr Asp Lys Val Asn Val Phe Leu Gly Ser Ser Gly Asp His
                35                  40                  45

Gly Gln Met Ser Pro Ser Ala Ser Thr Pro Phe Asn Met Met Ser Ile
            50                  55                  60

Gly Pro His Thr Asn Pro His Asn His Thr Gly Tyr Glu His Tyr Ala
65              70                  75                  80

Lys Glu Phe Asp Gly Phe Thr His Thr His Leu Glu Gly Val Gly Cys

```
                    85                  90                  95
Thr Gly Ser Gly Gly Asn Ile Leu Ile Lys Pro Ile Leu Asn Asp Asn
                100                 105                 110

Lys Glu Thr Glu Leu Arg Lys Val Thr Glu His Ala Lys Pro Gly Phe
            115                 120                 125

Tyr Glu Val Ser Phe Glu Asn Gly Ile Asp Ala Ala Met Ser Val Thr
        130                 135                 140

His Asn Phe Gly Ile His Gln Tyr Asn Phe Asn Gly Glu Lys Gly Gly
145                 150                 155                 160

Leu Phe Ile Asp Leu Ser Phe Ala Leu Ser Asn Arg Phe Val Ser Glu
                165                 170                 175

Glu His Glu Ile Lys Asp Asn Lys Ile Ser Gly Val Ile Ala Thr Lys
            180                 185                 190

Thr Thr Cys His Ala Gly Thr Tyr Arg Phe Tyr Glu Ile Gln Leu
        195                 200                 205

Lys Asn Met Ala Glu Ile Ala Gln Ile Ser Asp His Glu Ile Met Ala
    210                 215                 220

Lys Ala Glu Asp Asn Ser Lys Glu Val Lys Val Leu Ile Gly Phe Ser
225                 230                 235                 240

Ser Val Ser Lys Glu Tyr Ala Ser Gln Lys Ile Glu Asn Ile Ser Tyr
                245                 250                 255

Glu Asn Leu Lys Lys Glu Ala Ser Ala Ala Trp Glu Lys Ala Leu Ser
            260                 265                 270

Arg Ile Ser Val Glu Gly Glu Glu Asp Arg Glu Asp Leu Phe Tyr Ser
        275                 280                 285

Leu Leu Tyr Arg Gly Leu Gln Ser Pro Tyr Ile Val Ser Glu Glu Asp
    290                 295                 300

Gly Thr Tyr Pro Ala Ile Asp Gly Thr Leu Gln Lys Thr Glu Gly Thr
305                 310                 315                 320

Ile Tyr Ser Gly Trp Ala Ile Trp Asp Asn Tyr Arg Glu Gln Leu Pro
                325                 330                 335

Met Leu Ser Met Ala Tyr Pro Asp Arg Tyr Arg Asp Ile Val Lys Ser
            340                 345                 350

Ile Glu Asn Leu Tyr Ala Phe Gly Lys Lys Asn Trp Ala Thr Asp Tyr
        355                 360                 365

Glu Pro Ala Pro Thr Val Arg Thr Glu His Ala Met Val Val Leu Leu
    370                 375                 380

Asp Ala Tyr Asn Lys Gly Tyr Glu Val Asp Ile Lys Arg Ile Lys Asp
385                 390                 395                 400

Ser Leu Ile Lys Asp Ala Glu Ser Leu Asp Tyr Arg Ala Pro Asp Lys
                405                 410                 415

Ala Leu Glu Ser Ser Tyr Asp Asn Trp Ala Met Ala Gln Leu Met Lys
            420                 425                 430

Ile Asp Gly Asp Thr Thr Leu Tyr Asn Lys Tyr Ile Thr Lys Ser Leu
        435                 440                 445

Asp Tyr Lys Glu Tyr Trp Asn Lys Asp Phe Lys Asp Ile Thr Arg Asn
    450                 455                 460

Asp Val Asp Arg Met Gln Ala Arg Gly Leu Tyr Gln Gly Thr Ile Trp
465                 470                 475                 480

Gln Tyr Arg Trp Phe Val Pro Phe Asp Leu Asn Gly Leu Lys Gln Leu
                485                 490                 495

Ala Gly Gly Glu Asp Gln Phe Leu Glu Glu Leu Asp Thr Phe Phe Arg
            500                 505                 510
```

```
Asn His Asn Tyr Asn His Ala Asn Gln Pro Asp Leu Gln Val Pro Gly
            515                 520                 525

Met Tyr Asn Ala Thr Lys Glu Pro Trp Lys Ser Gln Glu Leu Tyr Arg
        530                 535                 540

Lys Ile Leu Leu Asp Thr Met Val Gln Ala Tyr Phe Asn Asp Asn Ser
545                 550                 555                 560

Lys Gly Ile Asp Pro Tyr Val Gly Arg Ile Tyr Gln Asn Lys Pro Lys
                565                 570                 575

Ala Tyr Leu Arg Thr Met Asp Asp Ala Gly Thr Met Ser Ser Trp
            580                 585                 590

Phe Val Met Arg Ser Leu Gly Leu Ser Pro Ala Asn Ile Gly Asp Pro
            595                 600                 605

Val Tyr Tyr Leu Thr Ala Pro Ile Phe Lys Glu Ile Ser Ile Asn Tyr
        610                 615                 620

Pro Lys Gly Lys Ala Phe Lys Ile Ser Val Thr Asn Tyr Asn Lys Asp
625                 630                 635                 640

His Tyr Tyr Val Glu Ser Ala Thr Leu Asn Gly Lys Pro Leu Asn Arg
                645                 650                 655

Asn Trp Leu Thr Gln Gln Glu Ile Leu Glu Gly Glu Leu Val Ile
            660                 665                 670

Lys Thr Ser Asp Thr Pro Asn Lys Glu Trp Gly Val Lys Glu Ala Trp
            675                 680                 685

Val Ser Ser Ile Arg Gln Tyr Leu
        690                 695

<210> SEQ ID NO 30
<211> LENGTH: 680
<212> TYPE: PRT
<213> ORGANISM: Chitinophaga pinensis

<400> SEQUENCE: 30

Met Lys Lys Ser Leu Ile Tyr Leu Leu Ser Leu Leu Ser Leu Thr Ala
  1               5                  10                  15

Val Ala Gln Gln Ser Gly Gln Val Asn Val Phe Leu Gly Ser Ser Gly
             20                  25                  30

Asp Asn Gly Gln Met Ser Pro Ala Ser Tyr Pro Phe Ser Met Val
         35                  40                  45

Ser Ile Gly Pro Glu Thr Tyr Pro Ser Thr His Thr Gly Tyr Glu Tyr
     50                  55                  60

Tyr Ala Lys Glu Phe Leu Gly Phe Thr His Asn Arg Met Glu Gly Val
 65                  70                  75                  80

Gly Cys Gln Gly Cys Gly Gly Asn Leu Leu Leu Arg Pro Phe Leu Gly
                 85                  90                  95

Asp Gly Pro Val Lys Ala Asp Leu Ile Lys Tyr Glu Glu Gln Ala Ser
            100                 105                 110

Pro Gly Tyr Tyr His Val Gly Phe Thr Asn Gly Ile Lys Ala Ser Phe
        115                 120                 125

Thr Val Tyr Lys Asn Ala Gly Leu His Gln Tyr Thr Phe Pro Glu Gly
    130                 135                 140

Lys Lys Gly Leu Leu Leu Asp Leu Gly Phe Ala His Val Gly Arg Phe
145                 150                 155                 160

Val Ala Glu Glu His Thr Ile Glu Gly Asn Ala Val Ser Gly Trp Val
                165                 170                 175

Glu Ser Arg Thr Thr Cys Ser Ala Gly Ile Tyr Arg Val Tyr Tyr Tyr
```

```
            180                 185                 190
Val Glu Thr Asp Arg Pro Val Lys Trp Thr Ala Thr Gln Ala His Glu
            195                 200                 205
Leu Val Ala Asp Val Thr Asp Asn Asn Leu Gly Val Arg Ile Gly Leu
            210                 215                 220
Ser Ser Val Asn Ala Thr Tyr Ala Lys Ala Ala Ile Thr Lys Asp Ala
225                 230                 235                 240
Phe Asp Met Val Lys Val Arg Ser Glu Lys Ala Trp Asn Asp Met Leu
                    245                 250                 255
Gly His Ile Lys Val Lys Gly Asp Pro Ala Arg Glu Lys Leu Phe Tyr
                    260                 265                 270
Ser Leu Phe Tyr Arg Ser Ile Gln Ser Pro Tyr Val Ser Glu Pro
            275                 280                 285
Asp Gly Ala Tyr Ala Ala Thr Asn Gly Thr Leu Gln His Thr Asn Ser
            290                 295                 300
Lys Met Tyr Asn Gly Trp Ala Ile Trp Asp Asn Tyr Arg Ala Gln Leu
305                 310                 315                 320
Pro Leu Leu Ser Ile Ala Phe Pro Gln Glu Tyr Gln Asp Met Thr Asn
                    325                 330                 335
Ser Ile Ala Gly Leu Tyr Ala His Gly Lys Lys Asp Tyr Ala Thr Leu
                    340                 345                 350
His Glu Pro Ser Ile Thr Val Arg Thr Glu His Ala Val Val Val Leu
                    355                 360                 365
Leu Asp Ala Leu Lys Lys Gly Tyr Lys Phe Asp Phe Asn Ala Ile Ala
            370                 375                 380
Asp Ser Val Glu Lys Glu Ile Lys Gly Leu Asp Tyr Ala His Pro Asp
385                 390                 395                 400
Lys Ala Leu Glu Ser Ser Tyr Asp Ala Trp Ala Leu Ala Glu Leu Tyr
                    405                 410                 415
Tyr Ala Gln Lys Asp Lys Ala His Gly Asp Gln Tyr Lys Val Gln Ala
                    420                 425                 430
Ala Asp Tyr Lys Lys Tyr Trp Leu Lys Asp Phe Gln Asp Leu Thr Lys
            435                 440                 445
Arg Asp Val Asp Arg Met Gln Ala Arg Gly Leu Tyr Gln Gly Thr Ile
450                 455                 460
Trp Gln Tyr Arg Trp Phe Val Pro Phe Asp Leu Lys Gly Leu Met Glu
465                 470                 475                 480
Leu Cys Gly Gly Glu Gln Ala Tyr Leu Ser Gln Leu Asp Glu Phe Phe
                    485                 490                 495
Asp Asn Asp Tyr Tyr Cys His Ala Asn Gln Pro Asp Leu Gln Thr Pro
            500                 505                 510
Phe Met Tyr Asn Val Thr Asn Gln Pro Trp Lys Ser Gln Ala Leu Val
            515                 520                 525
His Lys Ile Ala Val Asp Thr Met Val Gln His Tyr Phe Asn Asp Asn
            530                 535                 540
Ser Arg Gly Ile Gly Ser Glu Ile Gly Pro Ile Tyr Lys Asn Gln Pro
545                 550                 555                 560
Ala Ala Tyr Val Arg Thr Met Asp Asp Ala Gly Thr Met Ser Ser
                    565                 570                 575
Trp Phe Val Leu Val Ser Thr Gly Ile Phe Pro Ala Cys Ile Gly Ser
            580                 585                 590
Pro Val Tyr Tyr Leu Asn Val Pro Leu Phe Glu Ser Val Glu Trp Gln
            595                 600                 605
```

```
Trp Pro Gly Ala Lys Pro Phe Ser Val Gln Val Lys Asn Phe Gly Pro
            610                 615                 620

Lys Asn Val Tyr Ile Lys Glu Val Trp Leu Asn Gly Arg Lys Leu Asp
625                 630                 635                 640

Arg Asn Trp Ile Thr His Ser Glu Ile Ala Lys Gly Gly Lys Leu Glu
                645                 650                 655

Ile Val Ala Ser Asp Gln Pro Asp Met Gln Gln Gly Leu Gly Asn Lys
                660                 665                 670

Trp Ile Ala Asp Ile Thr Arg Gln
                675                 680

<210> SEQ ID NO 31
<211> LENGTH: 867
<212> TYPE: PRT
<213> ORGANISM: Caulobacter crescentus

<400> SEQUENCE: 31

Met Asn Pro Gly Lys Gly Pro Val Leu Arg Phe Arg Val Gln Leu Leu
1               5                   10                  15

Val Val Gly Phe Ala Leu Ala Leu Gly Ala Ala His Gln Ala Gln Ala
                20                  25                  30

Ala Pro Gly Arg Ala Leu Tyr Lys Leu Pro Asp Leu Arg Val Gly Leu
            35                  40                  45

Gly Asp Asp Asn Gln Gly Asp Thr Ile Pro Gly Pro Thr Arg Pro Asn
50                  55                  60

Gly Ser Ile His Pro Ser Pro Asp Thr Leu Lys Ala Ser Asn Ala Gly
65                  70                  75                  80

Tyr Asn Pro Ala Glu Pro Ile Ser Gly Phe Ala Gln Leu His Ser Gln
                85                  90                  95

Gly Ser Gly Gly Val Thr Thr Tyr Gly Thr Phe Leu Leu Ser Pro Gln
            100                 105                 110

Val Gly Glu Pro Val Phe Asp Glu Ala Ala His Leu Ser Pro Lys Ala
        115                 120                 125

Asp Glu Thr Leu Ala Ala Asp Ala Tyr Ser Val Arg Leu Thr Arg Tyr
130                 135                 140

Asp Thr Lys Val Glu Ile Thr Ser Ala His Tyr Ala Ala Ile Tyr Arg
145                 150                 155                 160

Leu Thr Tyr Pro Thr Thr Asp Gln Ala Gln Val Val Leu Asp Val Thr
                165                 170                 175

Arg Lys Val Gly Gly Leu Val Ala Ser Glu Gln Ala Asp Val Gln Leu
            180                 185                 190

Phe Pro Glu Gln Gly Arg Ile Val Gly His Val Lys Ala Lys Gly Tyr
        195                 200                 205

Trp Asn Pro Ala Leu Ile Asp Ile Trp Phe Val Ala Glu Phe Asp Gln
210                 215                 220

Asn Pro Thr Ala Trp Gly Val Phe Asp Lys Ala Glu Arg Arg Asp Gly
225                 230                 235                 240

Ala Leu Ser Gly Arg Thr Gly Ser Asp Glu Arg Leu Gly Ala Trp Leu
                245                 250                 255

Thr Phe Lys Thr Thr Pro Thr Lys Pro Leu Leu Val Lys Ile Ala Val
            260                 265                 270

Ser Phe Val Ser Ala Glu Met Ala Lys Ala Leu Leu Asp Arg Glu Ile
        275                 280                 285

Pro Asp Trp Asp Phe Glu Arg Val Arg Arg Asp Thr Gln Ala Ala Trp
```

```
                290                 295                 300
Asn Asp Arg Leu Gly Gln Val Arg Val Glu Gly Met Thr Glu Ser Gln
305                 310                 315                 320

Gln Arg Arg Phe Tyr Ser Ala Leu Tyr His Ala Ser Thr His Pro Arg
                325                 330                 335

Asp Arg Ser Leu Asp Gln Pro Ala Ala Arg Leu Gly Arg Pro Asn Trp
                340                 345                 350

Asp Glu His Tyr Thr Leu Trp Asp Thr Tyr Arg Thr Leu Phe Pro Leu
                355                 360                 365

Ile Ser Val Leu Arg Pro Ser Leu Tyr Thr Ala Asn Val Asn Ser Leu
                370                 375                 380

Ile His Thr Phe Asp Lys Phe Gly Ala Ala Asp Thr Ala Ile Ile Gly
385                 390                 395                 400

Gly Gln Asn Tyr His Val Gly Gln Gly Gly Asp Glu Val Asp Asn Val
                405                 410                 415

Leu Gly Glu Ala Leu Leu Arg Gly Ala Glu Gly Val Asn Trp Arg Asp
                420                 425                 430

Ala Trp Arg Val Ala Arg Phe Asn Ala Phe Glu Arg Arg Pro Arg
                435                 440                 445

Tyr Leu Glu Ser Gly Tyr Phe Ala Val Gly Asp Arg Ser Pro Glu Pro
                450                 455                 460

Asn Asn Gln Arg Ala Lys Ser Gly Ser Ser Thr Leu Gly Phe Ala Leu
465                 470                 475                 480

Asn Asp Phe Tyr Ala Ala Gln Val Ala Ala Lys Ala Gly Gln Thr Asp
                485                 490                 495

Glu Ala Lys Ile Leu Thr Glu Arg Ser Ala Asn Trp Arg Lys Ile Trp
                500                 505                 510

Asn Pro Asp Ala Thr Ser Asp Gly Phe Ser Gly Phe Leu Met Pro Arg
                515                 520                 525

Tyr Ala Asp Gly Lys Phe Gln Asp Ile Asp Pro Lys Leu Gly Trp Asp
                530                 535                 540

Gly Lys Val His Asn Asn Val Gly Tyr Tyr Glu Gly Thr Ala Trp Ile
545                 550                 555                 560

Tyr Ser Tyr Gly Val Leu His Asp Leu Pro Gly Leu Val Glu Ala Met
                565                 570                 575

Gly Gly Arg Val Arg Phe Asn Glu Arg Leu Asn His Ala Leu Asp Ala
                580                 585                 590

Gly Leu Ile Asp Ile Thr Asn Glu Pro Ser Phe Ala Thr Pro Trp Leu
                595                 600                 605

Phe His Ala Ile Gly Arg Ala Asp Leu Ser Ser Arg Trp Ala Gly Glu
                610                 615                 620

Val Val Lys His Phe Thr Ala Asp Ala Tyr Pro Gly Asp Glu Asp Ala
625                 630                 635                 640

Gly Ala Met Ser Ser Asn Phe Val Phe Asn Ser Leu Gly Leu Phe Pro
                645                 650                 655

Lys Leu Gly Ser Asp Leu Tyr Tyr Leu His Gly Pro Arg His Gly Arg
                660                 665                 670

Thr Val Ile Gln Leu Glu Asn Gly Lys Thr Leu Glu Ile Leu Ala Ala
                675                 680                 685

Lys Ala Gly Ala Ser Arg Pro Tyr Ile Ala Ser Ala Ser Phe Asn Gly
                690                 695                 700

Lys Pro Leu Ala Gly Pro Tyr Val Ser Gln Ala Gln Leu Leu Gly Gly
705                 710                 715                 720
```

-continued

```
Gly Val Leu Ser Leu Ser Met Ser Asp Gln Pro Gln Trp Ile Tyr
            725                 730                 735

Glu Gly Ala Val Leu Thr Val Arg Ala Asp Gln Pro Ser Leu Val Asp
        740                 745                 750

Gly Lys Thr Ser Thr Gly Trp Arg Ala Ala Ser Gly Gln Ser Val Thr
            755                 760                 765

Phe Ser Leu Lys Ala Pro Ala Cys Ile Ala Ala Tyr Ser Val Ser Val
770                 775                 780

Gly Pro Asp Gln Ala Asp Pro Ser His Trp Thr Leu Gln Ala Tyr Asp
785                 790                 795                 800

Gly Arg Ala Trp Val Ser Val Asp Gln Gln Ser Asn Val Val Phe Asp
            805                 810                 815

His Arg His Ala Thr Arg Thr Phe Pro Leu Ala Pro Gly Arg Tyr Ala
        820                 825                 830

Arg Leu Arg Trp Val Leu Asp Gly Gly Ser Glu Ala Ser Val Ser Glu
            835                 840                 845

Val Glu Leu Ile Ala Gly Ala Ser Cys Ala Ala Pro Thr Ser Gly Ala
    850                 855                 860

Pro Leu Leu
865

<210> SEQ ID NO 32
<211> LENGTH: 867
<212> TYPE: PRT
<213> ORGANISM: Caulobacter crescentus

<400> SEQUENCE: 32

Met Asn Pro Gly Lys Gly Pro Val Leu Arg Phe Arg Val Gln Leu Leu
1               5                   10                  15

Val Val Gly Phe Ala Leu Ala Leu Gly Ala Ala His Gln Ala Gln Ala
            20                  25                  30

Ala Pro Gly Arg Ala Leu Tyr Lys Leu Pro Asp Leu Arg Val Gly Leu
        35                  40                  45

Gly Asp Asp Asn Gln Gly Asp Thr Ile Pro Gly Pro Thr Arg Pro Asn
    50                  55                  60

Gly Ser Ile His Pro Ser Pro Asp Thr Leu Lys Ala Ser Asn Ala Gly
65                  70                  75                  80

Tyr Asn Pro Ala Glu Pro Ile Ser Gly Phe Ala Gln Leu His Ser Gln
                85                  90                  95

Gly Ser Gly Gly Val Thr Thr Tyr Gly Thr Phe Leu Leu Ser Pro Gln
            100                 105                 110

Val Gly Glu Pro Val Phe Asp Glu Ala Ala His Leu Ser Pro Lys Ala
        115                 120                 125

Asp Glu Thr Leu Ala Ala Asp Ala Tyr Ser Val Arg Leu Thr Arg Tyr
    130                 135                 140

Asp Thr Lys Val Glu Ile Thr Ser Ala His Tyr Ala Ala Ile Tyr Arg
145                 150                 155                 160

Leu Thr Tyr Pro Thr Thr Asp Gln Ala Gln Val Val Leu Asp Val Thr
                165                 170                 175

Arg Lys Val Gly Gly Leu Val Ala Ser Glu Gln Ala Asp Val Gln Leu
            180                 185                 190

Phe Pro Glu Gln Gly Arg Ile Val Gly His Val Lys Ala Lys Gly Tyr
        195                 200                 205

Trp Asn Pro Ala Leu Ile Asp Ile Trp Phe Val Ala Glu Phe Asp Gln
```

```
            210                 215                 220
Asn Pro Thr Ala Trp Gly Val Phe Asp Lys Ala Glu Arg Arg Asp Gly
225                 230                 235                 240

Ala Leu Ser Gly Arg Thr Gly Ser Asp Glu Arg Leu Gly Ala Trp Leu
                245                 250                 255

Thr Phe Lys Thr Thr Pro Thr Lys Pro Leu Leu Val Lys Ile Ala Val
            260                 265                 270

Ser Phe Val Ser Ala Glu Met Ala Lys Ala Leu Leu Asp Arg Glu Ile
        275                 280                 285

Pro Asp Trp Asp Phe Glu Arg Val Arg Arg Asp Thr Gln Ala Ala Trp
    290                 295                 300

Asn Asp Arg Leu Gly Gln Val Arg Val Glu Gly Met Thr Glu Ser Gln
305                 310                 315                 320

Gln Arg Arg Phe Tyr Ser Ala Leu Tyr His Ala Ser Thr His Pro Arg
                325                 330                 335

Asp Arg Ser Leu Asp Gln Pro Ala Ala Arg Leu Gly Arg Pro Asn Trp
            340                 345                 350

Asp Glu His Tyr Thr Leu Trp Asp Thr Tyr Arg Thr Leu Phe Pro Leu
        355                 360                 365

Ile Ser Val Leu Arg Pro Ser Leu Tyr Thr Ala Asn Val Asn Ser Leu
    370                 375                 380

Ile His Thr Phe Asp Lys Phe Ala Ala Asp Thr Ala Ile Ile Gly
385                 390                 395                 400

Gly Gln Asn Tyr His Val Gly Gln Gly Gly Asp Glu Val Asp Asn Val
                405                 410                 415

Leu Gly Glu Ala Leu Leu Arg Gly Ala Glu Gly Val Asn Trp Arg Asp
            420                 425                 430

Ala Trp Arg Val Ala Arg Phe Asn Ala Phe Glu Arg Arg Pro Arg
        435                 440                 445

Tyr Leu Glu Ser Gly Tyr Phe Ala Val Gly Asp Arg Ser Pro Glu Pro
    450                 455                 460

Asn Asn Gln Arg Ala Lys Ser Gly Ser Ser Thr Leu Gly Phe Ala Leu
465                 470                 475                 480

Asn Asp Phe Tyr Ala Ala Gln Val Ala Ala Lys Ala Gly Gln Thr Asp
                485                 490                 495

Glu Ala Lys Ile Leu Thr Glu Arg Ser Ala Asn Trp Arg Lys Ile Trp
            500                 505                 510

Asn Pro Asp Ala Thr Ser Asp Gly Phe Ser Gly Phe Leu Met Pro Arg
        515                 520                 525

Tyr Ala Asp Gly Lys Phe Gln Asp Ile Asp Pro Lys Leu Gly Trp Asp
    530                 535                 540

Gly Lys Val His Asn Asn Val Gly Tyr Tyr Glu Gly Thr Ala Trp Ile
545                 550                 555                 560

Tyr Ser Tyr Gly Val Leu His Asp Leu Pro Gly Leu Val Glu Ala Met
                565                 570                 575

Gly Gly Arg Val Arg Phe Asn Glu Arg Leu Asn His Ala Leu Asp Ala
            580                 585                 590

Gly Leu Ile Asp Ile Thr Asn Glu Pro Ser Phe Ala Thr Pro Trp Leu
        595                 600                 605

Phe His Ala Ile Gly Arg Ala Asp Leu Ser Ser Arg Trp Ala Gly Glu
    610                 615                 620

Val Val Lys His Phe Thr Ala Asp Ala Tyr Pro Gly Asp Glu Asp Ala
625                 630                 635                 640
```

```
Gly Ala Met Ser Ser Asn Phe Val Phe Asn Ser Leu Gly Leu Phe Pro
                645                 650                 655

Lys Leu Gly Ser Asp Leu Tyr Tyr Leu His Gly Pro Arg His Gly Arg
            660                 665                 670

Thr Val Ile Gln Leu Glu Asn Gly Lys Thr Leu Glu Ile Leu Ala Ala
        675                 680                 685

Lys Ala Gly Ala Ser Arg Pro Tyr Ile Ala Ser Ala Ser Phe Asn Gly
    690                 695                 700

Lys Pro Leu Ala Gly Pro Tyr Val Ser Gln Ala Gln Leu Leu Gly Gly
705                 710                 715                 720

Gly Val Leu Ser Leu Ser Met Ser Asp Gln Pro Gly Gln Trp Ile Tyr
                725                 730                 735

Glu Gly Ala Val Leu Thr Val Arg Ala Asp Gln Pro Ser Leu Val Asp
            740                 745                 750

Gly Lys Thr Ser Thr Gly Trp Arg Ala Ala Ser Gly Gln Ser Val Thr
        755                 760                 765

Phe Ser Leu Lys Ala Pro Ala Cys Ile Ala Ala Tyr Ser Val Ser Val
    770                 775                 780

Gly Pro Asp Gln Ala Asp Pro Ser His Trp Thr Leu Gln Ala Tyr Asp
785                 790                 795                 800

Gly Arg Ala Trp Val Ser Val Asp Gln Gln Ser Asn Val Val Phe Asp
                805                 810                 815

His Arg His Ala Thr Arg Thr Phe Pro Leu Ala Pro Gly Arg Tyr Ala
            820                 825                 830

Arg Leu Arg Trp Val Leu Asp Gly Gly Ser Glu Ala Ser Val Ser Glu
        835                 840                 845

Val Glu Leu Ile Ala Gly Ala Ser Cys Ala Ala Pro Thr Ser Gly Ala
    850                 855                 860

Pro Leu Leu
865

<210> SEQ ID NO 33
<211> LENGTH: 1937
<212> TYPE: PRT
<213> ORGANISM: Paenibacillus sp.

<400> SEQUENCE: 33

Met Phe Lys Lys Leu Phe Ala Val Ala Met Thr Val Met Cys Leu Thr
1               5                   10                  15

Gly Ile Leu Val Pro Val Gly Ser Asn Ala Ala Phe Ala Ala Ala Ala
            20                  25                  30

Glu Gly Ile Thr Thr Arg Asn Val Ala Ile Asn Ala Ala Ala Thr Ala
        35                  40                  45

Ser Gly Gln Cys Asn Ala Asn Glu Ser Ala Ser Asn Ala Val Asp Gly
    50                  55                  60

Lys Thr Asp Thr Lys Trp Cys Asp Asn Thr Ser Ala Gln Lys Lys Trp
65                  70                  75                  80

Leu Lys Leu Asp Leu Gly Lys Glu Tyr Leu Val Asn Glu Trp Val Leu
                85                  90                  95

Gln Asn Ala Ala Ile Asn Glu Ser Gly Asn Ser Pro Phe Trp Asn Thr
            100                 105                 110

Lys Asn Phe Arg Leu Gln Lys Ser Asp Asp Gly Glu Thr Trp Thr Asp
        115                 120                 125

Val Asp Ile Val Thr Asn Asn Ala Gln Thr Ile Val Asp Arg Phe Val
```

-continued

```
            130                 135                 140
Thr Pro Phe Thr Thr Arg Tyr Leu Arg Leu Tyr Ile Asp Lys Ala Ala
145                 150                 155                 160

Tyr Asp Ser Asn Ile Ala Arg Ile Tyr Glu Leu Glu Val Tyr Gly Val
                165                 170                 175

Glu Ala Asp Gln Ile Pro Ala Glu Pro Glu Thr Asn Leu Ala Pro Ile
            180                 185                 190

Asp Tyr Val Asp Pro Phe Ile Asn Thr Leu Gly Asp Asn Gly Gln Thr
        195                 200                 205

Asn Pro Gly Pro Thr Thr Pro Phe Gly Leu Val Ser Leu Gly Pro Asp
210                 215                 220

Ser Asp Gly Gly Ala Phe Ser Gly Tyr Tyr Glu Asn Lys Asn Leu
225                 230                 235                 240

Lys Gly Phe Ser His Leu Arg Phe Ser Gly Val Gly Cys Ser Gly Gly
                245                 250                 255

Gly Gly Asn Ile Leu Met Met Pro Glu Thr Arg Asp Phe Thr Lys Asn
            260                 265                 270

Val Ala Asp Tyr Lys Gln Lys Tyr Asp Lys Ser Ser Glu Gln Ala Ser
        275                 280                 285

Ala Gly Phe Tyr Gly Val Thr Leu Ala Ser Gly Ile Asn Val Gln Leu
290                 295                 300

Thr Ser Ser Asp Asn Val Gly Phe His Lys Tyr Thr Phe Pro Asp Thr
305                 310                 315                 320

Ala Asn Thr Gly Ser Val Leu Val Asp Leu Ser Asn Ser Tyr Ala Gly
                325                 330                 335

Met Val Asp Ala Asn Leu Lys Val Thr Gly Ser Asn Glu Ile Thr Gly
            340                 345                 350

Met Ile Lys Ser Gln Asn Val Cys Gly His Gly Tyr Tyr Thr Ile Tyr
        355                 360                 365

Tyr Ser Ile Gln Phe Asp His Asp Phe Asp Ser Tyr Ser Ser Trp Gln
370                 375                 380

Gly Asp Ser Val Gly Ala Val Ala Gln Arg Ser Gly Ser Asn Ser Gly
385                 390                 395                 400

Val Trp Leu Asn Phe Asn Thr Ala Gly Ser Lys Thr Val Gln Ala Lys
                405                 410                 415

Val Gly Leu Ser Thr Ile Ser Val Glu Gln Ala Gln Ala Glu Arg Gly
            420                 425                 430

Leu Tyr Ser Asp Trp Asn Phe Asp Ala Arg His Glu Glu Ala Arg Ala
        435                 440                 445

Ala Trp Ser Asn Val Leu Asn Lys Val Glu Ile Thr Asp Ala Asp Glu
450                 455                 460

Gln Asn Lys Arg Val Phe Tyr Thr Gln Met Tyr His Ser Tyr Leu Ser
465                 470                 475                 480

Pro Lys Asn Val Thr Ser Ser Ala Gly Thr Phe Lys Ala Gly Arg Asp
                485                 490                 495

Glu Asn Thr Val Arg Gln Ala Ser Glu Leu Gly Asp Asp Phe Glu Tyr
            500                 505                 510

Tyr Asn Gly Trp Thr Thr Trp Asp Asp Phe Arg Lys Tyr Ala Met Phe
        515                 520                 525

Ser Leu Phe Glu Pro Gln Arg Tyr Asn Asn Met Val Lys Ser Leu Val
530                 535                 540

Asp Leu Tyr Asn Thr Arg Gly Tyr Thr Gln Trp Gly Asp Gly Tyr
545                 550                 555                 560
```

-continued

```
Trp Pro Ser Pro Thr Val Arg Asn Glu Phe Asn Gly Gln Val Ile Leu
                565                 570                 575

Asp Ala Tyr Ala Lys Gly Phe Gln Asp Phe Asp Val Tyr Lys Ala Leu
            580                 585                 590

Lys Gly Met Ala Val Asp Ala Asp Asn Phe Ser Ile Ser Asp Gly Glu
        595                 600                 605

Ile Ser Gly Lys Leu Glu Lys Ala Asn Ser Ala Ser Phe Pro Met Lys
    610                 615                 620

Leu Ala Gln Leu Ile Gly Asp Lys Ala Thr Phe Glu Lys Tyr Lys Glu
625                 630                 635                 640

Leu Ala Leu Ser Tyr Lys Lys Leu Trp Asn Pro Thr Gln Val Asp Glu
                645                 650                 655

Lys Gly Thr Pro Thr Gly Phe Phe Thr Pro Asn Gly Thr Thr Val Gly
            660                 665                 670

Ala Gly Asp Ile Gln Ala Val Asp Arg Tyr Ala Tyr Gln Gly Asn Leu
        675                 680                 685

Trp Gln Tyr Arg Trp Ser Ala Pro Gln Asp Ile Asn Gly Leu Ala Gln
    690                 695                 700

Leu Met Gly Gly Lys Thr Glu Met Ala Lys Gln Leu Lys His Phe Phe
705                 710                 715                 720

Glu Ile Asp Glu Tyr Met Ala Ile Asn Glu Glu Asp Ile Ser Ala Pro
                725                 730                 735

Tyr Leu Phe Asn Tyr Leu Gly Tyr Pro Tyr Leu Thr Gln Tyr Tyr Ala
            740                 745                 750

Arg Glu Phe Thr Thr Glu Val Val Thr Gln Lys Tyr His Asn His Gly
        755                 760                 765

Ala Tyr Ala Tyr Pro Leu Lys Ser Arg Val Tyr Arg Asp Asp Pro Glu
    770                 775                 780

Gly Tyr Leu Ser Ser Met Asp Asp Ala Gly Gly Met Ser Trp
785                 790                 795                 800

Tyr Val Phe Ser Ala Leu Gly Leu Phe Pro Gly Asn Pro Gly Glu Gly
                805                 810                 815

Tyr Phe Leu Ile Gly Ser Pro Ile Phe Ser Glu Val Lys Leu His Met
            820                 825                 830

Gly Ser Gly Lys Thr Leu Val Ile Lys Ala Asp Asn Val Ser Ser Glu
        835                 840                 845

Asn Arg Phe Ile Gln Ser Ala Lys Leu Asn Gly Lys Asp Phe Asn Gln
    850                 855                 860

Ser Trp Ile Lys Tyr Asp Asp Leu Met Ala Gly Gly Thr Leu Glu Phe
865                 870                 875                 880

Gln Met Ser Ser Thr Pro Asn Met Ser Trp Gly Ala Lys Ala Ser Ala
                885                 890                 895

Ala Pro Pro Thr Val Asp Tyr Asn Ala Asp Met Asp Asn Asp Phe Asn
            900                 905                 910

His Glu Gln Leu Ile Pro Glu Lys Ser Thr Trp Lys Tyr Asp Asp Lys
        915                 920                 925

Gly Lys Glu Ala Gly Gly Trp Thr Gln Val Asp Phe Asp Ser
    930                 935                 940

Ser Trp Ser Ser Gly Lys Ala Met Leu Gly Tyr Asp Ser Tyr Gly Lys
945                 950                 955                 960

Pro Ala Thr Thr Val Ser Tyr Gly Pro Asn Ala Asn Asn Lys Tyr Val
                965                 970                 975
```

```
Thr Thr Tyr Phe Arg Lys Thr Phe Asp Ala Lys Asp Leu Asp Gly Ile
            980                 985                 990

Leu Glu Leu Asp Gly Ser Leu Ile Arg Asp Gly Ala Ile Val Tyr
        995                 1000                1005

Leu Asn Gly His Glu Ile Phe Arg Thr Asn Met Pro Thr Gly Ala Val
        1010                1015                1020

Asn Tyr Ser Thr Phe Ala Asn Ala Thr Val Gly Asp Glu Arg Asp Lys
1025                1030                1035                1040

Asn Gly Phe Ile Ile Asp Pro Ser Tyr Leu Val Glu Gly Lys Asn Val
            1045                1050                1055

Leu Thr Ala Glu Val His Gln Val Asn Ala Thr Ser Ser Asp Ile Ala
        1060                1065                1070

Phe Glu Phe Ser Leu Glu Ala Val Arg Lys Leu Asn Ile Pro Ala Ala
        1075                1080                1085

Pro Thr His Pro Val Val Asp Asp Lys Ala Asn Thr Ile Gly Trp Thr
        1090                1095                1100

Pro Val Glu Gly Ile Asn Asn Ala Ser Asp Tyr Glu Phe Ser Thr Asp
1105                1110                1115                1120

Gly Gly Lys Ser Trp Lys Gln Ala Lys Ala Asn Pro Gln Thr Val Gly
            1125                1130                1135

Pro Leu Asn Tyr Ala Pro Gly Ile Val Gln Val Arg Val Met Ala Asn
        1140                1145                1150

Ala Ala Ala Asn Arg Ala Ala Gly Glu Ala Leu Leu Ser Thr Glu Ala
        1155                1160                1165

Tyr Thr Ser Asp Val Lys Trp Asp Val Tyr Asp Leu Asp Ala Asp Ile
        1170                1175                1180

His Gln Asp Gly Asn Met Val Val Asp Val Thr Gly Thr Leu Lys Gly
1185                1190                1195                1200

Asp Tyr Thr Asp Ser Ala Val Val Phe Gln Leu Met Asp Gly Lys
            1205                1210                1215

Glu His Ala Trp Val Ser Ser Ala Val Pro Val Gln Thr Gly Ser Phe
        1220                1225                1230

Asp Ile Ser Gln Ile Tyr Asn Val Asp Ala Ser Lys Tyr Lys Val Asn
        1235                1240                1245

Val Tyr Leu Val Asn Glu Phe Asn Gly Asp Ile Tyr Glu Ser Pro Leu
        1250                1255                1260

Trp Leu Ala Asp Pro Ile Val Gln Gln Ser Glu Pro Gly Ser Leu Pro
1265                1270                1275                1280

Asp Pro Glu Gly Pro Pro Val Thr Glu Glu Pro Leu Pro Glu Pro Ile
            1285                1290                1295

Pro Leu Pro Asp Pro Lys Pro Asp Glu Pro Glu Glu Pro Val Pro
        1300                1305                1310

Glu Thr Gly Met Lys Ile Gln Phe Glu Asp Arg Ala Glu Trp Thr Ser
        1315                1320                1325

Ala Ala His Pro Asn Gly Gly Gly Leu Ser Thr Glu Ala Gly Asn
        1330                1335                1340

Gly Gly Thr Val Val Ala His Thr Phe Gly Gly Ala Trp Leu Ala Tyr
1345                1350                1355                1360

Asn Val Asp Phe Gly Thr Thr Gly Tyr Asn Asn Val Thr Val Gln Tyr
            1365                1370                1375

Asp Ala Pro Thr Asp Lys Val Pro Ala Gly Ser Lys Leu Glu Phe Arg
        1380                1385                1390

Leu Gly Ser Val Ser Gly Glu Leu Val Gly Thr Val Asn Met Glu Asp
```

```
            1395                1400                1405
Lys Asn Ala Gly Trp Gly Ser Tyr Ile Thr Lys Ala Asn Leu Thr
    1410                1415                1420

Arg Thr Leu Thr Gly Gln Gln Lys Leu Tyr Val Val Met Val Ala Gly
1425                1430                1435                1440

Thr Pro Asn Asn Leu Pro Tyr Ile Gly Asn Phe Asp Trp Phe Lys Phe
                1445                1450                1455

Asp Tyr Glu Lys Ile Arg Ser Asp Tyr Ala Lys Leu Glu Leu Glu Ser
            1460                1465                1470

Tyr Asp Glu Trp Thr Thr Asp Val Asn Thr Gly Asn Asn Thr Pro
        1475                1480                1485

Leu Lys Thr Glu Ala Gly Lys Gly Val Gly Gln Gln Val Ala Asn
    1490                1495                1500

Thr Phe Asn Gly Ala Trp Leu Ala Tyr Lys Arg Met Asp Phe Gly Ser
1505                1510                1515                1520

Glu Gly Val Asp Lys Phe Ser Ile Glu Tyr Ala Gly Asn Ser Thr Asn
                1525                1530                1535

Thr Phe Asn Asn Ser Ala Val Glu Val Arg Leu Gly Ser Pro Thr Gly
                1540                1545                1550

Thr Leu Val Gly Thr Val Ala Thr Pro Pro Thr Ala Ala Ala Trp Gly
            1555                1560                1565

Thr Tyr Ala Thr Val Ser Gly Ser Leu Thr Gln Lys Leu Thr Gly Leu
        1570                1575                1580

Gln Asp Val Tyr Leu Val Phe Thr Gly Ser Ala Ala Asn Gly Glu Thr
1585                1590                1595                1600

Gly Lys Lys Tyr Ile Gly Asn Phe Asp Asn Ala Ser Phe Ser Leu Ser
                1605                1610                1615

Val Gln Glu Pro Glu Pro Glu Gln Pro Gln Pro Glu Gln Glu
            1620                1625                1630

Gln Ile Thr Val Gln Phe Glu Ser Lys Thr Glu Trp Asn Thr Ala Leu
        1635                1640                1645

Asn Thr Phe Asn Asn Gln Ala Met Lys Ile Glu Asn Asn Asn Gly Gly
1650                1655                1660

Gln Thr Val Gly Asn Thr Tyr Thr Gly Ala Trp Leu Gly Phe Lys Asp
1665                1670                1675                1680

Val Asp Phe Gly Ser Glu Lys Gly Lys Asn Gln Val Ser Ile Val Tyr
                1685                1690                1695

Asp Ala Pro Thr Asn Arg Val Pro Ala Asp Val Lys Ala Glu Ile Arg
            1700                1705                1710

Leu Gly Ser Pro Thr Gly Thr Leu Val Gly Thr Val Ala Ile Pro Asn
    1715                1720                1725

Thr Gly Ser Thr Trp Gly Gln Tyr Asn Thr Ala Thr Ala Asp Leu Asn
        1730                1735                1740

Thr Thr Ile Lys Gly Lys Gln Asp Leu Tyr Ile Val Met Thr Gly Ser
1745                1750                1755                1760

Thr Thr Ser Ser Leu Leu Tyr Val Gly Asn Tyr Asp Ser Leu Thr Phe
                1765                1770                1775

Gly Tyr Lys Pro Val Arg Ser Asp Tyr Ala Lys Leu Glu Leu Glu Ser
            1780                1785                1790

Tyr Asp Glu Trp Thr Thr Ala Val Asn Pro Leu Asn Ser Asn Thr Pro
        1795                1800                1805

Leu Lys Thr Glu Ala Gly Lys Gly Gly Ala Gly Lys Gln Val Ala Asn
    1810                1815                1820
```

```
Thr Phe Asn Gly Ala Trp Leu Ala Tyr Lys Arg Met Asp Phe Gly Thr
1825                1830                1835                1840

Glu Gly Val Asn Thr Phe Ala Val Glu Tyr Ala Gly Asn Thr Thr Asn
            1845                1850                1855

Cys Phe Thr Asn Ser Ala Val Glu Ile Arg Leu Gly Ser Pro Thr Gly
        1860                1865                1870

Thr Leu Val Gly Lys Ile Ser Thr Pro Pro Lys Ala Gly Asn Trp Thr
    1875                1880                1885

Thr Tyr Asp Thr Val Ser Gly Thr Leu Thr Gln Lys Leu Thr Gly Ile
1890                1895                1900

Gln Asp Val Tyr Leu Val Leu Thr Gly Ser Ala Gly Asn Gly Glu Thr
1905                1910                1915                1920

Gly Lys Lys Tyr Ile Gly Asn Phe Asp Asn Ala Ala Phe Ser Leu Lys
            1925                1930                1935

Val

<210> SEQ ID NO 34
<211> LENGTH: 751
<212> TYPE: PRT
<213> ORGANISM: Chitinophaga pinensis

<400> SEQUENCE: 34

Met Lys Arg Asn Arg Tyr Leu Ile Ser Thr Ile Leu Val Leu Gly
  1               5                  10                  15

Ile Thr Thr Ser Ala Leu Ala Gln Val Gly Ala Gly Ser Thr Trp Lys
            20                  25                  30

Pro Thr Gly Asn Leu Thr Tyr Val Asp Pro Thr Ile Gly Ser Val Gly
        35                  40                  45

Leu Ile Leu Glu Pro Thr Arg Pro Ala Met Tyr Leu Pro Asn Ser Met
 50                  55                  60

Val Arg Val Phe Pro Ser Arg Lys Asp Gln Leu Glu Asp Gln Ile Asn
 65                  70                  75                  80

Phe Phe Pro Leu Thr Ile Ala Ser His Arg Gln Gln Ser Leu Phe Gly
                85                  90                  95

Phe Met Pro Leu Ser Gly Glu Val Asn Thr Glu Asn Trp Lys Arg Ser
            100                 105                 110

Arg Val Tyr Asp Arg Glu Lys Ile Ser Pro Cys Lys Tyr Ser Ala Tyr
        115                 120                 125

Leu Asp Asp Thr Asp Glu Ile Thr Phe Ala Pro Ala Ala His Ser Gly
130                 135                 140

Tyr Phe Glu Ile Asp Phe Thr Gly Asn Thr Pro His Tyr Leu Arg Leu
145                 150                 155                 160

Ser Ile Leu Asn Arg Asp Gly Asp Leu Thr Val Asp Gly Lys Arg Ala
                165                 170                 175

Ile Ser Gly Arg Glu Thr Phe Asn Gly Met Ser Ala Tyr Phe Tyr Ala
            180                 185                 190

Glu Val Asn Ala Asp Ile Ile Gly Thr Glu Tyr Arg Gly Asp Lys Lys
        195                 200                 205

Gln His Leu Phe Ala Ala Leu Gly Asn Asn Pro Gln Lys Ile Ala Val
    210                 215                 220

Arg Tyr Gly Val Ser Phe Ile Ser Val Glu Gln Ala Lys Ala Asn Leu
225                 230                 235                 240

Lys Lys Glu Ile Pro Leu Trp Thr Ile Ser Pro Leu Val Ile Lys Gly
                245                 250                 255
```

```
Ala Ala Ala Trp Asn Lys Val Leu Gly Gln Ile Asn Val Lys Gly Gly
            260                 265                 270

Thr Asp Ala Gln Lys Arg Val Phe Tyr Thr Ser Leu Tyr Arg Ala Tyr
            275                 280                 285

Glu Arg Met Val Asn Ile Asn Glu Tyr Gly Tyr Tyr Ser Ala Tyr
            290                 295                 300

Asp His Lys Val His Thr Ser Asp Lys Pro Phe Tyr Val Asp Asn Trp
305                 310                 315                 320

Leu Trp Asp Thr Tyr Ile Ala Leu Glu Pro Leu Gln Thr Leu Leu Asn
                325                 330                 335

Pro Glu Met Glu Ala Asp Lys Ile Arg Ser Tyr Val Asp Met Tyr Glu
            340                 345                 350

Gln Ser Gly Trp Met Pro Ser Phe Ala Val Ala His Gly Asp Met Pro
            355                 360                 365

Cys Met Thr Gly Asn His Ala Ala Ala Trp Met Ala Asp Ala Trp Phe
            370                 375                 380

Lys Gly Val Arg Asn Phe Asp Ile Ala Lys Ala Tyr Glu Gly Leu Lys
385                 390                 395                 400

Lys Asn Ser Leu Gln Ala Thr Leu Leu Pro Trp Arg Asn Gly Pro Ala
                405                 410                 415

Thr Ser Leu Asp Thr Phe Tyr Thr Glu His Gly Tyr Met Pro Ser Leu
            420                 425                 430

Lys Pro Asp Glu Lys Glu Thr Val Lys Glu Val Asp Asp Phe Glu Arg
            435                 440                 445

Arg Gln Ala Val Ala Val Thr Leu Glu Asn Ser Tyr Asp Asp Trp Cys
            450                 455                 460

Ile Ala Gln Leu Ala Lys Ala Gly His Pro Glu Asp Ile Pro Leu
465                 470                 475                 480

Phe Leu Lys Arg Ala Thr Asn Tyr Lys Asn Val Tyr Arg Ala Asp Lys
                485                 490                 495

Gly Phe Met Trp Pro Lys Asp Ala Asp Gly Asn Trp Ile Glu Pro Phe
            500                 505                 510

Asp Pro Lys Phe Ser Gly Gly Gln Gly Gly Arg Asp Tyr Phe Thr Glu
            515                 520                 525

Asn Asn Ala Tyr Thr Tyr Asn Trp Asp Val Lys His Asp Leu Thr Gly
            530                 535                 540

Leu Phe Asp Leu Met Gly Gly Lys Ala Lys Ala Glu Glu Lys Leu Asp
545                 550                 555                 560

Gln Leu Phe Arg Glu Asn Leu Gly Arg Ser Lys Tyr Asn Leu Trp Tyr
                565                 570                 575

Thr Phe Pro Asp Ala Thr Gly Met Val Gly Gln Phe Val Met Gly Asn
            580                 585                 590

Glu Pro Ser Phe His Ile Pro Tyr Leu Tyr Asn Tyr Thr Gly Ala Pro
            595                 600                 605

Trp Lys Thr Gln Lys Arg Ile Arg Met Leu Leu Asp Thr Trp Tyr Thr
            610                 615                 620

Asp Asn Leu Phe Gly Ile Pro Gly Asp Glu Asp Gly Gly Met Thr
625                 630                 635                 640

Ala Phe Val Val Phe Ser Met Met Gly Phe Cys Pro Val Thr Pro Gly
                645                 650                 655

Ile Pro Val Tyr Asn Ile Gly Ser Pro Val Phe Ser Glu Ile Thr Ile
            660                 665                 670
```

-continued

```
Lys Leu Phe Ser Gly Lys Thr Phe Thr Ile Ser Ala Pro Gly Ser Ser
            675                 680                 685

Ala Thr Lys Lys Tyr Ile Gln Arg Ala Thr Leu Asn Gly Gln Pro Leu
        690                 695                 700

Asn Val Pro Trp Phe Thr His Glu Asp Leu Leu Lys Gly Gly Val Leu
705                 710                 715                 720

Glu Leu Val Met Ser Glu Ser Pro Asn Lys Glu Trp Gly Thr Gly Ala
                725                 730                 735

Gln Ala Ala Pro Pro Ser Ser Leu Asn Tyr Ser Pro Ala Gly Lys
            740                 745                 750

<210> SEQ ID NO 35
<211> LENGTH: 728
<212> TYPE: PRT
<213> ORGANISM: Pedobacter heparinus

<400> SEQUENCE: 35

Met Lys Asn Ser Ile Lys Leu Met Leu Leu Cys Leu Leu Ser Gln
 1               5                  10                  15

Ser Arg Leu Lys Ala Gln Glu Val Thr Ser Asn Leu Gln Tyr Val Asp
                20                  25                  30

Pro Thr Ile Gly Ala Val Gly His Ile Leu Glu Pro Thr Arg Pro Thr
            35                  40                  45

Met His Leu Pro Asn Ser Met Val Arg Val Tyr Pro Val Arg Lys Asp
        50                  55                  60

Gln Leu Asp Asp Gln Ile Ser Tyr Phe Pro Leu Asn Met Tyr Ser His
65                  70                  75                  80

Arg Ile Gly Asn Val Phe Ala Leu Met Pro Tyr Asn Gly Val Val Asn
                85                  90                  95

Glu Lys Ser Trp Lys Gln Arg Phe Thr Tyr Asp Leu Glu Lys Thr Ala
            100                 105                 110

Pro His Tyr Tyr Thr Ala Val Leu Glu Glu Ser Gly Ile Lys Val Glu
        115                 120                 125

Phe Ser Pro Ser Glu Arg Ser Gly Tyr Tyr Arg Phe Lys Phe Pro Ser
130                 135                 140

Ala Ser Ala Asn Trp Leu Arg Leu Gly Val Val Asn Glu Thr Gly Glu
145                 150                 155                 160

Leu Lys Val Ser Gly Lys Arg Ile Leu Ser Gly Ser Glu Asp Phe Gln
                165                 170                 175

Gly Met Lys Ala Tyr Phe Tyr Gly Glu Leu Asn Ala Asp Val Thr Glu
            180                 185                 190

Ser Lys Tyr Lys Asp Gly Thr Gly Asn Lys Asn Leu Phe Leu Lys Val
        195                 200                 205

Gly Asn Ser His Gly Val Glu Phe Arg Tyr Gly Ile Ser Tyr Ile Ser
210                 215                 220

Val Glu Gln Ala Lys Ile Asn Leu Glu Lys Glu Ile Pro Asn Trp Gly
225                 230                 235                 240

Phe Glu Lys Val Lys Ser Thr Ala Lys Gln Val Trp Glu Glu Ala Leu
                245                 250                 255

Asn Gln Ile Thr Val Glu Gly Gly Thr Leu Ala Tyr Lys Arg Ser Phe
            260                 265                 270

Tyr Thr Ala Leu Tyr Arg Thr Tyr Glu Arg Met Val Asn Ile Asn Glu
        275                 280                 285

Tyr Gly Arg Tyr Tyr Ser Ala Tyr Asp His Lys Val Ser Asp Ser
            290                 295                 300
```

```
Arg Pro Phe Tyr Val Asp Asn Trp Ile Trp Asp Ser Tyr Leu Ala His
305                 310                 315                 320

Gln Pro Leu His Met Ile Leu Asn Pro Asp Arg Gln Ala Asp Met Ile
            325                 330                 335

Ser Ser Tyr Val Asn Met Tyr Glu Gln Ser Gly Trp Met Pro Ser Phe
            340                 345                 350

Ala Leu Val Phe Gly Asp Asn Pro Cys Met Thr Gly Asn His Ala Ala
            355                 360                 365

Ala Trp Ile Thr Asp Ala Trp Phe Lys Gly Ile Arg Asn Phe Asn Val
370                 375                 380

Glu Lys Ala Tyr Ala Gly Leu Lys Lys Asn Ser Leu Glu Ala Thr Leu
385                 390                 395                 400

Leu Pro Trp Arg Asn Gly Pro Ala Ile Gly Leu Asp Ser Phe Tyr Ala
                405                 410                 415

Glu Lys Gly Tyr Phe Pro Ala Leu Arg Pro Gly Glu Lys Glu Ser Val
                420                 425                 430

Asn Glu Val His Asp Phe Glu Lys Arg Gln Ser Val Ala Val Thr Leu
            435                 440                 445

Gln Gln Ser Tyr Asp Asp Trp Cys Ile Ser Lys Leu Ala Gly Thr Leu
450                 455                 460

Gly Lys Ala Ala Asp Ser Lys Leu Phe Leu Ala Lys Ala Glu Asn Tyr
465                 470                 475                 480

Lys Asn Val Phe Arg Glu Ser Lys Gly Phe Met Trp Pro Lys Asp Asp
                485                 490                 495

Lys Gly Gln Trp Ile Glu Pro Phe Asp Pro Lys Phe Ser Gly Gly Gln
                500                 505                 510

Gly Gly Arg Glu Tyr Phe Thr Glu Asn Asn Ala Tyr Thr Tyr Asn Trp
            515                 520                 525

Asp Val Lys His Asp Leu Glu Gly Leu Phe Lys Leu Met Gly Gly Lys
            530                 535                 540

Gln Ala Ala Glu Asn Lys Leu Asp Asn Leu Phe Arg Glu Asp Leu Gly
545                 550                 555                 560

Arg Ser Lys Tyr Val Leu Trp Asn Thr Phe Pro Asp Ala Thr Gly Leu
                565                 570                 575

Val Gly Gln Phe Val Met Gly Asn Glu Pro Ser Phe His Ile Pro Tyr
            580                 585                 590

Leu Tyr Asn Asp Leu Gly Ser Pro Trp Lys Thr Gln Lys Arg Ile Arg
            595                 600                 605

Met Leu Met Asp Thr Trp Phe Thr Asp Asn Leu Phe Ser Ile Pro Gly
            610                 615                 620

Asp Glu Asp Gly Gly Met Ser Ala Phe Val Val Phe Ser Met Met
625                 630                 635                 640

Gly Phe Tyr Pro Val Thr Pro Gly Ile Pro Val Tyr His Ile Gly Ser
                645                 650                 655

Pro Val Phe Asn Lys Ile Ser Leu Leu Lys Asn Gly Lys Thr Phe
                660                 665                 670

Thr Val Val Ala Arg Asn Asn Ser Ser Thr Ala Lys Tyr Ile Gln Ser
            675                 680                 685

Ala Lys Leu Asn Gly Val Asn Trp Asp Lys His Ser Phe Asn His Ala
            690                 695                 700

Asp Ile Leu Lys Gly Gly Asn Leu Glu Leu Val Met Gly Glu Thr Pro
705                 710                 715                 720
```

-continued

Asn Lys Gln Trp Gly Lys Thr Lys
                    725

<210> SEQ ID NO 36
<211> LENGTH: 2234
<212> TYPE: PRT
<213> ORGANISM: Streptomyces

<400> SEQUENCE: 36

Met Leu Val Met Pro Asp Arg Ser Lys Arg Pro Ile Arg Ser Ser
 1               5                  10                  15

Ser Pro Arg Ala Ala Leu Arg Ala Thr Val Ala Ala Val Leu Ala Gly
            20                  25                  30

Ala Leu Gly Leu Ala Ala Leu Thr Gly Gly Thr Ala Val Ala Val
            35                  40                  45

Pro Val Thr Lys Ala Ser Pro Ala Gly Glu Arg Ser Gly Gly Thr
     50                  55                  60

Asp Tyr Thr Lys Leu Val Asp Pro Phe Val Ser Thr Ala Gly Asp Tyr
 65                  70                  75                  80

Gly Asn Asp Leu Pro Gly Ala Gln Ala Pro His Ser Leu Ala Lys Val
                85                  90                  95

Asn Pro Met Thr Thr Pro Gly Arg Asn His Ser Gly Tyr Asp Tyr Asn
            100                 105                 110

Glu Asp His Ile Ala Gly Phe Thr Ala Thr Asn Leu Asp Gly Val Gly
            115                 120                 125

Gly Ser Gly Gly Gly Gly Asp Leu Leu Val Val Pro Thr Ser Gln Gln
        130                 135                 140

Tyr Asp Lys Arg Pro Ala Thr Ser Thr Tyr Ala His Pro Tyr Ser His
145                 150                 155                 160

Asp Asp Glu Ser Ala Thr Pro Gly Ser Tyr Arg Val Gly Leu Gly Ser
                165                 170                 175

Pro Ser Gly Thr Ile Asp Ala Glu Met Thr Ala Thr Arg Thr Ala
            180                 185                 190

Leu Glu Arg Tyr Ala Phe Pro Ala Lys Ala Arg Pro Gln Leu Val Leu
            195                 200                 205

Asp Leu Ala Asn Asn Phe Thr Ser Arg Thr Arg Ala Thr Leu Asp Ala
        210                 215                 220

Thr Arg Leu Lys Asp Gly Thr Thr Ala Ile Ser Gly Leu Val Ala Gly
225                 230                 235                 240

Ser Phe Asn Gly Ala Ser Tyr Arg Leu Tyr Tyr Tyr Ala Thr Thr Asn
                245                 250                 255

Val Pro Val Thr Ser Leu Arg Thr Trp Gly Asp Asp Gly Ala Leu Gly
            260                 265                 270

Asp Ala Thr Ala Arg Asp Gly Thr Asp Thr Gly Ala Val Leu Gly Phe
        275                 280                 285

Asp Pro Ala Asp Gly Asp Val Glu Leu Arg Val Thr Leu Ser Pro
    290                 295                 300

Ile Ser Ala Glu Gln Ala Ala Thr Asp Gln His Glu Glu Val Ala Gly
305                 310                 315                 320

Arg Thr Phe Glu Glu Val Arg Ala Gln Thr Lys Ala Asp Trp Asn Arg
                325                 330                 335

Thr Leu Gly Ala Val Ala Val Lys Ala Ser Lys Lys Ala Asp Pro Asp
            340                 345                 350

Ser Thr Leu Thr Lys Gln Phe Tyr Thr His Leu Tyr Arg Met Tyr Ala
        355                 360                 365

```
Leu Pro Val Asn Ala Thr Ser Thr Ser Gly Thr Tyr Arg Gly Val Asp
            370                 375                 380

Gly Ala Val His Lys Ala Asn Gly Phe Thr Tyr Tyr Asp Gly Trp Ser
385                 390                 395                 400

Thr Trp Asp Asp Phe Arg Lys Tyr Ser Val Ala Ala Tyr Ile Asp Pro
                405                 410                 415

Ala Thr Tyr Arg Asp Met Val Gln Ser Ala Val Ile Leu Phe Ala Asp
                420                 425                 430

Ala His Ala Ala Gly Lys Ser Leu Gly Ser Leu Thr His Ser Val Pro
            435                 440                 445

Thr Val Arg Trp Glu Arg Ser Ala Val Val Ile Ala Asp Ala Leu Ser
450                 455                 460

Lys Gly Phe Lys Asp Phe Asp Arg Leu Asp Glu Ala Tyr Pro Ala Leu
465                 470                 475                 480

Lys Ser Tyr Thr Gly Tyr Tyr Thr Gly Thr Gln Leu Arg Gln Gly Tyr
                485                 490                 495

Ile Ala Gly Asp Pro Gly Thr Thr Val Gln Arg Gly Tyr Asp Gln Trp
                500                 505                 510

Ala Leu Ser Val Val Ala Asp Ala Leu Gly Glu Asp Ala Glu Ala Lys
            515                 520                 525

Lys Leu Arg Glu Gln Ala Thr Met Ala Thr Asp Asn Leu Val Lys Pro
530                 535                 540

Asp Ala Trp Thr Ala Ala Asp Gly Thr Ala Val Gly Leu Leu Thr Pro
545                 550                 555                 560

Arg Asp Gly Glu Gly Asp Trp Gln Gly Val Asp Tyr Glu Lys Phe Glu
                565                 570                 575

Glu Ala Arg Leu Tyr Gln Gly Thr Leu Trp Gln Tyr His Trp Tyr Asp
                580                 585                 590

Ala Tyr Asp Met Gly Gly Leu Val Glu Ala Met Gly Gly Glu Gln Ala
                595                 600                 605

Gly Arg Ala Ala Ile Arg His Met Phe Gly Glu Asp Ser Asp Ala Asp
610                 615                 620

Asp Gly Ser Thr Met Leu His Ser Asn Ala Asn Glu Ile Asp Leu Gln
625                 630                 635                 640

Ala Pro Tyr Leu Phe Asn Tyr Val Gly Glu Pro Ser Leu Thr Gln Lys
                645                 650                 655

Trp Val Arg Ala Ile Tyr Thr Gly Glu Thr Trp Asn Arg Tyr Ile Ala
                660                 665                 670

Thr Gly Ser Thr Asn Glu Ala Pro Ser Ser Gly Gly Glu Phe Arg Pro
            675                 680                 685

Pro Val Lys Thr Lys Ala Tyr Glu Leu Ala Pro Asp Gly Phe Leu Pro
            690                 695                 700

Thr Met Asp Asn Asp Ala Gly Thr Met Ser Thr Met Phe Val Ala Ala
705                 710                 715                 720

Ala Leu Gly Leu Phe Pro Val Thr Ala Gly Ser Ser Gln Phe Gln Ile
                725                 730                 735

Gly Ser Pro Phe Phe Asp Ser Thr Thr Ile Thr Tyr Pro Asn Gly Ala
                740                 745                 750

Glu Phe Thr Val Glu Ala Asp Gly Val Ser Pro Lys Asn Tyr Tyr Val
            755                 760                 765

Thr Val Asp Ala Ser Val Glu Leu Arg Leu Ser Gly Arg Ala Ser Phe
770                 775                 780
```

```
Ala Ala Arg Lys Gly Thr Ser Leu Thr Arg Thr Gly Ala Ala Ser Val
785                 790                 795                 800

Thr Gly Leu Pro Asp Gly Val Thr Ala Asp Leu Arg Val Thr Gly Lys
            805                 810                 815

Arg Thr Ala Ser Leu Arg Leu Thr Gly Thr Thr Arg Thr Asp Ala Arg
        820                 825                 830

Phe Gly Ile Thr Phe Arg Asp Arg Ala Phe Pro His Gly Ile Pro Ala
    835                 840                 845

Ser Thr Val Thr Gly Thr Gly Val Ser Val Thr Asp Pro Leu Ile Val
850                 855                 860

Ser Ala Ala Val His Arg Gly Ser Leu Ala Ala Leu Val Asp Glu
865                 870                 875                 880

Ala Ser Leu Val Arg Glu Gly Asn Tyr Ser Asp Gly Ser Tyr Gly Ile
            885                 890                 895

Phe Arg Thr Ala Leu Glu Arg Ala Arg Thr Val Leu Ala Asp Ser Ala
        900                 905                 910

Ser Pro Thr Gly Thr Leu Met Ala Ala His Asp Ala Leu Arg Ser Ala
    915                 920                 925

Val Asp Ala Leu Thr Leu Asp Glu Gly Tyr Ala Val Leu Gln Ala
930                 935                 940

Glu Asp Pro Asp Arg Met Glu Gly Pro Ser Leu Val Lys Glu Ala Tyr
945                 950                 955                 960

Tyr Ser Asp Gly Asp Leu Gly Gly Val Thr Glu Gly Ala Trp Glu Gln
            965                 970                 975

Tyr Thr Asp Leu Asp Phe Gly Gly Val Pro Pro Arg Ser Val Ser Val
        980                 985                 990

Arg Tyr Ala Asn Ser Gln Ala Ala Ala Glu Pro Ser Ser Val Asp
    995                 1000                1005

Ile His Ala Gly Asp Ala Asp Gly Pro Val Val Ala Thr Val Ser Leu
1010                1015                1020

Pro Gly Thr Gly Gly Trp Gln Tyr Tyr Thr Thr Val Arg Ala Ala Val
1025                1030                1035                1040

Ser Asp Pro Gln Ala Leu Leu Lys Ala Ser Ser Ala Thr Phe Val Phe
            1045                1050                1055

His Ala Pro Ser Gly Arg Gln Trp Val Ser Asn Phe Asp Trp Tyr Gln
        1060                1065                1070

Phe Ser Pro Glu Ala Ala Pro Ser Ser Ser Pro Ile Thr Thr Leu Ala
    1075                1080                1085

Thr Leu Thr Thr Ala Asn Thr Thr Ser Thr Gly Asp Gly Ala Leu Pro
1090                1095                1100

Leu Lys Val Ser Gly Gly Val Phe Glu Asn Val Thr Asn Gly Ala Trp
1105                1110                1115                1120

Ala Glu Trp Arg Asp Thr Asp Leu Gly Asp Gly Ala Asp Thr Val Thr
            1125                1130                1135

Val Ser Tyr Asp Lys Pro Arg Arg Ala Ala Ser Asp Ser His Ile
        1140                1145                1150

Glu Leu Arg Pro Gly Ala Lys Asp Gly Pro Thr Ala Val Thr Val Pro
    1155                1160                1165

Leu Asp Tyr Thr Gly Ser Gly Trp Gly Thr Val Ala Ser Thr Ser Val
1170                1175                1180

Arg Leu Asp Pro Asp Val Phe Glu Gly Thr Gln Asp Val Tyr Ala Val
1185                1190                1195                1200

Phe Val Ser Ser Thr Gln Thr Asp Ala Gln Pro Tyr Val Ala Asn Val
```

-continued

```
                1205                1210                1215

His Ser Leu Thr Leu Thr Arg Gln Ala Asp Ala Pro Val Val Phe Asp
            1220                1225                1230

Ala Thr Ala Phe Glu Gly Ser Ser Gly Gly Leu Lys Ser Glu Pro
            1235                1240            1245

Ala Thr Trp Ser Gly Ala Gly Ser Ala Thr Ser Leu Gly Gly Thr Tyr
            1250                1255                1260

Asp Gly Ala Trp Leu Asp Tyr Gly Asp Val Asp Phe Gly Asp Ser Pro
1265                1270                1275                1280

Lys Asn Thr Val Thr Leu Thr Tyr Val Asn Asn Ser Ala Arg Cys Gly
                1285                1290                1295

Thr Gly Ser Ala Val Gln Leu Tyr Leu Asp Ser Phe Asp Pro Asp Ala
            1300                1305                1310

Pro Gly Thr Pro Tyr Ala Thr Val Pro Leu Pro Val Thr Gly Ser Ser
            1315                1320                1325

Trp Ser Ser Gly Gly Thr Thr Ser Leu Thr Leu Pro Glu Ala Ile Thr
            1330                1335                1340

Gly Thr His Ala Val His Leu Arg Leu Thr Asp Ala Asp Ser Ser
1345                1350                1355                1360

His Pro Tyr Val Ala Asn Leu Gly Gln Val Thr Phe Asp Arg Val Glu
                1365                1370                1375

Ala Pro Ala Gln Thr Asp Leu Ser Ala Leu Arg Lys Ala Ile Glu Gln
            1380                1385                1390

Tyr Glu Gly Leu Ser Glu Asp Ala Asp Arg Tyr Gly Thr Ile Asp Phe
            1395                1400                1405

Gly Val Phe Arg Arg Glu Leu Thr Ala Ala Arg Asp Leu Leu Gly Thr
            1410                1415                1420

Glu Asp Ala Thr Gln Leu Glu Asp Leu Arg Thr Arg Ser Leu Thr
1425                1430                1435                1440

Leu Ala Ala Asn Gln Leu Val Pro Leu Pro Arg Leu Arg Leu Glu Ser
                1445                1450                1455

Leu Val Ala Thr Ala Ser Ala Leu Ala Asp Glu Arg Tyr Thr Asp Ala
            1460                1465                1470

Ser Trp Lys Ala Phe Thr Thr Ala Leu Thr Ala Ala Lys Thr Ala Val
            1475                1480                1485

Ala Asp Glu Thr Ala Thr Asp Arg Thr Leu Thr Glu Arg Tyr Ala Ala
            1490                1495                1500

Leu Asp Arg Ala Arg Ser Ser Leu Thr Thr Lys Arg Arg Thr Val Pro
1505                1510                1515                1520

Ala Ala Pro Gly Ala Val Ser Ala Ala Pro Ser Gly Thr Ser Val Gln
                1525                1530                1535

Val Thr Trp Ser Ala Pro Glu Asp Gly Gly Ser Pro Val Thr Gly
            1540                1545                1550

Tyr Glu Ile Thr Leu Ser Gly Gly Arg Gln Val Glu Ile Ala Asp Pro
            1555                1560                1565

Asp Ser Arg Ser Thr Val Phe Thr Arg Leu Lys Asp Gly Thr Ser Tyr
            1570                1575                1580

Thr Ala Arg Val Arg Ala Val Asn Ala Leu Gly Asp Ser Pro Trp Ser
1585                1590                1595                1600

Ala Arg Thr Gln Pro Ala Val Thr Gly Asp Asn Arg Pro Gln Ala Pro
                1605                1610                1615

Thr Val Thr Gly Val Val Thr Asp Gly Glu Arg Val Arg Val Asn Trp
            1620                1625                1630
```

-continued

Arg Pro Ala Gly Asp Gly Gly Phe Pro Val Val Gly Tyr Thr Val Ala
                1635                1640                1645

Leu Asp Asp Gly Thr Thr Ala His Val Pro Gly Thr Thr Ser Thr Ala
    1650                1655                1660

Val Leu Thr Ala Ala Gly Gly Ala Lys Ala His Thr Ala Thr Val Thr
1665                1670                1675                1680

Ala Val Thr Arg Ala Gly Ser Ser Asp Gly Ser Gly Ala Thr Val Ser
                1685                1690                1695

Thr Ala Pro Ala Thr Ser Thr Thr Ser Ala Thr Ser Ala Gly Asp Pro
                1700                1705                1710

Ala Glu Tyr Glu Pro Ser Pro Phe Pro Gly Asp Thr Leu Asp Ala Thr
                1715                1720                1725

Tyr Ala Ser Asp Ala Trp Pro Glu Thr Gly Asp Gly Ser Asp Trp Phe
                1730                1735                1740

Thr His Leu Leu Ser Gly Phe Asp Asp Leu Gly Pro Ala Thr Leu Gly
1745                1750                1755                1760

Ala Asn Ser Glu Val Pro Ala Gly Thr Pro Leu Gly Ala Glu Asn Asp
                1765                1770                1775

Arg Ile Thr Val Arg Val Asn Asn Ala Ala Thr Gln Gln Gln Val Asp
                1780                1785                1790

Arg Ala Glu Val Asp Ala Ser Asn Ser Ala Thr Val Thr Met Ala Asp
                1795                1800                1805

Gly Leu Gly Ser Arg Leu Gly Pro Leu Tyr Gly Glu Ala Leu Lys Glu
                1810                1815                1820

Gly Arg Leu Pro Lys Thr Ser Ala Leu Phe Ser Arg Val Asn Glu Asn
1825                1830                1835                1840

Leu Asp Thr His Asp Ala Ala Lys Asn His Tyr Gln Tyr Leu Arg Pro
                1845                1850                1855

Tyr Val Arg Leu Gly Phe Ala Gly Asp Gly Gly Ala Val Tyr Glu Ser
                1860                1865                1870

Gln Asp Ser Ser Tyr Ser Gly Leu Ala Gly Gln Gly Ser Tyr Pro Ser
                1875                1880                1885

Gly His Thr Tyr Gly Gly Tyr Glu Ala Gly Thr Ile Leu Ala Thr Leu
                1890                1895                1900

Leu Pro Asp Leu Ala Pro Ser Ile Leu Ala Arg Thr Ser Glu Tyr Gly
1905                1910                1915                1920

Asp Asn Arg Ile Val Leu Gly Phe His Tyr Pro Leu Asp Val Met Gly
                1925                1930                1935

Gly Arg Ile Thr Ala Gln Ala Thr Val Ala His Arg Trp Ala Asp Pro
                1940                1945                1950

Glu Phe Ala Lys Leu Leu Gly Gln Ala His Thr Glu Ile Glu Asn Val
                1955                1960                1965

Leu Leu Ala Arg Cys Glu Glu Glu Gly Tyr Gly Asp Thr Leu Thr Ala
1970                1975                1980

Cys Ala Gly Asp Pro Tyr Ala Gly Leu Ser Thr Ala Gln Gln Val Asp
1985                1990                1995                2000

Arg Tyr Thr Gln Arg Leu Thr Tyr Gly Phe Ser Arg Thr Gly Glu Ala
                2005                2010                2015

Gly Gln Ala Leu Asp Ala Pro Ser Asp Ala Ala Ala Leu Leu Ile Thr
                2020                2025                2030

Ala Phe Pro Asp Leu Thr Ala Glu Gln Arg Thr Gln Val Leu Glu Gln
                2035                2040                2045

-continued

Thr Ala Thr Asp Ser Gly Tyr Pro Leu Asp Leu Thr Gly Ser Gly Gly
    2050                2055                2060

Pro Gly Trp Gln Arg Ile Asn Leu Ala Ala Met Ala Ala Asp Val
2065            2070                2075                2080

Val Val Asn Ala Asp Gly Ser Val Thr Val Thr Asn Phe Pro Asp Ala
            2085                2090                2095

Thr Ala Ala Ser Ala Ala Glu Ala Val Ala Ile Thr Val Gly Gly Val
                2100                2105                2110

Ala Leu Asp Gly Phe Asp Pro Asp Val Ser Thr Tyr Val Asp Trp
        2115                2120                2125

Pro Arg Asn Gly Gly Arg Ile Pro Ala Val Gly Ala Val Thr Ala Ala
        2130                2135                2140

Ser Gly Ala Arg Val Lys Val Thr Ser Gly Ser Ser Thr Val Ser Ser
2145                2150                2155                2160

Ser Gln Arg Gly Phe Ser Thr Arg Thr Leu Thr Val Thr Ser Ala Asp
                2165                2170                2175

Gly Glu Phe Thr Arg Thr Tyr Thr Val Gly Phe Arg Pro Val Glu Gln
                2180                2185                2190

His Pro His Arg Pro Gly Ala Leu Arg Asp Thr Gly Gly Gly Gly Thr
        2195                2200                2205

Ala Gly Gly Ser Gly Gly Gly Gly Asp Val Gly Gly Leu Trp Ser
    2210                2215                2220

Pro Ala Arg Glu Trp Glu Gln Thr Val Asn
2225                2230

<210> SEQ ID NO 37
<211> LENGTH: 2202
<212> TYPE: PRT
<213> ORGANISM: Streptomyces lividans

<400> SEQUENCE: 37

Met Leu Ala Gly Ala Leu Gly Leu Ala Ala Leu Thr Gly Gly Gly Thr
1               5                   10                  15

Ala Val Ala Val Pro Val Thr Lys Ala Ser Pro Pro Ala Gly Glu Arg
            20                  25                  30

Ser Gly Gly Thr Asp Tyr Thr Lys Leu Val Asp Pro Phe Val Ser Thr
        35                  40                  45

Ala Gly Asp Tyr Gly Asn Asp Leu Pro Gly Ala Gln Ala Pro His Ser
    50                  55                  60

Leu Ala Lys Val Asn Pro Met Thr Thr Pro Gly Arg Asn His Ser Gly
65                  70                  75                  80

Tyr Asp Tyr Asn Glu Asp His Ile Ala Gly Phe Thr Ala Thr Asn Leu
                85                  90                  95

Asp Gly Val Gly Gly Ser Gly Gly Gly Asp Leu Leu Val Val Pro
            100                 105                 110

Thr Ser Gln Gln Tyr Asp Lys Arg Pro Ala Thr Ser Thr Tyr Ala His
        115                 120                 125

Pro Tyr Ser His Asp Asp Glu Ser Ala Thr Pro Gly Ser Tyr Arg Val
    130                 135                 140

Gly Leu Gly Ser Pro Ser Gly Thr Ile Asp Ala Glu Met Thr Ala Thr
145                 150                 155                 160

Thr Arg Thr Ala Leu Glu Arg Tyr Ala Phe Pro Ala Lys Ala Arg Pro
                165                 170                 175

Gln Leu Val Leu Asp Leu Ala Asn Asn Phe Thr Ser Arg Thr Arg Ala
            180                 185                 190

```
Thr Leu Asp Ala Thr Arg Leu Lys Asp Gly Thr Thr Ala Ile Ser Gly
        195                 200                 205

Leu Val Ala Gly Ser Phe Asn Gly Ala Ser Tyr Arg Leu Tyr Tyr Tyr
    210                 215                 220

Ala Thr Thr Asn Val Pro Val Thr Ser Leu Arg Thr Trp Gly Asp Asp
225                 230                 235                 240

Gly Ala Leu Gly Asp Ala Thr Ala Arg Asp Gly Thr Asp Thr Gly Ala
                245                 250                 255

Val Leu Gly Phe Asp Pro Ala Asp Gly Asp Val Glu Leu Arg Val
                260                 265                 270

Thr Leu Ser Pro Ile Ser Ala Glu Gln Ala Ala Thr Asp Gln His Glu
        275                 280                 285

Glu Val Ala Gly Arg Thr Phe Glu Glu Val Arg Ala Gln Thr Lys Ala
    290                 295                 300

Asp Trp Asn Arg Thr Leu Gly Ala Val Ala Val Lys Ala Ser Lys Lys
305                 310                 315                 320

Ala Asp Pro Asp Ser Thr Leu Thr Lys Gln Phe Tyr Thr His Leu Tyr
                325                 330                 335

Arg Met Tyr Ala Leu Pro Val Asn Ala Thr Ser Thr Ser Gly Thr Tyr
                340                 345                 350

Arg Gly Val Asp Gly Ala Val His Lys Ala Asn Gly Phe Thr Tyr Tyr
            355                 360                 365

Asp Gly Trp Ser Thr Trp Asp Asp Phe Arg Lys Tyr Ser Val Ala Ala
        370                 375                 380

Tyr Ile Asp Pro Ala Thr Tyr Arg Asp Met Val Gln Ser Ala Val Ile
385                 390                 395                 400

Leu Phe Ala Asp Ala His Ala Ala Gly Lys Ser Leu Gly Ser Leu Thr
                405                 410                 415

His Ser Val Pro Thr Val Arg Trp Glu Arg Ser Ala Val Val Ile Ala
            420                 425                 430

Asp Ala Leu Ser Lys Gly Phe Lys Asp Phe Asp Arg Leu Asp Glu Ala
        435                 440                 445

Tyr Pro Ala Leu Lys Ser Tyr Thr Gly Tyr Tyr Thr Gly Thr Gln Leu
    450                 455                 460

Arg Gln Gly Tyr Ile Ala Gly Asp Pro Gly Thr Thr Val Gln Arg Gly
465                 470                 475                 480

Tyr Asp Gln Trp Ala Leu Ser Val Val Ala Asp Ala Leu Gly Glu Asp
                485                 490                 495

Ala Glu Ala Lys Lys Leu Arg Glu Gln Ala Thr Met Ala Thr Asp Asn
                500                 505                 510

Leu Val Lys Pro Asp Ala Trp Thr Ala Ala Asp Gly Thr Ala Val Gly
        515                 520                 525

Leu Leu Thr Pro Arg Asp Gly Glu Gly Asp Trp Gln Gly Val Asp Tyr
    530                 535                 540

Glu Lys Phe Glu Glu Ala Arg Leu Tyr Gln Gly Thr Leu Trp Gln Tyr
545                 550                 555                 560

His Trp Tyr Asp Ala Tyr Asp Met Gly Gly Leu Val Glu Ala Met Gly
                565                 570                 575

Gly Glu Gln Ala Gly Arg Ala Ala Ile Arg His Met Phe Gly Glu Asp
            580                 585                 590

Ser Asp Ala Asp Asp Gly Ser Thr Met Leu His Ser Asn Ala Asn Glu
        595                 600                 605
```

```
Ile Asp Leu Gln Ala Pro Tyr Leu Phe Asn Tyr Val Gly Glu Pro Ser
610                 615                 620
Leu Thr Gln Lys Trp Val Arg Ala Ile Tyr Thr Gly Glu Thr Trp Asn
625                 630                 635                 640
Arg Tyr Ile Ala Thr Gly Ser Thr Asn Glu Ala Pro Ser Ser Gly Gly
                645                 650                 655
Glu Phe Arg Pro Pro Val Lys Thr Lys Ala Tyr Glu Leu Ala Pro Asp
            660                 665                 670
Gly Phe Leu Pro Thr Met Asp Asn Asp Ala Gly Thr Met Ser Thr Met
                675                 680                 685
Phe Val Ala Ala Ala Leu Gly Leu Phe Pro Val Thr Ala Gly Ser Ser
690                 695                 700
Gln Phe Gln Ile Gly Ser Pro Phe Phe Asp Ser Thr Thr Ile Thr Tyr
705                 710                 715                 720
Pro Asn Gly Ala Glu Phe Thr Val Glu Ala Asp Gly Val Ser Pro Lys
                725                 730                 735
Asn Tyr Tyr Val Thr Val Asp Ala Ser Val Glu Leu Arg Leu Ser Gly
                740                 745                 750
Arg Ala Ser Phe Ala Ala Arg Lys Gly Thr Ser Leu Thr Arg Thr Gly
            755                 760                 765
Ala Ala Ser Val Thr Gly Leu Pro Asp Gly Val Thr Ala Asp Leu Arg
770                 775                 780
Val Thr Gly Lys Arg Thr Ala Ser Leu Arg Leu Thr Gly Thr Thr Arg
785                 790                 795                 800
Thr Asp Ala Arg Phe Gly Ile Thr Phe Arg Asp Arg Ala Phe Pro His
                805                 810                 815
Gly Ile Pro Ala Ser Thr Val Thr Gly Thr Gly Val Ser Val Thr Asp
                820                 825                 830
Pro Leu Ile Val Ser Ala Ala Val His Arg Gly Ser Leu Ala Ala
            835                 840                 845
Leu Val Asp Glu Ala Ser Leu Val Arg Glu Gly Asn Tyr Ser Asp Gly
            850                 855                 860
Ser Tyr Gly Ile Phe Arg Thr Ala Leu Glu Arg Ala Arg Thr Val Leu
865                 870                 875                 880
Ala Asp Ser Ala Ser Pro Thr Gly Thr Leu Met Ala Ala His Asp Ala
                885                 890                 895
Leu Arg Ser Ala Val Asp Ala Leu Thr Leu Asp Glu Gly Gly Tyr Ala
            900                 905                 910
Val Leu Gln Ala Glu Asp Pro Asp Arg Met Glu Gly Pro Ser Leu Val
            915                 920                 925
Lys Glu Ala Tyr Tyr Ser Asp Gly Asp Leu Gly Gly Ala Trp Glu Gln
            930                 935                 940
Tyr Thr Asp Leu Asp Phe Gly Gly Val Pro Pro Arg Ser Val Ser Val
945                 950                 955                 960
Arg Tyr Ala Asn Ser Gln Ala Ala Ala Glu Pro Ser Ser Val Asp
                965                 970                 975
Ile His Ala Gly Asp Ala Asp Gly Pro Val Val Ala Thr Val Ser Leu
            980                 985                 990
Pro Gly Thr Gly Gly Trp Gln Tyr Tyr Thr Thr Val Arg Ala Ala Val
            995                 1000                1005
Ser Asp Pro Gln Ala Leu Leu Lys Ala Ser Ser Ala Thr Phe Val Phe
1010                1015                1020
His Ala Pro Ser Gly Arg Gln Trp Val Ser Asn Phe Asp Trp Tyr Gln
```

```
1025                1030                1035                1040
Phe Ser Pro Glu Ala Ala Pro Ser Ser Pro Ile Thr Thr Leu Ala
                1045                1050                1055
Thr Leu Thr Thr Ala Asn Thr Thr Ser Thr Gly Asp Gly Ala Leu Pro
                1060                1065                1070
Leu Lys Val Ser Gly Gly Val Phe Glu Asn Val Thr Asn Gly Ala Trp
                1075                1080                1085
Ala Glu Trp Arg Asp Thr Asp Leu Gly Asp Gly Ala Asp Thr Val Thr
                1090                1095                1100
Val Ser Tyr Asp Lys Pro Arg Ser Arg Ala Ala Ser Asp Ser His Ile
1105                1110                1115                1120
Glu Leu Arg Pro Gly Ala Lys Asp Gly Pro Thr Ala Val Thr Val Pro
                1125                1130                1135
Leu Asp Tyr Thr Gly Ser Gly Trp Gly Thr Val Ala Ser Thr Ser Val
                1140                1145                1150
Arg Leu Asp Pro Asp Val Phe Glu Gly Thr Gln Asp Val Tyr Ala Val
                1155                1160                1165
Phe Val Ser Ser Thr Gln Thr Asp Ala Gln Pro Tyr Val Ala Asn Val
                1170                1175                1180
His Ser Leu Thr Leu Thr Arg Gln Ala Asp Ala Pro Val Val Phe Asp
1185                1190                1195                1200
Ala Thr Ala Phe Glu Gly Ser Ser Gly Gly Gly Leu Lys Ser Glu Pro
                1205                1210                1215
Ala Thr Trp Ser Gly Ala Gly Ser Ala Thr Ser Leu Gly Gly Thr Tyr
                1220                1225                1230
Asp Gly Ala Trp Leu Asp Tyr Gly Asp Val Asp Phe Gly Asp Ser Pro
                1235                1240                1245
Lys Asn Thr Val Thr Leu Thr Tyr Val Asn Asn Ser Ala Arg Cys Gly
                1250                1255                1260
Thr Gly Ser Ala Val Gln Leu Tyr Leu Asp Ser Phe Asp Pro Asp Ala
1265                1270                1275                1280
Pro Gly Thr Pro Tyr Ala Thr Val Pro Leu Pro Val Thr Gly Ser Ser
                1285                1290                1295
Trp Ser Ser Gly Gly Thr Thr Ser Leu Thr Leu Pro Glu Ala Ile Thr
                1300                1305                1310
Gly Thr His Ala Val His Leu Arg Leu Thr Thr Asp Ala Asp Ser Ser
                1315                1320                1325
His Pro Tyr Val Ala Asn Leu Gly Gln Val Thr Phe Asp Arg Val Glu
                1330                1335                1340
Ala Pro Ala Gln Thr Asp Leu Ser Ala Leu Arg Lys Ala Ile Glu Gln
1345                1350                1355                1360
Tyr Glu Gly Leu Ser Glu Asp Ala Asp Arg Tyr Gly Thr Ile Asp Phe
                1365                1370                1375
Gly Val Phe Arg Arg Glu Leu Thr Ala Ala Arg Asp Leu Leu Gly Thr
                1380                1385                1390
Glu Asp Ala Thr Gln Leu Glu Ala Asp Leu Arg Thr Arg Ser Leu Thr
                1395                1400                1405
Leu Ala Ala Asn Gln Leu Val Pro Leu Pro Arg Leu Arg Leu Glu Ser
                1410                1415                1420
Leu Val Ala Thr Ala Ser Ala Leu Ala Asp Glu Arg Tyr Thr Asp Ala
1425                1430                1435                1440
Ser Trp Lys Ala Phe Thr Thr Ala Leu Thr Ala Ala Lys Thr Ala Val
                1445                1450                1455
```

```
Ala Asp Glu Thr Ala Thr Asp Arg Thr Leu Thr Glu Arg Tyr Ala Ala
            1460                1465                1470

Leu Asp Arg Ala Arg Ser Ser Leu Thr Thr Lys Arg Thr Val Pro
        1475                1480                1485

Ala Ala Pro Gly Ala Val Ser Ala Ala Pro Ser Gly Thr Ser Val Gln
        1490                1495                1500

Val Thr Trp Ser Ala Pro Glu Asp Asp Gly Gly Ser Pro Val Thr Gly
1505                1510                1515                1520

Tyr Glu Ile Thr Leu Ser Gly Gly Arg Gln Val Glu Ile Ala Asp Pro
            1525                1530                1535

Asp Ser Arg Ser Thr Val Phe Thr Arg Leu Lys Asp Gly Thr Ser Tyr
        1540                1545                1550

Thr Ala Arg Val Arg Ala Val Asn Ala Leu Gly Asp Ser Pro Trp Ser
        1555                1560                1565

Ala Arg Thr Gln Pro Ala Val Thr Gly Asp Asn Arg Pro Gln Ala Pro
        1570                1575                1580

Thr Val Thr Gly Val Val Thr Asp Gly Glu Arg Val Arg Val Asn Trp
1585                1590                1595                1600

Arg Pro Ala Gly Asp Gly Gly Phe Pro Val Val Gly Tyr Thr Val Ala
            1605                1610                1615

Leu Asp Asp Gly Thr Thr Ala His Val Pro Gly Thr Thr Ser Thr Ala
            1620                1625                1630

Val Leu Thr Ala Ala Gly Gly Ala Lys Ala His Thr Ala Thr Val Thr
            1635                1640                1645

Ala Val Thr Arg Ala Gly Ser Ser Asp Gly Ser Gly Ala Thr Val Ser
        1650                1655                1660

Thr Ala Pro Ala Thr Ser Thr Thr Ser Ala Thr Ser Ala Gly Asp Pro
1665                1670                1675                1680

Ala Glu Tyr Glu Pro Ser Pro Phe Pro Gly Asp Thr Leu Asp Ala Thr
            1685                1690                1695

Tyr Ala Ser Asp Ala Trp Pro Glu Thr Gly Asp Gly Ser Asp Trp Phe
        1700                1705                1710

Thr His Leu Leu Ser Gly Phe Asp Asp Leu Gly Pro Ala Thr Leu Gly
        1715                1720                1725

Ala Asn Ser Glu Val Pro Ala Gly Thr Pro Leu Gly Ala Glu Asn Asp
        1730                1735                1740

Arg Ile Thr Val Arg Val Asn Asn Ala Ala Thr Gln Gln Gln Val Asp
1745                1750                1755                1760

Arg Ala Glu Val Asp Ala Ser Asn Ser Ala Thr Val Thr Met Ala Asp
            1765                1770                1775

Gly Leu Gly Ser Arg Leu Gly Pro Leu Tyr Gly Glu Ala Leu Lys Glu
            1780                1785                1790

Gly Arg Leu Pro Lys Thr Ser Ala Leu Phe Ser Arg Val Asn Glu Asn
        1795                1800                1805

Leu Asp Thr His Asp Ala Ala Lys Asn His Tyr Gln Tyr Leu Arg Pro
        1810                1815                1820

Tyr Val Arg Leu Gly Phe Ala Gly Asp Gly Gly Ala Val Tyr Glu Ser
1825                1830                1835                1840

Gln Asp Ser Ser Tyr Ser Gly Leu Ala Gly Gln Gly Ser Tyr Pro Ser
            1845                1850                1855

Gly His Thr Tyr Gly Gly Tyr Glu Ala Gly Thr Ile Leu Ala Thr Leu
            1860                1865                1870
```

```
Leu Pro Asp Leu Ala Pro Ser Ile Leu Ala Arg Thr Glu Tyr Gly
        1875                1880                1885

Asp Asn Arg Ile Val Leu Gly Phe His Tyr Pro Leu Asp Val Met Gly
    1890                1895                1900

Gly Arg Ile Thr Ala Gln Ala Thr Val Ala His Arg Trp Ala Asp Pro
1905                1910                1915                1920

Glu Phe Ala Lys Leu Leu Gly Gln Ala His Thr Glu Ile Glu Asn Val
            1925                1930                1935

Leu Leu Ala Arg Cys Glu Glu Gly Tyr Gly Asp Thr Leu Thr Ala
        1940                1945                1950

Cys Ala Gly Asp Pro Tyr Ala Gly Leu Ser Thr Ala Gln Gln Val Asp
    1955                1960                1965

Arg Tyr Thr Gln Arg Leu Thr Tyr Gly Phe Ser Arg Thr Gly Glu Ala
    1970                1975                1980

Gly Gln Ala Leu Asp Ala Pro Ser Asp Ala Ala Ala Leu Leu Ile Thr
1985                1990                1995                2000

Ala Phe Pro Asp Leu Thr Ala Glu Gln Arg Thr Gln Val Leu Glu Gln
            2005                2010                2015

Thr Ala Thr Asp Ser Gly Tyr Pro Leu Asp Leu Thr Gly Ser Gly Gly
            2020                2025                2030

Pro Gly Trp Gln Arg Ile Asn Leu Ala Ala Ala Met Ala Ala Asp Val
        2035                2040                2045

Val Val Asn Ala Asp Gly Ser Val Thr Val Thr Asn Phe Pro Asp Ala
    2050                2055                2060

Thr Ala Ala Ser Ala Ala Glu Ala Val Ala Ile Thr Val Gly Gly Val
2065                2070                2075                2080

Ala Leu Asp Gly Phe Asp Pro Asp Val Ser Thr Tyr Val Val Asp Trp
            2085                2090                2095

Pro Arg Asn Gly Gly Arg Ile Pro Ala Val Gly Ala Val Thr Ala Ala
            2100                2105                2110

Ser Gly Ala Arg Val Lys Val Thr Ser Gly Ser Ser Thr Val Ser Ser
        2115                2120                2125

Ser Gln Arg Gly Phe Ser Thr Arg Thr Leu Thr Val Thr Ser Ala Asp
        2130                2135                2140

Gly Glu Phe Thr Arg Thr Tyr Thr Val Gly Phe Arg Pro Val Glu Gln
2145                2150                2155                2160

His Pro His Arg Pro Gly Ala Leu Arg Asp Thr Gly Gly Gly Thr
            2165                2170                2175

Ala Gly Gly Ser Gly Gly Gly Asp Val Gly Gly Leu Trp Ser
        2180                2185                2190

Pro Ala Arg Glu Trp Glu Gln Thr Val Asn
        2195                2200

<210> SEQ ID NO 38
<211> LENGTH: 1856
<212> TYPE: PRT
<213> ORGANISM: Paenibacillus sp.

<400> SEQUENCE: 38

Met Phe Lys Lys Leu Phe Ala Val Ala Met Thr Val Met Cys Leu Thr
 1               5                  10                  15

Gly Ile Leu Val Pro Val Gly Ser Asn Ala Ala Phe Ala Ala Ala Ala
            20                  25                  30

Glu Gly Ile Thr Thr Arg Asn Val Ala Ile Asn Ala Ala Ala Thr Ala
        35                  40                  45
```

```
Ser Gly Gln Cys Asn Ala Asn Glu Ser Ala Ser Asn Ala Val Asp Gly
     50                  55                  60

Lys Thr Asp Thr Lys Trp Cys Asp Asn Thr Ser Ala Gln Lys Lys Trp
 65              70                  75                      80

Leu Lys Leu Asp Leu Gly Lys Glu Tyr Leu Val Asn Glu Trp Val Leu
                 85                  90                  95

Gln Asn Ala Ala Ile Asn Glu Ser Gly Asn Ser Pro Phe Trp Asn Thr
             100                 105                 110

Lys Asn Phe Arg Leu Gln Lys Ser Asp Asp Gly Glu Thr Trp Thr Asp
             115                 120                 125

Val Asp Ile Val Thr Asn Ala Gln Thr Ile Val Asp Arg Phe Val
             130                 135                 140

Thr Pro Phe Thr Thr Arg Tyr Leu Arg Leu Tyr Ile Asp Lys Ala Ala
145                 150                 155                 160

Tyr Asp Ser Asn Ile Ala Arg Ile Tyr Glu Leu Glu Val Tyr Gly Val
                 165                 170                 175

Glu Ala Asp Gln Ile Pro Ala Glu Pro Glu Thr Asn Leu Ala Pro Ile
             180                 185                 190

Asp Tyr Val Asp Pro Phe Ile Asn Thr Leu Gly Asp Asn Gly Gln Thr
             195                 200                 205

Asn Pro Gly Pro Thr Thr Pro Phe Gly Leu Val Ser Leu Gly Pro Asp
210                 215                 220

Ser Asp Gly Gly Ala Phe Ser Gly Tyr Tyr Glu Asn Lys Asn Leu
225                 230                 235                 240

Lys Gly Phe Ser His Leu Arg Phe Ser Gly Val Gly Cys Ser Gly Gly
                 245                 250                 255

Gly Gly Asn Ile Leu Met Met Pro Glu Thr Arg Asp Phe Thr Lys Asn
             260                 265                 270

Val Ala Asp Tyr Lys Gln Lys Tyr Asp Lys Ser Ser Glu Gln Ala Ser
             275                 280                 285

Ala Gly Phe Tyr Gly Val Thr Leu Ala Ser Gly Ile Asn Val Gln Leu
             290                 295                 300

Thr Ser Ser Asp Asn Val Gly Phe His Lys Tyr Thr Phe Pro Asp Thr
305                 310                 315                 320

Ala Asn Thr Gly Ser Val Leu Val Asp Leu Ser Asn Ser Tyr Ala Gly
                 325                 330                 335

Met Val Asp Ala Asn Leu Lys Val Thr Gly Ser Asn Glu Ile Thr Gly
             340                 345                 350

Met Ile Lys Ser Gln Asn Val Cys Gly His Gly Tyr Tyr Thr Ile Tyr
             355                 360                 365

Tyr Ser Ile Gln Phe Asp His Asp Phe Asp Ser Tyr Ser Ser Trp Gln
             370                 375                 380

Gly Asp Ser Val Gly Ala Val Ala Gln Arg Ser Gly Ser Asn Ser Gly
385                 390                 395                 400

Val Trp Leu Asn Phe Asn Thr Ala Gly Ser Lys Thr Val Gln Ala Lys
                 405                 410                 415

Val Gly Leu Ser Thr Ile Ser Val Glu Gln Ala Gln Ala Glu Arg Gly
             420                 425                 430

Leu Tyr Ser Asp Trp Asn Phe Asp Ala Arg His Glu Glu Ala Arg Ala
             435                 440                 445

Ala Trp Ser Asn Val Leu Asn Lys Val Glu Ile Thr Asp Ala Asp Glu
450                 455                 460
```

Gln Asn Lys Arg Val Phe Tyr Thr Gln Met Tyr His Ser Tyr Leu Ser
465                 470                 475                 480

Pro Lys Asn Val Thr Ser Ser Ala Gly Thr Phe Lys Ala Gly Arg Asp
            485                 490                 495

Glu Asn Thr Val Arg Gln Ala Ser Glu Leu Gly Asp Asp Phe Glu Tyr
                500                 505                 510

Tyr Asn Gly Trp Thr Thr Trp Asp Asp Phe Arg Lys Tyr Ala Met Phe
            515                 520                 525

Ser Leu Phe Glu Pro Gln Arg Tyr Asn Asn Met Val Lys Ser Leu Val
        530                 535                 540

Asp Leu Tyr Asn Thr Arg Gly Thr Tyr Thr Gln Trp Gly Asp Gly Tyr
545                 550                 555                 560

Trp Pro Ser Pro Thr Val Arg Asn Glu Phe Asn Gly Gln Val Ile Leu
                565                 570                 575

Asp Ala Tyr Ala Lys Gly Phe Gln Asp Phe Asp Val Tyr Lys Ala Leu
            580                 585                 590

Lys Gly Met Ala Val Asp Ala Asp Asn Phe Ser Ile Ser Asp Gly Glu
        595                 600                 605

Ile Ser Gly Lys Leu Glu Lys Ala Asn Ser Ala Ser Phe Pro Met Lys
    610                 615                 620

Leu Ala Gln Leu Ile Gly Asp Lys Ala Thr Phe Glu Lys Tyr Lys Glu
625                 630                 635                 640

Leu Ala Leu Ser Tyr Lys Lys Leu Trp Asn Pro Thr Gln Val Asp Glu
                645                 650                 655

Lys Gly Thr Pro Thr Gly Phe Phe Thr Pro Asn Gly Thr Thr Val Gly
            660                 665                 670

Ala Gly Asp Ile Gln Ala Val Asp Arg Tyr Ala Tyr Gln Gly Asn Leu
        675                 680                 685

Trp Gln Tyr Arg Trp Ser Ala Pro Gln Asp Ile Asn Gly Leu Ala Gln
    690                 695                 700

Leu Met Gly Gly Lys Thr Glu Met Ala Lys Gln Leu Lys His Phe Phe
705                 710                 715                 720

Glu Ile Asp Glu Tyr Met Ala Ile Asn Glu Glu Asp Ile Ser Ala Pro
                725                 730                 735

Tyr Leu Phe Asn Tyr Leu Gly Tyr Pro Tyr Leu Thr Gln Tyr Tyr Ala
            740                 745                 750

Arg Glu Phe Thr Thr Glu Val Thr Gln Lys Tyr His Asn His Gly
        755                 760                 765

Ala Tyr Ala Tyr Pro Leu Lys Ser Arg Val Tyr Arg Asp Asp Pro Glu
    770                 775                 780

Gly Tyr Leu Ser Ser Met Asp Asp Ala Gly Gly Met Ser Ser Trp
785                 790                 795                 800

Tyr Val Phe Ser Ala Leu Gly Leu Phe Pro Gly Asn Pro Gly Glu Gly
                805                 810                 815

Tyr Phe Leu Ile Gly Ser Pro Ile Phe Ser Glu Val Lys Leu His Met
            820                 825                 830

Gly Ser Gly Lys Thr Leu Val Ile Lys Ala Asp Asn Val Ser Ser Glu
        835                 840                 845

Asn Arg Phe Ile Glu Gly Trp Thr Gln Val Asp Phe Asp Ser Ser
    850                 855                 860

Trp Ser Ser Gly Lys Ala Met Leu Gly Tyr Asp Ser Tyr Gly Lys Pro
865                 870                 875                 880

Ala Thr Thr Val Ser Tyr Gly Pro Asn Ala Asn Asn Lys Tyr Val Thr

```
            885                 890                 895
Thr Tyr Phe Arg Lys Thr Phe Asp Ala Lys Asp Leu Asp Gly Ile Leu
            900                 905                 910
Glu Leu Asp Gly Ser Leu Ile Arg Asp Asp Gly Ala Ile Val Tyr Leu
            915                 920                 925
Asn Gly His Glu Ile Phe Arg Thr Asn Met Pro Thr Gly Ala Val Asn
            930                 935                 940
Tyr Ser Thr Phe Ala Asn Ala Thr Val Gly Asp Glu Arg Asp Lys Asn
945                 950                 955                 960
Gly Phe Ile Ile Asp Pro Ser Tyr Leu Val Glu Gly Lys Asn Val Leu
            965                 970                 975
Thr Ala Glu Val His Gln Val Asn Ala Thr Ser Ser Asp Ile Ala Phe
            980                 985                 990
Glu Phe Ser Leu Glu Ala Val Arg Lys Leu Asn Ile Pro Ala Ala Pro
            995                 1000                1005
Thr His Pro Val Val Asp Asp Lys Ala Asn Thr Ile Gly Trp Thr Pro
            1010                1015                1020
Val Glu Gly Ile Asn Asn Ala Ser Asp Tyr Glu Phe Ser Thr Asp Gly
1025                1030                1035                1040
Gly Lys Ser Trp Lys Gln Ala Lys Ala Asn Pro Gln Thr Val Gly Pro
            1045                1050                1055
Leu Asn Tyr Ala Pro Gly Ile Val Gln Val Arg Val Met Ala Asn Ala
            1060                1065                1070
Ala Ala Asn Arg Ala Ala Gly Glu Ala Leu Leu Ser Thr Glu Ala Tyr
            1075                1080                1085
Thr Ser Asp Val Lys Trp Asp Val Tyr Asp Leu Asp Ala Asp Ile His
            1090                1095                1100
Gln Asp Gly Asn Met Val Val Asp Val Thr Gly Thr Leu Lys Gly Asp
1105                1110                1115                1120
Tyr Thr Asp Ser Ala Val Val Val Phe Gln Leu Met Asp Gly Lys Glu
            1125                1130                1135
His Ala Trp Val Ser Ser Ala Val Pro Val Gln Thr Gly Ser Phe Asp
            1140                1145                1150
Ile Ser Gln Ile Tyr Asn Val Asp Ala Ser Lys Tyr Lys Val Asn Val
            1155                1160                1165
Tyr Leu Val Asn Glu Phe Asn Gly Asp Ile Tyr Glu Ser Pro Leu Trp
            1170                1175                1180
Leu Ala Asp Pro Ile Val Gln Gln Ser Glu Pro Gly Ser Leu Pro Asp
1185                1190                1195                1200
Pro Glu Gly Pro Pro Val Thr Glu Glu Pro Leu Pro Glu Pro Ile Pro
            1205                1210                1215
Leu Pro Asp Pro Lys Pro Asp Glu Pro Glu Pro Glu Pro Val Pro Glu
            1220                1225                1230
Thr Gly Met Lys Ile Gln Phe Glu Asp Arg Ala Glu Trp Thr Ser Ala
            1235                1240                1245
Ala His Pro Asn Gly Gly Gly Leu Ser Thr Glu Ala Gly Asn Gly
            1250                1255                1260
Gly Thr Val Val Ala His Thr Phe Gly Ala Trp Leu Ala Tyr Asn
1265                1270                1275                1280
Val Asp Phe Gly Thr Thr Gly Tyr Asn Asn Val Thr Val Gln Tyr Asp
            1285                1290                1295
Ala Pro Thr Asp Lys Val Pro Ala Gly Ser Lys Leu Glu Phe Arg Leu
            1300                1305                1310
```

-continued

```
Gly Ser Val Ser Gly Glu Leu Val Gly Thr Val Asn Met Glu Asp Lys
            1315                1320                1325
Asn Ala Gly Trp Gly Ser Tyr Ile Thr Thr Lys Ala Asn Leu Thr Arg
    1330                1335                1340
Thr Leu Thr Gly Gln Gln Lys Leu Tyr Val Val Met Val Ala Gly Thr
1345                1350                1355                1360
Pro Asn Asn Leu Pro Tyr Ile Gly Asn Phe Asp Trp Phe Lys Phe Asp
                1365                1370                1375
Tyr Glu Lys Ile Arg Ser Asp Tyr Ala Lys Leu Glu Leu Glu Ser Tyr
            1380                1385                1390
Asp Glu Trp Thr Thr Asp Val Asn Thr Gly Asn Asn Thr Pro Leu
        1395                1400                1405
Lys Thr Glu Ala Gly Lys Gly Gly Val Gly Gln Gln Val Ala Asn Thr
    1410                1415                1420
Phe Asn Gly Ala Trp Leu Ala Tyr Lys Arg Met Asp Phe Gly Ser Glu
1425                1430                1435                1440
Gly Val Asp Lys Phe Ser Ile Glu Tyr Ala Gly Asn Ser Thr Asn Thr
                1445                1450                1455
Phe Asn Asn Ser Ala Val Glu Val Arg Leu Gly Ser Pro Thr Gly Thr
            1460                1465                1470
Leu Val Gly Thr Val Ala Thr Pro Pro Thr Ala Ala Ala Trp Gly Thr
        1475                1480                1485
Tyr Ala Thr Val Ser Gly Ser Leu Thr Gln Lys Leu Thr Gly Leu Gln
    1490                1495                1500
Asp Val Tyr Leu Val Phe Thr Gly Ser Ala Ala Asn Gly Glu Thr Gly
1505                1510                1515                1520
Lys Lys Tyr Ile Gly Asn Phe Asp Asn Ala Ser Phe Ser Leu Ser Val
                1525                1530                1535
Gln Glu Pro Glu Glu Pro Glu Gln Pro Gln Gln Pro Glu Gln Glu Gln
            1540                1545                1550
Ile Thr Val Gln Phe Glu Ser Lys Thr Glu Trp Asn Thr Ala Leu Asn
        1555                1560                1565
Thr Phe Asn Asn Gln Ala Met Lys Ile Glu Asn Asn Gly Gly Gln
    1570                1575                1580
Thr Val Gly Asn Thr Tyr Thr Gly Ala Trp Leu Gly Phe Lys Asp Val
1585                1590                1595                1600
Asp Phe Gly Ser Glu Lys Gly Lys Asn Gln Val Ser Ile Val Tyr Asp
                1605                1610                1615
Ala Pro Thr Asn Arg Val Pro Ala Asp Val Lys Ala Glu Ile Arg Leu
            1620                1625                1630
Gly Ser Pro Thr Gly Thr Leu Val Gly Thr Val Ala Ile Pro Asn Thr
        1635                1640                1645
Gly Ser Thr Trp Gly Gln Tyr Asn Thr Ala Thr Ala Asp Leu Asn Thr
    1650                1655                1660
Thr Ile Lys Gly Lys Gln Asp Leu Tyr Ile Val Met Thr Gly Ser Thr
1665                1670                1675                1680
Thr Ser Ser Leu Leu Tyr Val Gly Asn Tyr Asp Ser Leu Thr Phe Gly
                1685                1690                1695
Tyr Lys Pro Val Arg Ser Asp Tyr Ala Lys Leu Glu Leu Glu Ser Tyr
            1700                1705                1710
Asp Glu Trp Thr Thr Ala Val Asn Pro Leu Asn Ser Asn Thr Pro Leu
        1715                1720                1725
```

```
Lys Thr Glu Ala Gly Lys Gly Gly Ala Gly Lys Gln Val Ala Asn Thr
    1730            1735            1740

Phe Asn Gly Ala Trp Leu Ala Tyr Lys Arg Met Asp Phe Gly Thr Glu
1745            1750            1755            1760

Gly Val Asn Thr Phe Ala Val Glu Tyr Ala Gly Asn Thr Thr Asn Cys
                1765            1770            1775

Phe Thr Asn Ser Ala Val Glu Ile Arg Leu Gly Ser Pro Thr Gly Thr
                1780            1785            1790

Leu Val Gly Lys Ile Ser Thr Pro Pro Lys Ala Gly Asn Trp Thr Thr
            1795            1800            1805

Tyr Asp Thr Val Ser Gly Thr Leu Thr Gln Lys Leu Thr Gly Ile Gln
    1810            1815            1820

Asp Val Tyr Leu Val Leu Thr Gly Ser Ala Gly Asn Gly Glu Thr Gly
1825            1830            1835            1840

Lys Lys Tyr Ile Gly Asn Phe Asp Asn Ala Ala Phe Ser Leu Lys Val
                1845            1850            1855

<210> SEQ ID NO 39
<211> LENGTH: 640
<212> TYPE: PRT
<213> ORGANISM: Bacteroides sp.

<400> SEQUENCE: 39

Met Lys Asn Asn Arg Ser Arg Trp Tyr Ala Leu Leu Leu Val Val Leu
1               5                   10                  15

Ser Ile Met Thr Pro Ser Val Ala Gln Asn Thr Lys Tyr Val Asn Leu
            20                  25                  30

Phe Ile Gly Thr Ser Gly Asp Asn Gly Gln Val Ala Pro Gly Ala Ala
        35                  40                  45

Ala Pro Phe Gly Met Val Cys Val Cys Pro Asp Asn Asp Pro Arg Ser
    50                  55                  60

His Ala Gly Tyr Asp Tyr Ala Val Thr Lys Val Ser Gly Ile Ser Val
65                  70                  75                  80

Asn Arg Leu Ser Gly Val Gly Cys Ser Gly Gly Gly Asn Leu Arg
                85                  90                  95

Ile Arg Pro Val Ala Pro Ser Gln Glu Leu His Ile Lys Lys Ser Arg
            100                 105                 110

Glu Lys Ala Thr Pro Gly Tyr Tyr Ser Thr Ala Phe Thr Asn Gly Ile
        115                 120                 125

Lys Thr Glu Leu Thr Ala Thr Asn Ala Met Ala Val Glu Arg Tyr Lys
    130                 135                 140

Phe Pro Arg Ser Leu Ser Ala Ala Leu Trp Ile Asp Phe Ala Ser Thr
145                 150                 155                 160

Phe Glu Asp Val Ala Thr Cys His Tyr Lys Arg Ile Ser Glu Thr Cys
                165                 170                 175

Ile Glu Gly Tyr Val Gln Ala Lys Asn Val Cys Gly His Gly Arg Tyr
            180                 185                 190

Lys Leu Tyr Phe Ser Leu Asn Thr Ser His Pro Phe Gln Leu Glu Glu
        195                 200                 205

Gln Lys Glu Thr Thr Ala Cys Leu Thr Phe Gly Lys Lys Val Arg Ser
    210                 215                 220

Val Glu Val Arg Ile Gly Leu Ser Ala Leu Ser Ser Glu Leu Ala Ser
225                 230                 235                 240

Trp Glu Cys Ala Arg Trp Glu Lys Met Asp Phe Glu Asp Val Lys Ser
                245                 250                 255
```

Arg Thr Ala Asp Gln Trp Glu Lys Gln Leu Ser Ala Ile Asp Val Lys
                260                 265                 270

Gly Gly Lys Asp Asp Arg Val Ile Phe Tyr Thr Ser Leu Tyr Arg
        275                 280                 285

Thr Tyr Leu Ser Pro Ala Asp Val Ser Ser Pro Asp Gly Ala Tyr Leu
    290                 295                 300

Gly Thr Asp Gly Lys Val Tyr Ile Ser Glu Asp Phe Arg Tyr Tyr Ser
305                 310                 315                 320

Asn Trp Ser Leu Trp Asp Thr Phe Arg Thr Lys Phe Pro Leu Leu Val
                325                 330                 335

Leu Thr Glu Pro Ala Lys Met Arg Asp Met Ala Thr Ser Leu Ile His
                340                 345                 350

Leu Tyr Ala Thr Gly Lys Lys Asp Trp Ser Thr Gly Phe Glu Ser Thr
                355                 360                 365

Pro Thr Val Arg Thr Glu His Ala Val Ile Leu Leu Asp Ala Tyr
    370                 375                 380

Arg Lys Gly Ile Thr Asn Leu Asp Phe Arg Lys Gly Tyr Ala Gly Met
385                 390                 395                 400

Lys Gln Glu Met Glu Arg Leu Pro Met Arg Ser Pro Asp Gln Lys Met
                405                 410                 415

Glu Ser Ala Tyr Asp Leu Trp Ala Met Ala Lys Ile Ala Glu Ile Ile
                420                 425                 430

Gly Glu Lys Ala Asp Ser Glu Gln Tyr Arg Gln Arg Ser Val Ser Leu
                435                 440                 445

Phe Glu Glu Thr Trp Lys Lys Glu Phe Met Asn Val Thr Pro Ala Phe
    450                 455                 460

Glu Val Met Lys Asn Asn Gly Leu Tyr Gln Gly Thr Arg Trp Gln Tyr
465                 470                 475                 480

Arg Trp Ala Ala Pro Gln Tyr Ile Asp Lys Met Ile Glu Trp Val Gly
                485                 490                 495

Gln Asp Ser Leu Arg Ser Gln Leu Thr Tyr Phe Phe Asp His His Leu
                500                 505                 510

Tyr Asn Gln Gly Asn Glu Pro Asp Ile His Val Pro Tyr Leu Phe Asn
                515                 520                 525

Arg Leu Gly Ala Pro Glu Lys Thr Gln Gln Ile Val Arg Ser Leu Met
    530                 535                 540

Thr Glu Pro Met Ile His Lys Tyr Gly Gly Asn Ser Glu Phe Lys Thr
545                 550                 555                 560

Pro Tyr Leu Gly Lys Ala Phe Lys Asn Ala Pro Glu Gly Tyr Ser Pro
                565                 570                 575

Glu Met Asp Glu Asp Asp Gly Thr Met Ser Ala Trp Tyr Val Phe Gly
                580                 585                 590

Ala Met Gly Phe Tyr Pro Leu Leu Val Gly Asp Glu Tyr Tyr Asp Leu
                595                 600                 605

Thr Ser Pro Leu Phe Asp Arg Val Leu Leu Arg Leu Thr Asn Gly Asn
    610                 615                 620

Val Leu Thr Ile Gln Thr Glu Gly Arg Lys Lys Lys Asp Ala Pro Ile
625                 630                 635                 640

<210> SEQ ID NO 40
<211> LENGTH: 624
<212> TYPE: PRT
<213> ORGANISM: Bacteroides cellulosilyticus

<400> SEQUENCE: 40

```
Met Val Gln Ala Gln Gln Thr Ser Phe Val Asn Pro Phe Ile Gly Thr
  1               5                  10                  15

Ser Asp Asp His Gly Gln Thr Asp Pro Ser Ala Thr Ile Pro Phe Gly
             20                  25                  30

Met Ile Lys Pro Gly Pro Glu Thr Ile Pro Arg Gly Asn Gly Gly Tyr
             35                  40                  45

Asp Tyr Gln Ser Gln Gln Leu Lys Gly Phe Ser Gln Thr Arg Met Ser
 50                  55                  60

Gly Val Gly Cys Ile Gly Val Gly Gly Asn Leu Leu Ile Thr Pro Phe
 65                  70                  75                  80

Val Gly Thr Ala Cys Lys Thr Leu Lys Met Asp Lys Ala Ser Glu Thr
             85                  90                  95

Ala Ile Pro Gly Tyr Tyr Ser Val Thr Leu Asp Asn Gln Leu Lys Val
            100                 105                 110

Glu Ile Thr Thr Gly Arg Thr Ala Ala Ile Tyr Arg Phe Thr Tyr Pro
            115                 120                 125

Ala Thr Glu Thr Ala Gly Ile Lys Ile Asn Phe Lys His Ser Tyr Gly
            130                 135                 140

Lys His Ile Ala Glu Glu His Ser Ile Ile Gly Asp Asn Ala Val Lys
145                 150                 155                 160

Gly Phe Val Arg Ser Ala Cys Thr Cys Asp Leu Gly Ser Tyr Lys Phe
            165                 170                 175

Tyr Tyr Tyr Ile Glu Lys Asp Lys Ser Thr Tyr Glu Pro Glu Asp Asn
            180                 185                 190

Asp Ser Glu Leu Leu Trp Lys Phe Gln Thr Glu Pro Asn Glu Gln Ile
            195                 200                 205

Ile Leu Lys Ile Gly Leu Ser Ser Val Ser Ala Glu Glu Ala Glu Ala
210                 215                 220

Asn Leu Lys Lys Glu Cys Ser Asn Gln Ser Phe Glu Gln Ile Arg Thr
225                 230                 235                 240

Asn Ala Arg Ile Ala Trp Glu Asn Leu Leu Gly Gln Ile Gln Val Glu
            245                 250                 255

Thr Ser Asp Glu Asp Leu Lys Thr Ser Phe Tyr Thr Arg Leu Tyr His
            260                 265                 270

Ala Cys Gln Thr Pro Phe Thr Ile Asn Asp Tyr Ser Gly Ser Tyr Lys
            275                 280                 285

Gly Ser Asp Gly Lys Val Tyr Lys Ser Gln Gln Leu Pro Tyr Tyr His
            290                 295                 300

Gly Trp Ser Ile Trp Asp Thr Tyr Arg Thr Lys Tyr Pro Leu Leu Ser
305                 310                 315                 320

Ile Val Cys Pro Thr Glu Tyr Lys His Met Ile Ser Ser Leu Ala Glu
            325                 330                 335

Leu Tyr Lys Gln Gly Lys Pro Arg Ser Ala Thr Lys Thr Glu Pro Phe
            340                 345                 350

Leu Thr Thr Arg Thr Glu His Ser Ile Ile Thr Ile Leu Asp Ala Leu
            355                 360                 365

Gln Lys Gly Met Phe Asp Gly Ser Leu Asp Leu Leu Pro Leu Met
            370                 375                 380

Leu Lys Glu Ala Glu Asp Ile Ser Asn Asp Ser Pro Asp Lys Ala Leu
385                 390                 395                 400

Glu Arg Gly Tyr Asp Phe Trp Gly Val Ser Glu Leu Ala Gly Lys Met
            405                 410                 415
```

```
Gly Asn Lys Glu Leu Lys Lys Glu Phe Ser Leu Arg Ser Lys Glu Tyr
            420                 425                 430

Arg Pro Ile Trp Leu Gln Lys Phe Lys Asp Ile Gly Pro Thr Ser Asp
            435                 440                 445

Ile Met His Gly Asp Gly Leu Tyr Glu Gly Thr Ile Trp Gln Tyr Arg
450                 455                 460

Trp Phe Val Pro His Asp Phe Asp Trp Val Ile Ala Thr Leu Gly Ser
465                 470                 475                 480

Lys Lys Lys Val Leu Ser Glu Leu Asp Tyr Phe Glu Asn Asn Leu
            485                 490                 495

Phe Asn Met Gly Asn Gln Pro Asp Ile His Val Pro Phe Leu Tyr Tyr
            500                 505                 510

Tyr Leu Gly Ala Pro Trp Lys Thr Gln Lys Leu Val His Gln Ile Leu
            515                 520                 525

Leu Glu Pro Thr Thr Asn Tyr Tyr Gly Thr His Glu Lys Trp Glu Lys
        530                 535                 540

Pro Tyr Ile Gly Lys Ile Phe Asn Thr Thr Pro Gln Gly Tyr Leu Lys
545                 550                 555                 560

Glu Met Asp Asp Asp Ala Gly Thr Met Ser Ser Trp Phe Val Leu Ser
                565                 570                 575

Ser Ile Gly Leu Phe Pro Val Cys Pro Gly Ile Pro Tyr Tyr Trp Ile
            580                 585                 590

Asn Ala Pro Val Phe Asp Thr Val Thr Leu His Pro Thr Ser Gln Gln
            595                 600                 605

Glu Phe Lys Ile Tyr Val Asn Arg Pro Asp Ala Glu Cys Ile Tyr Ile
        610                 615                 620

<210> SEQ ID NO 41
<211> LENGTH: 631
<212> TYPE: PRT
<213> ORGANISM: Leeuwenhoekiella blandensis

<400> SEQUENCE: 41

Met Lys Asn Tyr Ile Ala Val Leu Phe Thr Leu Val Leu Ala Phe Thr
1               5                   10                  15

Ser Val Ala Gln Glu Ser Leu Thr Asp Tyr Val Asn Val Phe Leu Gly
            20                  25                  30

Thr Ser Gly Asp His Gly Gln Met Ser Pro Ser Ala Thr Thr Pro Phe
        35                  40                  45

Asn Met Met Asn Leu Gly Pro Gln Thr Asn Pro His Gln His Thr Gly
50                  55                  60

Tyr Glu Tyr Tyr Ala Lys Gln Phe Asp Gly Phe Thr His Thr Arg Met
65                  70                  75                  80

Glu Gly Val Gly Cys Thr Gly Ser Gly Gly Asn Ile Leu Ile Lys Pro
                85                  90                  95

Ile Leu Asn Ala Glu Val Ser Thr Lys Leu Ile Lys Lys Thr Gln Asp
            100                 105                 110

Ala Val Pro Gly Phe Tyr His Val Asn Phe Glu Asn Gly Ile Asp Ala
        115                 120                 125

Lys Leu Thr Val Ala Gln Asn Leu Gly Met His Gln Tyr Ser Phe Pro
130                 135                 140

Asn Ala Asn Ser Gly Leu Tyr Ile Asp Leu Ser Phe Ala Leu Ser Asn
145                 150                 155                 160

Arg Phe Val Ala Glu Thr His Glu Ile Arg Arg Asn Leu Ile Ser Gly
```

```
                165                 170                 175
Tyr Met Asp Thr Lys Thr Thr Cys His Ala Gly Thr Tyr Arg Ile Tyr
            180                 185                 190

Tyr Ala Ile Lys Leu Pro Glu Glu Ala Gln Ile Gln Asn Val Gly Glu
        195                 200                 205

His Gln Leu Met Val Lys Gly Leu Gly Asp Ala Ala Glu Val Gln Val
    210                 215                 220

Gly Phe Ser Ser Val Asn Glu Gly Tyr Ala Lys Lys Arg Ile Thr Ser
225                 230                 235                 240

Asp Asp Phe Glu Thr Leu Lys Gly Lys Ala Ser Ala Ser Trp Asn Ala
                245                 250                 255

Tyr Leu Asn Thr Ile Glu Val Ser Gly Glu Lys Asp Arg Leu Gln Leu
            260                 265                 270

Phe Tyr Ser Leu Leu Tyr Arg Thr Ala Gln Ser Pro Phe Leu Val Ser
        275                 280                 285

Glu Glu Asp Gly Thr Phe Arg Ala Thr Asp Gly Ser Val Gln Asn Glu
    290                 295                 300

Asp Tyr Lys Val Tyr Asn Gly Trp Ala Ile Trp Asp Asn Tyr Arg Glu
305                 310                 315                 320

Gln Leu Pro Phe Leu Ser Leu Ala His Pro Glu Val Tyr Gln Asp Ile
                325                 330                 335

Thr Thr Ser Ile Ala Asn Leu Tyr Arg Phe Gly Lys Lys Asn Trp Ala
            340                 345                 350

Thr Glu His Glu Thr Ser Pro Thr Val Arg Thr Glu His Ala Met Val
        355                 360                 365

Val Leu Leu Asp Ala Tyr Lys Lys Gly Tyr Asp Val Asp Phe Glu Ala
    370                 375                 380

Ile Lys Asp Ser Leu Leu Tyr Glu Ala Asp His Leu Asp Phe Gly Ala
385                 390                 395                 400

Pro Asp Lys Ala Leu Glu Ser Ser Tyr Asp Leu Trp Ala Met Ser Glu
                405                 410                 415

Ile Leu Lys Ala Thr Gly Asp Gln Thr Ala Ser Lys Lys Tyr Leu Asp
            420                 425                 430

Lys Ala Leu Asp Tyr Lys Ala Tyr Trp Asp Lys Asp Phe Lys Asp Leu
        435                 440                 445

Ser Lys Ser Asp Val Asp Arg Met Gln Ala Arg Gly Leu Tyr Gln Gly
    450                 455                 460

Thr Ile Trp Gln Tyr Arg Trp Phe Val Pro Trp Asp Val Asn Gly Leu
465                 470                 475                 480

Gln Glu Leu Ala Gly Gly Ala Glu Thr Phe Glu Asn Gln Leu Asp Gln
                485                 490                 495

Phe Phe Glu Glu Phe Asn Tyr Asn His Ala Asn Gln Pro Asp Leu Gln
            500                 505                 510

Val Pro Gly Leu Tyr Asn Ala Thr Ser Gln Pro Trp Lys Ser Gln Lys
        515                 520                 525

Leu Phe Arg Glu Ile Leu Leu Asp Thr Val Val Gln Thr Tyr Phe Asn
    530                 535                 540

Asp Asn Ser Lys Gly Ile Asp Pro Tyr Val Gly Arg Ile Tyr Gln Asn
545                 550                 555                 560

Lys Pro Lys Ala Tyr Leu Arg Thr Met Asp Asp Ala Gly Thr Met
                565                 570                 575

Ser Ser Trp Phe Val Leu His Ser Met Gly Leu Ser Val Ala Asn Val
            580                 585                 590
```

Gly Ser Pro Val Tyr Tyr Leu Thr Ala Pro Ile Phe Lys Glu Val Lys
        595                 600                 605

Leu Asn Leu Ala Pro Gly Lys Thr Phe Ser Ile Ser Val Lys Asn Tyr
    610                 615                 620

Asn Lys Glu His Phe Tyr Val
625                 630

<210> SEQ ID NO 42
<211> LENGTH: 646
<212> TYPE: PRT
<213> ORGANISM: Sphingobacterium spiritivorum

<400> SEQUENCE: 42

Met Gln Val Leu Thr Asp Leu Leu Val Ser Met Lys Asn Phe Leu
 1               5                  10                  15

Ser Gln Phe Ser Val Cys Val Leu Ile Leu Ser Ser Gln Gln Phe
                20                  25                  30

Val Tyr Ala Gln Ser Arg Ser Leu Thr Asn Val Phe Leu Gly Ser
            35                  40                  45

Ser Gly Asp Tyr Gly Gln Met Ser Pro Ala Ala Ser Pro Phe His
50                  55                  60

Gln Met Ser Ile Ala Pro Gln Thr Tyr Pro Thr Leu His Met Gly Tyr
65                  70                  75                  80

Glu Tyr Leu Ala Lys Glu Ile Leu Gly Phe Thr His Asn Arg Phe Glu
                85                  90                  95

Gly Val Gly Cys Lys Gly Ser Gly Leu Ile Leu Val Lys Pro Phe
            100                 105                 110

Leu Gly Gly Gln Asp Asp Gln Gln Pro Leu Leu Lys Val Thr Glu Gln
            115                 120                 125

Ala Gly Pro Gly Phe Tyr Glu Ile Gly Leu Lys Asn Arg Ile Lys Ala
130                 135                 140

Ala Phe Ala Val Asp Gln Asn Phe Gly Ile His Glu Tyr Ser Phe Pro
145                 150                 155                 160

Lys Gly Lys Lys Gly Phe Ser Ile Asp Leu Ala His Ala Phe Asn Gly
                165                 170                 175

Ala Phe Val Ser Asn Thr Tyr Asp Met Asp Ala Lys Gly Met Leu Lys
            180                 185                 190

Gly Ser Val Arg Ala Arg Thr Thr Cys Gly Val Gly Ile Tyr Thr Ile
            195                 200                 205

His Tyr Ala Ile Lys Val Ser Ser His Val Trp Glu Gly Lys Gly
    210                 215                 220

Asn Gln Leu Thr Leu His Leu Glu Glu Asn Ser Glu Lys Val Thr Ile
225                 230                 235                 240

Gln Ile Ala Phe Ser Ala Val Ser Val Gln Lys Ala Val Glu Thr Leu
                245                 250                 255

Leu His Asn Ala Asp Arg Ser Tyr Ser Glu Val Arg Asn Ala Ser Gln
            260                 265                 270

Gln Gln Trp Asp Ile Cys Leu Ser His Ile Glu Val Lys Gly Asp Pro
            275                 280                 285

Glu Arg Glu Lys Leu Phe Tyr Ser Leu Phe Tyr Arg Thr Leu Gln Ser
        290                 295                 300

Pro Tyr Gln Thr Ser Glu Ala Asp Gly Gln Tyr Ala Gly Thr Asp Gly
305                 310                 315                 320

Lys Met His Ser Ala Lys Gly Lys Arg Tyr His Gly Trp Ala Ile Trp

```
            325                 330                 335
Asp Asn Tyr Lys Thr Gln Leu Pro Leu Leu Glu Leu Leu Tyr Pro Gln
            340                 345                 350

Leu Tyr Gln Asp Val Val Ser Ser Ile Ser Asp Leu Tyr Arg Tyr Gly
        355                 360                 365

Lys Tyr Asp Phe Ala Gly Pro Asn Glu Pro Ala Asn Ser Val Arg Thr
    370                 375                 380

Glu His Ala Ala Val Val Leu Leu Asp Ala Arg Asn Lys Gly Tyr Asp
385                 390                 395                 400

Ile His Phe Asp Ala Val Lys Asp Ser Leu Ile Arg Asp Thr Ala Arg
            405                 410                 415

Phe Asp Phe Ser Lys Pro Asp Lys Ala Leu Glu Ala Ala Tyr Asp Met
            420                 425                 430

Trp Ala Met Ala Gln Leu Phe Asp Lys Lys Gly Thr His Tyr Ala Gln
        435                 440                 445

Arg Ala Gly Ser Tyr Lys Thr Val Trp Gln Lys Glu Phe Lys Asp Leu
    450                 455                 460

Ser Arg Asn Asp Val Asp Arg Met Ser Ala Arg Asn Met Tyr Gln Gly
465                 470                 475                 480

Thr Ile Arg Gln Tyr Arg Trp Asn Val Pro Phe Asp Ile Gly Gly Leu
            485                 490                 495

Val Asp Leu Ala Gly Gly Lys Lys Ala Leu Thr Glu Gln Leu Asp Glu
            500                 505                 510

Phe Phe Asp Glu His Tyr Phe Asn Arg Ala Asn Glu Pro Asp Met Gln
        515                 520                 525

Ser Pro Thr Leu Tyr Tyr Ala Ser Asp Lys Pro Trp Lys Tyr Gln Ser
    530                 535                 540

Leu Val His Gln Leu Ala Val Asp Thr Val Ile Gln Tyr Tyr Phe Asn
545                 550                 555                 560

Asp Asn Ser Arg Gly Ile Asp Pro Phe Ile Asp Arg Ile Tyr Lys Asn
            565                 570                 575

Glu Ser Lys Ala Tyr Ile Arg Thr Met Asp Asp Ala Gly Ala Met
            580                 585                 590

Ser Gly Trp Phe Val Leu Thr Ala Leu Gly Leu His Gln Pro Val Ile
        595                 600                 605

Gly His Pro Val Tyr Tyr Leu Ser Val Pro Leu Phe Pro Glu Ile Asn
    610                 615                 620

Leu Arg Arg Ala Asp Asn Thr Leu Gln Ile Arg Val His Asn Phe Gly
625                 630                 635                 640

Ser Gln Asn Lys Tyr Ile
            645

<210> SEQ ID NO 43
<211> LENGTH: 642
<212> TYPE: PRT
<213> ORGANISM: Pedobacter sp.

<400> SEQUENCE: 43

Met Phe Phe Met Leu Lys Met Asn Leu Arg Leu Leu Ala Phe Phe Leu
 1               5                  10                  15

Leu Leu Leu Val Asn Lys Thr Ile Tyr Ala Gln Gln Thr Gly Lys Asp
            20                  25                  30

Lys Leu Val Asn Val Phe Leu Gly Ser Ser Gly Asp His Gly Gln Met
        35                  40                  45
```

-continued

```
Ser Pro Ala Ala Ser Tyr Pro Phe Ser Ala Leu Ser Ile Ala Pro Gln
    50                  55                  60

Thr Tyr Pro Met Thr His Thr Gly Tyr Glu His Leu Ala Lys Glu Val
65              70                  75                  80

Phe Gly Phe Thr His Asn Arg Phe Glu Gly Val Gly Cys Gln Gly Ser
                85                  90                  95

Gly Gly Ile Ile Leu Val Lys Pro Phe Leu Gly Ala Glu Asn Asp Glu
            100                 105                 110

Leu Pro Leu Val Lys Ala Ser Glu Thr Ala Ala Pro Gly Tyr Tyr Asp
        115                 120                 125

Ile Ala Phe Thr Asn Gly Ile Lys Ala Gly Phe Val Val Asn Lys Gln
    130                 135                 140

Thr Ala Met His Asp Tyr Ile Met Pro Ala Gly Lys Lys Gly Phe Ser
145                 150                 155                 160

Ile Asp Leu Gly His Thr Phe Asn Asn Ala Leu Val Asp Glu Ser His
                165                 170                 175

Thr Ile Asp Gly Asn Val Ile Lys Gly Trp Val Ala Ala Lys Thr Thr
            180                 185                 190

Cys His Ala Gly Thr Tyr Arg Ile Tyr Tyr Gln Leu Ser Phe Asn Gln
        195                 200                 205

Ser Val Lys Trp Lys Asp Leu Gly Glu His Arg Leu Val Ala Val Pro
    210                 215                 220

Ala Asp Asp Ala Thr Ala Val Gln Leu Arg Val Asp Ile Ser Ala Val
225                 230                 235                 240

Ser Thr Glu Tyr Ala Val Lys Ala Ser Lys Lys Leu Ser Phe Glu
                245                 250                 255

Glu Ala Lys Lys Asn Ser Ala Met Ala Trp Asp Glu Leu Leu Ser Ser
            260                 265                 270

Val Asp Val Lys Gly Asn Ala Glu Arg Glu Arg Leu Phe Tyr Ser Leu
        275                 280                 285

Leu Tyr Arg Thr Ile Gln Ser Pro Tyr Thr Ile Ser Glu Pro Asp Gly
    290                 295                 300

Thr Tyr Lys Ala Ile Asn Gly Ser Thr Gln Lys Ser Lys Glu Met Arg
305                 310                 315                 320

Tyr Asn Gly Trp Ala Ile Trp Asp Asn Tyr Lys Thr Gln Leu Pro Leu
                325                 330                 335

Leu Ser Val Leu Tyr Pro Lys Arg Tyr Gly Asp Ile Val Gly Ser Ile
            340                 345                 350

Ala Asn Leu Tyr Pro Tyr Gly Lys Lys Asp Tyr Ala Gly Pro Asn Glu
        355                 360                 365

Pro Ser Asn Thr Val Arg Thr Glu His Ala Met Val Val Leu Tyr Asp
    370                 375                 380

Ala Met Lys Lys Gly Tyr Lys Ile Asp Phe Pro Ala Ile Lys Asp Ser
385                 390                 395                 400

Val Leu Ala Glu Val Gln Arg Leu Asp Phe Ser Lys Pro Asp Lys Ser
                405                 410                 415

Leu Glu Ala Ser Tyr Asp Leu Trp Ala Val Ser Gly Met Phe Lys Leu
            420                 425                 430

Ser Gly Asp Ala Ala Met Ser Glu Lys Tyr Lys Thr Met Ala Met Asp
        435                 440                 445

Tyr Lys Lys Tyr Trp Asp Lys Asp Phe Lys Asp Leu Ser Lys Lys Asp
    450                 455                 460

Val Asp Arg Met Gly Ala Arg Ser Leu Tyr Gln Gly Thr Ile Arg Gln
```

```
                465                 470                 475                 480
Tyr Arg Trp Ala Val Pro Phe Asp Val Lys Gly Leu Val Glu Leu Thr
                    485                 490                 495
Gly Gly Ala Gln Ala Phe Thr Glu Gln Leu Asp Asp Phe Phe Asp Asn
                500                 505                 510
Asp Tyr Phe Asn Lys Ala Asn Glu Pro Asp Leu Gln Thr Gln Glu Leu
            515                 520                 525
Tyr Asn Gly Ser Ala Lys Pro Trp Lys Tyr Gln Ser Leu Val His Lys
        530                 535                 540
Leu Ala Leu Asp Thr Val Ile Gln His Tyr Phe Asn Asp Asn Ser Arg
545                 550                 555                 560
Gly Val Gly Ser Phe Ile Asp Arg Ile Tyr Lys Asn Glu Pro Lys Ala
                565                 570                 575
Phe Val Arg Thr Met Asp Asp Ala Gly Ala Met Ser Gly Trp Phe
                580                 585                 590
Val Leu Thr Ala Met Gly Ile Gln Pro Ala Cys Val Gly Thr Pro Ile
                595                 600                 605
Tyr Tyr Leu Asn Val Pro Leu Phe Glu Ser Val Thr Ile Lys Ser Gly
        610                 615                 620
Ala Lys Pro Leu Gln Ile Lys Val Glu His Phe Ser Asp Gln Asn Val
625                 630                 635                 640
Tyr Ile

<210> SEQ ID NO 44
<211> LENGTH: 810
<212> TYPE: PRT
<213> ORGANISM: Magnaporthe grisea

<400> SEQUENCE: 44

Met Ala Leu Ile His Ile Phe Phe Leu Leu Ser Ser Leu Val Ser Leu
1               5                   10                  15
Ala Gln Gln Ala Glu Leu Ala Asp Tyr Val Phe Thr Asn Thr Gly Ser
                20                  25                  30
Glu Gly Gly Gly Asn Thr Phe Pro Gly Val Ser Glu Pro Phe Gly Met
            35                  40                  45
Val Lys Leu Gly Pro Asp Val Phe Gln Asp Arg Val Asp Ser Tyr Ser
    50                  55                  60
Gly Tyr Leu Pro Asn Gly Lys Ile Lys Ala Phe Ser Met Leu His Leu
65                  70                  75                  80
Ser Gly Thr Gly Gly Ala Pro Lys Tyr Gly Val Val Ala Gln Met Pro
                85                  90                  95
Val Val Gly Asn Ile Ala Asn Pro Leu Asp Asp Tyr Leu Ala Ala Arg
            100                 105                 110
Asp Ala Pro Asp Met Thr Glu Val Gly Tyr Tyr Lys Ser Arg Leu Ala
        115                 120                 125
Thr Gly Ile Thr Val Glu Leu Ala Ala Ser Ser Arg Ala Gly Met Leu
    130                 135                 140
Gln Tyr Thr Phe Pro Ser Gly Pro Thr Pro Arg Asn Val Ile Val Asp
145                 150                 155                 160
Val Ser His Val Leu Pro Ser Tyr Arg Gly Gln Gly Leu Gly Gln Arg
                165                 170                 175
Tyr Leu Gly Gly Ser Ile Ser Val Asp Arg Asp Asp Ser Gly Asn Val
            180                 185                 190
Gln Tyr Lys Gly Ser Gly Ser Tyr Asp Asn Gly Trp Asn Arg Ala Pro
```

```
            195                 200                 205
Lys Trp Thr Val Tyr Phe Cys Gly Ala Phe Asn Ser Ser Ala Thr Phe
210                 215                 220

Lys Thr Phe Val Gly Thr Asn Ala Thr Ala Asn Thr Leu Ser Lys Phe
225                 230                 235                 240

Ser Asn Asp Asn Lys Val Glu Ser Leu Ser Arg Leu Gly Ala Val Phe
                245                 250                 255

Thr Phe Asp Ala Ala Asn Val Val Ser Arg Val Gly Val Ser Phe Ile
                260                 265                 270

Ser Glu Asp Gln Ala Cys Thr Asn Leu Asp Gln Gln Ile Pro Glu Ser
            275                 280                 285

Thr Ser Ile Ser Gln Leu Arg Gln Lys Thr Arg Asp Val Trp Asn Thr
        290                 295                 300

Asp Val Leu Ser Arg Val Ala Ser Asn Asp Lys Asn Thr Thr Lys Leu
305                 310                 315                 320

Gln His Leu Tyr Thr Ser Met Tyr Phe Met His Leu Met Pro Ile Asn
                325                 330                 335

Lys Thr Gly Glu Asn Pro Glu Trp Lys Ser Thr Glu Pro Tyr Tyr Asp
                340                 345                 350

Asp Ile Phe Thr Leu Trp Asp Leu Phe Arg Cys Thr Thr Ala Leu Leu
            355                 360                 365

His Val Phe Gln Pro Lys Val Tyr Glu Glu Phe Ile Arg Ser Leu Ile
        370                 375                 380

Asp Thr Trp Arg His Glu Gly Tyr Leu Pro Asp Ala Arg Ser Ser Phe
385                 390                 395                 400

Phe Asn Gly Ala Thr Gln Gly Gly Ser Asn Ala Asp Thr Val Leu Ala
                405                 410                 415

Asp Ala Tyr Val Lys Gly Val Arg Gly Gln Ile Asn Trp Glu Asp Gly
                420                 425                 430

Phe Ala Ala Met Val Lys Asp Ala Glu Val Val Pro Ala Leu Asn Asp
            435                 440                 445

Asp Pro Arg Asp Lys Thr Gly Ser Thr Lys Glu Gly Arg Gly Ala Leu
450                 455                 460

Pro Asp Trp Lys Glu Arg Gly Phe Leu Ser Thr Lys Phe Glu Arg Ser
465                 470                 475                 480

Val Ser Arg Ala Val Glu Tyr Ser Gln Asn Asp Phe Gly Leu Ser Gln
                485                 490                 495

Val Ala Lys Gly Leu Gly Lys Thr Ala Glu Ala Glu Lys Tyr Met Lys
                500                 505                 510

Arg Ser Arg Gln Trp Arg Ser His Trp Asn Lys Asp Met Lys Ala Leu
            515                 520                 525

Gly Phe Ser Gly Phe Leu Gly Pro Lys Gly Glu Asp Gly Gln Phe Glu
        530                 535                 540

Glu Gln Asp Pro Leu Asn Cys Arg Gly Cys Tyr Trp Gly Asp Asn Tyr
545                 550                 555                 560

Tyr Glu Ala Leu Pro Trp Glu Tyr Thr Phe Gly Pro His His Asp Ile
                565                 570                 575

Ser Thr Leu Ile Asp Tyr Ser Gly Gly Pro Arg Arg Phe Ala Ser Arg
                580                 585                 590

Leu Gln Trp Thr Phe Glu Pro Asn Val Arg Pro Lys Gly His Glu Arg
            595                 600                 605

Phe Asn Arg Met Ile Phe Asp Pro Gly Asn Glu Pro Ser Phe Thr Thr
        610                 615                 620
```

```
Pro Tyr Leu Tyr Asn Phe Val Gly Arg Gln Asp Met Thr Val Asn Thr
625                 630                 635                 640

Thr Arg Tyr Leu Gly Lys Thr Tyr Tyr Gly Val Arg Pro Asn Gly Leu
            645                 650                 655

Pro Gly Asn Ser Asp Ala Gly Ala Met Glu Ser Trp Ile Leu Trp Val
        660                 665                 670

Met Leu Gly Leu Tyr Pro Met Thr Gly Gln Thr Thr Phe Leu Ile Gly
            675                 680                 685

Ser Pro Trp Leu Asp Asp Ile Thr Ile Ser Leu Gly Asp Gly Lys Ser
        690                 695                 700

Leu Gln Ile Thr Ser Thr Gly Gly Ser Glu Asp Ser Phe Tyr Val Pro
705                 710                 715                 720

Val Ala Val Thr Val Pro Ile Val Val Ala Ala Phe Ala Ile Cys
            725                 730                 735

Val Thr Phe Phe Phe Ile Arg Arg Arg Arg Ala Ala Ala Gln Lys
            740                 745                 750

Ala Leu Ser Ser Gly Ser Gly Thr Pro Glu Ser Gly Ile Glu Thr Leu
        755                 760                 765

Thr Pro Thr Ser Gln Pro Val Asp Thr Ser Lys Thr Asn Val Gln Val
    770                 775                 780

Glu Ile Val Gly Ala Pro Pro Leu Asp Ser Thr Gln Gly Ala Asn Ile
785                 790                 795                 800

Ala Gln Leu Pro Pro Pro Val Ala Asn Arg
                805                 810

<210> SEQ ID NO 45
<211> LENGTH: 701
<212> TYPE: PRT
<213> ORGANISM: Bacteroides sp.

<400> SEQUENCE: 45

Met Lys Ile Leu His Phe Cys Ala Ala Ile Thr Met Ala Ala Met Leu
1               5                   10                  15

Ser Gly Cys Asn Gly Gly Gln Ser Gln Thr Ala Asn Arg Thr Pro Val
            20                  25                  30

Asp Tyr Val Asn Pro Tyr Ile Gly Asn Ile Ser His Leu Leu Val Pro
        35                  40                  45

Thr Phe Pro Thr Ile Gln Leu Pro Asn Ser Met Leu Arg Val Tyr Pro
    50                  55                  60

Glu Arg Ala Asp Tyr Thr Thr Glu Leu Leu Asn Gly Leu Pro Leu Ile
65                  70                  75                  80

Val Thr Asn His Arg Glu Arg Ser Ala Phe Asn Leu Ser Pro Tyr Gln
                85                  90                  95

Gly Lys Glu Leu Gln Pro Ile Ile Thr Tyr Asn Tyr Asp Asn Glu His
            100                 105                 110

Leu Thr Pro Tyr Ser Tyr Glu Val Asp Leu Asn Asp Asn Ser Met Lys
        115                 120                 125

Ala Glu Tyr Ala Leu Ser His Gln Ser Ala Leu Tyr Arg Ile Thr Phe
    130                 135                 140

Glu Ala Asp Lys Pro Ala Tyr Ile Ile Val Asn Ser Arg Asn Gly Ser
145                 150                 155                 160

Ile His Val Gly Glu Asn Phe Ile Ser Gly His Gln Gln Leu Ser Ala
                165                 170                 175

Asn Thr Asn Val Tyr Val Tyr Ile Glu Pro Gln Glu Lys Pro Val Ser
```

```
              180                 185                 190
Thr Gly Ile Leu Lys Asp Gly Val Ile Glu Ala Ser Lys Asp Asn Ala
              195                 200                 205
Glu Gly Ile Asn Ala Cys Ala Ala Trp Arg Phe Ala Asp Gly Thr Thr
              210                 215                 220
Thr Val Ser Leu Arg Tyr Gly Ile Ser Phe Ile Ser Glu Glu Gln Ala
225                 230                 235                 240
Glu Lys Asn Met Arg Asn Glu Leu Lys Asp Tyr Asn Ile Lys Asn Leu
              245                 250                 255
Ala Lys Thr Gly Arg Gln Ile Trp Asn Glu Ala Leu Gly Arg Ile Lys
              260                 265                 270
Val Glu Gly Gly Thr Glu Asp Asp Lys Thr Val Leu Tyr Ser Ser Phe
              275                 280                 285
Tyr Arg Thr Phe Glu Arg Pro Ile Cys Met Ser Glu Ala Gly Gly Arg
              290                 295                 300
Tyr Phe Ser Ala Phe Asp Gly Glu Val His Asp Asp Asn Gly Thr Pro
305                 310                 315                 320
Phe Tyr Asn Asp Asp Trp Ile Trp Asp Thr Tyr Arg Ala Ala His Pro
              325                 330                 335
Leu Arg Thr Leu Ile Asp Gln Lys Lys Glu Glu Asp Ile Ile Ala Ser
              340                 345                 350
Phe Leu Leu Met Ala Glu Gln Met Gly Thr Met Trp Met Pro Thr Phe
              355                 360                 365
Pro Glu Val Thr Gly Asp Ser Arg Arg Met Asn Ser Asn His Ala Val
              370                 375                 380
Ala Thr Ile Ala Asp Ala Leu Ala Lys Gly Leu Asn Val Asp Ala Ala
385                 390                 395                 400
Lys Ala Tyr Glu Ala Cys Arg Lys Gly Ile Glu Glu Lys Thr Leu Ala
              405                 410                 415
Pro Trp Ser Gly Ala Ala Ala Gly Trp Leu Asp Asn Phe Tyr Arg Glu
              420                 425                 430
Asn Gly Tyr Ile Pro Ala Leu Arg Pro Asp Glu Lys Glu Thr Asp Pro
              435                 440                 445
Asn Val His Pro Phe Glu Lys Arg Gln Pro Val Ala Val Thr Leu Gly
              450                 455                 460
Thr Ser Tyr Asp Gln Trp Cys Leu Ser Arg Ile Ala Glu Ile Leu Gly
465                 470                 475                 480
Lys Lys Asp Glu Ala Ala His Tyr Leu Gln Cys Ser Tyr Asn Tyr Arg
              485                 490                 495
Asn Leu Phe Asn Lys Glu Thr Gly Phe Phe His Pro Lys Asp Lys Glu
              500                 505                 510
Gly Asn Trp Ile Thr Pro Phe Asp Tyr Arg Tyr Ala Gly Gly Met Gly
              515                 520                 525
Ala Arg Glu Tyr Tyr Gly Glu Asn Asn Gly Trp Val Tyr Arg Trp Asp
              530                 535                 540
Val Pro His Asn Val Ala Asp Leu Ile Asn Leu Met Gly Gly Lys Glu
545                 550                 555                 560
Gln Phe Ile Ala Asn Leu Asp Arg Thr Phe Ser Glu Pro Leu Gly Arg
              565                 570                 575
Ser Lys Tyr Glu Phe Tyr Ala Gln Leu Pro Asp His Thr Gly Asn Val
              580                 585                 590
Gly Gln Phe Ser Met Ala Asn Glu Pro Ser Leu His Val Pro Tyr Leu
              595                 600                 605
```

```
Tyr Asn Tyr Ala Gly Gln Pro Trp Lys Thr Gln Lys Arg Ile Arg Gln
        610                 615                 620

Met Leu Lys Thr Trp Phe Arg Asn Asp Leu Met Gly Met Pro Gly Asp
625                 630                 635                 640

Glu Asp Gly Gly Gly Met Thr Ser Phe Val Val Phe Ser Ser Leu Gly
                645                 650                 655

Phe Tyr Pro Val Thr Pro Gly Ala Pro Val Tyr Asn Ile Gly Ser Pro
            660                 665                 670

Leu Phe Thr His Ala Glu Ile Thr Leu Ser Asn Gly Ser Val Phe Glu
        675                 680                 685

Ile Glu Ala Pro Asn Val Ser Glu Glu Asn Lys Tyr Ile
690                 695                 700

<210> SEQ ID NO 46
<211> LENGTH: 701
<212> TYPE: PRT
<213> ORGANISM: Bacteroides sp.

<400> SEQUENCE: 46

Met Lys Ile Leu His Phe Cys Ala Ala Ile Thr Met Ala Ala Met Leu
1               5                   10                  15

Ser Gly Cys Asn Gly Gly Gln Ser Gln Thr Ala Asn Arg Ala Pro Val
            20                  25                  30

Asp Tyr Val Asn Pro Tyr Ile Gly Asn Ile Ser His Leu Leu Val Pro
        35                  40                  45

Thr Phe Pro Thr Ile Gln Leu Pro Asn Ser Met Leu Arg Val Tyr Pro
    50                  55                  60

Glu Arg Ala Asp Tyr Thr Thr Glu Leu Leu Asn Gly Leu Pro Leu Ile
65                  70                  75                  80

Val Thr Asn His Arg Glu Arg Ser Ala Phe Asn Leu Ser Pro Tyr Gln
                85                  90                  95

Gly Lys Glu Leu Arg Pro Ile Ile Thr Tyr Asn Tyr Asp Asn Glu His
            100                 105                 110

Leu Thr Pro Tyr Ser Tyr Glu Val Asp Leu Asn Asp Asn Ser Met Lys
        115                 120                 125

Ala Glu Tyr Ala Leu Ser His Gln Ser Ala Leu Tyr Arg Ile Thr Phe
    130                 135                 140

Glu Ala Asp Lys Pro Ala Tyr Ile Val Asn Ser Arg Asn Gly Ser
145                 150                 155                 160

Ile His Val Gly Glu Asn Phe Ile Ser Gly His Gln Gln Leu Ser Ala
                165                 170                 175

Asn Thr Asn Val Tyr Val Tyr Ile Glu Pro Gln Glu Lys Pro Val Ser
            180                 185                 190

Thr Gly Ile Leu Lys Asp Gly Val Ile Glu Ala Ser Lys Asp Asn Ala
        195                 200                 205

Glu Gly Ile Asn Ala Cys Ala Ala Trp Arg Phe Ala Asp Gly Thr Thr
    210                 215                 220

Thr Val Ser Leu Arg Tyr Gly Ile Ser Phe Ile Ser Glu Glu Gln Ala
225                 230                 235                 240

Glu Lys Asn Met Arg Asn Glu Leu Lys Asp Tyr Asn Ile Lys Asn Leu
                245                 250                 255

Ala Lys Ala Gly Arg Gln Ile Trp Asn Glu Ala Leu Gly Arg Ile Lys
            260                 265                 270

Val Glu Gly Gly Thr Glu Asp Asp Lys Thr Val Leu Tyr Ser Ser Phe
```

-continued

```
            275                 280                 285
Tyr Arg Thr Phe Glu Arg Pro Ile Cys Met Ser Glu Ala Gly Gly Arg
290                 295                 300
Tyr Phe Ser Ala Phe Asp Gly Glu Val His Asp Asn Gly Thr Pro
305                 310                 315                 320
Phe Tyr Asn Asp Asp Trp Ile Trp Asp Thr Tyr Arg Ala Ala His Pro
            325                 330                 335
Leu Arg Thr Leu Ile Asp Gln Lys Lys Glu Glu Asp Ile Ile Ala Ser
            340                 345                 350
Phe Leu Leu Met Ala Glu Gln Met Gly Thr Met Trp Met Pro Thr Phe
            355                 360                 365
Pro Glu Val Thr Gly Asp Ser Arg Arg Met Asn Ser Asn His Ala Val
370                 375                 380
Ala Thr Ile Ala Asp Ala Leu Ala Lys Gly Leu Asn Ile Asp Ala Ala
385                 390                 395                 400
Lys Ala Tyr Glu Ala Cys Arg Lys Gly Ile Glu Glu Lys Thr Leu Ala
            405                 410                 415
Pro Trp Ser Gly Ala Ala Ala Gly Trp Leu Asp Asn Phe Tyr Arg Glu
            420                 425                 430
Asn Gly Tyr Ile Pro Ala Leu Arg Pro Asp Glu Lys Glu Thr Asp Pro
            435                 440                 445
Asn Val His Pro Phe Glu Lys Arg Gln Pro Val Ala Val Thr Leu Gly
450                 455                 460
Thr Ser Tyr Asp Gln Trp Cys Leu Ser Arg Ile Ala Glu Ile Leu Gly
465                 470                 475                 480
Lys Lys Asp Glu Ala Ala His Tyr Leu Gln Cys Ser Tyr Asn Tyr Arg
            485                 490                 495
Asn Leu Phe Asn Lys Glu Thr Gly Phe Phe His Pro Lys Asp Lys Glu
            500                 505                 510
Gly Asn Trp Ile Thr Pro Phe Asp Tyr Arg Tyr Ala Gly Gly Met Gly
            515                 520                 525
Ala Arg Glu Tyr Tyr Gly Glu Asn Asn Gly Trp Val Tyr Arg Trp Asp
530                 535                 540
Val Pro His Asn Val Ala Asp Leu Ile Asn Leu Met Gly Gly Lys Glu
545                 550                 555                 560
Gln Phe Ile Ala Asn Leu Asp Arg Thr Phe Ser Glu Pro Leu Gly Arg
            565                 570                 575
Ser Lys Tyr Glu Phe Tyr Ala Gln Leu Pro Asp His Thr Gly Asn Val
            580                 585                 590
Gly Gln Phe Ser Met Ala Asn Glu Pro Ser Leu His Val Pro Tyr Leu
            595                 600                 605
Tyr Asn Tyr Ala Gly Gln Pro Trp Lys Thr Gln Lys Arg Ile Arg Gln
            610                 615                 620
Met Leu Lys Thr Trp Phe Arg Asn Asp Leu Met Gly Met Pro Gly Asp
625                 630                 635                 640
Glu Asp Gly Gly Gly Met Thr Ser Phe Val Val Phe Ser Ser Leu Gly
                        645                 650                 655
Phe Tyr Pro Val Thr Pro Gly Ala Pro Val Tyr Asn Ile Gly Ser Pro
                    660                 665                 670
Leu Phe Thr His Ala Glu Ile Thr Leu Ser Asn Gly Ser Val Phe Glu
            675                 680                 685
Ile Glu Ala Pro Asn Val Ser Glu Glu Asn Lys Tyr Ile
            690                 695                 700
```

<210> SEQ ID NO 47
<211> LENGTH: 706
<212> TYPE: PRT
<213> ORGANISM: Bacteroides sp.

<400> SEQUENCE: 47

```
Met Lys Thr Lys Leu Lys Thr Ser Met Ala Leu Leu Ala Ser Ala Phe
 1               5                  10                  15

Leu Trp Val Ser Cys Ala Gly Gly Gly Thr Pro Pro Ser Ala Met
             20                  25                  30

Asp Pro Val Asp Tyr Val Asn Pro Tyr Met Gly Asn Ile Ser His Leu
             35                  40                  45

Leu Val Pro Thr Phe Pro Thr Val His Leu Pro Asn Ser Met Leu Arg
         50                  55                  60

Val Tyr Pro Glu Arg Ala Asp Phe Thr Gly Asp Arg Leu Gly Gly Leu
 65                  70                  75                  80

Pro Ile Ile Val Thr Asn His Arg Glu Arg Ser Ala Phe Asn Leu Cys
                 85                  90                  95

Pro Tyr Gln Gly Asp Glu Ser Gly Leu Arg Pro Val Ile Ala Tyr Ser
            100                 105                 110

Tyr Asp Arg Glu Lys Ile Leu Pro Tyr Arg Tyr Gln Val Tyr Leu Asp
            115                 120                 125

Asn Gly Glu Ile Asp Val Asp Phe Ala Pro Ser His Gln Ser Ala Val
        130                 135                 140

Tyr Ser Leu Thr Phe Glu Lys Glu Gly Pro Ala Tyr Leu Val Phe Asn
145                 150                 155                 160

Ser Arg Asn Gly Gln Leu Gln Val Asn Gly Asn Ala Val Ser Gly Tyr
                165                 170                 175

Gln Tyr Ile Asp Lys Lys Thr Lys Val Phe Leu Tyr Ala Glu Thr Asn
            180                 185                 190

Gln Lys Pro Val Lys Ala Gly Val Leu Ser Asn Gly Ser Val Lys Tyr
            195                 200                 205

Asp Glu Thr Ser Val Glu Gly Thr Asn Ala Ala Ile Ala Leu Ser Phe
        210                 215                 220

Gly Glu Asp Val Lys Lys Leu Gly Val Arg Tyr Gly Ile Ser Phe Ile
225                 230                 235                 240

Ser Glu Glu Gln Ala Lys Lys Asn Leu Glu Arg Glu Ile Ala Ala Tyr
                245                 250                 255

Asp Val Asp Val Val Ala Lys Ile Ala Arg Asn Asp Trp Asn Asp Ala
            260                 265                 270

Leu Gly Lys Ile Gln Val Gln Gly Gly Thr Lys Asp Glu Lys Thr Val
        275                 280                 285

Phe Tyr Thr Ser Leu Tyr Arg Cys Tyr Glu Arg Pro Ile Asn Leu Ser
290                 295                 300

Glu Asp Gly His Tyr Tyr Ser Ala Phe Asp Gly Lys Ile His Glu Asp
305                 310                 315                 320

Gly Gly Arg Pro Phe Tyr Thr Asp Asp Trp Ile Trp Asp Thr Tyr Arg
                325                 330                 335

Ala Thr His Pro Leu Arg Val Leu Ile Asp Asn Glu Arg Glu Asn Asp
            340                 345                 350

Ile Ile Asn Ser Tyr Leu Leu Met Ala Glu Gln Met Gly Thr Asp Trp
        355                 360                 365

Met Pro Thr Phe Pro Glu Val Thr Gly Asp Thr Arg Arg Met Asn Ser
```

```
                370                 375                 380
Asn His Ala Val Ala Thr Val Ile Asp Ala Tyr Arg Lys Gly Leu Arg
385                 390                 395                 400

Gly Phe Glu Leu Glu Lys Ala Tyr Ile Ala Cys Lys Lys Gly Ile Glu
                405                 410                 415

Glu Lys Thr Leu Ile Pro Trp Ser Ala Pro Ala Gly Trp Leu Asp
                420                 425                 430

Asp Phe Tyr Lys Glu His Gly Tyr Ile Pro Ala Leu Arg Pro Gly Glu
                435                 440                 445

Lys Glu Thr Val Pro Asn Val Ser Ile Trp Glu Lys Arg Gln Pro Ile
450                 455                 460

Ala Val Thr Leu Gly Thr Ser Tyr Asp Glu Trp Cys Leu Ser Gln Ile
465                 470                 475                 480

Ala Gln Glu Leu Gly Lys Lys Asp Glu Ala Asp Tyr Tyr Leu Arg Arg
                485                 490                 495

Ser Tyr Asn Tyr Arg Asn Val Phe Asn Pro Glu Thr Gly Phe Phe His
                500                 505                 510

Pro Lys Asp Lys Asp Gly Lys Phe Ile Tyr Pro Leu Asp Tyr Arg Tyr
                515                 520                 525

Asp Gly Gly Leu Gly Ala Arg Asp Tyr Tyr Asp Glu Asn Asn Gly Tyr
                530                 535                 540

Ile Tyr Arg Trp Asp Val Gln His Asn Ile Gly Asp Leu Ile Ser Leu
545                 550                 555                 560

Ile Gly Asn Glu Ala Phe Thr Ser Ala Leu Asp Ser Met Phe Asn
                565                 570                 575

Thr Pro Leu Gly Met Ser Lys Trp Gln Phe Tyr Ser Thr Leu Pro Asp
                580                 585                 590

His Thr Gly Asn Val Gly Met Phe Ser Met Ala Asn Glu Pro Ser Leu
                595                 600                 605

His Ile Pro Tyr Leu Tyr Asn Tyr Ala Gly Lys Pro Trp Met Thr Gln
                610                 615                 620

Lys Arg Ile Arg Thr Leu Leu Asn Gln Trp Phe Arg Asn Asp Leu Met
625                 630                 635                 640

Gly Val Pro Gly Asp Glu Asp Gly Gly Met Ser Ala Phe Val Val
                645                 650                 655

Phe Ser Gln Met Gly Phe Tyr Pro Val Thr Pro Gly Ser Pro Thr Tyr
                660                 665                 670

Asn Ile Gly Ser Pro Met Phe Thr Asp Val Lys Val Asp Met Gly Asn
                675                 680                 685

Gly Asn Thr Phe Glu Ile Arg Ala Asn Asn Ala Ser Asp Glu Asn Lys
690                 695                 700

Tyr Val
705

<210> SEQ ID NO 48
<211> LENGTH: 691
<212> TYPE: PRT
<213> ORGANISM: Bacteroides sp.

<400> SEQUENCE: 48

Met Ala Ser Ser Cys Val Tyr Ser Pro Pro Lys Glu Pro Val Asp Tyr
1               5                   10                  15

Val Asn Pro Asn Ile Gly Thr Ile Gly His Leu Leu Val Ala Thr Ala
                20                  25                  30
```

```
Ser Met Val Gln Leu Pro His Gly Met Val Gln Ile Gly Gln Asn Pro
         35                  40                  45
Tyr Pro Pro Leu Ala Asp Arg Tyr Leu Ala Asp Arg Ile Ser Gly Phe
 50                  55                  60
Ser Val Arg Ala Leu Pro Lys Tyr Thr Thr Lys Pro Phe Ser Trp Ile
 65                  70                  75                  80
Met Ala Thr Thr Gly Ala Pro Arg Ile Asn Pro Asn Asp Tyr Ala Ser
                 85                  90                  95
Gly Phe Asp His Asp Phe Glu Lys Val Thr Pro Tyr Tyr Ser Trp Ile
             100                 105                 110
Leu Leu Glu Asp Tyr Asp Ile Glu Ala Ala Met Thr Val Thr Gln His
             115                 120                 125
Ser Ser Phe Tyr Lys Phe Lys Tyr Pro Lys Ser Ser Glu Ser Asn Ile
 130                 135                 140
Leu Met Asn Asn Asn Gln Cys Val Arg Val Val Gly Asn Asn Cys Ile
 145                 150                 155                 160
Glu Ser Val Glu Ala Val Asp Ser Thr Gln Thr Ala Tyr Tyr Tyr Ala
             165                 170                 175
Ile Phe Ser Lys Pro Phe Arg Ser Tyr Val Thr Trp Lys Asp Ser Leu
             180                 185                 190
Ile Ser Gln Asp Val Lys Gln Glu Gly Leu Asp Ile Gly Ala Leu Val
             195                 200                 205
Thr Phe Asp Thr Ser Gln Asp Glu Glu Ile Met Val Lys Ile Gly Val
             210                 215                 220
Ser Phe Ile Asp Met Glu Gln Ala Lys Arg Asn Leu Glu Met Glu Ile
 225                 230                 235                 240
Pro Ala Trp Asp Phe Asp Lys Val Lys Asn Asp Gly Arg Glu Ile Trp
             245                 250                 255
Asn Asn Ala Leu Gly Lys Ile Lys Ile Glu Gly Gly Thr Asp Lys Gln
             260                 265                 270
Lys Thr Ile Phe Tyr Ser Ala Leu Tyr Arg Val Met Leu Gly Ser Gln
             275                 280                 285
Thr Leu Asp Arg Ser Glu Tyr Gly Arg Tyr Tyr Ser Arg Leu Asp Lys
             290                 295                 300
Gln Val His Asp Thr Glu Gly His Ala Phe Tyr Gln Val Gly Ser Asn
 305                 310                 315                 320
Trp Gly Ser His His Ser Leu Phe Pro Leu Val Leu Leu Glu Pro
                 325                 330                 335
Glu Ile Gln Asn Asp Ile Met Arg Ser Tyr Ile Arg Met Gln Asp Glu
             340                 345                 350
Gly Asp Trp Leu Val Asn Ser Gly Tyr Arg Asn Met Ile Gly Arg
             355                 360                 365
His Glu Val Ala Thr Ile Thr Asp Thr Tyr Met Lys Gly Phe Arg Asp
             370                 375                 380
Phe Asp Ile Glu Lys Ala Tyr Glu Ala Met Lys Arg Asn Ser Lys Glu
 385                 390                 395                 400
Ala Thr Met Leu Ser Arg His Ile Gly Lys Asp Trp Arg Leu Asn Glu
                 405                 410                 415
Leu Asp Lys Val Tyr Leu Glu Lys Gly Phe Tyr Pro Ala Lys Pro Ser
             420                 425                 430
Asp Gln Pro Glu Trp Val Lys Glu Val Gly Phe Gly Arg Gln Ser Val
             435                 440                 445
Ala Leu Thr Leu Glu Asn Cys Tyr Asp Asp Trp Cys Met Ser Ile Leu
```

```
            450                 455                 460
Ala Lys Glu Leu Gly Lys Glu Asp Asp Tyr Gln Tyr Tyr Leu Asn Arg
465                 470                 475                 480

Ala Tyr Asn Tyr Arg Asn Val Phe Asp Ser Lys Ser Gly Phe Met Arg
                485                 490                 495

Pro Lys Thr Ala Asp Gly Lys Trp Ile Glu Pro Phe Asp Pro Ile Trp
            500                 505                 510

Ser Gly Gly Gln Gly Gly Arg Asp Phe Tyr Thr Glu Asn Asn Gly Trp
            515                 520                 525

Asn Tyr Thr Trp Tyr Val Leu His Asp Pro Gln Gly Leu Ile Asn Leu
            530                 535                 540

Met Gly Gly Gln Glu Pro Phe Val Ala Lys Leu Gln Gln Met Phe Glu
545                 550                 555                 560

Thr Asn Val Pro Leu Tyr Lys Lys Tyr Asp Phe Leu Lys Gln Tyr Pro
                565                 570                 575

Asp Met Thr Gly Trp Ile Gly Met Tyr Ser His Gly Asn Glu Ile Thr
            580                 585                 590

Trp His Ile Pro Tyr Leu Tyr Asn Tyr Ala Gly Lys Pro Trp Met Thr
            595                 600                 605

Gln Arg Arg Ile Arg Gln Ile Leu Asp Leu Trp Tyr Gly Asp Gly Pro
610                 615                 620

Leu Gly Phe Cys Gly Asp Glu Asp Tyr Gly Glu Met Ser Ser Trp Tyr
625                 630                 635                 640

Ile Leu Ser Ala Met Gly Phe Tyr Thr Val Ala Pro Gly Arg Pro Val
                645                 650                 655

Tyr Asp Ile Gly Ser Pro Leu Phe Glu Lys Ser Thr Ile Asp Ile Gly
            660                 665                 670

Asp Gly Lys Lys Phe Thr Ile Glu Cys Arg Asn Ile Ser Thr Gln Asn
            675                 680                 685

Lys Tyr Ile
    690

<210> SEQ ID NO 49
<211> LENGTH: 706
<212> TYPE: PRT
<213> ORGANISM: Parabacteroides distasoni

<400> SEQUENCE: 49

Met Lys Thr Lys Leu Lys Thr Ser Met Ala Leu Leu Ala Ser Val Phe
1               5                   10                  15

Leu Trp Val Ser Cys Ala Gly Gly Gly Thr Ser Pro Ser Ala Met
                20                  25                  30

Asp Pro Val Asp Tyr Val Asn Pro Tyr Met Gly Asn Ile Ser His Leu
            35                  40                  45

Leu Val Pro Thr Phe Pro Thr Val His Leu Pro Asn Ser Met Leu Arg
50                  55                  60

Val Tyr Pro Glu Arg Ala Asp Phe Thr Gly Asp Arg Leu Gly Gly Leu
65                  70                  75                  80

Pro Ile Ile Val Thr Asn His Arg Glu Arg Ser Ala Phe Asn Leu Cys
                85                  90                  95

Pro Tyr Gln Gly Asp Glu Ser Gly Leu Arg Pro Val Ile Ala Tyr Ser
            100                 105                 110

Tyr Asp Arg Glu Lys Ile Leu Pro Tyr Arg Tyr Gln Val Tyr Leu Asp
            115                 120                 125
```

```
Asn Glu Glu Ile Asp Val Asp Phe Ala Pro Ser His Gln Ser Ala Val
    130                 135                 140

Tyr Ser Leu Thr Phe Lys Glu Gly Pro Ala Tyr Leu Val Phe Asn
145                 150                 155                 160

Ser Arg Asn Gly Gln Leu Gln Val Asn Gly Asn Ala Val Ser Gly Tyr
                165                 170                 175

Gln Tyr Ile Asp Lys Lys Thr Lys Val Phe Leu Tyr Ala Glu Thr Asn
            180                 185                 190

Gln Lys Pro Val Lys Ala Gly Val Leu Ser Asn Gly Ser Val Asn Tyr
        195                 200                 205

Asn Glu Thr Ser Val Glu Gly Ile Asn Ala Ala Ile Ala Leu Ser Phe
210                 215                 220

Gly Glu Asp Val Lys Lys Leu Gly Val Arg Tyr Gly Ile Ser Phe Ile
225                 230                 235                 240

Ser Glu Glu Gln Ala Lys Lys Asn Leu Glu Arg Glu Ile Ala Ala Tyr
                245                 250                 255

Asp Val Asp Val Ala Lys Ile Ala Arg Asn Asp Trp Asn Asp Ala
            260                 265                 270

Leu Gly Lys Ile Gln Val Gln Gly Gly Thr Lys Asp Glu Lys Thr Val
        275                 280                 285

Phe Tyr Thr Ser Leu Tyr Arg Cys Tyr Glu Arg Pro Ile Asn Leu Ser
290                 295                 300

Glu Asp Gly His Tyr Tyr Ser Ala Phe Asp Gly Lys Ile His Glu Asp
305                 310                 315                 320

Gly Gly Arg Ser Phe Tyr Thr Asp Asp Trp Ile Trp Asp Thr Tyr Arg
                325                 330                 335

Ala Thr His Pro Leu Arg Val Leu Ile Asp Asn Glu Arg Glu Asn Asp
            340                 345                 350

Ile Ile Asn Ser Tyr Leu Leu Met Ala Glu Gln Met Gly Thr Asp Trp
        355                 360                 365

Met Pro Thr Phe Pro Glu Val Thr Gly Asp Thr Arg Arg Met Asn Ser
370                 375                 380

Asn His Ala Val Ala Thr Val Ile Asp Ala Tyr Arg Lys Gly Leu Arg
385                 390                 395                 400

Gly Phe Glu Leu Glu Lys Ala Tyr Ile Ala Cys Lys Lys Gly Ile Glu
                405                 410                 415

Glu Lys Thr Leu Ile Pro Trp Ser Ala Ala Pro Ala Gly Trp Leu Asp
            420                 425                 430

Asp Phe Tyr Lys Glu His Gly Tyr Ile Pro Ala Leu Arg Pro Gly Glu
        435                 440                 445

Lys Glu Thr Val Pro Asn Val Ser Ile Trp Glu Lys Arg Gln Pro Ile
450                 455                 460

Ala Val Thr Leu Gly Thr Ser Tyr Asp Glu Trp Cys Leu Ser Gln Ile
465                 470                 475                 480

Ala Gln Glu Leu Gly Lys Lys Asp Glu Ala Asp Tyr Tyr Leu Arg Arg
                485                 490                 495

Ser Tyr Asn Phe Asn Thr Pro Leu Gly Met Ser Lys Trp Gln Phe Tyr
            500                 505                 510

Ser Thr Leu Pro Asp His Thr Gly Asn Val Gly Met Phe Ser Met Ala
        515                 520                 525

Asn Glu Pro Ser Leu His Ile Pro Tyr Leu Tyr Asn Tyr Ala Gly Lys
530                 535                 540

Pro Trp Met Thr Gln Lys Arg Ile Arg Thr Leu Leu Asn Gln Trp Phe
```

```
              545                 550                 555                 560
Arg Asn Asp Leu Met Gly Val Tyr Arg Asn Val Phe Asn Pro Glu Thr
                    565                 570                 575
Gly Phe Phe His Pro Lys Asp Lys Asp Gly Lys Phe Ile Tyr Pro Leu
                580                 585                 590
Asp Tyr Arg Tyr Asp Gly Gly Leu Gly Ala Arg Asp Tyr Tyr Asp Glu
                595                 600                 605
Asn Asn Gly Tyr Ile Tyr Arg Trp Asp Val Gln His Asn Ile Gly Asp
                610                 615                 620
Leu Ile Ser Leu Ile Gly Gly Asn Glu Ala Phe Thr Ser Ala Leu Asp
625                 630                 635                 640
Ser Met Pro Gly Asp Glu Asp Gly Gly Met Ser Ala Phe Val Val
                    645                 650                 655
Phe Ser Gln Met Gly Phe Tyr Pro Val Thr Pro Gly Ser Pro Thr Tyr
                660                 665                 670
Asn Ile Gly Ser Pro Met Phe Thr Asp Val Lys Val Asp Met Gly Asn
                675                 680                 685
Gly Asn Thr Phe Glu Ile Arg Ala Asn Asn Ala Ser Asp Glu Asn Lys
                690                 695                 700
Tyr Val
705

<210> SEQ ID NO 50
<211> LENGTH: 1650
<212> TYPE: PRT
<213> ORGANISM: Cellulosimicrobium cellulans

<400> SEQUENCE: 50

Ala Pro Glu Pro Pro Ser Ala Asp Tyr Ala Ser Leu Val Asp Val Phe
1               5                  10                  15
Val Gly Thr Glu Gly Asp Phe Gly Asn Asp Met Pro Ala Ala Gln Ala
                20                  25                  30
Pro Asn Gly Leu Ala Lys Val Asn Pro Arg Thr Thr Pro Gly Arg Asn
                35                  40                  45
Asn Thr Gly Tyr Asp Tyr Ala Gln Ser Lys Ile Ser Gly Phe Thr His
            50                  55                  60
Thr Asn Leu Asp Gly Val Gly Gly Ser Gly Gly Gly Asp Leu Leu
65                  70                  75                  80
Val Val Pro Thr Ser Gly Ser Tyr Thr Ala Arg Pro Gly Thr Gly Thr
                    85                  90                  95
Tyr Ala His Pro Phe Ser His Asp Asp Glu Asp Ala Gly Pro Gly Phe
                100                 105                 110
Tyr Ser Val Gly Leu Gly Asn Val Ala Gly Thr Asp Gly Ala Ile Thr
            115                 120                 125
Gly Ala Pro Gly Thr Ile Glu Ala Glu Val Ala Ala Thr Arg Ser
130                 135                 140
Gly Val His Arg Tyr Ala Phe Pro Ala Gly Ser Thr Pro Ser Leu Val
145                 150                 155                 160
Val Asp Leu Glu Thr Asn Asn Thr Ser Arg Arg Ser Ser Val Gln
                165                 170                 175
Val Glu Thr Arg Ala Asp Gly Thr Val Glu Leu Ser Gly Gln Val Thr
                180                 185                 190
Gly Tyr Phe Tyr Asn Ala Ala Tyr Thr Leu Tyr Tyr Thr Ala Arg Thr
            195                 200                 205
```

```
Leu Gln Pro Ala Thr Val Gln Thr Trp Gly Asp Asp Arg Leu Val
    210                 215                 220

Asp Ala Thr Ala Gln Asp Gly Val Asp Thr Gly Ala Ile Leu Thr Phe
225                 230                 235                 240

Asp Pro Ala Asp Ala Gly Glu Ile Gly Leu Gln Val Thr Leu Ser Pro
                245                 250                 255

Val Ser Val Glu Gln Ala Arg Ile Asp Gln Gln Val Glu Leu Gly Asp
            260                 265                 270

Leu Ser Phe Asp Ala Ile Arg Asp Arg Thr Arg Ala Glu Trp Asn Ala
        275                 280                 285

Thr Leu Gly Arg Val Ala Ile Asp Ala Ser Thr Ala Thr Asp Pro Thr
290                 295                 300

Gly Glu Leu Gln Arg Leu Phe Tyr Thr His Leu Tyr Arg Met Phe Ala
305                 310                 315                 320

Met Pro Met Asn Ala Thr Ser Thr Ser Gly Thr Tyr Arg Gly Val Asp
                325                 330                 335

Gly Ala Val His Ala Ala Gln Gly Phe Thr Tyr Tyr Asp Ser Trp Ala
            340                 345                 350

Thr Trp Asp Asp Phe Arg Lys Phe Ser Val Ile Ala Tyr Ile Asp Pro
        355                 360                 365

Ala Leu Tyr Arg Asp Met Val Gln Ser Leu Val Tyr Leu Phe Ala Asp
370                 375                 380

Ala Glu Ala Thr Gly Thr Gly Gly Leu Gly Gly Phe Val His Ser
385                 390                 395                 400

Val Pro Thr Val Arg Trp Glu Arg Ser Ser Val Val Ala Asp Ala
                405                 410                 415

Ile Ala Lys Gly Phe Asp Gly Phe Asp Arg Leu Asp Glu Ala Tyr Pro
            420                 425                 430

Ala Leu Gln Arg Leu Val Gly Gln Tyr Ser Ala Asp Glu Leu Arg Arg
        435                 440                 445

Gly Tyr Val Ala Gly Asn Pro Gly Ala Ser Val Gln Arg Gly Tyr Asp
450                 455                 460

Gln Tyr Gly Leu Ser Val Ile Ala Asp Glu Leu Gly Leu Thr Glu Glu
465                 470                 475                 480

Ala Glu Thr Leu Arg Glu Gln Ala Ser Trp Pro Ile Glu Lys Leu Thr
                485                 490                 495

Lys Pro Gly Ala Trp Thr Ala Ala Asp Gly Thr Gln Val Gly Leu Leu
            500                 505                 510

Thr Pro Arg Ala Ala Asp Gly Ser Trp Gln Ser Ala Asp His Ala Lys
        515                 520                 525

Phe Glu Ala Ala Gly Leu Tyr Gln Gly Thr Leu Trp Gln Tyr His Trp
530                 535                 540

Tyr Asp Ala Tyr Asp Met Asp Ala Leu Val Glu Ala Met Gly Gly His
545                 550                 555                 560

Glu Ala Ala Arg Leu Gly Met Arg His Met Phe Gly Glu His Ala Pro
                565                 570                 575

Asp Asp Gly Lys Ala Met Leu His Ser Asn Ala Asn Glu Ile Asp Leu
            580                 585                 590

Gln Ala Pro Tyr Leu Phe Asn Tyr Thr Gly Glu Pro Ser Leu Thr Gln
        595                 600                 605

Lys Trp Ala Arg Ala Ile Tyr Thr Lys Glu Thr Trp Asn Arg Tyr Ile
610                 615                 620

Ala Thr Gly Ser Ser Ser Ala Val Pro Ser Gly Gly Gly Glu Phe Thr
```

```
                625                 630                 635                 640
        Pro Pro Leu Lys Thr Lys Val Tyr Arg Leu Asp Pro Arg Gly Met Leu
                        645                 650                 655

Pro Thr Met Asp Asn Asp Ala Gly Thr Met Ser Thr Met Phe Val Ala
                        660                 665                 670

Ala Ala Val Gly Leu Phe Pro Val Thr Ala Gly Ser Ser Gln Phe Gln
                        675                 680                 685

Val Gly Ser Pro Phe Phe Asp Ser Thr Thr Ile Thr Tyr Asp Asp Gly
                        690                 695                 700

Ser Ala Phe Thr Val Thr Ala Asp Gly Val Ser Glu Asp Ala Phe Tyr
        705                 710                 715                 720

Val Gln Ser Ala Thr Leu Asp Gly Ala Thr Phe Gly Asn Thr Trp Val
                        725                 730                 735

Asp Tyr Ala Thr Val Val Gly Gly Ala Asp Leu Ala Phe Arg Met Gly
                        740                 745                 750

Glu Gln Pro Ser Asp Trp Gly Thr Asp Thr Ala Pro Ala Phe Ser Met
                        755                 760                 765

Ser Thr Ala Thr Asp Glu Pro Ala Glu Gly Pro Arg Val Ser Ala Glu
                        770                 775                 780

Pro Thr Thr Val Gln Thr Gly Asp Gly Gly Ala Leu Asp Ala Thr Val
        785                 790                 795                 800

Thr Leu Thr Leu Asp Gly Ala Arg Leu Ala Pro Ala Gly Thr Asp
                        805                 810                 815

Leu Val Thr Ser Gly Ala Ala Ser Val Val Gly Leu Pro Asp Gly Val
                        820                 825                 830

Thr Ala Ala Val Thr Val Ala Ser Pro Thr Ala Leu Thr Val Ser Leu
                        835                 840                 845

Thr Gly Thr Ala Ser Ala Asp Ala Arg Phe Phe Val His Leu Arg Asp
                        850                 855                 860

Ala Ala Leu Ala Asp Gly Val Ala Ala Ala Ser Leu Gln Gly Gln Gly
        865                 870                 875                 880

Val Ser Val Arg Ser Pro Leu Arg Leu Ser Val Ala Ser Ala Glu Arg
                        885                 890                 895

Asp Ala Leu Ala Ala Leu Val Asp Asp Ala Val Leu Val Arg His Gly
                        900                 905                 910

Asn Tyr Ser Ser Val Thr Phe Asp Arg Phe Ser Thr Ala Leu Thr Lys
                        915                 920                 925

Ala Gln Glu Ala Leu Gly Asp Glu Ala Ala Thr Ser Ile Ala Leu Arg
        930                 935                 940

Phe Ala Ala Asp Arg Leu Gly Ala Ala Ala Asp Ala Leu Asp Leu Thr
        945                 950                 955                 960

Gly Gly Gly Tyr Arg Thr Leu Glu Ala Glu Gln Ser Glu Ala Trp Ser
                        965                 970                 975

Gly Gly Glu Leu Lys Asn Glu Ala Asn Ser Ser Ser Gly Asn Leu Gly
                        980                 985                 990

Gly Val Arg Ser Gly Ser Trp Val Gln Tyr Arg Asp Met Thr Phe Glu
                        995                 1000                1005

Thr Ala Ala Gly Asp Thr Pro Pro Arg Phe Leu Thr Val Arg Tyr Asp
        1010                1015                1020

Thr Ser Phe Ala Pro Thr Asp Thr Pro Ser Thr Val Arg Val His Ala
        1025                1030                1035                1040

Gly Asp Val Ser Gly Pro Val Val Ala Thr Val Asp Leu Lys Gly Thr
                        1045                1050                1055
```

```
Ser Gly Trp Gly Lys Tyr Thr Glu Val Thr Ala Glu Leu Gly Asp Val
            1060                1065                1070

Gln Ala Leu Val Asp Ala Gln Val Val Thr Phe Glu Leu Leu Ala Pro
            1075                1080                1085

Ser Gly Arg Ser Trp Val Gly Asn Phe Asp Trp Phe Arg Phe Ser Ala
            1090                1095                1100

Glu Asp Pro Ala Ala Pro Gly Gln Pro Gly Glu Ser Pro Thr Val Thr
1105                1110                1115                1120

Ile Glu Ala Glu Asp Trp Thr Ala Ser Ser Gly Arg Gly Leu Lys Lys
                1125                1130                1135

Glu Ser Ser Thr Trp Thr Ser Gly Pro Val Thr Asn Val Gly Gly Thr
            1140                1145                1150

Ala Asp Gly Asp Trp Ile Ala Tyr Gly Glu Val Asp Leu Gly Glu Leu
            1155                1160                1165

Pro Leu Gly Glu Leu Ser Val His Tyr Val His Asn Ser Asn Arg Ser
            1170                1175                1180

Gly Asn Asn Ser Ala Leu Ser Val Tyr Leu Asp Ala Phe Asp Pro Ala
1185                1190                1195                1200

Asn Pro Gly Glu Pro Phe Val Thr Val Pro Leu Pro Thr Thr Gly Ser
            1205                1210                1215

Ser Trp Thr Ala Asp Gly Thr Ala Thr Val Val Leu Pro Glu Thr Val
            1220                1225                1230

Gln Gly Thr His Glu Val Phe Val Arg Leu Ser Thr Glu Pro Tyr Ala
            1235                1240                1245

Asp His Pro Tyr Val Ala Asn Leu Asp Ser Leu Thr Phe Ala Pro Gly
            1250                1255                1260

Gly Pro Thr Ser Val Val Val Glu Ser Glu Ala Trp Thr Ser Asn Ser
1265                1270                1275                1280

Gly Arg Gly Leu Lys Asn Glu Ser Ser Thr Trp Thr Ser Gly Pro Val
                1285                1290                1295

Thr Asn Val Gly Gly Thr Ala Asp Gly Asp Trp Leu Ala Tyr Gly Glu
            1300                1305                1310

Ile Asp Leu Gly Ser Ala Ala Leu Asp Gln Leu Ser Val His Tyr Val
            1315                1320                1325

His Asn Ser Asn Arg Ser Gly Arg Asn Ser Ala Leu Ser Val Tyr Leu
            1330                1335                1340

Asp Ala Phe Asp Pro Ala Asn Pro Gly Glu Pro Phe Val Thr Val Pro
1345                1350                1355                1360

Leu Ala Asn Thr Gly Ser Ser Trp Thr Thr Asp Gly Thr Ala Val Val
                1365                1370                1375

Asp Leu Pro Ser Thr Val Arg Gly Lys His Gln Val Trp Val Arg Leu
            1380                1385                1390

Ser Thr Glu Ala Tyr Ala Asp His Pro Tyr Val Ala Asn Leu Asp Ser
            1395                1400                1405

Met Arg Phe Phe Thr Asp Ala Tyr Asp Val Glu Val Pro Pro Thr Asp
            1410                1415                1420

Thr Ala Leu Ala Ala Val Val Asp Ala Ala Gly Thr Pro Glu Ala
1425                1430                1435                1440

Glu Ile Ala Arg Tyr Gly Arg Ile Asp Ala Arg Val Phe Thr Arg Glu
                1445                1450                1455

Leu Ala Ala Arg Ser Val Leu Ala Asp Ala Gly Ala Thr Gln Ala
            1460                1465                1470
```

-continued

```
Gln Ala Asp Glu Arg Ala Arg Arg Leu Gly Leu Ala Thr Asp Gln Leu
        1475                1480                1485

Val Pro Ala Glu Arg Arg Leu Glu Asn Leu Val Ala Ser Ala Glu
    1490                1495                1500

Ala Leu Thr Asp Glu Gly Tyr Ser Pro Glu Ser Trp Gln Ala Phe Arg
1505                1510                1515                1520

Thr Ala Leu Ala Ala Ala Thr Gly Thr Leu Asp Asp Ala Ala Ser
            1525                1530                1535

Asp Glu Ala Leu His Asp Ala Arg Leu Ala Leu Gln Gly Ala Val Asp
                1540                1545                1550

Ala Leu Glu Glu Pro Ala Asp Val Val Leu Val Glu Val Glu Val Ser
        1555                1560                1565

Pro Arg Cys Leu Ala Gly Lys Pro Tyr Val Ala Val Arg Ala Val Asn
    1570                1575                1580

Val Ser Asp Ala Ala Val Asp Val Glu Leu Ala Ser Ser Leu Gly Thr
1585                1590                1595                1600

Arg Ser Phe Val Gly Val Ala Pro Gly Ala Ser Ala Tyr Gln Ser Phe
                1605                1610                1615

Ala Ala Arg Ser Ala Thr Gly Asp Leu Asp Val Thr Val Thr Ala Thr
            1620                1625                1630

Gly Ala Asp Gly Thr Gln Thr Val Glu Gln Val Val Thr Val Pro Ser
        1635                1640                1645

Cys Ser
    1650

<210> SEQ ID NO 51
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 4, 5, 7
<223> OTHER INFORMATION: Xaa = Gly, Ala, Ser, Thr, or Cys

<400> SEQUENCE: 51

Gly Val Gly Xaa Xaa Gly Xaa Gly Gly
  1               5

<210> SEQ ID NO 52
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 3
<223> OTHER INFORMATION: Xaa = Any amino acid except Pro

<400> SEQUENCE: 52

Val Arg Xaa Glu
  1

<210> SEQ ID NO 53
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
```

```
<222> LOCATION: 1, 5
<223> OTHER INFORMATION: Xaa = Leu, Ile, Val, Ala, Phe, Tyr, or Met

<400> SEQUENCE: 53

Xaa Tyr Gln Gly Xaa
 1               5

<210> SEQ ID NO 54
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 3
<223> OTHER INFORMATION: Xaa = Any amino acid except Pro

<400> SEQUENCE: 54

Gly Asp Xaa Gly Asn
 1               5

<210> SEQ ID NO 55
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 4, 5, 7
<223> OTHER INFORMATION: Xaa = Gly, Ser, Thr, Val, Ala, Cys, or Gln

<400> SEQUENCE: 55

Gly Val Gly Xaa Xaa Gly Xaa Gly Gly
 1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 56

His His His His His His
 1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide

<400> SEQUENCE: 57

Leu Tyr Gln Gly Thr
 1               5

<210> SEQ ID NO 58
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 58

Asp Glu Val Asp
  1
```

UNITED STATES PATENT AND TRADEMARK OFFICE
CERTIFICATE OF CORRECTION

PATENT NO.         : 9,598,682 B2
APPLICATION NO.    : 13/499061
DATED              : March 21, 2017
INVENTOR(S)        : Nico Luc Marc Callewaert et al.

Page 1 of 1

It is certified that error appears in the above-identified patent and that said Letters Patent is hereby corrected as shown below:

In the Specification

Column 1, Line 13: Delete "PCT/IB2010/002589and" and insert -- PCT/IB2010/002589 and --, therefor.

Column 1, Line 14: Delete "61/246,846" and insert -- 61/246,847 --, therefor.

In the Claims

Column 265, Line 60, in Claim 12: Delete "Oogataea" and insert -- Ogataea --, therefor.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*